US012509431B2

(12) United States Patent
Hawryluk et al.

(10) Patent No.: US 12,509,431 B2
(45) Date of Patent: Dec. 30, 2025

(54) 1,4-DIHYDROQUINAZOLINONE COMPOUNDS AND USES THEREOF

(71) Applicant: Edgewise Therapeutics, Inc., Boulder, CO (US)

(72) Inventors: Natalie Anne Hawryluk, Nederland, CO (US); Stephen Thomas Schlachter, Boulder, CO (US); Marc Justin Evanchik, Boulder, CO (US); Carlos Luis Del Rio, San Mateo, CA (US); Alan James Russell, Boulder, CO (US); Kevin Koch, Niwot, CO (US); Michael Mark DuVall, Vancouver, WA (US); Michael Joseph Luzzio, Groton, CT (US); Kevin Hunt, Boulder, CO (US)

(73) Assignee: EDGEWISE THERAPEUTICS, INC., Boulder, CO (US)

( * ) Notice: Subject to any disclaimer, the term of this patent is extended or adjusted under 35 U.S.C. 154(b) by 0 days.

(21) Appl. No.: 18/882,649

(22) Filed: Sep. 11, 2024

(65) Prior Publication Data

US 2025/0154111 A1 May 15, 2025

Related U.S. Application Data

(63) Continuation of application No. PCT/US2023/075138, filed on Sep. 26, 2023.

(60) Provisional application No. 63/377,175, filed on Sep. 26, 2022.

(51) Int. Cl.

| | |
|---|---|
| ***C07D 239/80*** | (2006.01) |
| ***A61K 31/517*** | (2006.01) |
| ***A61K 31/519*** | (2006.01) |
| ***A61K 31/527*** | (2006.01) |
| ***A61K 31/5383*** | (2006.01) |
| ***A61P 9/00*** | (2006.01) |
| ***C07D 401/12*** | (2006.01) |
| ***C07D 401/14*** | (2006.01) |
| ***C07D 403/12*** | (2006.01) |
| ***C07D 405/12*** | (2006.01) |
| ***C07D 405/14*** | (2006.01) |
| ***C07D 409/12*** | (2006.01) |
| ***C07D 413/12*** | (2006.01) |
| ***C07D 413/14*** | (2006.01) |
| ***C07D 417/12*** | (2006.01) |
| ***C07D 471/04*** | (2006.01) |
| ***C07D 471/18*** | (2006.01) |
| ***C07D 487/04*** | (2006.01) |
| ***C07D 487/10*** | (2006.01) |
| ***C07D 491/048*** | (2006.01) |
| ***C07D 491/052*** | (2006.01) |
| ***C07D 491/056*** | (2006.01) |
| ***C07D 491/20*** | (2006.01) |
| ***C07D 498/04*** | (2006.01) |

(52) U.S. Cl.

CPC .......... *C07D 239/80* (2013.01); *A61K 31/517* (2013.01); *A61K 31/519* (2013.01); *A61K 31/527* (2013.01); *A61K 31/5383* (2013.01); *A61P 9/00* (2018.01); *C07D 401/12* (2013.01); *C07D 401/14* (2013.01); *C07D 403/12* (2013.01); *C07D 405/12* (2013.01); *C07D 405/14* (2013.01); *C07D 409/12* (2013.01); *C07D 413/12* (2013.01); *C07D 413/14* (2013.01); *C07D 417/12* (2013.01); *C07D 471/04* (2013.01); *C07D 471/18* (2013.01); *C07D 487/04* (2013.01); *C07D 487/10* (2013.01); *C07D 491/048* (2013.01); *C07D 491/052* (2013.01); *C07D 491/056* (2013.01); *C07D 491/20* (2013.01); *C07D 498/04* (2013.01)

(58) Field of Classification Search

CPC .................................................... C07D 239/80
USPC .................................................... 514/210.18
See application file for complete search history.

(56) References Cited

U.S. PATENT DOCUMENTS

| | | | |
|---|---|---|---|
| 5,846,514 | A | 12/1998 | Foster et al. |
| 6,334,997 | B1 | 1/2002 | Foster et al. |
| 7,429,604 | B2 | 9/2008 | Corte et al. |
| 7,875,636 | B2 | 1/2011 | Barrow et al. |
| 9,464,065 | B2 | 10/2016 | Schultz et al. |
| 9,522,140 | B2 | 12/2016 | Inoue et al. |
| 9,585,883 | B2 | 3/2017 | Oslob et al. |
| 11,052,092 | B2 | 7/2021 | Delhomel et al. |
| 11,306,098 | B2 | 4/2022 | Letourneau et al. |
| 11,931,358 | B2 | 3/2024 | Honarpour et al. |
| 11,945,803 | B2 | 4/2024 | Lennek et al. |
| 2007/0148185 | A1 | 6/2007 | Rathore et al. |

(Continued)

FOREIGN PATENT DOCUMENTS

| | | | |
|---|---|---|---|
| CN | 1521171 | A | 8/2004 |
| CN | 109836477 | A | 6/2019 |

(Continued)

OTHER PUBLICATIONS

Arranz, Esther. et al. Synthesis And Pharmacological Evaluationof 2,3-dihydro-3-oxo-4h-thieno[3,4-e][1,2,4]Thiadiazine 1,1-Dioxidesas Voltage-Dependent Calcium Channel Blockers. European Journal of Medicinal Chemistry 35(7-8):751-759 (2000).

(Continued)

*Primary Examiner* — Kahsay Habte
(74) *Attorney, Agent, or Firm* — WILSON SONSINI GOODRICH & ROSATI

(57) ABSTRACT

Provided dihydroquinazolinone and azadihydroquinazolinone compounds for treating cardiac indications such as hypertrophic cardiomyopathy and diastolic dysfunction.

40 Claims, No Drawings

(56) References Cited

U.S. PATENT DOCUMENTS

| | | | |
|---|---|---|---|
| 2009/0023169 | A1 | 1/2009 | Hartman et al. |
| 2010/0113391 | A1 | 5/2010 | Koga et al. |
| 2012/0108597 | A1 | 5/2012 | Guo et al. |
| 2016/0176868 | A1 | 6/2016 | Oslob et al. |
| 2019/0077793 | A1 | 3/2019 | Ashcraft et al. |
| 2020/0369626 | A1 | 11/2020 | Tu et al. |
| 2021/0276991 | A1 | 9/2021 | Morgan et al. |
| 2022/0106265 | A1 | 4/2022 | Thiele et al. |
| 2023/0012449 | A1 | 1/2023 | Bondy et al. |
| 2023/0149394 | A1 | 5/2023 | Honarpour et al. |
| 2024/0164138 | A1 | 5/2024 | Ham et al. |
| 2024/0279206 | A1 | 8/2024 | Lennek et al. |

FOREIGN PATENT DOCUMENTS

| | | | |
|---|---|---|---|
| CN | 114149423 | A | 3/2022 |
| EP | 0561252 | A1 | 9/1993 |
| EP | 0585913 | A2 | 3/1994 |
| EP | 1724264 | A1 | 11/2006 |
| EP | 2010493 | A2 | 1/2009 |
| EP | 2729448 | B1 | 9/2015 |
| EP | 3573960 | B1 | 8/2023 |
| JP | S6463518 | A | 3/1989 |
| JP | H01125369 | A | 5/1989 |
| MA | 30462 | B1 | 6/2009 |
| WO | WO-0032587 | A1 | 6/2000 |
| WO | WO-0142216 | A2 | 6/2001 |
| WO | WO-0206264 | A1 | 1/2002 |
| WO | WO-02064578 | A1 | 8/2002 |
| WO | WO-2005085210 | A1 | 9/2005 |
| WO | WO-2007078839 | A2 | 7/2007 |
| WO | WO-2007120729 | A2 | 10/2007 |
| WO | WO-2007124617 | A1 | 11/2007 |
| WO | WO-2008010964 | A1 | 1/2008 |
| WO | WO-2008016648 | A2 | 2/2008 |
| WO | WO-2008016669 | A2 | 2/2008 |
| WO | WO-2008076225 | A2 | 6/2008 |
| WO | WO-2008107436 | A1 | 9/2008 |
| WO | WO-2009023655 | A1 | 2/2009 |
| WO | WO-2009054983 | A1 | 4/2009 |
| WO | WO-2010002779 | A2 | 1/2010 |
| WO | WO-2010056549 | A1 | 5/2010 |
| WO | WO-2010137351 | A1 | 12/2010 |
| WO | WO-2013006738 | A1 | 1/2013 |
| WO | WO-2014205223 | A1 | 12/2014 |
| WO | WO-2016004417 | A1 | 1/2016 |
| WO | WO-2016162390 | A1 | 10/2016 |
| WO | WO-2017161119 | A1 | 9/2017 |
| WO | WO-2019028360 | A1 | 2/2019 |
| WO | WO-2020005888 | A1 | 1/2020 |
| WO | WO-2020033413 | A2 | 2/2020 |
| WO | WO-2020097265 | A1 | 5/2020 |
| WO | WO-2020123675 | A1 | 6/2020 |
| WO | WO-2020172565 | A1 | 8/2020 |
| WO | WO-2020210032 | A1 | 10/2020 |
| WO | WO-2020221376 | A1 | 11/2020 |
| WO | WO-2021092598 | A1 | 5/2021 |
| WO | WO-2021231546 | A1 | 11/2021 |
| WO | WO-2021231565 | A1 | 11/2021 |
| WO | WO-2022212902 | A1 | 10/2022 |
| WO | WO-2023277605 | A1 | 1/2023 |
| WO | WO-2023159234 | A2 | 8/2023 |
| WO | WO-2023208165 | A1 | 11/2023 |
| WO | WO-2023240134 | A1 | 12/2023 |
| WO | WO-2024050139 | A1 | 3/2024 |
| WO | WO-2024073426 | A1 | 4/2024 |
| WO | WO-2024138042 | A1 | 6/2024 |
| WO | WO-2024182469 | A1 | 9/2024 |
| WO | WO-2024206339 | A1 | 10/2024 |
| WO | WO-2024206345 | A1 | 10/2024 |
| WO | WO-2024206347 | A1 | 10/2024 |

OTHER PUBLICATIONS

Awinda et al., Mavacamten decreases maximal force and $Ca^{2+}$ sensitivity in the N47K-myosin regulatory light chain mouse model of hypertrophic cardiomyopathy. Am J. Physio. Heart Cir. Physiol., 320(2): Feb. 1, 2021;H881-H890.

Chatterjee, Tanmay. et al. Base-Promoted Synthesis of 2-Aryl Quinazolines from 2-Aminobenzylamines in Water. The Journal of Organic Chemistry 83(14):7423-7430 (2018).

Chem, Ji-Wang. et al. Studies on 1, 2, 4-Benzothiadiazine 1, 1-Dioxide IX.1 Synthesis and Pharmacological Evaluation of 1, 2, 4-Benzothiadiazine 1, 1-Dioxide Biphenyl Tetrazoles as Angiotensin II Antagonists. Journal of the Chinese Chemical Society 45(6):805-810 (1998).

Davis, J. S. et al., The Overall pattern of Cardiac contraction depends on a spatial gradient of Myosin Regulatory Light Chain Phosphorylation. Cell, vol. 107, 631-641, Nov. 30, 2001.

Engler, Thomas A. et al. Substituted 3-imidazo[1,2-a]pyridin-3-yl-4-(1,2,3,4-tetrahydro-[1,4]diazepino-[6,7,1-hi]indol-7-yl)pyrrole-2,5-diones as highly selective and potent inhibitors of glycogen synthase kinase-3. Journal of Medicinal Chemistry 47(16):3934-3937 (2004).

Evans, Anthony E. Synthesis of Radiolabeled Compounds. Journal of Radioanalytical and Nuclear Chemistry 64(1-2):9-32 (1981).

Fedorak, Richard N. et al. A novel colon-specific steroid prodrug enhances sodium chloride absorption in rat colitis. American Journal of Physiology 269(2 Pt 1):G210-G218 (1995).

Fieser, Louis. F, and Mary Fieser. Reagents for Organic Synthesis. John Wiley and Sons:119-121 (1994).

Highlights of Prescribing Information These highlights do not include all the information needed to use CAMZYOS safely and effectively. Apr. 2022, 27 Pages.

Higuchi, T, and V. Stella. Pro-Drugs as Novel Delivery Systems, vol. 14 of the A.C.S. Symposium Series. American Chemical Society (1975).

Hochhaus, Gunther. et al. A Selective HPLC/RIA for Dexamethasone and its Prodrug Dexamethasone-21-sulphobenzoate Sodium in Biological Fluids. Biomedical Chromatography 6(6):283-286 (1992).

Kabalka, George W. et al. The Synthesis of Radiolabeled Compounds via Organometallic Intermediates. Tetrahedron 45(21):6601-6621 (1989).

Larsen, Jorn Drustrup, and Hans Bundgaard. Prodrug forms for the sulfonamide group. I. Evaluation of N-acyl derivatives, N-sulfonylamidines, N-sulfonylsulfilimines and sulfonylureas as possible prodrug derivatives. International Journal of pharmaceutics 37(1-2):87-95 (1987).

Larsen, Jorn Drustrup et al. Prodrug forms for the Sulfonamide Group. II. Water-soluble Amino Acid Derivatives of N-methylsulfonamides as Possible Prodrugs. International Journal of Pharmaceutics 47:103-110 (1988).

Liu, Dazhi. et al. Design, synthesis and evaluation of 1, 2-benzisothiazol-3-one derivatives as potent caspase-3 inhibitors. Bioorganic & medicinal chemistry 21(11):2960-2967 (2013).

Mcleod, Andrew D. et al. A glucocorticoid prodrug facilitates normal mucosal function in rat colitis without adrenal suppression. Gastroenterology 106(2):405-413 (1994).

PCT/US2023/075138 International Search Report and Written Opinion dated Nov. 28, 2023.

PCT/US2024/021528 International Search Report and Written Opinion dated Aug. 6, 2024.

PCT/US2024/021537 International Search Report and Written Opinion dated Jul. 18, 2024.

PCT/US2024/021539 International Search Report and Written Opinion dated Aug. 12, 2024.

Ro, R. et al., Vector Flow Mapping in Obstructive Hypertrophic Cardiomyopathy to Assess the Relationship of Early Systolic Left Ventricular Flow and the Mitral Valve. Journal of the American College of Cardiology, 2014, vol. 64. No. 19; 1984-95.

Sinkula, A A, and Samuel H. Yalkowsky. Rationale for design of biologically reversible drug derivatives: prodrugs. Journal of pharmaceutical sciences 64(2):181-210 (1975).

Smith, Joshua D. Isoform selectivities of novel 4-hydroxycoumarin imines as inhibitors of myosin II. European journal of medicinal chemistry 247:115008, 1-38 (2023).

(56) References Cited

OTHER PUBLICATIONS

Sun, Lin. et al. Design, Synthesis, and Mechanism Study of Benzenesulfonamide-Containing Phenylalanine Derivatives as Novel HIV-1 Capsid Inhibitors with Improved Antiviral Activities. Journal of Medicinal Chemistry 63(9):4790-4810 (2020).
Wang, Min. et al. [11C]GSK2126458 and [18F]GSK2126458, The First Radiosynthesis Of New Potential PET Agents For Imaging Of PI3K And mTOR In Cancers. Bioorganic & Medicinal Chemistry Letters 22(4):1569-1574 (2012).
Zhang, J. et al., Hypertrophic cardiomyopathy associated E22K mutation in myosin regulatory light chain decreases calcium-activated tension and stiffness and reduces myofilament Ca2+ sensitivity. FEBS J. Aug. 2021 ; 288(15): 4596-4613. doi:10.1111/febs.15753.
Ukrainets, I.V. et al. 4-Hydroxyquinolin-2-ones. 45. Synthesis, Structure, and Biological Activity of N-Substituted 1H-4-Hydroxy-2-oxoquinoline-3-acetic Acid Amides. Chemistry of Heterocyclic Compounds 36:1319-1325 (2000).
DATABASE CaPlus [Online] ChemicA1 Abstracts Service, Jan. 1, 1990 (Jan. 1, 1990). Chen Qingping ET A1: Proton NMR spectra of 7[beta]-(6-substituted-2-quinolone-3-aceta mido)- and 7[beta]-(6-substituted-4-hydroxyquinoline-3-formamido)-cephA1osporins. XP093279164, Database accession No. 1991:631920.
Database Registry, ChemicA1 Abstracts Service; (Nov. 9, 2021), Database accession No. 2727956-55-8, XP093279204.
Database Registry, Chemical Abstracts Service (Aug. 2, 2012), Database accession No. 1385267-38-8, XP093279922.
Database Registry, Chemical Abstracts Service (Jun. 18, 2015), Database accession No. 1783105-24-7, XP093279920.
Database Registry, Chemical Abstracts Service; (Dec. 16, 2015), Database accession No. 1831179-14-6, XP093277426.
Database Registry, Chemical Abstracts Service; (Dec. 18, 2015), Database accession No. 1832193-03-9, XP093277424.
Database Registry, Chemical Abstracts Service; (Jul. 6, 2016), Database accession No. 1946404-58-5, XP093277421.
Database Registry, Chemical Abstracts Service; (Jul. 10, 2016), Database accession No. 1948573-95-2, XP093277416.
Database Registry, Chemical Abstracts Service (Jan. 25, 2017), Database accession No. 2058772-64-6, XP093279919.
Database Registry, Chemical Abstracts Service; (Jan. 27, 2017), Database accession No. 2060133-05-1, XP093277413.
Database Registry, Chemical Abstracts Service; (Jul. 26, 2017), Database accession No. 2103065-64-9, XP093277409.
Database Registry, Chemical Abstracts Service; (Feb. 15, 2018), Database accession No. 2173908-64-8, XP093277398.
Database Registry, Chemical Abstracts Service; (Mar. 12, 2018), Database accession No. 2189172-68-5, XP093277394.
Database Registry, Chemical Abstracts Service; (Jul. 28, 2019), Database accession No. 2361760-55-4, XP093277429.
Database Registry, Chemical Abstracts Service; (Jul. 28, 2019), Database accession No. 2361838-41-5, XP093277392.
Database Registry, Chemical Abstracts Service; (Jul. 28, 2019), Database accession No. 2361907-19-7, XP093277513.
Database Registry, Chemical Abstracts Service (Aug. 29, 2019), Database accession No. 2369930-64-1, XP093279918.
Database Registry, Chemical Abstracts Service (Jan. 1, 2020), Database accession No. 2398077-26-2, XP093279916.
Database Registry, Chemical Abstracts Service (Jan. 2, 2020), Database accession No. 2398164-43-5, XP093279914.
Database Registry, Chemical Abstracts Service (Jan. 8, 2020), Database accession No. 2402509-76-4, XP093279912.
Database Registry, Chemical Abstracts Service (Jan. 10, 2020), Database accession No. 2404419-52-7, XP093279910.
Database Registry, Chemical Abstracts Service (Jan. 13, 2020), Database accession No. 2405463-55-8, XP093279908.
Database Registry, Chemical Abstracts Service (Jun. 8, 2020), Database accession No. 2420362-92-9, XP093279906.
Database Registry, Chemical Abstracts Service (Jun. 9, 2020), Database accession No. 2421242-17-1, XP093279905.
Database Registry, Chemical Abstracts Service (Jun. 22, 2020), Database accession No. 2431889-47-1, XP093279901.
Database Registry, Chemical Abstracts Service (Jun. 23, 2020), Database accession No. 2432461-84-0, XP093279900.
Database Registry, Chemical Abstracts Service (Aug. 31, 2020), Database accession No. 2468117-82-8, XP093279897.
Database Registry, Chemical Abstracts Service; (Sep. 23, 2021), Database accession No. 2699886-11-6, XP093277387.
Database Registry, Chemical Abstracts Service; (Oct. 14, 2021), Database accession No. 2712289-98-8, XP093277386.
Database Registry, Chemical Abstracts Service; (Oct. 15, 2021), Database accession No. 2712788-51-5, XP093277508.
Database Registry, Chemical Abstracts Service; (Oct. 17, 2021), Database accession No. 2713664-04-9, XP093277384.
Database Registry, Chemical Abstracts Service (Jul. 26, 2022), Database accession No. 2797160-72-4, XP093279894.
Database Registry, Chemical Abstracts Service; (Sep. 1, 2022), Database accession No. 2816805-43-1, X P093277382.
Database Registry, Chemical Abstracts Service; (Jun. 23, 2023), Database accession No. 2935080-68-3, XP093277525.
Database Registry, Chemical Abstracts Service; (Aug. 29, 2023), Database accession No. 2966899-34-1, XP093277520.
Database Registry, Chemical Abstracts Service; (Aug. 31, 2023), Database accession No. 2968160-16-7, XP093277515.
Database Registry, Chemical Abstracts Service; (Oct. 18, 2023), Database accession No. 2990803-91-1, XP093277379.
Database Registry, Chemical Abstracts Service; (Dec. 1, 2023), Database accession No. 3009361-40-1, XP093277454.
Madhu, Desagoni. et al. 3-Trifluoroacetyl-quinolin-2(1 H)-ones as Carbonyl and Acid Surrogates in the Passerini-/Ugi-Type Reaction. The Journal of Organic Chemistry 87(5):2301-2314 (2022).
Okuzumi, Tatsuya. et al. Efficient solid-phase synthesis of quinazoline-2, 4-diones with various substituents on aromatic rings. Tetrahedron 59(29):5603-5608 (2003).
PCT/US2025/021324 International Search Report and Written Opinion dated Jun. 13, 2025.
PCT/US2025/021387 International Search Report and Written Opinion dated Jun. 13, 2025.
PCT/US2025/021402 International Search Report and Written Opinion dated Jun. 13, 2025.
PCT/US2025/021405 International Search Report and Written Opinion dated Jun. 16, 2025.
Sivakamasundari, S. et al. Pyrroloquinolines: Part IV—Synthesis of 1-Aryl-1H-pyrrolo [2,3-b]quinolines. Indian Journal of Chemistry XP002950352, 26B 744-747 (1987).
Ukrainets, I. et al. 4 Hydroxy-2-quinolones. 35. Synthesis and Study of Antithyroid Properties of 1H-2-OxO-3-(coumarin-3-yl)-4-hydroxyquinolines. Chemistry of Heterocyclic Compounds, Xp093278695 33(8):959-963 (1999).
Ukrainets I. V. et al. 4-Hydroxyquinolin-2-ones. 45. Synthesis, Structure, and Biological Activity of N-Substituted 1H-4-Hydroxy-2-oxoquinoline-3-acetic Acid Amides. Chemistry of Heterocyclic Compounds XP093278700, 36(11):1319-1325 (2000).

1,4-DIHYDROQUINAZOLINONE COMPOUNDS AND USES THEREOF

CROSS-REFERENCE

This application is a continuation application of International Patent Application No PCT/US2023/075138, filed Sep. 26, 2023, which claims the benefit of U.S. Provisional Patent Application No. 63/377,175, filed Sep. 26, 2022, each of which is incorporated herein by reference in its entirety.

BACKGROUND OF THE INVENTION

Hypertrophic cardiomyopathy HCM is a chronic, progressive disease of the cardiac sarcomere. The etiology of HCM is multifactorial; a significant portion of affected people have at least one mutation in the genes that encode cardiac sarcomere proteins. Regardless of the cause of HCM, in many cases, excess myosin-actin crossbridge formation in systole and diastole leads to hyperdynamic contraction and impaired relaxation. Over time this excess stress leads to tissue remodeling characterized histologically by myocyte hypertrophy, myofilament disarray, microvascular remodeling, and fibrosis. HCM may be genetic (e.g., heritable) or not genetic. HCM includes a group of highly penetrant, monogenic, autosomal dominant myocardial diseases. Such HCM may be caused by one or more of over 1,000 known point mutations in any one of the proteins contributing to the functional unit of myocardium, the sarcomere. About 1 in 500 individuals in the general population are found to have left ventricular hypertrophy unexplained by other known causes (e.g., hypertension or valvular disease), and many of these can be shown to have HCM, e.g., once other heritable (e.g., lysosomal storage diseases), metabolic, or infiltrative causes have been excluded.

Medical therapy for HCM is limited and many patients symptoms are empirically managed with beta-blockers, non-dihydropyridine calcium channel blockers, and/or disopyramide. None of these agents carry labeled indications for treating HCM, and essentially no rigorous clinical trial evidence is available to guide their use. In approximately 60% of patients with HCM, the left ventricular outflow tract becomes obstructed, impeding the flow of blood and creating a pressure gradient between the LV cavity and the aorta. For patients with hemodynamically significant outflow tract obstruction (gradient >50 mmHg), surgical myectomy or alcohol septal ablation can be utilized to alleviate the hemodynamic obstruction albeit with significant clinical morbidity and mortality. Provided herein are new therapeutic agents and methods that remedy the long-felt need for improved treatment of HCM and related cardiac disorders.

SUMMARY OF THE INVENTION

The disclosure provides compound and salts thereof for use in treating disease. In certain aspects, the disclosure provides a compounds of Formula (I), (II), and (III), pharmaceutical compositions thereof as well as methods of use in the treatment of disease.

Disclosed here is a compound represented by Formula (I):

(I)

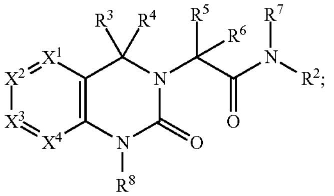

or a salt thereof, wherein:

$X^1$, $X^2$, $X^3$, and $X^4$ are each independently selected from $C(R^1)$, N, and $N^+(—O^-)$, wherein at least one of $X^1$, $X^2$, $X^3$, or $X^4$ is N; and no more than two of $X^1$, $X^2$, $X^3$, and $X^4$ are N;

each $R^1$ is independently selected from:

hydrogen;

halogen, $—NO_2$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$;

$C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2R^{10a}$, $—NO_2$, =O, =S, $=N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, =O, =S, $=N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$;

$R^2$ is selected from:

$C_{1-6}$ alkyl, $C_{2-6}$ alkenyl, and $C_{2-6}$ alkynyl, each of which is optionally substituted with one or more substituents independently selected from halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—C(O)OR^{10b}$, $—OC(O)R^{10b}$, $—N(R^{10b})C(O)N(R^{10b})_2$, $—OC(O)N(R^{10b})_2$, $—N(R^{10b})C(O)OR^{10b}$, $—S(O)R^{10b}$, $—S(O)_2R^{10b}$, $—NO_2$, =O, =S, $=N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—N(R^{10b})C(O)N(R^{10b})_2$, $—OC(O)N(R^{10b})_2$, $—N(R^{10b})C(O)OR^{10b}$, $—C(O)OR^{10b}$, $—OC(O)R^{10b}$, $—S(O)R^{10b}$, $—S(O)_2R^{10b}$, $—NO_2$, =O, =S, $=N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$;

$R^3$ and $R^4$ are each independently selected from:

hydrogen, halogen, —$OR^{10c}$, —$SR^{10c}$, —$N(R^{10c})_2$, —$NO_2$, and —CN; and $C_{1-6}$ alkyl optionally substituted with one or more substituents independently selected from halogen, —$OR^{10c}$, —$SR^{10c}$, —$N(R^{10c})_2$, —$NO_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$;

$R^5$ and $R^6$ are each independently selected from:

hydrogen, halogen, —$OR^{10c}$, —$SR^{10c}$, —$N(R^{10c})_2$, —$NO_2$, and —CN;

$C_{1-6}$ alkyl, optionally substituted with one or more substituents independently selected from halogen, —$OR^{10c}$, —$SR^{10c}$, —$N(R^{10c})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10c}$, —$SR^{10c}$, —$N(R^{10c})_2$, —$NO_2$, and —CN; and $C_{3-10}$ carbocycle and 3- to 10-membered heterocycle, each of which is optionally substituted with one or more substituents independently selected from halogen, —$OR^{10c}$, —$SR^{10c}$, —$N(R^{10c})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$.

$R^7$ is selected from:

hydrogen and $C_{1-6}$ alkyl optionally substituted with one or more substituents independently selected from halogen, —$OR^{10d}$, —$SR^{10d}$, —$N(R^{10d})_2$, —$NO_2$, and —CN;

$R^8$ is selected from:

hydrogen; and $C_{1-6}$ alkyl optionally substituted with one or more substituents independently selected from halogen, —$OR^{10e}$, —$SR^{10e}$, —$N(R^{10e})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10e}$, —$SR^{10e}$, —$N(R^{10e})_2$, —$NO_2$, and —CN;

each $R^{9a}$ is independently selected from:

halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN;

each $R^{9b}$ is independently selected from:

halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN;

each $R^{9c}$ is independently selected from:

halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10b})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN; and each $R^{10a}$, $R^{10b}$, $R^{10c}$, $R^{10d}$, and $R^{10e}$ is independently selected from:

hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

wherein if $X^3$ and $X^1$ are both N, then $R^8$ is selected from hydrogen and $C_{1-4}$ alkyl optionally substituted with one or more substituents independently selected from halogen, —$OR^{10}$, —$SR^{10}$, —$N(R^{10})_2$, —$NO_2$, and —CN; and wherein if $X^4$ and $X^2$ are both N, then $R^8$ is selected from hydrogen and $C_{1-4}$ alkyl optionally substituted with one or more substituents independently selected from halogen, —$OR^{10}$, —$SR^{10}$, —$N(R^{10})_2$, —$NO_2$, and —CN. The compound or salt of claim 1, wherein $X^1$, $X^2$, $X^3$, and $X^4$ are each independently selected from $C(R^1)$ and N.

Disclosed here is a compound represented by Formula (II):

(II)

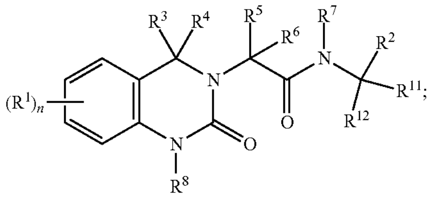

or a salt thereof, wherein:

n is 0, 1, 2, 3, or 4;

each $R^1$ is independently selected from:

halogen, —$NO_2$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, and —$S(O)_2R^{10a}$;

$C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, =O, =S, =$N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$;

$R^2$ is selected from:

halogen, —$NO_2$, —CN, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, and —$S(O)_2R^{10b}$;

$C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$;

$R^3$ and $R^4$ are each independently selected from:

hydrogen, halogen, —$OR^{10c}$, —$SR^{10c}$, —$N(R^{10c})_2$, —$NO_2$, and —CN; and $C_{1-6}$ alkyl optionally substituted with one or more substituents independently selected from halogen, —$OR^{10c}$, —$SR^{10c}$, —$N(R^{10c})_2$, —$NO_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$;

$R^5$ and $R^6$ are each independently selected from:

hydrogen, halogen, —$OR^{10d}$, —$SR^{10d}$, —$N(R^{10d})_2$, —$NO_2$, and —CN; and $C_{1-6}$ alkyl optionally substituted with one or more substituents independently selected from halogen, —$OR^{10d}$, —$SR^{10d}$, —$N(R^{10d})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9d}$;

$R^7$ is selected from:

hydrogen and $C_{1-6}$ alkyl optionally substituted with one or more substituents independently selected from halogen, —$OR^{10e}$, —$SR^{10e}$, —$N(R^{10e})_2$, —$NO_2$, and —CN;

$R^8$ is selected from:

hydrogen and $C_{1-6}$ alkyl optionally substituted with one or more substituents independently selected from halogen, —$OR^{10f}$, —$SR^{10f}$, —$N(R^{10f})_2$, —$NO_2$, and —CN;

$R^{11}$ is selected from:

halogen, —$NO_2$, —CN, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, and —$S(O)_2R^{10g}$; and $C_{1-6}$ alkyl, $C_{2-6}$ alkenyl, and $C_{2-6}$ alkynyl, each of which is optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, —$OC(O)R^{10g}$, —$N(R^{10g})C(O)N(R^{10g})_2$, —$OC(O)N(R^{10g})_2$, —$N(R^{10g})C(O)OR^{10g}$, —$S(O)R^{10g}$, —$S(O)_2R^{10g}$, —$NO_2$, =S, =$N(R^{10g})$, —CN, $C_{3-10}$ carbocycle and 3- to 10-membered heterocycle, wherein the $C_{3-10}$ carbocycle and 3- to 10-membered heterocycle are each optionally substituted with one or more $R^{9g}$.

$R^{12}$ is selected from hydrogen;

$C_{1-6}$ alkyl optionally substituted with one or more substituents independently selected from the group consisting of halogen, CN, OH, $OR^{10h}$, $N(R^{10h})_2$, $NO_2$, $C(O)R^{10h}$, $SR^{10h}$, and $S(O)R^{10h}$; and $C_{3-6}$ carbocycle and 3- to 10-membered heterocycle each optionally substituted with one or more substituents independently selected from the group consisting of halogen, CN, OH, $OR^{10h}$, $N(R^{10h})_2$, $NO_2$, $C(O)R^{10h}$, $SR^{10h}$, and $S(O)R^{10h}$; or $R^{12}$, $R^{11}$, and $R^2$ come together to form a $C_5$-$C_{10}$ bridged ring system;

each $R^{9a}$ is independently selected from:

halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN;

each $R^{9b}$ is independently selected from:

halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN;

each $R^{9b'}$ is independently selected from:

halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN;

each $R^{9c}$ is independently selected from:

halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN;

each $R^{9d}$ is independently selected from:

halogen, —$OR^{10d}$, —$SR^{10d}$, —$N(R^{10d})_2$, —$C(O)R^{10d}$, —$C(O)N(R^{10d})_2$, —$N(R^{10d})C(O)R^{10d}$, —$N(R^{10d})C(O)N(R^{10d})_2$, —$OC(O)N(R^{10d})_2$, —$N(R^{10d})C(O)OR^{10d}$, —$C(O)OR^{10d}$, —$OC(O)R^{10d}$, —$S(O)R^{10d}$, —$S(O)_2R^{10d}$, —$NO_2$, =O, =S, =$N(R^{10d})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10d}$, —$SR^{10d}$, $N(R^{10d})_2$, —$C(O)R^{10d}$, —$C(O)N(R^{10d})_2$, —$N(R^{10d})C(O)R^{10d}$, —$N(R^{10d})C(O)N(R^{10d})_2$, —$OC(O)N(R^{10d})_2$, —$N(R^{10d})C(O)OR^{10d}$, —$C(O)OR^{10d}$, —$OC(O)R^{10d}$, —$S(O)R^{10d}$, —$S(O)_2R^{10d}$, —$NO_2$, =O, =S, =$N(R^{10d})$, and —CN;

each $R^{9g}$ is independently selected from:

halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, —$S(O)_2R^{10g}$, —$NO_2$, =O, =S, =$N(R^{10g})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, —$S(O)_2R^{10g}$, —$NO_2$, =O, =S, =$N(R^{10g})$, and —CN;

each $R^{10a}$, $R^{10b}$, $R^{10b}$, $R^{10c}$, $R^{10b}$, $R^{10e}$, $R^{10f}$, $R^{10g}$, $R^{10h}$ is independently selected from:

hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

Disclosed herein is a method of treating a cardiovascular disease or a related condition comprising administering to a subject in need thereof a compound or salt of Formula (III):

(III)

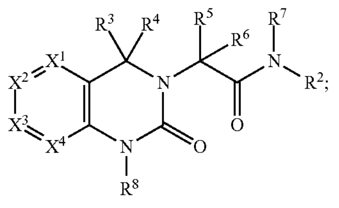

or a salt thereof, wherein $X^1$, $X^2$, $X^3$, and $X^4$ are each independently selected from $C(R^1)$, N, and $N^+(—O^-)$;

each $R^1$ is independently selected from:

hydrogen;

halogen, —$NO_2$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, and —$S(O)_2R^{10a}$;

$C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, =O, =S, =$N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$;

$R^2$ is selected from:

$C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$;

$R^3$ and $R^4$ are each independently selected from:

hydrogen, halogen, —$OR^{10c}$, —$SR^{10c}$, —$N(R^{10c})_2$, —$NO_2$, and —CN; and $C_{1-6}$ alkyl optionally substituted with one or more substituents independently selected from halogen, —$OR^{10c}$, —$SR^{10c}$, —$N(R^{10c})_2$, —$NO_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$;

$R^5$ and $R^6$ are each independently selected from:

hydrogen, halogen, —$OR^{10c}$, —$SR^{10c}$, —$N(R^{10c})_2$, —$NO_2$, and —CN;

$C_{1-6}$ alkyl, $C_{2-6}$ alkenyl, and $C_{2-6}$ alkynyl, any of which is optionally substituted at each occurrence with one or more substituents independently selected from halogen, —$OR^{10c}$, —$SR^{10c}$, —$N(R^{10c})_2$, —$NO_2$, —CN, and $C_{3-10}$ carbocycle and 3- to 10-membered heterocycle, each of which is optionally substituted with one or more substituents independently selected from halogen, —$OR^{10c}$, —$SR^{10c}$, —$N(R^{10c})_2$, —$NO_2$, and —CN; and $C_{3-10}$ carbocycle and 3- to 10-membered heterocycle, each of which is optionally substituted with one or more substituents independently selected from halogen, —$OR^{10c}$, —$SR^{10c}$, —$N(R^{10c})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$;

$R^7$ is selected from:

hydrogen and $C_{1-6}$ alkyl optionally substituted with one or more substituents independently selected from halogen, —$OR^{10d}$, —$SR^{10d}$, —$N(R^{10d})_2$, —$NO_2$, and —CN;

$R^8$ is selected from:

hydrogen; and $C_{1-6}$ alkyl optionally substituted with one or more substituents independently selected from halogen, —$OR^{10e}$, —$SR^{10e}$, —$N(R^{10e})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10e}$, —$SR^{10e}$, —$N(R^{10e})_2$, —$NO_2$, and —CN;

each $R^{9a}$ is independently selected from:

halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN;

each $R^{9b}$ is independently selected from:

halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C$ $(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN;

each $R^{9c}$ is independently selected from:

halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN;

each $R^{10a}$, $R^{10b}$, $R^{10c}$, $R^{10d}$, $R^{10e}$ is independently selected from:

hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}\ alkyl)_2$, —$NH(C_{1-6}\ alkyl)$, $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}\ alkyl)_2$, —$NH(C_{1-6}\ alkyl)$, $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

In certain aspects, the disclosure provides methods for treating a cardiac disease in an individual in need thereof, the method comprising administering a therapeutically effective amount of a compound of Formulas (I), (II), or (III).

Diseases treated by the methods described herein include, but are not limited to, cardiac diseases. Cardiac diseases treated by the methods described herein include, but are not limited to, heart muscle disease (cardiomyopathy), hypertrophic cardiomyopathy (HCM), abnormal heart rhythms, aorta disease, Marfan syndrome, coronary artery disease, heart attack, heart failure, rheumatic heart disease, peripheral vascular disease, stroke, deep vein thrombosis and pulmonary embolism.

Cardiomyopathy is a heart disease wherein the heart may be abnormally enlarged, thickened, and/or stiffened and may have few or no symptoms early on. As the disease gets worse, symptoms may include, but are not limited to, shortness of breath, feeling tired, irregular heartbeat, fainting, and onset of heart failure. Types of cardiomyopathy include, but are not limited to arrhythmogenic right ventricular dysplasia, dilated cardiomyopathy, hypertrophic cardiomyopathy, restrictive cardiomyopathy, and Takotsubo cardiomyopathy. Hypertrophic cardiomyopathy (HCM) may be genetic (e.g., heritable) or not genetic. HCM may be obstructive or nonobstructive. Genetic hypertrophic cardiomyopathy (HCM) comprises a group of highly penetrant, monogenic, autosomal dominant myocardial diseases. HCM may be caused by one or more of over 1,000 known point mutations in any one of the proteins contributing to the functional unit of myocardium, the sarcomere.

In approximately two-thirds of HCM subjects, the path followed by blood exiting the heart, known as the left ventricular outflow tract (LVOT), becomes obstructed by the enlarged and diseased muscle, restricting the flow of blood from the heart to the rest of the body (obstructive HCM). In other subjects, the thickened heart muscle does not block the LVOT, and their disease is driven by diastolic impairment due to the enlarged and stiffened heart muscle (non-obstructive HCM). In either obstructive or non-obstructive HCM subjects, exertion can result in fatigue or shortness of breath, interfering with a subject's ability to participate in activities of daily living. HCM has also been associated with increased risks of atrial fibrillation, stroke, heart failure and sudden cardiac death.

Currently available therapies for HCM are variably effective in alleviating symptoms but typically show decreased efficacy with increasing disease duration. Patients are thus empirically managed with beta-blockers, non-dihydropyridine calcium channel blockers, and/or disopyramide. In approximately 60% of patients with HCM, the left ventricular outflow tract becomes obstructed, impeding the flow of blood and creating a pressure gradient between the LV cavity and the aorta. For patients with hemodynamically significant outflow tract obstruction (gradient >50 mmHg), surgical myectomy or alcohol septal ablation can be utilized to alleviate the hemodynamic obstruction albeit with significant clinical morbidity and mortality. Provided are new therapeutic agents and methods that remedy the long-felt need for improved treatment of HCM and related cardiac disorders.

The compounds of the invention or their pharmaceutically acceptable salts can alter the natural history of HCM and other diseases rather than merely palliating symptoms. The mechanisms conferring clinical benefit to HCM patients can extend to patients with other forms of heart disease sharing similar pathophysiology, with or without demonstrable genetic influence. For example, an effective treatment for HCM, by improving ventricular relaxation during diastole, can also be effective in a broader population characterized by diastolic dysfunction. The compounds of the invention or their pharmaceutically acceptable salts can specifically target the root causes of the conditions or act upon other downstream pathways. Accordingly, the compounds of the invention or their pharmaceutically acceptable salts can also confer benefit to patients suffering from diastolic heart failure with preserved ejection fraction, ischemic heart disease, angina pectoris, or restrictive cardiomyopathy. Compounds of the invention or their pharmaceutically acceptable salts can also promote salutary ventricular remodeling of left ventricular hypertrophy due to volume or pressure overload; e.g., chronic mitral regurgitation, chronic aortic stenosis, or chronic systemic hypertension; in conjunction with therapies aimed at correcting or alleviating the primary cause of volume or pressure overload (valve repair/replacement, effective antihypertensive therapy). By reducing left ventricular filling pressures, the compounds could reduce the risk of pulmonary edema and respiratory failure. Reducing or eliminating functional mitral regurgitation and/or lowering left atrial pressures may reduce the risk of paroxysmal or permanent atrial fibrillation, and with it reduce the attendant risk of arterial thromboembolic complications including but not limited to cerebral arterial embolic stroke. Reducing or eliminating either dynamic and/or static left ventricular outflow obstruction may reduce the likelihood of requiring septal reduction therapy, either surgical or percutaneous, with their attendant risks of short- and long-term complications. The compounds or their pharmaceutically acceptable salts may reduce the severity of the chronic ischemic state associated with HCM and may thereby reduce the risk of Sudden Cardiac Death (SCD) or its equivalent in patients with implantable cardioverter-defibrillators (frequent and/or repeated ICD discharges) and/or the need for potentially toxic antiarrhythmic medications. The compounds or their pharmaceutically acceptable salts could be valuable in reducing or eliminating the need for concomitant medications with their attendant potential toxicities, drug—drug interactions, and/or side effects. The compounds or their pharmaceutically acceptable salts may reduce interstitial myocardial fibrosis and/or slow the progression, arrest, or reverse left ventricular hypertrophy.

Definitions

Unless defined otherwise, all technical and scientific terms used herein have the same meaning as is commonly understood by one of skill in the art to which this invention belongs.

As used in the specification and claims, the singular form "a", "an" and "the" includes plural references unless the context clearly dictates otherwise.

The term "$C_{x-y}$" or "$C_x$-$C_y$" (e.g., when used in conjunction with a chemical moiety, such as alkyl, alkenyl, or alkynyl) is meant to include groups that comprise a number of carbon atoms greater than or equal to x carbon atoms and less than or equal to y carbon atoms in the chemical moiety, subject to the following. The term "$C_{x-y}$" or "$C_x$-$C_y$" is not meant to limit the number of carbon atoms which may be attached to the chemical moiety when the chemical moiety is substituted with a second chemical moiety. For example, the term "$C_{1-6}$ alkyl" or "$C_1$ to $C_6$ alkyl" refers to saturated, substituted or unsubstituted, hydrocarbon groups, including straight-chain alkyl groups (e.g., linear alkyl groups) and branched alkyl groups that contain 1, 2, 3, 4, 5, or 6 carbon atoms, plus however many carbon atoms may be present in any substituents of the $C_{1-6}$ alkyl. For example, if a $C_{1-6}$ alkyl is optionally substituted with a second chemical moiety comprising two carbon atoms, then it will be understood that the $C_{1-6}$ alkyl can include between 1 and 8 carbon atoms.

The terms "$C_{x-y}$alkenyl" and "$C_{x-y}$alkynyl" refer to substituted or unsubstituted unsaturated aliphatic groups analogous in length and possible substitution to the alkyls described above, but that contain at least one double or triple bond, respectively.

"Amino" refers to the —$NH_2$ moiety.

"Cyano" refers to the —CN moiety.

"Nitro" refers to the —$NO_2$ moiety.

"Oxa" refers to the —O— moiety.

"Oxo" refers to the =O moiety.

"Thioxo" refers to the =S moiety.

"Imino" refers to the =N—H moiety.

"Oximo" refers to the =N—OH moiety.

"Hydrazino" refers to the =N—$NH_2$ moiety.

"Alkyl" refers to a straight (e.g., linear) or branched hydrocarbon moiety consisting solely of carbon and hydrogen atoms, fully saturated. In certain embodiments, "alkyl" comprises one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In certain embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl, e.g., methyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (2-propyl, iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond.

"Aminoalkyl" refers to a moiety boded through a nitrogen atom of the form —N(H)(alkyl) or N(alkyl)(alkyl), wherein when the moiety is N(alkyl)(alkyl), the two alkyl groups bonded to nitrogen can be the same alkyl groups or different alkyl groups.

"Alkoxy" refers to a moiety bonded through an oxygen atom of the formula —O-alkyl, where alkyl is an alkyl chain as defined above.

"Alkenyl" refers to a straight (e.g., linear) or branched hydrocarbon moiety consisting solely of carbon and hydrogen atoms, the moiety comprising at least one carbon-carbon double bond. In certain embodiments, an alkenyl comprises two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

"Alkynyl" refers to a straight (e.g., linear) or branched hydrocarbon moiety consisting solely of carbon and hydrogen atoms, the moiety comprising at least one carbon-carbon triple bond. In some embodiments, an alkynyl comprises from two to twelve carbon atoms. In some embodiments, an alkynyl optionally further comprises at least one carbon-carbon double bond. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like.

"Alkylene" or "alkylene chain" refers to a linear (e.g., straight), or branched, divalent, hydrocarbon moiety. An "alkylene" or "alkylene chain" can link a portion of the molecule to a second moiety. An "alkylene" or "alkylene chain" consists solely of carbon and hydrogen atoms (substitution of an alkylene with one or more substituents comprising atoms other than hydrogen, such as N, O, and S, may be specified). An "alkylene" or "alkylene chain" can contain no unsaturation (notwithstanding the points of attachment of an alkylene to the rest of the molecule). In certain embodiments, the "alkylene" or "alkylene chain" and comprises one to twelve carbon atoms, for example, methylene, ethylene, propylene, n-butylene, and the like. The alkylene chain can be attached to the portion of the molecule through a single bond and to the second moiety through a single bond. The points of attachment of an alkylene chain to the rest of the molecule and to the second moiety can be through one carbon atom in the alkylene chain or can be through any two carbon atoms within the alkylene. In certain embodiments, an alkylene comprises one to eight carbon atoms (e.g., $C_1$-$C_5$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_5$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene).

"Alkenylene" or "alkenylene chain" refers to a linear (e.g., straight), or branched, divalent, hydrocarbon moiety. An "alkenylene" or "alkenylene chain" can link a portion of the molecule to a second moiety. An "alkenylene" or "alkenylene chain" consists solely of carbon and hydrogen atoms (substitution of an alkenylene with one or more substituents comprising atoms other than hydrogen, such as N, O, and S, may be specified). An "alkenylene" or "alkenylene chain" comprises at least one carbon-carbon double bond. In certain embodiments, an "alkenylene" or "alkenylene chain" comprises from two to twelve carbon atoms. The alkenylene chain can be attached to the portion of the molecule through a single bond and to the second moiety through a single bond. The points of attachment of an alkenylene chain to the rest of the molecule and to the second moiety can be through one carbon in the alkenylene chain or through any two carbons within the alkenylene chain. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises five to eight carbon atoms (e.g., $C_5$-$C_8$ alkenylene). In other embodiments, an alkenylene comprises two to five carbon atoms (e.g., $C_2$-$C_5$ alkenylene). In other embodiments, an alkenylene comprises three to five carbon atoms (e.g., $C_3$-$C_5$ alkenylene).

"Alkynylene" or "alkynylene chain" refers to a linear (e.g., straight), or branched, divalent, hydrocarbon moiety. An "alkynylene" or "alkynylene chain" can link a portion of the molecule to a second moiety. An "alkynylene" or "alkynylene chain" consists solely of carbon and hydrogen (substitution of an alkynylene with one or more substituents comprising atoms other than hydrogen, such as N, O, and S, may be specified). An "alkynylene" or "alkynylene chain" comprises at least one carbon-carbon triple bond. In certain embodiments, an "alkynylene" or "alkynylene chain" comprises from two to twelve carbon atoms. An alkynylene chain can be attached to the portion of the molecule through a single bond and to the second moiety through a single bond. The points of attachment of an alkynylene chain to the rest of the molecule and to the second moiety can be through one carbon in the alkynylene chain or through any two carbons within the alkynylene chain. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atom (e.g., $C_2$ alkylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene).

The term "carbocycle" as used herein refers to a saturated or unsaturated (e.g., aromatic or nonaromatic unsaturated) ring or ring system in which each atom of the ring is carbon. For example, the term "carbocycle" includes 3- to 12-membered monocyclic rings (e.g., 3- to 10-membered monocyclic rings) and 4- to 20-membered polycyclic ring systems (e.g., 5- to 15-membered spiro polycyclic ring systems, 5- to 15-membered bridged polycyclic ring systems, or 4- to 15-membered fused polycyclic ring systems). For example, carbocycle includes 4- to 15-membered bicyclic rings (e.g., 5- to 15-membered spiro bicycles, 5- to 15-membered bridged bicyclic ring systems, or 4- to 15-membered fused bicyclic ring systems). For example, carbocycle includes tricyclic ring systems, which may be bridged, fused, spiro, or a combination thereof. For example, carbocycle includes tetracyclic ring systems, which may be bridged, fused, spiro, or a combination thereof. For example, carbocycle includes ring systems that are both fused and bridged; ring systems that are both fused and spiro; ring systems that are both bridged and spiro; and ring systems that are both fused and bridged and are also spiro. Each ring of a polycyclic carbocycle may be selected from saturated and unsaturated (e.g., aromatic or nonaromatic unsaturated) rings. In an exemplary embodiment, an aromatic ring (e.g., phenyl) of a polycyclic carbocycle may be fused to a saturated or unsaturated ring (e.g., cyclohexane, cyclopentane, cyclohexene, or phenyl). A polycyclic carbocycle includes any combination of saturated and unsaturated (e.g., aromatic or nonaromatic unsaturated) rings, as valence permits. For example, polycyclic carbocycles can be spiro bicyclic rings, such as spiropentane. For example, a polycyclic carbocycle includes any combination of ring sizes such as 2-2 spiro ring systems (e.g., spiro[2.2]pentane), 3-3 spiro ring systems, 4-4 spiro ring systems, 4-5 fused ring systems (e.g., bicyclo[4.5.0] fused ring systems), 5-5 fused ring systems, 5-6 fused ring systems, 6-6 fused ring systems (e.g., naphthalene), 5-7 fused ring systems, 6-7 fused ring systems, 5-8 fused ring systems, and 6-8 fused ring systems. Exemplary carbocycles include cyclopentyl, cyclohexyl, cyclohexenyl, adamantyl, phenyl, indanyl, naphthyl, trans-bicyclo[4.4.0]decane, cis-bicylo[4.4.0]decane, spiro[3.4]octane, fluoranthene, and bicyclo[1.1.1]pentanyl.

The term "aryl" refers to an aromatic monocyclic or aromatic polycyclic hydrocarbon ring system comprising at least one cyclic, delocalized (4n+2) π-electronic system, wherein n is an integer greater than or equal to 0, in accordance with Hückel theory. In some embodiments, the aromatic monocyclic or aromatic polycyclic hydrocarbon ring system comprises only hydrogen atoms and carbon atoms. In some embodiments, the aromatic monocyclic or polycyclic system contains from three to twenty carbon atoms. In some embodiments, at least one of the rings in the polycyclic aromatic ring system is aromatic. In some embodiments, the aromatic monocyclic or aromatic polycyclic hydrocarbon ring system comprises a cyclic, delocalized (4n+2) π-electronic system in accordance with Hückel theory. In some embodiments, the ring system from which aryl groups are derived include, but are not limited to, groups such as benzene, fluorene, indane, indene, anthracene, tetralin, and naphthalene. In some embodiments, the aryl substituent is not charged (e.g., neutral). In some embodiments, the aryl substituent bears no net charge. In some embodiments, the aryl substituent bears no net charge and is not zwitterionic. In some embodiments, none of the carbon atoms of the aryl substituent are charged. In some embodiments, none of the carbon atoms of the aryl substituent are charged. Alternatively, in some embodiments, the aryl substituent is positively or negatively charged or zwitterionic.

The term "cycloalkyl" refers to a saturated ring in which each atom of the ring is carbon. Cycloalkyl may include monocyclic and polycyclic rings such as 3- to 10-membered monocyclic rings, 5- to 12-membered bicyclic rings, 5- to 12-membered spiro bicycles, and 5- to 12-membered bridged rings. In certain embodiments, a cycloalkyl comprises three to ten carbon atoms. In other embodiments, a cycloalkyl comprises three to seven carbon atoms. In other embodiments, a cycloalkyl comprises five to seven carbon atoms. The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl. Examples of polycyclic cycloalkyls include, but are not limited to, adamantyl, spiropentane, norbomyl (i.e., bicyclo[2.2.1]heptanyl), decalinyl, 7,7 dimethyl bicyclo[2.2.1]heptanyl, bicyclo[1.1.1]pentanyl, spiropentane, and the like.

The term "cycloalkenyl" refers to a saturated ring in which each atom of the ring is carbon, and there is at least one double bond between two ring carbons. Cycloalkenyl may include monocyclic and polycyclic rings, such as 3- to 10-membered monocyclic rings and 4- to 12-membered bicyclic rings (e.g., 5- to 12-membered bridged bicyclic rings, fused 4- to 12-membered bicyclic rings, and spiro 5- to 12-membered bicyclic rings). In other embodiments, a cycloalkenyl comprises five to seven carbon atoms. The cycloalkenyl may be attached to the rest of the molecule by a single bond. Examples of monocyclic cycloalkenyls include, e.g., cyclopentenyl, cyclohexenyl, cycloheptenyl, and cyclooctenyl.

The term "halo" or, alternatively, "halogen" or "halide," means fluoro, chloro, bromo or iodo. In some embodiments, halo is fluoro, chloro, or bromo. In some embodiments, halo is fluoro or chloro.

The term "haloalkyl" refers to an alkyl, as defined above, that is substituted by one or more halogens, for example, trifluoromethyl, dichloromethyl, bromomethyl, 2,2,2-trifluoroethyl, 1-chloromethyl-2-fluoroethyl, and the like. In some embodiments, the alkyl part of the haloalkyl is optionally further substituted as described herein.

The term "heterocycle" as used herein refers to a saturated or unsaturated (e.g., aromatic or nonaromatic unsaturated) ring or ring system in which one or more heteroatom(s) is(are) member(s) of the ring or ring system. Exemplary heteroatoms include N, O, Si, P, B, and S atoms. For example, heterocycles include 3- to 12-membered monocyclic rings (e.g., 3- to 10-membered monocyclic rings) and 4- to 20-membered polycyclic ring systems (e.g., 4- to 15-membered fused poly ring systems, 5- to 15-membered spiro polycyclic ring systems, and 5- to 15-membered bridged polycyclic ring systems). For example, heterocycles include 4- to 20-membered bicyclic ring systems (e.g., 4- to 15-membered fused bicyclic ring systems, 5- to 15-membered spiro bicyclic ring systems, and 5- to 15-membered bridged bicyclic ring systems). For example, heterocycle includes tricyclic ring systems, which may be bridged, fused, spiro, or a combination thereof. For example, heterocycle includes tetracyclic ring systems, which may be bridged, fused, spiro, or a combination thereof. For example, heterocycle includes ring systems that are both fused and bridged; ring systems that are both fused and spiro; ring systems that are both bridged and spiro; and ring systems that are both fused and bridged and are also spiro. Each ring of a polycyclic heterocycle may be selected from saturated and unsaturated (e.g., aromatic or nonaromatic unsaturated) rings. A polycyclic heterocycle includes any combination of saturated, and unsaturated (e.g., aromatic or nonaromatic unsaturated) rings, as valence permits. In an exemplary embodiment, an aromatic ring, e.g., pyridyl or phenyl, may be fused to a saturated or unsaturated ring, e.g., cyclohexane, cyclopentane, morpholine, piperidine or cyclohexene, in a heterocycle, as long as at least one atom in the resulting fused ring system is a heteroatom. A polycyclic heterocycle includes any combination of ring sizes such as 3-3 spiro, 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. A bicyclic heterocycle further includes spiro bicyclic rings, e.g., 5 to 12-membered spiro bicycles, such as 2-oxa-6-azaspiro[3.3]heptane. In some embodiments, a heterocycle comprises multiple heteroatoms. In some embodiments, a heterocycle comprises an atom selected from nitrogen, oxygen, and sulfur. In some embodiments, a heterocycle comprises multiple atoms selected from nitrogen, oxygen, and sulfur. Nonlimiting examples of heterocycles include pyridine, pyrrole, indole, carbazole, piperidine, oxazole, morpholine, thiophene, benzothiophene, furan, tetrahydrofuran, and pyran. Nonlimiting examples of heterocycles include azepinyl, acridinyl, benzimidazolyl, benzindolyl, 1,3-benzodioxolyl, benzofuranyl, benzoxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). In some embodiments, the heterocycle is attached to the molecule by a carbon atom. In some embodiments, the heterocycle is attached to the molecule by a nitrogen atom. In some embodiments, the heterocycle comprises a moiety selected from a heteroaryl, a heterocycloalkyl, and a heterocycloalkenyl. In some embodiments, the heterocycle is a heteroaryl. In some embodiments, the heterocycle is a heterocycloalkyl. In some embodiments, the heterocycle is a heterocycloalkenyl.

In some embodiments, a heterocycle comprises an atom selected from nitrogen and oxygen. In some embodiments, a heterocycle comprises an atom selected from nitrogen and sulfur. In some embodiments, a heterocycle comprises an atom selected from oxygen and sulfur. In some embodiments, a heterocycle comprises an atom selected from nitrogen. In some embodiments, a heterocycle comprises an atom selected from oxygen. In some embodiments, a heterocycle comprises an atom selected from sulfur.

In some embodiments, the heterocycle comprises 1 to 8 heteroatoms. In some embodiments, the heterocycle comprises 1 to 5 heteroatoms. In some embodiments, the heterocycle comprises 1 to 3 heteroatoms. In some embodiments, the heterocycle comprises 1 to 2 heteroatoms. In some embodiments, the heterocycle is monosubstituted, disubstituted, trisubstituted, tetrasubstituted, or pentasubstituted.

In the molecule (e.g., in a heterocycle), one or more nitrogen atoms, if present, can be optionally quaternized. In some embodiments, the heterocycle substituent is positively charged. In some embodiments, the heterocycle substituent is negatively charged. In some embodiments, the heterocycle substituent is neutral. In some embodiments, the heterocycle substituent is zwitterionic. Alternatively, or in addition, in some embodiments, the heterocycle substituent is not charged. In some embodiments, the heterocycle substituent bears no charges. In some embodiments, the heterocycle substituent bears no net charge. In some embodiments, no atoms within the heterocycle substituent bear any net charge. In some embodiments, the heterocycle substituent bears no net charge and is not zwitterionic.

The term "heteroaryl" refers to a moiety derived from an aromatic monocyclic or aromatic polycyclic ring system, in which one or more heteroatom(s) is(are) member(s) of the ring system, and the ring system comprises at least one cyclic, delocalized (4n+2) π-electronic system, wherein n is an integer greater than or equal to 0, in accordance with Hückel theory. Exemplary heteroatoms include N, O, Si, P, B, and S atoms. In some embodiments, a heteroaryl includes one or more heteroatoms selected from nitrogen, oxygen, and sulfur. In some embodiments, a heteroaryl includes multiple heteroatoms selected from nitrogen, oxygen, and sulfur. In certain embodiments, "heteroaryl" includes rings and ring systems comprising 3 to 20 atoms. In some embodiments, "heteroaryl" includes rings and ring systems that comprise two to seventeen carbon atoms and from one to six heteroatoms selected from nitrogen, oxygen and sulfur. As used herein, the heteroaryl moiety is a monocyclic or polycyclic (e.g., bicyclic, tricyclic or tetracyclic) ring system, wherein at least one of the rings in the ring system is aromatic, i.e., it contains a cyclic, delocalized (4n+2) π-electron system in accordance with the Hückel theory. Heteroaryl includes fused, bridged, and spiro ring systems. The heteroatom(s) in the heteroaryl moiety is(are) optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzoxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-TH-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). In some embodiments, the heteroaryl substituent is positively or negatively charged. In some embodiments, the heteroaryl substituent is neutral. In some embodiments, the heteroaryl substituent is zwitterionic; alternatively, or in addition, in some embodiments, the heteroaryl substituent is not charged. In some embodiments, the heteroaryl substituent bears no charges. In some embodiments, the heteroaryl substituent bears no net charge. In some embodiments, the heteroaryl substituent bears no net charge and is not zwitterionic.

The term "heterocycle" comprises "heteroaryls" and "heterocycloalkyls." The term "carbocycle" comprises "aryls" and "cycloalkyls."

The term "heterocycloalkyl" refers to a saturated ring with carbon atoms and at least one heteroatom. Exemplary heteroatoms include N, O, Si, P, B, and S atoms. Heterocycloalkyl may include monocyclic and polycyclic rings such as 3- to 10-membered monocyclic rings, 6- to 12-membered bicyclic rings, 5- to 12-membered spiro bicycles, or 5- to 12-membered bridged rings. The heteroatoms in the heterocycloalkyl radical are optionally oxidized. One or more nitrogen atoms, if present, are optionally quaternized. The heterocycloalkyl is attached to the rest of the molecule through any atom of the heterocycloalkyl, valence permitting, such as any carbon or nitrogen atoms of the heterocycloalkyl. Examples of heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 2-oxa-6-azaspiro[3.3]heptane, and 1,1-dioxo-thiomorpholinyl. In some embodiments, a heterocycloalkyl comprises one heteroatom. In some embodiments, a heterocycloalkyl comprises one heteroatom selected from N, O, and S. In some embodiments, a heterocycloalkyl comprises multiple heteroatoms. In some embodiments, a heterocycloalkyl comprises multiple heteroatoms selected from N, O, and S.

The term "heterocycloalkenyl" refers to an unsaturated ring with carbon atoms and at least one heteroatom and there is at least one double bond between two ring carbons. Heterocycloalkenyl does not include heteroaryl rings. Exemplary heteroatoms include N, O, Si, P, B, and S atoms. Heterocycloalkenyl may include monocyclic and polycyclic rings such as 3- to 10-membered monocyclic rings, 6- to 12-membered bicyclic rings, and 5- to 12-membered bridged rings. In other embodiments, a heterocycloalkenyl comprises five to seven ring atoms. The heterocycloalkenyl may be attached to the rest of the molecule by a single bond. Examples of monocyclic cycloalkenyls include, e.g., pyrroline (dihydropyrrole), pyrazoline (dihydropyrazole), imidazoline (dihydroimidazole), triazoline (dihydrotriazole), dihydrofuran, dihydrothiophene, oxazoline (dihydrooxazole), isoxazoline (dihydroisoxazole), thiazoline (dihydrothiazole), isothiazoline (dihydroisothiazole), oxadiazoline (dihydrooxadiazole), thiadiazoline (dihydrothiadiazole), dihydropyridine, tetrahydropyridine, dihydropyridazine, tetrahydropyridazine, dihydropyrimidine, tetrahydropyrimidine, dihydropyrazine, tetrahydropyrazine, pyran, dihydropyran, thiopyran, dihydrothiopyran, dioxine, dihydrodioxine, oxazine, dihydrooxazine, thiazine, and dihydrothiazine.

The term "substituted" refers to moieties having substituents replacing a hydrogen on one or more carbons or substitutable heteroatoms, e.g., an NH or $NH_2$ of a compound. It will be understood that "substitution" or "substituted with" includes the implicit proviso that such substitution is in accordance with permitted valence of the substituted atom and the substituent and further includes the proviso that the substitution results in a stable compound, e.g., a compound which does not rapidly undergo rearrangement, cyclization, elimination, etc. In certain embodiments, substituted refers to moieties having substituents replacing two hydrogen atoms on the same carbon atom, such as substituting the two hydrogen atoms on a single carbon with an oxo, imino, oxime, hydrazone, or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

In some embodiments, substituents may include any substituents described herein, for example: halogen, hydroxy, oxo (=O), thioxo (=S), cyano (—CN), nitro (—$NO_2$), imino (=N—H), oximo (=N—OH), hydrazino (=N—$NH_2$), —$R^b$—$OR^a$, —$R^b$—OC(O)—$R^a$, —$R^b$—OC(O)—$OR^a$, —$R^b$—OC(O)—$N(R^a)_2$, —$R^b$, —$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$, —$N(R^a)$C(O)$OR^a$, —$R^b$, —$N(R^a)$C(O)$R^a$, —$R^b$, —$N(R^a)S(O)_tR^a$ (where t is 1 or 2), —$R^b$—$S(O)_tR^a$ (where t is 1 or 2), —$R^b$—$S(O)_tOR^a$ (where t is 1 or 2), and —$R^b$—$S(O)_tN(R^a)_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl, any of which may be optionally substituted by alkyl, alkenyl, alkynyl, halogen, haloalkyl, haloalkenyl, haloalkynyl, oxo (=O), thioxo (=S), cyano (—CN), nitro (—$NO_2$), imino (=N—H), oximo (=N—OH), hydrazine (=N—$NH_2$), —R—$OR^a$, —$R^b$—OC(O)—$R^a$, —$R^b$—OC(O)—$OR^a$, —$R^b$—OC(O)—$N(R^a)_2$, —$R^b$, —$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$, —$N(R^a)$C(O)$OR^a$, —$R^b$, —$N(R^a)$C(O)$R^a$, —$R^b$, —$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2); wherein each $R^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each $R^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—$NO_2$), imino (=N—H), oximo (=N—OH), hydrazine (=N—$NH_2$), —$R^b$—$OR^a$, —$R^b$—OC(O)—$R^a$, —$R^b$—OC(O)—$OR^a$, —$R^b$—OC(O)—$N(R^a)_2$, —$R^b$, —$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$, —$N(R^a)$C(O)$OR^a$, —$R^b$, —$N(R^a)$C(O)$R^a$, —$R^b$, —$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2); and wherein each $R^b$ is independently selected from a direct bond or a straight or branched alkylene, alkenylene, or alkynylene chain, and each $R^c$ is a straight or branched alkylene, alkenylene or alkynylene chain.

Double bonds to oxygen atoms, such as oxo groups, are represented herein as both "=O" and "(0)". Double bonds to nitrogen atoms are represented as both "=NR" and "(NR)". Double bonds to sulfur atoms are represented as both "=S" and "(S)".

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "salt" or "pharmaceutically acceptable salt" refers to salts derived from a variety of organic and inorganic counter ions well known in the art. Pharmaceutically acceptable acid addition salts can be formed with inorganic acids and/or organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and/or organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is selected from ammonium, potassium, sodium, calcium, and magnesium salts.

As used herein, "treatment" or "treating" refers to an approach for obtaining beneficial or desired results with respect to a disease, disorder, or medical condition including but not limited to a therapeutic benefit and/or a prophylactic benefit. A therapeutic benefit can include, for example, the eradication or amelioration of the underlying disorder being treated. Also, a therapeutic benefit can include, for example, the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made. Treatment via administration of a compound described herein does not require the involvement of a medical professional.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, all structures described herein are intended to disclose, implicitly or explicitly, all Z-, E-, and tautomeric forms as well.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibria include, but are not limited to:

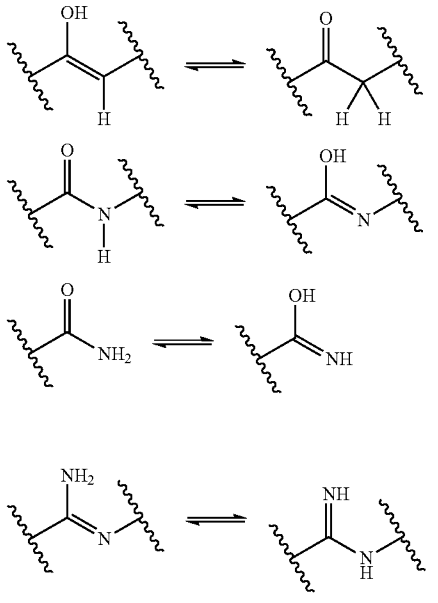

-continued

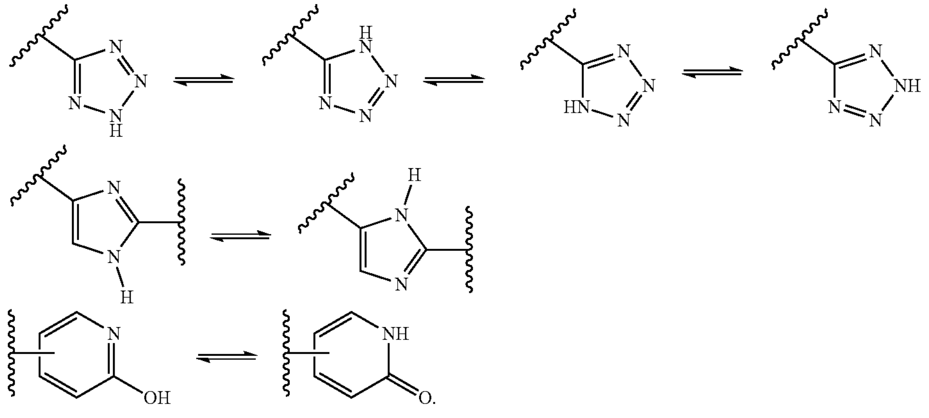

The compounds disclosed herein, in some embodiments, are used in different enriched isotopic forms, e.g., enriched in the content of $^{2}H$, $^{3}H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy of drugs, thus increasing the duration of action of drugs.

Unless otherwise stated, compounds described herein are intended to include compounds which differ only in the presence of one or more isotopically enriched atoms. For example, compounds having the present structures except for the replacement of one or more proton(s) by one or more deuterium (deuteria) or tritium (tritia), or combinations thereof, or except for the replacement of one or more $^{12}C$ atom(s) in the structure by one or more $^{13}C$ atom(s), one or more $^{14}C$ atom(s), or combinations thereof, in the structure are within the scope of the present disclosure.

The compounds of the present disclosure optionally comprise unnatural proportions of atomic isotopes at one or more atom(s) that constitute such compounds. For example, the compounds may be labeled with one or more isotope(s), such as for example, deuterium ($^{2}H$), tritium ($^{3}H$), iodine-125 ($^{125}I$) or carbon-14 ($^{14}C$). Isotopic substitution with $^{2}H$, $^{11}C$, $^{13}C$, $^{14}C$, $^{15}C$, $^{12}N$, $^{13}N$, $^{15}N$, $^{16}N$, $^{17}O$, $^{18}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, and $^{125}I$ are all contemplated. All isotopic variations of the compounds of the present invention, whether radioactive or not, are encompassed within the scope of the present invention.

In certain embodiments, the compounds disclosed herein have some or all of the $^{1}H$ atoms replaced with $^{2}H$ atoms. The methods of synthesis for deuterium-containing compounds are known in the art and include, by way of non-limiting example only, the following synthetic methods.

Deuterium-substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)]2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as MilliporeSigma.

Included in the present disclosure are salts, particularly pharmaceutically acceptable salts, of the compounds described herein. The compounds of the present disclosure that comprise one or more sufficiently acidic functional group(s), one or more sufficiently basic functional group(s), or both one or more sufficiently acidic functional group(s) and one or more sufficiently basic functional group(s) to form a salt (particularly a pharmaceutically acceptable salt), can react with any of a number of inorganic organic bases or inorganic or organic acids, to form a salt.; combinations thereof); or combinations thereof. Alternatively, compounds that are inherently charged, such as those with a quaternary nitrogen, can form a salt with an appropriate counterion.

The compounds and salts described herein may in some cases exist as diastereomers, enantiomers, or other stereoisomeric forms. Unless otherwise specified (e.g., in tables of biological data), the structures disclosed herein are intended to include, explicitly or implicitly, disclosure of all diastereomeric (e.g., epimeric) and enantiomeric forms as well as mixtures thereof. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

In certain embodiments, the compounds or salts of the compounds may be prodrugs. For example, in some embodiments, a hydroxyl in the parent compound is presented as an ester or a carbonate, or carboxylic acid present in the parent compound is presented as an ester. The term "prodrug" is intended to encompass compounds which, under physiologic conditions, are converted into pharmaceutical agents of the present disclosure. One method for making a prodrug is to include one or more selected moieties which are hydrolyzed under physiologic conditions to reveal the desired molecule. In other embodiments, the prodrug is converted by an enzymatic activity of the host animal such as specific target cells in the host animal. For example, esters or carbonates (e.g., esters or carbonates of alcohols or carboxylic acids and esters of phosphonic acids) may be prodrugs of the present disclosure. In some embodiments, a prodrug for an amine might rely on enzymatic activation. In some embodiments, a prodrug for an amine might rely on physiological chemical conditions for release of the drugs. In some embodiments, a prodrug for an amine may be selected from an amide, a carbonate, an N-acyloxy alkyl derivative, an N-acyloxy carbonyl derivative, a beta-aminoketone, an (oxodioxolenyl)methyl derivative, an N-Mannich base, an imine (e.g., a Schiff base), an enamine, an enaminone, an azo compound, a system capable of undergoing lactonization, a tetrahydrothiadiazine-2-thione, a redox system, or a PEG.

Prodrug forms of the herein described compounds, wherein the prodrug is metabolized in vivo to produce a compound as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. Prodrugs may help enhance the cell permeability of a compound relative to the parent drug. The prodrug may also have improved solubility in pharmaceutical compositions over the parent drug. Prodrugs may be designed as reversible drug derivatives, for use as modifiers to enhance drug transport to site-specific tissues or to increase drug residence inside of a cell.

In some embodiments, the design of a prodrug increases the lipophilicity of the pharmaceutical agent. In some embodiments, the design of a prodrug increases the effective water solubility. See, e.g., Fedorak et al., *Am. J Physiol.,* 269:G210-218 (1995); McLoed et al., *Gastroenterol,* 106: 405-413 (1994); Hochhaus et al., *Biomed. Chrom.,* 6:283-286 (1992); J. Larsen and H. Bundgaard, *Int. J Pharmaceutics,* 37, 87 (1987); J. Larsen et al., *Int. J Pharmaceutics,* 47, 103 (1988); Sinkula et al., *J Pharm. Sci.,* 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein for such disclosure). According to another embodiment, the present disclosure provides methods of producing the above-defined compounds. The compounds may be synthesized using conventional techniques.

Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis,* 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

Compounds

The following comprises a discussion of compounds and salts thereof that may be used in the methods of the disclosure. In certain embodiments, the compounds and salts are described in Formulas (I), (II), and (III).

In one aspect, disclosed herein is a compound represented by Formula (I):

(I)

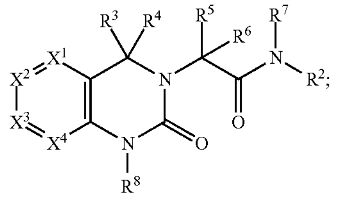

or a salt thereof, wherein:

$X^1$, $X^2$, $X^3$, and $X^4$ are each independently selected from $C(R^1)$, N, and N+(—O–), wherein at least one of $X^1$, $X^2$, $X^3$, or $X^4$ is N; and no more than two of $X^1$, $X^2$, $X^3$, and $X^4$ are N;

each $R^1$ is independently selected from:

hydrogen;

halogen, —$NO_2$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, and —$S(O)_2R^{10a}$;

$C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, =O, =S, =$N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$;

$R^2$ is selected from:

$C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$;

$R^3$ and $R^4$ are each independently selected from:

hydrogen, halogen, —$OR^{10c}$, —$SR^{10c}$, —$N(R^{10c})_2$, —$NO_2$, and —CN; and $C_{1-6}$ alkyl optionally substituted with one or more substituents independently selected from halogen, —$OR^{10c}$, —$SR^{10c}$, —$N(R^{10c})_2$, —$NO_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$.

$R^5$ and $R^6$ are each independently selected from:

hydrogen, halogen, —$OR^{10c}$, —$SR^{10c}$, —$N(R^{10c})_2$, —$NO_2$, and —CN;

$C_{1-6}$ alkyl, optionally substituted with one or more substituents independently selected from halogen, —$OR^{10c}$, —$SR^{10c}$, —$N(R^{10c})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10c}$, —$SR^{10c}$, —$N(R^{10c})_2$, —$NO_2$, and —CN; and $C_{3-10}$ carbocycle and 3- to 10-membered heterocycle, each of which is optionally substituted with one or more substituents independently selected from halogen, —$OR^{10c}$, —$SR^{10c}$, —$N(R^{10c})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$;

$R^7$ is selected from:

hydrogen and $C_{1-6}$ alkyl optionally substituted with one or more substituents independently selected from halogen, —$OR^{10d}$, —$SR^{10d}$, —$N(R^{10d})_2$, —$NO_2$, and —CN;

$R^8$ is selected from:

hydrogen; and $C_{1-6}$ alkyl optionally substituted with one or more substituents independently selected from halogen, —$OR^{10e}$, —$SR^{10e}$, —$N(R^{10e})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10e}$, —$SR^{10e}$, —$N(R^{10e})_2$, —$NO_2$, and —CN;

each $R^{9a}$ is independently selected from:

halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN;

each $R^{9b}$ is independently selected from:

halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN;

each $R^{9c}$ is independently selected from:

halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN; and each $R^{10a}$, $R^{10b}$, $R^{10c}$, $R^{10d}$, and $R^{10e}$ is independently selected from:

hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In one aspect, disclosed herein is a compound represented by Formula (I):

(I)

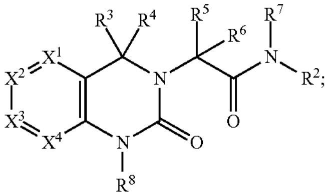

or a salt thereof, wherein:

$X^1$, $X^2$, $X^3$, and $X^4$ are each independently selected from $C(R^1)$, N, and $N^+(—O^-)$, wherein at least one of $X^1$, $X^2$, $X^3$, or $X^4$ is N; and no more than two of $X^1$, $X^2$, $X^3$, and $X^4$ are N;

each $R^1$ is independently selected from:

hydrogen;

halogen, $—NO_2$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$;

$C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2R^{10a}$, $—NO_2$, =O, =S, $=N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, =O, =S, $=N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$;

$R^2$ is selected from:

$C_{1-6}$ alkyl, $C_{2-6}$ alkenyl, and $C_{2-6}$ alkynyl, each of which is optionally substituted with one or more substituents independently selected from halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—C(O)OR^{10b}$, $—OC(O)R^{10b}$, $—N(R^{10b})C(O)N(R^{10b})_2$, $—OC(O)N(R^{10b})_2$, $—N(R^{10b})C(O)OR^{10b}$, $—S(O)R^{10b}$, $—S(O)_2R^{10b}$, $—NO_2$, =O, =S, $=N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—N(R^{10b})C(O)N(R^{10b})_2$, $—OC(O)N(R^{10b})_2$, $—N(R^{10b})C(O)OR^{10b}$, $—C(O)OR^{10b}$, $—OC(O)R^{10b}$, $—S(O)R^{10b}$, $—S(O)_2R^{10b}$, $—NO_2$, =O, =S, $=N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$;

$R^3$ and $R^4$ are each independently selected from:

hydrogen, halogen, $—OR^{10c}$, $—SR^{10c}$, $—N(R^{10c})_2$, $—NO_2$, and —CN; and $C_{1-6}$ alkyl optionally substituted with one or more substituents independently selected from halogen, $—OR^{10c}$, $—SR^{10c}$, $—N(R^{10c})_2$, $—NO_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$;

$R^5$ and $R^6$ are each independently selected from:

hydrogen, halogen, $—OR^{10c}$, $—SR^{10c}$, $—N(R^{10c})_2$, $—NO_2$, and —CN;

$C_{1-6}$ alkyl, optionally substituted with one or more substituents independently selected from halogen, $—OR^{10c}$, $—SR^{10c}$, $—N(R^{10c})_2$, $—NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, $—OR^{10c}$, $—SR^{10c}$, $—N(R^{10c})_2$, $—NO_2$, and —CN; and $C_{3-10}$ carbocycle and 3- to 10-membered heterocycle, each of which is optionally substituted with one or more substituents independently selected from halogen, $—OR^{10c}$, $—SR^{10c}$, $—N(R^{10c})_2$, $—NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$;

$R^7$ is selected from:

hydrogen and $C_{1-6}$ alkyl optionally substituted with one or more substituents independently selected from halogen, $—OR^{10d}$, $—SR^{10d}$, $—N(R^{10d})_2$, $—NO_2$, and —CN;

$R^8$ is selected from:

hydrogen; and $C_{1-6}$ alkyl optionally substituted with one or more substituents independently selected from halogen, $—OR^{10e}$, $—SR^{10e}$, $—N(R^{10e})_2$, $—NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, $—OR^{10e}$, $—SR^{10e}$, $—N(R^{10e})_2$, $—NO_2$, and —CN;

each $R^{9a}$ is independently selected from:

halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, =O, =S, $=N(R^{10a})$, and —CN; and $C_{1-3}$ alkyl, $C_{2-3}$ alkenyl, and $C_{2-3}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, =O, =S, $=N(R^{10a})$, and —CN;

each $R^{9b}$ is independently selected from:

halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—N(R^{10b})C(O)N(R^{10b})_2$, $—OC(O)N(R^{10b})_2$, $—N(R^{10b})C(O)OR^{10b}$, $—C(O)OR^{10b}$, $—OC(O)R^{10b}$, $—S(O)R^{10b}$, $—S(O)_2R^{10b}$, $—NO_2$, =O, =S, $=N(R^{10b})$, and —CN; and $C_{1-3}$ alkyl, $C_{2-3}$ alkenyl, and $C_{2-3}$ alkynyl, each of which is optionally substituted with one or more substituents independently selected from halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—N(R^{10b})C$ (O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$), and —CN;

each $R^{9c}$ is independently selected from:

halogen, —O$R^{10c}$, —S$R^{10c}$, —N($R^{10c}$)$_2$, —C(O)$R^{10c}$, —C(O)N($R^{10c}$)$_2$, —N($R^{10c}$)C(O)$R^{10c}$, —N($R^{10c}$)C(O)N($R^{10c}$)$_2$, —OC(O)N($R^{10c}$)$_2$, —N($R^{10c}$)C(O)O$R^{10c}$, —C(O)O$R^{10c}$, —OC(O)$R^{10c}$, —S(O)$R^{10c}$, —S(O)$_2R^{10c}$, —$NO_2$, =O, =S, =N($R^{10c}$), and —CN; and $C_{1-3}$ alkyl, $C_{2-3}$ alkenyl, and $C_{2-3}$ alkynyl, each of which is optionally substituted with one or more substituents independently selected from halogen, —O$R^{10c}$, —S$R^{10c}$, —N($R^{10c}$)$_2$, —C(O)$R^{10c}$, —C(O)N($R^{10c}$)$_2$, —N($R^{10c}$)C(O)$R^{10c}$, —N($R^{10c}$)C(O)N($R^{10c}$)$_2$, —OC(O)N($R^{10c}$)$_2$, —N($R^{10c}$)C(O)O$R^{10c}$, —C(O)O$R^{10c}$, —OC(O)$R^{10c}$, —S(O)$R^{10c}$, —S(O)$_2R^{10c}$, —$NO_2$, =O, =S, =N($R^{10c}$), and —CN; and each $R^{10a}$, $R^{10b}$, $R^{10c}$, $R^{10d}$, and $R^{10e}$ is independently selected from:

hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

wherein if $X^3$ and $X^1$ are both N, then $R^8$ is selected from hydrogen and $C_{1-4}$ alkyl optionally substituted with one or more substituents independently selected from halogen, —O$R^{10}$, —S$R^{10}$, —N($R^{10}$)$_2$, —$NO_2$, and —CN.

In one aspect, disclosed herein is a compound represented by Formula (IX):

(IX)

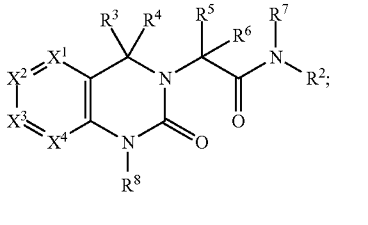

or a salt thereof, wherein:

$X^1$, $X^2$, $X^3$, and $X^4$ are each independently selected from C($R^1$), N, and $N^+$(—$O^-$), wherein at least one of $X^1$, $X^2$, $X^3$, or $X^4$ is N; and no more than two of $X^1$, $X^2$, $X^3$, and $X^4$ are N;

each $R^1$ is independently selected from:

hydrogen;

halogen, —$NO_2$, —CN, —O$R^{10a}$, —S$R^{10a}$, —N($R^{10a}$)$_2$, —C(O)$R^{10a}$, and —C(O)N($R^{10a}$)$_2$;

$C_{1-6}$ alkyl, optionally substituted with one or more substituents independently selected from halogen, —O$R^{10a}$, —S$R^{10a}$, —N($R^{10a}$)$_2$, —C(O)$R^{10a}$, —$NO_2$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —O$R^{10a}$, —S$R^{10a}$, —N($R^{10a}$)$_2$, —C(O)$R^{10a}$, —C(O)N($R^{10a}$)$_2$, —CN, $C_{1-6}$ alkyl optionally substituted with one or more $R^{9a}$;

$R^2$ is selected from:

$C_{1-6}$ alkyl, optionally substituted with one or more substituents independently selected from halogen, —O$R^{10b}$, —S$R^{10b}$, —N($R^{10b}$)$_2$, —CN, =O, $C_{3-10}$ carbocycle, and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —O$R^{10b}$, —S$R^{10b}$, —N($R^{10b}$)$_2$, =O, —CN, and $C_{1-6}$ alkyl, wherein each $C_{1-6}$ alkyl is optionally substituted with one or more $R^{9b}$;

$R^3$ and $R^4$ are each independently selected from:

hydrogen and —OH; and $C_{1-6}$ alkyl optionally substituted with one or more substituents independently selected from halogen, —O$R^{10b}$, —S$R^{10c}$, —N($R^{10c}$)$_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$;

$R^5$ and $R^6$ are each independently selected from:

hydrogen, halogen, —O$R^{10b}$, —S$R^{10c}$, —N($R^{10c}$)$_2$, —$NO_2$, and —CN; and $C_{1-6}$ alkyl; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$;

$R^7$ is selected from hydrogen and $C_{1-6}$ alkyl;

$R^8$ is selected from hydrogen and $C_{1-6}$ alkyl;

each $R^{9a}$, $R^{9b}$, $R^{9c}$, is independently selected from halogen, —OH, —OMe —CN, and $C_{1-3}$ alkyl;

each $R^{10a}$, $R^{10b}$, $R^{10c}$, $R^{10d}$, and $R^{10e}$ is independently selected from:

hydrogen;

$C_{1-6}$ alkyl optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle.

In one aspect, disclosed herein is a compound represented by Formula (IY):

(IY)

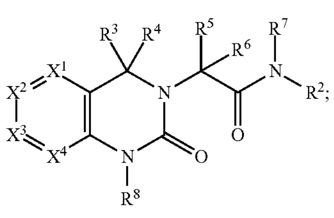

or a salt thereof, wherein:

$X^1$, $X^2$, $X^3$, and $X^4$ are each independently selected from $C(R^1)$, N, and $N^+(—O^-)$, wherein at least one of $X^1$, $X^2$, $X^3$, or $X^4$ is N; and no more than two of $X^1$, $X^2$, $X^3$, and $X^4$ are N;

each $R^1$ is independently selected from:

hydrogen, fluoro, chloro, bromo, —CN, —OH, —O($C_{1-6}$ alkyl), —O($C_{1-6}$ haloalkyl), —O($C_{3-10}$ carbocycle), —O(3- to 10-membered heterocycle), —$C(O)NH_2$, $C_{1-6}$ alkyl, $C_{1-6}$ haloalkyl, and $C_{3-10}$ carbocycle, wherein the $C_{3-10}$ carbocycle is optionally substituted with one or more halogen;

$R^2$ is selected from:

$C_{1-6}$ alkyl, optionally substituted with one or more substituents independently selected from —F, Cl, —OH, and $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from —F, —Cl, and —CN;

$R^3$ and $R^4$ are each independently selected from: hydrogen, —OH, and methyl;

$R^5$ and $R^6$ are each independently selected from hydrogen and $C_{1-3}$ alkyl;

$R^7$ is selected from: hydrogen and $C_{1-6}$ alkyl;

$R^8$ is selected from hydrogen and $C_{1-6}$ alkyl; and each $R^{9a}$, $R^{9b}$, $R^{9c}$, is independently selected from halogen, —OH, —OMe —CN, and $C_{1-3}$ alkyl.

In certain embodiments, for a compound or salt of Formula (I), $X^1$, $X^2$, $X^3$, and $X^4$ are each independently selected from $C(R^1)$, N, and $N^+(—O^-)$. In some embodiments, at least one of $X^1$, $X^2$, $X^3$, or $X^4$ is N. In some embodiments, no more than two of $X^1$, $X^2$, $X^3$, and $X^4$ are N. In some embodiments, $X^1$, $X^2$, $X^3$, and $X^4$ are each independently selected from $C(R^1)$, N, and $N^+(—O^-)$, wherein at least one of $X^1$, $X^2$, $X^3$, or $X^4$ is N; and no more than two of $X^1$, $X^2$, $X^3$, and $X^4$ are N. In some embodiments, no more than one of $X^1$, $X^2$, $X^3$, and $X^4$ is N. In some embodiments, no more than two of $X^1$, $X^2$, $X^3$, and $X^4$ is N. In some embodiments, no more than three of $X^1$, $X^2$, $X^3$, and $X^4$ is N. In some embodiments, at least one of $X^1$, $X^2$, $X^3$, or $X^4$ is N. In some embodiments, at least two of $X^1$, $X^2$, $X^3$, or $X^4$ is N. In some embodiments, at least three of $X^1$, $X^2$, $X^3$, or $X^4$ is N. In some embodiments, at least one of $X^1$, $X^2$, $X^3$, or $X^4$ is N, and no more than two of $X^1$, $X^2$, $X^3$, and $X^4$ are N. In some embodiments, $X^1$, $X^2$, $X^3$, and $X^4$ are each independently selected from $C(R^1)$, N, and $N^+(—O^-)$. In some embodiments, $X^1$, $X^2$, $X^3$, and $X^4$ are each independently selected from $C(R^1)$ and N. In some embodiments, $X^1$, $X^2$, $X^3$, and $X^4$ are each independently selected from $C(R^1)$. In some embodiments, one of $X^1$, $X^2$, $X^3$, or $X^4$ is N. In some embodiments, two of $X^1$, $X^2$, $X^3$, and $X^4$ are N. In some embodiments, three of $X^1$, $X^2$, $X^3$, and $X^4$ are N. In some embodiments, one of $X^1$, $X^2$, $X^3$, or $X^4$ is $C(R^1)$. In some embodiments, two of $X^1$, $X^2$, $X^3$, and $X^4$ are $C(R^1)$. In some embodiments, three of $X^1$, $X^2$, $X^3$, and $X^4$ are $C(R^1)$. In some embodiments, four of $X^1$, $X^2$, $X^3$, and $X^4$ are $C(R^1)$. In some embodiments, $X^1$ is N. In some embodiments, $X^2$ is N. In some embodiments, $X^3$ is N. In some embodiments, $X^4$ is N. In some embodiments, $X^1$ is $C(R^1)$. In some embodiments, $X^2$ is $C(R^1)$. In some embodiments, $X^3$ is $C(R^1)$. In some embodiments, $X^4$ is $C(R^1)$. In some embodiments, $X^1$ is C(H). In some embodiments, $X^2$ is C(H). In some embodiments, $X^3$ is C(H). In some embodiments, $X^4$ is C(H). In some embodiments, two of $X^1$, $X^2$, $X^3$, and $X^4$ are N. In some embodiments, two of $X^1$, $X^2$, $X^3$, and $X^4$ are N, and the two of two of $X^1$, $X^2$, $X^3$, and $X^4$ which are N are not bound (e.g., covalently) to each other. In some embodiments, $X^1$ and $X^3$ are N. In some embodiments, $X^2$ and $X^4$ are N. In some embodiments, $X^1$ is N, and $X^2$, $X^3$, and $X^4$ are $C(R^1)$. In some embodiments, $X^2$ is N, and $X^1$, $X^3$, and $X^4$ are $C(R^1)$. In some embodiments, $X^3$ is N, and $X^1$, $X^2$, and $X^4$ are $C(R^1)$. In some embodiments, $X^4$ is N, and $X^1$, $X^2$, and $X^3$ are $C(R^1)$. In some embodiments, $X^1$ is N, and $X^2$, $X^3$, and $X^4$ are C(H). In some embodiments, $X^2$ is N, and $X^1$, $X^3$, and $X^4$ are C(H). In some embodiments, $X^3$ is N, and $X^1$, $X^2$, and $X^4$ are C(H). In some embodiments, $X^4$ is N, and $X^1$, $X^2$, and $X^3$ are C(H).

In some embodiments, $X^2$ is N, and $X^1$ is $C(CF_3)$. In some embodiments $X^2$ is N, $X^1$ is $C(CF_3)$, $X^3$ is C(H), and $X^4$ is C(H). In some embodiments, $X^2$ is N, and $R^2$ is

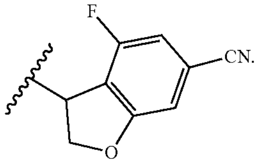 [SMILES: *C1COc2cc(C#N)cc(F)c21]

In some embodiments, $X^2$ is N, $R^2$ is

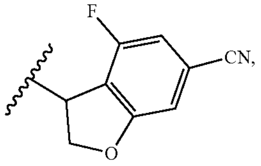 [SMILES: *C1COc2cc(C#N)cc(F)c21]

and $X^1$ is $C(CF_3)$. In some embodiments, $X^2$ is N, $R^2$ is

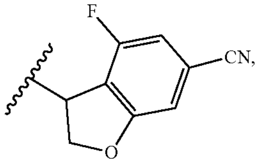 [SMILES: *C1COc2cc(C#N)cc(F)c21]

$X^1$ is $C(CF_3)$, $X^3$ is C(H), and $X^4$ is C(H). In some embodiments, $X^2$ is N, and $X^1$ is C(CN). In some embodiments, $X^2$ is N, $X^1$ is C(CN), $X^3$ is C(H), and $X^4$ is C(H). In some embodiments, $X^2$ is N, and $R^2$ is

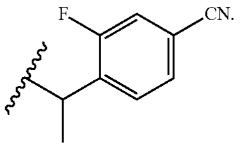 [SMILES: *C(C)c1ccc(C#N)cc1F]

In some embodiments, $X^2$ is N, $R^2$ is

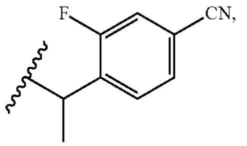 [SMILES: *C(C)c1ccc(C#N)cc1F]

and $X^1$ is C(F). In some embodiments, $X^2$ is N, $R^2$ is

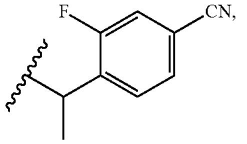 [SMILES: *C(C)c1ccc(C#N)cc1F]

$X^1$ is C(F), $X^3$ is C(H), and $X^4$ is C(H).

In some embodiments, $X^2$ is C(O($C_{1-6}$ alkyl)). In some embodiments, $X^2$ is C(OMe). In some embodiments, $X^1$ is N, and $X^2$ is C(O($C_{1-6}$ alkyl)). In some embodiments, $X^1$ is N, $X^2$ is C(O($C_{1-6}$ alkyl)), $X^3$ is C(H), and $X^4$ C(H). In some embodiments, $X^1$ is N, and $X^2$ is C(OMe). In some embodiments, $X^1$ is N, $X^2$ is C(OMe), $X^3$ is C(H), and $X^4$ C(H). In some embodiments, $X^1$ is N, and $X^2$ is C(O($C_{1-6}$ alkyl)), and $R^3$ and $R^4$ come together to form a cyclopropyl. In some embodiments, $X^1$ is N, $X^2$ is C(O($C_{1-6}$ alkyl)), $X^3$ is C(H), and $X^4$ C(H), and $R^3$ and $R^4$ come together to form a cyclopropyl. In some embodiments, $X^1$ is N, and $X^2$ is C(OMe), and $R^3$ and $R^4$ come together to form a cyclopropyl. In some embodiments, $X^1$ is N, $X^2$ is C(OMe), $X^3$ is C(H), and $X^4$ C(H), and $R^3$ and $R^4$ come together to form a cyclopropyl.

In some embodiments, $X^2$ is N, and $X^1$ is C(F). In some embodiments, $X^2$ is N, $X^1$ is

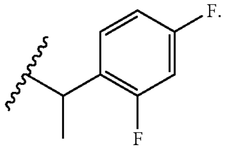 [SMILES: *C(C)c1ccc(F)cc1F]

In some embodiments, $X^2$ is N, and $R^2$ is F. In some embodiments, $X^2$ is N, $R^2$ is

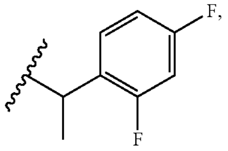 [SMILES: *C(C)c1ccc(F)cc1F]

and $X^1$ is C(F). In some embodiments, $X^2$ is N, $R^2$ is

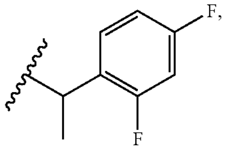 [SMILES: *C(C)c1ccc(F)cc1F]

$X^1$ is C(F), $X^3$ is C(H), and $X^4$ is C(H). In some embodiments, $X^2$ is N, and $X^1$ is C(Cl). In some embodiments, $X^2$ is N, $X^1$ is C(Cl), $X^3$ is C(H), and $X^4$ is C(H). In some embodiments, $X^2$ is N, $R^2$ is

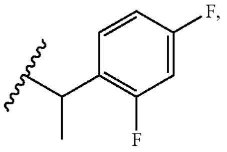 [SMILES: *C(C)c1ccc(F)cc1F]

and $X^1$ is C(Cl). In some embodiments, $X^2$ is N, $R^2$ is

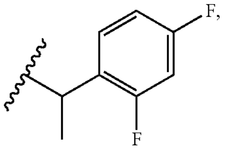 [SMILES: *C(C)c1ccc(F)cc1F]

$X^1$ is C(Cl), $X^3$ is C(H), and $X^4$ is C(H). In some embodiments, $X^2$ is N, and $X^1$ is C(CN). In some embodiments, $X^2$ is N, $X^1$ is C(CN), $X^3$ is C(H), and $X^4$ is C(H). In some embodiments, $X^2$ is N, and $R^2$ is

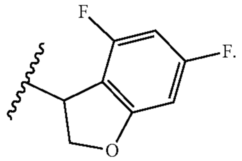 [SMILES: *C1COc2cc(F)cc(F)c21]

In some embodiments, $X^2$ is N, $R^2$ is

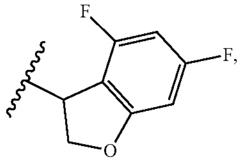 [SMILES: *C1COc2cc(F)cc(F)c21]

and $X^1$ is C(CN). In some embodiments, $X^2$ is N, $R^2$ is

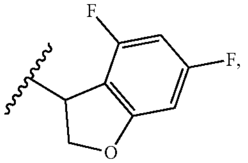 [SMILES: *C1COc2cc(F)cc(F)c21]

$X^1$ is C(CN), $X^3$ is C(H), and $X^4$ is C(H).

In some embodiments, $X^2$, $X^3$, and $X^4$ are each independently selected from C(H). In some embodiments, $X^1$ is N, and $X^2$, $X^3$, and $X^4$ are each independently selected from C($R^1$). In some embodiments, $X^1$ is N, and $X^2$, $X^3$, and $X^4$ are each independently selected from C(H). In some embodiments, $X^1$ is N, and $X^2$, $X^3$, and $X^4$ are each independently selected from C($R^1$), and $R^3$ and $R^4$ come together to form a cyclopropyl. In some embodiments, $X^1$ is N, and $X^2$, $X^3$, and $X^4$ are each independently selected from C(H), and $R^3$ and $R^4$ come together to form a cyclopropyl.

In some embodiments, $X^2$ is C(CN). In some embodiments, $X^1$ is N, and $X^2$ is C(Cl). In some embodiments, $X^1$ is N, and $X^2$ is C(Cl), and $X^3$ and $X^4$ are each independently selected from C($R^1$). In some embodiments, $X^1$ is N, and $X^2$ is C(Cl), and $X^3$ and $X^4$ are each independently selected from C(H).

In some embodiments, $X^1$ is N, and $X^2$ is C(CN). In some embodiments, $X^1$ is N, and $X^2$ is C(CN), and $X^3$ and $X^4$ are each independently selected from C($R^1$). In some embodiments, $X^1$ is N, and $X^2$ is C(CN), and $X^3$ and $X^4$ are each independently selected from C(H).

In some embodiments, $X^1$ is C(Br). In some embodiments, $X^1$ is N, and $X^2$ is C(Br). In some embodiments, $X^1$ is N, and $X^2$ is C(Br), and $X^3$ and $X^4$ are each independently selected from C($R^1$). In some embodiments, $X^1$ is N, and $X^2$ is C(Br), and $X^3$ and $X^4$ are each independently selected from C(H). In some embodiments, $X^1$ is N, and $X^2$ is C(Br), and $R^5$ is H, and $R^6$ is methyl. In some embodiments, $X^1$ is N, and $X^2$ is C(Br), and $X^3$ and $X^4$ are each independently selected from C($R^1$), and $R^5$ is H, and $R^6$ is methyl. In some embodiments, $X^1$ is N, and $X^2$ is C(Br), and $X^3$ and $X^4$ are each independently selected from C(H), and $R^5$ is H, and $R^6$ is methyl.

In some embodiments, $X^2$ is C(F). In some embodiments, $X^1$ is N, and $X^2$ is C(F). In some embodiments, $X^1$ is N, and $X^2$ is C(F), and $X^3$ and $X^4$ are each independently selected from C($R^1$). In some embodiments, $X^1$ is N, and $X^2$ is C(F), and $X^3$ and $X^4$ are each independently selected from C(H).

In some embodiments, $X^1$ is C($CF_3$). In some embodiments, $X^2$ is N, and $X^1$ is C($CF_3$). In some embodiments, $X^2$ is N, and $X^1$ is C($CF_3$), and $X^3$ and $X^4$ are each independently selected from C($R^1$). In some embodiments, $X^2$ is N, and $X^1$ is C($CF_3$), and $X^3$ and $X^4$ are each independently selected from C(H).

In some embodiments, $X^1$ is C($OCF_3$). In some embodiments, $X^2$ is N, and $X^1$ is C($OCF_3$). In some embodiments, $X^2$ is N, and $X^1$ is C($OCF_3$), and $X^3$ and $X^4$ are each independently selected from C($R^1$). In some embodiments, $X^2$ is N, and $X^1$ is C($OCF_3$), and $X^3$ and $X^4$ are each independently selected from C(H).

In some embodiments, $X^2$ is N, and $X^1$ is C(CN). In some embodiments, $X^2$ is N, $X^1$ is C(CN), $X^3$ is C(H), and $X^4$ is C(H). In some embodiments, $X^2$ is N, and $R^2$ is

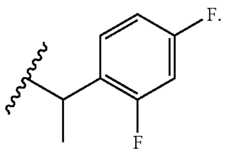 [SMILES: *C(C)c1ccc(F)cc1F]

In some embodiments, $X^2$ is N, $R^2$ is

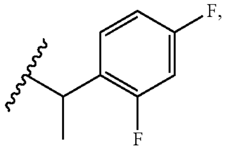 [SMILES: *C(C)c1ccc(F)cc1F]

and $X^1$ is C(CN). In some embodiments, $X^2$ is N, $R^2$ is

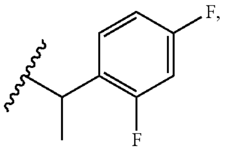 [SMILES: *C(C)c1ccc(F)cc1F]

$X^1$ is C(CN), $X^3$ is C(H), and $X^4$ is C(H). In some embodiments, $X^1$ is N, and $X^2$ is C($OR^{10a}$). In some embodiments, $X^1$ is N, and $X^2$ is C(OMe). In some embodiments, $X^1$ is N, $X^2$ is C($OR^{10a}$), $X^3$ is C(H), and $X^4$ is C(H). In some embodiments, $X^1$ is N, $X^2$ is C(OMe), $X^3$ is C(H), and $X^4$ is C(H). In some embodiments, $X^1$ is N, and $R^2$ is

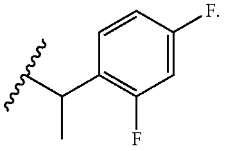 [SMILES: *C(C)c1ccc(F)cc1F]

In some embodiments, $X^1$ is N, $R^2$ is

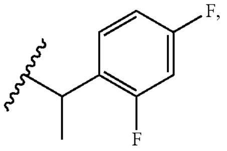 [SMILES: *C(C)c1ccc(F)cc1F]

and $X^2$ is C($OR^{10a}$). In some embodiments, $X^1$ is N, $R^2$ is

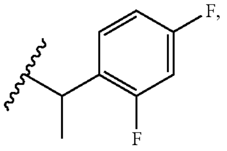 [SMILES: *C(C)c1ccc(F)cc1F]

and $X^2$ is C(OMe). In some embodiments, $X^1$ is N, $R^2$ is

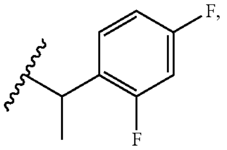 [SMILES: *C(C)c1ccc(F)cc1F]

$X^2$ is C($OR^{10a}$), $X^3$ is C(H), and $X^4$ is C(H). In some embodiments, $X^1$ is N, $R^2$ is

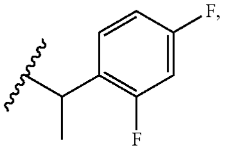 [SMILES: *C(C)c1ccc(F)cc1F]

$X^2$ is C(OMe), $X^3$ is C(H), and $X^4$ is C(H). In some embodiments, $X^1$ is N, $R^2$ is

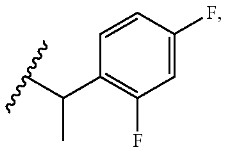 [SMILES: *C(C)c1ccc(F)cc1F]

$X^2$ is C(OMe), $X^3$ is C(H), $X^4$ is C(H), and $R^3$ and $R^4$ come together to form a cyclopropyl ring. In some embodiments, $X^1$ is N, $X^2$ is C(H), $X^3$ is C(H), and $X^4$ is C(H). In some embodiments, $X^1$ is N, and $R^2$ is

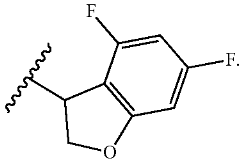 [SMILES: *C1COc2cc(F)cc(F)c21]

In some embodiments, $X^1$ is N, $R^2$ is

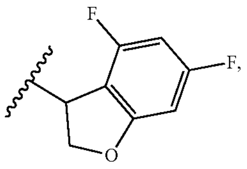 [SMILES: *C1COc2cc(F)cc(F)c21]

$X^3$ is C(H), and $X^4$ is C(H). In some embodiments, $X^1$ is N, $R^2$ is

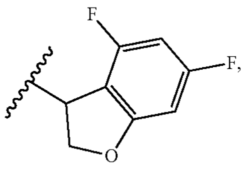 [SMILES: *C1COc2cc(F)cc(F)c21]

$X^3$ is C(H), $X^4$ is C(H), and $R^3$ and $R^4$ come together to form a cyclopropyl ring. In some embodiments, $X^1$ is N, and $X^2$ is C(Cl). In some embodiments, $X^1$ is N, $X^2$ is C(Cl), $X^3$ is C(H), and $X^4$ is C(H). In some embodiments, $X^1$ is N, and $R^2$ is

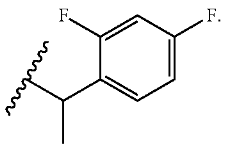 [SMILES: *C(C)c1ccc(F)cc1F]

In some embodiments, $X^1$ is N, $R^2$ is

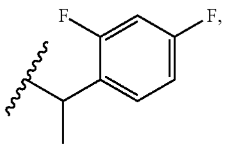

and $X^2$ is C(CN). In some embodiments, $X^1$ is N, $R^2$ is

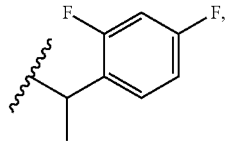 [SMILES: *C(C)c1ccc(F)cc1F]

$X^2$ is C(CN), $X^3$ is C(H), and $X^4$ is C(H). In some embodiments, $X^1$ is N, and $X^2$ is C(CN). In some embodiments, $X^1$ is N, $X^2$ is C(CN), $X^3$ is C(H), and $X^4$ is C(H). In some embodiments, $X^1$ is N, and $R^2$ is

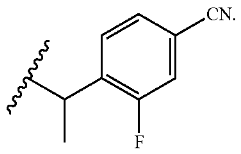 [SMILES: *C(C)c1ccc(C#N)cc1F]

In some embodiments, $X^1$ is N, $R^2$ is

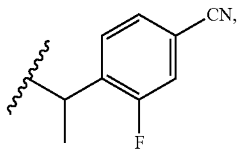 [SMILES: *C(C)c1ccc(C#N)cc1F]

and $X^2$ is C(CN). In some embodiments, $X^1$ is N, $R^2$ is

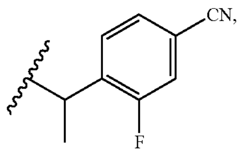 [SMILES: *C(C)c1ccc(C#N)cc1F]

$X^2$ is C(CN), $X^3$ is C(H), and $X^4$ is C(H). In some embodiments, $X^1$ is N, $R^2$ is

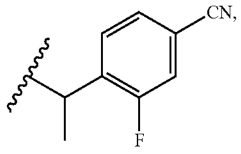 [SMILES: *C(C)c1ccc(C#N)cc1F]

$X^2$ is C(CN), $X^3$ is C(H), $X^4$ is C(H), and $R^3$ and $R^4$ come together to form a cyclopropyl ring. In some embodiments, $X^1$ is N, $X^2$ is C(H), $X^3$ is C(H), and $X^4$ is C(H). In some embodiments, $X^1$ is N, and $R^2$ is

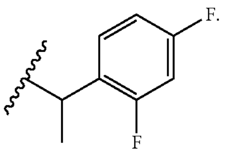 [SMILES: *C(C)c1ccc(F)cc1F]

In some embodiments, $X^1$ is N, $R^2$ is

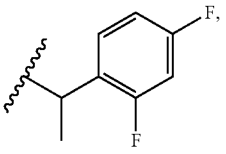 [SMILES: *C(C)c1ccc(F)cc1F]

and $X^2$ is C(H). In some embodiments, $X^1$ is N, $R^2$ is

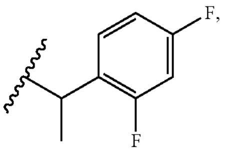 [SMILES: *C(C)c1ccc(F)cc1F]

$X^2$ is C(H), $X^3$ is C(H), and $X^4$ is C(H). In some embodiments, some embodiments, $X^1$ is N, and $X^2$ is C(CN). In some embodiments, $X^1$ is N, $X^2$ is C(CN), $X^3$ is C(H), and $X^4$ is C(H). In some embodiments, $X^1$ is N, and $R^2$ is

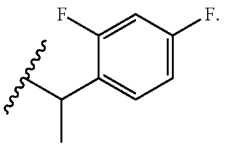 [SMILES: *C(C)c1ccc(F)cc1F]

In some embodiments, $X^1$ is N, $R^2$ is

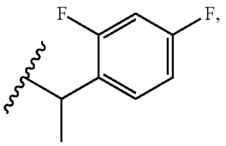

$X^2$ is C(CN). In some embodiments, $X^1$ is N, $R^2$ is

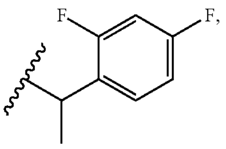

$X^2$ is C(CN), $X^3$ is C(H), and $X^4$ is C(H). In some embodiments, some embodiments, $X^1$ is N, and $X^2$ is C(F). In some embodiments, $X^1$ is N, $X^2$ is C(F), $X^3$ is C(H), and $X^4$ is C(H). In some embodiments, $X^1$ is N, and $R^2$ is

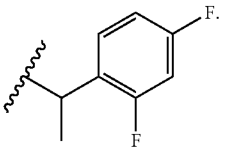 [SMILES: *C(C)c1ccc(F)cc1F]

In some embodiments, $X^1$ is N, $R^2$ is

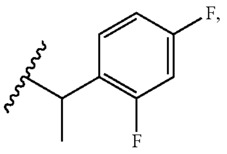 [SMILES: *C(C)c1ccc(F)cc1F]

and $X^2$ is C(F). In some embodiments, $X^1$ is N, $R^2$ is

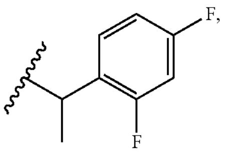 [SMILES: *C(C)c1ccc(F)cc1F]

$X^2$ is C(F), $X^3$ is C(H), and $X^4$ is C(H).

In some embodiments, $X^2$ is C(F). In some embodiments, for a compound or salt of Formula (I), $X^1$ is N, $X^2$ is F, $R^5$ is methyl, and $R^6$ is hydrogen.

In some embodiments, $X^2$ is $C(CF_3)$. In some embodiments, $X^1$ is N, and $X^2$ is $C(CF_3)$. In some embodiments, $X^1$ is N, and $X^2$ is $C(CF_3)$, and $X^3$ and $X^4$ are each independently selected from $C(R^1)$. In some embodiments, $X^1$ is N, and $X^2$ is $C(CF_3)$, and $X^3$ and $X^4$ are each independently selected from C(H).

In some embodiments, $X^1$ is C(Cl). In some embodiments, $X^3$ is N, and $X^1$ is $C(R^1)$. In some embodiments, $X^3$ is N, and $X^1$ is $C(R^1)$, and $X^2$ and $X^4$ are each independently selected from $C(R^1)$. In some embodiments, $X^3$ is N, and $X^1$ is C(Cl). In some embodiments, $X^3$ is N, and $X^1$ is C(Cl), and $X^2$ is $C(R^1)$. In some embodiments, $X^3$ is N, and $X^1$ is C(Cl), and $X^2$ is $C(R^1)$, and $X^4$ is $C(R^1)$. In some embodiments, $X^3$ is N, and $X^1$ is C(Cl), and $X^2$ is C(H). In some embodiments, $X^3$ is N, and $X^1$ is C(Cl), and $X^2$ is C(H), and $X^4$ is C(H).

In some embodiments, $X^1$ is $C(OCH_2CHF_2)$ (e.g., in some embodiments, $X^1$ is a carbon bearing a 2,2-difluoroethoxy moiety). In some embodiments, $X^2$ is N, and $X^1$ is $C(OCH_2CHF_2)$.

In some embodiments, $X^2$ is N, and $X^1$ is $C(OCH_2CHF_2)$, and $X^3$ and $X^4$ are each independently selected from $C(R^1)$. In some embodiments, $X^2$ is N, and $X^1$ is $C(OCH_2CHF_2)$, and $X^3$ and $X^4$ are each independently selected from C(H).

In some embodiments, $X^1$ is $C(OCH_2CH_3)$. In some embodiments, $X^2$ is N, and $X^1$ is $C(OCH_2CH_3)$. In some embodiments, $X^2$ is N, and $X^1$ is $C(OCH_2CH_3)$, and $X^3$ and $X^4$ are each independently selected from $C(R^1)$. In some embodiments, $X^2$ is N, and $X^1$ is $C(OCH_2CH_3)$, and $X^3$ and $X^4$ are each independently selected from C(H).

In some embodiments, $X^2$ is $C(OCH_2CH_3)$. In some embodiments, $X^1$ is N, and $X^2$ is $C(OCH_2CH_3)$. In some embodiments, $X^1$ is N, and $X^2$ is $C(OCH_2CH_3)$, and $X^3$ and $X^4$ are each independently selected from $C(R^1)$. In some embodiments, $X^1$ is N, and $X^2$ is $C(OCH_2CH_3)$, and $X^3$ and $X^4$ are each independently selected from C(H).

In some embodiments, $X^1$ is

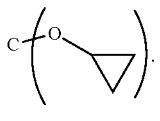

In some embodiments, $X^2$ is N, and $X^1$ is

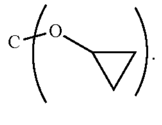

In some embodiments, $X^2$ is N, and $X^1$ is

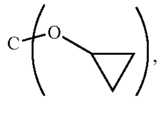

and $X^3$ and $X^4$ are each independently selected from $C(R^1)$.

In some embodiments, $X^2$ is N, and $X^1$ is

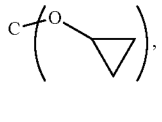

and $X^3$ and $X^4$ are each independently selected from C(H).

In certain embodiments, for a compound or salt of Formula (I), each $R^1$ is independently selected from:

hydrogen;

halogen, $—NO_2$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$;

$C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2R^{10a}$, $—NO_2$, =O, =S, $=N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, =O, =S, $=N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$.

In certain embodiments, for a compound or salt of Formula (I), each $R^1$ is independently selected from: hydrogen; halogen, $—NO_2$, —CN, $—OR^{10a}$, $—SR^{10a}$, $—N(R^{10a})_2$, $—C(O)R^{10a}$, and $—C(O)N(R^{10a})_2$; $C_{1-6}$ alkyl, optionally substituted with one or more substituents independently selected from halogen, $—OR^{10a}$, $—SR^{10a}$, $—N(R^{10a})_2$, $—C(O)R^{10a}$, $—NO_2$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, —CN, $C_{1-6}$ alkyl optionally substituted with one or more $R^{9a}$.

In some embodiments, each $R^1$ is independently selected from: hydrogen; halogen, $—NO_2$, —CN, $—OR^{10a}$, $—SR^{10a}$, $—N(R^{10a})_2$, $—C(O)R^{10a}$, and $—C(O)N(R^{10a})_2$; $C_{1-6}$ alkyl, optionally substituted with one or more substituents independently selected from halogen, $—OR^{10a}$, $—SR^{10a}$, and $—N(R^{10a})_2$; and $C_{3-10}$ carbocycle and 3- to 10-membered heterocycle, each of which is optionally substituted with one or more substituents independently selected from halogen, $—OR^{10a}$, $—SR^{10a}$ and $—N(R^{10a})_2$.

In some embodiments, each $R^1$ is independently selected from: hydrogen; halogen, CN, $—OR^{10a}$ and $—C(O)N(R^{10a})_2$; $C_{1-6}$ alkyl, optionally substituted with one or more substituents independently selected from halogen, and $C_{3-10}$ carbocycle optionally substituted with one or more substituents independently selected from halogen.

In some embodiments, $R^1$ is independently selected from hydrogen.

In some embodiments, each $R^1$ is independently selected from hydrogen, halogen, $—NO_2$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$ and $—S(O)_2R^{10a}$;

In some embodiments, each $R^1$ is independently selected from hydrogen, $C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2R^{10a}$, $—NO_2$, =O, =S, $=N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$.

In some embodiments, each $R^1$ is independently selected from hydrogen, $C_{3-10}$ carbocycle and 3- to 10-membered heterocycle, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, =O, =S, $=N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$.

In some embodiments, each $R^1$ is independently selected from: hydrogen; halogen, $—NO_2$, —CN, —CN, —OH, —SH, $—NO_2$, $—NH_2$, $—O—C_{1-6}$ alkyl, $—S—C_{1-6}$ alkyl, $—N(C_{1-6}$ alkyl$)_2$, and $—NH(C_{1-6}$ alkyl); $C_{1-6}$ alkyl, $C_{2-6}$ alkenyl, and $C_{2-6}$ alkynyl, each of which is optionally substituted with one or more substituents independently selected from halogen, $—NO_2$, —CN, —CN, —OH, —SH, $—NO_2$, $—NH_2$, $—O—C_{1-6}$ alkyl, $—S—C_{1-6}$ alkyl, $—N(C_{1-6}$ alkyl$)_2$, $—NH(C_{1-6}$ alkyl), $C_{3-10}$ carbocycle and 3- to 10-membered heterocycle; and $C_{3-10}$ carbocycle and 3- to 10-membered heterocycle, each of which is optionally substituted with one or more substituents independently selected from halogen, $—NO_2$, —CN, —CN, —OH, —SH, $—NO_2$, $—NH_2$, $—O—C_{1-6}$ alkyl, $—S—C_{1-6}$ alkyl, $—N(C_{1-6}$ alkyl$)_2$, $—NH(C_{1-6}$ alkyl), $C_{1-6}$ alkyl, $C_{2-6}$ alkenyl, and $C_{2-6}$ alkynyl.

In some embodiments, each $R^1$ is independently selected from $C_{1-3}$ alkyl optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle and 3- to 10-membered heterocycle. In some embodiments, each $R^1$ is independently selected from $C_{3-5}$ carbocycle is optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, and $C_{2-6}$ alkynyl. In some embodiments, each $R^1$ is independently selected from hydrogen, —CN, —OH, —OMe, —OEt, —OiPr, —F, —Cl, —Br, -Me, -Et, —$CF_3$, —$CHF_2$, —$CH_2F$, $OCF_3$, —$OCHF_2$, —$OCH_2F$, —C(O)$NH_2$,

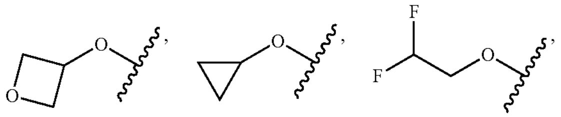

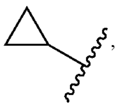
and
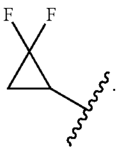

In some embodiments, each $R^1$ is independently selected from hydrogen, —CN, —OH, —OMe, —OEt, —OiPr, —F, —Cl, —Br, -Me, -Et, —$CF_3$, —$CHF_2$, —$CH_2F$, $OCF_3$, —C(O)$NH_2$,

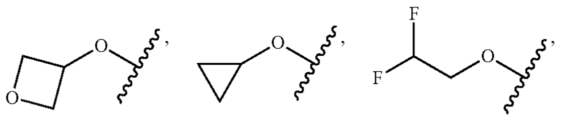

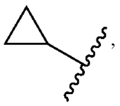
and
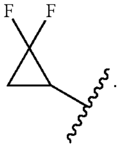

In some embodiments, each $R^1$ is independently selected from hydrogen, —CN, —OH, —OMe, —OEt, —OiPr, —F, —Cl, —Br, -Me, -Et, —$CF_3$, $OCF_3$, —C(O)$NH_2$,

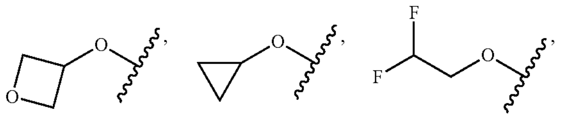

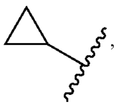
and
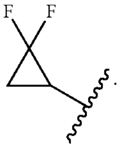

In some embodiments, each $R^1$ is independently selected from hydrogen, —CN, —OH, —OMe, —OEt, —OiPr, —F, —Cl, —Br, -Me, —$CF_3$, $OCF_3$, —C(O)$NH_2$,

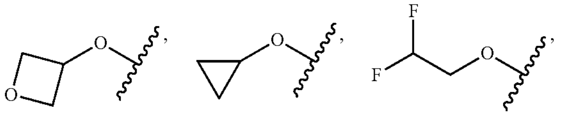

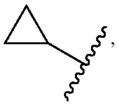
and
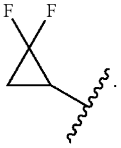

In some embodiments, each $R^1$ is independently selected from hydrogen, —$CF_3$, —CN, —$OR^{10a}$ (e.g., —OMe), —F, —Cl, —$OCF_3$, and methyl. In some embodiments, each $R^1$ is independently selected from hydrogen, —$CF_3$, —CN, —OMe, —F, —Cl, —$OCF_3$, and methyl. In some embodiments, each $R^1$ is independently selected from hydrogen, —$CF_3$, —CN, —$OR^{10a}$ (e.g., —OMe), —F, —Cl, and —$OCF_3$. In some embodiments, each $R^1$ is independently selected from hydrogen, —$CF_3$, —CN, —OMe, —F, —Cl, and —$OCF_3$. In some embodiments, each $R^1$ is independently selected from hydrogen, —$CF_3$, —CN, —OMe, —F, and —Cl. In some embodiments, each $R^1$ is independently selected from hydrogen, —$CF_3$, —CN, —OMe, and —F. In some embodiments, each $R^1$ is independently selected from hydrogen, —$CF_3$, —CN, and —OMe. In some embodiments, each $R^1$ is independently selected from hydrogen, —$CF_3$, and —CN. In some embodiments, each $R^1$ is independently selected from hydrogen and —CN. In some embodiments, each $R^1$ is independently selected from hydrogen and —$CF_3$. In some embodiments, each $R^1$ is independently selected from hydrogen and —CN. In some embodiments, each $R^1$ is independently selected from hydrogen and —$OR^{10a}$. In some embodiments, each $R^1$ is independently selected from hydrogen and —OMe. In some embodiments, each $R^1$ is independently selected from hydrogen and —F. In some embodiments, each $R^1$ is independently selected from hydrogen and —Cl. In some embodiments, each $R^1$ is independently selected from hydrogen and —$OCF_3$. In some embodiments, each $R^1$ is independently selected from hydrogen and $C_{1-6}$ alkyl. In some embodiments, each $R^1$ is independently selected from hydrogen and methyl. In some embodiments, each $R^1$ is independently selected from hydrogen, F, and CN. In some embodiments, each $R^1$ is independently selected from hydrogen and $CF_2H$. In some embodiments, each $R^1$ is independently selected from hydrogen, halogen, and —CN. In some embodiments, each $R^1$ is independently selected from hydrogen, F, and —CN. In some embodiments, each $R^1$ is independently selected from hydrogen and F. In some embodiments, each $R^1$ is independently selected from hydrogen and CN. In some embodiments, each $R^1$ is independently selected from hydrogen.

In certain embodiments, for a compound or salt of Formula (I), $R^2$ is selected from: $C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —N($R^{10b}$)C(O)N($R^{10b}$)$_2$, —OC(O)N($R^{10b}$)$_2$, —N($R^{10b}$)C(O)O$R^{10b}$, —S(O)$R^{10b}$, —S(O)$_2R^{10b}$, —$NO_2$, =O, =S, =N($R^{10b}$), —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$.

In some embodiments, $R^2$ is selected from $C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$.

In some embodiments, $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$.

In some embodiments, $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$.

In some embodiments, $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$.

In some embodiments, $R^2$ is selected from $C_{1-6}$ alkyl, optionally substituted with one or more substituents independently selected from halogen, —$OR^{10b}$, —$SR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$.

In some embodiments, $R^2$ is $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is $C_{1-6}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is $C_{1-6}$ alkyl, optionally substituted with one or more substituents independently selected from halogen, —$OR^{10b}$, —$SR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is $C_{1-6}$ alkyl, optionally substituted with one or more substituents independently selected from halogen, —$OR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is $C_{1-6}$ alkyl, optionally substituted with one or more substituents independently selected from halogen, —$OR^{10b}$, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is $C_{1-6}$ alkyl, optionally substituted with one or more substituents independently selected from F, OH, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is $C_{1-6}$ alkyl, optionally substituted with one or more substituents independently selected from F, OH, $C_{3-10}$ carbocycle and 3- to 10-membered heterocycle, wherein each $C_{3-10}$ carbocycle and 3- to 10-membered heterocycle is independently selected from phenyl, 2-pyridyl, and 3-pyridyl, and each phenyl, 2-pyridyl, and 3-pyridyl is optionally substituted with one or more $R^{9b}$. In some embodiments, $R^2$ is $C_2$ alkyl, optionally substituted with one or more substituents independently selected from halogen, —$OR^{10b}$, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is $C_2$ alkyl, optionally substituted with one or more substituents independently selected from F, OH, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is $C_2$ alkyl, optionally substituted with one or more substituents independently selected from F, OH, $C_{3-10}$ carbocycle and 3- to 10-membered heterocycle, wherein each $C_{3-10}$ carbocycle and 3- to 10-membered heterocycle is independently selected from phenyl, 2-pyridyl, and 3-pyridyl, and each phenyl, 2-pyridyl, and 3-pyridyl is optionally substituted with one or more $R^{9b}$.

In some embodiments, $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$.

In some embodiments, $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl, wherein the $C_{1-6}$ alkyl is optionally substituted with one or more $R^{9b}$.

In some embodiments, $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl.

In some embodiments, $R^2$ is selected from $C_{1-6}$ alkyl, optionally substituted with one or more substituents independently selected from halogen, —$OR^{10b}$, —$SR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl.

In some embodiments, $R^2$ is selected from $C_{1-6}$ alkyl, optionally substituted with one or more substituents independently selected from halogen, —$OR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl.

In some embodiments, $R^2$ is selected from $C_{1-6}$ alkyl, optionally substituted with one or more substituents independently selected from halogen, —$OR^{10b}$, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, and —CN.

In some embodiments, $R^2$ is selected from $C_{1-6}$ alkyl, optionally substituted with one or more substituents independently selected from F, OH, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from F, and —CN.

In some embodiments, $R^2$ is selected from $C_{1-6}$ alkyl, optionally substituted with one or more substituents independently selected from F, OH, $C_{3-10}$ carbocycle and 3- to 10-membered heterocycle, wherein each $C_{3-10}$ carbocycle and 3- to 10-membered heterocycle is independently selected from phenyl, 2-pyridyl, and 3-pyridyl, and each phenyl, 2-pyridyl, and 3-pyridyl is optionally substituted with one or more $R^{9b}$; and $C_{3-10}$ carbocycle and 3- to 10-membered heterocycle, each of which is optionally substituted with one or more substituents independently selected from F, and —CN.

In some embodiments, $R^2$ is selected from $C_2$ alkyl, optionally substituted with one or more substituents independently selected from halogen, —$OR^{10b}$, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from F, and —CN.

In some embodiments, $R^2$ is selected from $C_2$ alkyl, optionally substituted with one or more substituents independently selected from F, OH, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from F, and —CN.

In some embodiments, $R^2$ is a substituent represented by the following:

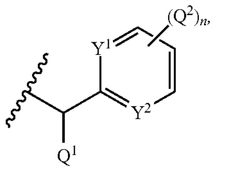

wherein, $Q^1$ is a $C_{1-3}$ alkyl optionally substituted with one or more substituents selected from OH and halo; $Y^1$ and $Y^2$ are each independently selected from N and $C(Q^3)$; and each $Q^2$ is independently selected from halo and CN; each $Q^3$ is independently selected from hydrogen, halo and CN; and n is 0, 1, or 2.

In some embodiments, $Q^1$ is a $C_1$ alkyl optionally substituted with one or more substituents selected from OH and fluoro; each $Q^2$ is independently selected from fluoro and CN; and each $Q^3$ is independently selected from hydrogen, fluoro and CN. In some embodiments, each $Q^2$ is selected from F and H. In some embodiments, each $Q^2$ is selected from CN and H. In some embodiments, each $Q^3$ is selected from F. In some embodiments, each $Q^3$ is selected from F and H. In some embodiments, each $Q^3$ is selected from CN and H. In some embodiments, each $Q^3$ is selected from F.

In some embodiments, $R^2$ is selected from

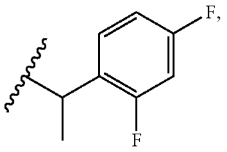
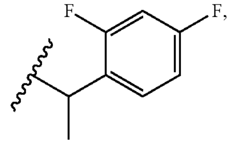
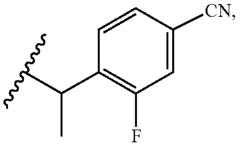
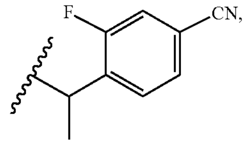
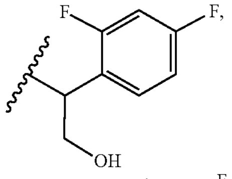
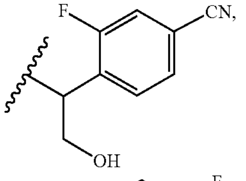
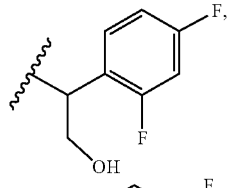
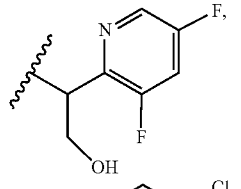
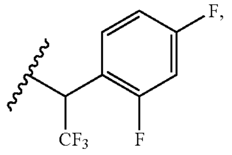
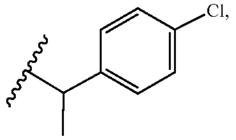
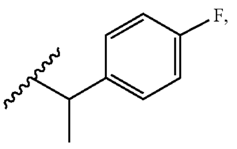
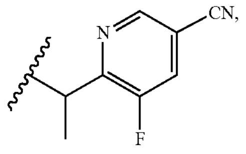

-continued

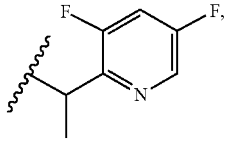
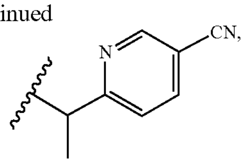
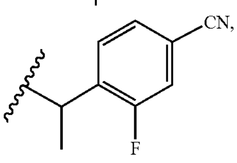
and
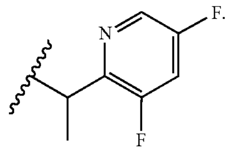

In some embodiments, $R^2$ is selected from

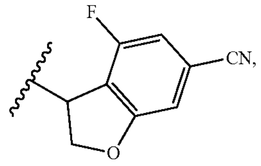
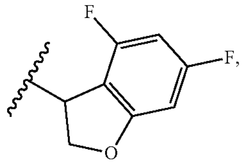
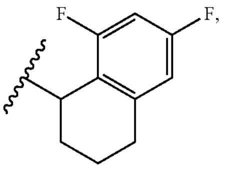
and
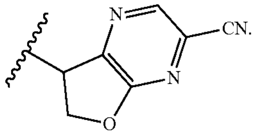

In some embodiments, $R^2$ is selected from $C_{1-6}$ alkyl optionally substituted with one or more substituents independently selected from OH and $C_{3-10}$ carbocycle, wherein the $C_{3-10}$ carbocycle is optionally substituted with one or more substituents independently selected from halogen and —CN; and $C_{3-10}$ carbocycle and 3- to 10-membered heterocycle optionally substituted with one or more substituents independently selected from halogen and —CN. In some embodiments, $R^2$ is selected from $C_{1-6}$ alkyl optionally substituted with one or more $C_{3-10}$ carbocycle, wherein each $C_{3-10}$ carbocycle is optionally substituted with one or more substituents independently selected from halogen and —CN; and $C_{3-10}$ carbocycle and 3- to 10-membered heterocycle optionally substituted with one or more substituents independently selected from halogen and —CN. In some embodiments, $R^2$ is selected from $C_{1-6}$ alkyl optionally substituted with one or more $C_{3-10}$ carbocycle, wherein each $C_{3-10}$ carbocycle is optionally substituted with one or more substituents independently selected from F and —CN; and $C_{3-10}$ carbocycle and 3- to 10-membered heterocycle optionally substituted with one or more substituents independently selected from —F and —CN. In some embodiments, $R^3$ is selected from $C_2$ alkyl optionally substituted with one or more $C_{3-10}$ carbocycle, wherein each $C_{3-10}$ carbocycle is optionally substituted with one or more substituents independently selected from halogen and —CN; and $C_{3-10}$ carbocycle and 3- to 10-membered heterocycle optionally substituted with one or more substituents independently selected from halogen and —CN.

In some embodiments, $R^2$ is selected from $C_2$ alkyl optionally substituted with one or more $C_{3-10}$ carbocycle, wherein each $C_{3-10}$ carbocycle is optionally substituted with one or more substituents independently selected from —F and —CN; and $C_{3-10}$ carbocycle and 3- to 10-membered heterocycle optionally substituted with one or more substituents independently selected from —F and —CN. In some embodiments, $R^2$ is a $C_2$ alkyl optionally substituted with one or more $C_{3-10}$ carbocycle, wherein each $C_{3-10}$ carbocycle is optionally substituted with one or more substituents independently selected from —F and —CN. In some embodiments, $R^2$ is a $C_2$ alkyl optionally substituted with one or more $C_{3-10}$ carbocycle, wherein each $C_{3-10}$ carbocycle is optionally substituted with one or more substituents independently selected from —F. In some embodiments, $R^2$ is a $C_2$ alkyl optionally substituted with one or more $C_{3-10}$ carbocycle, wherein each $C_{3-10}$ carbocycle is optionally substituted with one or more substituents independently selected from —CN.

In some embodiments, $R^2$ is a $C_{3-10}$ carbocycle and 3- to 10-membered heterocycle optionally substituted with one or more substituents independently selected from —F and —CN.

In certain embodiments, for a compound or salt of Formula (I), $R^3$ and $R^4$ are each independently selected from:

hydrogen, halogen, —$OR^{10c}$, —$SR^{10c}$, —$N(R^{10c})_2$, —$NO_2$, and —CN; and $C_{1-6}$ alkyl optionally substituted with one or more substituents independently selected from halogen, —$OR^{10c}$, —$SR^{10c}$, —$N(R^{10c})_2$, —$NO_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$.

In some embodiments, $R^3$ and $R^4$ are each independently selected from: hydrogen, halogen, —$OR^{10c}$, —$SR^{10c}$, —$N(R^{10c})_2$, —$NO_2$, and —CN; and $C_{1-6}$ alkyl optionally substituted with one or more substituents independently selected from halogen, —$OR^{10c}$, —$SR^{10c}$, —$N(R^{10c})_2$, —$NO_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$.

In some embodiments, $R^3$ and $R^4$ are each independently selected from: hydrogen, halogen, —$NO_2$, and —CN; and $C_{1-6}$ alkyl optionally substituted with one or more halogen; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$. In some embodiments, $R^3$ and $R^4$ are each independently selected from: hydrogen, halogen, —$NO_2$, and —CN; and $C_{1-6}$ alkyl optionally substituted with one or more halogen; or $R^3$ together with $R^4$ form a 3- to 10-membered heterocycle or $C_{3-10}$ carbocycle.

In some embodiments, $R^3$ and $R^4$ are each independently selected from: hydrogen; and $C_{1-6}$ alkyl optionally substituted with one or more halogen; or $R^3$ together with $R^4$ form a 3- to 10-membered heterocycle or $C_{3-10}$ carbocycle. In some embodiments, $R^3$ and $R^4$ are each independently selected from: hydrogen; and $C_{1-6}$ alkyl optionally substituted with one or more halogen. In some embodiments, $R^3$ and $R^4$ are each independently selected from: hydrogen; and $C_{1-6}$ alkyl. In some embodiments, $R^3$ and $R^4$ are each independently selected from: hydrogen; and $C_1$ alkyl. In some embodiments, $R^3$ and $R^4$ are each independently selected from: hydrogen.

In some embodiments, $R^3$ together with $R^4$ form a 3- to 10-membered heterocycle or $C_{3-10}$ carbocycle. In some embodiments, the 3- to 10-membered heterocycle or $C_{3-10}$ carbocycle formed by $R^3$ together with $R^4$ is selected from cyclopropyl and oxetanyl. In some embodiments, $R^3$ and $R^4$ are each independently selected from: hydrogen; and $C_1$ alkyl; or $R^3$ together with $R^4$ form a 3- to 10-membered heterocycle or $C_{3-10}$ carbocycle. In some embodiments, $R^3$ and $R^4$ are each independently selected from: hydrogen; and $C_1$ alkyl; or $R^3$ together with $R^4$ form a $C_{3-10}$ carbocycle. In some embodiments, $R^3$ and $R^4$ are each independently selected from: hydrogen; and $C_1$ alkyl; or $R^3$ together with $R^4$ form a $C_{3-10}$ carbocycle, wherein the $C_{3-10}$ carbocycle is cyclopropane.

In some embodiments, $R^3$ and $R^4$ are each hydrogen. In some embodiments, $R^3$ is hydrogen. In some embodiments, $R^4$ is hydrogen. In some embodiments, $R^3$ is hydrogen, and $R^4$ is methyl. In some embodiments, $R^3$ is hydrogen, and $R^4$ is $C_{1-6}$ alkyl. In some embodiments, $R^3$ is —H, and $R^4$ is —OH. In some embodiments, $R^3$ is —OH, and $R^4$ is —H. In some embodiments, $R^3$ is —OH.

In certain embodiments, for a compound or salt of Formula (I), $R^5$ and $R^6$ are each independently selected from:

hydrogen, halogen, —$OR^{10c}$, —$SR^{10c}$, —$N(R^{10c})_2$, —$NO_2$, and —CN;

$C_{1-6}$ alkyl, optionally substituted with one or more substituents independently selected from halogen, —$OR^{10c}$, —$SR^{10c}$, —$N(R^{10c})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10c}$, —$SR^{10c}$, —$N(R^{10c})_2$, —$NO_2$, and —CN; and $C_{3-10}$ carbocycle and 3- to 10-membered heterocycle, each of which is optionally substituted with one or more substituents independently selected from halogen, —$OR^{10c}$, —$SR^{10c}$, —$N(R^{10c})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$.

In some embodiments, $R^5$ and $R^6$ are each independently selected from: hydrogen, halogen, —$OR^{10c}$, —$SR^{10c}$, —$N(R^{10c})_2$, —$NO_2$, and —CN; $C_{1-6}$ alkyl, optionally substituted with one or more substituents independently selected from halogen, —$OR^{10c}$, —$SR^{10c}$, —$N(R^{10c})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10c}$, —$SR^{10c}$, —$N(R^{10c})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$.

In some embodiments, $R^5$ and $R^6$ are each independently selected from: hydrogen, halogen, —$OR^{10c}$, —$SR^{10c}$, —$N(R^{10c})_2$, —$NO_2$, and —CN; and $C_{1-6}$ alkyl; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$. In some embodiments, $R^5$ and $R^6$ are each independently selected from: hydrogen, halogen, —$OR^{10c}$, —$SR^{10c}$, —$N(R^{10c})_2$, —$NO_2$, and —CN; and $C_{1-6}$ alkyl. In some embodiments, $R^5$ and $R^6$ are each independently selected from: hydrogen and $C_{1-3}$ alkyl. In some embodiments, $R^5$ is hydrogen. In some embodiments, $R^6$ is hydrogen. In some embodiments, $R^5$ and $R^6$ are each hydrogen. In some embodiments, $R^5$ is hydrogen, and $R^6$ is $C_{1-6}$ alkyl optionally substituted with one or more substituents independently selected from $C_{3-10}$ carbocycle and 3- to 10-membered heterocycle. In some embodiments, $R^5$ is hydrogen, and $R^6$ is methyl.

In some embodiments, the compound or salt of Formula (I) is a compound or salt of Formula (I-Q):

(I-Q)

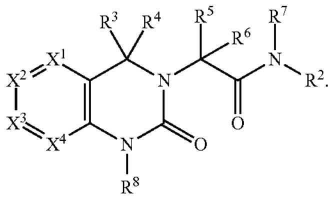

In some embodiments, the compound or salt of formula (I-Q is an activator of skeletal myosin. In some embodiments, the compound or salt of formula (I-Q) is used to treat obesity or to induce weight loss. In some embodiments, for a compound or salt of formula (I-Q), $R^5$ and $R^6$ are each independently selected from: hydrogen, halogen, —$OR^{10c}$, —$SR^{10c}$, —$N(R^{10c})_2$, —$NO_2$, and —CN; $C_{1-10}$ alkyl, optionally substituted with one or more substituents independently selected from halogen, —$OR^{10c}$, —$SR^{10c}$, —$N(R^{10c})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10c}$, —$SR^{10c}$, —$N(R^{10c})_2$, —$NO_2$, and —CN; and $C_{3-10}$ carbocycle and 3- to 10-membered heterocycle, each of which is optionally substituted with one or more substituents independently selected from halogen, —$OR^{10c}$, —$SR^{10c}$, —$N(R^{10c})_2$, —$NO_2$, and —CN. In some embodiments, $R^5$ is —H, and $R^6$ is selected from: $C_{1-10}$ alkyl, optionally substituted with one or more substituents independently selected from halogen, —$OR^{10c}$, —$SR^{10c}$, —$N(R^{10c})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10c}$, —$SR^{10c}$, —$N(R^{10c})_2$, —$NO_2$, and —CN; and $C_{3-10}$ carbocycle and 3- to 10-membered heterocycle, each of which is optionally substituted with one or more substituents independently selected from halogen, —$OR^{10c}$, —$SR^{10c}$, —$N(R^{10c})_2$, —$NO_2$, and —CN. In some embodiments, $R^5$ is —H, and $R^6$ is selected from: $C_{1-10}$ alkyl, optionally substituted with one or more substituents independently selected from halogen, —$OR^{10c}$, —$SR^{10c}$, —$N(R^{10c})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10c}$, —$SR^{10c}$, —$N(R^{10c})_2$, —$NO_2$, and —CN. In some embodiments, $R^5$ is —H, and $R^6$ is selected from: $C_{1-6}$ alkyl, optionally substituted with one or more substituents independently selected from halogen, —$OR^{10c}$, —$SR^{10c}$, —$N(R^{10c})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10c}$, —$SR^{10c}$, —$N(R^{10c})_2$, —$NO_2$, and —CN. In some embodiments, $R^5$ is —H, and $R^6$ is a branched (e.g., nonlinear, e.g., primary, secondary, or tertiary) $C_{1-6}$ alkyl, optionally substituted with one or more substituents independently selected from halogen, —$OR^{10c}$, —$SR^{10c}$, —$N(R^{10c})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10c}$, —$SR^{10c}$, —$N(R^{10c})_2$, —$NO_2$, and —CN. In some embodiments, $R^5$ is —H, and $R^6$ is a methyl, ethyl, n-propyl, i-propyl, n-butyl, s-butyl, i-butyl, t-butyl, n-pentyl, tert-pentyl, neopentyl, isopentyl, sec-pentyl, 3-pentyl, sec-isopentyl, or 2-methylbutyl moiety optionally substituted with one or more substituents independently selected from halogen, —$OR^{10c}$, —$SR^{10c}$, —$N(R^{10c})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10c}$, —$SR^{10c}$, —$N(R^{10c})_2$, —$NO_2$, and —CN. In some embodiments, $R^5$ is —H, and $R^6$ is a methyl, ethyl, n-propyl, i-propyl, n-butyl, s-butyl, i-butyl, t-butyl, n-pentyl, tert-pentyl, neopentyl, isopentyl, sec-pentyl, 3-pentyl, sec-isopentyl, or 2-methylbutyl moiety optionally substituted with one or more substituents independently selected from $C_{3-10}$ carbocycle, wherein each $C_{3-10}$ carbocycle is optionally substituted with one or more substituents independently selected from halogen and —CN. In some embodiments, $R^5$ is —H, and $R^6$ is a methyl, ethyl, n-propyl, i-propyl, n-butyl, s-butyl, i-butyl, t-butyl, n-pentyl, tert-pentyl, neopentyl, isopentyl, sec-pentyl, 3-pentyl, sec-isopentyl, or 2-methylbutyl moiety optionally substituted with one or more substituents independently selected from $C_{3-10}$ carbocycle. In some embodiments, $R^5$ is —H, and $R^6$ is a n-propyl, i-propyl, n-butyl, s-butyl, i-butyl, t-butyl, n-pentyl, tert-pentyl, neopentyl, isopentyl, sec-pentyl, 3-pentyl, sec-isopentyl, or 2-methylbutyl moiety.

In certain embodiments, for a compound or salt of Formula (I), $R^7$ is selected from: hydrogen and $C_{1-6}$ alkyl optionally substituted with one or more substituents independently selected from halogen, —$OR^{10d}$, —$SR^{10d}$, —$N(R^{10d})_2$, —$NO_2$, and —CN. In some embodiments, $R^7$ is selected from hydrogen and $C_{1-6}$ alkyl optionally substituted with one or more substituents independently selected from halogen, CN, $C_{3-10}$ carbocycle, and 3- to 10-membered heterocycle. In some embodiments, $R^7$ is selected from hydrogen and $C_{1-6}$ alkyl optionally substituted with one or more substituents independently selected from halogen and CN. In some embodiments, $R^7$ is selected from hydrogen and $C_{1-6}$ alkyl optionally substituted with one or more substituents independently selected from halogen. In some embodiments, $R^7$ is selected from hydrogen and $C_{1-6}$ alkyl. In some embodiments, $R^7$ is selected from hydrogen and methyl. In some embodiments, $R^7$ is selected from hydrogen.

In certain embodiments, for a compound or salt of Formula (I), $R^8$ is selected from:

- hydrogen; and
- $C_{1-6}$ alkyl optionally substituted with one or more substituents independently selected from halogen, —$OR^{10e}$, —$SR^{10e}$, —$N(R^{10e})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10e}$, —$SR^{10e}$, —$N(R^{10e})_2$, —$NO_2$, and —CN.

In some embodiments, $R^8$ is selected from: hydrogen; and $C_{1-6}$ alkyl optionally substituted with one or more substituents independently selected from halogen, —$OR^{10e}$, —$SR^{10e}$, —$N(R^{10e})_2$, —$NO_2$, and —CN. In some embodiments, $R^8$ is selected from hydrogen and $C_{1-6}$ alkyl optionally substituted with one or more substituents independently selected from halogen, CN, $C_{3-10}$ carbocycle, and 3- to 10-membered heterocycle. In some embodiments, $R^8$ is selected from hydrogen and $C_{1-6}$ alkyl optionally substituted with one or more substituents independently selected from halogen and CN. In some embodiments, $R^8$ is selected from hydrogen and $C_{1-6}$ alkyl optionally substituted with one or more substituents independently selected from halogen.

In some embodiments, $R^8$ is selected from hydrogen and $C_{1-6}$ alkyl. In some embodiments, $R^8$ is selected from hydrogen.

In certain embodiments, for a compound or salt of Formula (I), each $R^{9a}$ is independently selected from:

halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN.

In some embodiments, each $R^{9a}$ is independently selected from: halogen, —$OR^{10a}$, —$SR^{10a}$, $N(R^{10a})_2$, —$C(O)R^{10a}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$NO_2$, =O, and —CN. In some embodiments, each $R^{9a}$ is independently selected from: halogen, —$OR^{10a}$, —$SR^{10a}$, —$N(R^{10a})_2$, —$C(O)R^{10a}$, —$NO_2$, =O, and —CN; and $C_{1-3}$ alkyl optionally substituted with one or more substituents independently selected from halogen, —$OR^{10a}$, —$SR^{10a}$, —$N(R^{10a})_2$, —$C(O)R^{10a}$, —$NO_2$, =O, and —CN. In some embodiments, each $R^{9a}$ is independently selected from: F, Cl, Br, —$OR^{10a}$, —$N(R^{10a})_2$, —$NO_2$, =O, and —CN; and $C_{1-3}$ alkyl optionally substituted with one or more substituents independently selected from F, Cl, Br, —$OR^{10a}$, —$N(R^{10a})_2$, —$NO_2$, =O, and —CN. In some embodiments, each $R^{9a}$ is independently selected from: F, Cl, —$OR^{10a}$, —$N(R^{10a})_2$, —$NO_2$, =O, and —CN; and $C_{1-3}$ alkyl optionally substituted with one or more substituents independently selected from F, Cl, —$OR^{10a}$, —$N(R^{10a})_2$, —$NO_2$, =O, and —CN. In some embodiments, each $R^{9a}$ is independently selected from: F, Cl, —$NO_2$, =O, and —CN; and $C_{1-3}$ alkyl optionally substituted with one or more substituents independently selected from F, Cl, —$NO_2$, =O, and —CN. In some embodiments, each $R^{9a}$ is independently selected from: F, Cl, and —CN; and $C_{1-3}$ alkyl optionally substituted with one or more substituents independently selected from F, Cl, and —CN. In some embodiments, each $R^{9a}$ is independently selected from: F, Cl, and —CN; and $C_{1-3}$ alkyl. In some embodiments, each $R^{9a}$ is independently selected from: F and —CN; and $C_{1-3}$ alkyl. In some embodiments, each $R^{9a}$ is independently selected from: F and —CN. In some embodiments, each $R^{9a}$ is independently selected from: F. In some embodiments, each $R^{9a}$ is independently selected from: —CN.

In certain embodiments, for a compound or salt of Formula (I), each $R^{9b}$ is independently selected from: halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN. In some embodiments, each $R^{9b}$ is independently selected from: halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, and —CN. In some embodiments, each $R^{9b}$ is independently selected from: halogen, —$OR^{10b}$, —$SR^{10b}$, —$N(R^{10b})_2$, —$NO_2$, =O, and —CN; and $C_{1-3}$ alkyl, optionally substituted with one or more substituents independently selected from halogen, —$OR^{10b}$, —$SR^{10b}$, —$N(R^{10b})_2$, —$NO_2$, =O, and —CN. In some embodiments, each $R^{9b}$ is independently selected from: halogen, —$OR^{10b}$, —$SR^{10b}$, —$N(R^{10b})_2$, —$NO_2$, =O, and —CN; and $C_{1-3}$ alkyl, optionally substituted with one or more substituents independently selected from halogen, —$OR^{10b}$, —$SR^{10b}$, —$N(R^{10b})_2$, —$NO_2$, =O, and —CN. In some embodiments, each $R^{9b}$ is independently selected from halogen and —CN. In some embodiments, each $R^{9b}$ is independently selected from —F, —Cl, and —CN. In some embodiments, each $R^{9b}$ is independently selected from —F and —CN. In some embodiments, each $R^{9b}$ is independently selected from —F. In some embodiments, each $R^{9b}$ is independently selected from —CN.

In certain embodiments, for a compound or salt of Formula (I), each $R^{9c}$ is independently selected from: halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN. In some embodiments, each $R^{9c}$ is independently selected from halogen, —$OR^{10c}$, —$SR^{10c}$, —$N(R^{10c})_2$, —$C(O)R^{10c}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10c}$, —$SR^{10c}$, —$N(R^{10c})_2$, —$C(O)R^{10c}$, —$NO_2$, =O, and —CN. In some embodiments, each $R^{9c}$ is independently selected from halogen, —$OR^{10c}$, —$SR^{10c}$, —$N(R^{10c})_2$, —$C(O)R^{10c}$, —$NO_2$, =O, and —CN; and $C_{1-3}$ alkyl, optionally substituted with one or more substituents independently selected from halogen, —$OR^{10c}$, —$SR^{10c}$, —$N(R^{10c})_2$, —$C(O)R^{10c}$, —$NO_2$, =O, and —CN. In some embodiments, each $R^{9c}$ is independently selected from F, Cl, Br, —$OR^{10c}$, —$SR^{10c}$, —$N(R^{10c})_2$, —$C(O)R^{10c}$, —$NO_2$, =O, and —CN; and $C_{1-3}$ alkyl, optionally substituted with one or more substituents independently selected from F, Cl, Br, —$OR^{10c}$, —$SR^{10c}$, —$N(R^{10c})_2$, —$C(O)R^{10c}$, —$NO_2$, =O, and —CN. In some embodiments, each $R^{9c}$ is independently selected from F, Cl, —$OR^{10c}$, —$SR^{10c}$, —$N(R^{10c})_2$, —$C(O)R^{10c}$, —$NO_2$, =O, and —CN; and $C_{1-3}$ alkyl, optionally substituted with one or more substituents independently selected from F, Cl, —$OR^{10c}$, —$SR^{10c}$, —$N(R^{10c})_2$, —$C(O)R^{10c}$, —$NO_2$, =O, and —CN. In some embodiments, each $R^{9c}$ is independently selected from F, Cl, Br, —$OR^{10c}$, —$N(R^{10c})_2$, —$C(O)R^{10c}$, —$NO_2$, =O, and —CN; and $C_{1-3}$ alkyl, optionally substituted with one or more substituents independently selected from F, Cl, Br, —$OR^{10c}$, —$N(R^{10c})_2$, —$C(O)R^{10c}$, —$NO_2$, =O, and —CN. In some embodiments, each $R^{9c}$ is independently selected from F, Cl, Br, —$NO_2$, =O, and —CN; and $C_{1-3}$ alkyl, optionally substituted with one or more substituents independently selected from F, Cl, Br, —$NO_2$, =O, and —CN. In some embodiments, each $R^{9c}$ is independently selected from F, Cl, —$NO_2$, =O, and —CN; and $C_{1-3}$ alkyl, optionally substituted with one or more substituents independently selected from F, Cl, —$NO_2$, =O, and —CN. In some embodiments, each $R^{9c}$ is independently selected from: F, Cl, and —CN; and $C_{1-3}$ alkyl optionally substituted with one or more substituents independently selected from F, Cl, and —CN. In some embodiments, each $R^{9c}$ is independently selected from: F, Cl, and —CN; and $C_{1-3}$ alkyl. In some embodiments, each $R^{9c}$ is independently selected from: F and —CN; and $C_{1-3}$ alkyl. In some embodiments, each $R^{9c}$ is independently selected from: F and —CN. In some embodiments, each $R^{9c}$ is independently selected from: F. In some embodiments, each $R^{9c}$ is independently selected from: —CN.

In certain embodiments, for a compound or salt of Formula (I), each $R^{10a}$, $R^{10b}$, $R^{10c}$, $R^{10d}$, and $R^{10e}$ is independently selected from:

hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In certain embodiments, for a compound or salt of Formula (I), each $R^{10a}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, each $R^{10a}$ is independently selected from hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —$N(C_{1-6}$ alkyl$)_2$, and —$NH(C_{1-6}$ alkyl); and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —$N(C_{1-6}$ alkyl$)_2$, —NH($C_{1-6}$ alkyl), $C_{1-6}$ alkyl, and $C_{1-6}$ haloalkyl. In some embodiments, each $R^{10a}$ is independently selected from hydrogen; and $C_{1-6}$ alkyl, optionally substituted with one or more substituents independently selected from halogen, —CN, —OH, —SH, —$NO_2$, —$NH_2$, and =O; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —$N(C_{1-6}$ alkyl$)_2$, —$NH(C_{1-6}$ alkyl), $C_{1-6}$ alkyl, and $C_{1-6}$ haloalkyl. In some embodiments, $R^{10a}$ is independently selected from hydrogen; and $C_{1-6}$ alkyl optionally substituted with one or more substituents independently selected from halogen; and $C_{3-10}$ carbocycle, and 3- to 10-membered heterocycle. In some embodiments, $R^{10a}$ is independently selected from hydrogen; and $C_{1-6}$ alkyl optionally substituted with one or more substituents independently selected from fluorine and chlorine; and $C_{3-10}$ carbocycle, and 3- to 10-membered heterocycle. In some embodiments, $R^{10a}$ is independently selected from hydrogen; and $C_{1-6}$ alkyl optionally substituted with fluorine; and $C_{3-10}$ carbocycle, and 3- to 10-membered heterocycle. In some embodiments, $R^{10a}$ is independently selected from hydrogen; and $C_{1-6}$ alkyl optionally substituted with fluorine; and $C_{3-10}$ carbocycle, and 3- to 10-membered heterocycle selected from cyclopropane and oxetane. In some embodiments, $R^{10a}$ is hydrogen. In some embodiments, $R^{10a}$ is methyl.

In certain embodiments, for a compound or salt of Formula (I), each $R^{10b}$ is independently selected from:

hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In some embodiments, each $R^{10b}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, and —$NH(C_{1-6}$ alkyl); and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —NH ($C_{1-6}$ alkyl), $C_{1-6}$ alkyl, $C_{2-6}$ alkenyl, and $C_{1-6}$ haloalkyl. In some embodiments, each $R^{10b}$ is independently selected from: hydrogen; and $C_{1-6}$ alkyl. In some embodiments, each $R^{10b}$ is hydrogen. In some embodiments, $R^{10b}$ is methyl.

In certain embodiments, for a compound or salt of Formula (I), each $R^{10c}$ is independently selected from:

hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In some embodiments, each $R^{10c}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH ($C_{1-6}$ alkyl); and $C_{3-10}$ carbocycle, and 3- to 10-membered heterocycle. In some embodiments, each $R^{10c}$ is independently selected from: hydrogen; and $C_{1-6}$ alkyl. In some embodiments, each $R^{10c}$ is hydrogen. In some embodiments, $R^{10c}$ is methyl.

In certain embodiments, for a compound or salt of Formula (I), each $R^{10d}$ is independently selected from:

hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In some embodiments, each $R^{10d}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH ($C_{1-6}$ alkyl); and $C_{3-10}$ carbocycle, and 3- to 10-membered heterocycle. In some embodiments, each $R^{10d}$ is independently selected from: hydrogen; and $C_{1-6}$ alkyl. In some embodiments, each $R^{10d}$ is hydrogen. In some embodiments, $R^{10d}$ is methyl.

In certain embodiments, for a compound or salt of Formula (I), each $R^{10e}$ is independently selected from:

hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In some embodiments, each $R^{10e}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH ($C_{1-6}$ alkyl); and $C_{3-10}$ carbocycle, and 3- to 10-membered heterocycle. In some embodiments, each $R^{10e}$ is independently selected from: hydrogen; and $C_{1-6}$ alkyl. In some embodiments, each $R^{10e}$ is hydrogen. In some embodiments, $R^{10e}$ is methyl.

In certain embodiments, for a compound or salt of Formula (I), if two of $X^1$, $X^2$, $X^3$, and $X^4$ are N, then $R^8$ is selected from hydrogen and $C_{1-4}$ alkyl optionally substituted with one or more substituents independently selected from halogen, —$OR^{10}$, —$SR^{10}$, —N($R^{10}$)$_2$, —$NO_2$, and —CN. In some embodiments, if two of $X^1$, $X^2$, $X^3$, and $X^4$ are N, then $R^8$ is selected from hydrogen and $C_{1-4}$ alkyl optionally substituted with one or more substituents independently selected from halogen, —$OR^{10}$, and —CN. In some embodiments, if two of $X^1$, $X^2$, $X^3$, and $X^4$ are N, then $R^8$ is selected from hydrogen and $C_{1-4}$ alkyl optionally substituted with one or more substituents independently selected from fluoro, —OH, and —CN. In some embodiments, if two of $X^1$, $X^2$, $X^3$, and $X^4$ are N, then $R^8$ is selected from hydrogen and $C_{1-4}$ alkyl. In some embodiments, if two of $X^1$, $X^2$, $X^3$, and $X^4$ are N, then $R^8$ is selected from hydrogen and $C_1$ alkyl. In some embodiments, if two of $X^1$, $X^2$, $X^3$, and $X^4$ are N, then $R^8$ is selected from hydrogen.

In certain embodiments, for a compound or salt of Formula (I), if $X^3$ and $X^1$ are both N, then $R^8$ is selected from hydrogen and $C_{1-4}$ alkyl optionally substituted with one or more substituents independently selected from halogen, —$OR^{10}$, —$SR^{10}$, —N($R^{10}$)$_2$, —$NO_2$, and —CN. In some embodiments, if $X^3$ and $X^1$ are both N, then $R^8$ is selected from hydrogen and $C_{1-4}$ alkyl optionally substituted with one or more substituents independently selected from halogen, —$OR^{10}$, and —CN. In some embodiments, if $X^3$ and $X^1$ are both N, then $R^8$ is selected from hydrogen and $C_{1-4}$ alkyl optionally substituted with one or more substituents independently selected from fluoro, —OH, and —CN. In some embodiments, if $X^3$ and $X^1$ are both N, then $R^8$ is selected from hydrogen and $C_{1-4}$ alkyl. In some embodiments, if $X^3$ and $X^1$ are both N, then $R^8$ is selected from hydrogen and $C_1$ alkyl. In some embodiments, if $X^3$ and $X^1$ are both N, then $R^8$ is selected from hydrogen.

In certain embodiments, for a compound or salt of Formula (I), if $X^2$ and $X^4$ are both N, then $R^8$ is selected from hydrogen and $C_{1-4}$ alkyl optionally substituted with one or more substituents independently selected from halogen, —$OR^{10}$, —$SR^{10}$, —N($R^{10}$)$_2$, —$NO_2$, and —CN. In some embodiments, if $X^2$ and $X^4$ are both N, then $R^8$ is selected from hydrogen and $C_{1-4}$ alkyl optionally substituted with one or more substituents independently selected from halogen, —$OR^{10}$, and —CN. In some embodiments, if $X^2$ and $X^4$ are both N, then $R^8$ is selected from hydrogen and $C_{1-4}$ alkyl optionally substituted with one or more substituents independently selected from fluoro, —OH, and —CN. In some embodiments, if $X^2$ and $X^4$ are both N, then $R^8$ is selected from hydrogen and $C_{1-4}$ alkyl. In some embodiments, if $X^2$ and $X^4$ are both N, then $R^8$ is selected from hydrogen and $C_1$ alkyl. In some embodiments, if $X^2$ and $X^4$ are both N, then $R^8$ is selected from hydrogen.

In certain embodiments, for a compound or salt of Formula (I), if two of $X^1$, $X^2$, $X^3$, and $X^4$ are N, then $R^7$ is selected from hydrogen and $C_{1-4}$ alkyl optionally substituted with one or more substituents independently selected from halogen, —$OR^{10}$, —$SR^{10}$, —N($R^{10}$)$_2$, —$NO_2$, and —CN. In some embodiments, if two of $X^1$, $X^2$, $X^3$, and $X^4$ are N, then $R^7$ is selected from hydrogen and $C_{1-4}$ alkyl optionally substituted with one or more substituents independently selected from halogen, —$OR^{10}$, and —CN. In some embodiments, if two of $X^1$, $X^2$, $X^3$, and $X^4$ are N, then $R^7$ is selected from hydrogen and $C_{1-4}$ alkyl optionally substituted with one or more substituents independently selected from fluoro, —OH, and —CN. In some embodiments, if two of $X^1$, $X^2$, $X^3$, and $X^4$ are N, then $R^7$ is selected from hydrogen and $C_{1-4}$ alkyl. In some embodiments, if two of $X^1$, $X^2$, $X^3$, and $X^4$ are N, then $R^7$ is selected from hydrogen and $C_1$ alkyl. In some embodiments, if two of $X^1$, $X^2$, $X^3$, and $X^4$ are N, then $R^7$ is selected from hydrogen.

In certain embodiments, for a compound or salt of Formula (I), if $X^3$ and $X^1$ are both N, then $R^7$ is selected from hydrogen and $C_{1-4}$ alkyl optionally substituted with one or more substituents independently selected from halogen, —$OR^{10}$, —$SR^{10}$, —$N(R^{10})_2$, —$NO_2$, and —CN. In some embodiments, if $X^3$ and $X^1$ are both N, then $R^7$ is selected from hydrogen and $C_{1-4}$ alkyl optionally substituted with one or more substituents independently selected from halogen, —$OR^{10}$, and —CN. In some embodiments, if $X^3$ and $X^1$ are both N, then $R^7$ is selected from hydrogen and $C_{1-4}$ alkyl optionally substituted with one or more substituents independently selected from fluoro, —OH, and —CN. In some embodiments, if $X^3$ and $X^1$ are both N, then $R^7$ is selected from hydrogen and $C_{1-4}$ alkyl. In some embodiments, if $X^3$ and $X^1$ are both N, then $R^7$ is selected from hydrogen and $C_1$ alkyl. In some embodiments, if $X^3$ and $X^1$ are both N, then $R^7$ is selected from hydrogen.

In certain embodiments, for a compound or salt of Formula (I), if $X^2$ and $X^4$ are both N, then $R^7$ is selected from hydrogen and $C_{1-4}$ alkyl optionally substituted with one or more substituents independently selected from halogen, —$OR^{10}$, —$SR^{10}$, —$N(R^{10})_2$, —$NO_2$, and —CN. In some embodiments, if $X^2$ and $X^4$ are both N, then $R^7$ is selected from hydrogen and $C_{1-4}$ alkyl optionally substituted with one or more substituents independently selected from halogen, —$OR^{10}$, and —CN. In some embodiments, if $X^2$ and $X^4$ are both N, then $R^7$ is selected from hydrogen and $C_{1-4}$ alkyl optionally substituted with one or more substituents independently selected from fluoro, —OH, and —CN. In some embodiments, if $X^2$ and $X^4$ are both N, then $R^7$ is selected from hydrogen and $C_{1-4}$ alkyl. In some embodiments, if $X^2$ and $X^4$ are both N, then $R^7$ is selected from hydrogen and $C_1$ alkyl. In some embodiments, if $X^2$ and $X^4$ are both N, then $R^7$ is selected from hydrogen.

In some embodiments, the compound or salt of Formula (I) is selected from: N87, N4, N5, N13, N15, N123, N33, N111, N124, and N128.

In some embodiments, the compound or salt of Formula (I) is selected from: N87, N4, N5, N13, N15, N123, N33, N111, N124, N128, N7, N18, N68, N88, N26, N103, N104, N117, N110, N37, N102, N94, N112, N81, N54, N101, N23, N136, N9, N98, N122, N31, N28, N115, N121, N74, N119, N16, N126, N47, N125, N83, N118, N10, and N62.

In some embodiments, the compound or salt of Formula (I) is selected from: N87, N4, N5, N13, N15, N123, N33, N111, N124, N128, N7, N18, N68, N88, N26, N103, N104, N117, N110, N37, N102, N94, N112, N81, N54, N101, N23, N136, N9, N98, N122, N31, N28, N115, N121, N74, N119, N16, N126, N47, N125, N83, N118, N10, N62, N41, N60, N14, N44, N108, N130, N93, N19, N77, N8, N114, N106, N3, N133, N6, N24, N127, N72, N84, N95, N132, N129, N21, N116, N55, N109, N35, N135, N59, N12, N36, N80, N99, N34, N39, and N50.

In some embodiments, the compound or salt of Formula (I) is selected from: N87, N4, N5, N13, N15, N123, N33, N111, N124, N128, N7, N18, N68, N88, N26, N103, N104, N117, N110, N37, N102, N94, N112, N81, N54, N101, N23, N136, N9, N98, N122, N31, N28, N115, N121, N74, N119, N16, N126, N47, N125, N83, N118, N10, N62, N41, N60, N14, N44, N108, N130, N93, N19, N77, N8, N114, N106, N3, N133, N6, N24, N127, N72, N84, N95, N132, N129, N21, N116, N55, N109, N35, N135, N59, N12, N36, N80, N99, N34, N39, N50, N57, N25, N45, N2, N85, N113, N64, N78, N66, N86, N43, N30, N131, N71, N91, N38, N1, N17, N40, and N52.

In some embodiments, the compound or salt of Formula (I) is selected from: N87, N4, N5, N13, N15, N123, N33, N111, N124, N128, N7, N18, N68, N88, N26, N103, N104, N117, N110, N37, N102, N94, N112, N81, N54, N101, N23, N136, N9, N98, N122, N31, N28, N115, N121, N74, N119, N16, N126, N47, N125, N83, N118, N10, N62, N41, N60, N14, N44, N108, N130, N93, N19, N77, N8, N114, N106, N3, N133, N6, N24, N127, N72, N84, N95, N132, N129, N21, N116, N55, N109, N35, N135, N59, N12, N36, N80, N99, N34, N39, N50, N57, N25, N45, N2, N85, N113, N64, N78, N66, N86, N43, N30, N131, N71, N91, N38, N1, N17, N40, N52, N11, N20, N22, N27, N29, N32, N42, N46, N48, N49, N51, N53, N56, N58, N61, N63, N65, N67, N69, N70, N73, N75, N76, N79, N82, N89, N90, N92, N96, N97, N100, N105, N107, and N120.

In some embodiments, the compound or salt of Formula (I) is selected from: N5, N23, N87, N124, N128, N7, N33, N117, N4, and N94

In some embodiments, the compound or salt of Formula (I) is selected from: N5, N23, N87, N124, N128, N7, N33, N117, N4, N94, N81, N88, N115, N13, and N123.

In some embodiments, the compound or salt of Formula (I) is selected from: N5, N23, N87, N124, N128, N7, N33, N117, N4, N94, N81, N88, N115, N13, N123, N31, N26, N18, N74, N68, N101, N102, N41, N125, N15, N54, N9, N119, N126, N104, N37, N129, N62, N118, N95, N121, N47, N28, N111, N114, N112, and N103.

In some embodiments, the compound or salt of Formula (I) is selected from: N5, N23, N87, N124, N128, N7, N33, N117, N4, N94, N81, N88, N115, N13, N123, N31, N26, N18, N74, N68, N101, N102, N41, N125, N15, N54, N9, N119, N126, N104, N37, N129, N62, N118, N95, N121, N47, N28, N111, N114, N112, N103, N136, N122, N19, N8, N10, N21, N133, N44, N110, N77, N36, N120, N78, N2, N24, N6, N72, N116, N108, N39, N98, N127, N113, N60, and N132.

In some embodiments, the compound or salt of Formula (I) is selected from: N5, N23, N87, N124, N128, N7, N33, N117, N4, N94, N81, N88, N115, N13, N123, N31, N26, N18, N74, N68, N101, N102, N41, N125, N15, N54, N9, N119, N126, N104, N37, N129, N62, N118, N95, N121, N47, N28, N111, N114, N112, N103, N136, N122, N19, N8, N10, N21, N133, N44, N110, N77, N36, N120, N78, N2, N24, N6, N72, N116, N108, N39, N98, N127, N113, N60, N132, N1, N3, N11, N12, N14, N16, N17, N20, N22, N25, N27, N29, N30, N32, N34, N35, N38, N40, N42, N43, N45, N46, N48, N49, N50, N51, N52, N53, N55, N56, N57, N58, N59, N61, N63, N64, N65, N66, N67, N69, N70, N71, N73, N75, N76, N79, N80, N82, N83, N84, N85, N86, N89, N90, N91, N92, N93, N96, N97, N99, N100, N105, N106, N107, N109, N130, N131, and N135.

In some embodiments, for a compound or salt of formula (I), each $R^1$ is independently selected from: hydrogen; deuterium, —$N_3$, halogen, —$NO_2$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, and —$S(O)_2R^{10a}$; $C_{1-6}$ alkyl, $C_{2-6}$ alkenyl, and $C_{2-6}$ alkynyl, each of which is optionally substituted with one or more substituents independently selected from deuterium, —$N_3$, halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, =O, =S, =$N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from deuterium, —$N_3$, halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$. In some embodiments, $R^2$ is selected from $C_{1-6}$ alkyl, $C_{2-6}$ alkenyl, and $C_{2-6}$ alkynyl, each of which is optionally substituted with one or more substituents independently selected from deuterium, —$N_3$, halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from deuterium, —$N_3$, halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. In some embodiments, $R^3$ and $R^4$ are each independently selected from: ·hydrogen, deuterium, —$N_3$, halogen, —$OR^{10c}$, —$SR^{10c}$, —$N(R^{10c})_2$, —$NO_2$, and —CN; and $C_{1-6}$ alkyl optionally substituted with one or more substituents independently selected from deuterium, —$N_3$, halogen, —$OR^{10c}$, —$SR^{10c}$, —$N(R^{10c})_2$, —$NO_2$, and —CN; or ·$R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$. In some embodiments, $R^5$ and $R^6$ are each independently selected from: hydrogen, deuterium, —$N_3$, halogen, —$OR^{10c}$, —$SR^{10c}$, —$N(R^{10c})_2$, —$NO_2$, and —CN; $C_{1-6}$ alkyl, optionally substituted with one or more substituents independently selected from deuterium, —$N_3$, halogen, —$OR^{10c}$, —$SR^{10c}$, —$N(R^{10c})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from deuterium, —$N_3$, halogen, —$OR^{10c}$, —$SR^{10c}$, —$N(R^{10c})_2$, —$NO_2$, and —CN; and $C_{3-10}$ carbocycle and 3- to 10-membered heterocycle, each of which is optionally substituted with one or more substituents independently selected from deuterium, —$N_3$, halogen, —$OR^{10c}$, —$SR^{10c}$, —$N(R^{10c})_2$, —$NO_2$, and —CN; or ·$R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$. In some embodiments, $R^7$ is selected from: ·hydrogen and $C_{1-6}$ alkyl optionally substituted with one or more substituents independently selected from deuterium, —$N_3$, halogen, —$OR^{10d}$, —$SR^{10d}$, —$N(R^{10d})_2$, —$NO_2$, and —CN. In some embodiments, $R^8$ is selected from: ·hydrogen; and $C_{1-6}$ alkyl optionally substituted with one or more substituents independently selected from deuterium, —$N_3$, halogen, —$OR^{10e}$, —$SR^{10e}$, —$N(R^{10e})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from deuterium, —$N_3$, halogen, —$OR^{10e}$, —$SR^{10e}$, —$N(R^{10e})_2$, —$NO_2$, and —CN. In some embodiments, each $R^{9a}$ is independently selected from: deuterium, —$N_3$, halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN; and $C_{1-3}$ alkyl, $C_{2-3}$ alkenyl, and $C_{2-3}$ alkynyl, each of which is optionally substituted with one or more substituents independently selected from deuterium, —$N_3$, halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN. In some embodiments, each $R^{9b}$ is independently selected from: deuterium, —$N_3$, halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN; and $C_{1-3}$ alkyl, $C_{2-3}$ alkenyl, and $C_{2-3}$ alkynyl, each of which is optionally substituted with one or more substituents independently selected from deuterium, —$N_3$, halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$ and —CN. In some embodiments, each $R^{9c}$ is independently selected from: deuterium, —$N_3$, halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN; and $C_{1-3}$ alkyl, $C_{2-3}$ alkenyl, and $C_{2-3}$ alkynyl, each of which is optionally substituted with one or more substituents independently selected from deuterium, —$N_3$, halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN. In some embodiments, each $R^{10a}$, $R^{10b}$, $R^{10c}$, $R^{10d}$, and $R^{10e}$ is independently selected from: hydrogen; $C_{1-6}$ alkyl, $C_{2-6}$ alkenyl, and $C_{2-6}$ alkynyl, each of which is optionally substituted with one or more substituents independently selected from deuterium, —$N_3$, halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from deuterium, —$N_3$, halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, $R^3$ is -D. In some embodiments, $R^4$ is -D. In some embodiments, $R^5$ is -D. In some embodiments, $R^6$ is -D. In some embodiments, $R^7$ is -D. In some embodiments, $R^8$ is -D.

In one aspect, the present disclosure provides a compound represented by Formula (II):

(II)

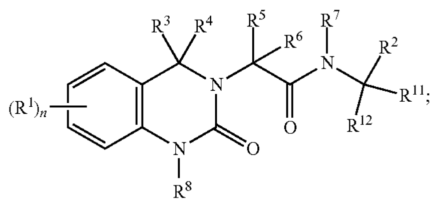

or a salt thereof, wherein:

n is 0, 1, 2, 3, or 4;

each $R^1$ is independently selected from:

halogen, —$NO_2$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, and —$S(O)_2R^{10a}$;

$C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, =O, =S, =$N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$;

$R^2$ is selected from:

halogen, —$NO_2$, —CN, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, and —$S(O)_2R^{10b}$;

$C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b}$';

$R^3$ and $R^4$ are each independently selected from:

hydrogen, halogen, —$OR^{10c}$, —$SR^{10c}$, —$N(R^{10c})_2$, —$NO_2$, and —CN; and $C_{1-6}$ alkyl optionally substituted with one or more substituents independently selected from halogen, —$OR^{10c}$, —$SR^{10c}$, —$N(R^{10c})_2$, —$NO_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$;

$R^5$ and $R^6$ are each independently selected from:

hydrogen, halogen, —$OR^{10d}$, $SR^{10d}$, —$N(R^{10d})_2$, —$NO_2$, and —CN; and $C_{1-6}$ alkyl optionally substituted with one or more substituents independently selected from halogen, —$OR^{10d}$, —$SR^{10d}$, —$N(R^{10d})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9d}$;

$R^7$ is selected from:

hydrogen and $C_{1-6}$ alkyl optionally substituted with one or more substituents independently selected from halogen, —$OR^{10e}$, —$SR^{10e}$, —$N(R^{10e})_2$, —$NO_2$, and —CN;

$R^8$ is selected from:

hydrogen;

and $C_{1-6}$ alkyl optionally substituted with one or more substituents independently selected from halogen, —$OR^{10f}$, —$SR^{10f}$, —$N(R^{10f})_2$, —$NO_2$, and —CN;

$R^{11}$ is selected from:

halogen, —$NO_2$, —CN, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, and —$S(O)_2R^{10g}$; and $C_{1-6}$ alkyl, $C_{2-6}$ alkenyl, and $C_{2-6}$ alkynyl, each of which is optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, —$OC(O)R^{10g}$, —$N(R^{10g})C(O)N(R^{10g})_2$, —$OC(O)N(R^{10g})_2$, —$N(R^{10g})C(O)OR^{10g}$, —$S(O)R^{10g}$, —$S(O)_2R^{10g}$, —$NO_2$, =S, =$N(R^{10g})$, —CN, $C_{3-10}$ carbocycle and 3- to 10-membered heterocycle, wherein the $C_{3-10}$ carbocycle and 3- to 10-membered heterocycle are each optionally substituted with one or more $R^{9g}$;

$R^{12}$ is selected from hydrogen;

$C_{1-6}$ alkyl optionally substituted with one or more substituents independently selected from the group consisting of halogen, CN, OH, $OR^{10h}$, $N(R^{10h})_2$, $NO_2$, $C(O)R^{10h}$, $SR^{10h}$, and $S(O)R^{10h}$; and $C_{3-6}$ carbocycle and 3- to 10-membered heterocycle each optionally substituted with one or more substituents independently selected from the group consisting of halogen, CN, OH, $OR^{10h}$, $N(R^{10h})_2$, $NO_2$, $C(O)R^{10h}$, $SR^{10h}$, and $S(O)R^{10h}$; or $R^{12}$, $R^{11}$, and $R^2$ come together to form a $C_5$-$C_{10}$ bridged ring system;

each $R^{9a}$ is independently selected from:

halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, $=O$, $=S$, $=N(R^{10a})$, and —CN; and $C_{1-3}$ alkyl, $C_{2-3}$ alkenyl, and $C_{2-3}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, $=O$, $=S$, $=N(R^{10a})$, and —CN;

each $R^{9b}$ is independently selected from:

halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—N(R^{10b})C(O)N(R^{10b})_2$, $—OC(O)N(R^{10b})_2$, $—N(R^{10b})C(O)OR^{10b}$, $—C(O)OR^{10b}$, $—OC(O)R^{10b}$, $—S(O)R^{10b}$, $—S(O)_2R^{10b}$, $—NO_2$, $=O$, $=S$, $=N(R^{10b})$, and —CN; and $C_{1-3}$ alkyl, $C_{2-3}$ alkenyl, and $C_{2-3}$ alkynyl, each of which is optionally substituted with one or more substituents independently selected from halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—N(R^{10b})C(O)N(R^{10b})_2$, $—OC(O)N(R^{10b})_2$, $—N(R^{10b})C(O)OR^{10b}$, $—C(O)OR^{10b}$, $—OC(O)R^{10b}$, $—S(O)R^{10b}$, $—S(O)_2R^{10b}$, $—NO_2$, $=O$, $=S$, $=N(R^{10b})$, and —CN;

each $R^{9b'}$ is independently selected from:

halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—N(R^{10b})C(O)N(R^{10b})_2$, $—OC(O)N(R^{10b})_2$, $—N(R^{10b})C(O)OR^{10b}$, $—C(O)OR^{10b}$, $—OC(O)R^{10b}$, $—S(O)R^{10b}$, $—S(O)_2R^{10b}$, $—NO_2$, $=O$, $=S$, $=N(R^{10b})$, and —CN; and $C_{1-3}$ alkyl, $C_{2-3}$ alkenyl, and $C_{2-3}$ alkynyl, each of which is optionally substituted with one or more substituents independently selected from halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—N(R^{10b})C(O)N(R^{10b})_2$, $—OC(O)N(R^{10b})_2$, $—N(R^{10b})C(O)OR^{10b}$, $—C(O)OR^{10b}$, $—OC(O)R^{10b}$, $—S(O)R^{10b}$, $—S(O)_2R^{10b}$, $—NO_2$, $=O$, $=S$, $=N(R^{10b})$, and —CN;

each $R^{9c}$ is independently selected from:

halogen, $—OR^{10c}$, $—SR^{10c}$, $—N(R^{10c})_2$, $—C(O)R^{10c}$, $—C(O)N(R^{10c})_2$, $—N(R^{10c})C(O)R^{10c}$, $—N(R^{10c})C(O)N(R^{10c})_2$, $—OC(O)N(R^{10c})_2$, $—N(R^{10c})C(O)OR^{10c}$, $—C(O)OR^{10c}$, $—OC(O)R^{10c}$, $—S(O)R^{10c}$, $—S(O)_2R^{10c}$, $—NO_2$, $=O$, $=S$, $=N(R^{10c})$, and —CN; and $C_{1-3}$ alkyl, $C_{2-3}$ alkenyl, and $C_{2-3}$ alkynyl, each of which is optionally substituted with one or more substituents independently selected from halogen, $—OR^{10c}$, $—SR^{10c}$, $—N(R^{10c})_2$, $—C(O)R^{10c}$, $—C(O)N(R^{10c})_2$, $—N(R^{10c})C(O)R^{10c}$, $—N(R^{10c})C(O)N(R^{10c})_2$, $—OC(O)N(R^{10c})_2$, $—N(R^{10c})C(O)OR^{10c}$, $—C(O)OR^{10c}$, $—OC(O)R^{10c}$, $—S(O)R^{10c}$, $—S(O)_2R^{10c}$, $—NO_2$, $=O$, $=S$, $=N(R^{10c})$, and —CN;

each $R^{9d}$ is independently selected from:

halogen, $—OR^{10d}$, $—SR^{10d}$, $—N(R^{10d})_2$, $—C(O)R^{10d}$, $—C(O)N(R^{10d})_2$, $—N(R^{10d})C(O)R^{10d}$, $—N(R^{10d})C(O)N(R^{10d})_2$, $—OC(O)N(R^{10d})_2$, $—N(R^{10d})C(O)OR^{10d}$, $—C(O)OR^{10d}$, $—OC(O)R^{10d}$, $—S(O)R^{10d}$, $—S(O)_2R^{10d}$, $—NO_2$, $=O$, $=S$, $=N(R^{10d})$, and —CN; and $C_{1-3}$ alkyl, $C_{2-3}$ alkenyl, and $C_{2-3}$ alkynyl, each of which is optionally substituted with one or more substituents independently selected from halogen, $—OR^{10d}$, $—SR^{10d}$, $N(R^{10d})_2$, $—C(O)R^{10d}$, $—C(O)N(R^{10d})_2$, $—N(R^{10d})C(O)R^{10d}$, $—N(R^{10d})C(O)N(R^{10d})_2$, $—OC(O)N(R^{10d})_2$, $—N(R^{10d})C(O)OR^{10d}$, $—C(O)OR^{10d}$, $—OC(O)R^{10d}$, $—S(O)R^{10d}$, $—S(O)_2R^{10d}$, $—NO_2$, $=O$, $=S$, $=N(R^{10d})$, and —CN;

each $R^{9g}$ is independently selected from:

halogen, $—OR^{10g}$, $—SR^{10g}$, $—N(R^{10g})_2$, $—C(O)R^{10g}$, $—C(O)N(R^{10g})_2$, $—N(R^{10g})C(O)R^{10g}$, $—N(R^{10g})C(O)N(R^{10g})_2$, $—OC(O)N(R^{10g})_2$, $—N(R^{10g})C(O)OR^{10g}$, $—C(O)OR^{10g}$, $—OC(O)R^{10g}$, $—S(O)R^{10g}$, $—S(O)_2R^{10g}$, $—NO_2$, $=O$, $=S$, $=N(R^{10g})$, and —CN; and $C_{1-3}$ alkyl, $C_{2-3}$ alkenyl, and $C_{2-3}$ alkynyl, each of which is optionally substituted with one or more substituents independently selected from halogen, $—OR^{10g}$, $—SR^{10g}$, $—N(R^{10g})_2$, $—C(O)R^{10g}$, $—C(O)N(R^{10g})_2$, $—N(R^{10g})C(O)R^{10g}$, $—N(R^{10g})C(O)N(R^{10g})_2$, $—OC(O)N(R^{10g})_2$, $—N(R^{10g})C(O)OR^{10g}$, $—C(O)OR^{10g}$, $—OC(O)R^{10g}$, $—S(O)R^{10g}$, $—S(O)_2R^{10g}$, $—NO_2$, $=O$, $=S$, $=N(R^{10g})$, and —CN;

each $R^{10a}$, $R^{10b}$, $R^{10c}$, $R^{10d}$, $R^{10e}$, $R^{10f}$, $R^{10g}$, $R^{10h}$ is independently selected from:

hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, $—NO_2$, $—NH_2$, $=O$, $=S$, $—O—C_{1-6}$ alkyl, $—S—C_{1-6}$ alkyl, $—N(C_{1-6}\ alkyl)_2$, $—NH(C_{1-6}\ alkyl)$, $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, $—NO_2$, $—NH_2$, $=O$, $=S$, $—O—C_{1-6}$ alkyl, $—S—C_{1-6}$ alkyl, $—N(C_{1-6}\ alkyl)_2$, $—NH(C_{1-6}\ alkyl)$, $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In some embodiments, the compound of Formula (II) is of Formula (II-X):

(II-X)

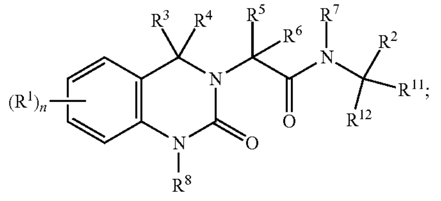

or a salt thereof, wherein:

n is 1, 2, 3, or 4;

each $R^1$ is independently selected from:

halogen, —$NO_2$, —CN, —$OR^{10a}$, —$SR^{10a}$, —$N(R^{10a})_2$, —$C(O)R^{10a}$;

$C_{1-6}$ alkyl, optionally substituted with one or more substituents independently selected from halogen, —$OR^{10a}$, —$SR^{10a}$, —$N(R^{10a})_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, =O, —CN, and $C_{1-6}$ alkyl, wherein each $C_{1-6}$ alkyl is optionally substituted with one or more $R^{9a}$;

$R^2$ is selected from:

$C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{1-6}$ alkyl, $C_{2-6}$ alkenyl, $C_{2-6}$ alkynyl, $C_{3-10}$ carbocycle and 3- to 10-membered heterocycle, wherein each $C_{1-6}$ alkyl, $C_{2-6}$ alkenyl, $C_{2-6}$ alkynyl, $C_{3-10}$ carbocycle, and 3- to 10-membered heterocycle is optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b\prime}$;

$R^3$ and $R^4$ are each independently selected from:

hydrogen, halogen, —OH, —OMe —SH, —$NH_2$, —$NO_2$, and —CN; and $C_{1-6}$ alkyl optionally substituted with one or more substituents independently selected from halogen, OH, —OMe —SH, —$NH_2$, —$NO_2$, and —CN; or;

$R^5$ and $R^6$ are each independently selected from:

hydrogen, halogen, —OH, —OMe —SH, —$NH_2$, —$NO_2$, and —CN; and $C_{1-6}$ alkyl optionally substituted with one or more substituents independently selected from halogen, —OH, —OMe —SH, —$NH_2$, —$NO_2$, and —CN;

$R^7$ is selected from:

hydrogen and $C_{1-6}$ alkyl optionally substituted with one or more substituents independently selected from halogen, —OH, —OMe —SH, —$NH_2$, —$NO_2$, and —CN;

$R^8$ is selected from:

hydrogen and $C_{1-6}$ alkyl optionally substituted with one or more substituents independently selected from halogen, —OH, —OMe —SH, —$NH_2$, —$NO_2$, and —CN;

$R^{11}$ is selected from:

halogen, —OH, —OMe —SH, —$NH_2$, —$NO_2$, and —CN; and $C_{1-6}$ alkyl optionally substituted with one or more substituents independently selected from halogen, —OH, —OMe —SH, —$NH_2$, —$NO_2$, and —CN;

$R^{12}$ is selected from hydrogen;

$C_{1-6}$ alkyl optionally substituted with one or more substituents independently selected from the group consisting of halogen, —OH, —OMe —SH, —$NH_2$, —$NO_2$, and —CN; and $C_{3-6}$ carbocycle and 3- to 10-membered heterocycle each optionally substituted with one or more substituents independently selected from the group consisting of halogen, —OH, —OMe —SH, —$NH_2$, —$NO_2$, and —CN; or $R^{12}$, $R^{11}$, and $R^2$ come together to form a $C_5$-$C_{10}$ bridged ring system;

each $R^{9a}$ is independently selected from halogen, —$OR^{10a}$, —CN, and $C_{1-6}$ alkyl;

each $R^{9b}$ is independently selected from halogen, —$OR^{10b}$, —CN, and $C_{1-6}$ alkyl;

each $R^{9b\prime}$ is independently selected from halogen, —$OR^{10b}$, —CN, and $C_{1-6}$ alkyl;

each $R^{10a}$, $R^{10b}$, is independently selected from hydrogen, $C_{1-6}$ alkyl, $C_{3-10}$ carbocycle, and 3- to 10-membered heterocycle.

In some embodiments, the compound of Formula II is of Formula (II-Y) Formula (II-Y):

(II-Y)

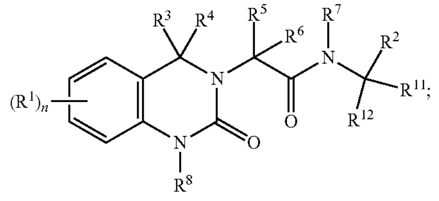

or a salt thereof, wherein:

n is 1 or 2;

each $R^1$ is independently selected from:

halogen, —CN, —$OR^{10a}$, —$SR^{10a}$, —$N(R^{10a})_2$; and $C_{1-6}$ alkyl, optionally substituted with one or more substituents independently selected from halogen, —$OR^{10a}$, —$SR^{10a}$, —$N(R^{10a})_2$, =O, and —CN;

$R^2$ is selected from:

$C_{3-10}$ carbocycle and 3- to 10-membered heterocycle, each of which is optionally substituted with one or more substituents independently selected from halogen, —$OR^{10b}$, =O, —CN, $C_{1-6}$ alkyl, $C_{2-6}$ alkynyl, $C_{3-10}$ carbocycle and 3- to 10-membered heterocycle, wherein each $C_{1-6}$ alkyl, $C_{2-6}$ alkynyl, $C_{3-10}$ carbocycle, and 3- to 10-membered heterocycle is optionally substituted with one or more $R^{9b}$;

$R^3$ and $R^4$ are each independently selected from:

hydrogen, halogen, —OH, —OMe- and —CN; and $C_{1-3}$ alkyl optionally substituted with one or more substituents independently selected from halogen, OH, —OMe and —CN;

$R^5$ and $R^6$ are each independently selected from:

hydrogen, halogen, —OH, —OMe- and —CN; and $C_{1-3}$ alkyl optionally substituted with one or more substituents independently selected from halogen, —OH, —OMe and —CN;

$R^7$ is selected from:

hydrogen and $C_{1-3}$ alkyl optionally substituted with one or more substituents independently selected from halogen, —OH, —OMe and —CN;

$R^8$ is selected from:

hydrogen and $C_{1-3}$ alkyl optionally substituted with one or more substituents independently selected from halogen, —OH, —OMe and —CN;

$R^{11}$ is selected from:

$C_{1-3}$ alkyl optionally substituted with one or more substituents independently selected from halogen, —OH, —OMe and —CN;

$R^{12}$ is selected from hydrogen, $C_{1-3}$ alkyl, $C_{3-6}$ carbocycle and 3- to 10-membered; or $R^{12}$, $R^{11}$, and $R^2$ come together to form a $C_5$-$C_{10}$ bridged ring system;

each $R^{9a}$ is independently selected from halogen, —OH, —OMe, —CN, and $C_{1-3}$ alkyl;

each $R^{9b}$ is independently selected from halogen, —OH, —OMe, —CN, and $C_{1-3}$ alkyl;

each $R^{9b\prime}$ is independently selected from halogen, —OH, —OMe, —CN, and $C_{1-3}$ alkyl;

each $R^{10a}$, $R^{10b}$, is independently selected from hydrogen, $C_{1-6}$ alkyl, $C_{6-10}$ carbocycle, and 5- to 10-membered heterocycle.

In some embodiments, for a compound or salt of Formula (II), n is 0, 1, 2, 3, or 4. In some embodiments, n is 0, 1, 2, or 3. In some embodiments, n is 0, 1, 2, or 4. In some embodiments, n is 0, 1, 3, or 4. In some embodiments, n is 0, 2, 3, or 4. In some embodiments, n is 1, 2, 3, or 4. In some embodiments, n is 0, 1, or 2. In some embodiments, n is 0, 1, or 3. In some embodiments, n is 0, 1, or 4. In some embodiments, n is 0, 2, or 3. In some embodiments, n is 0, 2, or 4. In some embodiments, n is 0, 3, or 4. In some embodiments, n is 1, 2, or 3. In some embodiments, n is 1, 2, or 4. In some embodiments, n is 0 or 1. In some embodiments, n is 0 or 2. In some embodiments, n is 0 or 3. In some embodiments, n is 0 or 4. In some embodiments, n is 1 or 2. In some embodiments, n is 1 or 3. In some embodiments, n is 1 or 4. In some embodiments, n is 2 or 3. In some embodiments, n is 2 or 4. In some embodiments, n is 3 or 4. In some embodiments, n is 0. In some embodiments, n is 1. In some embodiments, n is 2. In some embodiments, n is 3. In some embodiments, n is 4. In some embodiments, n is 0. In some embodiments, n is 1 or 2. In some embodiments, n is 1. In some embodiments, n is 2. In some embodiments, n is 0 or 1. In some embodiments, n is 0 or 2.

In some embodiments, for a compound or salt of Formula (II), each $R^1$ is independently selected from:

halogen, —$NO_2$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, and —$S(O)_2R^{10a}$;

$C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, =O, =S, =$N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$;

In some embodiments, each $R^1$ is independently selected from: halogen, —$NO_2$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, and —$OC(O)R^{10a}$; $C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, $N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$NO_2$, =O, —CN, $C_{1-6}$ alkyl, and $C_{2-6}$ alkenyl, wherein $C_{1-6}$ alkyl, and $C_{2-6}$ alkenyl, are each optionally substituted with one or more $R^{9a}$.

In some embodiments, each $R^1$ is independently selected from: halogen, —$NO_2$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, and —$OC(O)R^{10a}$; $C_{1-6}$ alkyl and $C_{2-6}$ alkenyl each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$NO_2$, =O, —CN, $C_{1-6}$ alkyl, and $C_{2-6}$ alkenyl, wherein $C_{1-6}$ alkyl, and $C_{2-6}$ alkenyl, are each optionally substituted with one or more $R^{9a}$. In some embodiments, each $R^1$ is independently selected from: halogen, —$NO_2$, —CN, —$OR^{10a}$, —$SR^{10a}$, —$N(R^{10a})_2$, and —$C(O)R^{10a}$; $C_{1-6}$ alkyl and $C_{2-6}$ alkenyl each of which is optionally substituted with one or more substituents independently selected from halogen, —$OR^{10a}$, —$SR^{10a}$, —$N(R^{10a})_2$, —$C(O)R^{10a}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$NO_2$, =O, —CN, $C_{1-6}$ alkyl, and $C_{2-6}$ alkenyl, wherein $C_{1-6}$ alkyl, and $C_{2-6}$ alkenyl, are each optionally substituted with one or more $R^{9a}$. In some embodiments, each $R^1$ is independently selected from: halogen, —$NO_2$, —CN, —$OR^{10a}$, —$SR^{10a}$, —$N(R^{10a})_2$, and —C(O)$R^{10a}$; $C_{1-6}$ alkyl and $C_{2-6}$ alkenyl each of which is optionally substituted with one or more substituents independently selected from halogen, —$OR^{10a}$, —$SR^{10a}$, —$N(R^{10a})_2$, —C(O)$R^{10a}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle. In some embodiments, each $R^1$ is independently selected from: halogen, —$NO_2$, —CN, —$OR^{10a}$, —$SR^{10a}$, —$N(R^{10a})_2$, and —C(O)$R^{10a}$; and $C_{1-6}$ alkyl optionally substituted with one or more substituents independently selected from halogen, —$OR^{10a}$, —$SR^{10a}$, —$N(R^{10a})_2$, —C(O)$R^{10a}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$. In some embodiments, each $R^1$ is independently selected from: halogen, —$NO_2$, —CN, —$OR^{10a}$, —$SR^{10a}$, —$N(R^{10a})_2$, and —C(O)$R^{10a}$; and $C_{1-6}$ alkyl optionally substituted with one or more substituents independently selected from halogen, —$OR^{10a}$, —$SR^{10a}$, —$N(R^{10a})_2$, —C(O)$R^{10a}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$. In some embodiments, each $R^1$ is independently selected from: halogen, —$NO_2$, —CN, —$OR^{10a}$, —$SR^{10a}$, —$N(R^{10a})_2$, and —C(O)$R^{10a}$; and $C_{1-6}$ alkyl optionally substituted with one or more substituents independently selected from halogen, —$OR^{10a}$, —$SR^{10a}$, —$N(R^{10a})_2$, —C(O)$R^{10a}$, —$NO_2$, =O, and —CN. In some embodiments, each $R^1$ is independently selected from: halogen, —$NO_2$, —CN, —$OR^{10a}$, —$SR^{10a}$, —$N(R^{10a})_2$, and —C(O)$R^{10a}$; and $C_{1-6}$ alkyl. In some embodiments, each $R^1$ is independently selected from: halogen, —$NO_2$, —CN, —$OR^{10a}$, —$SR^{10a}$, and —$N(R^{10a})_2$. In some embodiments, each $R^1$ is independently selected from: halogen and —CN. In some embodiments, each $R^1$ is independently selected from: fluoro, bromo, and —CN. In some embodiments, each $R^1$ is independently selected from fluoro and CN. In some embodiments, each $R^1$ is independently selected from fluoro and bromo. In some embodiments, each $R^1$ is independently selected from bromo and CN. some embodiments, each $R^1$ is independently selected from fluoro. In some embodiments, each $R^1$ is independently selected from bromo. In some embodiments, each $R^1$ is independently selected from CN. In some embodiments, each $R^1$ is independently selected from: halogen, —CN, —$OR^{10a}$, and $C_{1-6}$ alkyl. In some embodiments, each $R^1$ is independently selected from: halogen, —CN, —$OR^{10a}$, and $C_{1-6}$ alkyl. In some embodiments, each $R^1$ is independently selected from: —F, —Br, —Cl, —CN, —OH, and —$CH_3$. In some embodiments, each $R^1$ is independently selected from: —F, —Br, —CN, —OH, and —$CH_3$.

In some embodiments, n is 2, and each $R^1$ is independently selected from —F, —Cl, and —CN. In some embodiments, n is 2, and each $R^1$ is independently selected from —F, and —CN. In some embodiments, n is 2, and each $R^1$ is independently selected from —F. In some embodiments, an $R^1$ ortho to the carbon bearing $R^3$ and $R^4$ is —F. In some embodiments, an $R^1$ meta to the carbon bearing $R^3$ and $R^4$ is —F. In some embodiments, an $R^1$ para to the carbon bearing $R^3$ and $R^4$ is —F. In some embodiments, an $R^1$ ortho to the carbon bearing $R^3$ and $R^4$ is —F, and an $R^1$ meta to the carbon bearing $R^3$ and $R^4$ is —F. In some embodiments, n is 2, and an $R^1$ ortho to the carbon bearing $R^3$ and $R^4$ is —F, and an $R^1$ meta to the carbon bearing $R^3$ and $R^4$ is —F.

In some embodiments, the compound of formula (II) is selected from Formula (II-A), (II-A)

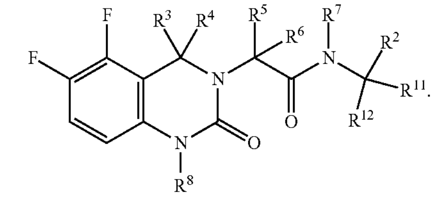

In some embodiments, the compound of formula (II) is selected from Formula (II-B)

(II-B)

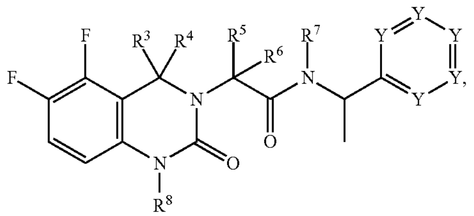

wherein each Y is selected from —($CR^{9b}$)— and N.

In some embodiments, the compound of formula (II) is selected from Formula (II-C), (II-C)

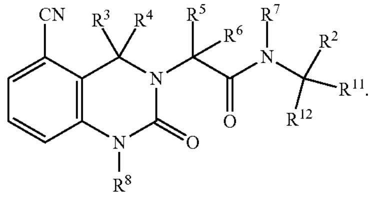

In some embodiments, the compound of formula (II) is selected from Formula (II-D)

(II-D)

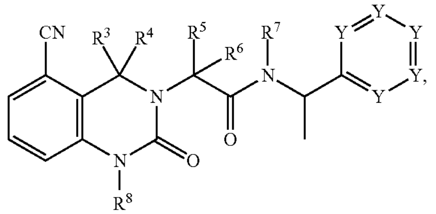

wherein each Y is selected from —($CR^{9b}$)— and N.

In some embodiments, the compound of formula (II) is selected from Formula (II-E), (II-E)

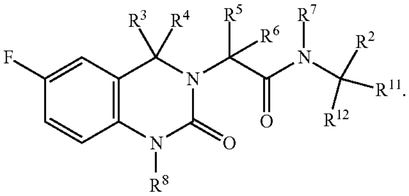

In some embodiments, the compound of formula (II) is selected from Formula (II-F)

(II-F)

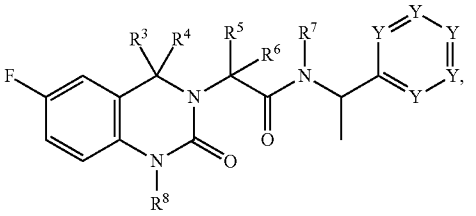

wherein each Y is selected from —($CR^{9b}$)— and N.

In some embodiments, for a compound or salt of Formula (II), $R^2$ is selected from:

halogen, —$NO_2$, —CN, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, and —$S(O)_2R^{10b}$;

$C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b\prime}$.

In some embodiments, $R^2$ together with $R^{11}$ and $R^{12}$ form a bridged 5- to 20-membered heterocycle or bridged $C_{5-20}$ carbocycle optionally substituted with one or more $R^{9b\prime}$. In some embodiments, $R^2$ together with $R^{11}$ and $R^{12}$ form a bridged 5- to 18-membered heterocycle or bridged $C_{5-18}$ carbocycle optionally substituted with one or more $R^{9b\prime}$. In some embodiments, $R^2$ together with $R^{11}$ and $R^{12}$ form a bridged 5- to 15-membered heterocycle or bridged $C_{5-15}$ carbocycle optionally substituted with one or more $R^{9b\prime}$. In some embodiments, $R^2$ together with $R^{11}$ and $R^{12}$ form a bridged 5- to 12-membered heterocycle or bridged $C_{5-12}$ carbocycle optionally substituted with one or more $R^{9b\prime}$. In some embodiments, $R^2$ together with $R^{11}$ and $R^{12}$ form a bridged 5- to 10-membered heterocycle or bridged $C_{5-10}$ carbocycle optionally substituted with one or more $R^{9b\prime}$.

In some embodiments, $R^2$ is selected from: halogen, —$NO_2$, —CN, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, and —$OC(O)R^{10b}$; $C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b\prime}$.

In some embodiments, for a compound or salt of Formula (II), $R^2$ is selected from: halogen, —$NO_2$, —CN, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, and —$OC(O)R^{10b}$; $C_{1-6}$ alkyl and $C_{2-6}$ alkenyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b\prime}$. In some embodiments, $R^2$ is selected from: halogen, —$NO_2$, —CN, —$OR^{10b}$, —$SR^{10b}$, and —$N(R^{10b})_2$; $C_{1-6}$ alkyl and $C_{2-6}$ alkenyl, each of which is optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. In some embodiments, $R^2$ is selected from: halogen, $—NO_2$, —CN, $—OR^{10b}$, $—SR^{10b}$, and $—N(R^{10b})_2$; $C_{1-6}$ alkyl, optionally substituted with one or more substituents independently selected from halogen, $—OR^{10b}$, $—SR^{10b}$, $—N(R^{10b})_2$, $—C(O)R^{10b}$, $—NO_2$, =O, —CN; and $C_{3-10}$ carbocycle and 3- to 10-membered heterocycle, each of which is optionally substituted with one or more substituents independently selected from halogen, $—OR^{10b}$, $—SR^{10b}$, $—N(R^{10b})_2$, $—C(O)R^{10b}$, $—NO_2$, =O, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. In some embodiments, $R^2$ is selected from: halogen, $—NO_2$, —CN, $—OR^{10b}$, $—SR^{10b}$, and $—N(R^{10b})_2$; $C_{1-6}$ alkyl, optionally substituted with one or more $—OR^{10b}$; and $C_{3-10}$ carbocycle and 3- to 10-membered heterocycle, each of which is optionally substituted with one or more substituents independently selected from halogen, $—OR^{10b}$, $—SR^{10b}$, $—N(R^{10b})_2$, $—C(O)R^{10b}$, $—NO_2$, =O, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$.

In some embodiments, $R^2$ is selected from: halogen, $—NO_2$, —CN, $—OR^{10b}$, $—SR^{10b}$, and $—N(R^{10b})_2$; $C_{1-6}$ alkyl; and $C_{3-10}$ carbocycle and 3- to 10-membered heterocycle, each of which is optionally substituted with one or more substituents independently selected from halogen, $—OR^{10b}$, $—SR^{10b}$, $—N(R^{10b})_2$, $—C(O)R^{10b}$, $—NO_2$, =O, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. In some embodiments, $R^2$ is selected from: $C_{3-10}$ carbocycle and 3- to 10-membered heterocycle, each of which is optionally substituted with one or more substituents independently selected from halogen, $—OR^{10b}$, $—SR^{10b}$, $—N(R^{10b})_2$, $—C(O)R^{10b}$, $—NO_2$, =O, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$.

In some embodiments, $R^2$ is selected from: $C_{3-10}$ carbocycle and 3- to 10-membered heterocycle, each of which is optionally substituted with one or more substituents independently selected from halogen, $—OR^{10b}$, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. In some embodiments, $R^2$ is selected from: $C_{3-10}$ carbocycle and 3- to 10-membered heterocycle, each of which is optionally substituted with one or more substituents independently selected from halogen, $—OR^{10b}$, —CN, and $C_{1-6}$ alkyl, wherein $C_{1-6}$ alkyl is optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. In some embodiments, $R^2$ is selected from: $C_{3-10}$ carbocycle and 3- to 10-membered heterocycle, each of which is optionally substituted with one or more substituents independently selected from fluoro, bromo, $—OR^{10b}$, —CN, and $C_{1-6}$ alkyl, wherein $C_{1-6}$ alkyl is optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. In some embodiments, $R^2$ is selected from: $C_{3-10}$ carbocycle and 3- to 10-membered heterocycle, each of which is optionally substituted with one or more substituents independently selected from fluoro, bromo, —OMe, —CN, and $C_{1-6}$ alkyl, wherein $C_{1-6}$ alkyl is optionally substituted with one or more $R^{9b}$. In some embodiments, $R^2$ is selected from: $C_{3-10}$ carbocycle and 3- to 10-membered heterocycle, each of which is optionally substituted with one or more substituents independently selected from fluoro, bromo, —OMe, —CN, and $C_{1-6}$ alkyl, wherein $C_{1-6}$ alkyl is optionally substituted with one or more fluoro. In some embodiments, $R^2$ is selected from: $C_{3-10}$ carbocycle and 3- to 10-membered heterocycle, each of which is optionally substituted with one or more substituents independently selected from fluoro, bromo, —OMe, —CN, and $C_1$ alkyl, wherein $C_1$ alkyl is optionally substituted with one or more fluoro.

In some embodiments, $R^2$ is selected from pyrazinyl (e.g., 2-pyrazinyl, 3-pyrazinyl), pyridazinyl (e.g., 3-, 4-, 5-, or 6-pyridazine), phenyl, pyridyl (e.g., 2-, 3-, or 4-pyridyl), and pyrimidyl (e.g., 2-, 4-, 5- or 6-pyrimidyl), wherein each pyrazinyl, pyridizyl, phenyl, pyridyl, and pyrimidyl is optionally substituted with one or more substituents independently selected from fluoro, bromo, —OMe, —CN, and $C_1$ alkyl, wherein each $C_1$ alkyl is optionally substituted with one or more fluoro. In some embodiments, $R^2$ is selected from phenyl, pyridyl, and pyrimidyl, wherein each phenyl, pyridyl, and pyrimidyl is optionally substituted with one or more substituents independently selected from fluoro, bromo, —OMe, —CN, and $C_1$ alkyl, wherein each $C_1$ alkyl is optionally substituted with one or more fluoro. In some embodiments, $R^2$ is selected from phenyl, 2-pyridyl, 2-pyrimidyl, and 6-pyrimidyl, wherein each phenyl, 2-pyridyl, 2-pyrimidyl, and 6-pyrimidyl is optionally substituted with one or more substituents independently selected from fluoro, bromo, —OMe, —CN, and $C_1$ alkyl, wherein each $C_1$ alkyl is optionally substituted with one or more fluoro. In some embodiments, $R^2$ is selected from: $C_{3-10}$ carbocycle and 3- to 10-membered heterocycle, each of which is optionally substituted with one or more substituents independently selected from halogen, $—OR^{10b}$, =O, —CN, $C_{1-6}$ alkyl, $C_{2-6}$ alkynyl, $C_{3-10}$ carbocycle and 3- to 10-membered heterocycle. In some embodiments, $R^2$ is selected from: $C_{3-10}$ carbocycle and 3- to 10-membered heterocycle, each of which is optionally substituted with one or more substituents independently selected from —F, —Cl, —Br, —CN, —OH, $—OCH_3$, $—CH_3$, $—CF_3$, $—C(O)NH_2$,

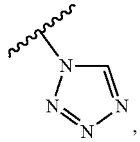,
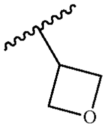, and —CCH.
In some embodiments, $R^2$ is selected from
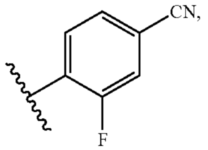
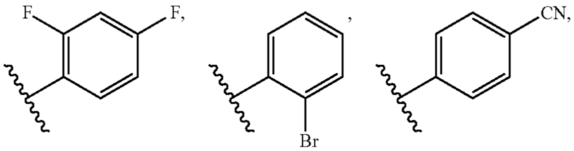
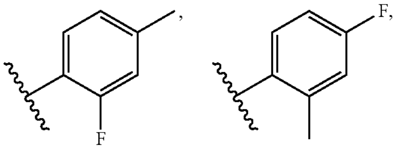
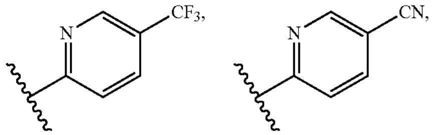
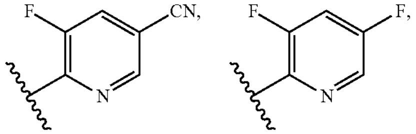
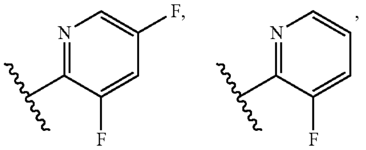
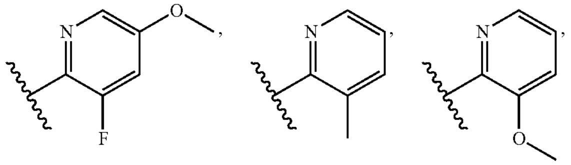
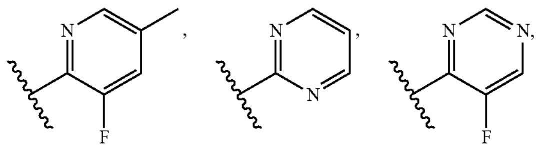
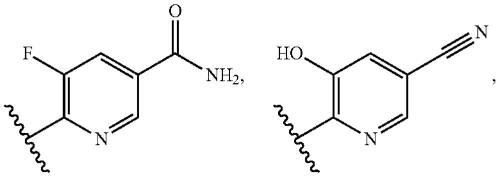
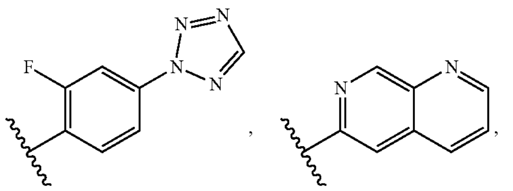
-continued
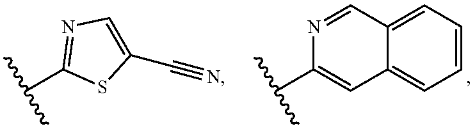
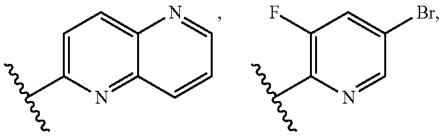
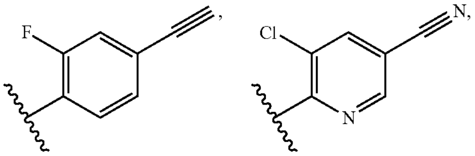
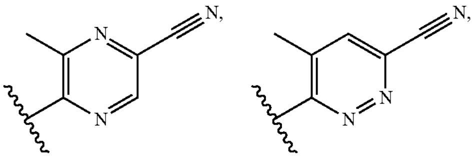
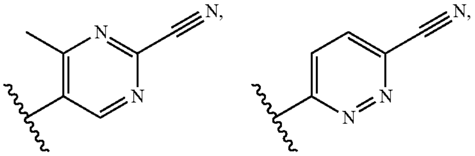
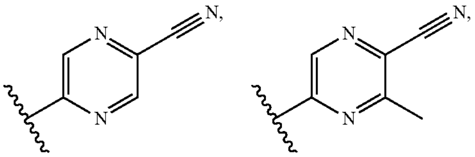
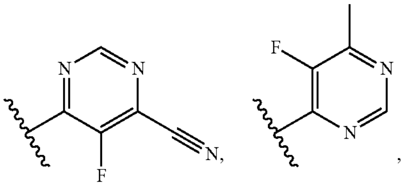
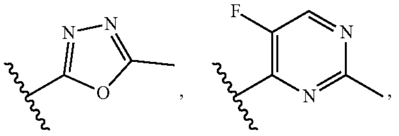
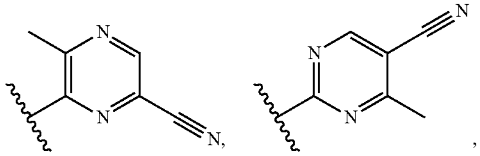
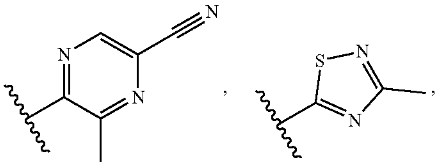
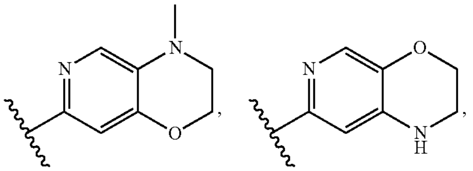 and -continued

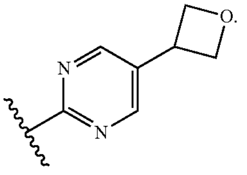

In some embodiments, $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. In some embodiments, wherein $R^2$ together with $R^{11}$ form a 3- to 10-membered heterocycle or $C_{3-10}$ carbocycle, and wherein the 3- to 10-membered heterocycle or $C_{3-10}$ carbocycle is optionally substituted with one or more fluoro or CN. In some embodiments, wherein $R^2$ together with $R^{11}$ form a $C_{3-10}$ carbocycle or 3- to 10-membered heterocycle selected from dihydrobenzofuran and indene, each of which is optionally substituted with one or more substituents independently selected from fluoro and CN.

In some embodiments, $R^2$ together with $R^{11}$ is selected from

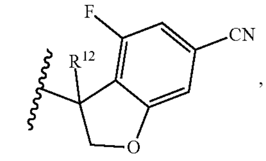
,
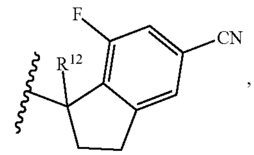
,
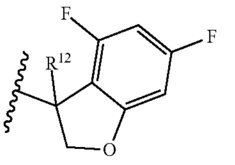
,
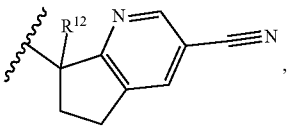
,
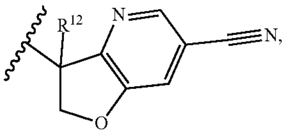
,
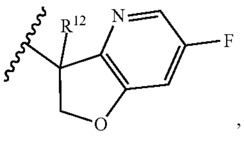
, and
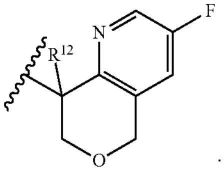
.

In some embodiments, $R^{12}$ is H and $R^2$ together with $R^{11}$ is selected from

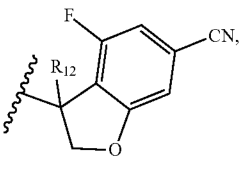

and

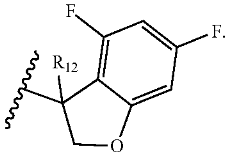

In some embodiments, $R^{12}$ is H and $R^2$ together with $R^{11}$ is selected from

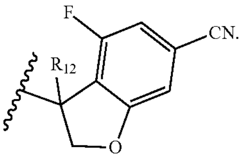

In some embodiments, $R^2$ and $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. In some embodiments, $R^2$ and $R^{11}$ form a 3- to 10-membered heterocycle or $C_{3-10}$ carbocycle, wherein the 3- to 10-membered heterocycle or $C_{3-10}$ carbocycle is optionally substituted with one or more substituents selected from halogen and CN. In some embodiments, $R^2$ and $R^{11}$ form a 3- to 10-membered heterocycle or $C_{3-10}$ carbocycle, wherein the 3- to 10-membered heterocycle or $C_{3-10}$ carbocycle is optionally substituted with one or more substituents selected from fluorine and CN. In some embodiments, $R^2$ and $R^{11}$ form a 3- to 10-membered heterocycle or $C_{3-10}$ carbocycle, wherein the 3- to 10-membered heterocycle or $C_{3-10}$ carbocycle is optionally substituted with one or more substituents selected from halogen. In some embodiments, $R^2$ and $R^{11}$ form a 3- to 10-membered heterocycle or $C_{3-10}$ carbocycle, wherein the 3- to 10-membered heterocycle or $C_{3-10}$ carbocycle is optionally substituted with one or more substituents selected from fluorine. In some embodiments, $R^2$ and $R^{11}$ form a 3- to 10-membered heterocycle or $C_{3-10}$ carbocycle, wherein the 3- to 10-membered heterocycle or $C_{3-10}$ carbocycle is optionally substituted with one or more substituents selected from CN.

In some embodiments, $R^2$ is selected from: $C_{3-10}$ carbocycle and 3- to 10-membered heterocycle, each of which is optionally substituted with one or more substituents independently selected from fluoro, bromo, —OMe, —CN, and $C_1$ alkyl, wherein $C_1$ alkyl is optionally substituted with one or more fluoro. In some embodiments, $R^2$ is selected from: $C_{3-10}$ carbocycle and 3- to 10-membered heterocycle, each of which is optionally substituted with one or more substituents independently selected from fluoro, bromo, —CN, and $C_1$ alkyl. In some embodiments, $R^2$ is selected from: $C_{3-10}$ carbocycle and 3- to 10-membered heterocycle, each of which is optionally substituted with one or more substituents independently selected from fluoro, bromo, —CN, and $C_1$ alkyl.

In some embodiments, $R^2$ is a $C_{3-10}$ carbocycle optionally substituted with one or more substituents independently selected from fluoro, bromo, —CN, and $C_1$ alkyl. In some embodiments, $R^2$ is a $C_{3-10}$ carbocycle optionally substituted with one or more substituents independently selected from fluoro, —CN, and $C_1$ alkyl. In some embodiments, $R^2$ is a $C_{3-10}$ carbocycle optionally substituted with one or more substituents independently selected from fluoro and —CN.

In some embodiments, $R^2$ is a $C_{3-10}$ carbocycle optionally substituted with one or more substituents independently selected from fluoro. In some embodiments, $R^2$ is a $C_{3-10}$ carbocycle optionally substituted with one or more substituents independently selected from chloro.

In some embodiments, for a compound or salt of Formula (II), $R^3$ and $R^4$ are each independently selected from:

hydrogen, halogen, —$OR^{10c}$, —$SR^{10c}$, —$N(R^{10c})_2$, —$NO_2$, and —CN; and $C_{1-6}$ alkyl optionally substituted with one or more substituents independently selected from halogen, —$OR^{10c}$, —$SR^{10c}$, —$N(R^{10c})_2$, —$NO_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$.

In some embodiments, $R^3$ and $R^4$ are each independently selected from: hydrogen; and $C_{1-6}$ alkyl optionally substituted with one or more substituents independently selected from halogen; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$. In some embodiments, $R^3$ and $R^4$ are each independently selected from: hydrogen; and $C_{1-6}$ alkyl optionally substituted with one or more substituents independently selected from halogen.

In some embodiments, $R^3$ and $R^4$ are each independently selected from: hydrogen; and $C_1$ alkyl optionally substituted with one or more substituents independently selected from fluoro.

In some embodiments, $R^3$ and $R^4$ are each independently selected from: hydrogen; and $C_1$ alkyl. In some embodiments, $R^3$ and $R^4$ are each independently selected from: hydrogen. In some embodiments, $R^3$ is selected from: hydrogen. In some embodiments, $R^4$ is selected from: hydrogen. In some embodiments, $R^3$ is —H, and $R^4$ is —OH. In some embodiments, $R^3$ is —OH, and $R^4$ is —H. In some embodiments, $R^3$ is —OH.

In some embodiments, $R^3$ together with $R^4$ form a 3- to 10-membered heterocycle or $C_{3-10}$ carbocycle, the 3- to 10-membered heterocycle or $C_{3-10}$ carbocycle is optionally substituted with one or more $R^{9c}$. In some embodiments, $R^3$ together with $R^4$ form a $C_{3-10}$ carbocycle, the $C_{3-10}$ carbocycle is optionally substituted with one or more $R^{9c}$. In some embodiments, $R^3$ together with $R^4$ form a $C_{3-10}$ carbocycle. In some embodiments, $R^3$ together with $R^4$ form a $C_{3-10}$ carbocycle selected from cyclopropyl, cyclobutyl, cyclopentyl, and cyclohexyl. In some embodiments, $R^3$ together with $R^4$ form a ring selected from

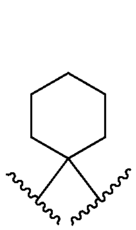,
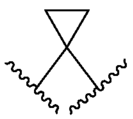,
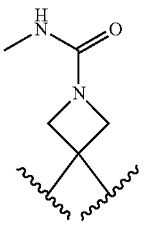, and
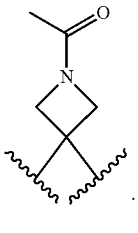.

In some embodiments, for a compound or salt of Formula (II), $R^5$ and $R^6$ are each independently selected from:

hydrogen, halogen, —$OR^{10d}$, —$SR^{10d}$, —$N(R^{10d})_2$, —$NO_2$, and —CN; and $C_{1-6}$ alkyl optionally substituted with one or more substituents independently selected from halogen, —$OR^{10d}$, $SR^{10d}$, —$N(R^{10d})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9d}$.

In some embodiments, $R^5$ and $R^6$ are each independently selected from: hydrogen, halogen, —$OR^{10d}$, —$SR^{10d}$, —$N(R^{10d})_2$, —$NO_2$, and —CN; and $C_{1-6}$ alkyl; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9d}$. In some embodiments, $R^5$ and $R^6$ are each independently selected from: hydrogen, halogen, —$OR^{10d}$, —$SR^{10d}$, —$N(R^{10d})_2$, —$NO_2$, and —CN; and $C_{1-6}$ alkyl; or $R^5$ together with $R^6$ form a 3- to 10-membered heterocycle or $C_{3-10}$ carbocycle. In some embodiments, $R^5$ and $R^6$ are each independently selected from: hydrogen, halogen, —$OR^{10d}$, —$SR^{10d}$, —$N(R^{10d})_2$, —$NO_2$, and —CN; and $C_{1-6}$ alkyl. In some embodiments, $R^5$ and $R^6$ are each independently selected from: hydrogen, halogen, —$OR^{10d}$, —$SR^{10d}$, —$N(R^{10d})_2$, —$NO_2$, and —CN. In some embodiments, $R^5$ and $R^6$ are hydrogen. In some embodiments, $R^5$ is hydrogen. In some embodiments, $R^6$ is hydrogen. In some embodiments, $R^5$ and $R^6$ are each independently selected from: hydrogen; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9d}$. In some embodiments, $R^5$ and $R^6$ are each independently selected from: hydrogen; or $R^5$ together with $R^6$ form a 3- to 10-membered heterocycle or $C_{3-10}$ carbocycle. In some embodiments, $R^5$ and $R^6$ are each independently selected from: hydrogen and —$CH_3$, or $R^5$ and $R^6$ together form a cyclopropyl.

In some embodiments, the compound or salt of Formula (II) is a compound or salt of Formula (II-Q):

(II-Q)

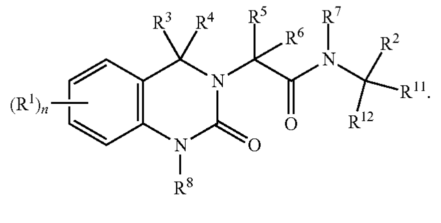

In some embodiments, the compound or salt of formula (II-Q is an activator of skeletal myosin. In some embodiments, the compound or salt of formula (II-Q) is used to treat obesity or to induce weight loss. In some embodiments, for a compound or salt of formula (I-Q), $R^5$ and $R^6$ are each independently selected from: hydrogen, halogen, —$OR^{10c}$, —$SR^{10c}$, —$N(R^{10c})_2$, —$NO_2$, and —CN; $C_{1-10}$ alkyl, optionally substituted with one or more substituents independently selected from halogen, —$OR^{10c}$, —$SR^{10c}$, —$N(R^{10c})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, $—OR^{10c}$, $—SR^{10c}$, $—N(R^{10c})_2$, $—NO_2$, and —CN; and $C_{3-10}$ carbocycle and 3- to 10-membered heterocycle, each of which is optionally substituted with one or more substituents independently selected from halogen, $—OR^{10c}$, $—SR^{10c}$, $—N(R^{10c})_2$, $—NO_2$, and —CN. In some embodiments, $R^5$ is —H, and $R^6$ is selected from: $C_{1-10}$ alkyl, optionally substituted with one or more substituents independently selected from halogen, $—OR^{10c}$, $—SR^{10c}$, $—N(R^{10c})_2$, $—NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, $—OR^{10c}$, $—SR^{10c}$, $—N(R^{10c})_2$, $—NO_2$, and —CN; and $C_{3-10}$ carbocycle and 3- to 10-membered heterocycle, each of which is optionally substituted with one or more substituents independently selected from halogen, $—OR^{10c}$, $—SR^{10c}$, $—N(R^{10c})_2$, $—NO_2$, and —CN. In some embodiments, $R^5$ is —H, and $R^6$ is selected from: $C_{1-10}$ alkyl, optionally substituted with one or more substituents independently selected from halogen, $—OR^{10c}$, $—SR^{10c}$, $—N(R^{10c})_2$, $—NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, $—OR^{10c}$, $—SR^{10c}$, $—N(R^{10c})_2$, $—NO_2$, and —CN. In some embodiments, $R^5$ is —H, and $R^6$ is selected from: $C_{1-6}$ alkyl, optionally substituted with one or more substituents independently selected from halogen, $—OR^{10c}$, $—SR^{10c}$, $—N(R^{10c})_2$, $—NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, $—OR^{10c}$, $—SR^{10c}$, $—N(R^{10c})_2$, $—NO_2$, and —CN. In some embodiments, $R^5$ is —H, and $R^6$ is a branched (e.g., nonlinear, e.g., primary, secondary, or tertiary) $C_{1-6}$ alkyl, optionally substituted with one or more substituents independently selected from halogen, $—OR^{10c}$, $—SR^{10c}$, $—N(R^{10c})_2$, $—NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, $—OR^{10c}$, $—SR^{10c}$, $—N(R^{10b})_2$, $—NO_2$, and —CN. In some embodiments, $R^5$ is —H, and $R^6$ is a methyl, ethyl, n-propyl, i-propyl, n-butyl, s-butyl, i-butyl, t-butyl, n-pentyl, tert-pentyl, neopentyl, isopentyl, sec-pentyl, 3-pentyl, sec-isopentyl, or 2-methylbutyl moiety optionally substituted with one or more substituents independently selected from halogen, $—OR^{10c}$, $—SR^{10c}$, $—N(R^{10c})_2$, $—NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, $—OR^{10c}$, $—SR^{10c}$, $—N(R^{10c})_2$, $—NO_2$, and —CN. In some embodiments, $R^5$ is —H, and $R^6$ is a methyl, ethyl, n-propyl, i-propyl, n-butyl, s-butyl, i-butyl, t-butyl, n-pentyl, tert-pentyl, neopentyl, isopentyl, sec-pentyl, 3-pentyl, sec-isopentyl, or 2-methylbutyl moiety optionally substituted with one or more substituents independently selected from $C_{3-10}$ carbocycle, wherein each $C_{3-10}$ carbocycle is optionally substituted with one or more substituents independently selected from halogen and —CN. In some embodiments, $R^5$ is —H, and $R^6$ is a methyl, ethyl, n-propyl, i-propyl, n-butyl, s-butyl, i-butyl, t-butyl, n-pentyl, tert-pentyl, neopentyl, isopentyl, sec-pentyl, 3-pentyl, sec-isopentyl, or 2-methylbutyl moiety optionally substituted with one or more substituents independently selected from $C_{3-10}$ carbocycle. In some embodiments, $R^5$ is —H, and $R^6$ is a n-propyl, i-propyl, n-butyl, s-butyl, i-butyl, t-butyl, n-pentyl, tert-pentyl, neopentyl, isopentyl, sec-pentyl, 3-pentyl, sec-isopentyl, or 2-methylbutyl moiety.

In some embodiments, for a compound or salt of Formula (II), $R^7$ is selected from: hydrogen and $C_{1-6}$ alkyl optionally substituted with one or more substituents independently selected from halogen, $—OR^{10e}$, $—SR^{10e}$, $—N(R^{10e})_2$, $—NO_2$, and —CN. In some embodiments, $R^7$ is selected from: hydrogen, and $C_{1-3}$ alkyl. In some embodiments, $R^7$ is selected from: hydrogen.

In some embodiments, for a compound or salt of formula (II), $R^8$ is selected from: hydrogen and $C_{1-6}$ alkyl optionally substituted with one or more substituents independently selected from halogen, $—OR^{10f}$, $—SR^{10f}$, $—N(R^{10f})_2$, $—NO_2$, and —CN. In some embodiments, $R^8$ is selected from: hydrogen and $C_{1-6}$ alkyl optionally substituted with one or more substituents independently selected from halogen, and —CN. In some embodiments, $R^8$ is selected from: hydrogen and $C_{1-6}$ alkyl optionally substituted with one or more substituents independently selected from fluoro and —CN. In some embodiments, $R^8$ is selected from: hydrogen and $C_{1-3}$ alkyl. In some embodiments, for a compound or salt of Formula (II), $R^8$ is selected from: hydrogen and $C_1$ alkyl. In some embodiments, $R^8$ is selected from: hydrogen.

In some embodiments, for a compound or salt of Formula (II), $R^{11}$ is selected from:

halogen, $—NO_2$, —CN, $—OR^{10g}$, $—SR^{10g}$, $—N(R^{10g})_2$, $—C(O)R^{10g}$, $—C(O)N(R^{10g})_2$, $—N(R^{10g})C(O)R^{10g}$, $—N(R^{10g})C(O)N(R^{10g})_2$, $—OC(O)N(R^{10g})_2$, $—N(R^{10g})C(O)OR^{10g}$, $—C(O)OR^{10g}$, $—OC(O)R^{10g}$, $—S(O)R^{10g}$, and $—S(O)_2R^{10g}$; and $C_{1-6}$ alkyl, $C_{2-6}$ alkenyl, and $C_{2-6}$ alkynyl, each of which is optionally substituted with one or more substituents independently selected from halogen, $—OR^{10g}$, $—SR^{10g}$, $—N(R^{10g})_2$, $—C(O)R^{10g}$, $—C(O)N(R^{10g})_2$, $—N(R^{10g})C(O)R^{10g}$, $—C(O)OR^{10g}$, $—OC(O)R^{10g}$, $—N(R^{10g})C(O)N(R^{10g})_2$, $—OC(O)N(R^{10g})_2$, $—N(R^{10g})C(O)OR^{10g}$, $—S(O)R^{10g}$, $—S(O)_2R^{10g}$, $—NO_2$, =S, $=N(R^{10g})$, —CN, $C_{3-10}$ carbocycle and 3- to 10-membered heterocycle, wherein the $C_{3-10}$ carbocycle and 3- to 10-membered heterocycle are each optionally substituted with one or more $R^{9g}$.

In some embodiments, $R^{11}$ is selected from: halogen, $—NO_2$, —CN, $—OR^{10g}$, $—SR^{10g}$, $—N(R^{10g})_2$, $—C(O)R^{10g}$, $—C(O)N(R^{10g})_2$, $—N(R^{10g})C(O)R^{10g}$, $—C(O)OR^{10g}$, and $—OC(O)R^{10g}$; and $C_{1-6}$ alkyl, $C_{2-6}$ alkenyl, and $C_{2-6}$ alkynyl, each of which is optionally substituted with one or more substituents independently selected from halogen, $—OR^{10g}$, $—SR^{10g}$, $—N(R^{10g})_2$, $—C(O)R^{10g}$, $—C(O)N(R^{10g})_2$, $—N(R^{10g})C(O)R^{10g}$, $—C(O)OR^{10g}$, $—OC(O)R^{10g}$, $—NO_2$, =O, —CN, and $C_{3-10}$ carbocycle and 3- to 10-membered heterocycle, wherein the $C_{3-10}$ carbocycle and 3- to 10-membered heterocycle are each optionally substituted with one or more $R^{9g}$. In some embodiments, $R^{11}$ is selected from: halogen, $—NO_2$, —CN, $—OR^{10g}$, $—SR^{10g}$, $—N(R^{10g})_2$, $—C(O)R^{10g}$, $—C(O)N(R^{10g})_2$, $—N(R^{10g})C(O)R^{10g}$, $—C(O)OR^{10g}$, and $—OC(O)R^{10g}$; and $C_{1-6}$ alkyl optionally substituted with one or more substituents independently selected from halogen, $—OR^{10g}$, $—SR^{10g}$, $—N(R^{10g})_2$, $—C(O)R^{10g}$, $—C(O)N(R^{10g})_2$, $—N(R^{10g})C(O)R^{10g}$, $—C(O)OR^{10g}$, $—OC(O)R^{10g}$, $—NO_2$, =O, —CN, and $C_{3-10}$ carbocycle and 3- to 10-membered heterocycle, wherein the $C_{3-10}$ carbocycle and 3- to 10-membered heterocycle are each optionally substituted with one or more $R^{9g}$. In some embodiments, $R^{11}$ is selected from: halogen, $—NO_2$, —CN, $—OR^{10g}$, $—SR^{10g}$, and $—N(R^{10g})_2$; and $C_{1-6}$ alkyl optionally substituted with one or more substituents independently selected from halogen, —$OR^{10g}$, —$SR^{10g}$, —$N(R^{10g})_2$, —$NO_2$, ═O, —CN, and $C_{3-10}$ carbocycle and 3- to 10-membered heterocycle, wherein the $C_{3-10}$ carbocycle and 3- to 10-membered heterocycle are each optionally substituted with one or more $R^{9g}$. In some embodiments, $R^{11}$ is selected from: halogen, —$NO_2$, —CN, —$OR^{10g}$, —$SR^{10g}$, and —$N(R^{10g})_2$; and $C_{1-6}$ alkyl optionally substituted with one or more substituents independently selected from halogen, —$OR^{10g}$, —$SR^{10g}$, —$N(R^{10g})_2$, —$NO_2$, ═O, and —CN. In some embodiments, $R^{11}$ is selected from: $C_{1-6}$ alkyl optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, —$OC(O)R^{10g}$, —$N(R^{10g})C(O)N(R^{10g})_2$, —$OC(O)N(R^{10g})_2$, —$N(R^{10g})C(O)OR^{10g}$, —$S(O)R^{10g}$, —$S(O)_2R^{10g}$, —$NO_2$, ═O, ═S, ═$N(R^{10g})$, —CN, $C_{3-10}$ carbocycle and 3- to 10-membered heterocycle, wherein the $C_{3-10}$ carbocycle and 3- to 10-membered heterocycle are each optionally substituted with one or more $R^{9g}$. In some embodiments, $R^{11}$ is selected from: $C_{1-6}$ alkyl optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, —$OC(O)R^{10g}$, —$NO_2$, ═O, —CN, and $C_{3-10}$ carbocycle and 3- to 10-membered heterocycle, wherein the $C_{3-10}$ carbocycle and 3- to 10-membered heterocycle are each optionally substituted with one or more $R^{9g}$. In some embodiments, $R^{11}$ is selected from: $C_{1-6}$ alkyl optionally substituted with one or more substituents independently selected from halogen, —$OR^{10g}$, —$SR^{10g}$, —$N(R^{10g})_2$, —$C(O)R^{10g}$, —$NO_2$, ═O, —CN, and $C_{3-10}$ carbocycle and 3- to 10-membered heterocycle, wherein the $C_{3-10}$ carbocycle and 3- to 10-membered heterocycle are each optionally substituted with one or more $R^{9g}$. In some embodiments, $R^{11}$ is selected from: $C_{1-6}$ alkyl optionally substituted with one or more substituents independently selected from halogen, —$OR^{10g}$, —$SR^{10g}$, —$N(R^{10g})_2$, —$C(O)R^{10g}$, —$NO_2$, ═O, —CN, and $C_{3-10}$ carbocycle and 3- to 10-membered heterocycle. In some embodiments, $R^{11}$ is selected from: $C_{1-6}$ alkyl optionally substituted with one or more substituents independently selected from halogen, —$OR^{10g}$, —$SR^{10g}$, —$N(R^{10g})_2$, —$C(O)R^{10g}$, —$NO_2$, ═O, and —CN. In some embodiments, $R^{11}$ is selected from: $C_{1-3}$ alkyl optionally substituted with one or more substituents independently selected from halogen and —$OR^{10g}$. In some embodiments, $R^{11}$ is selected from: $C_{1-3}$ alkyl optionally substituted with one or more —$OR^{10g}$. In some embodiments, $R^{11}$ is selected from: $C_{1-3}$ alkyl optionally substituted with one or more —OH.

In some embodiments, for a compound or salt of Formula (II), $R^{12}$ is selected from hydrogen;

$C_{1-6}$ alkyl optionally substituted with one or more substituents independently selected from the group consisting of halogen, CN, OH, $OR^{10h}$, $N(R^{10h})_2$, $NO_2$, $C(O)R^{10h}$ $SR^{10h}$, and $S(O)R^{10h}$; and $C_{3-6}$ carbocycle and 3- to 10-membered heterocycle each optionally substituted with one or more substituents independently selected from the group consisting of halogen, CN, OH, $OR^{10h}$, $N(R^{10h})_2$, $NO_2$, $C(O)R^{10h}$, $SR^{10h}$, and $S(O)R^{10h}$; or $R^{12}$, $R^{11}$, and $R^2$ come together to form a $C_5$-$C_{10}$ bridged ring system.

In some embodiments, $R^{12}$ is selected from hydrogen; $C_{1-6}$ alkyl optionally substituted with one or more substituents independently selected from the group consisting of halogen, CN, OH, $OR^{10h}$, $N(R^{10h})_2$, $NO_2$, $C(O)R^{10h}$, $SR^{10h}$, and $S(O)R^{10h}$; and $C_{3-6}$ carbocycle and 3- to 10-membered heterocycle each optionally substituted with one or more substituents independently selected from the group consisting of halogen, CN, OH, $OR^{10h}$, $N(R^{10h})_2$, $NO_2$, $C(O)R^{10h}$, $SR^{10h}$, and $S(O)R^{10h}$; or $R^{12}$, $R^{11}$, and $R^2$ come together to form a $C_5$-$C_{10}$ bridged ring system. In some embodiments, $R^{12}$ is selected from hydrogen; $C_{1-6}$ alkyl optionally substituted with one or more substituents independently selected from the group consisting of halogen, CN, OH, $OR^{10h}$ $N(R^{10h})_2$, $NO_2$, $C(O)R^{10h}$, $SR^{10h}$, and $S(O)R^{10h}$; and $C_{3-6}$ carbocycle and 3- to 10-membered heterocycle each optionally substituted with one or more substituents independently selected from the group consisting of halogen, CN, OH, $OR^{10h}$, $N(R^{10h})_2$, $NO_2$, $C(O)R^{10h}$, $SR^{10h}$, and $S(O)R^{10h}$. In some embodiments, $R^{12}$ is selected from hydrogen; and $C_{1-6}$ alkyl optionally substituted with one or more substituents independently selected from the group consisting of halogen, CN, OH, $OR^{10h}$, $N(R^{10h})_2$, $NO_2$, $C(O)R^{10h}$, and $SR^{10h}$. In some embodiments, $R^{12}$ is selected from hydrogen; and $C_{1-6}$ alkyl.

In some embodiments, $R^{12}$ is hydrogen. In some embodiments, $R^{12}$ is methyl. In some embodiments, $R^{12}$ is ethyl. In some embodiments, $R^{12}$, $R^{11}$, and $R^2$ come together to form a $C_5$-$C_{10}$ bridged ring system. In some embodiments, $R^{12}$, $R^{11}$, and $R^2$ come together to form a $C_5$-$C_{10}$ bridged ring system selected from [1.1.1]bicyclopentane.

In some embodiments, for a compound or salt of Formula (II), each $R^{9a}$ is independently selected from: halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, ═O, ═S, ═$N(R^{10a})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, ═O, ═S, ═$N(R^{10a})$, and —CN. In some embodiments, each $R^{9a}$ is independently selected from: halogen, —$OR^{10a}$, —$SR^{10a}$, —$N(R^{10a})_2$, —$C(O)R^{10a}$, —$NO_2$, ═O, —CN; and $C_{1-3}$ alkyl, optionally substituted with one or more substituents independently selected from halogen, —$OR^{10a}$, —$SR^{10a}$, —$N(R^{10a})_2$, —$C(O)R^{10a}$, —$NO_2$, ═O, and —CN. In some embodiments, each $R^{9a}$ is independently selected from: halogen, —$NO_2$, ═O, —CN; and $C_{1-3}$ alkyl, optionally substituted with one or more substituents independently selected from halogen, —$NO_2$, ═O, and —CN. In some embodiments, each $R^{9a}$ is independently selected from: halogen and —CN; and $C_{1-3}$ alkyl, optionally substituted with one or more substituents independently selected from halogen, and —CN. In some embodiments, each $R^{9a}$ is independently selected from: fluoro and —CN; and $C_1$ alkyl, optionally substituted with one or more substituents independently selected from fluoro, and —CN. In some embodiments, each $R^{9a}$ is independently selected from: fluoro and —CN; and $C_1$ alkyl. In some embodiments, each $R^{9a}$ is independently selected from: fluoro and —CN. In some embodiments, each $R^{9a}$ is independently selected from: fluoro. In some embodiments, each $R^{9a}$ is independently selected from: —CN.

In some embodiments, for a compound or salt of Formula (II), each $R^{9b}$ is independently selected from:

halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —C(O)OR$^{10b}$, —OC(O)R$^{10b}$, —S(O)R$^{10b}$, —S(O)$_2$R$^{10b}$, —NO$_2$, =O, =S, =N(R$^{10b}$), and —CN; and $C_{1-3}$ alkyl, $C_{2-3}$ alkenyl, and $C_{2-3}$ alkynyl, each of which is optionally substituted with one or more substituents independently selected from halogen, —OR$^{10b}$, —SR$^{10b}$, —N(R$^{10b}$)$_2$, —C(O)R$^{10b}$, —C(O)N(R$^{10b}$)$_2$, —N(R$^{10b}$)C(O)R$^{10b}$, —N(R$^{10b}$)C(O)N(R$^{10b}$)$_2$, —OC(O)N(R$^{10b}$)$_2$, —N(R$^{10b}$)C(O)OR$^{10b}$, —C(O)OR$^{10b}$, —OC(O)R$^{10b}$, —S(O)R$^{10b}$, —S(O)$_2$R$^{10b}$, —NO$_2$, =O, =S, =N(R$^{10b}$), and —CN.

In some embodiments, each R$^{9b}$ is independently selected from: halogen, —OR$^{10b}$, —SR$^{10b}$, —N(R$^{10b}$)$_2$, —C(O)R$^{10b}$, —NO$_2$, =O, —CN; and $C_{1-3}$ alkyl, optionally substituted with one or more substituents independently selected from halogen, —OR$^{10b}$, —SR$^{10b}$, —N(R$^{10b}$)$_2$, —C(O)R$^{10b}$, —NO$_2$, =O, and —CN. In some embodiments, each R$^{9b}$ is independently selected from: halogen, —NO$_2$, =O, —CN; and $C_{1-3}$ alkyl, optionally substituted with one or more substituents independently selected from halogen, —NO$_2$, =O, and —CN. In some embodiments, each R$^{9b}$ is independently selected from: halogen. In some embodiments, each R$^{9b}$ is independently selected from: fluoro. In some embodiments, each R$^{9b}$ is independently selected from: halogen and —CN; and $C_{1-3}$ alkyl, optionally substituted with one or more substituents independently selected from halogen, and —CN. In some embodiments, each R$^{9b}$ is independently selected from: fluoro and —CN; and $C_1$ alkyl, optionally substituted with one or more substituents independently selected from fluoro, and —CN. In some embodiments, each R$^{9b}$ is independently selected from: fluoro and —CN; and $C_1$ alkyl. In some embodiments, each R$^{9b}$ is independently selected from: fluoro and —CN. In some embodiments, each R$^{9b}$ is independently selected from: fluoro. In some embodiments, each R$^{9b}$ is independently selected from: —CN. In some embodiments, each R$^{9b}$ is independently selected from: —F, —Cl, —Br, —CN, —OH, —OCH$_3$, —CH$_3$, —CF$_3$, —C(O)NH$_2$,

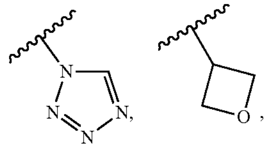 [SMILES: *n1cnnn1 ; *C1COC1 ; ","]

and —CCH. In some embodiments, each R$^{9b}$ is independently selected from: —F, —Cl, —Br, —CN, —OH, —OCH$_3$, —CH$_3$, and —CF$_3$.

In some embodiments, for a compound or salt of Formula (II), each R$^{9b'}$ is independently selected from:

halogen, —OR$^{10b}$, —SR$^{10b}$, —N(R$^{10b}$)$_2$, —C(O)R$^{10b}$, —C(O)N(R$^{10b}$)$_2$, —N(R$^{10b}$)C(O)R$^{10b}$, —N(R$^{10b}$)C(O)N(R$^{10b}$)$_2$, —OC(O)N(R$^{10b}$)$_2$, —N(R$^{10b}$)C(O)OR$^{10b}$, —C(O)OR$^{10b}$, —OC(O)R$^{10b}$, —S(O)R$^{10b}$, —S(O)$_2$R$^{10b}$, —NO$_2$, =O, =S, =N(R$^{10b}$), and —CN; and $C_{1-3}$ alkyl, $C_{2-3}$ alkenyl, and $C_{2-3}$ alkynyl, each of which is optionally substituted with one or more substituents independently selected from halogen, —OR$^{10b}$, —SR$^{10b}$, —N(R$^{10b}$)$_2$, —C(O)R$^{10b}$, —C(O)N(R$^{10b}$)$_2$, —N(R$^{10b}$)C(O)R$^{10b}$, —N(R$^{10b}$)C(O)N(R$^{10b}$)$_2$, —OC(O)N(R$^{10b}$)$_2$, —N(R$^{10b}$)C(O)OR$^{10b}$, —C(O)OR$^{10b}$, —OC(O)R$^{10b}$, —S(O)R$^{10b}$, —S(O)$_2$R$^{10b}$, —NO$_2$, =O, =S, =N(R$^{10b}$), and —CN.

In some embodiments, each R$^{9b'}$ is independently selected from: halogen, —OR$^{10b}$, —SR$^{10b}$, —N(R$^{10b}$)$_2$, —C(O)R$^{10b}$, —NO$_2$, =O, —CN; and $C_{1-3}$ alkyl, optionally substituted with one or more substituents independently selected from halogen, —OR$^{10b}$, —SR$^{10b}$, —N(R$^{10b}$)$_2$, —C(O)R$^{10b}$, —NO$_2$, =O, and —CN. In some embodiments, each R$^{9b'}$ is independently selected from: halogen, —NO$_2$, =O, —CN; and $C_{1-3}$ alkyl, optionally substituted with one or more substituents independently selected from halogen, —NO$_2$, =O, and —CN. In some embodiments, each R$^{9b'}$ is independently selected from: halogen and CN. In some embodiments, each R$^{9b'}$ is independently selected from: fluoro and CN. In some embodiments, each R$^{9b'}$ is independently selected from: fluoro. In some embodiments, each R$^{9b'}$ is independently selected from: fluoro, bromo, and CN. In some embodiments, each R$^{9b'}$ is independently selected from: halogen and —CN; and $C_{1-3}$ alkyl, optionally substituted with one or more substituents independently selected from halogen, and —CN. In some embodiments, each R$^{9b'}$ is independently selected from: fluoro and —CN; and $C_1$ alkyl, optionally substituted with one or more substituents independently selected from fluoro, and —CN. In some embodiments, each R$^{9b'}$ is independently selected from: fluoro and —CN; and $C_1$ alkyl. In some embodiments, each R$^{9b'}$ is independently selected from: fluoro and —CN. In some embodiments, each R$^{9b'}$ is independently selected from: fluoro. In some embodiments, each R$^{9b'}$ is independently selected from: —CN.

In some embodiments, for a compound or salt of Formula (II), each R$^{9c}$ is independently selected from:

halogen, —OR$^{10c}$, —SR$^{10c}$, —N(R$^{10c}$)$_2$, —C(O)R$^{10c}$, —C(O)N(R$^{10c}$)$_2$, —N(R$^{10c}$)C(O)R$^{10c}$, —N(R$^{10c}$)C(O)N(R$^{10}$)$_2$, —OC(O)N(R$^{10c}$)$_2$, —N(R$^{10c}$)C(O)OR$^{10c}$, —C(O)OR$^{10c}$, —OC(O)R$^{10c}$, —S(O)R$^{10c}$, —S(O)$_2$R$^{10c}$, —NO$_2$, =O, =S, =N(R$^{10c}$), and —CN; and $C_{1-3}$ alkyl, $C_{2-3}$ alkenyl, and $C_{2-3}$ alkynyl, each of which is optionally substituted with one or more substituents independently selected from halogen, —OR$^{10c}$, —SR$^{10c}$, —N(R$^{10c}$)$_2$, —C(O)R$^{10c}$, —C(O)N(R$^{10c}$)$_2$, —N(R$^{10c}$)C(O)R$^{10c}$, —N(R$^{10c}$)C(O)N(R$^{10c}$)$_2$, —OC(O)N(R$^{10c}$)$_2$, —N(R$^{10c}$)C(O)OR$^{10c}$, —C(O)OR$^{10c}$, —OC(O)R$^{10c}$, —S(O)R$^{10c}$, —S(O)$_2$R$^{10c}$, —NO$_2$, =O, =S, =N(R$^{10c}$), and —CN.

In some embodiments, each R$^{9c}$ is independently selected from: halogen, —OR$^{10c}$, —SR$^{10c}$, —N(R$^{10c}$)$_2$, —C(O)R$^{10c}$, —NO$_2$, =O, —CN; and $C_{1-3}$ alkyl, optionally substituted with one or more substituents independently selected from halogen, —OR$^{10c}$, —SR$^{10c}$, —N(R$^{10c}$)$_2$, —C(O)R$^{10c}$, —NO$_2$, =O, and —CN. In some embodiments, each R$^{9c}$ is independently selected from: halogen, —NO$_2$, =O, —CN; and $C_{1-3}$ alkyl, optionally substituted with one or more substituents independently selected from halogen, —NO$_2$, =O, and —CN. In some embodiments, each R$^{9c}$ is independently selected from: halogen and —CN; and $C_{1-3}$ alkyl, optionally substituted with one or more substituents independently selected from halogen, and —CN. In some embodiments, each R$^{9c}$ is independently selected from: fluoro and —CN; and $C_1$ alkyl, optionally substituted with one or more substituents independently selected from fluoro, and —CN. In some embodiments, each R$^{9c}$ is independently selected from: fluoro and —CN; and $C_1$ alkyl. In some embodiments, each R$^{9c}$ is independently selected from: fluoro and —CN. In some embodiments, each R$^{9c}$ is independently selected from: fluoro. In some embodiments, each R$^{9c}$ is independently selected from: —CN.

In some embodiments, for a compound or salt of Formula (II), each R$^{9d}$ is independently selected from:

halogen, —OR$^{10d}$, —SR$^{10d}$, —N(R$^{10d}$)$_2$, —C(O)R$^{10d}$, —C(O)N(R$^{10d}$)$_2$, —N(R$^{10d}$)C(O)R$^{10d}$, —N(R$^{10d}$)C(O)N(R$^{10d}$)$_2$, —OC(O)N(R$^{10d}$)$_2$, —N(R$^{10d}$)C(O)OR$^{10d}$, —$C(O)OR^{10d}$, —$OC(O)R^{10d}$, —$S(O)R^{10d}$, —$S(O)_2R^{10d}$, —$NO_2$, =O, =S, =$N(R^{10d})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10d}$, $SR^{10d}$, —$N(R^{10d})_2$, —$C(O)R^{10d}$, —$C(O)N(R^{10d})_2$, —$N(R^{10d})C(O)R^{10d}$, —$N(R^{10d})C(O)N(R^{10d})_2$, —$OC(O)N(R^{10d})_2$, —$N(R^{10d})C(O)OR^{10d}$, —$C(O)OR^{10d}$, —$OC(O)R^{10d}$, —$S(O)R^{10d}$, —$S(O)_2R^{10d}$, —$NO_2$, =O, =S, =$N(R^{10d})$, and —CN;

In some embodiments, each $R^{9d}$ is independently selected from: halogen, —$OR^{10d}$, —$SR^{10d}$, —$N(R^{10d})_2$, —$C(O)R^{10d}$, —$NO_2$, =O, —CN; and $C_{1-3}$ alkyl, optionally substituted with one or more substituents independently selected from halogen, —$OR^{10d}$, $SR^{10d}$, —$N(R^{10d})_2$, —$C(O)R^{10d}$, —$NO_2$, =O, and —CN. In some embodiments, each $R^{9d}$ is independently selected from: halogen, —$NO_2$, =O, —CN; and $C_{1-3}$ alkyl, optionally substituted with one or more substituents independently selected from halogen, —$NO_2$, =O, and —CN. In some embodiments, each $R^{9d}$ is independently selected from: halogen and —CN; and $C_{1-3}$ alkyl, optionally substituted with one or more substituents independently selected from halogen, and —CN. In some embodiments, each $R^{9d}$ is independently selected from: fluoro and —CN; and $C_1$ alkyl, optionally substituted with one or more substituents independently selected from fluoro, and —CN. In some embodiments, each $R^{9d}$ is independently selected from: fluoro and —CN; and $C_1$ alkyl. In some embodiments, each $R^{9d}$ is independently selected from: fluoro and —CN. In some embodiments, each $R^{9d}$ is independently selected from: fluoro. In some embodiments, each $R^{9d}$ is independently selected from: —CN.

In some embodiments, for a compound or salt of Formula (II), each $R^{98}$ is independently selected from:

halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, —$S(O)_2R^{10g}$, —$NO_2$, =O, =S, =$N(R^{10g})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, —$S(O)_2R^{10g}$, —$NO_2$, =O, =S, =$N(R^{10g})$, and —CN.

In some embodiments, each $R^{9g}$ is independently selected from: halogen, —$OR^{10g}$, —$SR^{10g}$, —$N(R^{10g})_2$, —$C(O)R^{10g}$, —$NO_2$, =O, —CN; and $C_{1-3}$ alkyl, optionally substituted with one or more substituents independently selected from halogen, —$OR^{10g}$, —$SR^{10g}$, —$N(R^{10g})_2$, —$C(O)R^{10g}$, —$NO_2$, =O, and —CN. In some embodiments, each $R^{9g}$ is independently selected from: halogen, —$NO_2$, =O, —CN; and $C_{1-3}$ alkyl, optionally substituted with one or more substituents independently selected from halogen, —$NO_2$, =O, and —CN. In some embodiments, each $R^{9g}$ is independently selected from: halogen and —CN; and $C_{1-3}$ alkyl, optionally substituted with one or more substituents independently selected from halogen, and —CN. In some embodiments, each $R^{9g}$ is independently selected from: fluoro and —CN; and $C_1$ alkyl, optionally substituted with one or more substituents independently selected from fluoro, and —CN. In some embodiments, each $R^{9g}$ is independently selected from: fluoro and —CN; and $C_1$ alkyl. In some embodiments, each $R^{9g}$ is independently selected from: fluoro and —CN. In some embodiments, each $R^{9g}$ is independently selected from: fluoro. In some embodiments, each $R^{9b}$ is independently selected from: —CN.

In some embodiments, for a compound or salt of Formula (II), each $R^{10a}$ is independently selected from:

hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In some embodiments, each $R^{10a}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle. In some embodiments, each $R^{10a}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle.

In some embodiments, each $R^{10a}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl). In some embodiments, each $R^{10a}$ is independently selected from: hydrogen; and $C_{1-6}$ alkyl. In some embodiments, each $R^{10a}$ is independently selected from: hydrogen.

In some embodiments, for a compound or salt of Formula (II), each $R^{10b}$ is independently selected from: each $R^{10b}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, each $R^{10b}$ is selected from hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, each $R^{10b}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle.

In some embodiments, each $R^{10b}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH ($C_{1-6}$ alkyl); and $C_{3-10}$ carbocycle, and 3- to 10-membered heterocycle. In some embodiments, each $R^{10b}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl). In some embodiments, each $R^{10b}$ is independently selected from: hydrogen; and $C_{1-6}$ alkyl. In some embodiments, each $R^{10b}$ is independently selected from: $C_{1-3}$ alkyl.

In some embodiments, each $R^{10b}$ is methyl. In some embodiments, each $R^{10b}$ is hydrogen.

In some embodiments, for a compound or salt of Formula (II), each $R^{10c}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In some embodiments, each $R^{10c}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH ($C_{1-6}$ alkyl), $C_{3-10}$ carbocycle, 3- to 10-membered heterocycle; and $C_{3-10}$ carbocycle, and 3- to 10-membered heterocycle. In some embodiments, each $R^{10c}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH ($C_{1-6}$ alkyl); and $C_{3-10}$ carbocycle, and 3- to 10-membered heterocycle. In some embodiments, each $R^{10c}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl). In some embodiments, each $R^{10c}$ is independently selected from: hydrogen; and $C_{1-6}$ alkyl. In some embodiments, each $R^{10c}$ is hydrogen.

In some embodiments, for a compound or salt of Formula (II), each $R^{10d}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, each $R^{10d}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle. In some embodiments, each $R^{10d}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. In some embodiments, each $R^{10d}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl). In some embodiments, each $R^{10d}$ is independently selected from: hydrogen; and $C_{1-6}$ alkyl. In some embodiments, each $R^{10d}$ is hydrogen.

In some embodiments, for a compound or salt of Formula (II), each $R^{10e}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, each $R^{10e}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle. In some embodiments, each $R^{10e}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. In some embodiments, each $R^{10e}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl). In some embodiments, each $R^{10e}$ is independently selected from: hydrogen; and $C_{1-6}$ alkyl. In some embodiments, each $R^{10e}$ is hydrogen.

In some embodiments, for a compound or salt of Formula (II), each $R^{10f}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, each $R^{10f}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle. In some embodiments, each $R^{10f}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. In some embodiments, each $R^{10f}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl). In some embodiments, each $R^{10f}$ is independently selected from: hydrogen; and $C_{1-6}$ alkyl. In some embodiments, each $R^{10f}$ is hydrogen.

In some embodiments, for a compound or salt of Formula (II), each $R^{10g}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, each $R^{10g}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, each $R^{10g}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle. In some embodiments, each $R^{10g}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. In some embodiments, each $R^{10g}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl). In some embodiments, each $R^{10g}$ is independently selected from: hydrogen; and $C_{1-6}$ alkyl. In some embodiments, each $R^{10g}$ is hydrogen.

In some embodiments, for a compound or salt of Formula (II), each $R^{10g}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, each $R^{10h}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle. In some embodiments, each $R^{10h}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. In some embodiments, each $R^{10h}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl). In some embodiments, each $R^{10h}$ is independently selected from: hydrogen; and $C_{1-6}$ alkyl. In some embodiments, each $R^{10h}$ is hydrogen.

In some embodiments, the compound or salt of Formula (II) is selected from: B75, B36, B31, B45, B39, B145, B33, B206, B92, B82, B189, B278, B221, B238, B236, B100, B103, B23, B9, B62, B123, B43, B324, B83, B142, B77, B57, B78, B191, B232, B79, B314, B110, B55, B307, B147, B315, B139, B355, B225, B248, B222, B272, and B266.

In some embodiments, the compound or salt of Formula (II) is selected from: B75, B36, B31, B45, B39, B145, B33, B206, B92, B82, B189, B278, B221, B238, B236, B100, B103, B23, B9, B62, B123, B43, B324, B83, B142, B77, B57, B78, B191, B232, B79, B314, B110, B55, B307, B147, B315, B139, B355, B225, B248, B222, B272, B266, B141, B120, B13, B332, B269, B281, B229, B65, B17, B227, B247, B176, B291, B80, B322, B319, B118, B4, B6, B214, B89, B126, B296, B249, B366, B133, B30, B303, B132, B330, B338, B1, B233, B81, B106, B94, B199, B53, B128, B356, B306, B312, B336, B323, B358, B164, and B102.

In some embodiments, the compound or salt of Formula (II) is selected from: B75, B36, B31, B45, B39, B145, B33, B206, B92, B82, B189, B278, B221, B238, B236, B100, B103, B23, B9, B62, B123, B43, B324, B83, B142, B77, B57, B78, B191, B232, B79, B314, B110, B55, B307, B147, B315, B139, B355, B225, B248, B222, B272, B266, B120, B13, B332, B269, B281, B229, B65, B17, B227, B247, B176, B291, B80, B322, B319, B118, B4, B6, B214, B89, B126, B296, B249, B366, B133, B30, B303, B132, B330, B338, B1, B233, B81, B106, B94, B199, B53, B128, B356, B306, B312, B336, B323, B358, B164, B102, B29, B279, B54, B241, B268, B105, B121, B114, B137, B217, B84, B181, B141, B226, B91, B14, B101, B169, B117, B326, B113, B310, B292, B34, B152, B321, B202, B210, B154, B267, B327, B87, B243, B329, B130, B231, B354, B116, B349, B346, B230, B339, B320, B16, B295, B290, B127, B234, B288, B129, B204, B37, B32, B237, B350, B367, B228, B70, B124, B160, B331, B76, B85, B136, B52, B188, B8, B155, B223, B44, B7, B88, B108, B135, B64, B264, B119, B286, B35, B334, B46, B42, B69, B352, B280, B59, B25, B99, B144, B341, B60, B148, B284, B12, B283, B342, B245, B2, B38, and B150.

In some embodiments, the compound or salt of Formula (II) is selected from: B75, B36, B31, B45, B39, B145, B33, B206, B92, B82, B189, B278, B221, B238, B236, B100, B103, B23, B9, B62, B123, B43, B324, B83, B142, B77, B57, B78, B191, B232, B79, B314, B110, B55, B307, B147, B315, B139, B355, B225, B248, B222, B272, B266, B120, B13, B332, B269, B281, B229, B65, B17, B227, B247, B176, B291, B80, B322, B319, B118, B4, B6, B214, B89, B126, B296, B249, B366, B133, B30, B303, B132, B330, B338, B1, B233, B81, B106, B94, B199, B53, B128, B356, B306, B312, B336, B323, B358, B164, B102, B29, B279, B54, B241, B268, B105, B121, B114, B137, B217, B84, B181, B141, B226, B91, B14, B101, B169, B117, B326, B113, B310, B292, B34, B152, B321, B202, B210, B154, B267, B327, B87, B243, B329, B130, B231, B354, B116, B349, B346, B230, B339, B320, B16, B295, B290, B127, B234, B288, B129, B204, B37, B32, B237, B350, B367, B228, B70, B124, B160, B331, B76, B85, B136, B52, B188, B8, B155, B223, B44, B7, B88, B108, B135, B64, B264, B119, B286, B35, B334, B46, B42, B69, B352, B280, B59, B25, B99, B144, B341, B60, B148, B284, B12, B283, B342, B245, B2, B38, B150, B337, B58, B325, B302, B140, B274, B304, B235, B270, B73, B74, B93, B344, B122, B300, B97, B112, B212, B146, B138, B328, B95, B357, B125, B56, B41, B63, B265, B96, B273, B297, B353, B68, B205, B163, B27, B18, B72, B182, B313, B200, B244, B104, B170, B172, B178, B194, B340, B156, B343, B161, B301, B134, B359, B203, B157, B28, B49, B275, B218, B251, and B335.

In some embodiments, the compound or salt of Formula (II) is selected from: B75, B36, B31, B45, B39, B145, B33, B206, B92, B82, B189, B278, B221, B238, B236, B100, B103, B23, B9, B62, B123, B43, B324, B83, B142, B77, B57, B78, B191, B232, B79, B314, B110, B55, B307, B147, B315, B139, B355, B225, B248, B222, B272, B266, B120, B13, B332, B269, B281, B229, B65, B17, B227, B247, B176, B291, B80, B322, B319, B118, B4, B6, B214, B89, B126, B296, B249, B366, B133, B30, B303, B132, B330, B338, B1, B233, B81, B106, B94, B199, B53, B128, B356, B306, B312, B336, B323, B358, B164, B102, B29, B279, B54, B241, B268, B105, B121, B114, B137, B217, B84, B181, B141, B226, B91, B14, B101, B169, B117, B326, B113, B310, B292, B34, B152, B321, B202, B210, B154, B267, B327, B87, B243, B329, B130, B231, B354, B116, B349, B346, B230, B339, B320, B16, B295, B290, B127, B234, B288, B129, B204, B37, B32, B237, B350, B367, B228, B70, B124, B160, B331, B76, B85, B136, B52, B188, B8, B155, B223, B44, B7, B88, B108, B135, B64, B264, B119, B286, B35, B334, B46, B42, B69, B352, B280, B59, B25, B99, B144, B341, B60, B148, B284, B12, B283, B342, B245, B2, B38, B150, B337, B58, B325, B302, B140, B274, B304, B235, B270, B73, B74, B93, B344, B122, B300, B97, B112, B212, B146, B138, B328, B95, B357, B125, B56, B41, B63, B265, B96, B273, B297, B353, B68, B205, B163, B27, B18, B72, B182, B313, B200, B244, B104, B170, B172, B178, B194, B340, B156, B343, B161, B301, B134, B359, B203, B157, B28, B49, B275, B218, B251, B335, B348, B309, B22, B90, B209, B109, B153, B165, B190, B197, B171, B364, B308, B240, B201, B193, B224, B3, B71, B67, B360, B174, B294, B51, B166, B162, B220, B345, B184, B242, B299, B187, B149, B287, B256, B277, B250, B252, B282, and B213.

In some embodiments, the compound or salt of Formula (II) is selected from: B75, B36, B31, B45, B39, B145, B33, B206, B92, B82, B189, B278, B221, B238, B236, B100, B103, B23, B9, B62, B123, B43, B324, B83, B142, B77, B57, B78, B191, B232, B79, B314, B110, B55, B307, B147, B315, B139, B355, B225, B248, B222, B272, B266, B120, B13, B332, B269, B281, B229, B65, B17, B227, B247, B176, B291, B80, B322, B319, B118, B4, B6, B214, B89, B126, B296, B249, B366, B133, B30, B303, B132, B330, B338, B1, B233, B81, B106, B94, B199, B53, B128, B356, B306, B312, B336, B323, B358, B164, B102, B29, B279, B54, B241, B268, B105, B121, B114, B137, B217, B84, B181, B141, B226, B91, B14, B101, B169, B117, B326, B113, B310, B292, B34, B152, B321, B202, B210, B154, B267, B327, B87, B243, B329, B130, B231, B354, B116, B349, B346, B230, B339, B320, B16, B295, B290, B127, B234, B288, B129, B204, B37, B32, B237, B350, B367, B228, B70, B124, B160, B331, B76, B85, B136, B52, B188, B8, B155, B223, B44, B7, B88, B108, B135, B64, B264, B119, B286, B35, B334, B46, B42, B69, B352, B280, B59, B25, B99, B144, B341, B60, B148, B284, B12, B283, B342, B245, B2, B38, B150, B337, B58, B325, B302, B140, B274, B304, B235, B270, B73, B74, B93, B344, B122, B300, B97, B112, B212, B146, B138, B328, B95, B357, B125, B56, B41, B63, B265, B96, B273, B297, B353, B68, B205, B163, B27, B18, B72, B182, B313, B200, B244, B104, B170, B172, B178, B194, B340, B156, B343, B161, B301, B134, B359, B203, B157, B28, B49, B275, B218, B251, B335, B348, B309, B22, B90, B209, B109, B153, B165, B190, B197, B171, B364, B308, B240, B201, B193, B224, B3, B71, B67, B360, B174, B294, B51, B166, B162, B220, B345, B184, B242, B299, B187, B149, B287, B256, B277, B250, B252, B282, B213, B362, B10, B40, B276, B50, B271, B48, B98, B246, B311, B47, B5, B11, B15, B19, B20, B21, B24, B26, B61, B66, B86, B107, B111, B115, B131, B143, B151, B158, B159, B167, B168, B173, B175, B177, B180, B183, B185, B186, B192, B195, B196, B198, B207, B208, B211, B215, B216, B219, B239, B253, B254, B255, B285, B289, B333, B347, B351, B361, B363, and B365.

In some embodiments, the compound or salt of Formula (II) is selected from: B75, B36, B31, B45, B39, B145, B33, B206, B92, B82, B189, B278, B221, B238, B236, B100, B103, B23, B9, B62, B123, B43, B324, B83, B142, B77, B57, B78, B191, B232, B79, B314, B110, B55, B307, B147, B315, B139, B355, B225, B248, B222, B272, B266, B120, B13, B332, B269, B281, B229, B65, B17, B227, B247, B176, B291, B80, B322, B319, B118, B4, B6, B214, B89, B126, B296, B249, B366, B133, B30, B303, B132, B330, B338, B1, B233, B81, B106, B94, B199, B53, B128, B356, B306, B312, B336, B323, B358, B164, B102, B29, B279, B54, B241, B268, B105, B121, B114, B137, B217, B84, B181, B141, B226, B91, B14, B101, B169, B117, B326, B113, B310, B292, B34, B152, B321, B202, B210, B154, B267, B327, B87, B243, B329, B130, B231, B354, B116, B349, B346, B230, B339, B320, B16, B295, B290, B127, B234, B288, B129, B204, B37, B32, B237, B350, B367, B228, B70, B124, B160, B331, B76, B85, B136, B52, B188, B8, B155, B223, B44, B7, B88, B108, B135, B64, B264, B119, B286, B35, B334, B46, B42, B69, B352, B280, B59, B25, B99, B144, B341, B60, B148, B284, B12, B283, B342, B245, B2, B38, B150, B337, B58, B325, B302, B140, B274, B304, B235, B270, B73, B74, B93, B344, B122, B300, B97, B112, B212, B146, B138, B328, B95, B357, B125, B56, B41, B63, B265, B96, B273, B297, B353, B68, B205, B163, B27, B18, B72, B182, B313, B200, B244, B104, B170, B172, B178, B194, B340, B156, B343, B161, B301, B134, B359, B203, B157, B28, B49, B275, B218, B251, B335, B348, B309, B22, B90, B209, B109, B153, B165, B190, B197, B171, B364, B308, B240, B201, B193, B224, B3, B71, B67, B360, B174, B294, B51, B166, B162, B220, B345, B184, B242, B299, B187, B149, B287, B256, B277, B250, B252, B282, B213, B362, B10, B40, B276, B50, B271, B48, B98, B246, B311, B47, B5, B11, B15, B19, B20, B21, B24, B26, B61, B66, B86, B107, B111, B115, B131, B143, B151, B158, B159, B167, B168, B173, B175, B177, B180, B183, B185, B186, B192, B195, B196, B198, B207, B208, B211, B215, B216, B219, B239, B253, B254, B255, B285, B289, B333, B347, B351, B361, B363, B365, B179, B257, B258, B259, B262, B263, and B293.

In some embodiments, the compound or salt of Formula (II) is selected from: B75, B36, B23, B9, B62, B31, B45, B123, B43, B206, B39, and B324.

In some embodiments, the compound or salt of Formula (II) is selected from: B75, B36, B23, B9, B62, B31, B45, B123, B43, B206, B39, B324, B145, B92, B83, B55, B142, B82, B1, B322, B326, B33, B307, B77, B189, B147, B120, B14, B13, B57, B278, B303, B315, B319, and B332.

In some embodiments, the compound or salt of Formula (II) is selected from: B75, B36, B23, B9, B62, B31, B45, B123, B43, B206, B39, B324, B145, B92, B83, B55, B142, B82, B1, B322, B326, B33, B307, B77, B189, B147, B120, B14, B13, B57, B278, B303, B315, B319, B332, B128, B221, B78, B118, B4, B139, B355, B356, B12, B238, B6, B269, B281, B229, B121, B65, B114, B132, B306, B312, B17, B225, B330, B191, B226, B236, B113, B320, B214, B89, B227, B233, B336, B248, B152, B247, B69, B323, B358, B164, B126, B76, B295, B341, B310, B176, B296, B232, B81, B329, B222, B284, B79, B106, B37, B314, B350, B44, B292, B94, B32, B367, B110, B199, B101, B64, B8, B249, B116, B29, B137, B279, B100, B272, B136, B366, B91, B349, B264, B217, B130, B35, B59, B54, and B321.

In some embodiments, the compound or salt of Formula (II) is selected from: B75, B36, B23, B9, B62, B31, B45, B123, B43, B206, B39, B324, B145, B92, B83, B55, B142, B82, B1, B322, B326, B33, B307, B77, B189, B147, B120, B14, B13, B57, B278, B303, B315, B319, B332, B128, B221, B78, B118, B4, B139, B355, B356, B12, B238, B6, B269, B281, B229, B121, B65, B114, B132, B306, B312, B17, B225, B330, B191, B226, B236, B113, B320, B214, B89, B227, B233, B336, B248, B152, B247, B69, B323, B358, B164, B126, B76, B295, B341, B310, B176, B296, B232, B81, B329, B222, B284, B79, B106, B37, B314, B350, B44, B292, B94, B32, B367, B110, B199, B101, B64, B8, B249, B116, B29, B137, B279, B100, B272, B136, B366, B91, B349, B264, B217, B130, B35, B59, B54, B321, B202, B362, B16, B70, B103, B68, B241, B169, B266, B327, B41, B204, B300, B52, B84, B234, B231, B334, B346, B338, B188, B230, B46, B291, B124, B181, B133, B117, B56, B87, B228, B339, B73, B297, B353, B210, B112, B88, B352, B25, B154, B80, B7, B302, B268, B141, B155, B42, B325, B108, B34, B223, B38, B354, B313, B267, B304, B58, B160, B97, B244, B342, B290, B288, B265, B93, B148, B102, B105, B22, B283, B280, B348, B337, B53, B119, B2, B237, B10, B286, B344, B67, and B360.

In some embodiments, the compound or salt of Formula (II) is selected from: B75, B36, B23, B9, B62, B31, B45, B123, B43, B206, B39, B324, B145, B92, B83, B55, B142, B82, B1, B322, B326, B33, B307, B77, B189, B147, B120, B14, B13, B57, B278, B303, B315, B319, B332, B128, B221, B78, B118, B4, B139, B355, B356, B12, B238, B6, B269, B281, B229, B121, B65, B114, B132, B306, B312, B17, B225, B330, B191, B226, B236, B113, B320, B214, B89, B227, B233, B336, B248, B152, B247, B69, B323, B358, B164, B126, B76, B295, B341, B310, B176, B296, B232, B81, B329, B222, B284, B79, B106, B37, B314, B350, B44, B292, B94, B32, B367, B110, B199, B101, B64, B8, B249, B116, B29, B137, B279, B100, B272, B136, B366, B91, B349, B264, B217, B130, B35, B59, B54, B321, B202, B362, B16, B70, B103, B68, B241, B169, B266, B327, B41, B204, B300, B52, B84, B234, B231, B334, B346, B338, B188, B230, B46, B291, B124, B181, B133, B117, B56, B87, B228, B339, B73, B297, B353, B210, B112, B88, B352, B25, B154, B80, B7, B302, B268, B141, B155, B42, B325, B108, B34, B223, B38, B354, B313, B267, B304, B58, B160, B97, B244, B342, B290, B288, B265, B93, B148, B102, B105, B22, B283, B280, B348, B337, B53, B119, B2, B237, B10, B286, B344, B67, B360, B309, B156, B243, B245, B301, B212, B27, B135, B205, B40, B172, B273, B150, B203, B276, B85, B163, B170, B294, B193, B71, B50, B161, B49, B256, B144, B190, B3, B271, B140, B184, B250, B252, B48, B331, B146, B98, B277, B246, B194, B200, B311, B134, B274, B127, and B47.

In some embodiments, the compound or salt of Formula (II) is selected from: B75, B36, B23, B9, B62, B31, B45, B123, B43, B206, B39, B324, B145, B92, B83, B55, B142, B82, B1, B322, B326, B33, B307, B77, B189, B147, B120, B14, B13, B57, B278, B303, B315, B319, B332, B128, B221, B78, B118, B4, B139, B355, B356, B12, B238, B6, B269, B281, B229, B121, B65, B114, B132, B306, B312, B17, B225, B330, B191, B226, B236, B113, B320, B214, B89, B227, B233, B336, B248, B152, B247, B69, B323, B358, B164, B126, B76, B295, B341, B310, B176, B296, B232, B81, B329, B222, B284, B79, B106, B37, B314, B350, B44, B292, B94, B32, B367, B110, B199, B101, B64, B8, B249, B116, B29, B137, B279, B100, B272, B136, B366, B91, B349, B264, B217, B130, B35, B59, B54, B321, B202, B362, B16, B70, B103, B68, B241, B169, B266, B327, B41, B204, B300, B52, B84, B234, B231, B334, B346, B338, B188, B230, B46, B291, B124, B181, B133, B117, B56, B87, B228, B339, B73, B297, B353, B210, B112, B88, B352, B25, B154, B80, B7, B302, B268, B141, B155, B42, B325, B108, B34, B223, B38, B354, B313, B267, B304, B58, B160, B97, B244, B342, B290, B288, B265, B93, B148, B102, B105, B22, B283, B280, B348, B337, B53, B119, B2, B237, B10, B286, B344, B67, B360, B309, B156, B243, B245, B301, B212, B27, B135, B205, B40, B172, B273, B150, B203, B276, B85, B163, B170, B294, B193, B71, B50, B161, B49, B256, B144, B190, B3, B271, B140, B184, B250, B252, B48, B331, B146, B98, B277, B246, B194, B200, B311, B134, B274, B127, B47, B5, B11, B15, B18, B19, B20, B21, B24, B26, B28, B30, B51, B60, B61, B63, B66, B72, B74, B86, B90, B95, B96, B99, B104, B107, B109, B111, B115, B122, B125, B129, B131, B138, B143, B149, B151, B153, B157, B158, B159, B162, B165, B166, B167, B168, B171, B173, B174, B175, B177, B178, B179, B180, B182, B183, B185, B186, B187, B192, B195, B196, B197, B198, B201, B207, B208, B209, B211, B213, B215, B216, B218, B219, B220, B224, B235, B239, B240, B242, B251, B253, B254, B255, B270, B275, B282, B285, B287, B289, B299, B308, B328, B333, B335, B340, B343, B345, B347, B351, B357, B359, B361, B363, B364, and B365.

In some embodiments, the compound or salt of Formula (II) is selected from: B75, B36, B23, B9, B62, B31, B45, B123, B43, B206, B39, B324, B145, B92, B83, B55, B142, B82, B1, B322, B326, B33, B307, B77, B189, B147, B120, B14, B13, B57, B278, B303, B315, B319, B332, B128, B221, B78, B118, B4, B139, B355, B356, B12, B238, B6, B269, B281, B229, B121, B65, B114, B132, B306, B312, B17, B225, B330, B191, B226, B236, B113, B320, B214, B89, B227, B233, B336, B248, B152, B247, B69, B323, B358, B164, B126, B76, B295, B341, B310, B176, B296, B232, B81, B329, B222, B284, B79, B106, B37, B314, B350, B44, B292, B94, B32, B367, B110, B199, B101, B64, B8, B249, B116, B29, B137, B279, B100, B272, B136, B366, B91, B349, B264, B217, B130, B35, B59, B54, B321, B202, B362, B16, B70, B103, B68, B241, B169, B266, B327, B41, B204, B300, B52, B84, B234, B231, B334, B346, B338, B188, B230, B46, B291, B124, B181, B133, B117, B56, B87, B228, B339, B73, B297, B353, B210, B112, B88, B352, B25, B154, B80, B7, B302, B268, B141, B155, B42, B325, B108, B34, B223, B38, B354, B313, B267, B304, B58, B160, B97, B244, B342, B290, B288, B265, B93, B148, B102, B105, B22, B283, B280, B348, B337, B53, B119, B2, B237, B10, B286, B344, B67, B360, B309, B156, B243, B245, B301, B212, B27, B135, B205, B40, B172, B273, B150, B203, B276, B85, B163, B170, B294, B193, B71, B50, B161, B49, B256, B144, B190, B3, B271, B140, B184, B250, B252, B48, B331, B146, B98, B277, B246, B194, B200, B311, B134, B274, B127, B47, B5, B11, B15, B18, B19, B20, B21, B24, B26, B28, B30, B51, B60, B61, B63, B66, B72, B74, B86, B90, B95, B96, B99, B104, B107, B109, B111, B115, B122, B125, B129, B131, B138, B143, B149, B151, B153, B157, B158, B159, B162, B165, B166, B167, B168, B171, B173, B174, B175, B177, B178, B179, B180, B182, B183, B185, B186, B187, B192, B195, B196, B197, B198, B201, B207, B208, B209, B211, B213, B215, B216, B218, B219, B220, B224, B235, B239, B240, B242, B251, B253, B254, B255, B270, B275, B282, B285, B287, B289, B299, B308, B328, B333, B335, B340, B343, B345, B347, B351, B357, B359, B361, B363, B364, B365, B257, B258, B259, B262, B263, and B293.

In some embodiments, for a compound or salt of Formula (II) each $R^1$ is independently selected from: deuterium, —$N_3$, halogen, —$NO_2$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, and —$S(O)_2R^{10a}$; $C_{1-6}$ alkyl, $C_{2-6}$ alkenyl, and $C_{2-6}$ alkynyl, each of which is optionally substituted with one or more substituents independently selected from deuterium, —$N_3$, halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, =O, =S, =$N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from deuterium, —$N_3$, halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$. $R^2$ is selected from: deuterium, —$N_3$, halogen, —$NO_2$, —CN, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, and —$S(O)_2R^{10b}$; $C_{1-6}$ alkyl, $C_{2-6}$ alkenyl, and $C_{2-6}$ alkynyl, each of which is optionally substituted with one or more substituents independently selected from deuterium, —$N_3$, halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from deuterium, —$N_3$, halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. $R^3$ and $R^4$ are each independently selected from: hydrogen, deuterium, —$N_3$, halogen, —$OR^{10c}$, —$SR^{10c}$, —$N(R^{10c})_2$, —$NO_2$, and —CN; and $C_{1-6}$ alkyl optionally substituted with one or more substituents independently selected from deuterium, —$N_3$, halogen, —$OR^{10c}$, —$SR^{10c}$, —$N(R^{10c})_2$, —$NO_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$. $R^5$ and $R^6$ are each independently selected from: hydrogen, deuterium, —$N_3$, halogen, —$OR^{10d}$, $SR^{10d}$, —$N(R^{10d})_2$, —$NO_2$, and —CN; and $C_{1-6}$ alkyl optionally substituted with one or more substituents independently selected from deuterium, —$N_3$, halogen, —$OR^{10d}$, —$SR^{10d}$, —$N(R^{10d})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9d}$. $R^7$ is selected from: hydrogen and $C_{1-6}$ alkyl optionally substituted with one or more substituents independently selected from deuterium, —$N_3$, halogen, —$OR^{10e}$, —$SR^{10e}$, —$N(R^{10e})_2$, —$NO_2$, and —CN. $R^8$ is selected from: hydrogen; and $C_{1-6}$ alkyl optionally substituted with one or more substituents independently selected from deuterium, —$N_3$, halogen, —OR$^{10f}$, —SR$^{10f}$, —N(R$^{10f}$)$_2$, —$NO_2$, and —CN. R$^{11}$ is selected from: deuterium, —$N_3$, halogen, —$NO_2$, —CN, —OR$^{10g}$, —SR$^{10g}$, —N(R$^{10g}$)$_2$, —C(O)R$^{10g}$, —C(O)N(R$^{10g}$)$_2$, —N(R$^{10g}$)C(O)R$^{10g}$, —N(R$^{10g}$)C(O)N(R$^{10g}$)$_2$, —OC(O)N(R$^{10g}$)$_2$, —N(R$^{10g}$)C(O)OR$^{10g}$, —C(O)OR$^{10g}$, —OC(O)R$^{10g}$, —S(O)R$^{10g}$, and —S(O)$_2$R$^{10g}$; and $C_{1-6}$ alkyl, $C_{2-6}$ alkenyl, and $C_{2-6}$ alkynyl, each of which is optionally substituted with one or more substituents independently selected from deuterium, —$N_3$, halogen, —OR$^{10g}$, —SR$^{10g}$, —N(R$^{10g}$)$_2$, —C(O)R$^{10g}$, —C(O)N(R$^{10g}$)$_2$, —N(R$^{10g}$)C(O)R$^{10g}$, —C(O)OR$^{10g}$, —OC(O)R$^{10g}$, —N(R$^{10g}$)C(O)N(R$^{10g}$)$_2$, —OC(O)N(R$^{10g}$)$_2$, —N(R$^{10g}$)C(O)OR$^{10g}$, —S(O)R$^{10g}$, —S(O)$_2$R$^{10g}$, —$NO_2$, =S, =N(R$^{10g}$), —CN, $C_{3-10}$ carbocycle and 3- to 10-membered heterocycle, wherein the $C_{3-10}$ carbocycle and 3- to 10-membered heterocycle are each optionally substituted with one or more R$^{9g}$. R$^{12}$ is selected from hydrogen; $C_{1-6}$ alkyl optionally substituted with one or more substituents independently selected from the group consisting of deuterium, —$N_3$, halogen, CN, OH, OR$^{10h}$, N(R$^{10h}$)$_2$, $NO_2$, C(O)R$^{10h}$, SR$^{10h}$, and S(O)R$^{10h}$; and $C_{3-6}$ carbocycle and 3- to 10-membered heterocycle each optionally substituted with one or more substituents independently selected from the group consisting of halogen, CN, OH, OR$^{10h}$, N(R$^{10h}$)$_2$, $NO_2$, C(O)R$^{10h}$, SR$^{10h}$, and S(O)R$^{10h}$; or R$^{12}$, R$^{11}$, and R$^2$ come together to form a $C_5$-$C_{10}$ bridged ring system. each R$^{9a}$ is independently selected from: deuterium, —$N_3$, halogen, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —N(R$^{10a}$)C(O)N(R$^{10a}$)$_2$, —OC(O)N(R$^{10a}$)$_2$, —N(R$^{10a}$)C(O)OR$^{10a}$, —C(O)OR$^{10a}$, —OC(O)R$^{10a}$, —S(O)R$^{10a}$, —S(O)$_2$R$^{10a}$, —$NO_2$, =O, =S, =N(R$^{10a}$), and —CN; and $C_{1-3}$ alkyl, $C_{2-3}$ alkenyl, and $C_{2-3}$ alkynyl, each of which is optionally substituted with one or more substituents independently selected from halogen, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —N(R$^{10a}$)C(O)N(R$^{10a}$)$_2$, —OC(O)N(R$^{10a}$)$_2$, —N(R$^{10a}$)C(O)OR$^{10a}$, —C(O)OR$^{10a}$, —OC(O)R$^{10a}$, —S(O)R$^{10a}$, —S(O)$_2$R$^{10a}$, —$NO_2$, =O, =S, =N(R$^{10a}$), and —CN. each R$^{9b}$ is independently selected from: deuterium, —$N_3$, halogen, —OR$^{10b}$, —SR$^{10b}$, —N(R$^{10b}$)$_2$, —C(O)R$^{10b}$, —C(O)N(R$^{10b}$)$_2$, —N(R$^{10b}$)C(O)R$^{10b}$, —N(R$^{10b}$)C(O)N(R$^{10b}$)$_2$, —OC(O)N(R$^{10b}$)$_2$, —N(R$^{10b}$)C(O)OR$^{10b}$, —C(O)OR$^{10b}$, —OC(O)R$^{10b}$, —S(O)R$^{10b}$, —S(O)$_2$R$^{10b}$, —$NO_2$, =O, =S, =N(R$^{10b}$) and —CN; and $C_{1-3}$ alkyl, $C_{2-3}$ alkenyl, and $C_{2-3}$ alkynyl, each of which is optionally substituted with one or more substituents independently selected from deuterium, —$N_3$, halogen, —OR$^{10b}$, —SR$^{10b}$, —N(R$^{10b}$)$_2$, —C(O)R$^{10b}$, —C(O)N(R$^{10b}$)$_2$, —N(R$^{10b}$)C(O)R$^{10b}$, —N(R$^{10b}$)C(O)N(R$^{10b}$)$_2$, —OC(O)N(R$^{10b}$)$_2$, —N(R$^{10b}$)C(O)OR$^{10b}$, —C(O)OR$^{10b}$, —OC(O)R$^{10b}$, —S(O)R$^{10b}$, —S(O)$_2$R$^{10b}$, —$NO_2$, =O, =S, =N(R$^{10b}$), and —CN. each R$^{9b'}$ is independently selected from: deuterium, —$N_3$, halogen, —OR$^{10b}$, —SR$^{10b}$, —N(R$^{10b}$)$_2$, —C(O)R$^{10b}$, —C(O)N(R$^{10b}$)$_2$, —N(R$^{10b}$)C(O)R$^{10b}$, —N(R$^{10b}$)C(O)N(R$^{10b}$)$_2$, —OC(O)N(R$^{10b}$)$_2$, —N(R$^{10b}$)C(O)OR$^{10b}$, —C(O)OR$^{10b}$, —OC(O)R$^{10b}$, —S(O)R$^{10b}$, —S(O)$_2$R$^{10b}$, —$NO_2$, =O, =S, =N(R$^{10b}$), and —CN; and $C_{1-3}$ alkyl, $C_{2-3}$ alkenyl, and $C_{2-3}$ alkynyl, each of which is optionally substituted with one or more substituents independently selected from deuterium, —$N_3$, halogen, —OR$^{10b}$, —SR$^{10b}$, —N(R$^{10b}$)$_2$, —C(O)R$^{10b}$, —C(O)N(R$^{10b}$)$_2$, —N(R$^{10b}$)C(O)R$^{10b}$, —N(R$^{10b}$)C(O)N(R$^{10b}$)$_2$, —OC(O)N(R$^{10b}$)$_2$, —N(R$^{10b}$)C(O)OR$^{10b}$, —C(O)OR$^{10b}$, —OC(O)R$^{10b}$, —S(O)R$^{10b}$, —S(O)$_2$R$^{10b}$, —$NO_2$, =O, =S, =N(R$^{10b}$), and —CN. each R$^{9c}$ is independently selected from: deuterium, —$N_3$, halogen, —OR$^{10c}$, —SR$^{10c}$, —N(R$^{10c}$)$_2$, —C(O)R$^{10c}$, —C(O)N(R$^{10c}$)$_2$, —N(R$^{10c}$)C(O)R$^{10c}$, —N(R$^{10c}$)C(O)N(R$^{10c}$)$_2$, —OC(O)N(R$^{10c}$)$_2$, —N(R$^{10c}$)C(O)OR$^{10c}$, —C(O)OR$^{10c}$, —OC(O)R$^{10c}$, —S(O)R$^{10c}$, —S(O)$_2$R$^{10c}$, —$NO_2$, =O, =S, =N(R$^{10c}$), and —CN; and $C_{1-3}$ alkyl, $C_{2-3}$ alkenyl, and $C_{2-3}$ alkynyl, each of which is optionally substituted with one or more substituents independently selected from deuterium, —$N_3$, halogen, —OR$^{10c}$, —SR$^{10c}$, —N(R$^{10c}$)$_2$, —C(O)R$^{10c}$, —C(O)N(R$^{10c}$)$_2$, —N(R$^{10c}$)C(O)R$^{10c}$, —N(R$^{10c}$)C(O)N(R$^{10c}$)$_2$, —OC(O)N(R$^{10c}$)$_2$, —N(R$^{10c}$)C(O)OR$^{10c}$, —C(O)OR$^{10c}$, —OC(O)R$^{10c}$, —S(O)R$^{10c}$, —S(O)$_2$R$^{10c}$, —$NO_2$, =O, =S, =N(R$^{10c}$), and —CN. each R$^{9d}$ is independently selected from: deuterium, —$N_3$, halogen, —OR$^{10d}$, —SR$^{10d}$, —N(R$^{10d}$)$_2$, —C(O)R$^{10d}$, —C(O)N(R$^{10d}$)$_2$, —N(R$^{10d}$)C(O)R$^{10d}$, —N(R$^{10d}$)C(O)N(R$^{10d}$)$_2$, —OC(O)N(R$^{10d}$)$_2$, —N(R$^{10d}$)C(O)OR$^{10d}$, —C(O)OR$^{10d}$, —OC(O)R$^{10d}$, —S(O)R$^{10d}$, —S(O)$_2$R$^{10d}$, —$NO_2$, =O, =S, =N(R$^{10d}$), and —CN; and $C_{1-3}$ alkyl, $C_{2-3}$ alkenyl, and $C_{2-3}$ alkynyl, each of which is optionally substituted with one or more substituents independently selected from deuterium, —$N_3$, halogen, —OR$^{10d}$, —SR$^{10d}$, —N(R$^{10d}$)$_2$, —C(O)R$^{10d}$, —C(O)N(R$^{10d}$)$_2$, —N(R$^{10d}$)C(O)R$^{10d}$, —N(R$^{10d}$)C(O)N(R$^{10d}$)$_2$, —OC(O)N(R$^{10d}$)$_2$, —N(R$^{10d}$)C(O)OR$^{10d}$, —C(O)OR$^{10d}$, —OC(O)R$^{10d}$, —S(O)R$^{10d}$, —S(O)$_2$R$^{10d}$, —$NO_2$, =O, =S, =N(R$^{10d}$), and —CN. each R$^{9g}$ is independently selected from: deuterium, —$N_3$, halogen, —OR$^{10g}$, —SR$^{10g}$, —N(R$^{10g}$)$_2$, —C(O)R$^{10g}$, —C(O)N(R$^{10g}$)$_2$, —N(R$^{10g}$)C(O)R$^{10g}$, —N(R$^{10g}$)C(O)N(R$^{10g}$)$_2$, —OC(O)N(R$^{10g}$)$_2$, —N(R$^{10g}$)C(O)OR$^{10g}$, —C(O)OR$^{10g}$, —OC(O)R$^{10g}$, —S(O)R$^{10g}$, —S(O)$_2$R$^{10g}$, —$NO_2$, =O, =S, =N(R$^{10g}$), and —CN; and $C_{1-3}$ alkyl, $C_{2-3}$ alkenyl, and $C_{2-3}$ alkynyl, each of which is optionally substituted with one or more substituents independently selected from deuterium, —$N_3$, halogen, —OR$^{10g}$, —SR$^{10g}$, —N(R$^{10g}$)$_2$, —C(O)R$^{10g}$, —C(O)N(R$^{10g}$)$_2$, —N(R$^{10g}$)C(O)R$^{10g}$, —N(R$^{10g}$)C(O)N(R$^{10g}$)$_2$, —OC(O)N(R$^{10g}$)$_2$, —N(R$^{10g}$)C(O)OR$^{10g}$, —C(O)OR$^{10g}$, —OC(O)R$^{10g}$, —S(O)R$^{10g}$, —S(O)$_2$R$^{10g}$, —$NO_2$, =O, =S, =N(R$^{10g}$), and —CN. each R$^{10a}$, R$^{10b}$, R$^{10c}$, R$^{10d}$, R$^{10e}$, R$^{10f}$, R$^{10g}$, R$^{10h}$ is independently selected from: hydrogen; $C_{1-6}$ alkyl, $C_{2-6}$ alkenyl, and $C_{2-6}$ alkynyl, each of which is optionally substituted with one or more substituents independently selected from deuterium, —$N_3$, halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, R$^3$ is -D. In some embodiments, R$^4$ is -D. In some embodiments, R$^5$ is -D. In some embodiments, $R^6$ is -D. In some embodiments, $R^7$ is -D. In some embodiments, $R^8$ is -D. In some embodiments, $R^{11}$ is -D. In some embodiments, $R^{12}$ is -D.

Therapeutic Applications

Methods of administration of a compound or salt of Formula (I), (II), or (III) discussed herein may be used for the treatment of cardiovascular diseases or disorders. Methods of administration of a compound or salt of Formula (I), (II), or (III) discussed herein may be used for the treatment of cardiac diseases and disorders. Methods of administration of a compound or salt of Formula (I), (II), or (III) discussed herein may be used for the treatment of myopathies.

Examples of cardiac diseases and disorders include but are not limited to heart attack, heart failure, heart infection, endocarditis, myocarditis, pericarditis, arrhythmia, abnormal heart rhythms, aorta disease, Marfan syndrome, vascular disease, stroke, congenital heart disease, coronary artery disease, rhematic heart disease, peripheral vascular disease, heart valve disease, pericardial disease, heart muscle disease, cardiomyopathy, and deep vein thrombosis and pulmonary embolism. Examples of heart infections include but are not limited to endocarditis, myocarditis, and pericarditis.

Methods of administration of a compound or salt of Formula (I), (II), or (III) discussed herein may be used for the treatment of myopathies. In some embodiments, the myopathy is a cardiac myopathy. In some embodiments, the present disclosure provides a method of treating a condition selected from hypertrophic cardiomyopathy (HCM). In some embodiments, the present disclosure provides a method of treating a condition selected from hypertrophic cardiomyopathy (HCM); heart failure with preserved ejection fraction (HFpEF); disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; ischemia; and andangina. In some embodiments, said heart failure with preserved ejection fraction (HFpEF) comprises one or more disorders selected from disorders of relaxation and disorders of chamber stiffness (diabetic HFpEF). In some embodiments, said left ventricular (LV) hypertrophy is malignant left ventricular (LV) hypertrophy. In some embodiments, said restrictive cardiomyopathy comprises one or more subgroups selected from inflammatory subgroups, infiltrative subgroups, storage subgroups, idiopathic/inherited subgroups, congenital heart disease subgroups. In some embodiments, said inflammatory subgroups comprise one or more subgroups selected from Loefilers and EMF. In some embodiments, said inflammatory subgroups comprise one or more subgroups selected from amyloid, sarcoid, and XRT. In some embodiments, said storage subgroups comprise one or more subgroups selected from hemochromatosis, Fabry, and glycogen storage disease. In some embodiments, said idiopathic/inherited subgroups comprise one or more subgroups selected from Trop I (beta myosin HC), Trop T (alpha cardiac actin), and desmin related subgroups. In some embodiments, said congenital heart disease subgroups comprise one or more subgroups selected from pressure-overloaded RV, Tetralogy of Fallot, and pulmonic stenosis. In an aspect, the present disclosure provides a method of treating hypertrophic cardiomyopathy or a related condition comprising administering to a subject in need thereof a compound or salt disclosed herein.

In an aspect, the present disclosure provides a method of treating obstructive hypertrophic cardiomyopathy comprising administering to a subject in need thereof a compound or salt disclosed herein. In an aspect, the present disclosure provides a method of treating non-obstructive hypertrophic cardiomyopathy comprising administering to a subject in need thereof a compound or salt of disclosed herein. In an aspect, the present disclosure provides a method of treating heart failure with preserved ejection fraction comprising administering to a subject in need thereof a compound or disclosed herein. In an aspect, the present disclosure provides a method of treating left ventricle stiffness comprising administering to a subject in need thereof a compound or salt disclosed herein.

In an aspect, the present disclosure provides a method of treating a condition selected from hypertrophic cardiomyopathy (HCM); disorders of relaxation; ischemic cardiomyopathy; cardiac transplant allograft vasculopathy; restrictive cardiomyopathy; left ventricular (LV) hypertrophy; ischemia; and andangin, the method comprising administering a ventricular-selective agent.

In an aspect, the present disclosure provides methods of treating atrial cardiopathy, Heart failure with ejection fraction (e.g., Heart failure with preserved ejection fraction (HFpEF), Heart failure with reduced ejection fraction (HFrEF)), arrhythmia (e.g., Atrial fibrillation), stroke (e.g., Cardioembolic stroke, Cryptogenic stroke), valve disease (e.g., Mitral valve disease, or Tricuspid valve disease), comprises administering an atrial-selective agent. In an aspect, the present disclosure provides methods of treating atrial cardiopathy, Heart failure with preserved ejection fraction (HFpEF), Heart failure with reduced ejection fraction (HFrEF), Atrial fibrillation, Cardioembolic stroke, Cryptogenic stroke, Mitral valve disease, or Tricuspid valve disease, comprises administering an atrial-selective agent. In an aspect, the present disclosure provides methods of treating atrial cardiopathy. In some embodiments, the present disclosure provides a method of treating HFpEF. In some embodiments, the present disclosure provides a method of treating HFrEF. In some embodiments, the present disclosure provides a method of treating Atrial fibrillation. In some embodiments, the present disclosure provides a method of treating Cardioembolic stroke. In some embodiments, the present disclosure provides a method of treating Cryptogenic stroke. In some embodiments, the present disclosure provides a method of treating Mitral valve disease. In some embodiments, the present disclosure provides a method of treating Tricuspid valve disease.

In some embodiments, the present disclosure provides a method of treating one or more diseases selected from atrial cardiopathy, HFpEF, HFrEF, Atrial fibrillation, Cardioembolic stroke, Cryptogenic stroke, Mitral valve disease, and Tricuspid valve disease. In some embodiments, the method comprises administering a compound of Formula (I), Formula (II), or Formula (III). In some embodiments, the compound of Formula (I), Formula (II), or Formula (III) for use in treating one or more diseases selected from atrial cardiopathy, HFpEF, HFrEF, Atrial fibrillation, Cardioembolic stroke, Cryptogenic stroke, Mitral valve disease, and Tricuspid valve disease, comprises an atrial-selective agent. In some embodiments, the atrial-selective agent selectively inhibits atrial myosin relative to ventricular myosin or relative to skeletal myosin. In some embodiments, the atrial-selective agent selectively inhibits atrial myosin regulatory light chain relative to ventricular myosin regulatory light chain, or relative to skeletal myosin regulatory light chain, or relative to both atrial myosin regulatory light chain and skeletal myosin regulatory light chain.

In some embodiments, disclosed herein are methods to treat cardiac disease by the administration of a compound or salt of Formula (I), (II), or (III).

In some embodiments, disclosed herein is a method of treating cardiac disease in an individual in need thereof, the method comprising administering a therapeutically effective amount of a compound of Formula (III): or a salt thereof, wherein

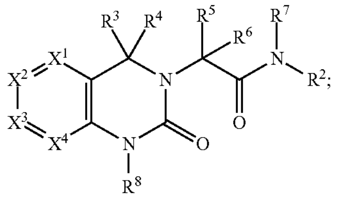

(III)

$X^1$, $X^2$, $X^3$, and $X^4$ are each independently selected from $C(R^1)$, N, and $N^+(—O^-)$;

each $R^1$ is independently selected from:

hydrogen;

halogen, $—NO_2$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$;

$C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2R^{10a}$, $—NO_2$, =O, =S, $=N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, =O, =S, $=N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$;

$R^2$ is selected from:

$C_{1-6}$ alkyl, $C_{2-6}$ alkenyl, and $C_{2-6}$ alkynyl, each of which is optionally substituted with one or more substituents independently selected from halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—C(O)OR^{10b}$, $—OC(O)R^{10b}$, $—N(R^{10b})C(O)N(R^{10b})_2$, $—OC(O)N(R^{10b})_2$, $—N(R^{10b})C(O)OR^{10b}$, $—S(O)R^{10b}$, $—S(O)_2R^{10b}$, $—NO_2$, =O, =S, $=N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—N(R^{10b})C(O)N(R^{10b})_2$, $—OC(O)N(R^{10b})_2$, $—N(R^{10b})C(O)OR^{10b}$, $—C(O)OR^{10b}$, $—OC(O)R^{10b}$, $—S(O)R^{10b}$, $—S(O)_2R^{10b}$, $—NO_2$, =O, =S, $=N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$;

$R^3$ and $R^4$ are each independently selected from:

hydrogen, halogen, $—OR^{10c}$, $—SR^{10c}$, $—N(R^{10c})_2$, $—NO_2$, and —CN; and $C_{1-6}$ alkyl optionally substituted with one or more substituents independently selected from halogen, $—OR^{10c}$, $—SR^{10c}$, $—N(R^{10c})_2$, $—NO_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$;

$R^5$ and $R^6$ are each independently selected from:

hydrogen, halogen, $—OR^{10c}$, $—SR^{10c}$, $—N(R^{10c})_2$, $—NO_2$, and —CN;

$C_{1-6}$ alkyl, $C_{2-6}$ alkenyl, and $C_{2-6}$ alkynyl, any of which is optionally substituted at each occurrence with one or more substituents independently selected from halogen, $—OR^{10c}$, $—SR^{10c}$, $—N(R^{10c})_2$, $—NO_2$, —CN, and $C_{3-10}$ carbocycle and 3- to 10-membered heterocycle, each of which is optionally substituted with one or more substituents independently selected from halogen, $—OR^{10c}$, $—SR^{10c}$, $—N(R^{10c})_2$, $—NO_2$, and —CN; and $C_{3-10}$ carbocycle and 3- to 10-membered heterocycle, each of which is optionally substituted with one or more substituents independently selected from halogen, $—OR^{10c}$, $—SR^{10c}$, $—N(R^{10c})_2$, $—NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$;

$R^7$ is selected from:

hydrogen and $C_{1-6}$ alkyl optionally substituted with one or more substituents independently selected from halogen, $—OR^{10d}$, $—SR^{10d}$, $—N(R^{10d})_2$, $—NO_2$, and —CN;

$R^8$ is selected from:

hydrogen; and $C_{1-6}$ alkyl optionally substituted with one or more substituents independently selected from halogen, $—OR^{10e}$, $—SR^{10e}$, $—N(R^{10e})_2$, $—NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, $—OR^{10e}$, $—SR^{10e}$, $—N(R^{10e})_2$, $—NO_2$, and —CN;

each $R^{9a}$ is independently selected from:

halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, =O, =S, $=N(R^{10a})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN;

each $R^{9b}$ is independently selected from:

halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN;

each $R^{9c}$ is independently selected from:

halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN;

each $R^{10a}$, $R^{10b}$, $R^{10c}$, $R^{10d}$, $R^{10e}$ is independently selected from:

hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In certain embodiments, for a compound or salt of Formula (III), $X^1$, $X^2$, $X^3$, and $X^4$ are each independently selected from $C(R^1)$, N, and $N^+(—O^-)$. In some embodiments, at least one of $X^1$, $X^2$, $X^3$, or $X^4$ is N. In some embodiments, no more than two of $X^1$, $X^2$, $X^3$, and $X^4$ are N. In some embodiments, $X^1$, $X^2$, $X^3$, and $X^4$ are each independently selected from $C(R^1)$, N, and $N^+(—O^-)$, wherein at least one of $X^1$, $X^2$, $X^3$, or $X^4$ is N; and no more than two of $X^1$, $X^2$, $X^3$, and $X^4$ are N.

In some embodiments, $X^1$, $X^2$, $X^3$, and $X^4$ are each independently selected from $C(R^1)$ and N. In some embodiments, $X^1$, $X^2$, $X^3$, and $X^4$ are each independently selected from $C(R^1)$.

In some embodiments, no more than one of $X^1$, $X^2$, $X^3$, and $X^4$ is N. In some embodiments, no more than two of $X^1$, $X^2$, $X^3$, and $X^4$ is N. In some embodiments, no more than three of $X^1$, $X^2$, $X^3$, and $X^4$ is N. In some embodiments, at least one of $X^1$, $X^2$, $X^3$, or $X^4$ is N. In some embodiments, at least two of $X^1$, $X^2$, $X^3$, or $X^4$ is N. In some embodiments, at least three of $X^1$, $X^2$, $X^3$, or $X^4$ is N.

In some embodiments, at least one of $X^1$, $X^2$, $X^3$, or $X^4$ is N, and no more than two of $X^1$, $X^2$, $X^3$, and $X^4$ are N. In some embodiments, $X^1$, $X^2$, $X^3$, and $X^4$ are each independently selected from $C(R^1)$, N, and $N^+(—O^-)$. In some embodiments, $X^1$, $X^2$, $X^3$, and $X^4$ are each independently selected from $C(R^1)$ and N. In some embodiments, $X^1$, $X^2$, $X^3$, and $X^4$ are each independently selected from $C(R^1)$. In some embodiments, one of $X^1$, $X^2$, $X^3$, or $X^4$ is N. In some embodiments, two of $X^1$, $X^2$, $X^3$, and $X^4$ are N. In some embodiments, three of $X^1$, $X^2$, $X^3$, and $X^4$ are N. In some embodiments, one of $X^1$, $X^2$, $X^3$, or $X^4$ is $C(R^1)$. In some embodiments, two of $X^1$, $X^2$, $X^3$, and $X^4$ are $C(R^1)$. In some embodiments, three of $X^1$, $X^2$, $X^3$, and $X^4$ are $C(R^1)$. In some embodiments, four of $X^1$, $X^2$, $X^3$, and $X^4$ are $C(R^1)$. In some embodiments, $X^1$ is N. In some embodiments, $X^2$ is N. In some embodiments, $X^3$ is N. In some embodiments, $X^4$ is N. In some embodiments, $X^1$ is $C(R^1)$. In some embodiments, $X^2$ is $C(R^1)$. In some embodiments, $X^3$ is $C(R^1)$. In some embodiments, $X^4$ is $C(R^1)$. In some embodiments, $X^1$ is C(H). In some embodiments, $X^2$ is C(H). In some embodiments, $X^3$ is C(H). In some embodiments, $X^4$ is C(H). In some embodiments, two of $X^1$, $X^2$, $X^3$, and $X^4$ are N. In some embodiments, two of $X^1$, $X^2$, $X^3$, and $X^4$ are N, and the two of two of $X^1$, $X^2$, $X^3$, and $X^4$ which are N are not bound (e.g., covalently) to each other. In some embodiments, $X^1$ and $X^3$ are N. In some embodiments, $X^2$ and $X^4$ are N. In some embodiments, $X^1$ is N, and $X^2$, $X^3$, and $X^4$ are $C(R^1)$. In some embodiments, $X^2$ is N, and $X^1$, $X^3$, and $X^4$ are $C(R^1)$. In some embodiments, $X^3$ is N, and $X^1$, $X^2$, and $X^4$ are $C(R^1)$. In some embodiments, $X^4$ is N, and $X^1$, $X^2$, and $X^3$ are $C(R^1)$. In some embodiments, $X^1$ is N, and $X^2$, $X^3$, and $X^4$ are C(H). In some embodiments, $X^2$ is N, and $X^1$, $X^3$, and $X^4$ are C(H). In some embodiments, $X^3$ is N, and $X^1$, $X^2$, and $X^4$ are C(H). In some embodiments, $X^4$ is N, and $X^1$, $X^2$, and $X^3$ are C(H).

In some embodiments, $X^2$ is N, and $X^1$ is $C(CF_3)$. In some embodiments $X^2$ is N, $X^1$ is $C(CF_3)$, $X^3$ is C(H), and $X^4$ is C(H). In some embodiments, $X^2$ is N, and $R^2$ is

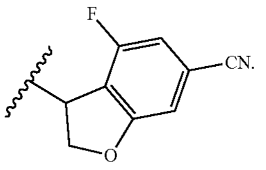 [SMILES: *C1COc2cc(C#N)cc(F)c21]

In some embodiments, $X^2$ is N, $R^2$ is

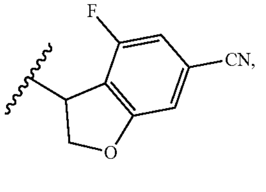 [SMILES: *C1COc2cc(C#N)cc(F)c21]

and $X^1$ is $C(CF_3)$. In some embodiments, $X^2$ is N, $R^2$ is

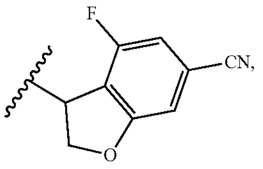 [SMILES: *C1COc2cc(C#N)cc(F)c21]

$X^1$ is $C(CF_3)$, $X^3$ is C(H), and $X^4$ is C(H). In some embodiments, $X^2$ is N, and $X^1$ is C(CN). In some embodiments, $X^2$ is N, $X^1$ is C(CN), $X^3$ is C(H), and $X^4$ is C(H). In some embodiments, $X^2$ is N, and $R^2$ is

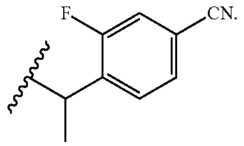 [SMILES: *C(C)c1ccc(C#N)cc1F]

In some embodiments, $X^2$ is N, $R^2$ is

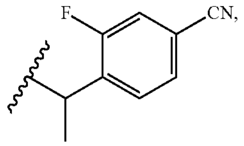 [SMILES: *C(C)c1ccc(C#N)cc1F]

and $X^1$ is C(F). In some embodiments, $X^2$ is N, $R^2$ is

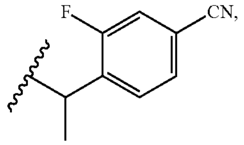 [SMILES: *C(C)c1ccc(C#N)cc1F]

$X^1$ is C(F), $X^3$ is C(H), and $X^4$ is C(H).

In some embodiments, $X^2$ is $C(O(C_{1-6}$ alkyl)). In some embodiments, $X^2$ is C(OMe). In some embodiments, $X^1$ is N, and $X^2$ is $C(O(C_{1-6}$ alkyl)). In some embodiments, $X^1$ is N, $X^2$ is $C(O(C_{1-6}$ alkyl)), $X^3$ is C(H), and $X^4$ C(H). In some embodiments, $X^1$ is N, and $X^2$ is C(OMe). In some embodiments, $X^1$ is N, $X^2$ is C(OMe), $X^3$ is C(H), and $X^4$ C(H). In some embodiments, $X^1$ is N, and $X^2$ is $C(O(C_{1-6}$ alkyl)), and $R^3$ and $R^4$ come together to form a cyclopropyl. In some embodiments, $X^1$ is N, $X^2$ is $C(O(C_{1-6}$ alkyl)), $X^3$ is C(H), and $X^4$ C(H), and $R^3$ and $R^4$ come together to form a cyclopropyl. In some embodiments, $X^1$ is N, and $X^2$ is C(OMe), and $R^3$ and $R^4$ come together to form a cyclopropyl. In some embodiments, $X^1$ is N, $X^2$ is C(OMe), $X^3$ is C(H), and $X^4$ C(H), and $R^3$ and $R^4$ come together to form a cyclopropyl.

In some embodiments, $X^2$ is N, and $X^1$ is C(F). In some embodiments, $X^2$ is N, $X^1$ is C(F), $X^3$ is C(H), and $X^4$ is C(H). In some embodiments, $X^2$ is N, and $R^2$ is

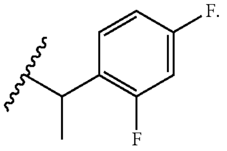 [SMILES: *C(C)c1ccc(F)cc1F]

In some embodiments, $X^2$ is N, $R^2$ is

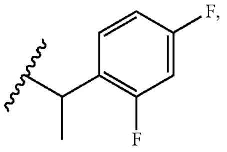 [SMILES: *C(C)c1ccc(F)cc1F]

and $X^1$ is C(F). In some embodiments, $X^2$ is N, $R^2$ is

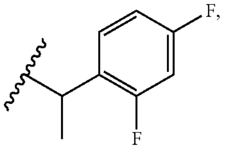 [SMILES: *C(C)c1ccc(F)cc1F]

$X^1$ is C(F), $X^3$ is C(H), and $X^4$ is C(H). In some embodiments, $X^2$ is N, and $X^1$ is C(Cl). In some embodiments, $X^2$ is N, $X^1$ is C(Cl), $X^3$ is C(H), and $X^4$ is C(H). In some embodiments, $X^2$ is N, $R^2$ is

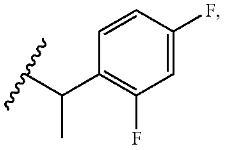 [SMILES: *C(C)c1ccc(F)cc1F]

and $X^1$ is C(Cl). In some embodiments, $X^2$ is N, $R^2$ is

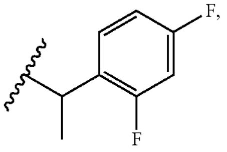 [SMILES: *C(C)c1ccc(F)cc1F]

$X^1$ is C(Cl), $X^3$ is C(H), and $X^4$ is C(H). In some embodiments, $X^2$ is N, and $X^1$ is C(CN). In some embodiments, $X^2$ is N, $X^1$ is C(CN), $X^3$ is C(H), and $X^4$ is C(H). In some embodiments, $X^2$ is N, and $R^2$ is

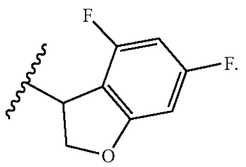 [SMILES: *C1COc2cc(F)cc(F)c21]

In some embodiments, $X^2$ is N, $R^2$ is

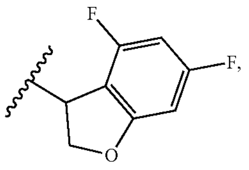 [SMILES: *C1COc2cc(F)cc(F)c21]

and $X^1$ is C(CN). In some embodiments, $X^2$ is N, $R^2$ is

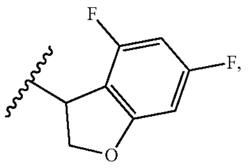 [SMILES: *C1COc2cc(F)cc(F)c21]

$X^1$ is C(CN), $X^3$ is C(H), and $X^4$ is C(H).

In some embodiments, $X^2$, $X^3$, and $X^4$ are each independently selected from C(H). In some embodiments, $X^1$ is N, and $X^2$, $X^3$, and $X^4$ are each independently selected from C($R^1$). In some embodiments, $X^1$ is N, and $X^2$, $X^3$, and $X^4$ are each independently selected from C(H). In some embodiments, $X^1$ is N, and $X^2$, $X^3$, and $X^4$ are each independently selected from C($R^1$), and $R^3$ and $R^4$ come together to form a cyclopropyl. In some embodiments, $X^1$ is N, and $X^2$, $X^3$, and $X^4$ are each independently selected from C(H), and $R^3$ and $R^4$ come together to form a cyclopropyl.

In some embodiments, $X^2$ is C(CN). In some embodiments, $X^1$ is N, and $X^2$ is C(Cl). In some embodiments, $X^1$ is N, and $X^2$ is C(Cl), and $X^3$ and $X^4$ are each independently selected from C($R^1$). In some embodiments, $X^1$ is N, and $X^2$ is C(Cl), and $X^3$ and $X^4$ are each independently selected from C(H).

In some embodiments, $X^1$ is N, and $X^2$ is C(CN). In some embodiments, $X^1$ is N, and $X^2$ is C(CN), and $X^3$ and $X^4$ are each independently selected from C($R^1$). In some embodiments, $X^1$ is N, and $X^2$ is C(CN), and $X^3$ and $X^4$ are each independently selected from C(H).

In some embodiments, $X^1$ is C(Br). In some embodiments, $X^1$ is N, and $X^2$ is C(Br). In some embodiments, $X^1$ is N, and $X^2$ is C(Br), and $X^3$ and $X^4$ are each independently selected from C($R^1$). In some embodiments, $X^1$ is N, and $X^2$ is C(Br), and $X^3$ and $X^4$ are each independently selected from C(H). In some embodiments, $X^1$ is N, and $X^2$ is C(Br), and $R^5$ is H, and $R^6$ is methyl. In some embodiments, $X^1$ is N, and $X^2$ is C(Br), and $X^3$ and $X^4$ are each independently selected from C($R^1$), and $R^5$ is H, and $R^6$ is methyl. In some embodiments, $X^1$ is N, and $X^2$ is C(Br), and $X^3$ and $X^4$ are each independently selected from C(H), and $R^5$ is H, and $R^6$ is methyl.

In some embodiments, $X^2$ is C(F). In some embodiments, $X^1$ is N, and $X^2$ is C(F). In some embodiments, $X^1$ is N, and $X^2$ is C(F), and $X^3$ and $X^4$ are each independently selected from C($R^1$). In some embodiments, $X^1$ is N, and $X^2$ is C(F), and $X^3$ and $X^4$ are each independently selected from C(H).

In some embodiments, $X^1$ is C($CF_3$). In some embodiments, $X^2$ is N, and $X^1$ is C($CF_3$). In some embodiments, $X^2$ is N, and $X^1$ is C($CF_3$), and $X^3$ and $X^4$ are each independently selected from C($R^1$). In some embodiments, $X^2$ is N, and $X^1$ is C($CF_3$), and $X^3$ and $X^4$ are each independently selected from C(H).

In some embodiments, $X^1$ is C($OCF_3$). In some embodiments, $X^2$ is N, and $X^1$ is C($OCF_3$). In some embodiments, $X^2$ is N, and $X^1$ is C($OCF_3$), and $X^3$ and $X^4$ are each independently selected from C($R^1$). In some embodiments, $X^2$ is N, and $X^1$ is C($OCF_3$), and $X^3$ and $X^4$ are each independently selected from C(H).

In some embodiments, $X^2$ is N, and $X^1$ is C(CN). In some embodiments, $X^2$ is N, $X^1$ is C(CN), $X^3$ is C(H), and $X^4$ is C(H). In some embodiments, $X^2$ is N, and $R^2$ is

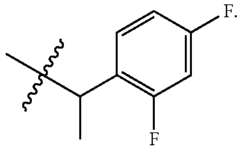 [SMILES: *C(C)c1ccc(F)cc1F]

In some embodiments, $X^2$ is N, $R^2$ is

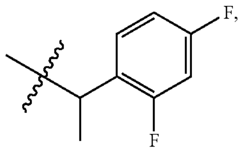 [SMILES: *C(C)c1ccc(F)cc1F]

and $X^1$ is C(CN). In some embodiments, $X^2$ is N, $R^2$ is

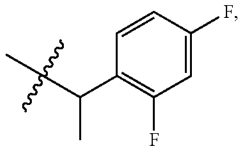 [SMILES: *C(C)c1ccc(F)cc1F]

$X^1$ is C(CN), $X^3$ is C(H), and $X^4$ is C(H). In some embodiments, $X^1$ is N, and $X^2$ is C($OR^{10a}$). In some embodiments, $X^1$ is N, and $X^2$ is C(OMe). In some embodiments, $X^1$ is N, $X^2$ is C($OR^{10a}$), $X^3$ is C(H), and $X^4$ is C(H). In some embodiments, $X^1$ is N, $X^2$ is C(OMe), $X^3$ is C(H), and $X^4$ is C(H). In some embodiments, $X^1$ is N, and $R^2$ is

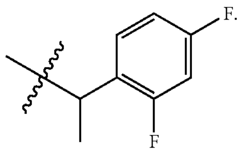 [SMILES: *C(C)c1ccc(F)cc1F]

In some embodiments, $X^1$ is N, $R^2$ is

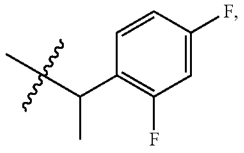 [SMILES: *C(C)c1ccc(F)cc1F]

and $X^2$ is $C(OR^{10a})$. In some embodiments, $X^1$ is N, $R^2$ is

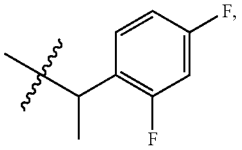 [SMILES: *C(C)c1ccc(F)cc1F]

and $X^2$ is C(OMe). In some embodiments, $X^1$ is N, $R^2$ is

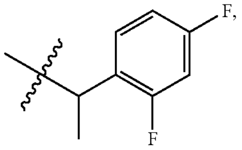 [SMILES: *C(C)c1ccc(F)cc1F]

$X^2$ is $C(OR^{10a})$, $X^3$ is C(H), and $X^4$ is C(H). In some embodiments, $X^1$ is N, $R^2$ is

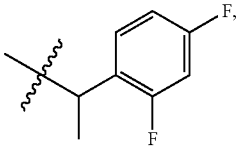 [SMILES: *C(C)c1ccc(F)cc1F]

$X^2$ is C(OMe), $X^3$ is C(H), and $X^4$ is C(H). In some embodiments, $X^1$ is N, $R^2$ is

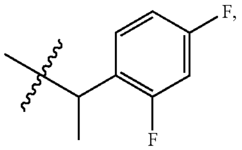 [SMILES: *C(C)c1ccc(F)cc1F]

$X^2$ is C(OMe), $X^3$ is C(H), $X^4$ is C(H), and $R^3$ and $R^4$ come together to form a cyclopropyl ring. In some embodiments, $X^1$ is N, $X^2$ is C(H), $X^3$ is C(H), and $X^4$ is C(H). In some embodiments, $X^1$ is N, and $R^2$ is

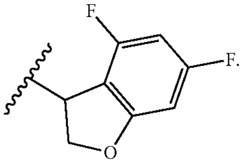 [SMILES: *C1COc2cc(F)cc(F)c21]

In some embodiments, $X^1$ is N, $R^2$ is

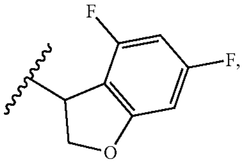 [SMILES: *C1COc2cc(F)cc(F)c21]

$X^3$ is C(H), and $X^4$ is C(H). In some embodiments, $X^1$ is N, $R^2$ is

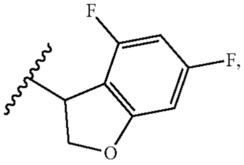 [SMILES: *C1COc2cc(F)cc(F)c21]

$X^3$ is C(H), $X^4$ is C(H), and $R^3$ and $R^4$ come together to form a cyclopropyl ring. In some embodiments, $X^1$ is N, and $X^2$ is C(Cl). In some embodiments, $X^1$ is N, $X^2$ is C(Cl), $X^3$ is C(H), and $X^4$ is C(H). In some embodiments, $X^1$ is N, and $R^2$ is

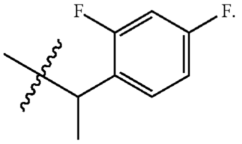 [SMILES: *C(C)c1ccc(F)cc1F]

In some embodiments, $X^1$ is N, $R^2$ is

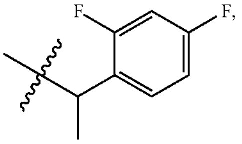 [SMILES: *C(C)c1ccc(F)cc1F]

and $X^2$ is C(CN). In some embodiments, $X^1$ is N, $R^2$ is

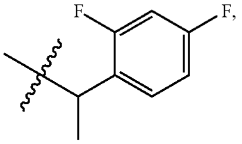 [SMILES: *C(C)c1ccc(F)cc1F]

$X^2$ is C(CN), $X^3$ is C(H), and $X^4$ is C(H). In some embodiments, $X^1$ is N, and $X^2$ is C(CN). In some embodiments, $X^1$ is N, $X^2$ is C(CN), $X^3$ is C(H), and $X^4$ is C(H). In some embodiments, $X^1$ is N, and $R^2$ is

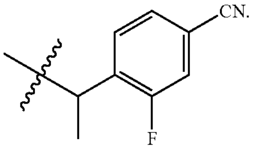 [SMILES: *C(C)c1ccc(C#N)cc1F]

In some embodiments, $X^1$ is N, $R^2$ is

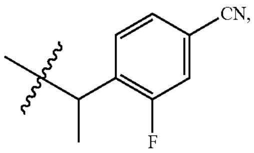 [SMILES: *C(C)c1ccc(C#N)cc1F]

and $X^2$ is C(CN). In some embodiments, $X^1$ is N, $R^2$ is

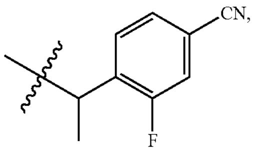 [SMILES: *C(C)c1ccc(C#N)cc1F]

$X^2$ is C(CN), $X^3$ is C(H), and $X^4$ is C(H). In some embodiments, $X^1$ is N, $R^2$ is

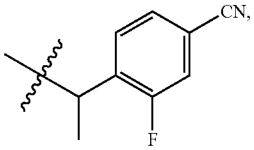 [SMILES: *C(C)c1ccc(C#N)cc1F]

$X^2$ is C(CN), $X^3$ is C(H), $X^4$ is C(H), and $R^3$ and $R^4$ come together to form a cyclopropyl ring. In some embodiments, $X^1$ is N, $X^2$ is C(H), $X^3$ is C(H), and $X^4$ is C(H). In some embodiments, $X^1$ is N, and $R^2$ is

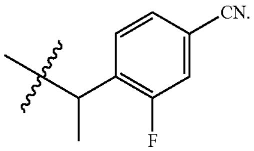 [SMILES: *C(C)c1ccc(C#N)cc1F]

In some embodiments, $X^1$ is N, $R^2$ is

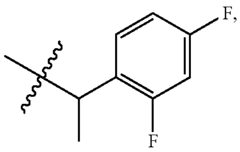 [SMILES: *C(C)c1ccc(F)cc1F]

and $X^2$ is C(H). In some embodiments, $X^1$ is N, $R^2$ is

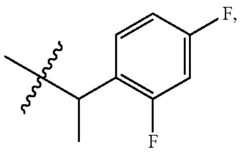 [SMILES: *C(C)c1ccc(F)cc1F]

$X^2$ is C(H), $X^3$ is C(H), and $X^4$ is C(H). In some embodiments, some embodiments, $X^1$ is N, and $X^2$ is C(CN). In some embodiments, $X^1$ is N, $X^2$ is C(CN), $X^3$ is C(H), and $X^4$ is C(H). In some embodiments, $X^1$ is N, and $R^2$ is

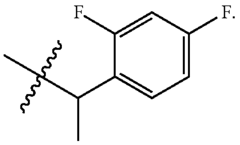 [SMILES: *C(C)c1ccc(F)cc1F]

In some embodiments, $X^1$ is N, $R^2$ is

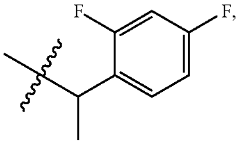 [SMILES: *C(C)c1ccc(F)cc1F]

$X^2$ is C(CN). In some embodiments, $X^1$ is N, $R^2$ is

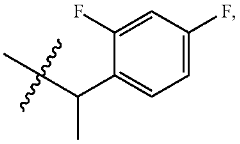 [SMILES: *C(C)c1ccc(F)cc1F]

$X^2$ is C(CN), $X^3$ is C(H), and $X^4$ is C(H). In some embodiments, some embodiments, $X^1$ is N, and $X^2$ is C(F). In some embodiments, $X^1$ is N, $X^2$ is C(F), $X^3$ is C(H), and $X^4$ is C(H). In some embodiments, $X^1$ is N, and $R^2$ is

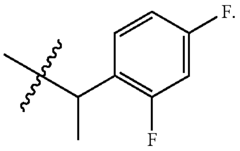 [SMILES: *C(C)c1ccc(F)cc1F]

In some embodiments, $X^1$ is N, $R^2$ is

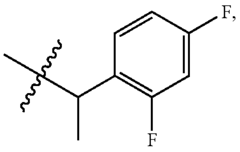 [SMILES: *C(C)c1ccc(F)cc1F]

and $X^2$ is C(F). In some embodiments, $X^1$ is N, $R^2$ is

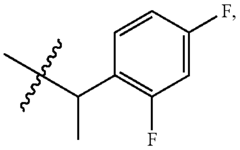

$X^2$ is C(F), $X^3$ is C(H), and $X^4$ is C(H).

In some embodiments, $X^2$ is C(F). In some embodiments, for a compound or salt of Formula (III), $X^1$ is N, $X^2$ is F, $R^5$ is methyl, and $R^6$ is hydrogen.

In some embodiments, $X^2$ is $C(CF_3)$. In some embodiments, $X^1$ is N, and $X^2$ is $C(CF_3)$. In some embodiments, $X^1$ is N, and $X^2$ is $C(CF_3)$, and $X^3$ and $X^4$ are each independently selected from $C(R^1)$. In some embodiments, $X^1$ is N, and $X^2$ is $C(CF_3)$, and $X^3$ and $X^4$ are each independently selected from C(H).

In some embodiments, $X^1$ is C(Cl). In some embodiments, $X^3$ is N, and $X^1$ is $C(R^1)$. In some embodiments, $X^3$ is N, and $X^1$ is $C(R^1)$, and $X^2$ and $X^4$ are each independently selected from $C(R^1)$. In some embodiments, $X^3$ is N, and $X^1$ is C(Cl). In some embodiments, $X^3$ is N, and $X^1$ is C(Cl), and $X^2$ is $C(R^1)$. In some embodiments, $X^3$ is N, and $X^1$ is C(Cl), and $X^2$ is $C(R^1)$, and $X^4$ is $C(R^1)$. In some embodiments, $X^3$ is N, and $X^1$ is C(Cl), and $X^2$ is C(H). In some embodiments, $X^3$ is N, and $X^1$ is C(Cl), and $X^2$ is C(H), and $X^4$ is C(H).

In some embodiments, $X^1$ is $C(OCH_2CHF_2)$ (e.g., in some embodiments, $X^1$ is a carbon bearing a 2,2-difluoroethoxy moiety). In some embodiments, $X^2$ is N, and $X^1$ is $C(OCH_2CHF_2)$. In some embodiments, $X^2$ is N, and $X^1$ is $C(OCH_2CHF_2)$, and $X^3$ and $X^4$ are each independently selected from $C(R^1)$. In some embodiments, $X^2$ is N, and $X^1$ is $C(OCH_2CHF_2)$, and $X^3$ and $X^4$ are each independently selected from C(H).

In some embodiments, $X^1$ is $C(OCH_2CH_3)$. In some embodiments, $X^2$ is N, and $X^1$ is $C(OCH_2CH_3)$. In some embodiments, $X^2$ is N, and $X^1$ is $C(OCH_2CH_3)$, and $X^3$ and $X^4$ are each independently selected from $C(R^1)$. In some embodiments, $X^2$ is N, and $X^1$ is $C(OCH_2CH_3)$, and $X^3$ and $X^4$ are each independently selected from C(H).

In some embodiments, $X^2$ is $C(OCH_2CH_3)$. In some embodiments, $X^1$ is N, and $X^2$ is $C(OCH_2CH_3)$. In some embodiments, $X^1$ is N, and $X^2$ is $C(OCH_2CH_3)$, and $X^3$ and $X^4$ are each independently selected from $C(R^1)$. In some embodiments, $X^1$ is N, and $X^2$ is $C(OCH_2CH_3)$, and $X^3$ and $X^4$ are each independently selected from C(H).

In some embodiments, $X^1$ is

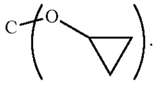.

In some embodiments, $X^2$ is N, and $X^1$ is

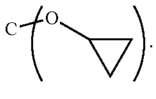.

In some embodiments, $X^2$ is N, and $X^1$ is

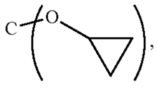, and $X^3$ and $X^4$ are each independently selected from $C(R^1)$. In some embodiments, $X^2$ is N, and $X^1$ is

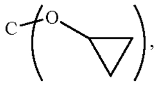, and $X^3$ and $X^4$ are each independently selected from C(H).

In certain embodiments, for a compound or salt of Formula (III), each $R^1$ is independently selected from:

hydrogen;

halogen, $-NO_2$, $-CN$, $-OR^{10a}$, $-SR^{10a}$, $-N(R^{10a})_2$, $-C(O)R^{10a}$, $-C(O)N(R^{10a})_2$, $-N(R^{10a})C(O)R^{10a}$, $-N(R^{10a})C(O)N(R^{10a})_2$, $-OC(O)N(R^{10a})_2$, $-N(R^{10a})C(O)OR^{10a}$, $-C(O)OR^{10a}$, $-OC(O)R^{10a}$, $-S(O)R^{10a}$, and $-S(O)_2R^{10a}$;

$C_{1-6}$ alkyl, $C_{2-6}$ alkenyl, and $C_{2-6}$ alkynyl, each of which is optionally substituted with one or more substituents independently selected from halogen, $-OR^{10a}$, $-SR^{10a}$, $-N(R^{10a})_2$, $-C(O)R^{10a}$, $-C(O)N(R^{10a})_2$, $-N(R^{10a})C(O)R^{10a}$, $-C(O)OR^{10a}$, $-OC(O)R^{10a}$, $-N(R^{10a})C(O)N(R^{10a})_2$, $-OC(O)N(R^{10a})_2$, $-N(R^{10a})C(O)OR^{10a}$, $-S(O)R^{10a}$, $-S(O)_2R^{10a}$, $-NO_2$, $=O$, $=S$, $=N(R^{10a})$, $-CN$, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, $-OR^{10a}$, $-SR^{10a}$, $-N(R^{10a})_2$, $-C(O)R^{10a}$, $-C(O)N(R^{10a})_2$, $-N(R^{10a})C(O)R^{10a}$, $-N(R^{10a})C(O)N(R^{10a})_2$, $-OC(O)N(R^{10a})_2$, $-N(R^{10a})C(O)OR^{10a}$, $-C(O)OR^{10a}$, $-OC(O)R^{10a}$, $-S(O)R^{10a}$, $-S(O)_2R^{10a}$, $-NO_2$, $=O$, $=S$, $=N(R^{10a})$, $-CN$, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$.

In certain embodiments, for a compound or salt of Formula (III), each $R^1$ is independently selected from: hydrogen; halogen, $-NO_2$, $-CN$, $-OR^{10a}$, $-SR^{10a}$, $-N(R^{10a})_2$, $-C(O)R^{10a}$, and $-C(O)N(R^{10a})_2$; $C_{1-6}$ alkyl, optionally substituted with one or more substituents independently selected from halogen, $-OR^{10a}$, $-SR^{10a}$, $-N(R^{10a})_2$, $-C(O)R^{10a}$, $-NO_2$, $-CN$, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, $-OR^{10a}$, $-SR^{10a}$, $-N(R^{10a})_2$, $-C(O)R^{10a}$, $-C(O)N(R^{10a})_2$, $-CN$, $C_{1-6}$ alkyl optionally substituted with one or more $R^{9a}$ In some embodiments, each $R^1$ is independently selected from: hydrogen; halogen, $-NO_2$, $-CN$, $-OR^{10a}$, $-SR^{10a}$, $-N(R^{10a})_2$, $-C(O)R^{10a}$, and $-C(O)N(R^{10a})_2$; $C_{1-6}$ alkyl, optionally substituted with one or more substituents independently selected from halogen, $-OR^{10a}$, $-SR^{10a}$, and $-N(R^{10a})_2$; and $C_{3-10}$ carbocycle and 3- to 10-membered heterocycle, each of which is optionally substituted with one or more substituents independently selected from halogen, $-OR^{10a}$, $-SR^{10a}$, and $-N(R^{10a})_2$. In some embodiments, each $R^1$ is independently selected from: hydrogen; halogen, CN, $-OR^{10a}$, and $-C(O)N(R^{10a})_2$; $C_{1-6}$ alkyl, optionally substituted with one or more substituents independently selected from halogen, and $C_{3-10}$ carbocycle optionally substituted with one or more substituents independently selected from halogen. In some embodiments, $R^1$ is hydrogen. In some embodiments, each $R^1$ is independently selected from hydrogen, halogen, $-NO_2$, $-CN$, $-OR^{10a}$, $-SR^{10a}$, $-N(R^{10a})_2$, $-C(O)R^{10a}$, $-C(O)N(R^{10a})_2$, $-N(R^{10a})C(O)R^{10a}$, $-N(R^{10a})C(O)N(R^{10a})_2$, $-OC(O)N(R^{10a})_2$, $-N(R^{10a})C(O)OR^{10a}$, $-C(O)OR^{10a}$, $-OC(O)R^{10a}$, $-S(O)R^{10a}$, and $-S(O)_2R^{10a}$. In some embodiments, each $R^1$ is independently selected from hydrogen, $C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, =O, =S, =$N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$. In some embodiments, each $R^1$ is independently selected from hydrogen, $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$. In some embodiments, each $R^1$ is independently selected from: hydrogen; halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, and —$NH(C_{1-6}$ alkyl); $C_{1-6}$ alkyl, $C_{2-6}$ alkenyl, and $C_{2-6}$ alkynyl, each of which is optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, and $C_{2-6}$ alkynyl. In some embodiments, each $R^1$ is independently selected from $C_{1-3}$ alkyl optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle and 3- to 10-membered heterocycle. In some embodiments, each $R^1$ is independently selected from $C_{3-5}$ carbocycle is optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, and $C_{2-6}$ alkynyl. In some embodiments, each $R^1$ is independently selected from hydrogen, —CN, —OH, —OMe, —OEt, —OiPr, —F, —Cl, —Br, —$CH_3$, —$CH_2CH_3$, —$CF_3$, —$CHF_2$, —$CH_2F$, $OCF_3$, —$OCHF_2$, —$OCH_2F$, —$C(O)NH_2$,

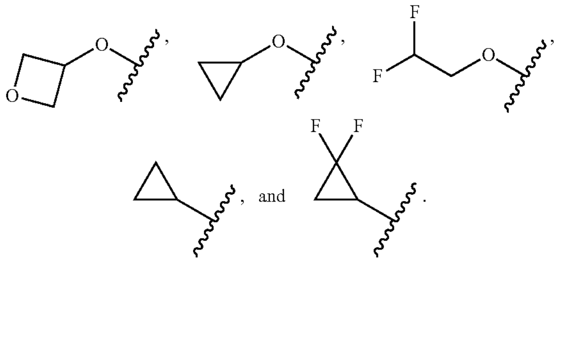

In some embodiments, each $R^1$ is independently selected from hydrogen, —CN, —OH, —OMe, —OEt, —OiPr, —F, —Cl, —Br, -Me, -Et, —$CF_3$, —$CHF_2$, —$CH_2F$, $OCF_3$, —$C(O)NH_2$,

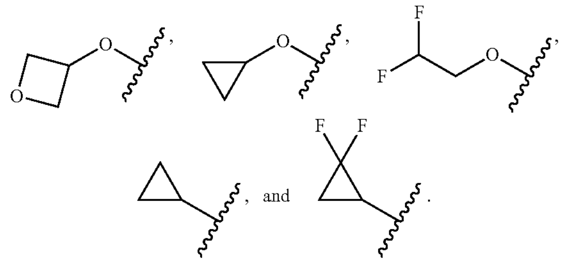

In some embodiments, each $R^1$ is independently selected from hydrogen, —CN, —OH, —OMe, —OEt, —OiPr, —F, —Cl, —Br, -Me, -Et, —$CF_3$, $OCF_3$, —$C(O)NH_2$,

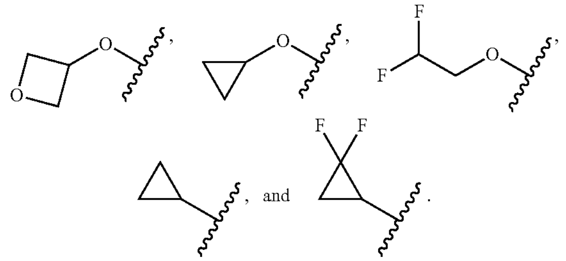

In some embodiments, each $R^1$ is independently selected from hydrogen, —CN, —OH, —OMe, —OEt, —OiPr, —F, —Cl, —Br, -Me, —$CF_3$, $OCF_3$, —$C(O)NH_2$,

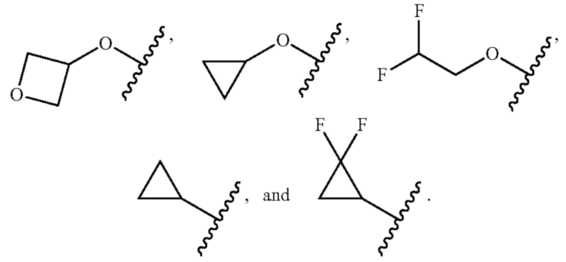

In some embodiments, each $R^1$ is independently selected from hydrogen, —$CF_3$, —CN, —$OR^{10a}$, —F, —Cl, —$OCF_3$, and methyl. In some embodiments, each $R^1$ is independently selected from hydrogen, —$CF_3$, —CN, —OMe, —F, —Cl, —$OCF_3$, and methyl. In some embodiments, each $R^1$ is independently selected from hydrogen, —$CF_3$, —CN, —$OR^{10a}$ (e.g., —OMe), —F, —Cl, and —$OCF_3$. In some embodiments, each $R^1$ is independently selected from hydrogen, —$CF_3$, —CN, —OMe, —F, —Cl, and —$OCF_3$. In some embodiments, each $R^1$ is independently selected from hydrogen, —$CF_3$, —CN, —OMe, —F, and —Cl. In some embodiments, each $R^1$ is independently selected from hydrogen, —$CF_3$, —CN, —OMe, and —F. In some embodiments, each $R^1$ is independently selected from hydrogen, —$CF_3$, —CN, and —OMe. In some embodiments, each $R^1$ is independently selected from hydrogen, —$CF_3$, and —CN. In some embodiments, each $R^1$ is independently selected from hydrogen and —CN. In some embodiments, each $R^1$ is independently selected from hydrogen and —$CF_3$. In some embodiments, each $R^1$ is independently selected from hydrogen and —CN. In some embodiments, each $R^1$ is independently selected from hydrogen and —$OR^{10a}$. In some embodiments, each $R^1$ is independently selected from hydrogen and —OMe. In some embodiments, each $R^1$ is independently selected from hydrogen and —F. In some embodiments, each $R^1$ is independently selected from hydrogen and —Cl. In some embodiments, each $R^1$ is independently selected from hydrogen and —$OCF_3$. In some embodiments, each $R^1$ is independently selected from hydrogen and $C_{1-6}$ alkyl. In some embodiments, each $R^1$ is independently selected from hydrogen and methyl. In some embodiments, each $R^1$ is independently selected from hydrogen, F, and CN. In some embodiments, each $R^1$ is independently selected from hydrogen and $CF_2H$.

In certain embodiments, for a compound or salt of Formula (III), $R^2$ is selected from:

$C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$.

In some embodiments, $R^2$ is selected from $C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. In some embodiments, $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. In some embodiments, $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. In some embodiments, $R^2$ is selected from $C_{1-6}$ alkyl, optionally substituted with one or more substituents independently selected from halogen, —$OR^{10b}$, —$SR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, $C_{1-6}$ alkyl, $C_{2-6}$ alkenyl, and $C_2$-6 alkynyl, wherein $C_{1-6}$ alkyl, $C_{2-6}$ alkenyl, and $C_{2-6}$ alkynyl are each optionally substituted with one or more $R^{9b}$. In some embodiments, for a compound or salt of formula (III), $R^2$ is $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is $C_{1-6}$ alkyl, optionally substituted with one or more substituents independently selected from halogen, —OROb, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is $C_{1-6}$ alkyl, optionally substituted with one or more substituents independently selected from halogen, —$OR^{10b}$, —$SR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is $C_{1-6}$ alkyl, optionally substituted with one or more substituents independently selected from halogen, —$OR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is $C_{1-6}$ alkyl, optionally substituted with one or more substituents independently selected from halogen, —$OR^{10b}$, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is $C_{1-6}$ alkyl, optionally substituted with one or more substituents independently selected from F, OH, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is $C_{1-6}$ alkyl, optionally substituted with one or more substituents independently selected from F, OH, $C_{3-10}$ carbocycle and 3- to 10-membered heterocycle, wherein each $C_{3-10}$ carbocycle and 3- to 10-membered heterocycle is independently selected from phenyl, 2-pyridyl, and 3-pyridyl, and each phenyl, 2-pyridyl, and 3-pyridyl is optionally substituted with one or more $R^{9b}$. In some embodiments, $R^2$ is $C_2$ alkyl, optionally substituted with one or more substituents independently selected from halogen, —$OR^{10b}$, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is $C_2$ alkyl, optionally substituted with one or more substituents independently selected from F, OH, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is $C_2$ alkyl, optionally substituted with one or more substituents independently selected from F, OH, $C_{3-10}$ carbocycle and 3- to 10-membered heterocycle, wherein each $C_{3-10}$ carbocycle and 3- to 10-membered heterocycle is independently selected from phenyl, 2-pyridyl, and 3-pyridyl, and each phenyl, 2-pyridyl, and 3-pyridyl is optionally substituted with one or more $R^{9b}$. In some embodiments, $R^2$ is $C_2$ alkyl, optionally substituted with one or more substituents independently selected from F, OH, $C_{3-10}$ carbocycle and 3- to 10-membered heterocycle, wherein each $C_{3-10}$ carbocycle and 3- to 10-membered heterocycle is independently selected from phenyl and 2-pyridyl, and each phenyl and 2-pyridyl is optionally substituted with one or more $R^{9b}$. In some embodiments, $R^2$ is $C_2$ alkyl, optionally substituted with one or more substituents independently selected from F, OH, $C_{3-10}$ carbocycle and 3- to 10-membered heterocycle, wherein each $C_{3-10}$ carbocycle and 3- to 10-membered heterocycle is independently selected from phenyl, pyridyl, and pyrimidyl, and each phenyl, pyridyl, and pyramidal is optionally substituted with one or more $R^{9b}$.

In some embodiments, $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. In some embodiments, $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl, wherein the $C_{1-6}$ alkyl is optionally substituted with one or more $R^{9b}$. In some embodiments, $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl. In some embodiments, $R^2$ is selected from $C_{1-6}$ alkyl, optionally substituted with one or more substituents independently selected from halogen, —$OR^{10b}$, —$SR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl. In some embodiments, $R^2$ is selected from $C_{1-6}$ alkyl, optionally substituted with one or more substituents independently selected from halogen, —$OR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl. In some embodiments, $R^2$ is selected from $C_{1-6}$ alkyl, optionally substituted with one or more substituents independently selected from halogen, —$OR^{10b}$, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, and —CN. In some embodiments, $R^2$ is selected from $C_{1-6}$ alkyl, optionally substituted with one or more substituents independently selected from F, OH, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from F, and —CN. In some embodiments, $R^2$ is selected from $C_{1-6}$ alkyl, optionally substituted with one or more substituents independently selected from F, OH, $C_{3-10}$ carbocycle and 3- to 10-membered heterocycle, wherein each $C_{3-10}$ carbocycle and 3- to 10-membered heterocycle is independently selected from phenyl, 2-pyridyl, and 3-pyridyl, and each phenyl, 2-pyridyl, and 3-pyridyl is optionally substituted with one or more $R^{9b}$; and $C_{3-10}$ carbocycle and 3- to 10-membered heterocycle, each of which is optionally substituted with one or more substituents independently selected from F, and —CN. In some embodiments, $R^2$ is selected from $C_2$ alkyl, optionally substituted with one or more substituents independently selected from halogen, —$OR^{10b}$, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from F, and —CN.

In some embodiments, $R^2$ is selected from $C_2$ alkyl, optionally substituted with one or more substituents independently selected from F, OH, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from F, and —CN.

In some embodiments, for a compound or salt of formula (III), $R^2$ is a substituent represented by the following:

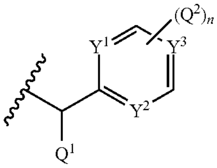

, wherein, $Q^1$ is a $C_{1-3}$ alkyl optionally substituted with one or more substituents selected from OH and halo; $Y^1$, $Y^2$, and $Y_3$ are selected from N and $C(Q^3)$; and each $Q^2$ is independently selected from halo, CN, $C_{1-6}$ alkoxy, and $C_{1-6}$ alkyl optionally substituted with one or more substituents selected from halogen; each $Q^3$ is independently selected from hydrogen, halo, CN, $C_{1-6}$ alkoxy, and $C_{1-6}$ alkyl optionally substituted with one or more substituents selected from halogen; and n is 0 or 1. In some embodiments, $Q^1$ is a $C_1$ alkyl optionally substituted with one or more substituents selected from OH and fluoro. In some embodiments, n is 0. In some embodiments, each $Q^3$ is independently selected from hydrogen, fluoro, chloro, bromo, CN, methoxy, methyl, and trifluoromethyl. In some embodiments, $Q^1$ is a $C_1$ alkyl optionally substituted with one or more substituents selected from OH and fluoro n is 0; and each $Q^3$ is independently selected from hydrogen, fluoro, chloro, bromo, CN, methoxy, methyl, and trifluoromethyl. In some embodiments, $Q^1$ is a $C_1$ alkyl; n is 0; and each $Q^3$ is independently selected from hydrogen, fluoro, and CN.

In some embodiments, $R^2$ is a substituent represented by the following:

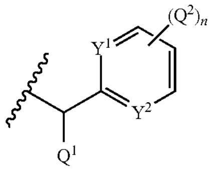

, wherein, $Q^1$ is a $C_{1-3}$ alkyl optionally substituted with one or more substituents selected from OH and halo; $Y^1$ and $Y^2$ are each independently selected from N and $C(Q^3)$; and each $Q^2$ is independently selected from halo and CN; each $Q^3$ is independently selected from hydrogen, halo and CN; and n is 0, 1, or 2. In some embodiments, $Q^1$ is a $C_1$ alkyl optionally substituted with one or more substituents selected from OH and fluoro; each $Q^2$ is independently selected from fluoro and CN; and each $Q^3$ is independently selected from hydrogen, fluoro and CN.

In some embodiments, $R^2$ is selected from

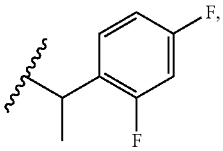
,
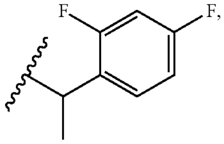
,
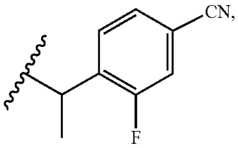
,
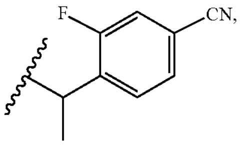
,
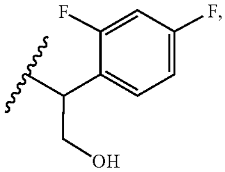
,
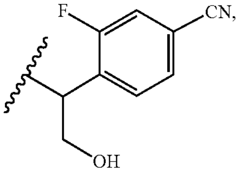
,
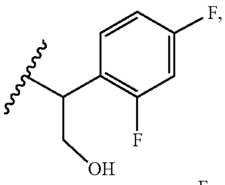
,
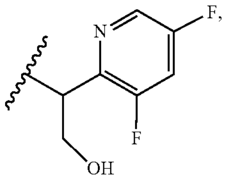
,
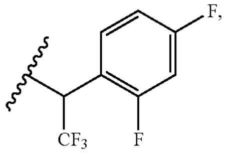
,
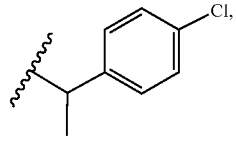
,
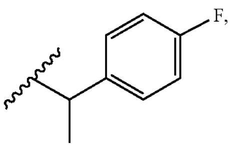
,
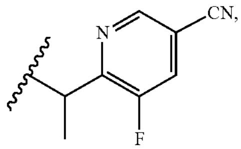
, -continued
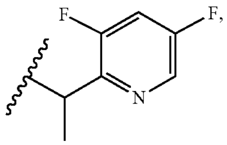 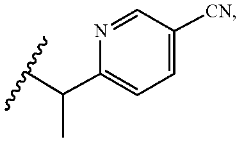
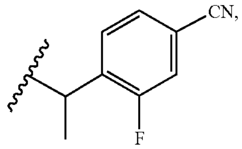 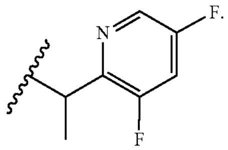
In some embodiments, $R^2$ is selected from
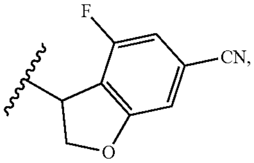 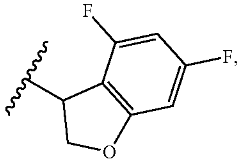
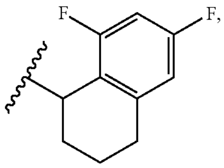 and 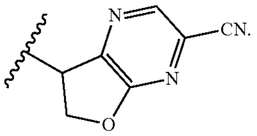
In some embodiments, $R^2$ is selected from,
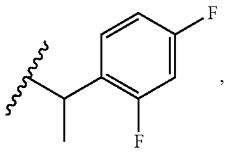, 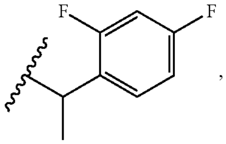,
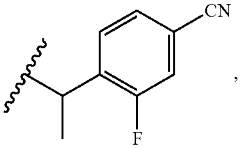, 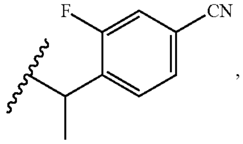,
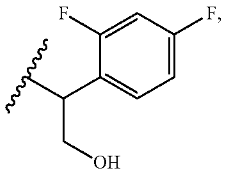 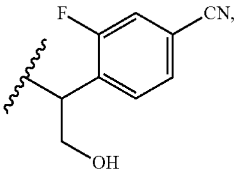
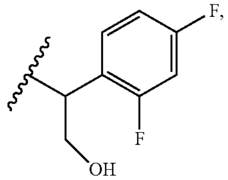 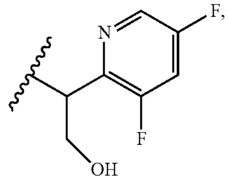
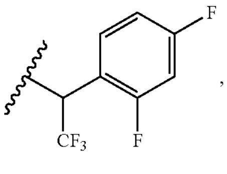, 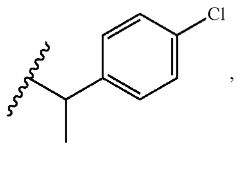,
-continued
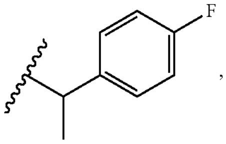, 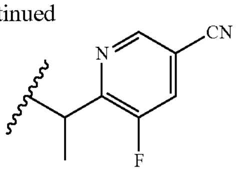,
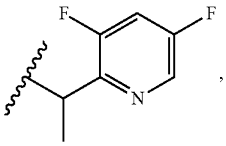, 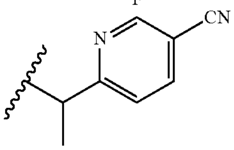,
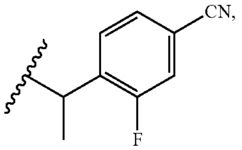 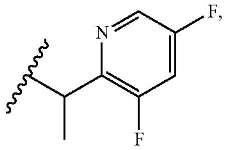
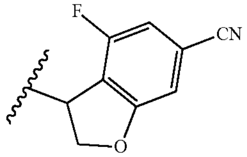, 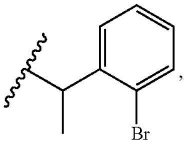
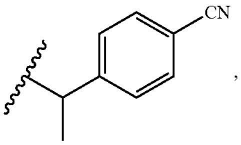, 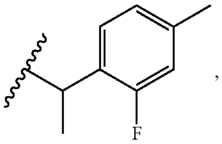,
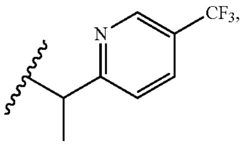 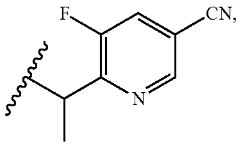
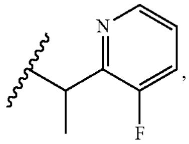 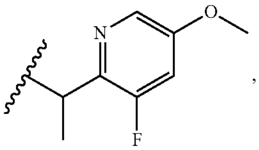,
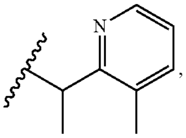 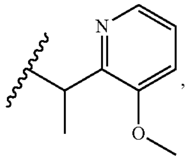
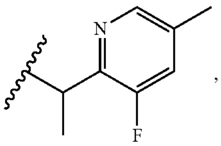, 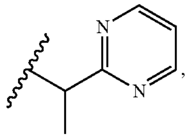
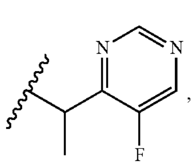 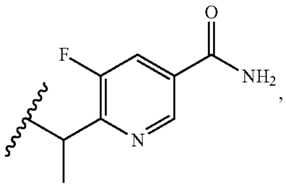
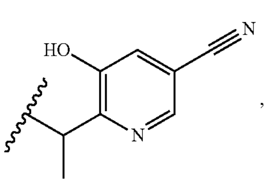, 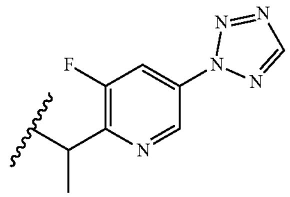, -continued

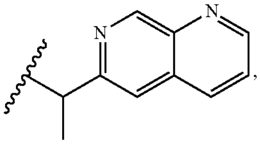,
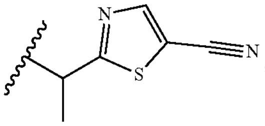,
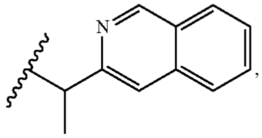,
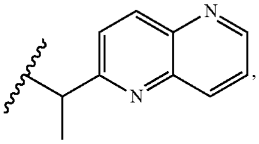,
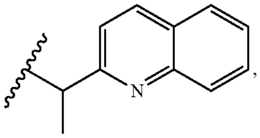,
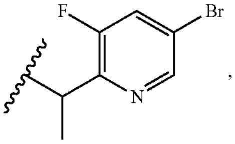,
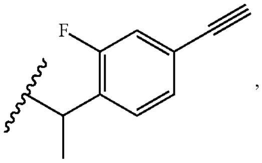,
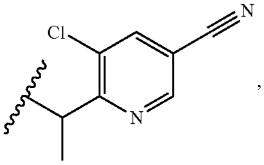,
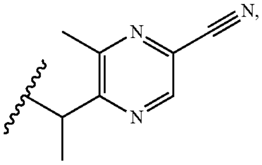
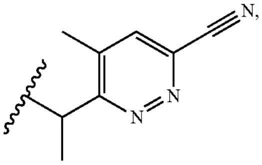
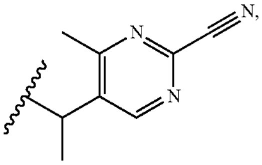
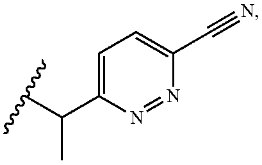
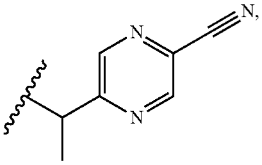
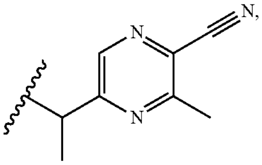
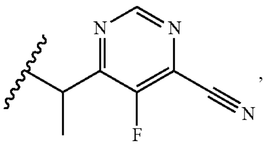,
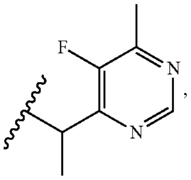,
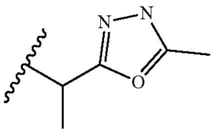,
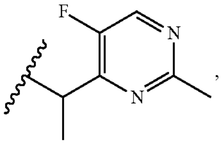,
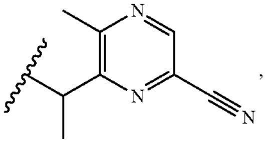,
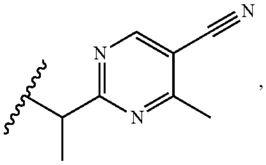, -continued

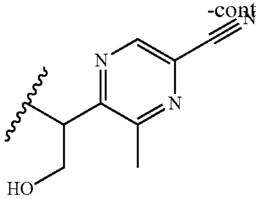,
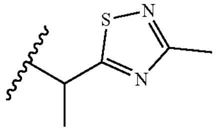,
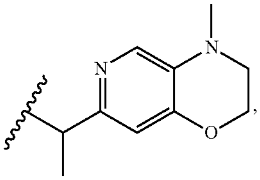,
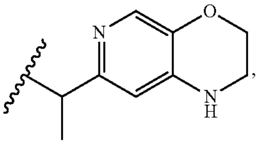, and
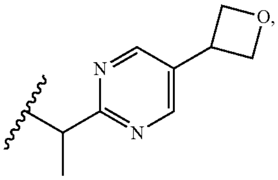

In some embodiments, $R^2$ is selected from

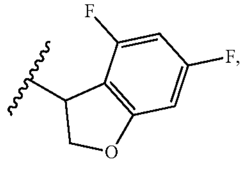
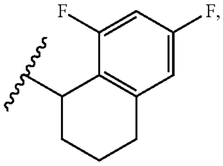
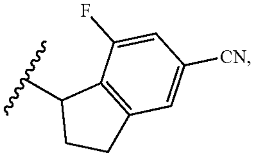
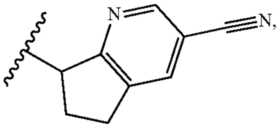
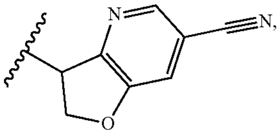
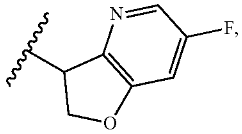
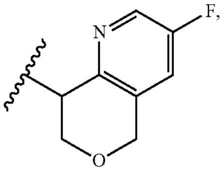 and
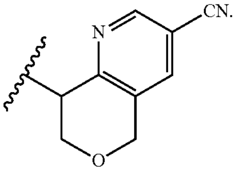

In some embodiments, $R^2$ is selected from $C_{1-6}$ alkyl optionally substituted with one or more substituents independently selected from OH and $C_{3-10}$ carbocycle, wherein the $C_{3-10}$ carbocycle is optionally substituted with one or more substituents independently selected from halogen and —CN; and $C_{3-10}$ carbocycle and 3- to 10-membered heterocycle optionally substituted with one or more substituents independently selected from halogen and —CN. In some embodiments, $R^2$ is selected from $C_{1-6}$ alkyl optionally substituted with one or more $C_{3-10}$ carbocycle, wherein each $C_{3-10}$ carbocycle is optionally substituted with one or more substituents independently selected from halogen and —CN; and $C_{3-10}$ carbocycle and 3- to 10-membered heterocycle optionally substituted with one or more substituents independently selected from halogen and —CN. In some embodiments, $R^2$ is selected from $C_{1-6}$ alkyl optionally substituted with one or more $C_{3-10}$ carbocycle, wherein each $C_{3-10}$ carbocycle is optionally substituted with one or more substituents independently selected from F and —CN; and $C_{3-10}$ carbocycle and 3- to 10-membered heterocycle optionally substituted with one or more substituents independently selected from —F and —CN. In some embodiments, $R^2$ is selected from $C_2$ alkyl optionally substituted with one or more $C_{3-10}$ carbocycle, wherein each $C_{3-10}$ carbocycle is optionally substituted with one or more substituents independently selected from halogen and —CN; and $C_{3-10}$ carbocycle and 3- to 10-membered heterocycle optionally substituted with one or more substituents independently selected from halogen and —CN. In some embodiments, $R^2$ is selected from $C_2$ alkyl optionally substituted with one or more $C_{3-10}$ carbocycle, wherein each $C_{3-10}$ carbocycle is optionally substituted with one or more substituents independently selected from —F and —CN; and $C_{3-10}$ carbocycle and 3- to 10-membered heterocycle optionally substituted with one or more substituents independently selected from —F and —CN. In some embodiments, $R^2$ is a $C_2$ alkyl optionally substituted with one or more $C_{3-10}$ carbocycle, wherein each $C_{3-10}$ carbocycle is optionally substituted with one or more substituents independently selected from —F and —CN.

In some embodiments, $R^2$ is a $C_{3-10}$ carbocycle and 3- to 10-membered heterocycle optionally substituted with one or more substituents independently selected from —F and —CN.

In certain embodiments, for a compound or salt of Formula (III), $R^3$ and $R^4$ are each independently selected from:

hydrogen, halogen, $—OR^{10c}$, $—SR^{10c}$, $—N(R^{10c})_2$, $—NO_2$, and —CN; and $C_{1-6}$ alkyl optionally substituted with one or more substituents independently selected from halogen, $—OR^{10c}$, $—SR^{10c}$, $—N(R^{10c})_2$, $—NO_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$.

In some embodiments, $R^3$ and $R^4$ are each independently selected from: hydrogen, halogen, $—OR^{10c}$, $—SR^{10c}$, $—N(R^{10c})_2$, $—NO_2$, and —CN; and $C_{1-6}$ alkyl optionally substituted with one or more substituents independently selected from halogen, $—OR^{10c}$, $—SR^{10c}$, $—N(R^{10c})_2$, $—NO_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$. In some embodiments, $R^3$ and $R^4$ are each independently selected from: hydrogen, halogen, $—NO_2$, and —CN; and $C_{1-6}$ alkyl optionally substituted with one or more halogen; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$. In some embodiments, $R^3$ and $R^4$ are each independently selected from: hydrogen, halogen, $—NO_2$, and —CN; and $C_{1-6}$ alkyl optionally substituted with one or more halogen; or $R^3$ together with $R^4$ form a 3- to 10-membered heterocycle or $C_{3-10}$ carbocycle. In some embodiments, $R^3$ and $R^4$ are each independently selected from: hydrogen; and $C_{1-6}$ alkyl optionally substituted with one or more halogen; or $R^3$ together with $R^4$ form a 3- to 10-membered heterocycle or $C_{3-10}$ carbocycle. In some embodiments, $R^3$ and $R^4$ are each independently selected from: hydrogen; and $C_{1-6}$ alkyl optionally substituted with one or more halogen. In some embodiments, $R^3$ and $R^4$ are each independently selected from: hydrogen; and $C_{1-6}$ alkyl. In some embodiments, $R^3$ and $R^4$ are each independently selected from: hydrogen; and $C_1$ alkyl. In some embodiments, $R^3$ is —H, and $R^4$ is —OH. In some embodiments, $R^3$ is —OH, and $R^4$ is —H. In some embodiments, $R^3$ is —OH.

In some embodiments, $R^3$ together with $R^4$ form a 3- to 10-membered heterocycle or $C_{3-10}$ carbocycle. In some embodiments, the 3- to 10-membered heterocycle or $C_{3-10}$ carbocycle formed by $R^3$ together with $R^4$ is selected from cyclopropyl, cyclohexyl, and oxetanyl. In some embodiments, $R^3$ and $R^4$ are each independently selected from: hydrogen; and $C_1$ alkyl; or $R^3$ together with $R^4$ form a 3- to 10-membered heterocycle or $C_{3-10}$ carbocycle. In some embodiments, $R^3$ and $R^4$ are each independently selected from: hydrogen; and $C_1$ alkyl; or $R^3$ together with $R^4$ form a $C_{3-10}$ carbocycle. In some embodiments, $R^3$ and $R^4$ are each independently selected from: hydrogen; and $C_1$ alkyl; or $R^3$ together with $R^4$ form a $C_{3-10}$ carbocycle, wherein the $C_{3-10}$ carbocycle is cyclopropane. In some embodiments, wherein $R^3$ together with $R^4$ form a ring selected from

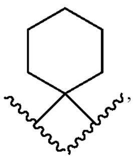, 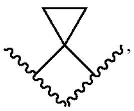, 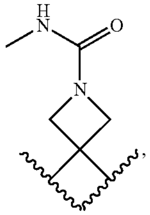, and

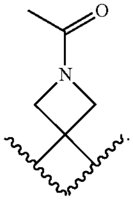.

In some embodiments, $R^3$ and $R^4$ are each hydrogen. In some embodiments, $R^3$ is hydrogen, and $R^4$ is methyl. In some embodiments, $R^3$ and $R^4$ are each independently selected from: hydrogen; and $C_{1-6}$ alkyl optionally substituted with one or more fluorine. In some embodiments, $R^3$ and $R^4$ are each independently selected from hydrogen. In some embodiments, $R^3$ and $R^4$ are each independently selected from hydrogen; and $C_1$ alkyl optionally substituted with one or more fluorine. In some embodiments, $R^3$ and $R^4$ are each independently selected from hydrogen, methyl, and trifluoromethyl. In some embodiments, $R^3$ and $R^4$ are each independently selected from hydrogen and $C_1$ alkyl. In some embodiments, $R^3$ and $R^4$ are each independently selected from $C_1$ alkyl.

In certain embodiments, for a compound or salt of Formula (III), $R^5$ and $R^6$ are each independently selected from:

hydrogen, halogen, $—OR^{10c}$, $—SR^{10c}$, $—N(R^{10c})_2$, $—NO_2$, and —CN;

$C_{1-6}$ alkyl, optionally substituted with one or more substituents independently selected from halogen, $—OR^{10c}$, $—SR^{10c}$, $—N(R^{10c})_2$, $—NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, $—OR^{10c}$, $—SR^{10c}$, $—N(R^{10c})_2$, $—NO_2$, and —CN; and $C_{3-10}$ carbocycle and 3- to 10-membered heterocycle, each of which is optionally substituted with one or more substituents independently selected from halogen, —$OR^{10c}$, —$SR^{10c}$, —$N(R^{10c})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$.

In some embodiments, $R^5$ and $R^6$ are each independently selected from: hydrogen, halogen, —$OR^{10c}$, —$SR^{10c}$, —$N(R^{10c})_2$, —$NO_2$, and —CN; $C_{1-6}$ alkyl, optionally substituted with one or more substituents independently selected from halogen, —$OR^{10c}$, —$SR^{10c}$, —$N(R^{10c})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10c}$, —$SR^{10c}$, —$N(R^{10c})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$. In some embodiments, $R^5$ and $R^6$ are each independently selected from: hydrogen, halogen, —$OR^{10c}$, —$SR^{10c}$, —$N(R^{10c})_2$, —$NO_2$, and —CN; and $C_{1-6}$ alkyl; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$. In some embodiments, $R^5$ and $R^6$ are each independently selected from: hydrogen, halogen, —$OR^{10c}$, —$SR^{10c}$, —$N(R^{10c})_2$, —$NO_2$, and —CN; and $C_{1-6}$ alkyl. In some embodiments, $R^5$ and $R^6$ are each independently selected from: hydrogen and $C_{1-3}$ alkyl. In some embodiments, $R^5$ is hydrogen. In some embodiments, $R^6$ is hydrogen. In some embodiments, $R^5$ and $R^6$ are each hydrogen. In some embodiments, $R^5$ and $R^6$ are each independently selected from: hydrogen and —$CH_3$, or $R^5$ and $R^6$ together form a cyclopropyl.

In certain embodiments, for a compound or salt of Formula (III), $R^7$ is selected from: hydrogen and $C_{1-6}$ alkyl optionally substituted with one or more substituents independently selected from halogen, —$OR^{10a}$, —$SR^{10d}$, —$N(R^{10a})_2$, —$NO_2$, and —CN. In some embodiments for a compound or salt of formula (III), $R^7$ is selected from hydrogen and $C_{1-6}$ alkyl optionally substituted with one or more substituents independently selected from halogen. In some embodiments, $R^7$ is selected from hydrogen.

In certain embodiments, for a compound or salt of Formula (III), $R^8$ is selected from:

hydrogen; and $C_{1-6}$ alkyl optionally substituted with one or more substituents independently selected from halogen, —$OR^{10e}$, —$SR^{10e}$, —$N(R^{10e})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10e}$, —$SR^{10e}$, —$N(R^{10e})_2$, —$NO_2$, and —CN.

In some embodiments, for a compound or salt of formula (III), $R^8$ is selected from: hydrogen; and $C_{1-6}$ alkyl optionally substituted with one or more substituents independently selected from halogen, —$OR^{10e}$, —$SR^{10e}$, —$N(R^{10e})_2$, —$NO_2$, and —CN. In some embodiments, for a compound or salt of formula (III), $R^8$ is selected from: hydrogen; and $C_{1-6}$ alkyl optionally substituted with one or more substituents independently selected from halogen and —CN. In some embodiments, $R^8$ is selected from hydrogen.

In certain embodiments, for a compound or salt of Formula (III), each $R^{9a}$ is independently selected from:

halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN.

In some embodiments, each $R^{9a}$ is independently selected from: halogen, —$OR^{10a}$, —$SR^{10a}$, —$N(R^{10a})_2$, —$C(O)R^{10a}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$NO_2$, =O, and —CN. In some embodiments, each $R^{9a}$ is independently selected from: halogen, —$OR^{10a}$, —$SR^{10a}$, —$N(R^{10a})_2$, —$C(O)R^{10a}$, —$NO_2$, =O, and —CN; and $C_{1-3}$ alkyl optionally substituted with one or more substituents independently selected from halogen, —$OR^{10a}$, —$SR^{10a}$, —$N(R^{10a})_2$, —$C(O)R^{10a}$, —$NO_2$, =O, and —CN. In some embodiments, each $R^{9a}$ is independently selected from: F, Cl, Br, —$OR^{10a}$, —$N(R^{10a})_2$, —$NO_2$, =O, and —CN; and $C_{1-3}$ alkyl optionally substituted with one or more substituents independently selected from F, Cl, Br, —$OR^{10a}$, —$N(R^{10a})_2$, —$NO_2$, =O, and —CN. In some embodiments, each $R^{9a}$ is independently selected from: F, Cl, —$OR^{10a}$, —$N(R^{10a})_2$, —$NO_2$, =O, and —CN; and $C_{1-3}$ alkyl optionally substituted with one or more substituents independently selected from F, Cl, —$OR^{10a}$, —$N(R^{10a})_2$, —$NO_2$, =O, and —CN. In some embodiments, each $R^{9a}$ is independently selected from: F, Cl, —$NO_2$, =O, and —CN; and $C_{1-3}$ alkyl optionally substituted with one or more substituents independently selected from F, Cl, —$NO_2$, =O, and —CN. In some embodiments, each $R^{9a}$ is independently selected from F and CN. In some embodiments, each $R^{9a}$ is independently selected from —F. In some embodiments, each $R^{9a}$ is independently selected from —CN.

In certain embodiments, for a compound or salt of Formula (III), each $R^{9b}$ is independently selected from:

halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN.

In some embodiments, each $R^{9b}$ is independently selected from: halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —C(O)OR$^{10b}$, —OC(O)R$^{10b}$, —NO$_2$, =O, and —CN. In some embodiments, each R$^{9b}$ is independently selected from: halogen, —OR$^{10b}$, —SR$^{10b}$, —N(R$^{10b}$)$_2$, —NO$_2$, =O, and —CN; and C$_{1-3}$ alkyl, optionally substituted with one or more substituents independently selected from halogen, —OR$^{10b}$, —SR$^{10b}$, —N(R$^{10b}$)$_2$, —NO$_2$, =O, and —CN. In some embodiments, each R$^{9b}$ is independently selected from: halogen, —OR$^{10b}$, —SR$^{10b}$, —N(R$^{10b}$)$_2$, —NO$_2$, =O, and —CN; and C$_{1-3}$ alkyl, optionally substituted with one or more substituents independently selected from halogen, —OR$^{10b}$, —SR$^{10b}$, —N(R$^{10b}$)$_2$, —NO$_2$, =O, and —CN. In some embodiments, each R$^{9b}$ is independently selected from fluoro, chloro, bromo, methoxy, methyl, and trifluoromethyl. In some embodiments, each R$^{9b}$ is independently selected from halogen and —CN. In some embodiments, each R$^{9b}$ is independently selected from —F, —Cl, and —CN. In some embodiments, each R$^{9b}$ is independently selected from —F and —CN. In some embodiments, each R$^{9b}$ is independently selected from —F. In some embodiments, each R$^{9b}$ is independently selected from —CN. In some embodiments, —F, —Cl, —Br, —CN, —OH, —OCH$_3$, —CH$_3$, —CF$_3$, —C(O)NH$_2$,

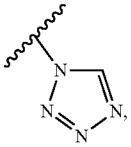, 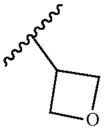, and —CCH.

In certain embodiments, for a compound or salt of Formula (III), each R$^{9c}$ is independently selected from:

halogen, —OR$^{10c}$, —SR$^{10c}$, —N(R$^{10c}$)$_2$, —C(O)R$^{10c}$, —C(O)N(R$^{10c}$)$_2$, —N(R$^{10c}$)C(O)R$^{10c}$, —N(R$^{10c}$)C(O)N(R$^{10c}$)$_2$, —OC(O)N(R$^{10c}$)$_2$, —N(R$^{10c}$)C(O)OR$^{10c}$, —C(O)OR$^{10c}$, —OC(O)R$^{10c}$, —S(O)R$^{10c}$, —S(O)$_2$R$^{10c}$, —NO$_2$, =O, =S, =N(R$^{10c}$), and —CN; and C$_{1-3}$ alkyl, C$_{2-3}$ alkenyl, and C$_{2-3}$ alkynyl, each of which is optionally substituted with one or more substituents independently selected from halogen, —OR$^{10c}$, —SR$^{10c}$, —N(R$^{10c}$)$_2$, —C(O)R$^{10c}$, —C(O)N(R$^{10c}$)$_2$, —N(R$^{10c}$)C(O)R$^{10c}$, —N(R$^{10c}$)C(O)N(R$^{10c}$)$_2$, —OC(O)N(R$^{10c}$)$_2$, —N(R$^{10c}$)C(O)OR$^{10c}$, —C(O)OR$^{10c}$, —OC(O)R$^{10c}$, —S(O)R$^{10c}$, —S(O)$_2$R$^{10c}$, —NO$_2$, =O, =S, =N(R$^{10c}$), and —CN.

In some embodiments, each R$^{9c}$ is independently selected from halogen, —OR$^{10c}$, —SR$^{10c}$, —N(R$^{10c}$)$_2$, —C(O)R$^{10c}$, —NO$_2$, =O, and —CN; and C$_{1-3}$ alkyl, C$_{2-3}$ alkenyl, and C$_{2-3}$ alkynyl, each of which is optionally substituted with one or more substituents independently selected from halogen, —OR$^{10c}$, —SR$^{10c}$, —N(R$^{10c}$)$_2$, —C(O)R$^{10c}$, —NO$_2$, =O, and —CN. In some embodiments, each R$^{9c}$ is independently selected from halogen, —OR$^{10c}$, —SR$^{10c}$, —N(R$^{10c}$)$_2$, —C(O)R$^{10c}$, —NO$_2$, =O, and —CN; and C$_{1-3}$ alkyl, optionally substituted with one or more substituents independently selected from halogen, —OR$^{10c}$, —SR$^{10c}$, —N(R$^{10c}$)$_2$, —C(O)R$^{10c}$, —NO$_2$, =O, and —CN. In some embodiments, each R$^{9c}$ is independently selected from F, Cl, Br, —OR$^{10c}$, —SR$^{10c}$, —N(R$^{10c}$)$_2$, —C(O)R$^{10c}$, —NO$_2$, =O, and —CN; and C$_{1-3}$ alkyl, optionally substituted with one or more substituents independently selected from F, Cl, Br, —OR$^{10c}$, —SR$^{10c}$, —N(R$^{10c}$)$_2$, —C(O)R$^{10c}$, —NO$_2$, =O, and —CN. In some embodiments, each R$^{9c}$ is independently selected from F, Cl, —OR$^{10c}$, —SR$^{10c}$, —N(R$^{10c}$)$_2$, —C(O)R$^{10c}$, —NO$_2$, =O, and —CN; and C$_{1-3}$ alkyl, optionally substituted with one or more substituents independently selected from F, Cl, —OR$^{10c}$, —SR$^{10c}$, —N(R$^{10c}$)$_2$, —C(O)R$^{10c}$, —NO$_2$, =O, and —CN. In some embodiments, each R$^{9c}$ is independently selected from F, Cl, Br, —OR$^{10c}$, —N(R$^{10c}$)$_2$, —C(O)R$^{10c}$, —NO$_2$, =O, and —CN; and C$_{1-3}$ alkyl, optionally substituted with one or more substituents independently selected from F, Cl, Br, —OR$^{10c}$, —N(R$^{10c}$)$_2$, —C(O)R$^{10c}$, —NO$_2$, =O, and —CN. In some embodiments, each R$^{9c}$ is independently selected from F, Cl, Br, —NO$_2$, =O, and —CN; and C$_{1-3}$ alkyl, optionally substituted with one or more substituents independently selected from F, Cl, Br, —NO$_2$, =O, and —CN. In some embodiments, each R$^{9c}$ is independently selected from F, Cl, —NO$_2$, =O, and —CN; and C$_{1-3}$ alkyl, optionally substituted with one or more substituents independently selected from F, Cl, —NO$_2$, =O, and —CN. In some embodiments, each R$^{9c}$ is independently selected from —F and —CN. In some embodiments, each R$^{9c}$ is independently selected from —F. In some embodiments, each R$^{9c}$ is independently selected from —CN.

In certain embodiments, for a compound or salt of Formula (III), each R$^{10a}$, R$^{10b}$, R$^{10c}$, R$^{10d}$, and R$^{10e}$ is independently selected from:

hydrogen;

C$_{1-6}$ alkyl, C$_{2-6}$ alkenyl, and C$_{2-6}$ alkynyl, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{3-10}$ carbocycle, 3- to 10-membered heterocycle; and C$_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and C$_{1-6}$ haloalkyl.

In certain embodiments, for a compound or salt of Formula (III), each R$^{10a}$ is independently selected from: hydrogen; C$_{1-6}$ alkyl, C$_{2-6}$ alkenyl, and C$_{2-6}$ alkynyl, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{3-10}$ carbocycle, 3- to 10-membered heterocycle; and C$_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and C$_{1-6}$ haloalkyl. In some embodiments, each R$^{10a}$ is independently selected from hydrogen; and C$_{1-6}$ alkyl, optionally substituted with one or more substituents independently selected from halogen, —CN, —OH, —SH, —NO$_2$, —NH$_2$, =O, —O—C$_{1-6}$ alkyl, —N(C$_{1-6}$ alkyl)$_2$, and —NH(C$_{1-6}$ alkyl); and C$_{3-10}$ carbocycle, and 3- to 10-membered heterocycle, each of which is optionally substituted with one or more substituents independently selected from halogen, —CN, —OH, —SH, —NO$_2$, —NH$_2$, =O, —O—C$_{1-6}$ alkyl, —N(C$_{1-6}$ alkyl)$_2$, —NH(C$_{1-6}$ alkyl), C$_{1-6}$ alkyl, and C$_{1-6}$ haloalkyl. In some embodiments, each R$^{10a}$ is independently selected from hydrogen; and C$_{1-6}$ alkyl, optionally substituted with one or more substituents independently selected from halogen, —CN, —OH, —SH, —NO$_2$, —NH$_2$, and =O; and C$_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —N($C_{1-6}$ alkyl)$_2$, —NH($C_{1-6}$ alkyl), $C_{1-6}$ alkyl, and $C_{1-6}$ haloalkyl. In some embodiments, each $R^{10a}$ is independently selected from hydrogen; and $C_{1-6}$ alkyl optionally substituted with one or more substituents independently selected from halogen; and $C_{3-10}$ carbocycle, and 3- to 10-membered heterocycle. In some embodiments, each $R^{10a}$ is independently selected from hydrogen; and $C_{1-6}$ alkyl optionally substituted with one or more substituents independently selected from fluorine and chlorine; and $C_{3-10}$ carbocycle, and 3- to 10-membered heterocycle. In some embodiments, each $R^{10a}$ is independently selected from hydrogen; and $C_{1-6}$ alkyl optionally substituted with fluorine; and $C_{3-10}$ carbocycle, and 3- to 10-membered heterocycle. In some embodiments, each $R^{10a}$ is independently selected from hydrogen; and $C_{1-6}$ alkyl optionally substituted with fluorine; and $C_{3-10}$ carbocycle, and 3- to 10-membered heterocycle selected from cyclopropane and oxetane. In some embodiments, each $R^{10a}$ is hydrogen. In some embodiments, each $R^{10a}$ is methyl.

In certain embodiments, for a compound or salt of Formula (III), each $R^{10b}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, each $R^{10b}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, and —NH($C_{1-6}$ alkyl); and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, and $C_{1-6}$ haloalkyl. In some embodiments, each $R^{10b}$ is independently selected from: hydrogen; and $C_{1-6}$ alkyl. In some embodiments, each $R^{10b}$ is hydrogen. In some embodiments, each $R^{10b}$ is methyl.

In certain embodiments, for a compound or salt of Formula (III), each $R^{10b}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, each $R^{10c}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. In some embodiments, each $R^{10c}$ is independently selected from: hydrogen; and $C_{1-6}$ alkyl. In some embodiments, each $R^{10c}$ is hydrogen. In some embodiments, each $R^{10c}$ is methyl.

In certain embodiments, for a compound or salt of Formula (III), each $R^{10d}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, each $R^{10d}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. In some embodiments, each $R^{10d}$ is independently selected from: hydrogen; and $C_{1-6}$ alkyl. In some embodiments, each $R^{10d}$ is hydrogen. In some embodiments, $R^{10d}$ is methyl.

In certain embodiments, for a compound or salt of Formula (III), each $R^{10e}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, each $R^{10e}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. In some embodiments, each $R^{10e}$ is independently selected from: hydrogen; and $C_{1-6}$ alkyl. In some embodiments, each $R^{10e}$ is hydrogen. In some embodiments, $R^{10e}$ is methyl.

In certain embodiments, for a compound or salt of Formula (III), if $X^3$ and $X^1$ are both N, then $R^8$ is selected from hydrogen and $C_{1-4}$ alkyl optionally substituted with one or more substituents independently selected from halogen, —$OR^{10}$, —$SR^{10}$, —N($R^{10}$)$_2$, —$NO_2$, and —CN. In some embodiments, if $X^3$ and $X^1$ are both N, then $R^8$ is selected from hydrogen and $C_{1-4}$ alkyl optionally substituted with one or more substituents independently selected from halogen, —$OR^{10}$, and —CN. In some embodiments, if $X^3$ and $X^1$ are both N, then $R^8$ is selected from hydrogen and $C_{1-4}$ alkyl optionally substituted with one or more substituents independently selected from fluoro, —OH, and —CN. In some embodiments, if $X^3$ and $X^1$ are both N, then $R^8$ is selected from hydrogen and $C_{1-4}$ alkyl. In some embodiments, if $X^3$ and $X^1$ are both N, then $R^8$ is selected from hydrogen and $C_1$ alkyl. In some embodiments, if $X^3$ and $X^1$ are both N, then $R^8$ is selected from hydrogen.

In some embodiments, the compound or salt of Formula (III) is selected from: $N_{87}$, $N_4$, $N_5$, $N_{13}$, $N_{15}$, $N_{123}$, $N_{33}$, $N_{111}$, $N_{124}$, $N_{128}$, B75, B36, B31, B45, B39, B145, B33, B206, B92, B82, B189, B278, B221, B238, B236, B100, B103, B23, B9, B62, B123, B43, B324, B83, B142, B77, B57, B78, B191, B232, B79, B314, B110, B55, B307, B147, B315, B139, B355, B225, B248, B222, B272, B266, B141, B120, B13, B332, B269, B281, B229, B65, B17, B227, B247, B176, B291, B80, B322, B319, B118, B4, B6, B214, B89, B126, B296, B249, B366, B133, B30, B303, B132, B330, B338, B1, B233, B81, B106, B94, B199, B53, B128, B356, B306, B312, B336, B323, B358, B164, and B102.

In some embodiments, the compound or salt of Formula (III) is selected from: N87, N4, N5, N13, N15, N123, N33, N111, N124, N128, N7, N18, N68, N88, N26, N103, N104, N117, N110, N37, N102, N94, N112, N81, N54, N101, N23, N136, N9, N98, N122, N31, N28, N115, N121, N74, N119, N16, N126, N47, N125, N83, N118, N10, and N62, B75, B36, B31, B45, B39, B145, B33, B206, B92, B82, B189, B278, B221, B238, B236, B100, B103, B23, B9, B62, B123, B43, B324, B83, B142, B77, B57, B78, B191, B232, B79, B314, B110, B55, B307, B147, B315, B139, B355, B225, B248, B222, B272, B266, B120, B13, B332, B269, B281, B229, B65, B17, B227, B247, B176, B291, B80, B322, B319, B118, B4, B6, B214, B89, B126, B296, B249, B366, B133, B30, B303, B132, B330, B338, B1, B233, B81, B106, B94, B199, B53, B128, B356, B306, B312, B336, B323, B358, B164, B102, B29, B279, B54, B241, B268, B105, B121, B114, B137, B217, B84, B181, B141, B226, B91, B14, B101, B169, B117, B326, B113, B310, B292, B34, B152, B321, B202, B210, B154, B267, B327, B87, B243, B329, B130, B231, B354, B116, B349, B346, B230, B339, B320, B16, B295, B290, B127, B234, B288, B129, B204, B37, B32, B237, B350, B367, B228, B70, B124, B160, B331, B76, B85, B136, B52, B188, B8, B155, B223, B44, B7, B88, B108, B135, B64, B264, B119, B286, B35, B334, B46, B42, B69, B352, B280, B59, B25, B99, B144, B341, B60, B148, B284, B12, B283, B342, B245, B2, B38, and B150.

In some embodiments, the compound or salt of Formula (III) is selected from: N87, N4, N5, N13, N15, N123, N33, N111, N124, N128, N7, N18, N68, N88, N26, N103, N104, N117, N110, N37, N102, N94, N112, N81, N54, N101, N23, N136, N9, N98, N122, N31, N28, N115, N121, N74, N119, N16, N126, N47, N125, N83, N118, N10, N62, N41, N60, N14, N44, N108, N130, N93, N19, N77, N8, N114, N106, N3, N133, N6, N24, N127, N72, N84, N95, N132, N129, N21, N116, N55, N109, N35, N135, N59, N12, N36, N80, N99, N34, N39, N50, B75, B36, B31, B45, B39, B145, B33, B206, B92, B82, B189, B278, B221, B238, B236, B100, B103, B23, B9, B62, B123, B43, B324, B83, B142, B77, B57, B78, B191, B232, B79, B314, B110, B55, B307, B147, B315, B139, B355, B225, B248, B222, B272, B266, B120, B13, B332, B269, B281, B229, B65, B17, B227, B247, B176, B291, B80, B322, B319, B118, B4, B6, B214, B89, B126, B296, B249, B366, B133, B30, B303, B132, B330, B338, B1, B233, B81, B106, B94, B199, B53, B128, B356, B306, B312, B336, B323, B358, B164, B102, B29, B279, B54, B241, B268, B105, B121, B114, B137, B217, B84, B181, B141, B226, B91, B14, B101, B169, B117, B326, B113, B310, B292, B34, B152, B321, B202, B210, B154, B267, B327, B87, B243, B329, B130, B231, B354, B116, B349, B346, B230, B339, B320, B16, B295, B290, B127, B234, B288, B129, B204, B37, B32, B237, B350, B367, B228, B70, B124, B160, B331, B76, B85, B136, B52, B188, B8, B155, B223, B44, B7, B88, B108, B135, B64, B264, B119, B286, B35, B334, B46, B42, B69, B352, B280, B59, B25, B99, B144, B341, B60, B148, B284, B12, B283, B342, B245, B2, B38, B150, B337, B58, B325, B302, B140, B274, B304, B235, B270, B73, B74, B93, B344, B122, B300, B97, B112, B212, B146, B138, B328, B95, B357, B125, B56, B41, B63, B265, B96, B273, B297, B353, B68, B205, B163, B27, B18, B72, B182, B313, B200, B244, B104, B170, B172, B178, B194, B340, B156, B343, B161, B301, B134, B359, B203, B157, B28, B49, B275, B218, B251, and B335.

In some embodiments, the compound or salt of Formula (III) is selected from: N87, N4, N5, N13, N15, N123, N33, N111, N124, N128, N7, N18, N68, N88, N26, N103, N104, N117, N110, N37, N102, N94, N112, N81, N54, N101, N23, N136, N9, N98, N122, N31, N28, N115, N121, N74, N119, N16, N126, N47, N125, N83, N118, N10, N62, N41, N60, N14, N44, N108, N130, N93, N19, N77, N8, N114, N106, N3, N133, N6, N24, N127, N72, N84, N95, N132, N129, N21, N116, N55, N109, N35, N135, N59, N12, N36, N80, N99, N34, N39, N50, N57, N25, N45, N2, N85, N113, N64, N78, N66, N86, N43, N30, N131, N71, N91, N38, N1, N17, N40, N52, B75, B36, B31, B45, B39, B145, B33, B206, B92, B82, B189, B278, B221, B238, B236, B100, B103, B23, B9, B62, B123, B43, B324, B83, B142, B77, B57, B78, B191, B232, B79, B314, B110, B55, B307, B147, B315, B139, B355, B225, B248, B222, B272, B266, B120, B13, B332, B269, B281, B229, B65, B17, B227, B247, B176, B291, B80, B322, B319, B118, B4, B6, B214, B89, B126, B296, B249, B366, B133, B30, B303, B132, B330, B338, B1, B233, B81, B106, B94, B199, B53, B128, B356, B306, B312, B336, B323, B358, B164, B102, B29, B279, B54, B241, B268, B105, B121, B114, B137, B217, B84, B181, B141, B226, B91, B14, B101, B169, B117, B326, B113, B310, B292, B34, B152, B321, B202, B210, B154, B267, B327, B87, B243, B329, B130, B231, B354, B116, B349, B346, B230, B339, B320, B16, B295, B290, B127, B234, B288, B129, B204, B37, B32, B237, B350, B367, B228, B70, B124, B160, B331, B76, B85, B136, B52, B188, B8, B155, B223, B44, B7, B88, B108, B135, B64, B264, B119, B286, B35, B334, B46, B42, B69, B352, B280, B59, B25, B99, B144, B341, B60, B148, B284, B12, B283, B342, B245, B2, B38, B150, B337, B58, B325, B302, B140, B274, B304, B235, B270, B73, B74, B93, B344, B122, B300, B97, B112, B212, B146, B138, B328, B95, B357, B125, B56, B41, B63, B265, B96, B273, B297, B353, B68, B205, B163, B27, B18, B72, B182, B313, B200, B244, B104, B170, B172, B178, B194, B340, B156, B343, B161, B301, B134, B359, B203, B157, B28, B49, B275, B218, B251, B335, B348, B309, B22, B90, B209, B109, B153, B165, B190, B197, B171, B364, B308, B240, B201, B193, B224, B3, B71, B67, B360, B174, B294, B51, B166, B162, B220, B345, B184, B242, B299, B187, B149, B287, B256, B277, B250, B252, B282, and B213.

In some embodiments, the compound or salt of Formula (III) is selected from: N87, N4, N5, N13, N15, N123, N33, N111, N124, N128, N7, N18, N68, N88, N26, N103, N104, N117, N110, N37, N102, N94, N112, N81, N54, N101, N23, N136, N9, N98, N122, N31, N28, N115, N121, N74, N119, N16, N126, N47, N125, N83, N118, N10, N62, N41, N60, N14, N44, N108, N130, N93, N19, N77, N8, N114, N106, N3, N133, N6, N24, N127, N72, N84, N95, N132, N129, N21, N116, N55, N109, N35, N135, N59, N12, N36, N80, N99, N34, N39, N50, N57, N25, N45, N2, N85, N113, N64, N78, N66, N86, N43, N30, N131, N71, N91, N38, N1, N17, N40, N52, N11, N20, N22, N27, N29, N32, N42, N46, N48, N49, N51, N53, N56, N58, N61, N63, N65, N67, N69, N70, N73, N75, N76, N79, N82, N89, N90, N92, N96, N97, N100, N105, N107, N120, B75, B36, B31, B45, B39, B145, B33, B206, B92, B82, B189, B278, B221, B238, B236, B100, B103, B23, B9, B62, B123, B43, B324, B83, B142, B77, B57, B78, B191, B232, B79, B314, B110, B55, B307, B147, B315, B139, B355, B225, B248, B222, B272, B266, B120, B13, B332, B269, B281, B229, B65, B17, B227, B247, B176, B291, B80, B322, B319, B118, B4, B6, B214, B89, B126, B296, B249, B366, B133, B30, B303, B132, B330, B338, B1, B233, B81, B106, B94, B199, B53, B128, B356, B306, B312, B336, B323, B358, B164, B102, B29, B279, B54, B241, B268, B105, B121, B114, B137, B217, B84, B181, B141, B226, B91, B14, B101, B169, B117, B326, B113, B310, B292, B34, B152, B321, B202, B210, B154, B267, B327, B87, B243, B329, B130, B231, B354, B116, B349, B346, B230, B339, B320, B16, B295, B290, B127, B234, B288, B129, B204, B37, B32, B237, B350, B367, B228, B70, B124, B160, B331, B76, B85, B136, B52, B188, B8, B155, B223, B44, B7, B88, B108, B135, B64, B264, B119, B286, B35, B334, B46, B42, B69, B352, B280, B59, B25, B99, B144, B341, B60, B148, B284, B12, B283, B342, B245, B2, B38, B150, B337, B58, B325, B302, B140, B274, B304, B235, B270, B73, B74, B93, B344, B122, B300, B97, B112, B212, B146, B138, B328, B95, B357, B125, B56, B41, B63, B265, B96, B273, B297, B353, B68, B205, B163, B27, B18, B72, B182, B313, B200, B244, B104, B170, B172, B178, B194, B340, B156, B343, B161, B301, B134, B359, B203, B157, B28, B49, B275, B218, B251, B335, B348, B309, B22, B90, B209, B109, B153, B165, B190, B197, B171, B364, B308, B240, B201, B193, B224, B3, B71, B67, B360, B174, B294, B51, B166, B162, B220, B345, B184, B242, B299, B187, B149, B287, B256, B277, B250, B252, B282, B213, B362, B10, B40, B276, B50, B271, B48, B98, B246, B311, B47, B5, B11, B15, B19, B20, B21, B24, B26, B61, B66, B86, B107, B111, B115, B131, B143, B151, B158, B159, B167, B168, B173, B175, B177, B180, B183, B185, B186, B192, B195, B196, B198, B207, B208, B211, B215, B216, B219, B239, B253, B254, B255, B285, B289, B333, B347, B351, B361, B363, B365, B179, B257, B258, B259, B262, B263, and B293.

In some embodiments, the compound or salt of Formula (III) is selected from: $N_5$, $N_{23}$, $N_{87}$, $N_{124}$, $N_{128}$, $N_7$, $N_{33}$, $N_{117}$, $N_4$, and $N_{94}$.

In some embodiments, the compound or salt of Formula (III) is selected from: $N_5$, $N_{23}$, $N_{87}$, $N_{124}$, $N_{128}$, $N_7$, $N_{33}$, $N_{117}$, $N_4$, $N_{94}$, $N_{81}$, $N_{88}$, $N_{115}$, $N_{13}$, $N_{123}$, B75, B36, B23, B9, B62, B31, B45, B123, B43, B206, B39, B324, B145, B92, B83, B55, B142, B82, B1, B322, B326, B33, B307, B77, B189, B147, B120, B14, B13, B57, B278, B303, B315, B319, B332, B128, B221, B78, B118, B4, B139, B355, B356, B12, B238, B6, B269, B281, B229, B121, B65, B114, B132, B306, B312, B17, B225, B330, B191, B226, B236, B113, B320, B214, B89, B227, B233, B336, B248, B152, B247, B69, B323, B358, B164, B126, B76, B295, B341, B310, B176, B296, B232, B81, B329, B222, B284, B79, B106, B37, B314, B350, B44, B292, B94, B32, B367, B110, B199, B101, B64, B8, B249, B116, B29, B137, B279, B100, B272, B136, B366, B91, B349, B264, B217, B130, B35, B59, B54, and B321.

In some embodiments, the compound or salt of Formula (III) is selected from: N5, N23, N87, N124, N128, N7, N33, N117, N4, N94, N81, N88, N115, N13, N123, N31, N26, N18, N74, N68, N101, N102, N41, N125, N15, N54, N9, N119, N126, N104, N37, N129, N62, N118, N95, N121, N47, N28, N111, N114, N112, and N103, B75, B36, B23, B9, B62, B31, B45, B123, B43, B206, B39, B324, B145, B92, B83, B55, B142, B82, B1, B322, B326, B33, B307, B77, B189, B147, B120, B14, B13, B57, B278, B303, B315, B319, B332, B128, B221, B78, B118, B4, B139, B355, B356, B12, B238, B6, B269, B281, B229, B121, B65, B114, B132, B306, B312, B17, B225, B330, B191, B226, B236, B113, B320, B214, B89, B227, B233, B336, B248, B152, B247, B69, B323, B358, B164, B126, B76, B295, B341, B310, B176, B296, B232, B81, B329, B222, B284, B79, B106, B37, B314, B350, B44, B292, B94, B32, B367, B110, B199, B101, B64, B8, B249, B116, B29, B137, B279, B100, B272, B136, B366, B91, B349, B264, B217, B130, B35, B59, B54, B321, B202, B362, B16, B70, B103, B68, B241, B169, B266, B327, B41, B204, B300, B52, B84, B234, B231, B334, B346, B338, B188, B230, B46, B291, B124, B181, B133, B117, B56, B87, B228, B339, B73, B297, B353, B210, B112, B88, B352, B25, B154, B80, B7, B302, B268, B141, B155, B42, B325, B108, B34, B223, B38, B354, B313, B267, B304, B58, B160, B97, B244, B342, B290, B288, B265, B93, B148, B102, B105, B22, B283, B280, B348, B337, B53, B119, B2, B237, B10, B286, B344, B67, and B360.

In some embodiments, the compound or salt of Formula (III) is selected from: N5, N23, N87, N124, N128, N7, N33, N117, N4, N94, N81, N88, N115, N13, N123, N31, N26, N18, N74, N68, N101, N102, N41, N125, N15, N54, N9, N119, N126, N104, N37, N129, N62, N118, N95, N121, N47, N28, N111, N114, N112, N103, N136, N122, N19, N8, N10, N21, N133, N44, N110, N77, N36, N120, N78, N2, N24, N6, N72, N116, N108, N39, N98, N127, N113, N60, N132, B75, B36, B23, B9, B62, B31, B45, B123, B43, B206, B39, B324, B145, B92, B83, B55, B142, B82, B1, B322, B326, B33, B307, B77, B189, B147, B120, B14, B13, B57, B278, B303, B315, B319, B332, B128, B221, B78, B118, B4, B139, B355, B356, B12, B238, B6, B269, B281, B229, B121, B65, B114, B132, B306, B312, B17, B225, B330, B191, B226, B236, B113, B320, B214, B89, B227, B233, B336, B248, B152, B247, B69, B323, B358, B164, B126, B76, B295, B341, B310, B176, B296, B232, B81, B329, B222, B284, B79, B106, B37, B314, B350, B44, B292, B94, B32, B367, B110, B199, B101, B64, B8, B249, B116, B29, B137, B279, B100, B272, B136, B366, B91, B349, B264, B217, B130, B35, B59, B54, B321, B202, B362, B16, B70, B103, B68, B241, B169, B266, B327, B41, B204, B300, B52, B84, B234, B231, B334, B346, B338, B188, B230, B46, B291, B124, B181, B133, B117, B56, B87, B228, B339, B73, B297, B353, B210, B112, B88, B352, B25, B154, B80, B7, B302, B268, B141, B155, B42, B325, B108, B34, B223, B38, B354, B313, B267, B304, B58, B160, B97, B244, B342, B290, B288, B265, B93, B148, B102, B105, B22, B283, B280, B348, B337, B53, B119, B2, B237, B10, B286, B344, B67, B360, B309, B156, B243, B245, B301, B212, B27, B135, B205, B40, B172, B273, B150, B203, B276, B85, B163, B170, B294, B193, B71, B50, B161, B49, B256, B144, B190, B3, B271, B140, B184, B250, B252, B48, B331, B146, B98, B277, B246, B194, B200, B311, B134, B274, B127, and B47.

In some embodiments, the compound or salt of Formula (III) is selected from: N5, N23, N87, N124, N128, N7, N33, N117, N4, N94, N81, N88, N115, N13, N123, N31, N26, N18, N74, N68, N101, N102, N41, N125, N15, N54, N9, N119, N126, N104, N37, N129, N62, N118, N95, N121, N47, N28, N111, N114, N112, N103, N136, N122, N19, N8, N10, N21, N133, N44, N110, N77, N36, N120, N78, N2, N24, N6, N72, N116, N108, N39, N98, N127, N113, N60, N132, N1, N3, N11, N12, N14, N16, N17, N20, N22, N25, N27, N29, N30, N32, N34, N35, N38, N40, N42, N43, N45, N46, N48, N49, N50, N51, N52, N53, N55, N56, N57, N58, N59, N61, N63, N64, N65, N66, N67, N69, N70, N71, N73, N75, N76, N79, N80, N82, N83, N84, N85, N86, N89, N90, N91, N92, N93, N96, N97, N99, N100, N105, N106, N107, N109, N130, N131, N135, B75, B36, B23, B9, B62, B31, B45, B123, B43, B206, B39, B324, B145, B92, B83, B55, B142, B82, B1, B322, B326, B33, B307, B77, B189, B147, B120, B14, B13, B57, B278, B303, B315, B319, B332, B128, B221, B78, B118, B4, B139, B355, B356, B12, B238, B6, B269, B281, B229, B121, B65, B114, B132, B306, B312, B17, B225, B330, B191, B226, B236, B113, B320, B214, B89, B227, B233, B336, B248, B152, B247, B69, B323, B358, B164, B126, B76, B295, B341, B310, B176, B296, B232, B81, B329, B222, B284, B79, B106, B37, B314, B350, B44, B292, B94, B32, B367, B110, B199, B101, B64, B8, B249, B116, B29, B137, B279, B100, B272, B136, B366, B91, B349, B264, B217, B130, B35, B59, B54, B321, B202, B362, B16, B70, B103, B68, B241, B169, B266, B327, B41, B204, B300, B52, B84, B234, B231, B334, B346, B338, B188, B230, B46, B291, B124, B181, B133, B117, B56, B87, B228, B339, B73, B297, B353, B210, B112, B88, B352, B25, B154, B80, B7, B302, B268, B141, B155, B42, B325, B108, B34, B223, B38, B354, B313, B267, B304, B58, B160, B97, B244, B342, B290, B288, B265, B93, B148, B102, B105, B22, B283, B280, B348, B337, B53, B119, B2, B237, B10, B286, B344, B67, B360, B309, B156, B243, B245, B301, B212, B27, B135, B205, B40, B172, B273, B150, B203, B276, B85, B163, B170, B294, B193, B71, B50, B161, B49, B256, B144, B190, B3, B271, B140, B184, B250, B252, B48, B331, B146, B98, B277, B246, B194, B200, B311, B134, B274, B127, B47, B5, B11, B15, B18, B19, B20, B21, B24, B26, B28, B30, B51, B60, B61, B63, B66, B72, B74, B86, B90, B95, B96, B99, B104, B107, B109, B111, B115, B122, B125, B129, B131, B138, B143, B149, B151, B153, B157, B158, B159, B162, B165, B166, B167, B168, B171, B173, B174, B175, B177, B178, B179, B180, B182, B183, B185, B186, B187, B192, B195, B196, B197, B198, B201, B207, B208, B209, B211, B213, B215, B216, B218, B219, B220, B224, B235, B239, B240, B242, B251, B253, B254, B255, B270, B275, B282, B285, B287, B289, B299, B308, B328, B333, B335, B340, B343, B345, B347, B351, B357, B359, B361, B363, B364, B365, B257, B258, B259, B262, B263, and B293.

In some embodiments, for a compound or salt of formula (III), each $R^1$ is independently selected from: hydrogen; deuterium, —N3, halogen, $—NO_2$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$; $C_{1-6}$ alkyl, $C_{2-6}$ alkenyl, and $C_{2-6}$ alkynyl, each of which is optionally substituted with one or more substituents independently selected from deuterium, —N3, halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2R^{10a}$, $—NO_2$, =O, =S, $=N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from deuterium, $—N_3$, halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, =O, =S, $=N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$. In some embodiments, $R^2$ is selected from $C_{1-6}$ alkyl, $C_{2-6}$ alkenyl, and $C_{2-6}$ alkynyl, each of which is optionally substituted with one or more substituents independently selected from deuterium, $—N_3$, halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—C(O)OR^{10b}$, $—OC(O)R^{10b}$, $—N(R^{10b})C(O)N(R^{10b})_2$, $—OC(O)N(R^{10b})_2$, $—N(R^{10b})C(O)OR^{10b}$, $—S(O)R^{10b}$, $—S(O)_2R^{10b}$, $—NO_2$, =O, =S, $=N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from deuterium, $—N_3$, halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—N(R^{10b})C(O)N(R^{10b})_2$, $—OC(O)N(R^{10b})_2$, $—N(R^{10b})C(O)OR^{10b}$, $—C(O)OR^{10b}$, $—OC(O)R^{10b}$, $—S(O)R^{10b}$, $—S(O)_2R^{10b}$, $—NO_2$, =O, =S, $=N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. In some embodiments, $R^3$ and $R^4$ are each independently selected from: ·hydrogen, deuterium, $—N_3$, halogen, $—OR^{10c}$, $—SR^{10c}$, $—N(R^{10c})_2$, $—NO_2$, and —CN; and $C_{1-6}$ alkyl optionally substituted with one or more substituents independently selected from deuterium, $—N_3$, halogen, $—OR^{10c}$, $—SR^{10c}$, $—N(R^{10c})_2$, $—NO_2$, and —CN; or ·$R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$. In some embodiments, $R^5$ and $R^6$ are each independently selected from: hydrogen, deuterium, $—N_3$, halogen, $—OR^{10c}$, $—SR^{10c}$, $—N(R^{10c})_2$, $—NO_2$, and —CN; $C_{1-6}$ alkyl, optionally substituted with one or more substituents independently selected from deuterium, $—N_3$, halogen, $—OR^{10c}$, $—SR^{10c}$, $—N(R^{10c})_2$, $—NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from deuterium, $—N_3$, halogen, $—OR^{10c}$, $—SR^{10c}$, $—N(R^{10c})_2$, $—NO_2$, and —CN; and $C_{3-10}$ carbocycle and 3- to 10-membered heterocycle, each of which is optionally substituted with one or more substituents independently selected from deuterium, $—N_3$, halogen, $—OR^{10c}$, $—SR^{10c}$, $—N(R^{10c})_2$, $—NO_2$, and —CN; or ·$R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$. In some embodiments, $R^7$ is selected from: ·hydrogen and $C_{1-6}$ alkyl optionally substituted with one or more substituents independently selected from deuterium, $—N_3$, halogen, $—OR^{10d}$, $—SR^{10d}$, $—N(R^{10d})_2$, $—NO_2$, and —CN. In some embodiments, $R^8$ is selected from: ·hydrogen; and $C_{1-6}$ alkyl optionally substituted with one or more substituents independently selected from deuterium, $—N_3$, halogen, $—OR^{10e}$, $—SR^{10e}$, $—N(R^{10e})_2$, $—NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from deuterium, $—N_3$, halogen, $—OR^{10e}$, $—SR^{10e}$, $—N(R^{10e})_2$, $—NO_2$, and —CN. In some embodiments, each $R^{9a}$ is independently selected from: deuterium, —$N_3$, halogen, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —N(R$^{10a}$)C(O)N(R$^{10a}$)$_2$, —OC(O)N(R$^{10a}$)$_2$, —N(R$^{10a}$)C(O)OR$^{10a}$, —C(O)OR$^{10a}$, —OC(O)R$^{10a}$, —S(O)R$^{10a}$, —S(O)$_2$R$^{10a}$, —NO$_2$, =O, =S, =N(R$^{10a}$), and —CN; and $C_{1-3}$ alkyl, $C_{2-3}$ alkenyl, and $C_{2-3}$ alkynyl, each of which is optionally substituted with one or more substituents independently selected from deuterium, —$N_3$, halogen, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —N(R$^{10a}$)C(O)N(R$^{10a}$)$_2$, —OC(O)N(R$^{10a}$)$_2$, —N(R$^{10a}$)C(O)OR$^{10a}$, —C(O)OR$^{10a}$, —OC(O)R$^{10a}$, —S(O)R$^{10a}$, —S(O)$_2$R$^{10a}$, —NO$_2$, =O, =S, =N(R$^{10a}$), and —CN. In some embodiments, each R$^{9b}$ is independently selected from: deuterium, —$N_3$, halogen, —OR$^{10b}$, —SR$^{10b}$, —N(R$^{10b}$)$_2$, —C(O)R$^{10b}$, —C(O)N(R$^{10b}$)$_2$, —N(R$^{10b}$)C(O)R$^{10b}$, —N(R$^{10b}$)C(O)N(R$^{10b}$)$_2$, —OC(O)N(R$^{10b}$)$_2$, —N(R$^{10b}$)C(O)OR$^{10b}$, —C(O)OR$^{10b}$, —OC(O)R$^{10b}$, —S(O)R$^{10b}$, —S(O)$_2$R$^{10b}$, —NO$_2$, =O, =S, =N(R$^{10b}$), and —CN; and $C_{1-3}$ alkyl, $C_{2-3}$ alkenyl, and $C_{2-3}$ alkynyl, each of which is optionally substituted with one or more substituents independently selected from deuterium, —$N_3$, halogen, —OR$^{10b}$, —SR$^{10b}$, —N(R$^{10b}$)$_2$, —C(O)R$^{10b}$, —C(O)N(R$^{10b}$)$_2$, —N(R$^{10b}$)C(O)R$^{10b}$, —N(R$^{10b}$)C(O)N(R$^{10b}$)$_2$, —OC(O)N(R$^{10b}$)$_2$, —N(R$^{10b}$)C(O)OR$^{10b}$, —C(O)OR$^{10b}$, —OC(O)R$^{10b}$, —S(O)R$^{10b}$, —S(O)$_2$R$^{10b}$, —NO$_2$, =O, =S, =N(R$^{10b}$) and —CN. In some embodiments, each R$^{9c}$ is independently selected from: deuterium, —$N_3$, halogen, —OR$^{10c}$, —SR$^{10c}$, —N(R$^{10c}$)$_2$, —C(O)R$^{10c}$, —C(O)N(R$^{10c}$)$_2$, —N(R$^{10c}$)C(O)R$^{10c}$, —N(R$^{10c}$)C(O)N(R$^{10c}$)$_2$, —OC(O)N(R$^{10c}$)$_2$, —N(R$^{10c}$)C(O)OR$^{10c}$, —C(O)OR$^{10c}$, —OC(O)R$^{10c}$, —S(O)R$^{10c}$, —S(O)$_2$R$^{10c}$, —NO$_2$, =O, =S, =N(R$^{10c}$), and —CN; and $C_{1-3}$ alkyl, $C_{2-3}$ alkenyl, and $C_{2-3}$ alkynyl, each of which is optionally substituted with one or more substituents independently selected from deuterium, —$N_3$, halogen, —OR$^{10c}$, —SR$^{10c}$, —N(R$^{10c}$)$_2$, —C(O)R$^{10c}$, —C(O)N(R$^{10c}$)$_2$, —N(R$^{10c}$)C(O)R$^{10c}$, —N(R$^{10c}$)C(O)N(R$^{10c}$)$_2$, —OC(O)N(R$^{10c}$)$_2$, —N(R$^{10c}$)C(O)OR$^{10c}$, —C(O)OR$^{10c}$, —OC(O)R$^{10c}$, —S(O)R$^{10c}$, —S(O)$_2$R$^{10c}$, —NO$_2$, =O, =S, =N(R$^{10c}$), and —CN. In some embodiments, each R$^{10a}$, R$^{10b}$, R$^{10c}$, R$^{10d}$, and R$^{10e}$ is independently selected from: hydrogen; $C_{1-6}$ alkyl, $C_{2-6}$ alkenyl, and $C_{2-6}$ alkynyl, each of which is optionally substituted with one or more substituents independently selected from deuterium, —$N_3$, halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from deuterium, —$N_3$, halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In some embodiments, for a compound or salt of formula (III), each R$^1$ is independently selected from: hydrogen; halogen, —NO$_2$, —CN, —OR$^{10a}$, —SR$^{10a}$, —N(R$^{10a}$)$_2$, —C(O)R$^{10a}$, and —C(O)N(R$^{10a}$)$_2$; $C_{1-6}$ alkyl, optionally substituted with one or more substituents independently selected from halogen, —OR$^{10a}$, —SR$^{10a}$, and —N(R$^{10a}$)$_2$; and $C_{3-10}$ carbocycle and 3- to 10-membered heterocycle, each of which is optionally substituted with one or more substituents independently selected from halogen, —OR$^{10a}$, —SR$^{10a}$, and —N(R$^{10a}$)$_2$. In some embodiments, each R$^1$ is independently selected from hydrogen, —CN, —OH, —OMe, —OEt, —OiPr, —F, —Cl, —Br, —CH$_3$, —CH$_2$CH$_3$, —CF$_3$, —CHF$_2$, —CH$_2$F, OCF$_3$, —OCHF$_2$, —OCH$_2$F, —C(O)NH$_2$,

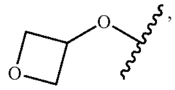, 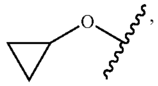, 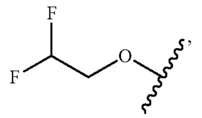,

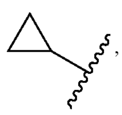, and 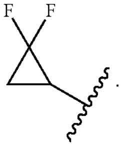.

In some embodiments, each R$^1$ is independently selected from —F and —CN. In some embodiments, R$^2$ is selected from $C_{1-6}$ alkyl, optionally substituted with one or more substituents independently selected from halogen, —OR$^{10b}$, —SR$^{10b}$, —N(R$^{10b}$)$_2$, —CN, =O, $C_{3-10}$ carbocycle, and 3- to 10-membered heterocycle, wherein the $C_{3-10}$ carbocycle and 3- to 10-membered heterocycle are each optionally substituted with one or more R$^{9b}$; and $C_{3-10}$ carbocycle and 3- to 10-membered heterocycle, each of which is optionally substituted with one or more substituents independently selected from halogen, —OR$^{10b}$, —SR$^{10b}$, —N(R$^{10b}$)$_2$, =O, —CN, and $C_{1-6}$ alkyl, wherein each $C_{1-6}$ alkyl is optionally substituted with one or more R$^{9b}$. In some embodiments, R$^2$ is selected from $C_{1-6}$ alkyl, optionally substituted with one or more substituents independently selected from halogen, —OR$^{10b}$, —SR$^{10b}$, —N(R$^{10b}$)$_2$, —CN, =O, $C_{3-10}$ carbocycle, and 3- to 10-membered heterocycle, wherein the $C_{3-10}$ carbocycle and 3- to 10-membered heterocycle are each optionally substituted with one or more R$^{9b}$; and $C_{3-10}$ carbocycle and 3- to 10-membered heterocycle, each of which is optionally substituted with one or more substituents independently selected from halogen, —OR$^{10b}$, —SR$^{10b}$, —N(R$^{10b}$)$_2$, =O, —CN, and $C_{1-6}$ alkyl, wherein each $C_{1-6}$ alkyl is optionally substituted with one or more R$^{9b}$. In some embodiments, R$^2$ is selected from $C_{1-6}$ alkyl, optionally substituted with one or more substituents independently selected from halogen, —OR$^{10b}$, —CN, $C_{3-10}$ carbocycle, and 3- to 10-membered heterocycle, wherein the $C_{3-10}$ carbocycle and 3- to 10-membered heterocycle are each optionally substituted with one or more R$^{9b}$; and $C_{3-10}$ carbocycle and 3- to 10-membered heterocycle, each of which is optionally substituted with one or more substituents independently selected from halogen, —OR$^{10b}$, and —CN. In some embodiments, R$^2$ is selected from $C_{1-6}$ alkyl, optionally substituted with one or more substituents independently selected from —F, Cl, —OH, and $C_{3-10}$ carbocycle and 3- to 10-membered heterocycle, wherein the $C_{3-10}$ carbocycle and 3- to 10-membered heterocycle are each optionally substituted with one or more R$^{9b}$; and $C_{3-10}$ carbocycle and 3- to 10-membered heterocycle, each of which is optionally substituted with one or more substituents independently selected from —F, —Cl, and —CN. In some embodiments, R$^2$ is selected from $C_2$ alkyl, optionally substituted with one or more substituents independently selected from —F, —OH, and $C_{3-10}$ carbocycle and 3- to 10-membered heterocycle, wherein the $C_{3-10}$ carbocycle and 3- to 10-membered heterocycle are each optionally substituted with one or more substituents independently selected from —F, —Cl, and —CN; and $C_{3-10}$ carbocycle and 3- to 10-membered heterocycle, each of which is optionally substituted with one or more substituents independently selected from —F and —CN. In some embodiments, $R^2$ is selected from $C_2$ alkyl, optionally substituted with one or more substituents independently selected from $C_{3-10}$ carbocycle and 3- to 10-membered heterocycle, wherein the $C_{3-10}$ carbocycle and 3- to 10-membered heterocycle are each optionally substituted with one or more substituents independently selected from —F, —Cl, and —CN. In some embodiments, $R^2$ is a substituent represented by the following:

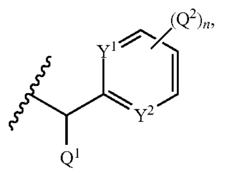

wherein, $Q^1$ is a $C_1$ alkyl optionally substituted with one or more substituents selected from —OH and —F; $Y^1$ and $Y^2$ are each independently selected from N and $C(Q^3)$; and each $Q^2$ is independently selected from halogen and —CN; each $Q^3$ is independently selected from hydrogen, halogen and —CN; and n is 0, 1, or 2. In some embodiments, $Q^1$ is —$CH_3$; each $Q^2$ is independently selected from —F and —CN; and each $Q^3$ is independently selected from hydrogen, —F, and —CN. In some embodiments, $R^3$ and $R^4$ are each independently selected from: hydrogen and —OH; and $C_{1-6}$ alkyl optionally substituted with one or more substituents independently selected from halogen, —$OR^{10c}$, —$SR^{10c}$, —$N(R^{10c})_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$. In some embodiments, $R^3$ and $R^4$ are each independently selected from: hydrogen, —OH, and $C_1$ alkyl. In some embodiments, $R^3$ is —OH, and $R^4$ is —H. In some embodiments, $R^3$ is —H, and $R^4$ is —H. In some embodiments, $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$. In some embodiments, $R^3$ together with $R^4$ form a 3- to 10-membered heterocycle or $C_{3-10}$ carbocycle, each of which is optionally substituted with one or more substituents independently selected from —$C(O)N(R^{10c})_2$ and —$C(O)R^{10c}$. In some embodiments, $R^3$ together with $R^4$ form a ring selected from

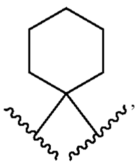,
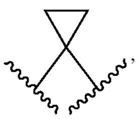,
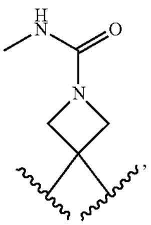, and
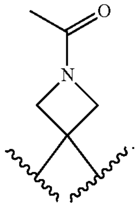.

In some embodiments, $R^5$ and $R^6$ are each independently selected from: hydrogen and $C_{1-6}$ alkyl. In some embodiments, $R^5$ and $R^6$ are each independently selected from: hydrogen and —$CH_3$, or $R^5$ and $R^6$ together form a cyclopropyl. In some embodiments, $R^5$ and $R^6$ are each hydrogen. In some embodiments, $R^7$ is selected from hydrogen and $C_{1-6}$ alkyl. In some embodiments, $R^7$ is selected from hydrogen. In some embodiments, $R^8$ is selected from: hydrogen; and $C_{1-6}$ alkyl. In some embodiments, $R^8$ is selected from hydrogen. In some embodiments, each $R^{9a}$ is independently selected from: halogen, —$OR^{10a}$, —CN, and $C_{1-3}$ alkyl. In some embodiments, each $R^{9b}$ is independently selected from: halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, and —CN; $C_{1-3}$ alkyl and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, and —CN; and $C_{3-10}$ carbocycle and 3- to 10-membered heterocycle. In some embodiments, each $R^{9b}$ is independently selected from: —F, —Cl, —Br, —CN, —OH, —$OCH_3$, —$CH_3$, —$CF_3$, —$C(O)NH_2$,

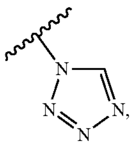,
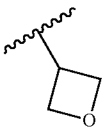, and —CCH. In some embodiments, each $R^{9b}$ is independently selected from halogen and —CN. In some embodiments, each $R^{9c}$ is independently selected from: halogen, —$OR^{10a}$, —CN, and $C_{1-3}$ alkyl. In some embodiments, each $R^{10a}$, $R^{10b}$, $R^{10c}$, $R^{10d}$, and $R^{10e}$ is independently selected from hydrogen, $C_{1-6}$ alkyl, $C_{3-10}$ carbocycle, and 3- to 10-membered heterocycle. In some embodiments, each $R^{10a}$, $R^{10b}$, $R^{10c}$, $R^{10d}$, and $R^{10e}$ is independently selected from hydrogen. In some embodiments, if $X^3$ and $X^1$ are both N, then $R^8$ is selected from hydrogen.

Methods of administration of a compound or salt of Formula (I), (II), or (III) discussed herein may be used for the treatment of cardiac conditions. Methods of administration of a compound or salt of Formula (I), (II), or (III) discussed herein may be used for the treatment of cardiac dysfunction. In an aspect, the present disclosure provides a method of treating a condition selected from hypertrophic cardiomyopathy (HCM); heart failure with preserved ejection fraction (HFpEF); disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; ischemia; and angina; and myocarditis. In some embodiments, the condition is cardiac dysfunction related to acute or chronic myocarditis. In some embodiments, the myocarditis is parasitic, bacterial, viral, or non-infectious. In some embodiments, the myocarditis is autoimmune myocarditis. In some embodiments, the myocarditis is eosinophilic myocarditis. In some embodiments, the condition is a cardiomyopathy. In some embodiments, the cardiomyopathy is a toxic cardiomyopathy. In some embodiments, the toxic cardiomyopathy is related to exposure to chemotherapeutic agents, ethanol, cocaine, other toxic substances, or any combination thereof. In some embodiments, said heart failure with preserved ejection fraction (HFpEF) comprises one or more disorders selected from disorders of relaxation and disorders of chamber stiffness (diabetic HFpEF). In some embodiments, said left ventricular (LV) hypertrophy is malignant left ventricular (LV) hypertrophy. In some embodiments, said restrictive cardiomyopathy comprises one or more subgroups selected from inflammatory subgroups, infiltrative subgroups, storage subgroups, idiopathic subgroups, inherited subgroups, congenital heart disease subgroups. In some embodiments, said inflammatory subgroups comprise one or more subgroups selected from Loefilers and EMF. In some embodiments, said inflammatory subgroups comprise one or more subgroups selected from amyloid, sarcoid, and radiation (e.g., XRT, radiation therapy, or radiation injury). In some embodiments, said storage subgroups comprise one or more subgroups selected from hemochromatosis, Fabry, and glycogen storage disease. In some embodiments, said inherited subgroups is related to conditions associated with Troponin I (e.g., beta myosin Heavy Chain), Troponin T (e.g., alpha cardiac actin), or desmin. In some embodiments, said congenital heart disease subgroups comprise one or more subgroups selected from pressure-overloaded right ventricle (RV), Tetralogy of Fallot, and pulmonic stenosis. In an aspect, the present disclosure provides a method of treating hypertrophic cardiomyopathy or a related condition comprising administering to a subject in need thereof a compound or salt disclosed herein.

In an aspect, the present disclosure provides a method of treating obstructive hypertrophic cardiomyopathy comprising administering to a subject in need thereof a compound or salt disclosed herein. In an aspect, the present disclosure provides a method of treating non-obstructive hypertrophic cardiomyopathy comprising administering to a subject in need thereof a compound or salt of disclosed herein. In an aspect, the present disclosure provides a method of treating heart failure with preserved ejection fraction comprising administering to a subject in need thereof a compound or disclosed herein. In an aspect, the present disclosure provides a method of treating left ventricle stiffness comprising administering to a subject in need thereof a compound or salt disclosed herein.

In some embodiments, the present disclosure provides a method of treating dilated (DCM) cardiomyopathy. In some embodiments, the present disclosure provides a method of treating sudden cardiac death.

In an aspect, the present disclosure provides a method of treating a cardiac disease or disorder, the method comprising administering a compound or salt of any one of Formula (I), (II), or (III) to a subject in need thereof. In some embodiments, administering the compound or salt of any one of Formula (I), (II), or (III) modulates the subject's heart rate (HR), end diastolic volume (EDV), or fractional shortening (FS). In some embodiments, administering the compound or salt of any one of Formula (I), (II), or (III) increases the subject's heart rate (HR). In some embodiments, administering the compound or salt of any one of Formula (I), (II), or (III) decreases the subject's heart rate (HR). In some embodiments, administering the compound or salt of any one of Formula (I), (II), or (III) decreases the subject's fractional shortening (FS). In some embodiments, administering the compound or salt of any one of Formula (I), (II), or (III) decreases the subject's end diastolic volume (EDV). Alternatively, in some embodiments, administering the compound or salt of any one of Formula (I), (II), or (III) increases the subject's end diastolic volume (EDV). Alternatively, in some embodiments, administering the compound or salt of any one of Formula (I), (II), or (III) does not change the subject's end diastolic volume (EDV). Alternatively, in some embodiments, administering the compound or salt of any one of Formula (I), (II), or (III) increases the subject's fractional shortening (FS). In some embodiments, administering the compound or salt of any one of Formula (I), (II), or (III) modulates an index of left-ventricular fractional shortening (FS) and systolic wall-thickening index (SWT). In some embodiments, administering the compound or salt of any one of Formula (I), (II), or (III) modulates an index of left-ventricular fractional shortening (FS). In some embodiments, administering the compound or salt of any one of Formula (I), (II), or (III) modulates an index of systolic wall-thickening index (SWT).

In some embodiments, the method comprising administering a compound of Formula (III) further comprises further comprising administering an additional active agent.

In an aspect, the present disclosure provides a pharmaceutical composition comprising the compound or salt of Formula (III) and one or more excipient(s) (e.g., a pharmaceutically acceptable excipient).

In an aspect, the present disclosure provides a method of modulating a light chain. In some embodiments, administering a compound or salt of Formula (I), Formula (II), or Formula (III) modulate a light chain. In some embodiments, administering a compound or salt of Formula (I), Formula (II), or Formula (III) modulates a regulatory light chain (RLC) (e.g., a myosin regulatory light chain). In some embodiments, administering a compound or salt of Formula (I), Formula (II), or Formula (III) modulates an essential light chain (ELC) (e.g., a myosin essential light chain). In some embodiments, the regulatory light chain is a cardiac myosin regulatory light chain. In some embodiments, the modulating the regulatory light chain is inhibiting the regulatory light chain (e.g., inhibiting the function of the RLC). Alternatively, or in addition, in some embodiments, the modulating the regulatory light chain is activating the regulatory light chain (e.g., activating the function of the RLC). In some embodiments, the method changes the ability of a myosin lever arm to develop force. In some embodiments, administering a compound or salt of the present disclosure overcomes a disturbance in an interaction between myosin regulatory light chain and myosin heavy chain. In some embodiments, the disturbance is caused by a genetic mutation. In some embodiments, the method of modulating an RLC is for use in treating hypertrophic cardiomyopathy.

In some embodiments, administering a compound of the present disclosure modulates ATP cycling rates of one or more sarcomeric protein(s) (e.g., actomyosin cycling). In some embodiments, administering a compound of the present disclosure activates ATP cycling rates of sarcomeric proteins. Alternatively, in some embodiments, administering a compound of the present disclosure inhibits ATP cycling rates of sarcomeric proteins. In some embodiments, the modulating ATP cycling rates of sarcomeric proteiens is through interactions (e.g., binding) with one or more sarcomere protein(s) (e.g., myosin, myosin regulatory light chain, myosin essential light chain, or myosin binding protein-c).

In some embodiments, administering a compound or salt of the present disclosure modulates actin floating on myosin. In some embodiments, administering a compound or salt of the present disclosure modulates actin floating on myosin in a different way than a direct myosin inhibitor modulates actin floating on myosin (e.g., as shown in a Motility assay).

In an aspect, administering a compound or salt of the disclosure (e.g., a compound or salt of any one of Formula (I), (II), or (III)) modulates one or more sarcomeric protein (s). In an aspect, administering a compound or salt of the disclosure (e.g., a compound or salt of any one of Formula (I), (II), or (III)) modulates a myosin (e.g., myosin in cardiac muscle, myosin in skeletal muscle). In an aspect, administering a compound or salt of the disclosure (e.g., a compound or salt of any one of Formula (I), (II), or (III)) modulates a myosin light chain (e.g., essential myosin light chain, regulatory myosin light chain). In some embodiments, administering a compound or salt of the disclosure (e.g., a compound or salt of any one of Formula (I), (II), or (III)) modulates a regulatory light chain (e.g., myosin regulatory light chain). In some embodiments, the compound or salt of the disclosure (e.g., a compound or salt of any one of Formula (I), (II), or (III)) inhibits a regulatory light chain. Alternatively, in some embodiments, the compound or salt of the disclosure (e.g., a compound or salt of any one of Formula (I), (II), or (III)) activates a myosin regulatory light chain.

In an aspect, administering a compound of the present disclosure treats a patient (e.g., with HCM) through modulation of a myosin regulatory light chain (e.g., cardiac myosin regulatory light chain).

In some embodiments, the patient to which a compound of the present disclosure is administered exhibits a myosin heavy chain mutation (e.g., on chromosome 14 q11.2-3, e.g., MYH7). In some embodiments, the patient exhibits a β-myosin heavy chain mutation (e.g., on chromosome 14 q11.2-3, e.g., MYH7). In some embodiments, the patient exhibits an insertion/deletion polymorphism in the gene encoding for angiotensin converting enzyme (e.g., ACE). In some embodiments, the patient with the insertion/deletion polymorphism in the gene encoding for ACE exhibits more marked hypertrophy of the left ventricle. In some embodiments, the patient exhibits a troponin mutation (e.g., troponin T or troponin C). In some embodiments, the patient exhibits a myosin binding protein C (MYBPC) mutation. In some embodiments, the patient exhibits a myosin 7 mutation. In some embodiments, the patient exhibits multiple mutations selected from troponin, RLC, MYBPC, myosin 7, myosin heavy chain, and ACE. In some embodiments, the patient exhibits multiple mutations selected from troponin, RLC, MYBPC, and myosin 7.

In some embodiments, the patient to which a compound of the present disclosure is administered exhibits a myosin regulatory light chain mutation (e.g., E22K mutation). In some embodiments, the myosin regulatory light chain mutation disturbs the interaction of myosin regulatory light chain with myosin heavy chain. In some embodiments, the disturbance in the interaction between myosin regulatory light chain and myosin heavy chain leads to structural abnormalities in the myosin cross bridge (e.g., in the myosin cross bridge, e.g., in the lever arm of the myosin cross bridge). In some embodiments, the mutation in the myosin regulatory light chain leads to reduced contractility. In some embodiments, the mutation in the myosin regulatory light chain leads to decreased cardiac output.

In some embodiments, modulation of the myosin regulatory light chain overcomes a disturbance in an interaction between myosin regulatory light chain and myosin heavy chain (e.g., which leads to structural abnormalities in the myosin cross bridge, e.g., in the lever arm of the myosin cross bridge). In some embodiments, administering a compound of the present disclosure (e.g., to a patient with an RLC mutation) changes a myosin lever arm's ability to develop force. In some embodiments, the myosin lever arm's changed ability to develop force results in slowed contraction. In some embodiments, the myosin lever arm's changed ability to develop force results in accelerated relaxation. In some embodiments, the myosin lever arm's changed ability to develop force results in slowed contraction and accelerated relaxation. In some embodiments, this helps overcome mutations (e.g., that enhance the proportion of force-developing myosin heads, e.g., HCM mutations). In some embodiments, this action (e.g., slowed contraction or accelerated relaxation) is greater at low calcium (e.g., diastolic) compared to high calcium (e.g., systolic) (e.g., which may modulate its inhibitory action as the heart contracts and relaxes). In some embodiments, modulation of the myosin regulatory light chain leads to reduced contractility. In some embodiments, modulation of the myosin regulatory light chain leads to decreased cardiac output. In some embodiments, modulation of the myosin regulatory light chain leads to slowing of early contraction (e.g., resulting from slower walking of myosin heads along actin). In some embodiments, the slowing of early contraction is used to treat HCM (e.g., obstructive HCM, oHCM). In some embodiments, treatment through this mechanism is administered for genetic HCM or non-genetic HCM.

In some embodiments, one or more cardiac mutation(s) (e.g., a mutation in the myosin regulatory light chain) in a patient (e.g., a patient with HCM) modulate(s) a spatial gradient of myosin regulatory light chain phosphorylation (e.g., modulate relative to that in the heart of a patient without HCM). In some embodiments, a mutation in the myosin regulatory light chain modulates the spatial gradient of myosin regulatory light chain phosphorylation. In some embodiments, a mutation in the myosin regulatory light chain decreases cardiac torsion (e.g., so that blood is less efficiently wrung out of the heart). In some embodiments, a mutation in the myosin regulatory light chain decreases cardiac torsion by altering the mechanism by which the spatial gradient of myosin light chain phosphorylation across the heart inversely alters tension production. In some embodiments, a mutation in the myosin regulatory light chain decreases cardiac torsion by altering the mechanism by which the spatial gradient of myosin light chain phosphorylation across the heart inversely alters the stretch activation response. In some embodiments, a mutation in the myosin regulatory light chain decreases cardiac torsion by modulating a mechanism by which the spatial gradient of myosin light chain phosphorylation across the heart inversely alters tension production and the stretch activation response. In some embodiments, treatment through this mechanism is administered for genetic HCM or non-genetic HCM.

In some embodiments, modulation of the myosin regulatory light chain increases cardiac torsion in a patient (e.g., with HCM) relative to a patient without HCM. In some embodiments, modulation of myosin regulatory light chain increases torsion by modulating the spatial gradient of myosin light chain phosphorylation across the heart.

In some embodiments, the myosin regulatory light chain mutation decreases calcium-activated tension. In some embodiments, the myosin regulatory light chain mutation decreases calcium-activated stiffness. In some embodiments, the myosin regulatory light chain mutation reduces myofilament $Ca^{2+}$ sensitivity. In some embodiments, modulation of the myosin regulatory light chain increases calcium-activated tension. In some embodiments, modulation of the myosin regulatory light chain increases calcium-activated stiffness. In some embodiments, modulation of the myosin regulatory light chain increases myofilament $Ca^{2+}$ sensitivity. In some embodiments, upon administration of a compound or salt of the present disclosure, changes in calcium sensitivity are length dependent. In some embodiments, upon administration of a compound or salt of the present disclosure, changes in calcium sensitivity are length dependent (e.g., except with decreases in calcium sensitivity at long sarcomere lengths). In some embodiments, administering a compound of the present disclosure changes calcium sensitivity. In some embodiments, administering a compound of the present disclosure changes calcium sensitivity when the sarcomere is stretched. In some embodiments, treatment through this mechanism is administered for genetic HCM or non-genetic HCM.

In an aspect, a compound of the present disclosure (e.g., a compound of Formula I, Formula II, or Formula III) selectively inhibits function of ventricular myosin. In some embodiments, a compound of the present disclosure selectively inhibits function of atrial myosin. In some embodiments, a compound of the present disclosure selectively inhibits function of skeletal myosin. In some embodiments, a compound of the present disclosure selectively inhibits function of ventricular myosin relative to atrial myosin. In some embodiments, a compound of the present disclosure selectively inhibits function of ventricular myosin relative to skeletal myosin. In some embodiments, a compound of the present disclosure selectively inhibits function of ventricular myosin relative to atrial myosin and skeletal myosin. In some embodiments, a compound of the present disclosure selectively inhibits function of atrial myosin relative to ventricular myosin. In some embodiments, a compound of the present disclosure selectively inhibits function of atrial myosin relative to skeletal myosin. In some embodiments, a compound of the present disclosure selectively inhibits function of atrial myosin relative to ventricular myosin and skeletal myosin. In some embodiments, a compound of the present disclosure selectively inhibits function of skeletal myosin relative to atrial myosin. In some embodiments, a compound of the present disclosure selectively inhibits function of skeletal myosin relative to ventricular myosin. In some embodiments, a compound of the present disclosure selectively inhibits function of skeletal myosin relative to atrial myosin and ventricular myosin.

In an aspect, a compound of the present disclosure (e.g., a compound of Formula I, Formula II, or Formula III) selectively activates function of ventricular myosin. In some embodiments, a compound of the present disclosure selectively activates function of atrial myosin. In some embodiments, a compound of the present disclosure selectively activates function of skeletal myosin. In some embodiments, a compound of the present disclosure selectively activates function of ventricular myosin relative to atrial myosin. In some embodiments, a compound of the present disclosure selectively activates function of ventricular myosin relative to skeletal myosin. In some embodiments, a compound of the present disclosure selectively activates function of ventricular myosin relative to atrial myosin and skeletal myosin. In some embodiments, a compound of the present disclosure selectively activates function of atrial myosin relative to ventricular myosin. In some embodiments, a compound of the present disclosure selectively activates function of atrial myosin relative to skeletal myosin. In some embodiments, a compound of the present disclosure selectively activates function of atrial myosin relative to ventricular myosin and skeletal myosin. In some embodiments, a compound of the present disclosure selectively activates function of skeletal myosin relative to atrial myosin. In some embodiments, a compound of the present disclosure selectively activates function of skeletal myosin relative to ventricular myosin. In some embodiments, a compound of the present disclosure selectively activates function of skeletal myosin relative to atrial myosin and ventricular myosin.

In some embodiments, administering a compound or salt of the present disclosure does not modulate myosin heavy chain. In some embodiments, the compound or salt of the present disclosure does not bind myosin heavy chain. In some embodiments, the compound or salt of the present disclosure does not inhibit myosin heavy chain. In some embodiments, the compound or salt of the present disclosure does not activate myosin heavy chain.

In some embodiments, the term selective inhibition refers to a 10-fold decrease in activity (e.g., in some embodiments, selective inhibition of ventricular myosin relative to atrial myosin refers to a state wherein the $IC_{25}$ value for ventricular myosin is 10-times lower than that of atrial myosin). In some embodiments, the term selective inhibition refers to a decrease in activity that is at least about 2-fold, at least about 3-fold, at least about 4-fold, at least about 5-fold, at least about 7-fold, at least about 10-fold, at least about 15-fold, at least about 20-fold, at least about 30-fold, at least about 40-fold, at least about 50-fold, at least about 60-fold, at least about 70-fold, at least about 80-fold, at least about 90-fold, at least about 100-fold, at least about 125-fold, at least about 150-fold, at least about 175-fold, at least about 200-fold, at least about 300-fold, at least about 400-fold, at least about 500-fold, at least about 600-fold, at least about 700-fold, at least about 800-fold, at least about 900-fold, at least about 1000-fold, at least about 2000-fold, at least about 10,000-fold, or more. Alternatively, or in addition, in some embodiments, the term selective inhibition refers to a decrease in activity that is at most about 2-fold, at most about 3-fold, at most about 4-fold, at most about 5-fold, at most about 7-fold, at most about 10-fold, at most about 15-fold, at most about 20-fold, at most about 30-fold, at most about 40-fold, at most about 50-fold, at most about 60-fold, at most about 70-fold, at most about 80-fold, at most about 90-fold, at most about 100-fold, at most about 125-fold, at most about 150-fold, at most about 175-fold, at most about 200-fold, at most about 300-fold, at most about 400-fold, at most about 500-fold, at most about 600-fold, at most about 700-fold, at most about 800-fold, at most about 900-fold, at most about 1000-fold, at most about 2000-fold, at most about 10,000-fold, or less. In some embodiments, the term selective inhibition refers to a decrease in activity that is about 1-fold to about 5,000-fold. In some embodiments, the term selective inhibition refers to a decrease in activity that is at least about 1-fold. In some embodiments, the term selective inhibition refers to a decrease in activity that is at most about 5,000-fold. In some embodiments, the term selective inhibition refers to a decrease in activity that is about 1-fold to about 2-fold, about 1-fold to about 5-fold, about 1-fold to about 10-fold, about 1-fold to about 25-fold, about 1-fold to about 50-fold, about 1-fold to about 75-fold, about 1-fold to about 100-fold, about 1-fold to about 200-fold, about 1-fold to about 500-fold, about 1-fold to about 1,000-fold, about 1-fold to about 5,000-fold, about 2-fold to about 5-fold, about 2-fold to about 10-fold, about 2-fold to about 25-fold, about 2-fold to about 50-fold, about 2-fold to about 75-fold, about 2-fold to about 100-fold, about 2-fold to about 200-fold, about 2-fold to about 500-fold, about 2-fold to about 1,000-fold, about 2-fold to about 5,000-fold, about 5-fold to about 10-fold, about 5-fold to about 25-fold, about 5-fold to about 50-fold, about 5-fold to about 75-fold, about 5-fold to about 100-fold, about 5-fold to about 200-fold, about 5-fold to about 500-fold, about 5-fold to about 1,000-fold, about 5-fold to about 5,000-fold, about 10-fold to about 25-fold, about 10-fold to about 50-fold, about 10-fold to about 75-fold, about 10-fold to about 100-fold, about 10-fold to about 200-fold, about 10-fold to about 500-fold, about 10-fold to about 1,000-fold, about 10-fold to about 5,000-fold, about 25-fold to about 50-fold, about 25-fold to about 75-fold, about 25-fold to about 100-fold, about 25-fold to about 200-fold, about 25-fold to about 500-fold, about 25-fold to about 1,000-fold, about 25-fold to about 5,000-fold, about 50-fold to about 75-fold, about 50-fold to about 100-fold, about 50-fold to about 200-fold, about 50-fold to about 500-fold, about 50-fold to about 1,000-fold, about 50-fold to about 5,000-fold, about 75-fold to about 100-fold, about 75-fold to about 200-fold, about 75-fold to about 500-fold, about 75-fold to about 1,000-fold, about 75-fold to about 5,000-fold, about 100-fold to about 200-fold, about 100-fold to about 500-fold, about 100-fold to about 1,000-fold, about 100-fold to about 5,000-fold, about 200-fold to about 500-fold, about 200-fold to about 1,000-fold, about 200-fold to about 5,000-fold, about 500-fold to about 1,000-fold, about 500-fold to about 5,000-fold, or about 1,000-fold to about 5,000-fold, or about 2-fold to about 10,000 fold. In some embodiments, the term selective inhibition refers to a decrease in activity that is about 1-fold, about 2-fold, about 5-fold, about 10-fold, about 25-fold, about 50-fold, about 75-fold, about 100-fold, about 200-fold, about 500-fold, about 1,000-fold, about 5,000-fold, about 10,000-fold, or 100,000-fold.

In some embodiments, the term selective activation refers to a 10-fold increase in activity (e.g., in some embodiments, selective activation of ventricular myosin relative to atrial myosin refers to a state wherein the $IC_{25}$ value for ventricular myosin is 10-times higher than that of atrial myosin). In some embodiments, the term selective activation refers to an increase in activity that is at least about 2-fold, at least about 3-fold, at least about 4-fold, at least about 5-fold, at least about 7-fold, at least about 10-fold, at least about 15-fold, at least about 20-fold, at least about 30-fold, at least about 40-fold, at least about 50-fold, at least about 60-fold, at least about 70-fold, at least about 80-fold, at least about 90-fold, at least about 100-fold, at least about 125-fold, at least about 150-fold, at least about 175-fold, at least about 200-fold, at least about 300-fold, at least about 400-fold, at least about 500-fold, at least about 600-fold, at least about 700-fold, at least about 800-fold, at least about 900-fold, at least about 1000-fold, at least about 2000-fold, at least about 10,000-fold, or more. Alternatively, or in addition, in some embodiments, the term selective activation refers to an increase in activity that is at most about 2-fold, at most about 3-fold, at most about 4-fold, at most about 5-fold, at most about 7-fold, at most about 10-fold, at most about 15-fold, at most about 20-fold, at most about 30-fold, at most about 40-fold, at most about 50-fold, at most about 60-fold, at most about 70-fold, at most about 80-fold, at most about 90-fold, at most about 100-fold, at most about 125-fold, at most about 150-fold, at most about 175-fold, at most about 200-fold, at most about 300-fold, at most about 400-fold, at most about 500-fold, at most about 600-fold, at most about 700-fold, at most about 800-fold, at most about 900-fold, at most about 1000-fold, at most about 2000-fold, at most about 10,000-fold, or less. In some embodiments, the term selective activation refers to an increase in activity that is about 1-fold to about 5,000-fold. In some embodiments, the term selective activation refers to an increase in activity that is at least about 1-fold. In some embodiments, the term selective activation refers to an increase in activity that is at most about 5,000-fold. In some embodiments, the term selective activation refers to an increase in activity that is about 1-fold to about 2-fold, about 1-fold to about 5-fold, about 1-fold to about 10-fold, about 1-fold to about 25-fold, about 1-fold to about 50-fold, about 1-fold to about 75-fold, about 1-fold to about 100-fold, about 1-fold to about 200-fold, about 1-fold to about 500-fold, about 1-fold to about 1,000-fold, about 1-fold to about 5,000-fold, about 2-fold to about 5-fold, about 2-fold to about 10-fold, about 2-fold to about 25-fold, about 2-fold to about 50-fold, about 2-fold to about 75-fold, about 2-fold to about 100-fold, about 2-fold to about 200-fold, about 2-fold to about 500-fold, about 2-fold to about 1,000-fold, about 2-fold to about 5,000-fold, about 5-fold to about 10-fold, about 5-fold to about 25-fold, about 5-fold to about 50-fold, about 5-fold to about 75-fold, about 5-fold to about 100-fold, about 5-fold to about 200-fold, about 5-fold to about 500-fold, about 5-fold to about 1,000-fold, about 5-fold to about 5,000-fold, about 10-fold to about 25-fold, about 10-fold to about 50-fold, about 10-fold to about 75-fold, about 10-fold to about 100-fold, about 10-fold to about 200-fold, about 10-fold to about 500-fold, about 10-fold to about 1,000-fold, about 10-fold to about 5,000-fold, about 25-fold to about 50-fold, about 25-fold to about 75-fold, about 25-fold to about 100-fold, about 25-fold to about 200-fold, about 25-fold to about 500-fold, about 25-fold to about 1,000-fold, about 25-fold to about 5,000-fold, about 50-fold to about 75-fold, about 50-fold to about 100-fold, about 50-fold to about 200-fold, about 50-fold to about 500-fold, about 50-fold to about 1,000-fold, about 50-fold to about 5,000-fold, about 75-fold to about 100-fold, about 75-fold to about 200-fold, about 75-fold to about 500-fold, about 75-fold to about 1,000-fold, about 75-fold to about 5,000-fold, about 100-fold to about 200-fold, about 100-fold to about 500-fold, about 100-fold to about 1,000-fold, about 100-fold to about 5,000-fold, about 200-fold to about 500-fold, about 200-fold to about 1,000-fold, about 200-fold to about 5,000-fold, about 500-fold to about 1,000-fold, about 500-fold to about 5,000-fold, or about 1,000-fold to about 5,000-fold, or about 2-fold to about 10,000 fold. In some embodiments, the term selective activation refers to an increase in activity that is about 1-fold, about 2-fold, about 5-fold, about 10-fold, about 25-fold, about 50-fold, about 75-fold, about 100-fold, about 200-fold, about 500-fold, about 1,000-fold, or about 5,000-fold.

In an aspect, the present disclosure provides methods of treating atrial cardiopathy, Heart failure with ejection fraction (e.g., Heart failure with preserved ejection fraction (HFpEF), Heart failure with reduced ejection fraction (HFrEF)), arrhythmia (e.g., Atrial fibrillation), stroke (e.g., Cardioembolic stroke, Cryptogenic stroke), valve disease (e.g., Mitral valve disease, or Tricuspid valve disease), comprises administering an atrial-selective agent. In an aspect, the present disclosure provides methods of treating atrial cardiopathy, Heart failure with preserved ejection fraction (HFpEF), Heart failure with reduced ejection fraction (HFrEF), Atrial fibrillation, Cardioembolic stroke, Cryptogenic stroke, Mitral valve disease, or Tricuspid valve disease, comprises administering an atrial-selective agent. In an aspect, the present disclosure provides methods of treating atrial cardiopathy. In some embodiments, the present disclosure provides a method of treating HFpEF. In some embodiments, the present disclosure provides a method of treating HFrEF. In some embodiments, the present disclosure provides a method of treating Atrial fibrillation. In some embodiments, the present disclosure provides a method of treating Cardioembolic stroke. In some embodiments, the present disclosure provides a method of treating Cryptogenic stroke. In some embodiments, the present disclosure provides a method of treating Mitral valve disease. In some embodiments, the present disclosure provides a method of treating Tricuspid valve disease.

In some embodiments, the present disclosure provides a method of treating one or more diseases selected from atrial cardiopathy, HFpEF, HFrEF, Atrial fibrillation, Cardioembolic stroke, Cryptogenic stroke, Mitral valve disease, and Tricuspid valve disease. In some embodiments, the method comprises administering a compound of Formula (I), Formula (II), or Formula (III). In some embodiments, the compound of Formula (I), Formula (II), or Formula (III) for use in treating one or more diseases selected from atrial cardiopathy, HFpEF, HFrEF, Atrial fibrillation, Cardioembolic stroke, Cryptogenic stroke, Mitral valve disease, and Tricuspid valve disease, comprises an atrial-selective agent. In some embodiments, the atrial-selective agent selectively inhibits atrial myosin relative to ventricular myosin or relative to skeletal myosin. In some embodiments, the atrial-selective agent selectively inhibits atrial myosin regulatory light chain relative to ventricular myosin regulatory light chain, or relative to skeletal myosin regulatory light chain, or relative to both atrial myosin regulatory light chain and skeletal myosin regulatory light chain.

In an aspect, the present disclosure provides a method of treating activity-induced muscle damage, a movement disorder, a neuromuscular condition, or a metabolic myopathy, the method comprising administering a compound or salt of any one of Formula (I), (II), or (III) to a subject in need thereof. In some embodiments, the compound or salt of any one of Formula (I), (II), or (III) inhibits skeletal muscle myosin II. In some embodiments, said movement disorder comprises muscle spasticity. In some embodiments, said muscle spasticity may be selected from spasticity associated with multiple sclerosis, Parkinson's disease, Alzheimer's disease, or cerebral palsy, or injury, or a traumatic event such as stroke, traumatic brain injury, spinal cord injury, hypoxia, meningitis, encephalitis, phenylketonuria, or amyotrophic lateral sclerosis.

Skeletal muscle is mainly composed of two types of fibers, slow-twitch muscle fiber (i.e., type I) and fast-twitch muscle fiber (i.e., type II). In each muscle, the two types of fibers are configured in a mosaic-like arrangement, with differences in fiber type composition in different muscles and at different points in growth and development. Slow-twitch muscle fibers have excellent aerobic energy production ability. Contraction rate of the slow-twitch muscle fiber is low but tolerance to fatigue is high. Slow-twitch muscle fibers typically have a higher concentration of mitochondria and myoglobin than do fast-twitch fibers and are surrounded by more capillaries than are fast-twitch fibers. Slow-twitch fibers contract at a slower rate due to lower myosin ATPase activity and produce less power compared to fast-twitch fibers, but they are able to maintain contractile function over longer-terms, such as in stabilization, postural control, and endurance exercises.

Fast twitch muscle fibers in humans are further divided into two main fiber types depending on the specific fast skeletal myosin they express (Type IIa, IIx/d). A third type of fast fiber (Type IIb) exists in other mammals but is rarely identified in human muscle. Fast-twitch muscle fibers have excellent anaerobic energy production ability and are able to generate high amounts of tension over a short period of time. Typically, fast-twitch muscle fibers have lower concentrations of mitochondria, myoglobin, and capillaries compared to slow-twitch fibers, and thus can fatigue more quickly. Fast-twitch muscles produce quicker force required for power and resistance activities.

The proportion of the type I and type II can vary in different individuals. For example, non-athletic individuals can have close to 50% of each muscle fiber types. Power athletes can have a higher ratio of fast-twitch fibers, e.g., 70-75% type II in sprinters. Endurance athletes can have a higher ratio of slow-twitch fibers, e.g., 70-80% in distance runners. The proportion of the type I and type II fibers can also vary depending on the age of an individual. The proportion of type II fibers, especially the type Ix, can decline as an individual ages, resulting in a loss in lean muscle mass.

The contractile action of skeletal muscle leads to muscle damage in subjects with neuromuscular disease, e.g., DMD, and this damage appears to be more prevalent in fast fibers.

It has been observed that acute force drop after lengthening injury is greater in predominantly fast type II fiber muscles compared to predominantly slow type I fiber muscles in dystrophy mouse models. It has also been demonstrated that the degree of acute force drop and histological damage in dystrophy mouse models is proportional to peak force development during lengthening injury. Excessive contraction-induced injuries, which precede the inflammation and irreversible fibrosis that characterizes late-stage DMD pathology. Contraction-induced muscle damage in these patients may be reduced by limiting peak force generation in type II fibers and possibly increasing reliance on healthier type I fibers.

Inhibitors of skeletal muscle myosin that are not selective for the type II fibers may lead to excessive inhibition of skeletal muscle contraction including respiratory function and unwanted inhibition of cardiac activity as the heart shares several structural components (such as type I myosin) with type I skeletal muscle fibers. While not wishing to be bound by a particular mechanistic theory, this disclosure provides selective inhibitors of fast-fiber skeletal muscle myosin as a treatment option for Becker muscular dystrophy (BMD), Duchenne muscular dystrophy (DMD), Limb-girdle muscular dystrophies (LGMD), McArdle disease, and other neuromuscular conditions. The targeted inhibition of type II skeletal muscle myosin may reduce skeletal muscle contractions while minimizing the impact on a subject's daily activities.

When healthy muscle is subjected to excessive, unaccustomed exercise, it develops soreness and sustained reductions in strength and range of motion. Proteins also leak from injured muscle fibers into circulation, including creatine kinase (CK), lactate dehydrogenase and myoglobin. These biomarkers are not unique to either fast or slow fibers and so do not provide detail regarding differences in fiber responses to injury. Troponin I (TNNI) is a component of the troponin complex that controls initiation of contraction of muscle by calcium. It is distinct in that there is a different isoform for each type of striated muscle: TNNI1 in slow skeletal muscle, TNNI2 in fast skeletal muscle and TNNI3 in cardiac muscle. Selective enzyme-linked immunosorbent assays (ELISAs) have been used to demonstrate that TNNI2 but not TNNI1 is elevated in circulation after injurious exercise, even under extreme conditions.

DMD and BMD are caused by an absence (DMD) or truncation (BMD) of the dystrophin protein5. Dystrophin provides a structural link between the actin cytoskeleton and the basement membrane through the dystrophin-glycoprotein complex. When dystrophin is absent or truncated, contraction of muscle leads to heightened muscle stress and injury with normal use. While the sensitivity to injury is much higher in DMD muscle than in BMD or healthy muscle, fast fibers still appear to be more susceptible than slow fibers, with young DMD patients exhibiting histological evidence of disruption in fast fibers7 and early loss of type IIx fibers. Example 21 shows the relative susceptibility of these fibers to leak muscle contents, such as troponin, creatine kinase, or myoglobin. In some embodiments, this disclosure provides selective inhibitors of fast-fiber skeletal muscle myosin as a treatment option for DMD, BMD, McArdle's disease, or Limb-girdle muscular dystrophies.

Methods of administration of a compound or salt of Formula (I), (II), or (III) discussed herein may be used for inhibiting muscle myosin II. In some embodiments, the compounds and salts thereof may be used to treat activity-induced muscle damage. In some embodiments, the compounds may be used to treat neuromuscular conditions and movement disorders (such as spasticity).

Methods of administration of a compound or salt of Formula (I), (II), or (III) discussed herein may be used for the treatment of activity-induced muscle damage, neuromuscular conditions, movement disorders, or metabolic myopathies. In some embodiments, activity-induced muscle damage, neuromuscular conditions, movement disorders, or metabolic myopathies are treated through administration of a skeletal inhibitor. Examples of neuromuscular conditions include but are not limited to Duchenne Muscular Dystrophy, Becker muscular dystrophy, myotonic dystrophy 1, myotonic dystrophy 2, facioscapulohumeral muscular dystrophy, oculopharyngeal muscular dystrophy, limb girdle muscular dystrophies, tendinitis and carpal tunnel syndrome. Examples of movement disorders include but are not limited to muscle spasticity disorders, spasticity associated with multiple sclerosis, Parkinson's disease, Alzheimer's disease, or cerebral palsy, or injury or a traumatic event such as stroke, traumatic brain injury, spinal cord injury, hypoxia, meningitis, encephalitis, phenylketonuria, or amyotrophic lateral sclerosis. Also included are other conditions that may respond to the inhibition of skeletal myosin II, skeletal troponin C, skeletal troponin I, skeletal tropomyosin, skeletal troponin T, skeletal regulatory light chains, skeletal myosin binding protein C or skeletal actin. In some embodiments, neuromuscular conditions and movement disorders are selected from muscular dystrophies and myopathies. In some embodiments, muscular dystrophies are diseases that cause progressive weakness and loss of muscle mass where abnormal genes (mutations) interfere with the production of proteins needed to form healthy muscle. In some embodiments, muscular dystrophies are selected from Becker muscular dystrophy (BMD), Congenital muscular dystrophies (CMD), Duchenne muscular dystrophy (DMD), Emery-Dreifuss muscular dystrophy (EDMD), Facioscapulohumeral muscular dystrophy (FSHD), Limb-girdle muscular dystrophies (LGMD), Myotonic dystrophy (DM), and Oculopharyngeal muscular dystrophy (OPMD). In some embodiments, Congenital muscular dystrophies (CMD) is selected from Bethlem CMD, Fukuyama CMD, Muscle-eye-brain diseases (MEBs), Rigid spine syndromes, Ullrich CMD, and Walker-Warburg syndromes (WWS). In some embodiments, myopathies are diseases of muscle that are not caused by nerve disorders. Myopathies cause the muscles to become weak or shrunken (atrophied). In some embodiments, myopathies are selected from congenital myopathies, distal myopathies, endocrine myopathies, inflammatory myopathies, metabolic myopathies, myofibrillar myopathies (MFM), scapuloperoneal myopathy, and cardiomyopathies. In some embodiments, congenital myopathies are selected from cap myopathies, centronuclear myopathies, congenital myopathies with fiber type disproportion, core myopathies, central core disease, multiminicore myopathies, myosin storage myopathies, myotubular myopathy, and nemaline myopathies. In some embodiments, distal myopathies are selected from, gne myopathy/Nonaka myopathy/hereditary inclusion-body myopathy (HIBM), laing distal myopathy, Markesbery-Griggs late-onset distal myopathy, Miyoshi myopathy, Udd myopathy/tibial muscular dystrophy, VCP myopathy/IBMPFD, vocal cord and pharyngeal distal myopathy, and Welander distal myopathy. In some embodiments, endocrine myopathies are selected from, hyperthyroid myopathy, and hypothyroid myopathy. In some embodiments, inflammatory myopathies are selected from, dermatomyositis, inclusion-body myositis, and polymyositis. In some embodiments, metabolic myopathies are selected from, von Gierke's disease, Anderson disease, Fanconi-Bickel syndrome, aldolase A deficiency, acid maltase deficiency (Pompe disease), carnitine deficiency, carnitine palmitoyltransferase deficiency, debrancher enzyme deficiency (Cori disease, Forbes disease), lactate dehydrogenase deficiency, myoadenylate deaminase deficiency, phosphofructokinase deficiency (Tarui disease), phosphoglycerate kinase deficiency, phosphoglycerate mutase deficiency (Her's disease), and phosphorylase deficiency (e.g., McArdle's disease). In some embodiments, metabolic myopathies are selected from McArdle's disease. In some embodiments, cardiomyopathies are selected from intrinsic cardiomyopathies and extrinsic cardiomyopathies. In some embodiments, intrinsic cardiomyopathies are selected from genetic myopathies and acquired myopathies. In some embodiments, genetic myopathies are selected from Hypertrophic cardiomyopathy, arrhythmogenic right ventricular cardiomyopathy (ARVC), LV non-compaction, ion channelopathies, dilated cardiomyopathy (DCM), and restrictive cardiomyopathy (RCM). In some embodiments, acquired myopathies are selected from stress cardiomyopathy, myocarditis, eosinophilic myocarditis, and ischemic cardiomyopathy. In some embodiments, extrinsic cardiomyopathies are selected from metabolic cardiomyopathies, endomyocardial cardiomyopathies, endocrine cardiomyopathies, and cardiofacial cardiomyopathies. In some embodiments, metabolic cardiomyopathies are selected from Fabry's disease and hemochromatosis. In some embodiments, endomyocardial cardiomyopathies are selected from endomyocardial fibrosis and Hypereosinophilic syndrome. In some embodiments, endocrine cardiomyopathies are selected from diabetes mellitus, hyperthyroidism, and acromegaly. In some embodiments, the Cardiofacial cardiomyopathy is Noonan syndrome. In some embodiments, the disease (e.g., activity-induced muscle damage, neuromuscular condition, movement disorder, or metabolic myopathy) comprises muscle wasting. In some embodiments, the muscle wasting comprises Cachexia. In some embodiments, the Cachexia is associated with one or more cancer(s). In some embodiments, the one or more cancer(s) is selected from renal cell carcinoma. In some embodiments, the muscle wasting arises from inactivity. In some embodiments, the muscle wasting comprises acute quadriplegic myopathy. In some embodiments, the muscle wasting arises from a reaction against anesthetics. In some embodiments, the muscle wasting comprises rhabdomyolysis. In some embodiments, the muscle wasting comprises Compartment syndrome. In some embodiments, the disease comprises muscle pain. In some embodiments, the disease comprises back pain. In some embodiments, the disease comprises lower-back pain. In some embodiments, the disease comprises chronic back pain. In some embodiments, the disease comprises insomnia. In some embodiments, the disease is insomnia. In some embodiments, the compound or salt is administered in a low dose. In some embodiments, the disease is insomnia, and the compound or salt is administered in a low dose. In some embodiments, the subject in need thereof experiences enhanced strength and enhanced fatiguability. In some embodiments, the subject in need thereof does not experience muscle leakiness.

In some embodiments, the present disclosure provides methods of treating a cardiomyopathy in a patient with a neuromuscular condition (e.g., Duchenne Muscular Dystrophy, Becker Muscular Dystrophy, Limb-Girdle Muscular Dystrophy, e.g., susceptible LGMD), the methods comprising administering a compound or salt of the present disclosure.

Combination Therapies

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually hours, days, weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

In certain embodiments, a compound or salt of the disclosure may be administered in combination with an atrial activator. In some embodiments, the combination of a compound or salt of the present disclosure with an atrial activator is administered to a patient with HFpEF.

In certain embodiments, a compound or salt of the disclosure may be administered in combination with an oral corticosteroid. In certain embodiments, a compound or salt of the disclosure is administered in combination with deflazacort. In certain embodiments, a compound or salt of the disclosure is administered in combination with prednisone. In certain embodiments, a compound or salt of the disclosure is administered in combination with a morpholino antisense oligomer. In certain embodiments, a compound or salt of the disclosure is administered in combination with and exon skipping therapy. In certain embodiments, the additional therapeutic agent is eteplirsen or ataluren.

In certain embodiments, a compound or salt of the disclosure is used in combination with a gene therapy. In certain embodiments, the compound or salt of the disclosure is used in combination with adeno-associated virus (AAV) containing genes encoding replacement proteins, e.g., dystrophin, or truncated version thereof, e.g., microdystrophin. In certain embodiments, a compound or salt of the disclosure is administered in combination with vamorolone.

Some numbered examples of embodiments follow. (1) A compound represented by Formula (I):

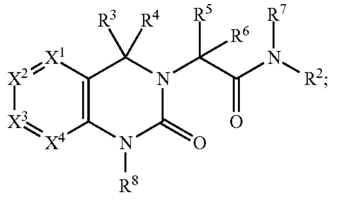

(I)

or a salt thereof, wherein: $X^1$, $X^2$, $X^3$, and $X^4$ are each independently selected from $C(R^1)$, N, and $N^+(—O^-)$, wherein at least one of $X^1$, $X^2$, $X^3$, or $X^4$ is N; and no more than two of $X^1$, $X^2$, $X^3$, and $X^4$ are N; each $R^1$ is independently selected from: hydrogen; halogen, $—NO_2$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$; $C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2R^{10a}$, $—NO_2$, =O, =S, $=N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, =O, =S, $=N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$; $R^2$ is selected from: $C_{1-6}$ alkyl, $C_{2-6}$ alkenyl, and $C_{2-6}$ alkynyl, each of which is optionally substituted with one or more substituents independently selected from halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—C(O)OR^{10b}$, $—OC(O)R^{10b}$, $—N(R^{10b})C(O)N(R^{10b})_2$, $—OC(O)N(R^{10b})_2$, $—N(R^{10b})C(O)OR^{10b}$, $—S(O)R^{10b}$, $—S(O)_2R^{10b}$, $—NO_2$, =O, =S, $=N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$; $R^3$ and $R^4$ are each independently selected from: hydrogen, halogen, —$OR^{10c}$, —$SR^{10c}$, —$N(R^{10c})_2$, —$NO_2$, and —CN; and $C_{1-6}$ alkyl optionally substituted with one or more substituents independently selected from halogen, —$OR^{10c}$, —$SR^{10c}$, —$N(R^{10c})_2$, —$NO_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$; $R^5$ and $R^6$ are each independently selected from: hydrogen, halogen, —$OR^{10c}$, —$SR^{10c}$, —$N(R^{10c})_2$, —$NO_2$, and —CN; $C_{1-6}$ alkyl, optionally substituted with one or more substituents independently selected from halogen, —$OR^{10c}$, —$SR^{10c}$, —$N(R^{10c})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10c}$, —$SR^{10c}$, —$N(R^{10c})_2$, —$NO_2$, and —CN; and $C_{3-10}$ carbocycle and 3- to 10-membered heterocycle, each of which is optionally substituted with one or more substituents independently selected from halogen, —$OR^{10c}$, —$SR^{10c}$, —$N(R^{10c})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$; $R^7$ is selected from: hydrogen and $C_{1-6}$ alkyl optionally substituted with one or more substituents independently selected from halogen, —$OR^{10d}$, —$SR^{10d}$, —$N(R^{10d})_2$, —$NO_2$, and —CN; $R^8$ is selected from: hydrogen; and $C_{1-6}$ alkyl optionally substituted with one or more substituents independently selected from halogen, —$OR^{10e}$, —$SR^{10e}$, —$N(R^{10e})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10e}$, —$SR^{10e}$, —$N(R^{10e})_2$, —$NO_2$, and —CN; each $R^{9a}$ is independently selected from: halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN; each $R^{9b}$ is independently selected from: halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$ and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN; each $R^{9c}$ is independently selected from: halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$ and —CN; and each $R^{10a}$, $R^{10b}$, $R^{10c}$, $R^{10d}$, and $R^{10e}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; wherein if $X^3$ and $X^1$ are both N, then $R^8$ is selected from hydrogen and $C_{1-4}$ alkyl optionally substituted with one or more substituents independently selected from halogen, —$OR^{10}$, —$SR^{10}$, —$N(R^{10})_2$, —$NO_2$, and —CN. (2) The compound or salt of embodiment 1, wherein $X^1$, $X^2$, $X^3$, and $X^4$ are each independently selected from $C(R^1)$ and N. (3) The compound or salt of embodiment 1 or 2, wherein one of $X^1$, $X^2$, $X^3$, or $X^4$ is N. (4) The compound or salt of embodiment 3, wherein $X^1$ is N. (5) The compound or salt of embodiment 3, wherein $X^2$ is N. (6) The compound or salt of embodiment 3, wherein $X^3$ is N. (7) The compound or salt of embodiment 3, wherein $X^4$ is N. (8) The compound or salt of embodiments 1 or 2, wherein two of $X^1$, $X^2$, $X^3$, and $X^4$ are N. (9) The compound or salt of embodiment 8, wherein $X^1$ and $X^3$ are N. (10) The compound or salt of embodiment 8, wherein $X^2$ and $X^4$ are N. (11) The compound or salt of any one of embodiments 1 to 10, wherein each $R^1$ is independently selected from: hydrogen; halogen, —$NO_2$, —CN, —$OR^{10a}$, —$SR^{10a}$, —$N(R^{10a})_2$, —$C(O)R^{10a}$, and —$C(O)N(R^{10a})_2$; $C_{1-6}$ alkyl, optionally substituted with one or more substituents independently selected from halogen, —$OR^{10a}$, —$SR^{10a}$, —$N(R^{10a})_2$, —$C(O)R^{10a}$, —$NO_2$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —CN, $C_{1-6}$ alkyl optionally substituted with one or more $R^{9a}$. (12) The compound or salt of any one of embodiments 1 to 11, wherein each $R^1$ is independently selected from: hydrogen; halogen, —$NO_2$, —CN, —$OR^{10a}$, —$SR^{10a}$, —$N(R^{10a})_2$, —$C(O)R^{10a}$, and —$C(O)N(R^{10a})_2$; $C_{1-6}$ alkyl, optionally substituted with one or more substituents independently selected from halogen, —$OR^{10a}$, —$SR^{10a}$, and —$N(R^{10a})_2$; and $C_{3-10}$ carbocycle and 3- to 10-membered heterocycle, each of which is optionally substituted with one or more substituents independently selected from halogen, —$OR^{10a}$, —$SR^{10a}$, and —$N(R^{10a})_2$. (13) The compound or salt of any one of embodiments 1 to 12, wherein each $R^1$ is independently selected from: hydrogen; halogen, CN, —$OR^{10a}$, and —$C(O)N(R^{10a})_2$; $C_{1-6}$ alkyl, optionally substituted with one or more substituents independently selected from halogen, and $C_{3-10}$ carbocycle optionally substituted with one or more substituents independently selected from halogen. (14) The compound or salt of any one of embodiments 1 to 13, wherein $R^1$ is hydrogen. (15) The compound or salt of any one of embodiments 1 to 10, wherein each $R^1$ is independently selected from hydrogen, halogen, —$NO_2$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, and —$S(O)_2R^{10a}$; (16) The compound or salt of any one of 1 to 10 or embodiment 15, wherein each $R^1$ is independently selected from hydrogen, $C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, =O, =S, =$N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$. (17) The compound or salt of any one of embodiments 1 to 10 or embodiments 15 to 16, wherein each $R^1$ is independently selected from hydrogen, $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$. (18) The compound or salt of any one of embodiments 1 to 10 or embodiments 15 to 17, wherein each $R^1$ is independently selected from: hydrogen; halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, and —$NH(C_{1-6}$ alkyl); $C_{1-6}$ alkyl, $C_{2-6}$ alkenyl, and $C_{2-6}$ alkynyl, each of which is optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, and $C_{2-6}$ alkynyl. (19) The compound or salt of any one of embodiments 1 to 10 or embodiments 15 to 18, wherein each $R^1$ is independently selected from $C_{1-3}$ alkyl optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, —NH($C_{1-6}$ alkyl), $C_{3-10}$ carbocycle and 3- to 10-membered heterocycle. (20) The compound or salt of any one of embodiments 1 to 10 or embodiments 15 to 19, wherein each $R^1$ is independently selected from $C_{3-5}$ carbocycle is optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, and $C_{2-6}$ alkynyl. (21) The compound or salt of any one of embodiments 1 to 10 or embodiments 15 to 20, wherein each $R^1$ is independently selected from hydrogen, —CN, —OH, —OMe, —OEt, —OiPr, —F, —Cl, —Br, -Me, -Et, —$CF_3$, —$CHF_2$, —$CH_2F$, $OCF_3$, —$OCHF_2$, —$OCH_2F$, —$C(O)NH_2$,

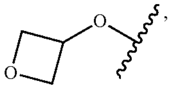, 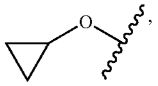, 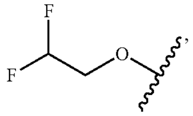,

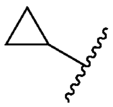, and 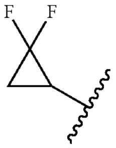.

(22) The compound or salt of any one of embodiments 1 to 21, wherein $R^2$ is selected from $C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (23) The compound or salt of any one of embodiments 1 to 22, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (24) The compound or salt of any one of embodiments 1 to 23, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (25) The compound or salt of any one of embodiments 1 to 24, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (26) The compound or salt of any one of embodiments 1 to 25, wherein $R^2$ is selected from $C_{1-6}$ alkyl, optionally substituted with one or more substituents independently selected from halogen, —$OR^{10b}$, —$SR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (27) The compound or salt of any one of embodiments 1 to 21, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (28) The compound or salt of any one of embodiments 1 to 21, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl, wherein the $C_{1-6}$ alkyl is optionally substituted with one or more $R^{9b}$. (29) The compound or salt of any one of embodiments 1 to 21 or embodiment 28, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl. (30) The compound or salt of any one of embodiments 1 to 21 or any one of embodiments 28 to 29, wherein $R^2$ is selected from $C_{1-6}$ alkyl, optionally substituted with one or more substituents independently selected from halogen, —$OR^{10b}$, —$SR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl. (31) The compound or salt of any one of embodiments 1 to 21 or any one of embodiments 28 to 30, wherein $R^2$ is selected from $C_{1-6}$ alkyl, optionally substituted with one or more substituents independently selected from halogen, —$OR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl. (32) The compound or salt of any one of embodiments 1 to 21 or any one of embodiments 28 to 31, wherein $R^2$ is selected from $C_{1-6}$ alkyl, optionally substituted with one or more substituents independently selected from halogen, —$OR^{10b}$, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, and —CN. (33) The compound or salt of any one of embodiments 1 to 21 or any one of embodiments 28 to 32, wherein $R^2$ is selected from $C_{1-6}$ alkyl, optionally substituted with one or more substituents independently selected from F, OH, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from F, and —CN. (34) The compound or salt of any one of embodiments 1 to 21 or any one of embodiments 28 to 33, wherein $R^2$ is selected from $C_{1-6}$ alkyl, optionally substituted with one or more substituents independently selected from F, OH, $C_{3-10}$ carbocycle and 3- to 10-membered heterocycle, wherein each $C_{3-10}$ carbocycle and 3- to 10-membered heterocycle is independently selected from phenyl, 2-pyridyl, and 3-pyridyl, and each phenyl, 2-pyridyl, and 3-pyridyl is optionally substituted with one or more $R^{9b}$; and $C_{3-10}$ carbocycle and 3- to 10-membered heterocycle, each of which is optionally substituted with one or more substituents independently selected from F, and —CN. (35) The compound or salt of any one of embodiments 1 to 21 or any one of embodiments 28 to 34, wherein $R^2$ is selected from $C_2$ alkyl, optionally substituted with one or more substituents independently selected from halogen, —$OR^{10b}$, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from F, and —CN. (36) The compound or salt of any one of embodiments 1 to 21 or any one of embodiments 28 to 35, wherein $R^2$ is selected from $C_2$ alkyl, optionally substituted with one or more substituents independently selected from F, OH, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from F, and —CN. (37) The compound or salt of any one of embodiments 1 to 21 or embodiments 28 to 36, wherein $R^2$ is $C_2$ alkyl, optionally substituted with one or more substituents independently selected from F, OH, $C_{3-10}$ carbocycle and 3- to 10-membered heterocycle, wherein each $C_{3-10}$ carbocycle and 3- to 10-membered heterocycle is independently selected from phenyl, 2-pyridyl, and 3-pyridyl, and each phenyl, 2-pyridyl, and 3-pyridyl is optionally substituted with one or more $R^{9b}$. (38) The compound or salt of any one of embodiments 1 to 34, wherein $R^2$ is a substituent represented by the following:

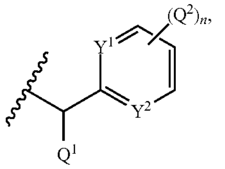

wherein, $Q^1$ is a $C_{1-3}$ alkyl optionally substituted with one or more substituents selected from OH and halo; $Y^1$ and $Y^2$ are each independently selected from N and $C(Q^3)$; and each $Q^2$ is independently selected from halo and CN; each $Q^3$ is independently selected from hydrogen, halo and CN; and n is 0, 1, or 2. (39) The compound or salt of embodiments 1 to 34 or embodiment 38, wherein $Q^1$ is a $C_1$ alkyl optionally substituted with one or more substituents selected from OH and fluoro; each $Q^2$ is independently selected from fluoro and CN; and each $Q^3$ is independently selected from hydrogen, fluoro and CN. (40) The compound or salt of any one of embodiments 1 to 36, wherein $R^2$ is selected from

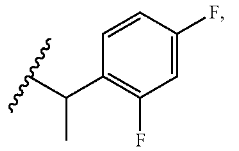
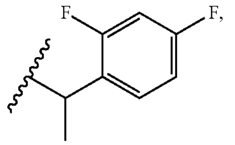
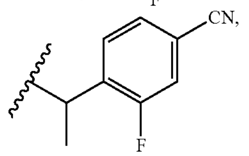
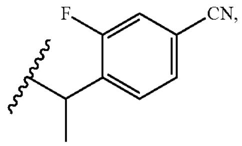

-continued

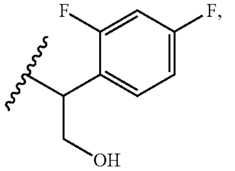
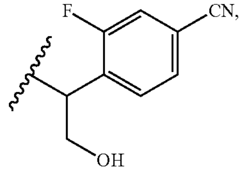
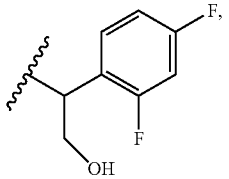
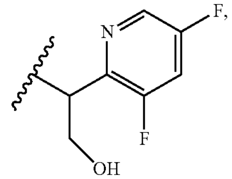
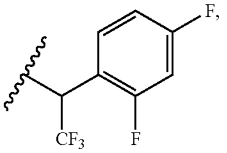
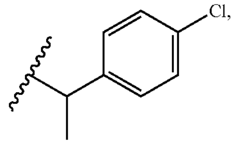
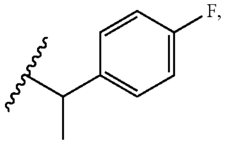
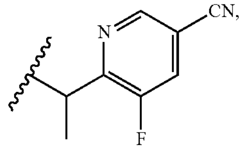
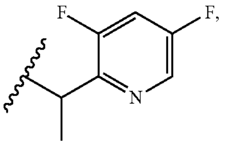
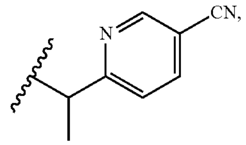
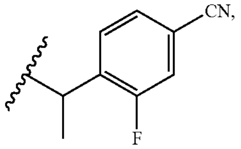
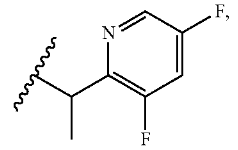
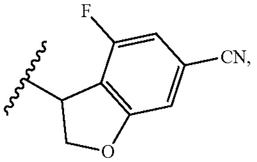
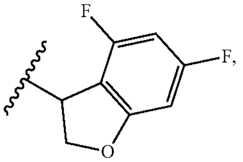

and

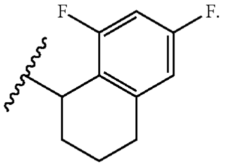

(41) The compound or salt of any one of embodiments 1 to 40, wherein $R^3$ and $R^4$ are each independently selected from: hydrogen, halogen, —$OR^{10c}$, —$SR^{10c}$, —$N(R^{10c})_2$, —$NO_2$, and —CN; and $C_{1-6}$ alkyl optionally substituted with one or more substituents independently selected from halogen, —$OR^{10c}$, —$SR^{10c}$, —$N(R^{10c})_2$, —$NO_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$. (42) The compound or salt of any one of embodiments 1 to 41, wherein $R^3$ and $R^4$ are each independently selected from: hydrogen, halogen, —$NO_2$, and —CN; and $C_{1-6}$ alkyl optionally substituted with one or more halogen; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$. (43) The compound or salt of any one of embodiments 1 to 42, wherein $R^3$ and $R^4$ are each independently selected from: hydrogen, halogen, —$NO_2$, and —CN; and $C_{1-6}$ alkyl optionally substituted with one or more halogen; or $R^3$ together with $R^4$ form a 3- to 10-membered heterocycle or $C_{3-10}$ carbocycle. (44) The compound or salt of any one of embodiments 1 to 43, wherein $R^3$ and $R^4$ are each independently selected from: hydrogen; and $C_{1-6}$ alkyl optionally substituted with one or more halogen; or $R^3$ together with $R^4$ form a 3- to 10-membered heterocycle or $C_{3-10}$ carbocycle. (45) The compound or salt of any one of embodiments 1 to 44, wherein $R^3$ and $R^4$ are each independently selected from: hydrogen; and $C_{1-6}$ alkyl optionally substituted with one or more halogen. (46) The compound or salt of any one of embodiments 1 to 45, wherein $R^3$ and $R^4$ are each independently selected from: hydrogen; and $C_{1-6}$ alkyl. (47) The compound or salt of any one of embodiments 1 to 46, wherein $R^3$ and $R^4$ are each independently selected from: hydrogen; and $C_1$ alkyl. (48) The compound or salt of any one of embodiments 1 to 44, wherein $R^3$ together with $R^4$ form a 3- to 10-membered heterocycle or $C_{3-10}$ carbocycle. (49) The compound or salt of any one of embodiments 1 to 44 or embodiment 48, wherein the 3- to 10-membered heterocycle or $C_{3-10}$ carbocycle formed by $R^3$ together with $R^4$ is selected from cyclopropyl and oxetanyl. (50) The compound or salt of any one of embodiments 1 to 49, wherein $R^5$ and $R^6$ are each independently selected from: hydrogen, halogen, —$OR^{10c}$, —$SR^{10c}$, —$N(R^{10c})_2$, —$NO_2$, and —CN; $C_{1-6}$ alkyl, optionally substituted with one or more substituents independently selected from halogen, —$OR^{10c}$, —$SR^{10c}$, —$N(R^{10c})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10c}$, —$SR^{10c}$, —$N(R^{10c})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$. (51) The compound or salt of any one of embodiments 1 to 50, wherein $R^5$ and $R^6$ are each independently selected from: hydrogen, halogen, —$OR^{10c}$, —$SR^{10c}$, —$N(R^{10c})_2$, —$NO_2$, and —CN; and $C_{1-6}$ alkyl; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$. (52) The compound or salt of any one of embodiments 1 to 51, wherein $R^5$ and $R^6$ are each independently selected from: hydrogen, halogen, —$OR^{10c}$, —$SR^{10c}$, —$N(R^{10c})_2$, —$NO_2$, and —CN; and $C_{1-6}$ alkyl. (53) The compound or salt of any one of embodiments 1 to 52, wherein $R^5$ and $R^6$ are each independently selected from: hydrogen and $C_{1-3}$ alkyl. (54) The compound or salt of any one of embodiments 1 to 53, wherein $R^5$ and $R^6$ are each hydrogen. (55) The compound or salt of any one of embodiments 1 to 54, wherein $R^7$ is selected from hydrogen and $C_{1-6}$ alkyl optionally substituted with one or more substituents independently selected from halogen. (56) The compound or salt of any one of embodiments 1 to 55, wherein $R^7$ is selected from hydrogen. (57) The compound or salt of any one of embodiments 1 to 56, wherein $R^8$ is selected from: hydrogen; and $C_{1-6}$ alkyl optionally substituted with one or more substituents independently selected from halogen, —$OR^{10e}$, —$SR^{10e}$, —$N(R^{10e})_2$, —$NO_2$, —CN, $C_{3-10}$ carbocycle, and 3- to 10-membered heterocycle. (58) The compound or salt of any one of embodiments 1 to 57, wherein $R^8$ is selected from: hydrogen; and $C_{1-6}$ alkyl optionally substituted with one or more substituents independently selected from halogen, —$OR^{10e}$, —$SR^{10e}$, —$N(R^{10e})_2$, —$NO_2$, and —CN. (59) The compound or salt of any one of embodiments 1 to 58, wherein $R^8$ is selected from hydrogen. (60) The compound or salt of any one of embodiments 1 to 59, wherein each $R^{9a}$ is independently selected from: halogen, —$OR^{10a}$, —$SR^{10a}$, —$N(R^{10a})_2$, —$C(O)R^{10a}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$NO_2$, =O, and —CN. (61) The compound or salt of any one of embodiments 1 to 60, wherein each $R^{9a}$ is independently selected from: halogen, —$OR^{10a}$, —$SR^{10a}$, —$N(R^{10a})_2$, —$C(O)R^{10a}$, —$NO_2$, =O, and —CN; and $C_{1-3}$ alkyl optionally substituted with one or more substituents independently selected from halogen, —$OR^{10a}$, —$SR^{10a}$, —$N(R^{10a})_2$, —$C(O)R^{10a}$, —$NO_2$, =O, and —CN. (62) The compound or salt of any one of embodiments 1 to 61, wherein each $R^{9b}$ is independently selected from: halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, and —CN. (63) The compound or salt of any one of embodiments 1 to 62, wherein each $R^{9b}$ is independently selected from: halogen, —$OR^{10b}$, —$SR^{10b}$, —$N(R^{10b})_2$, —$NO_2$, =O, and —CN; and $C_{1-3}$ alkyl, optionally substituted with one or more substituents independently selected from halogen, —$OR^{10b}$, —$SR^{10b}$, —$N(R^{10b})_2$, —$NO_2$, =O, and —CN. (64) The compound or salt of any one of embodiments 1 to 63, wherein each $R^{9b}$ is independently selected from: halogen, —$OR^{10b}$, —$SR^{10b}$, —$N(R^{10b})_2$, —$NO_2$, =O, and —CN; and $C_{1-3}$ alkyl, optionally substituted with one or more substituents independently selected from halogen, —$OR^{10b}$, —$SR^{10b}$, —$N(R^{10b})_2$, —$NO_2$, =O, and —CN. (65) The compound or salt of any one of embodiments 1 to 64, wherein each $R^{9b}$ is independently selected from halogen and —CN. (66) The compound or salt of any one of embodiments 1 to 65, wherein each $R^{9c}$ is independently selected from halogen, —$OR^{10c}$, —$SR^{10c}$, —$N(R^{10c})_2$, —$C(O)R^{10c}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10c}$, —$SR^{10c}$, —$N(R^{10c})_2$, —$C(O)R^{10c}$, —$NO_2$, =O, and —CN. (67) The compound or salt of any one of embodiments 1 to 66, wherein each $R^{9c}$ is independently selected from halogen, —$OR^{10c}$, —$SR^{10c}$, —$N(R^{10c})_2$, —$C(O)R^{10c}$, —$NO_2$, =O, and —CN; and $C_{1-3}$ alkyl, optionally substituted with one or more substituents independently selected from halogen, —$OR^{10c}$, —$SR^{10c}$, —$N(R^{10c})_2$, —$C(O)R^{10c}$, —$NO_2$, =O, and —CN. (68) The compound or salt of any one of embodiments 1 to 67, wherein each $R^{10a}$ is independently selected from hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —NH($C_{1-6}$ alkyl), $C_{1-6}$ alkyl, $C_{3-10}$ carbocycle, 3- to 10-membered heterocycle, and $C_{1-6}$ haloalkyl. (69) The compound or salt of any one of embodiments 1 to 68, wherein each $R^{10a}$ is independently selected from hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —N($C_{1-6}$ alkyl)$_2$, and —NH($C_{1-6}$ alkyl); and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —N($C_{1-6}$ alkyl)$_2$, —NH($C_{1-6}$ alkyl), $C_{1-6}$ alkyl, and $C_{1-6}$haloalkyl. (70) The compound or salt of any one of embodiments 1 to 69, wherein each $R^{10a}$ is independently selected from hydrogen; and $C_{1-6}$ alkyl, optionally substituted with one or more substituents independently selected from halogen, —CN, —OH, —SH, —$NO_2$, —$NH_2$, and =O; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —N($C_{1-6}$ alkyl)$_2$, —NH($C_{1-6}$ alkyl), $C_{1-6}$ alkyl, and $C_{1-6}$ haloalkyl. (71) The compound or salt of any one of embodiments 1 to 70, wherein each $R^{10a}$ is independently selected from hydrogen; and $C_{1-6}$ alkyl optionally substituted with one or more substituents independently selected from halogen; and $C_{3-10}$ carbocycle, and 3- to 10-membered heterocycle. (72) The compound or salt of any one of embodiments 1 to 71, wherein each $R^{10b}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, and —NH($C_{1-6}$ alkyl); and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, and $C_{1-6}$ haloalkyl. (73) The compound or salt of any one of embodiments 1 to 72, wherein each $R^{10b}$ is independently selected from: hydrogen; and $C_{1-6}$ alkyl. (74) The compound or salt of any one of embodiments 1 to 73, wherein each $R^{10b}$ is hydrogen. (75) The compound or salt of any one of embodiments 1 to 74, wherein each $R^{10c}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. (76) The compound or salt of any one of embodiments 1 to 75, wherein each $R^{10c}$ is independently selected from: hydrogen; and $C_{1-6}$ alkyl. (77) The compound or salt of any one of embodiments 1 to 76, wherein each $R^{10c}$ is hydrogen. (78) The compound or salt of any one of embodiments 1 to 77, wherein each $R^{10d}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. (79) The compound or salt of any one of embodiments 1 to 78, wherein each $R^{10d}$ is independently selected from: hydrogen; and $C_{1-6}$ alkyl. (80) The compound or salt of any one of embodiments 1 to 79, wherein each $R^{10d}$ is hydrogen. (81) The compound or salt of any one of embodiments 1 to 80, wherein each $R^{10e}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. (82) The compound or salt of any one of embodiments 1 to 81, wherein each $R^{10b}$ is independently selected from: hydrogen; and $C_{1-6}$ alkyl. (83) The compound or salt of any one of embodiments 1 to 82, wherein each $R^{10e}$ is hydrogen. (84) The compound or salt of any one of embodiments 1 to 83, wherein if $X^3$ and $X^1$ are both N, then $R^8$ is selected from hydrogen and $C_{1-4}$ alkyl optionally substituted with one or more substituents independently selected from halogen, —$OR^{10}$, and —CN. (85) The compound or salt of any one of embodiments 1 to 84, wherein if $X^3$ and $X^1$ are both N, then $R^8$ is selected from hydrogen and $C_{1-4}$ alkyl optionally substituted with one or more substituents independently selected from fluoro, —OH, and —CN. (86) The compound or salt of any one of embodiments 1 to 85, wherein if $X^3$ and $X^1$ are both N, then $R^8$ is selected from hydrogen and $C_{1-4}$ alkyl. (87) The compound or salt of any one of embodiments 1 to 86, wherein if $X^3$ and $X^1$ are both N, then $R^8$ is selected from hydrogen and $C_1$ alkyl. (88) The compound or salt of any one of embodiments 1 to 87, wherein if $X^3$ and $X^1$ are both N, then $R^8$ is selected from hydrogen. Embodiments (89), (90), (91), (89A), (90A), (91A), (89B), (90B): In some embodiments, the compound of formula (I) is selected from compound N1, N2, N3, N4, N5, N6, N7, N8, N9, N10, N11, N12, N13, N14, N15, N16, N17, N18, N19, N20, N21, N22, N23, N24, N25, N26, N27, N28, N29, N30, N31, N32, N33, N34, N35, N36, N37, N38, N39, N40, N41, N42, N43, N44, N45, N46, N47, N48, N49, N50, N51, N52, N53, N54, N55, N56, N57, N58, N59, N60, N61, N62, N63, N64, N65, N66, N67, N68, N69, N70, N71, N72, N73, N74, N75, N76, N77, N78, N79, N80, N81, N82, N83, N84, N85, N86, N87, N88, N89, N90, N91, N92, N93, N94, N95, N96, N97, N98, N99, N100, N101, N102, N103, N104, N105, N106, N107, N108, N109, N110, N111, N112, N113, N114, N115, N116, N117, N118, N119, N120, N121, N122, N123, N124, N125, N126, N127, N128, N129, N130, N131, N132, N133, and a salt of any one thereof. In some embodiments, the compound of formula (I) is selected from compound N2, N4, N5, N6, N7, N8, N9, N10, N13, N15, N18, N19, N21, N23, N24, N26, N28, N31, N33, N36, N37, N39, N41, N44, N47, N54, N60, N62, N68, N72, N74, N77, N78, N81, N87, N88, N94, N95, N98, N101, N102, N103, N104, N108, N110, N111, N112, N113, N114, N115, N116, N117, N118, N119, N120, N121, N122, N123, N124, N125, N126, N127, N128, N129, N132, N133, and a salt of any one thereof. In some embodiments, the compound of formula (I) is selected from compound N4, N5, N7, N9, N13, N15, N18, N23, N26, N28, N31, N33, N37, N41, N47, N54, N62, N68, N74, N81, N87, N88, N94, N95, N101, N102, N103, N104, N111, N112, N114, N115, N117, N118, N119, N121, N123, N124, N125, N126, N128, N129, and a salt of any one thereof. In some embodiments, the compound of formula (I) is selected from compound N4, N5, N7, N13, N23, N33, N81, N87, N88, N94, N115, N117, N123, N124, N128, and a salt of any one thereof. In some embodiments, the compound of formula (I) is selected from compound N1, N2, N3, N4, N5, N6, N7, N8, N9, N10, N12, N13, N14, N15, N16, N17, N18, N19, N21, N23, N24, N25, N26, N28, N30, N31, N33, N34, N35, N36, N37, N38, N39, N40, N41, N43, N44, N45, N47, N50, N52, N54, N55, N57, N59, N60, N62, N64, N66, N68, N71, N72, N74, N77, N78, N80, N81, N83, N84, N85, N86, N87, N88, N91, N93, N94, N95, N98, N99, N101, N102, N103, N104, N106, N108, N109, N110, N111, N112, N113, N114, N115, N116, N117, N118, N119, N121, N122, N123, N124, N125, N126, N127, N128, N129, N130, N131, N132, N133, and a salt of any one thereof. In some embodiments, the compound of formula (I) is selected from compound N3, N4, N5, N6, N7, N8, N9, N10, N12, N13, N14, N15, N16, N18, N19, N21, N23, N24, N26, N28, N31, N33, N34, N35, N36, N37, N39, N41, N44, N47, N50, N54, N55, N59, N60, N62, N68, N72, N74, N77, N80, N81, N83, N84, N87, N88, N93, N94, N95, N98, N99, N101, N102, N103, N104, N106, N108, N109, N110, N111, N112, N114, N115, N116, N117, N118, N119, N121, N122, N123, N124, N125, N126, N127, N128, N129, N130, N132, N133, and a salt of any one thereof. In some embodiments, the compound of formula (I) is selected from compound N4, N5, N7, N9, N10, N13, N15, N16, N18, N23, N26, N28, N31, N33, N37, N47, N54, N62, N68, N74, N81, N83, N87, N88, N94, N98, N101, N102, N103, N104, N110, N111, N112, N115, N117, N118, N119, N121, N122, N123, N124, N125, N126, N128, and a salt of any one thereof. In some embodiments, the compound of formula (I) is selected from compound N4, N5, N13, N15, N33, N87, N111, N123, N124, N128, and a salt of any one thereof.

(92) A compound represented by Formula (II):

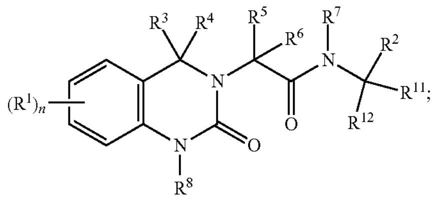

(II)

or a salt thereof, wherein: n is 0, 1, 2, 3, or 4; each $R^1$ is independently selected from: halogen, —$NO_2$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$ and —$S(O)_2R^{10a}$; $C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, =O, =S, =$N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$; $R^2$ is selected from: halogen, —$NO_2$, —CN, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, and —$S(O)_2R^{10b}$; $C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b}$'; $R^3$ and $R^4$ are each independently selected from: hydrogen, halogen, —$OR^{10c}$, —$SR^{10c}$, —$N(R^{10c})_2$, —$NO_2$, and —CN; and $C_{1-6}$ alkyl optionally substituted with one or more substituents independently selected from halogen, —$OR^{10c}$, —$SR^{10c}$, —$N(R^{10c})_2$, —$NO_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$; $R^5$ and $R^6$ are each independently selected from: hydrogen, halogen, —$OR^{10d}$, $SR^{10d}$, —$N(R^{10d})_2$, —$NO_2$, and —CN; and $C_{1-6}$ alkyl optionally substituted with one or more substituents independently selected from halogen, —$OR^{10d}$, —$SR^{10d}$, —$N(R^{10d})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9d}$; $R^7$ is selected from: hydrogen and $C_{1-6}$ alkyl optionally substituted with one or more substituents independently selected from halogen, —$OR^{10e}$, —$SR^{10e}$, —$N(R^{10e})_2$, —$NO_2$, and —CN; $R^8$ is selected from: hydrogen and $C_{1-6}$ alkyl optionally substituted with one or more substituents independently selected from halogen, —$OR^{10f}$, —$SR^{10f}$, —$N(R^{10f})_2$, —$NO_2$, and —CN; $R^{11}$ is selected from: halogen, —$NO_2$, —CN, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, and —$S(O)_2R^{10g}$; and $C_{1-6}$ alkyl, $C_{2-6}$ alkenyl, and $C_{2-6}$ alkynyl, each of which is optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, —$OC(O)R^{10g}$, —$N(R^{10g})C(O)N(R^{10g})_2$, —$OC(O)N(R^{10g})_2$, —$N(R^{10g})C(O)OR^{10g}$, —$S(O)R^{10g}$, —$S(O)_2R^{10g}$, —$NO_2$, =S, =$N(R^{10g})$, —CN, $C_{3-10}$ carbocycle and 3- to 10-membered heterocycle, wherein the $C_{3-10}$ carbocycle and 3- to 10-membered heterocycle are each optionally substituted with one or more $R^{9g}$; $R^{12}$ is selected from hydrogen; $C_{1-6}$ alkyl optionally substituted with one or more substituents independently selected from the group consisting of halogen, CN, OH, $OR^{10h}$, $N(R^{10h})_2$, $NO_2$, $C(O)R^{10h}$, $SR^{10h}$, and $S(O)R^{10h}$; and $C_{3-6}$ carbocycle and 3- to 10-membered heterocycle each optionally substituted with one or more substituents independently selected from the group consisting of halogen, CN, OH, $OR^{10h}$ $N(R^{10h})_2$, $NO_2$, $C(O)R^{10h}$, $SR^{10h}$, and $S(O)R^{10h}$; or $R^{12}$, $R^{11}$, and $R^2$ come together to form a $C_5$-$C_{10}$ bridged ring system; each $R^{9a}$ is independently selected from: halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN; each $R^{9b}$ is independently selected from: halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$ and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$ and —CN; each $R^{9b'}$ is independently selected from: halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$ and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$ and —CN; each $R^{9c}$ is independently selected from: halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10c}$, —$SR^{10c}$, $N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$ and —CN; each $R^{9d}$ is independently selected from: halogen, —$OR^{10d}$, —$SR^{10d}$, —$N(R^{10d})_2$, —$C(O)R^{10d}$, —$C(O)N(R^{10d})_2$, —$N(R^{10d})C(O)R^{10d}$, —$N(R^{10d})C(O)N(R^{10d})_2$, —$OC(O)N(R^{10d})_2$, —$N(R^{10d})C(O)OR^{10d}$, —$C(O)OR^{10d}$, —$OC(O)R^{10d}$, —$S(O)R^{10d}$, —$S(O)_2R^{10d}$, —$NO_2$, =O, =S, =$N(R^{10d})$ and —CN; and $C_{1-3}$ alkyl, $C_{2-3}$ alkenyl, and $C_{2-3}$ alkynyl, each of which is optionally substituted with one or more substituents independently selected from halogen, —$OR^{10d}$, $SR^{10d}$, —$N(R^{10d})_2$, $C(O)R^{10d}$, —$C(O)N(R^{10d})_2$, —$N(R^{10d})C(O)R^{10d}$, —$N(R^{10d})C(O)N(R^{10d})_2$, —$OC(O)N(R^{10d})_2$, —$N(R^{10d})C(O)OR^{10d}$, —$C(O)OR^{10d}$, —$OC(O)R^{10d}$, —$S(O)R^{10d}$, $S(O)_2R^{10d}$, —$NO_2$, =O, =S, =$N(R^{10d})$ and —CN; each $R^{9g}$ is independently selected from: halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, —$S(O)_2R^{10g}$, —$NO_2$, =O, =S, =$N(R^{10g})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, —$S(O)_2R^{10g}$, —$NO_2$, =O, =S, =$N(R^{10g})$, and —CN; each $R^{10a}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10b}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10c}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10d}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10b}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10f}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10g}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; and each $R^{10h}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH ($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. (93) The compound or salt of embodiment 92, wherein n is 0, 1, or 2. (94) The compound or salt of any one of embodiments 92 to 93, wherein n is 0. (95) The compound or salt of any one of embodiments 92 to 94, wherein n is 1 or 2. (96) The compound or salt of any one of embodiments 92 to 95, wherein n is 1. (97) The compound or salt of any one of embodiments 92 to 96, wherein n is 2. (98) The compound or salt of any one of embodiments 92 to 97, wherein each $R^1$ is independently selected from: halogen, —$NO_2$, —CN, —$OR^{10a}$, —$SR^{10a}$, —$N(R^{10a})_2$, —C(O)$R^{10a}$, —C(O)N($R^{10a}$)$_2$, —N($R^{10a}$)C(O)$R^{10a}$, —C(O)O$R^{10a}$, and —OC(O)$R^{10a}$; $C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —C(O)$R^{10a}$, —C(O)N($R^{10a}$)$_2$, —N($R^{10a}$)C(O)$R^{10a}$, —C(O)O$R^{10a}$, —OC(O)$R^{10a}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —C(O)$R^{10a}$, —C(O)N($R^{10a}$)$_2$, —N($R^{10a}$)C(O)$R^{10a}$, —C(O)O$R^{10a}$, —OC(O)$R^{10a}$, —$NO_2$, =O, —CN, $C_{1-6}$ alkyl, and $C_{2-6}$ alkenyl, wherein $C_{1-6}$ alkyl, and $C_{2-6}$ alkenyl, are each optionally substituted with one or more $R^{9a}$. (99) The compound or salt of any one of embodiments 92 to 98, wherein each $R^1$ is independently selected from: halogen, —$NO_2$, —CN, —$OR^{10a}$, —$SR^{10a}$, —$N(R^{10a})_2$, —C(O)$R^{10a}$, —C(O)N($R^{10a}$)$_2$, —N($R^{10a}$)C(O) $R^{10a}$, —C(O)O$R^{10a}$, and —OC(O)$R^{10a}$; $C_{1-6}$ alkyl and $C_{2-6}$ alkenyl each of which is optionally substituted with one or more substituents independently selected from halogen, —$OR^{10a}$, —$SR^{10a}$, —$N(R^{10a})_2$, —C(O)$R^{10a}$, —C(O)N ($R^{10a}$)$_2$, —N($R^{10a}$)C(O)$R^{10a}$, —C(O)O$R^{10a}$, —OC(O)$R^{10a}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —C(O)$R^{10a}$, —C(O)N($R^{10a}$)$_2$, —N($R^{10a}$)C(O)$R^{10a}$, —C(O)O$R^{10a}$, —OC(O)$R^{10a}$, —$NO_2$, =O, —CN, $C_{1-6}$ alkyl, and $C_{2-6}$ alkenyl, wherein $C_{1-6}$ alkyl, and $C_{2-6}$ alkenyl, are each optionally substituted with one or more $R^{9a}$. (100) The compound or salt of any one of embodiments 92 to 99, wherein each $R^1$ is independently selected from: halogen, —$NO_2$, —CN, —$OR^{10a}$, —$SR^{10a}$, —$N(R^{10a})_2$, and —C(O) $R^{10a}$; $C_{1-6}$ alkyl and $C_{2-6}$ alkenyl each of which is optionally substituted with one or more substituents independently selected from halogen, —$OR^{10a}$, —$SR^{10a}$, —$N(R^{10a})_2$, —C(O)$R^{10a}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —C(O)$R^{10a}$, —$NO_2$, =O, —CN, $C_{1-6}$ alkyl, and $C_{2-6}$ alkenyl, wherein $C_{1-6}$ alkyl, and $C_{2-6}$ alkenyl, are each optionally substituted with one or more $R^{9a}$. (101) The compound or salt of any one of embodiments 92 to 100, wherein each $R^1$ is independently selected from: halogen, —$NO_2$, —CN, —$OR^{10a}$, —$SR^{10a}$, —$N(R^{10a})_2$, and —C(O)$R^{10a}$; $C_{1-6}$ alkyl and $C_{2-6}$ alkenyl each of which is optionally substituted with one or more substituents independently selected from halogen, —$OR^{10a}$, —$SR^{10a}$, —$N(R^{10a})_2$, —C(O)$R^{10a}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle. (102) The compound or salt of any one of embodiments 92 to 101, wherein each $R^1$ is independently selected from: halogen, —$NO_2$, —CN, —$OR^{10a}$, —$SR^{10a}$, —$N(R^{10a})_2$, and —C(O)$R^{10a}$; and $C_{1-6}$ alkyl optionally substituted with one or more substituents independently selected from halogen, —$OR^{10a}$, —$SR^{10a}$, —$N(R^{10a})_2$, —C(O)$R^{10a}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$. (103) The compound or salt of any one of embodiments 92 to 102, wherein each $R^1$ is independently selected from: halogen, —$NO_2$, —CN, —$OR^{10a}$, —$SR^{10a}$, —$N(R^{10a})_2$, and —C(O)$R^{10a}$; and $C_{1-6}$ alkyl optionally substituted with one or more substituents independently selected from halogen, —$OR^{10a}$, —$SR^{10a}$, —$N(R^{10a})_2$, —C(O)$R^{10a}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$. (104) The compound or salt of any one of embodiments 92 to 103, wherein each $R^1$ is independently selected from: halogen, —$NO_2$, —CN, —$OR^{10a}$, —$SR^{10a}$, —$N(R^{10a})_2$, and —C(O)$R^{10a}$; and $C_{1-6}$ alkyl optionally substituted with one or more substituents independently selected from halogen, —$OR^{10a}$, —$SR^{10a}$, —$N(R^{10a})_2$, —C(O)$R^{10a}$, —$NO_2$, =O, and —CN. (105) The compound or salt of any one of embodiments 92 to 104, wherein each $R^1$ is independently selected from: halogen, —$NO_2$, —CN, —$OR^{10a}$, —$SR^{10a}$, —$N(R^{10a})_2$, and —C(O)$R^{10a}$; and $C_{1-6}$ alkyl. (106) The compound or salt of any one of embodiments 92 to 105, wherein each $R^1$ is independently selected from: halogen, —$NO_2$, —CN, —$OR^{10a}$, —$SR^{10a}$, and —$N(R^{10a})_2$. (107) The compound or salt of any one of embodiments 92 to 106, wherein each $R^1$ is independently selected from: halogen and —CN. (108) The compound or salt of any one of embodiments 92 to 107, wherein each $R^1$ is independently selected from: fluoro, bromo, and —CN. (109) The compound or salt of any one of embodiments 92 to 108, wherein $R^2$ is selected from: halogen, —$NO_2$, —CN, —$OR^{10b}$, —$SR^{10b}$, —$N(R^{10b})_2$, —C(O)$R^{10b}$, —C(O)$N(R^{10b})_2$, —$N(R^{10b})$C(O)$R^{10b}$, —C(O)$OR^{10b}$, and —OC(O)$R^{10b}$; $C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —C(O)$R^{10b}$, —C(O)$N(R^{10b})_2$, —$N(R^{10b})$C(O)$R^{10b}$, —C(O)$OR^{10b}$, —OC(O)$R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —C(O)$R^{10b}$, —C(O)$N(R^{10b})_2$, —$N(R^{10b})$C(O)$R^{10b}$, —C(O)$OR^{10b}$, —OC(O)$R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. (110) The compound or salt of any one of embodiments 92 to 109, wherein $R^2$ is selected from: halogen, —$NO_2$, —CN, —$OR^{10b}$, —$SR^{10b}$, —$N(R^{10b})_2$, —C(O)$R^{10b}$, —C(O)N$(R^{10b})_2$, —$N(R^{10b})$C(O)$R^{10b}$, —C(O)$OR^{10b}$, and —OC(O)$R^{10b}$; $C_{1-6}$ alkyl and $C_{2-6}$ alkenyl, each of which is optionally substituted with one or more substituents independently selected from halogen, —$OR^{10b}$, —$SR^{10b}$, —$N(R^{10b})_2$, —C(O)$R^{10b}$, —C(O)$N(R^{10b})_2$, —$N(R^{10b})$C(O)$R^{10b}$, —C(O)$OR^{10b}$, —OC(O)$R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —C(O)$R^{10b}$, —C(O)$N(R^{10b})_2$, —$N(R^{10b})$C(O)$R^{10b}$, —C(O)$OR^{10b}$, —OC(O)$R^{10b}$, —$NO_2$, =O, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. (111) The compound or salt of any one of embodiments 92 to 110, wherein $R^2$ is selected from: halogen, —$NO_2$, —CN, —$OR^{10b}$, —$SR^{10b}$, and —$N(R^{10b})_2$; $C_{1-6}$ alkyl and $C_{2-6}$ alkenyl, each of which is optionally substituted with one or more substituents independently selected from halogen, —$OR^{10b}$, —$SR^{10b}$, —$N(R^{10b})_2$, —C(O)$R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —C(O)$R^{10b}$, —$NO_2$, =O, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. (112) The compound or salt of any one of embodiments 92 to 111, wherein $R^2$ is selected from: halogen, —$NO_2$, —CN, —$OR^{10b}$, —$SR^{10b}$, and —$N(R^{10b})_2$; $C_{1-6}$ alkyl, optionally substituted with one or more substituents independently selected from halogen, —$OR^{10b}$, —$SR^{10b}$, —$N(R^{10b})_2$, —C(O)$R^{10b}$, —$NO_2$, =O, —CN; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —C(O)$R^{10b}$, —$NO_2$, =O, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. (113) The compound or salt of any one of embodiments 92 to 112, wherein $R^2$ is selected from: halogen, —$NO_2$, —CN, —$OR^{10b}$, —$SR^{10b}$, and —$N(R^{10b})_2$; $C_{1-6}$ alkyl, optionally substituted with one or more —$OR^{10b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —C(O)$R^{10b}$, —$NO_2$, =O, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. (114) The compound or salt of any one of embodiments 92 to 113, wherein $R^2$ is selected from: halogen, —$NO_2$, —CN, —$OR^{10b}$, —$SR^{10b}$, and —$N(R^{10b})_2$; $C_{1-6}$ alkyl; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —C(O)$R^{10b}$, —$NO_2$, =O, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. (115) The compound or salt of any one of embodiments 92 to 114, wherein $R^2$ is selected from: $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —C(O)$R^{10b}$, —$NO_2$, =O, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b\prime}$. (116) The compound or salt of any one of embodiments 92 to 115, wherein $R^2$ is selected from: $C_{3-10}$ carbocycle and 3- to 10-membered heterocycle, each of which is optionally substituted with one or more substituents independently selected from halogen, —$OR^{10b}$, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b\prime}$. (117) The compound or salt of any one of embodiments 92 to 116, wherein $R^2$ is selected from: $C_{3-10}$ carbocycle and 3- to 10-membered heterocycle, each of which is optionally substituted with one or more substituents independently selected from halogen, —$OR^{10b}$, —CN, and $C_{1-6}$ alkyl, wherein $C_{1-6}$ alkyl is optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b\prime}$. (118) The compound or salt of any one of embodiments 92 to 117, wherein $R^2$ is selected from: $C_{3-10}$ carbocycle and 3- to 10-membered heterocycle, each of which is optionally substituted with one or more substituents independently selected from fluoro, bromo, —$OR^{10b}$, —CN, and $C_{1-6}$ alkyl, wherein $C_{1-6}$ alkyl is optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b\prime}$. (119) The compound or salt of any one of embodiments 92 to 118, wherein $R^2$ is selected from: $C_{3-10}$ carbocycle and 3- to 10-membered heterocycle, each of which is optionally substituted with one or more substituents independently selected from fluoro, bromo, —OMe, —CN, and $C_{1-6}$ alkyl, wherein $C_{1-6}$ alkyl is optionally substituted with one or more $R^{9b}$. (120) The compound or salt of any one of embodiments 92 to 119, wherein $R^2$ is selected from: $C_{3-10}$ carbocycle and 3- to 10-membered heterocycle, each of which is optionally substituted with one or more substituents independently selected from fluoro, bromo, —OMe, —CN, and $C_{1-6}$ alkyl, wherein $C_{1-6}$ alkyl is optionally substituted with one or more fluoro. (121) The compound or salt of any one of embodiments 92 to 120, wherein $R^2$ is selected from: $C_{3-10}$ carbocycle and 3- to 10-membered heterocycle, each of which is optionally substituted with one or more substituents independently selected from fluoro, bromo, —OMe, —CN, and $C_1$ alkyl, wherein $C_1$ alkyl is optionally substituted with one or more fluoro. (122) The compound or salt of any one of embodiments 92 to 121, wherein $R^2$ is selected from phenyl, pyridyl, and pyrimidyl, wherein each phenyl, pyridyl, and pyrimidyl is optionally substituted with one or more substituents independently selected from fluoro, bromo, —OMe, —CN, and $C_1$ alkyl, wherein each $C_1$ alkyl is optionally substituted with one or more fluoro. (123) The compound or salt of any one of embodiments 92 to 122, wherein $R^2$ is selected from phenyl, 2-pyridyl, 2-pyrimidyl, and 6-pyrimidyl, wherein each phenyl, 2-pyridyl, 2-pyrimidyl, and 6-pyrimidyl is optionally substituted with one or more substituents independently selected from fluoro, bromo, —OMe, —CN, and $C_1$ alkyl, wherein each $C_1$ alkyl is optionally substituted with one or more fluoro. (124) The compound or salt of any one of embodiments 92 to 123, wherein $R^2$ is selected from

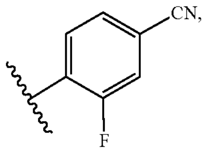 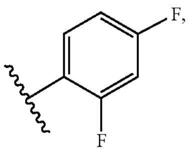

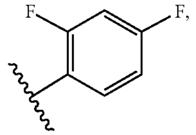 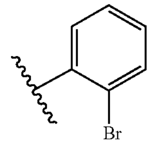

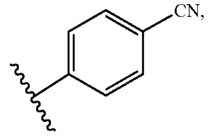 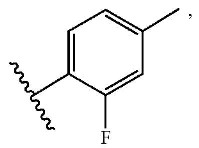

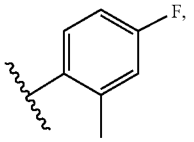 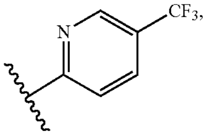

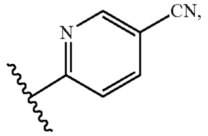 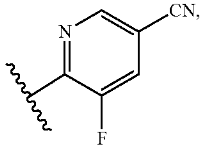

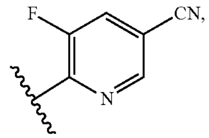 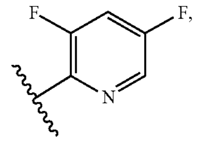

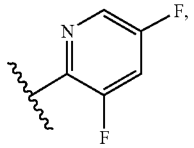 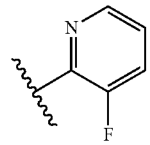

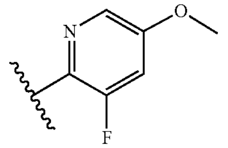 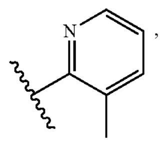

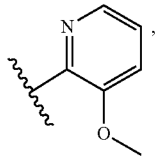 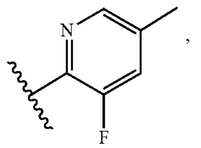

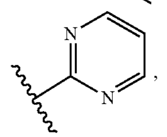, and 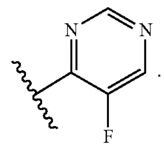.

(125) The compound or salt of any one of embodiments 92 to 118, wherein $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b\prime}$. (126) The compound or salt of any one of embodiments 92 to 118 or any one of embodiments 125, wherein $R^2$ together with $R^{11}$ form a 3- to 10-membered heterocycle or $C_{3-10}$ carbocycle, and wherein the 3- to 10-membered heterocycle or $C_{3-10}$ carbocycle is optionally substituted with one or more fluoro or CN. (127) The compound or salt of any one of embodiments 92 to 118 or any one of embodiments 125 to 126, wherein $R^2$ together with $R^{11}$ form a $C_{3-10}$ carbocycle or 3- to 10-membered heterocycle selected from dihydrobenzofuran and indene, each of which is optionally substituted with one or more substituents independently selected from fluoro and CN. (128) The compound or salt of any one of embodiments 92 to 118 or any one of embodiments 125 to 127, wherein $R^{12}$ is H and $R^2$ together with $R^{11}$ is selected from

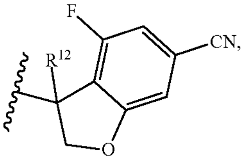

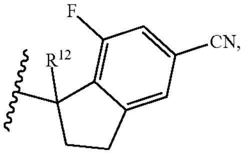

and

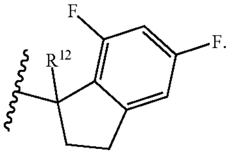

(129) The compound or salt of any one of embodiments 92 to 128, wherein $R^3$ and $R^4$ are each independently selected from: hydrogen; and $C_{1-6}$ alkyl optionally substituted with one or more substituents independently selected from halogen; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$. (130) The compound or salt of any one of embodiments 92 to 129, wherein $R^3$ and $R^4$ are each independently selected from: hydrogen; and $C_{1-6}$ alkyl optionally substituted with one or more substituents independently selected from halogen. (131) The compound or salt of any one of embodiments 92 to 130, wherein $R^3$ and $R^4$ are each independently selected from: hydrogen; and $C_1$ alkyl optionally substituted with one or more substituents independently selected from fluoro. (132) The compound or salt of any one of embodiments 92 to 129, wherein $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$. (133) The compound or salt of any one of embodiments 92 to 129 or embodiment 132, wherein $R^3$ together with $R^4$ form a $C_{3-10}$ carbocycle, wherein the $C_{3-10}$ carbocycle is optionally substituted with one or more $R^{9c}$. (134) The compound or salt of any one of embodiments 92 to 129 or any one of embodiments 132 to 133, wherein $R^3$ together with $R^4$ form a $C_{3-10}$ carbocycle. (135) The compound or salt of any one of embodiments 92 to 129 or any one of embodiments 132 to 134, wherein $R^3$ together with $R^4$ form a $C_{3-10}$ carbocycle selected from cyclopropyl, cyclobutyl, cyclopentyl, and cyclohexyl. (136) The compound or salt of any one of embodiments 92 to 135, wherein $R^5$ and $R^6$ are each independently selected from: hydrogen, halogen, —$OR^{10d}$, $SR^{10d}$, —$N(R^{10d})_2$, —$NO_2$, and —CN; and $C_{1-6}$ alkyl; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9d}$. (137) The compound or salt of any one of embodiments 92 to 136, wherein $R^5$ and $R^6$ are each independently selected from: hydrogen, halogen, —$OR^{10d}$, —$SR^{10}$ d, —$N(R^{10d})_2$, —$NO_2$, and —CN; and $C_{1-6}$ alkyl; or $R^5$ together with $R^6$ form a 3- to 10-membered heterocycle or $C_{3-10}$ carbocycle. (138) The compound or salt of any one of embodiments 92 to 137, wherein $R^5$ and $R^6$ are each independently selected from: hydrogen, halogen, —$OR^{10d}$, —$SR^{10d}$, —$N(R^{10d})_2$, —$NO_2$, and —CN; and $C_{1-6}$ alkyl. (139) The compound or salt of any one of embodiments 92 to 138, wherein $R^5$ and $R^6$ are each independently selected from: hydrogen, halogen, —$OR^{10d}$, —$SR^{10d}$, —$N(R^{10d})_2$, —$NO_2$, and —CN. (140) The compound or salt of any one of embodiments 92 to 139, wherein $R^5$ and $R^6$ are hydrogen. (141) The compound or salt of any one of embodiments 92 to 137, wherein $R^5$ and $R^6$ are each independently selected from: hydrogen; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9d}$. (142) The compound or salt of any one of embodiments 92 to 137 or embodiment 141, wherein $R^5$ and $R^6$ are each independently selected from: hydrogen; or $R^5$ together with $R^6$ form a 3- to 10-membered heterocycle or $C_{3-10}$ carbocycle. (143) The compound or salt of any one of embodiments 92 to 142, wherein $R^7$ is selected from: hydrogen, and $C_{1-3}$ alkyl. (144) The compound or salt of any one of embodiments 92 to 143, wherein $R^7$ is selected from: hydrogen. (145) The compound or salt of any one of embodiments 92 to 144, wherein $R^8$ is selected from: hydrogen and $C_{1-3}$ alkyl. (146) The compound or salt of any one of embodiments 92 to 145, wherein $R^8$ is selected from: hydrogen. (147) The compound or salt of any one of embodiments 92 to 146, wherein $R^{11}$ is selected from: halogen, —$NO_2$, —CN, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, and —$OC(O)R^{10g}$; and $C_{1-6}$ alkyl, $C_{2-6}$ alkenyl, and $C_{2-6}$ alkynyl, each of which is optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, —$OC(O)R^{10g}$, —$NO_2$, =O, —CN, and $C_{3-10}$ carbocycle and 3- to 10-membered heterocycle, wherein the $C_{3-10}$ carbocycle and 3- to 10-membered heterocycle are each optionally substituted with one or more $R^{9g}$. (148) The compound or salt of any one of embodiments 92 to 147, wherein $R^{11}$ is selected from: halogen, —$NO_2$, —CN, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, and —$OC(O)R^{10g}$; and $C_{1-6}$ alkyl optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, —$OC(O)R^{10g}$, —$NO_2$, =O, —CN, and $C_{3-10}$ carbocycle and 3- to 10-membered heterocycle, wherein the $C_{3-10}$ carbocycle and 3- to 10-membered heterocycle are each optionally substituted with one or more $R^{9g}$. (149) The compound or salt of any one of embodiments 92 to 148, wherein $R^{11}$ is selected from: halogen, —$NO_2$, —CN, —$OR^{10g}$, —$SR^{10g}$, and —$N(R^{10g})_2$; and $C_{1-6}$ alkyl optionally substituted with one or more substituents independently selected from halogen, —$OR^{10g}$, —$SR^{10g}$, —$N(R^{10g})_2$, —$NO_2$, =O, —CN, and $C_{3-10}$ carbocycle and 3- to 10-membered heterocycle, wherein the $C_{3-10}$ carbocycle and 3- to 10-membered heterocycle are each optionally substituted with one or more $R^{9g}$. (150) The compound or salt of any one of embodiments 92 to 149, wherein $R^{11}$ is selected from: halogen, —$NO_2$, —CN, —$OR^{10g}$, —$SR^{10g}$, and —$N(R^{10g})_2$; and $C_{1-6}$ alkyl optionally substituted with one or more substituents independently selected from halogen, —$OR^{10g}$, —$SR^{10g}$, —$N(R^{10g})_2$, —$NO_2$, =O, and —CN. (151) The compound or salt of any one of embodiments 92 to 146, wherein $R^{11}$ is selected from: $C_{1-6}$ alkyl optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, —$OC(O)R^{10g}$, —$N(R^{10g})C(O)N(R^{10g})_2$, —$OC(O)N(R^{10g})_2$, —$N(R^{10g})C(O)OR^{10g}$, —$S(O)R^{10g}$, —$S(O)_2R^{10g}$, —$NO_2$, =O, =S, =$N(R^{10g})$, —CN, $C_{3-10}$ carbocycle and 3- to 10-membered heterocycle, wherein the $C_{3-10}$ carbocycle and 3- to 10-membered heterocycle are each optionally substituted with one or more $R^{9g}$. (152) The compound or salt of any one of embodiments 92 to 146 or embodiment 151, wherein $R^{11}$ is selected from: $C_{1-6}$ alkyl optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, —$OC(O)R^{10g}$, —$NO_2$, =O, —CN, and $C_{3-10}$ carbocycle and 3- to 10-membered heterocycle, wherein the $C_{3-10}$ carbocycle and 3- to 10-membered heterocycle are each optionally substituted with one or more $R^{9g}$. (153) The compound or salt of any one of embodiments 92 to 146 or any one of embodiments 151 to 152, wherein $R^{11}$ is selected from: $C_{1-6}$ alkyl optionally substituted with one or more substituents independently selected from halogen, —$OR^{10g}$, —$SR^{10g}$, —$N(R^{10g})_2$, —$C(O)R^{10g}$, —$NO_2$, =O, —CN, and $C_{3-10}$ carbocycle and 3- to 10-membered heterocycle, wherein the $C_{3-10}$ carbocycle and 3- to 10-membered heterocycle are each optionally substituted with one or more $R^{9g}$. (154) The compound or salt of any one of embodiments 92 to 146 or any one of embodiments 151 to 153, wherein $R^{11}$ is selected from: $C_{1-6}$ alkyl optionally substituted with one or more substituents independently selected from halogen, —$OR^{10g}$, —$SR^{10b}$, —$N(R^{10c})_2$, —$C(O)R^{10g}$, —$NO_2$, =O, —CN, and $C_{3-10}$ carbocycle and 3- to 10-membered heterocycle. (155) The compound or salt of any one of embodiments 92 to 146 or any one of embodiments 151 to 154, wherein $R^{11}$ is selected from: $C_{1-6}$ alkyl optionally substituted with one or more substituents independently selected from halogen, —$OR^{10g}$, —$SR^{10g}$, —$N(R^{10g})_2$, —$C(O)R^{10g}$, —$NO_2$, =O, and —CN. (156) The compound or salt of any one of embodiments 92 to 146 or any one of embodiments 151 to 155, wherein $R^{11}$ is selected from: $C_{1-3}$ alkyl optionally substituted with one or more substituents independently selected from halogen and —$OR^{10g}$. (157) The compound or salt of any one of embodiments 92 to 146 or any one of embodiments 151 to 156, wherein $R^{11}$ is selected from: $C_{1-3}$ alkyl optionally substituted with one or more —$OR^{10g}$. (158) The compound or salt of any one of embodiments 92 to 146 or any one of embodiments 151 to 157, wherein $R^{11}$ is selected from: $C_{1-3}$ alkyl optionally substituted with one or more —OH. (159) The compound or salt of any one of embodiments 92 to 158, wherein $R^{12}$ is selected from hydrogen; $C_{1-6}$ alkyl optionally substituted with one or more substituents independently selected from the group consisting of halogen, CN, OH, $OR^{10h}$, $N(R^{10h})_2$, $NO_2$, $C(O)R^{10h}$, $SR^{10h}$, and $S(O)R^{10h}$; and $C_{3-6}$ carbocycle and 3- to 10-membered heterocycle each optionally substituted with one or more substituents independently selected from the group consisting of halogen, CN, OH, $OR^{10h}$, $N(R^{10h})_2$, $NO_2$, $C(O)R^{10h}$, $SR^{10h}$, and $S(O)R^{10h}$. (160) The compound or salt of any one of embodiments 92 to 159, wherein $R^{12}$ is selected from hydrogen; and $C_{1-6}$ alkyl optionally substituted with one or more substituents independently selected from the group consisting of halogen, CN, OH, $OR^{10h}$, $N(R^{10h})_2$, $NO_2$, $C(O)R^{10h}$, and $SR^{10h}$. (161) The compound or salt of any one of embodiments 92 to 160, wherein $R^{12}$ is selected from hydrogen; and $C_{1-6}$ alkyl. (162) The compound or salt of any one of embodiments 92 to 161, wherein $R^{12}$ is hydrogen. (163) The compound or salt of any one of embodiments 92 to 158, wherein $R^{12}$, $R^{11}$, and $R^2$ come together to form a $C_5$-$C_{10}$ bridged ring system. (164) The compound or salt of any one of embodiments 92 to 158 or embodiment 163, wherein $R^{12}$, $R^{11}$, and $R^2$ come together to form a $C_5$-$C_{10}$ bridged ring system selected from [1.1.1]bicyclopentane. (165) The compound or salt of any one of embodiments 92 to 164, wherein each $R^{9a}$ is independently selected from: halogen, —$OR^{10a}$, —$SR^{10a}$, —$N(R^{10a})_2$, —$C(O)R^{10a}$, —$NO_2$, =O, —CN; and $C_{1-3}$ alkyl, optionally substituted with one or more substituents independently selected from halogen, —$OR^{10a}$, —$SR^{10a}$, —$N(R^{10a})_2$, —$C(O)R^{10a}$, —$NO_2$, =O, and —CN. (166) The compound or salt of any one of embodiments 92 to 165, wherein each $R^{9a}$ is independently selected from: halogen, —$NO_2$, =O, —CN; and $C_{1-3}$ alkyl, optionally substituted with one or more substituents independently selected from halogen, —$NO_2$, =O, and —CN. (167) The compound or salt of any one of embodiments 92 to 166, wherein each $R^{9b}$ is independently selected from: halogen, —$OR^{10b}$, —$SR^{10b}$, —$N(R^{10b})_2$, —$C(O)R^{10b}$, —$NO_2$, =O, —CN; and $C_{1-3}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, and —CN. (168) The compound or salt of any one of embodiments 92 to 167, wherein each $R^{9b}$ is independently selected from: halogen, —$NO_2$, =O, —CN; and $C_{1-3}$ alkyl, optionally substituted with one or more substituents independently selected from halogen, —$NO_2$, =O, and —CN. (169) The compound or salt of any one of embodiments 92 to 168, wherein each $R^{9b}$ is independently selected from: halogen. (170) The compound or salt of any one of embodiments 92 to 169, wherein each $R^{9b}$ is independently selected from: fluoro. (171) The compound or salt of any one of embodiments 92 to 170, wherein each $R^{9b'}$ is independently selected from: halogen, —$OR^{10b}$, —$SR^{10b}$, —$N(R^{10b})_2$, —$C(O)R^{10b}$, —$NO_2$, =O, —CN; and $C_{1-3}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, and —CN. (172) The compound or salt of any one of embodiments 92 to 171, wherein each $R^{9b'}$ is independently selected from: halogen, —$NO_2$, =O, —CN; and $C_{1-3}$ alkyl, optionally substituted with one or more substituents independently selected from halogen, —$NO_2$, =O, and —CN. (173) The compound or salt of any one of embodiments 92 to 172, wherein each $R^{9b'}$ is independently selected from: halogen and CN. (174) The compound or salt of any one of embodiments 92 to 173, wherein each $R^{9b'}$ is independently selected from: fluoro and CN. (175) The compound or salt of any one of embodiments 92 to 174, wherein each $R^{9c}$ is independently selected from: halogen, —$OR^{10c}$, —$SR^{10c}$, —$N(R^{10c})_2$, —$C(O)R^{10c}$, —$NO_2$, =O, —CN; and $C_{1-3}$ alkyl, optionally substituted with one or more substituents independently selected from halogen, —$OR^{10c}$, —$SR^{10c}$, —$N(R^{10c})_2$, —$C(O)R^{10b}$, —$NO_2$, =O, and —CN. (176) The compound or salt of any one of embodiments 92 to 175, wherein each $R^{9c}$ is independently selected from: halogen, —$NO_2$, =O, —CN; and $C_{1-3}$ alkyl, optionally substituted with one or more substituents independently selected from halogen, —$NO_2$, =O, and —CN. (177) The compound or salt of any one of embodiments 92 to 176, wherein each $R^{9d}$ is independently selected from: halogen, —$OR^{10d}$, $SR^{10d}$, —$N(R^{10d})_2$, —$C(O)R^{10d}$, —$NO_2$, =O, —CN; and $C_{1-3}$ alkyl, optionally substituted with one or more substituents independently selected from halogen, —$OR^{10d}$, —$SR^{10d}$, —$N(R^{10d})_2$, —$C(O)R^{10d}$, —$NO_2$, =O, and —CN. (178) The compound or salt of any one of embodiments 92 to 177, wherein each $R^{9d}$ is independently selected from: halogen, —$NO_2$, ═O, —CN; and $C_{1-3}$ alkyl, optionally substituted with one or more substituents independently selected from halogen, —$NO_2$, ═O, and —CN. (179) The compound or salt of any one of embodiments 92 to 178, wherein each $R^{9g}$ is independently selected from: halogen, —$OR^{10g}$, —$SR^{10g}$, —$N(R^{10g})_2$, —$C(O)R^{10g}$, —$NO_2$, ═O, —CN; and $C_{1-3}$ alkyl, optionally substituted with one or more substituents independently selected from halogen, —$OR^{10g}$, —$SR^{10g}$, —$N(R^{10g})_2$, —$C(O)R^{10g}$, —$NO_2$, ═O, and —CN. (180) The compound or salt of any one of embodiments 92 to 179, wherein each $R^{9g}$ is independently selected from: halogen, —$NO_2$, ═O, —CN; and $C_{1-3}$ alkyl, optionally substituted with one or more substituents independently selected from halogen, —$NO_2$, ═O, and —CN. (181) The compound or salt of any one of embodiments 92 to 180, wherein each $R^{10a}$ is independently selected from: hydrogen; and $C_{1-6}$ alkyl, optionally substituted with one or more substituents independently selected from halogen, —CN, —OH, —SH, —$NO_2$, —$NH_2$, ═O, —O—$C_{1-6}$ alkyl, —S—$C_{1-6}$ alkyl, —$N(C_{1-6}$ alkyl$)_2$, —NH($C_{1-6}$ alkyl), $C_{3-10}$ carbocycle, 3- to 10-membered heterocycle; and $C_{3-10}$ carbocycle, and 3- to 10-membered heterocycle. (182) The compound or salt of any one of embodiments 92 to 181, wherein each $R^{10a}$ is independently selected from: hydrogen; and $C_{1-6}$ alkyl, optionally substituted with one or more substituents independently selected from halogen, —CN, —OH, —SH, —$NO_2$, —$NH_2$, ═O, —O—$C_{1-6}$ alkyl, —S—$C_{1-6}$ alkyl, —$N(C_{1-6}$ alkyl$)_2$, —NH($C_{1-6}$ alkyl); and $C_{3-10}$ carbocycle, and 3- to 10-membered heterocycle. (183) The compound or salt of any one of embodiments 92 to 182, wherein each $R^{10a}$ is independently selected from: hydrogen; and $C_{1-6}$ alkyl, optionally substituted with one or more substituents independently selected from halogen, —CN, —OH, —SH, —$NO_2$, —$NH_2$, ═O, —O—$C_{1-6}$ alkyl, —S—$C_{1-6}$ alkyl, —$N(C_{1-6}$ alkyl$)_2$, —NH($C_{1-6}$ alkyl). (184) The compound or salt of any one of embodiments 92 to 183, wherein each $R^{10a}$ is independently selected from: hydrogen; and $C_{1-6}$ alkyl. (185) The compound or salt of any one of embodiments 92 to 184, wherein each $R^{10a}$ is independently selected from: hydrogen. (186) The compound or salt of any one of embodiments 92 to 185, wherein each $R^{10b}$ is independently selected from: hydrogen; and $C_{1-6}$ alkyl, optionally substituted with one or more substituents independently selected from halogen, —CN, —OH, —SH, —$NO_2$, —$NH_2$, ═O, —O—$C_{1-6}$ alkyl, —S—$C_{1-6}$ alkyl, —$N(C_{1-6}$ alkyl$)_2$, —NH ($C_{1-6}$ alkyl), $C_{3-10}$ carbocycle, 3- to 10-membered heterocycle; and $C_{3-10}$ carbocycle, and 3- to 10-membered heterocycle. (187) The compound or salt of any one of embodiments 92 to 186, wherein each $R^{10b}$ is independently selected from: hydrogen; and $C_{1-6}$ alkyl, optionally substituted with one or more substituents independently selected from halogen, —CN, —OH, —SH, —$NO_2$, —$NH_2$, ═O, —O—$C_{1-6}$ alkyl, —S—$C_{1-6}$ alkyl, —$N(C_{1-6}$ alkyl$)_2$, —NH ($C_{1-6}$ alkyl); and $C_{3-10}$ carbocycle, and 3- to 10-membered heterocycle. (188) The compound or salt of any one of embodiments 92 to 187, wherein each $R^{10b}$ is independently selected from: hydrogen; and $C_{1-6}$ alkyl, optionally substituted with one or more substituents independently selected from halogen, —CN, —OH, —SH, —$NO_2$, —$NH_2$, ═O, —O—$C_{1-6}$ alkyl, —S—$C_{1-6}$ alkyl, —$N(C_{1-6}$ alkyl$)_2$, —NH ($C_{1-6}$ alkyl). (189) The compound or salt of any one of embodiments 92 to 188, wherein each $R^{10b}$ is independently selected from: hydrogen; and $C_{1-6}$ alkyl. (190) The compound or salt of any one of embodiments 92 to 189, wherein each $R^{10b}$ is independently selected from: $C_{1-3}$ alkyl. (191) The compound or salt of any one of embodiments 92 to 190, wherein each $R^{10b}$ is methyl. (192) The compound or salt of any one of embodiments 92 to 191, wherein each $R^{10c}$ is independently selected from: hydrogen; and $C_{1-6}$ alkyl, optionally substituted with one or more substituents independently selected from halogen, —CN, —OH, —SH, —$NO_2$, —$NH_2$, ═O, —O—$C_{1-6}$ alkyl, —S—$C_{1-6}$ alkyl, —$N(C_{1-6}$ alkyl$)_2$, —NH($C_{1-6}$ alkyl), $C_{3-10}$ carbocycle, 3- to 10-membered heterocycle; and $C_{3-10}$ carbocycle, and 3- to 10-membered heterocycle. (193) The compound or salt of any one of embodiments 92 to 192, wherein each $R^{10c}$ is independently selected from: hydrogen; and $C_{1-6}$ alkyl, optionally substituted with one or more substituents independently selected from halogen, —CN, —OH, —SH, —$NO_2$, —$NH_2$, ═O, —O—$C_{1-6}$ alkyl, —S—$C_{1-6}$ alkyl, —$N(C_{1-6}$ alkyl$)_2$, —NH($C_{1-6}$ alkyl); and $C_{3-10}$ carbocycle, and 3- to 10-membered heterocycle. (194) The compound or salt of any one of embodiments 92 to 193, wherein each $R^{10c}$ is independently selected from: hydrogen; and $C_{1-6}$ alkyl, optionally substituted with one or more substituents independently selected from halogen, —CN, —OH, —SH, —$NO_2$, —$NH_2$, ═O, —O—$C_{1-6}$ alkyl, —S—$C_{1-6}$ alkyl, —$N(C_{1-6}$ alkyl$)_2$, —NH($C_{1-6}$ alkyl). (195) The compound or salt of any one of embodiments 92 to 194, wherein each $R^{10c}$ is independently selected from: hydrogen; and $C_{1-6}$ alkyl. (196) The compound or salt of any one of embodiments 92 to 195, wherein each $R^{10c}$ is hydrogen. (197) The compound or salt of any one of embodiments 92 to 196, wherein each $R^{10d}$ is independently selected from: hydrogen; and $C_{1-6}$ alkyl, optionally substituted with one or more substituents independently selected from halogen, —CN, —OH, —SH, —$NO_2$, —$NH_2$, ═O, —O—$C_{1-6}$ alkyl, —S—$C_{1-6}$ alkyl, —$N(C_{1-6}$ alkyl$)_2$, —NH($C_{1-6}$ alkyl), $C_{3-10}$ carbocycle, 3- to 10-membered heterocycle; and $C_{3-10}$ carbocycle, and 3- to 10-membered heterocycle. (198) The compound or salt of any one of embodiments 92 to 197, wherein each $R^{10d}$ is independently selected from: hydrogen; and $C_{1-6}$ alkyl, optionally substituted with one or more substituents independently selected from halogen, —CN, —OH, —SH, —$NO_2$, —$NH_2$, ═O, —O—$C_{1-6}$ alkyl, —S—$C_{1-6}$ alkyl, —$N(C_{1-6}$ alkyl$)_2$, —NH($C_{1-6}$ alkyl); and $C_{3-10}$ carbocycle, and 3- to 10-membered heterocycle. (199) The compound or salt of any one of embodiments 92 to 198, wherein each $R^{10d}$ is independently selected from: hydrogen; and $C_{1-6}$ alkyl, optionally substituted with one or more substituents independently selected from halogen, —CN, —OH, —SH, —$NO_2$, —$NH_2$, ═O, —O—$C_{1-6}$ alkyl, —S—$C_{1-6}$ alkyl, —$N(C_{1-6}$ alkyl$)_2$, —NH($C_{1-6}$ alkyl). (200) The compound or salt of any one of embodiments 92 to 199, wherein each $R^{10d}$ is independently selected from: hydrogen; and $C_{1-6}$ alkyl. (201) The compound or salt of any one of embodiments 92 to 200, wherein each $R^{10d}$ is hydrogen. (202) The compound or salt of any one of embodiments 92 to 201, wherein each $R^{10e}$ is independently selected from: hydrogen; and $C_{1-6}$ alkyl, optionally substituted with one or more substituents independently selected from halogen, —CN, —OH, —SH, —$NO_2$, —$NH_2$, ═O, —O—$C_{1-6}$ alkyl, —S—$C_{1-6}$ alkyl, —$N(C_{1-6}$ alkyl$)_2$, —NH($C_{1-6}$ alkyl), $C_{3-10}$ carbocycle, 3- to 10-membered heterocycle; and $C_{3-10}$ carbocycle, and 3- to 10-membered heterocycle. (203) The compound or salt of any one of embodiments 92 to 202, wherein each $R^{10e}$ is independently selected from: hydrogen; and $C_{1-6}$ alkyl, optionally substituted with one or more substituents independently selected from halogen, —CN, —OH, —SH, —$NO_2$, —$NH_2$, ═O, —O—$C_{1-6}$ alkyl, —S—$C_{1-6}$ alkyl, —$N(C_{1-6}$ alkyl$)_2$, —NH($C_{1-6}$ alkyl); and $C_{3-10}$ carbocycle, and 3- to 10-membered heterocycle. (204) The compound or salt of any one of embodiments 92 to 203, wherein each $R^{10e}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl). (205) The compound or salt of any one of embodiments 92 to 204, wherein each $R^{10e}$ is independently selected from: hydrogen; and $C_{1-6}$ alkyl. (206) The compound or salt of any one of embodiments 92 to 205, wherein each $R^{10e}$ is hydrogen. (207) The compound or salt of any one of embodiments 92 to 206, wherein each $R^{10f}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle. (208) The compound or salt of any one of embodiments 92 to 207, wherein each $R^{10f}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. (209) The compound or salt of any one of embodiments 92 to 208, wherein each $R^{10f}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl). (210) The compound or salt of any one of embodiments 92 to 209, wherein each $R^{10f}$ is independently selected from: hydrogen; and $C_{1-6}$ alkyl. (211) The compound or salt of any one of embodiments 92 to 210, wherein each $R^{10f}$ is hydrogen. (212) The compound or salt of any one of embodiments 92 to 211, wherein each $R^{10g}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle. (213) The compound or salt of any one of embodiments 92 to 212, wherein each $R^{10g}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. (214) The compound or salt of any one of embodiments 92 to 213, wherein each $R^{10g}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl). (215) The compound or salt of any one of embodiments 92 to 214, wherein each $R^{10g}$ is independently selected from: hydrogen; and $C_{1-6}$ alkyl. (216) The compound or salt of any one of embodiments 92 to 215, wherein each $R^{10g}$ is hydrogen. (217) The compound or salt of any one of embodiments 92 to 216, wherein each $R^{10h}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle. (218) The compound or salt of any one of embodiments 92 to 217, wherein each $R^{10h}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. (219) The compound or salt of any one of embodiments 92 to 218, wherein each $R^{10h}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl). (220) The compound or salt of any one of embodiments 92 to 219, wherein each $R^{10h}$ is independently selected from: hydrogen; and $C_{1-6}$ alkyl. (221) The compound or salt of any one of embodiments 92 to 220, wherein each $R^{10h}$ is hydrogen. (222), (223), (224), (222A), (223A), (224A), (222B), (223B), (224B): In some embodiments, the compound of formula (II) is selected from compound B1, B2, B3, B4, B5, B6, B7, B8, B9, B10, B11, B12, B13, B14, B15, B16, B17, B18, B19, B20, B21, B22, B23, B24, B25, B26, B27, B28, B29, B30, B31, B32, B33, B34, B35, B36, B37, B38, B39, B40, B41, B42, B43, B44, B45, B46, B47, B48, B49, B50, B51, B52, B53, B54, B55, B56, B57, B58, B59, B60, B61, B62, B63, B64, B65, B66, B67, B68, B69, B70, B71, B72, B73, B74, B75, B76, B77, B78, B79, B80, B81, B82, B83, B84, B85, B86, B87, B88, B89, B90, B91, B92, B93, B94, B95, B96, B97, B98, B99, B100, B101, B102, B103, B104, B105, B106, B107, B108, B109, B110, B111, B112, B113, B114, B115, B116, B117, B118, B119, B120, B121, B122, B123, B124, B125, B126, B127, B128, B129, B130, B131, B132, B133, B134, B135, B136, B137, B138, B139, B140, B141, B142, B143, B144, B145, B146, B147, B148, B149, B150, B151, B152, B153, B154, B155, B156, B157, B158, B159, B160, B161, B162, B163, B164, B165, B166, B167, B168, B169, B170, B171, B172, B173, B174, B175, B176, B177, B178, B179, B180, B181, B182, B183, B184, B185, B186, B187, B188, B189, B190, B191, B192, B193, B194, B195, B196, B197, B198, B199, B200, B201, B202, B203, B204, B205, B206, B207, B208, B209, B210, B211, B212, B213, B214, B215, B216, B217, B218, B219, B220, B221, B222, B223, B224, B225, B226, B227, B228, B229, B230, B231, B232, B233, B234, B235, B236, B237, B238, B239, B240, B241, B242, B243, B244, B245, B246, B247, B248, B249, or a salt of any one thereof. In some embodiments, the compound of formula (II) is selected from compound B1, B2, B3, B4, B6, B7, B8, B9, B10, B12, B13, B14, B16, B17, B22, B23, B25, B27, B29, B31, B32, B33, B34, B35, B36, B37, B38, B39, B40, B41, B42, B43, B44, B45, B46, B47, B48, B49, B50, B52, B53, B54, B55, B56, B57, B58, B59, B62, B64, B65, B67, B68, B69, B70, B71, B73, B75, B76, B77, B78, B79, B80, B81, B82, B83, B84, B85, B87, B88, B89, B91, B92, B93, B94, B97, B98, B100, B101, B102, B103, B105, B106, B108, B110, B112, B113, B114, B116, B117, B118, B119, B120, B121, B123, B124, B126, B127, B128, B130, B132, B133, B134, B135, B136, B137, B139, B140, B141, B142, B144, B145, B146, B147, B148, B150, B152, B154, B155, B156, B160, B161, B163, B164, B169, B170, B172, B176, B181, B184, B188, B189, B190, B191, B193, B194, B199, B200, B202, B203, B204, B205, B206, B210, B212, B214, B217, B221, B222, B223, B225, B226, B227, B228, B229, B230, B231, B232, B233, B234, B236, B237, B238, B241, B243, B244, B245, B246, B247, B248, B249, and a salt of any one thereof. In some embodiments the compound of formula (II) is selected from compound B1, B2, B4, B6, B7, B8, B9, B10, B12, B13, B14, B16, B17, B22, B23, B25, B29, B31, B32, B33, B34, B35, B36, B37, B38, B39, B41, B42, B43, B44, B45, B46, B52, B53, B54, B55, B56, B57, B58, B59, B62, B64, B65, B67, B68, B69, B70, B73, B75, B76, B77, B78, B79, B80, B81, B82, B83, B84, B87, B88, B89, B91, B92, B93, B94, B97, B100, B101, B102, B103, B105, B106, B108, B110, B112, B113, B114, B116, B117, B118, B119, B120, B121, B123, B124, B126, B128, B130, B132, B133, B136, B137, B139, B141, B142, B145, B147, B148, B152, B154, B155, B160, B164, B169, B176, B181, B188, B189, B191, B199, B202, B204, B206, B210, B214, B217, B221, B222, B223, B225, B226, B227, B228, B229, B230, B231, B232, B233, B234, B236, B237, B238, B241, B244, B247, B248, B249, and a salt of any one thereof. In some embodiments, the compound of formula (II) is selected from compound B1, B4, B6, B8, B9, B12, B13, B14, B17, B23, B29, B31, B32, B33, B35, B36, B37, B39, B43, B44, B45, B54, B55, B57, B59, B62, B64, B65, B69, B75, B76, B77, B78, B79, B81, B82, B83, B89, B91, B92, B94, B100, B101, B106, B110, B113, B114, B116, B118, B120, B121, B123, B126, B128, B130, B132, B136, B137, B139, B142, B145, B147, B152, B164, B176, B189, B191, B199, B206, B214, B217, B221, B222, B225, B226, B227, B229, B232, B233, B236, B238, B247, B248, B249, and a salt of any one thereof. In some embodiments, the compound of formula (II) is selected from compound B1, B9, B13, B14, B23, B31, B33, B36, B39, B43, B45, B55, B57, B62, B75, B77, B82, B83, B92, B120, B123, B142, B145, B147, B189, B206, and a salt of any one thereof. In some embodiments, the compound of formula (II) is selected from compound B1, B2, B3, B4, B6, B7, B8, B9, B12, B13, B14, B16, B17, B18, B22, B23, B25, B27, B28, B29, B30, B31, B32, B33, B34, B35, B36, B37, B38, B39, B41, B42, B43, B44, B45, B46, B49, B51, B52, B53, B54, B55, B56, B57, B58, B59, B60, B62, B63, B64, B65, B67, B68, B69, B70, B71, B72, B73, B74, B75, B76, B77, B78, B79, B80, B81, B82, B83, B84, B85, B87, B88, B89, B90, B91, B92, B93, B94, B95, B96, B97, B99, B100, B101, B102, B103, B104, B105, B106, B108, B109, B110, B12, B113, B114, B116, B117, B118, B119, B120, B121, B122, B123, B124, B125, B126, B127, B128, B129, B130, B132, B133, B134, B135, B136, B137, B138, B139, B140, B141, B142, B144, B145, B146, B147, B148, B149, B150, B152, B153, B154, B155, B156, B157, B160, B161, B162, B163, B164, B165, B166, B169, B170, B171, B172, B174, B176, B178, B181, B182, B184, B187, B188, B189, B190, B191, B193, B194, B197, B199, B200, B201, B202, B203, B204, B205, B206, B209, B210, B212, B213, B214, B217, B218, B220, B221, B222, B223, B224, B225, B226, B227, B228, B229, B230, B231, B232, B233, B234, B235, B236, B237, B238, B240, B241, B242, B243, B244, B245, B247, B248, B249, and a salt of any one thereof. In some embodiments, the compound of formula (II) is selected from compound B1, B2, B4, B6, B7, B8, B9, B12, B13, B14, B16, B17, B18, B23, B25, B27, B28, B29, B30, B31, B32, B33, B34, B35, B36, B37, B38, B39, B41, B42, B43, B44, B45, B46, B49, B52, B53, B54, B55, B56, B57, B58, B59, B60, B62, B63, B64, B65, B68, B69, B70, B72, B73, B74, B75, B76, B77, B78, B79, B80, B81, B82, B83, B84, B85, B87, B88, B89, B91, B92, B93, B94, B95, B96, B97, B99, B100, B101, B102, B103, B104, B105, B106, B108, B110, B112, B113, B114, B116, B117, B118, B119, B120, B121, B122, B123, B124, B125, B126, B127, B128, B129, B130, B132, B133, B134, B135, B136, B137, B138, B139, B140, B141, B142, B144, B145, B146, B147, B148, B150, B152, B154, B155, B156, B157, B160, B161, B163, B164, B169, B170, B172, B176, B178, B181, B182, B188, B189, B191, B194, B199, B200, B202, B203, B204, B205, B206, B210, B212, B214, B217, B218, B221, B222, B223, B225, B226, B227, B228, B229, B230, B231, B232, B233, B234, B235, B236, B237, B238, B241, B243, B244, B245, B247, B248, B249, and a salt of any one thereof. In some embodiments, the compound of formula (II) is selected from compound B1, B2, B4, B6, B7, B8, B9, B12, B13, B14, B16, B17, B23, B25, B29, B30, B31, B32, B33, B34, B35, B36, B37, B38, B39, B42, B43, B44, B45, B46, B52, B53, B54, B55, B57, B59, B60, B62, B64, B65, B69, B70, B75, B76, B77, B78, B79, B80, B81, B82, B83, B84, B85, B87, B88, B89, B91, B92, B94, B99, B100, B101, B102, B103, B105, B106, B108, B110, B113, B114, B116, B117, B118, B119, B120, B121, B123, B124, B126, B127, B128, B129, B130, B132, B133, B135, B136, B137, B139, B141, B142, B144, B145, B147, B148, B150, B152, B154, B155, B160, B164, B169, B176, B181, B188, B189, B191, B199, B202, B204, B206, B210, B214, B217, B221, B222, B223, B225, B226, B227, B228, B229, B230, B231, B232, B233, B234, B236, B237, B238, B241, B243, B245, B247, B248, B249, and a salt of any one thereof. In some embodiments, the compound of formula (II) is selected from compound B1, B4, B6, B9, B13, B17, B23, B30, B31, B33, B36, B39, B43, B45, B53, B54, B55, B57, B62, B65, B75, B77, B78, B79, B80, B81, B82, B83, B89, B92, B94, B100, B103, B106, B110, B118, B120, B123, B126, B128, B132, B133, B139, B142, B145, B147, B164, B176, B189, B191, B199, B206, B214, B221, B222, B225, B227, B229, B232, B233, B236, B238, B247, B248, B249, and a salt of any one thereof.

(225) A method of treating cardiovascular disease or a related condition comprising administering to a subject in need thereof a compound or salt of any one of embodiments 1 to 210. (226) A method of treating diastolic dysfunction or a related condition comprising administering to a subject in need thereof a compound or salt of any one of embodiments 1 to 210. (227) A method of treating a condition selected from hypertrophic cardiomyopathy (HCM); heart failure with preserved ejection fraction (HFpEF); heart failure with mid ranged ejection fraction disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; right ventricular (RV) hypertrophy; acute myocardial infarction; acute revascularization; ischemia; and angina; the method comprising administering to a subject in need thereof a compound or salt of any one of embodiments 1 to 210. (228) The method of embodiment 227, wherein said heart failure with preserved ejection fraction (HFpEF) comprises one or more disorders selected from disorders of relaxation and disorders of chamber stiffness (diabetic HFpEF). (229) The method of embodiment 227, wherein said left ventricular (LV) hypertrophy is malignant left ventricular (LV) hypertrophy. (230) The method of embodiment 227, wherein said restrictive cardiomyopathy comprises one or more subgroups selected from inflammatory subgroups, infiltrative subgroups, storage subgroups, idiopathic/inherited subgroups, congenital heart disease subgroups. (231) The method of embodiment 229, wherein said inflammatory subgroups comprise one or more subgroups selected from Loefilers and EMF. (232) The method of embodiment 229, wherein said inflammatory subgroups comprise one or more subgroups selected from amyloid, sarcoid, and XRT. (233) The method of embodiment 229, wherein said storage subgroups comprise one or more subgroups selected from hemochromatosis, Fabry, and glycogen storage disease. (234) The method of embodiment 229, wherein said idiopathic/inherited subgroups comprise one or more subgroups selected from Trop I (beta myosin HC), Trop T (alpha cardiac actin), and desmin related subgroups. (235) The method of embodiment 229, wherein said congenital heart disease subgroups comprise one or more subgroups selected from pressure-overloaded RV, Tetralogy of Fallot, and pulmonic stenosis. (236) A method of treating hypertrophic cardiomyopathy or a related condition comprising administering to a subject in need thereof a compound or salt of any one of embodiments 1 to 210. (237) A method of treating obstructive hypertrophic cardiomyopathy comprising administering to a subject in need thereof a compound or salt of any one of embodiments 1 to 210. (238) A method of treating non-obstructive hypertrophic cardiomyopathy comprising administering to a subject in need thereof a compound or salt of any one of embodiments 1 to 210. (239) A method of treating heart failure with preserved ejection fraction comprising administering to a subject in need thereof a compound or salt of any one of embodiments 1 to 210. (240) A method of treating left ventricle stiffness comprising administering to a subject in need thereof a compound or salt of any one of embodiments 1 to 210.

(241) A method of treating a cardiovascular disease or a related condition comprising administering to a subject in need thereof a compound or salt of Formula (III):

(III)

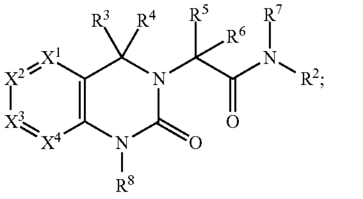

or a salt thereof, wherein $X^1$, $X^2$, $X^3$, and $X^4$ are each independently selected from $C(R^1)$, N, and $N^+(—O^-)$; each $R^1$ is independently selected from: hydrogen; halogen, $—NO_2$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$; $C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2R^{10a}$, $—NO_2$, =O, =S, $=N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, =O, =S, $=N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$; $R^2$ is selected from: $C_{1-6}$ alkyl, $C_{2-6}$ alkenyl, and $C_{2-6}$ alkynyl, each of which is optionally substituted with one or more substituents independently selected from halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—C(O)OR^{10b}$, $—OC(O)R^{10b}$, $—N(R^{10b})C(O)N(R^{10b})_2$, $—OC(O)N(R^{10b})_2$, $—N(R^{10b})C(O)OR^{10b}$, $—S(O)R^{10b}$, $—S(O)_2R^{10b}$, $—NO_2$, =O, =S, $=N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—N(R^{10b})C(O)N(R^{10b})_2$, $—OC(O)N(R^{10b})_2$, $—N(R^{10b})C(O)OR^{10b}$, $—C(O)OR^{10b}$, $—OC(O)R^{10b}$, $—S(O)R^{10b}$, $—S(O)_2R^{10b}$, $—NO_2$, =O, =S, $=N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$; $R^3$ and $R^4$ are each independently selected from: hydrogen, halogen, $—OR^{10c}$, $—SR^{10c}$, $—N(R^{10c})_2$, $—NO_2$, and —CN; and $C_{1-6}$ alkyl optionally substituted with one or more substituents independently selected from halogen, $—OR^{10c}$, $—SR^{10c}$, $—N(R^{10c})_2$, $—NO_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$; $R^5$ and $R^6$ are each independently selected from: hydrogen, halogen, $—OR^{10c}$, $—SR^{10c}$, $—N(R^{10c})_2$, $—NO_2$, and —CN; $C_{1-6}$ alkyl, $C_{2-6}$ alkenyl, and $C_{2-6}$ alkynyl, any of which is optionally substituted at each occurrence with one or more substituents independently selected from halogen, $—OR^{10c}$, $—SR^{10c}$, $—N(R^{10c})_2$, $—NO_2$, —CN, and $C_{3-10}$ carbocycle and 3- to 10-membered heterocycle, each of which is optionally substituted with one or more substituents independently selected from halogen, $—OR^{10c}$, $—SR^{10c}$, $—N(R^{10c})_2$, $—NO_2$, and —CN; and $C_{3-10}$ carbocycle and 3- to 10-membered heterocycle, each of which is optionally substituted with one or more substituents independently selected from halogen, $—OR^{10c}$, $—SR^{10c}$, $—N(R^{10c})_2$, $—NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$; $R^7$ is selected from: hydrogen and $C_{1-6}$ alkyl optionally substituted with one or more substituents independently selected from halogen, $—OR^{10d}$, $—SR^{10d}$, $—N(R^{10d})_2$, $—NO_2$, and —CN; $R^8$ is selected from: hydrogen; and $C_{1-6}$ alkyl optionally substituted with one or more substituents independently selected from halogen, $—OR^{10e}$, $—SR^{10e}$, $—N(R^{10e})_2$, $—NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, $—OR^{10e}$, $—SR^{10e}$, $—N(R^{10e})_2$, $—NO_2$, and —CN; each $R^{9a}$ is independently selected from: halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, =O, =S, $=N(R^{10a})$, and —CN; and $C_{1-3}$ alkyl, $C_{2-3}$ alkenyl, and $C_{2-3}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, =O, =S, $=N(R^{10a})$, and —CN; each $R^{9b}$ is independently selected from: halogen, $—OR^{10b}$, $—SR^{10b}$, $—N(R^{10b})_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$) and —CN; and $C_{1-3}$ alkyl, $C_{2-3}$ alkenyl, and $C_{2-3}$ alkynyl, each of which is optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$) and —CN; each $R^{9c}$ is independently selected from: halogen, —O$R^{10c}$, —S$R^{10c}$, —N($R^{10c}$)$_2$, —C(O)$R^{10c}$, —C(O)N($R^{10c}$)$_2$, —N($R^{10c}$)C(O)$R^{10c}$, —N($R^{10c}$)C(O)N($R^{10c}$, —OC(O)N($R^{10c}$)$_2$, —N($R^{10c}$)C(O)O$R^{10c}$, —C(O)O$R^{10c}$, —OC(O)$R^{10c}$, —S(O)$R^{10c}$, —S(O)$_2R^{10c}$, —$NO_2$, =O, =S, =N($R^{10c}$), and —CN; and $C_{1-3}$ alkyl, $C_{2-3}$ alkenyl, and $C_{2-3}$ alkynyl, each of which is optionally substituted with one or more substituents independently selected from halogen, —O$R^{10c}$, —S$R^{10c}$, —N($R^{10c}$)$_2$, —C(O)$R^{10c}$, —C(O)N($R^{10c}$)$_2$, —N($R^{10c}$)C(O)$R^{10c}$, —N($R^{10c}$)C(O)N($R^{10c}$)$_2$, —OC(O)N($R^{10c}$)$_2$, —N($R^{10c}$)C(O)O$R^{10c}$, —C(O)O$R^{10c}$, —OC(O)$R^{10c}$, —S(O)$R^{10c}$, —S(O)$_2R^{10c}$, —$NO_2$, =O, =S, =N($R^{10c}$) and —CN; each $R^{10a}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10b}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10c}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10d}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10b}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. (242) The method of embodiment 241, wherein $X^1$, $X^2$, $X^3$, and $X^4$ are each independently selected from C($R^1$) and N. (243) The method of embodiment 241 or 242, wherein one of $X^1$, $X^2$, $X^3$, or $X^4$ is N. (244) The method of embodiment 243, wherein $X^1$ is N. (245) The method of embodiment 243, wherein $X^2$ is N. (246) The method of embodiment 243, wherein $X^3$ is N. (247) The method of embodiment 243, wherein $X^4$ is N. (248) The method of embodiments 241 or 242, wherein two of $X^1$, $X^2$, $X^3$, or $X^4$ is N. (249) The method of embodiment 248, wherein $X^1$ and $X^3$ are N; or $X^2$ and $X^4$ are N. (250) The method of embodiment 248, wherein $X^1$, $X^2$, $X^3$, and $X^4$ are each independently selected from C($R^1$). (251) The method of any one of embodiments 241 to 250, wherein each $R^1$ is independently selected from: hydrogen; halogen, —$NO_2$, —CN, —O$R^{10a}$, —S$R^{10a}$, —N($R^{10a}$)$_2$, —C(O)$R^{10a}$, and —C(O)N($R^{10a}$)$_2$; $C_{1-6}$ alkyl, optionally substituted with one or more substituents independently selected from halogen, —O$R^{10a}$, —S$R^{10a}$, —N($R^{10a}$)$_2$, —C(O)$R^{10a}$, —$NO_2$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —O$R^{10a}$, —S$R^{10a}$, —N($R^{10a}$)$_2$, —C(O)$R^{10a}$, —C(O)N($R^{10a}$)$_2$, —CN, $C_{1-6}$ alkyl optionally substituted with one or more $R^{9a}$ (252) The method of any one of embodiments 241 to 251, wherein each $R^1$ is independently selected from: hydrogen; halogen, —$NO_2$, —CN, —O$R^{10a}$, —S$R^{10a}$, —N($R^{10a}$)$_2$, —C(O)$R^{10a}$, and —C(O)N($R^{10a}$)$_2$; $C_{1-6}$ alkyl, optionally substituted with one or more substituents independently selected from halogen, —O$R^{10a}$, —S$R^{10a}$, and —N($R^{10a}$)$_2$; and $C_{3-10}$ carbocycle and 3- to 10-membered heterocycle, each of which is optionally substituted with one or more substituents independently selected from halogen, —O$R^{10a}$, —S$R^{10a}$, and —N($R^{10a}$)$_2$. (253) The method of any one of embodiments 241 to 252, wherein each $R^1$ is independently selected from: hydrogen; halogen, CN, —O$R^{10a}$, and —C(O)N($R^{10a}$)$_2$; $C_{1-6}$ alkyl, optionally substituted with one or more substituents independently selected from halogen, and $C_{3-10}$ carbocycle optionally substituted with one or more substituents independently selected from halogen. (254) The method of any one of embodiments 241 to 253, wherein $R^1$ is hydrogen. (255) The method of any one of embodiments 241 to 250, wherein each $R^1$ is independently selected from hydrogen, halogen, —$NO_2$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$ and —$S(O)_2R^{10a}$; (256) The method of any one of embodiments 241 to 250 or embodiment 255, wherein each $R^1$ is independently selected from hydrogen, $C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, ═O, ═S, ═$N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$. (257) The method of any one of embodiments 241 to 250 or embodiments 255 to 256, wherein each $R^1$ is independently selected from hydrogen, $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, ═O, ═S, ═$N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$. (258) The method of any one of embodiments 241 to 250 or embodiments 255 to 257, wherein each $R^1$ is independently selected from: hydrogen; halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, and —$NH(C_{1-6}$ alkyl); $C_{1-6}$ alkyl, $C_{2-6}$ alkenyl, and $C_{2-6}$ alkynyl, each of which is optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, and $C_{2-6}$ alkynyl. (259) The method of any one of embodiments 241 to 250 or embodiments 255 to 258, wherein each $R^1$ is independently selected from $C_{1-3}$ alkyl optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle and 3- to 10-membered heterocycle. (260) The method of any one of embodiments 241 to 250 or embodiments 255 to 259, wherein each $R^1$ is independently selected from $C_{3-5}$ carbocycle is optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, and $C_{2-6}$ alkynyl. (261) The method of any one of embodiments 241 to 250 or embodiments 255 to 260, wherein each $R^1$ is independently selected from hydrogen, —CN, —OH, —OMe, —OEt, —OiPr, —F, —Cl, —Br, -Me, -Et, —$CF_3$, —$CHF_2$, —$CH_2F$, $OCF_3$, —$OCHF_2$, —$OCH_2F$, —$C(O)NH_2$,

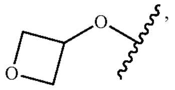, 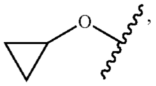, 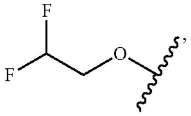,

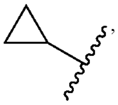, and 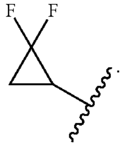.

(262) The method of any one of embodiments 241 to 261, wherein $R^2$ is selected from $C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, ═O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, ═O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (263) The method of any one of embodiments 241 to 262, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, ═O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, ═O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (264) The method of any one of embodiments 241 to 263, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$NO_2$, ═O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, ═O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (265) The method of any one of embodiments 241 to 264, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (266) The method of any one of embodiments 241 to 265, wherein $R^2$ is selected from $C_{1-6}$ alkyl, optionally substituted with one or more substituents independently selected from halogen, —$OR^{10b}$, —$SR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (267) The method of any one of embodiments 241 to 261, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (268) The method of any one of embodiments 241 to 261, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl, wherein the $C_{1-6}$ alkyl is optionally substituted with one or more $R^{9b}$. (269) The method of any one of embodiments 241 to 261 or embodiment 268, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl. (270) The method of any one of embodiments 241 to 261 or any one of embodiments 268 to 269, wherein $R^2$ is selected from $C_{1-6}$ alkyl, optionally substituted with one or more substituents independently selected from halogen, —$OR^{10b}$, —$SR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl. (271) The method of any one of embodiments 241 to 261 or any one of embodiments 268 to 270, wherein $R^2$ is selected from $C_{1-6}$ alkyl, optionally substituted with one or more substituents independently selected from halogen, —$OR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl. (272) The method of any one of embodiments 241 to 261 or any one of embodiments 268 to 271, wherein $R^2$ is selected from $C_{1-6}$ alkyl, optionally substituted with one or more substituents independently selected from halogen, —$OR^{10b}$, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, and —CN. (273) The method of any one of embodiments 241 to 261 or any one of embodiments 268 to 272, wherein $R^2$ is selected from $C_{1-6}$ alkyl, optionally substituted with one or more substituents independently selected from F, OH, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from F, and —CN. (274) The method of any one of embodiments 241 to 261 or any one of embodiments 268 to 273, wherein $R^2$ is selected from $C_{1-6}$ alkyl, optionally substituted with one or more substituents independently selected from F, OH, $C_{3-10}$ carbocycle and 3- to 10-membered heterocycle, wherein each $C_{3-10}$ carbocycle and 3- to 10-membered heterocycle is independently selected from phenyl, 2-pyridyl, and 3-pyridyl, and each phenyl, 2-pyridyl, and 3-pyridyl is optionally substituted with one or more $R^{9b}$; and $C_{3-10}$ carbocycle and 3- to 10-membered heterocycle, each of which is optionally substituted with one or more substituents independently selected from F, and —CN. (275) The method of any one of embodiments 241 to 261 or any one of embodiments 268 to 274, wherein $R^2$ is selected from $C_2$ alkyl, optionally substituted with one or more substituents independently selected from halogen, —$OR^{10b}$, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from F, and —CN. (276) The method of any one of embodiments 241 to 261 or any one of embodiments 268 to 275, wherein $R^2$ is selected from $C_2$ alkyl, optionally substituted with one or more substituents independently selected from F, OH, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from F, and —CN. (277) The method of any one of embodiments 241 to 261 or embodiment 268 to 276, wherein $R^2$ is $C_2$ alkyl, optionally substituted with one or more substituents independently selected from F, OH, $C_{3-10}$ carbocycle and 3- to 10-membered heterocycle, wherein each $C_{3-10}$ carbocycle and 3- to 10-membered heterocycle is independently selected from phenyl, pyridyl, and pyrimidyl, and each phenyl, pyridyl, and pyrimidyl is optionally substituted with one or more $R^{9b}$. (278) The method of any one of embodiments 241 to 274, wherein $R^2$ is a substituent represented by the following:

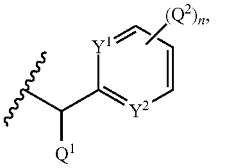

wherein, $Q^1$ is a $C_{1-3}$ alkyl optionally substituted with one or more substituents selected from OH and halo; $Y^1$, $Y^2$, and $Y_3$ are selected from N and $C(Q^3)$; and each $Q^2$ is independently selected from halo, CN, $C_{1-6}$ alkoxy, and $C_{1-6}$ alkyl optionally substituted with one or more substituents selected from halogen; each $Q^3$ is independently selected from hydrogen, halo, CN, $C_{1-6}$ alkoxy, and $C_{1-6}$ alkyl optionally substituted with one or more substituents selected from halogen; and n is 0 or 1. (279) The method of embodiments 241 to 274 or embodiment 278, wherein $Q^1$ is a $C_1$ alkyl optionally substituted with one or more substituents selected from OH and fluoro; n is 0; and each $Q^3$ is independently selected from hydrogen, fluoro, chloro, bromo, CN, methoxy, methyl, and trifluoromethyl. (280) The method of any one of embodiments 241 to 276, wherein $R^2$ is selected from

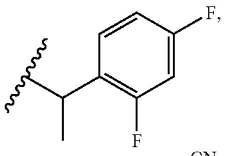
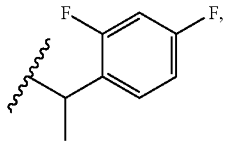
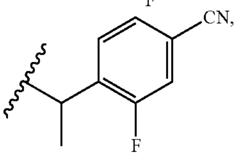
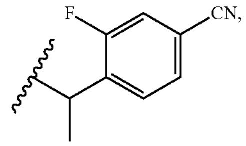
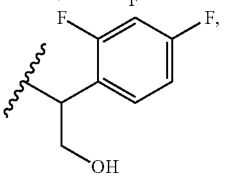
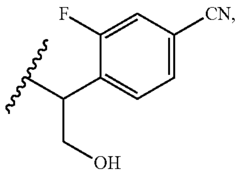

-continued

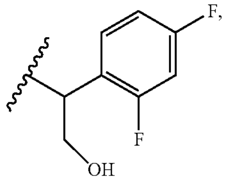
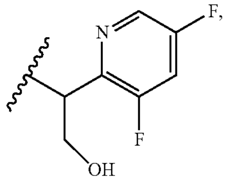
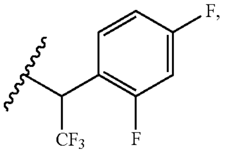
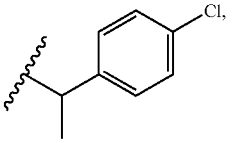
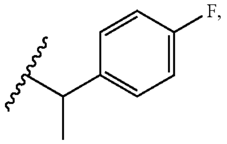
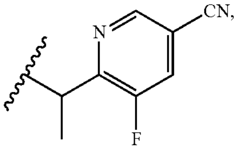
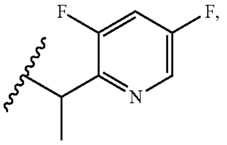
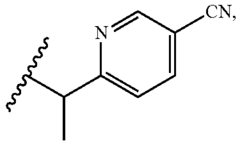
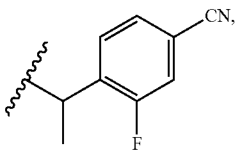
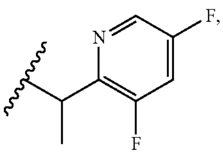
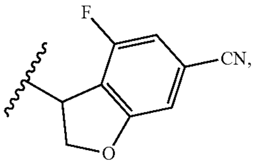
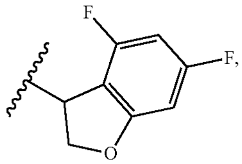
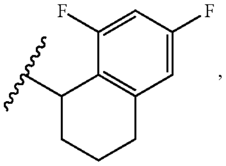
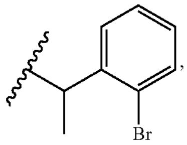
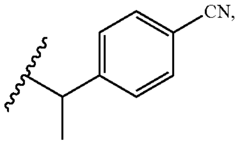
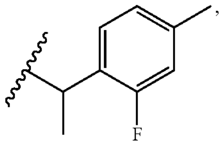
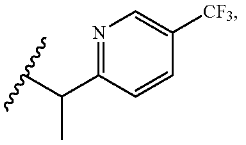
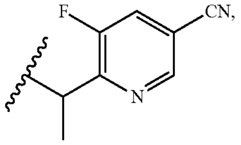
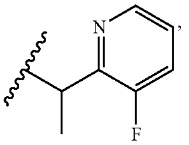
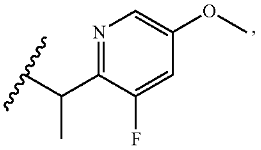
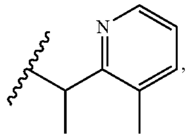
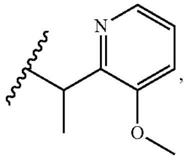

-continued

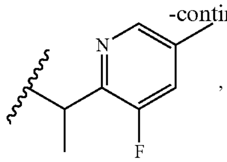, 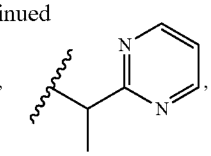, 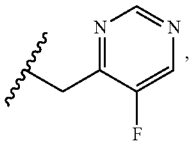, and 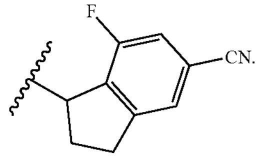

(281) The method of any one of embodiments 241 to 280, wherein $R^3$ and $R^4$ are each independently selected from: hydrogen, halogen, —$OR^{10c}$, —$SR^{10c}$, —$N(R^{10c})_2$, —$NO_2$, and —CN; and $C_{1-6}$ alkyl optionally substituted with one or more substituents independently selected from halogen, —$OR^{10c}$, —$SR^{10c}$, —$N(R^{10c})_2$, —$NO_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$. (282) The method of any one of embodiments 241 to 281, wherein $R^3$ and $R^4$ are each independently selected from: hydrogen, halogen, —$NO_2$, and —CN; and $C_{1-6}$ alkyl optionally substituted with one or more halogen; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more $R^{9c}$. (283) The method of any one of embodiments 241 to 282, wherein $R^3$ and $R^4$ are each independently selected from: hydrogen, halogen, —$NO_2$, and —CN; and $C_{1-6}$ alkyl optionally substituted with one or more halogen; or $R^3$ together with $R^4$ form a 3- to 10-membered heterocycle or $C_{3-10}$ carbocycle. (284) The method of any one of embodiments 241 to 283, wherein $R^3$ and $R^4$ are each independently selected from: hydrogen; and $C_{1-6}$ alkyl optionally substituted with one or more halogen; or $R^3$ together with $R^4$ form a 3- to 10-membered heterocycle or $C_{3-10}$ carbocycle. (285) The method of any one of embodiments 241 to 284, wherein $R^3$ and $R^4$ are each independently selected from: hydrogen; and $C_{1-6}$ alkyl optionally substituted with one or more halogen. (286) The method of any one of embodiments 241 to 285, wherein $R^3$ and $R^4$ are each independently selected from: hydrogen; and $C_{1-6}$ alkyl optionally substituted with one or more fluorine. (287) The method of any one of embodiments 241 to 286, wherein $R^3$ and $R^4$ are each independently selected from hydrogen. ( ) The method of any one of embodiments 241 to XX, wherein $R^3$ and $R^4$ are each independently selected from hydrogen; and $C_1$ alkyl optionally substituted with one or more fluorine. ( ) The method of any one of embodiments 241 to XX, wherein $R^3$ and $R^4$ are each independently selected from hydrogen, methyl, and trifluoromethyl. ( ) The method of any one of embodiments 241 to XX, wherein $R^3$ and $R^4$ are each independently selected from hydrogen and $C_1$ alkyl. ( ) The method of any one of embodiments 241 to XX, wherein $R^3$ and $R^4$ are each independently selected from $C_1$ alkyl. (288) The method of any one of embodiments 241 to 284, wherein $R^3$ together with $R^4$ form a 3- to 10-membered heterocycle or $C_{3-10}$ carbocycle. (289) The method of any one of embodiments 241 to 284 or embodiment 288, wherein the 3- to 10-membered heterocycle or $C_{3-10}$ carbocycle formed by $R^3$ together with $R^4$ is selected from cyclopropyl, oxetanyl, and cyclohexyl. (290) The method of any one of embodiments 241 to 289, wherein $R^5$ and $R^6$ are each independently selected from: hydrogen, halogen, —$OR^{10c}$, —$SR^{10c}$, —$N(R^{10c})_2$, —$NO_2$, and —CN; $C_{1-6}$ alkyl, optionally substituted with one or more substituents independently selected from halogen, —$OR^{10c}$, —$SR^{10c}$, —$N(R^{10c})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10c}$, —$SR^{10c}$, —$N(R^{10c})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$. (291) The method of any one of embodiments 241 to 290, wherein $R^5$ and $R^6$ are each independently selected from: hydrogen, halogen, —$OR^{10c}$, —$SR^{10c}$, —$N(R^{10c})_2$, —$NO_2$, and —CN; and $C_{1-6}$ alkyl; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$. (292) The method of any one of embodiments 241 to 291, wherein $R^5$ and $R^6$ are each independently selected from: hydrogen, halogen, —$OR^{10c}$, —$SR^{10c}$, —$N(R^{10c})_2$, —$NO_2$, and —CN; and $C_{1-6}$ alkyl. (293) The method of any one of embodiments 241 to 292, wherein $R^5$ and $R^6$ are each independently selected from: hydrogen and $C_{1-3}$ alkyl. (294) The method of any one of embodiments 241 to 293, wherein $R^5$ and $R^6$ are each hydrogen. (295) The method of any one of embodiments 241 to 294, wherein $R^7$ is selected from hydrogen and $C_{1-6}$ alkyl optionally substituted with one or more substituents independently selected from halogen. (296) The method of any one of embodiments 241 to 295, wherein $R^7$ is selected from hydrogen. (297) The method of any one of embodiments 241 to 296, wherein $R^8$ is selected from: hydrogen; and $C_{1-6}$ alkyl optionally substituted with one or more substituents independently selected from halogen, —$OR^{10e}$, —$SR^{10e}$, —$N(R^{10e})_2$, —$NO_2$, —CN, $C_{3-10}$ carbocycle, and 3- to 10-membered heterocycle. (298) The method of any one of embodiments 241 to 297, wherein $R^8$ is selected from: hydrogen; and $C_{1-6}$ alkyl optionally substituted with one or more substituents independently selected from halogen, —$OR^{10e}$, —$SR^{10e}$, —$N(R^{10e})_2$, —$NO_2$, and —CN. (299) The method of any one of embodiments 241 to 298, wherein $R^8$ is selected from hydrogen. (300) The method of any one of embodiments 241 to 299, wherein each $R^{9a}$ is independently selected from: halogen, —$OR^{10a}$, —$SR^{10a}$, —$N(R^{10a})_2$, —$C(O)R^{10a}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$NO_2$, =O, and —CN. (301) The method of any one of embodiments 241 to 300, wherein each $R^{9a}$ is independently selected from: halogen, —$OR^{10a}$, —$SR^{10a}$, —$N(R^{10a})_2$, —$C(O)R^{10a}$, —$NO_2$, =O, and —CN; and $C_{1-3}$ alkyl optionally substituted with one or more substituents independently selected from halogen, —$OR^{10a}$, —$SR^{10a}$, —$N(R^{10a})_2$, —$C(O)R^{10a}$, —$NO_2$, =O, and —CN. (302) The method of any one of embodiments 241 to 301, wherein each $R^{9b}$ is independently selected from: halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, and —CN. (303) The method of any one of embodiments 241 to 302, wherein each $R^{9b}$ is independently selected from: halogen, —$OR^{10b}$, —$SR^{10b}$, —$N(R^{10b})_2$, —$NO_2$, =O, and —CN; and $C_{1-3}$ alkyl, optionally substituted with one or more substituents independently selected from halogen, —$OR^{10b}$, —$SR^{10b}$, —$N(R^{10b})_2$, —$NO_2$, =O, and —CN. (304) The method of any one of embodiments 241 to 303, wherein each $R^{9b}$ is independently selected from: halogen, —$OR^{10b}$, —$SR^{10b}$, —$N(R^{10b})_2$, —$NO_2$, =O, and —CN; and $C_{1-3}$ alkyl, optionally substituted with one or more substituents independently selected from halogen, —$OR^{10b}$, —$SR^{10b}$, —$N(R^{10b})_2$, —$NO_2$, =O, and —CN. (305) The method of any one of embodiments 241 to 304, wherein each $R^{9b}$ is independently selected from halogen and —CN. (306) The method of any one of embodiments 241 to 305, wherein each $R^{9c}$ is independently selected from halogen, —$OR^{10c}$, —$SR^{10c}$, —$N(R^{10c})_2$, —$C(O)R^{10c}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10c}$, —$SR^{10c}$, —$N(R^{10c})_2$, —$C(O)R^{10c}$, —$NO_2$, =O, and —CN. (307) The method of any one of embodiments 241 to 306, wherein each $R^{9c}$ is independently selected from halogen, —$OR^{10c}$, —$SR^{10c}$, —$N(R^{10c})_2$, —$C(O)R^{10c}$, —$NO_2$, =O, and —CN; and $C_{1-3}$ alkyl, optionally substituted with one or more substituents independently selected from halogen, —$OR^{10}$, —$SR^{10c}$, —$N(R^{10c})_2$, —$C(O)R^{10c}$, —$NO_2$, =O, and —CN. (308) The method of any one of embodiments 241 to 307, wherein each $R^{10a}$ is independently selected from hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl$)_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl$)_2$, —NH($C_{1-6}$ alkyl), $C_{1-6}$ alkyl, $C_{3-10}$ carbocycle, 3- to 10-membered heterocycle, and $C_{1-6}$ haloalkyl. (309) The method of any one of embodiments 241 to 308, wherein each $R^{10a}$ is independently selected from hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —N($C_{1-6}$ alkyl$)_2$, and —NH($C_{1-6}$ alkyl); and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —N($C_{1-6}$ alkyl$)_2$, —NH($C_{1-6}$ alkyl), $C_{1-6}$ alkyl, and $C_{1-6}$ haloalkyl. (310) The method of any one of embodiments 241 to 309, wherein each $R^{10a}$ is independently selected from hydrogen; and $C_{1-6}$ alkyl, optionally substituted with one or more substituents independently selected from halogen, —CN, —OH, —SH, —$NO_2$, —$NH_2$, and =O; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —N($C_{1-6}$ alkyl$)_2$, —NH ($C_{1-6}$ alkyl), $C_{1-6}$ alkyl, and $C_{1-6}$ haloalkyl. (311) The method of any one of embodiments 241 to 310, wherein each $R^{10a}$ is independently selected from hydrogen; and $C_{1-6}$ alkyl optionally substituted with one or more substituents independently selected from halogen; and $C_{3-10}$ carbocycle, and 3- to 10-membered heterocycle. (312) The method of any one of embodiments 241 to 311, wherein each $R^{10b}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl$)_2$, and —NH($C_{1-6}$ alkyl); and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl$)_2$, —NH($C_{1-6}$ alkyl), $C_{1-6}$ alkyl, $C_{2-6}$ alkenyl, and $C_{1-6}$ haloalkyl. (313) The method of any one of embodiments 241 to 312, wherein each $R^{10b}$ is independently selected from: hydrogen; and $C_{1-6}$ alkyl. (314) The method of any one of embodiments 241 to 313, wherein each $R^{10b}$ is hydrogen. (315) The method of any one of embodiments 241 to 314, wherein each $R^{10c}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl$)_2$, —NH($C_{1-6}$ alkyl); and $C_{3-10}$ carbocycle, and 3- to 10-membered heterocycle. (316) The method of any one of embodiments 241 to 315, wherein each $R^{10c}$ is independently selected from: hydrogen; and $C_{1-6}$ alkyl. (317) The method of any one of embodiments 241 to 316, wherein each $R^{10c}$ is hydrogen. (318) The method of any one of embodiments 241 to 317, wherein each $R^{10d}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl$)_2$, —NH($C_{1-6}$ alkyl); and $C_{3-10}$ carbocycle, and 3- to 10-membered heterocycle. (319) The method of any one of embodiments 241 to 318, wherein each $R^{10d}$ is independently selected from: hydrogen; and $C_{1-6}$ alkyl. (320) The method of any one of embodiments 241 to 319, wherein each $R^{10d}$ is hydrogen. (321) The method of any one of embodiments 241 to 320, wherein each $R^{10e}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl$)_2$, —NH($C_{1-6}$ alkyl); and $C_{3-10}$ carbocycle, and 3- to 10-membered heterocycle. (322) The method of any one of embodiments 241 to 321, wherein each $R^{10e}$ is independently selected from: hydrogen; and $C_{1-6}$ alkyl. (323) The method of any one of embodiments 241 to 322, wherein each $R^{10e}$ is hydrogen. (324) The method of any one of embodiments 241 to 323, wherein if $X^3$ and $X^1$ are both N, then $R^8$ is selected from hydrogen and $C_{1-4}$ alkyl optionally substituted with one or more substituents independently selected from halogen, —$OR^{10}$, —$SR^{10}$, —$N(R^{10})_2$, —$NO_2$, and —CN. (325) The method of any one of embodiments 241 to 324, wherein if $X^3$ and $X^1$ are both N, then $R^8$ is selected from hydrogen and $C_{1-4}$ alkyl optionally substituted with one or more substituents independently selected from halogen, —$OR^{10}$, and —CN. (326) The method of any one of embodiments 241 to 325, wherein if $X^3$ and $X^1$ are both N, then $R^8$ is selected from hydrogen and $C_{1-4}$ alkyl optionally substituted with one or more substituents independently selected from fluoro, —OH, and —CN. (327) The method of any one of embodiments 241 to 326, wherein if $X^3$ and $X^1$ are both N, then $R^8$ is selected from hydrogen and $C_{1-4}$ alkyl. (328) The method of any one of embodiments 241 to 327, wherein if $X^3$ and $X^1$ are both N, then $R^8$ is selected from hydrogen and $C_1$ alkyl. (329) The method of any one of embodiments 241 to 328, wherein if $X^3$ and $X^1$ are both N, then $R^8$ is selected from hydrogen. (330), (331), (332), (330A), (331A), (332A), (330B), (331B), (332B): In some embodiments, the compound of formula (III) is selected from compound N1, N2, N3, N4, N5, N6, N7, N8, N9, N10, N11, N12, N13, N14, N15, N16, N17, N18, N19, N20, N21, N22, N23, N24, N25, N26, N27, N28, N29, N30, N31, N32, N33, N34, N35, N36, N37, N38, N39, N40, N41, N42, N43, N44, N45, N46, N47, N48, N49, N50, N51, N52, N53, N54, N55, N56, N57, N58, N59, N60, N61, N62, N63, N64, N65, N66, N67, N68, N69, N70, N71, N72, N73, N74, N75, N76, N77, N78, N79, N80, N81, N82, N83, N84, N85, N86, N87, N88, N89, N90, N91, N92, N93, N94, N95, N96, N97, N98, N99, N100, N101, N102, N103, N104, N105, N106, N107, N108, N109, N110, N111, N112, N113, N114, N115, N116, N117, N118, N119, N120, N121, N122, N123, N124, N125, N126, N127, N128, N129, N130, N131, N132, N133, B1, B2, B3, B4, B5, B6, B7, B8, B9, B10, B11, B12, B13, B14, B15, B16, B17, B18, B19, B20, B21, B22, B23, B24, B25, B26, B27, B28, B29, B30, B31, B32, B33, B34, B35, B36, B37, B38, B39, B40, B41, B42, B43, B44, B45, B46, B47, B48, B49, B50, B51, B52, B53, B54, B55, B56, B57, B58, B59, B60, B61, B62, B63, B64, B65, B66, B67, B68, B69, B70, B71, B72, B73, B74, B75, B76, B77, B78, B79, B80, B81, B82, B83, B84, B85, B86, B87, B88, B89, B90, B91, B92, B93, B94, B95, B96, B97, B98, B99, B100, B101, B102, B103, B104, B105, B106, B107, B108, B109, B110, B111, B112, B113, B114, B115, B116, B117, B118, B119, B120, B121, B122, B123, B124, B125, B126, B127, B128, B129, B130, B131, B132, B133, B134, B135, B136, B137, B138, B139, B140, B141, B142, B143, B144, B145, B146, B147, B148, B149, B150, B151, B152, B153, B154, B155, B156, B157, B158, B159, B160, B161, B162, B163, B164, B165, B166, B167, B168, B169, B170, B171, B172, B173, B174, B175, B176, B177, B178, B179, B180, B181, B182, B183, B184, B185, B186, B187, B188, B189, B190, B191, B192, B193, B194, B195, B196, B197, B198, B199, B200, B201, B202, B203, B204, B205, B206, B207, B208, B209, B210, B211, B212, B213, B214, B215, B216, B217, B218, B219, B220, B221, B222, B223, B224, B225, B226, B227, B228, B229, B230, B231, B232, B233, B234, B235, B236, B237, B238, B239, B240, B241, B242, B243, B244, B245, B246, B247, B248, B249, and a salt of any one thereof. In some embodiments, the compound of formula (III) is selected from compound N2, N4, N5, N6, N7, N8, N9, N10, N13, N15, N18, N19, N21, N23, N24, N26, N28, N31, N33, N36, N37, N39, N41, N44, N47, N54, N60, N62, N68, N72, N74, N77, N78, N81, N87, N88, N94, N95, N98, N101, N102, N103, N104, N108, N110, N111, N112, N113, N114, N115, N116, N117, N118, N119, N120, N121, N122, N123, N124, N125, N126, N127, N128, N129, N132, N133, B1, B2, B3, B4, B6, B7, B8, B9, B10, B12, B13, B14, B16, B17, B22, B23, B25, B27, B29, B31, B32, B33, B34, B35, B36, B37, B38, B39, B40, B41, B42, B43, B44, B45, B46, B47, B48, B49, B50, B52, B53, B54, B55, B56, B57, B58, B59, B62, B64, B65, B67, B68, B69, B70, B71, B73, B75, B76, B77, B78, B79, B80, B81, B82, B83, B84, B85, B87, B88, B89, B91, B92, B93, B94, B97, B98, B100, B101, B102, B103, B105, B106, B108, B110, B112, B113, B114, B116, B117, B118, B119, B120, B121, B123, B124, B126, B127, B128, B130, B132, B133, B134, B135, B136, B137, B139, B140, B141, B142, B144, B145, B146, B147, B148, B150, B152, B154, B155, B156, B160, B161, B163, B164, B169, B170, B172, B176, B181, B184, B188, B189, B190, B191, B193, B194, B199, B200, B202, B203, B204, B205, B206, B210, B212, B214, B217, B221, B222, B223, B225, B226, B227, B228, B229, B230, B231, B232, B233, B234, B236, B237, B238, B241, B243, B244, B245, B246, B247, B248, and B249. In some embodiments, the compound of formula (III) is selected from compound N4, N5, N7, N9, N13, N15, N18, N23, N26, N28, N31, N33, N37, N41, N47, N54, N62, N68, N74, N81, N87, N88, N94, N95, N101, N102, N103, N104, N111, N112, N114, N115, N117, N118, N119, N121, N123, N124, N125, N126, N128, N129, B1, B2, B4, B6, B7, B8, B9, B10, B12, B13, B14, B16, B17, B22, B23, B25, B29, B31, B32, B33, B34, B35, B36, B37, B38, B39, B41, B42, B43, B44, B45, B46, B52, B53, B54, B55, B56, B57, B58, B59, B62, B64, B65, B67, B68, B69, B70, B73, B75, B76, B77, B78, B79, B80, B81, B82, B83, B84, B87, B88, B89, B91, B92, B93, B94, B97, B100, B101, B102, B103, B105, B106, B108, B110, B112, B113, B114, B116, B117, B118, B119, B120, B121, B123, B124, B126, B128, B130, B132, B133, B136, B137, B139, B141, B142, B145, B147, B148, B152, B154, B155, B160, B164, B169, B176, B181, B188, B189, B191, B199, B202, B204, B206, B210, B214, B217, B221, B222, B223, B225, B226, B227, B228, B229, B230, B231, B232, B233, B234, B236, B237, B238, B241, B244, B247, B248, B249, and a salt of any one thereof. In some embodiments, the compound of formula (III) is selected from compound N4, N5, N7, N13, N23, N33, N81, N87, N88, N94, N115, N117, N123, N124, N128, B1, B4, B6, B8, B9, B12, B13, B14, B17, B23, B29, B31, B32, B33, B35, B36, B37, B39, B43, B44, B45, B54, B55, B57, B59, B62, B64, B65, B69, B75, B76, B77, B78, B79, B81, B82, B83, B89, B91, B92, B94, B100, B101, B106, B110, B113, B114, B116, B118, B120, B121, B123, B126, B128, B130, B132, B136, B137, B139, B142, B145, B147, B152, B164, B176, B189, B191, B199, B206, B214, B217, B221, B222, B225, B226, B227, B229, B232, B233, B236, B238, B247, B248, B249, and a salt of any one thereof. In some embodiments, the compound of formula (III) is selected from compound B1, B9, B13, B14, B23, B31, B33, B36, B39, B43, B45, B55, B57, B62, B75, B77, B82, B83, B92, B120, B123, B142, B145, B147, B189, B206, and a salt of any one thereof. In some embodiments, the compound of formula (III) is selected from compound N1, N2, N3, N4, N5, N6, N7, N8, N9, N10, N12, N13, N14, N15, N16, N17, N18, N19, N21, N23, N24, N25, N26, N28, N30, N31, N33, N34, N35, N36, N37, N38, N39, N40, N41, N43, N44, N45, N47, N50, N52, N54, N55, N57, N59, N60, N62, N64, N66, N68, N71, N72, N74, N77, N78, N80, N81, N83, N84, N85, N86, N87, N88, N91, N93, N94, N95, N98, N99, N101, N102, N103, N104, N106, N108, N109, N110, N111, N112, N113, N114, N115, N116, N117, N118, N119, N121, N122, N123, N124, N125, N126, N127, N128, N129, N130, N131, N132, N133, B1, B2, B3, B4, B6, B7, B8, B9, B12, B13, B14, B16, B17, B18, B22, B23, B25, B27, B28, B29, B30, B31, B32, B33, B34, B35, B36, B37, B38, B39, B41, B42, B43, B44, B45, B46, B49, B51, B52, B53, B54, B55, B56, B57, B58, B59, B60, B62, B63, B64, B65, B67, B68, B69, B70, B71, B72, B73, B74, B75, B76, B77, B78, B79, B80, B81, B82, B83, B84, B85, B87, B88, B89, B90, B91, B92, B93, B94, B95, B96, B97, B99, B100, B101, B102, B103, B104, B105, B106, B108, B109, B110, B112, B113, B114, B116, B117, B118, B119, B120, B121, B122, B123, B124, B125, B126, B127, B128, B129, B130, B132, B133, B134, B135, B136, B137, B138, B139, B140, B141, B142, B144, B145, B146, B147, B148, B149, B150, B152, B153, B154, B155, B156, B157, B160, B161, B162, B163, B164, B165, B166, B169, B170, B171, B172, B174, B176, B178, B181, B182, B184, B187, B188, B189, B190, B191, B193, B194, B197, B199, B200, B201, B202, B203, B204, B205, B206, B209, B210, B212, B213, B214, B217, B218, B220, B221, B222, B223, B224, B225, B226, B227, B228, B229, B230, B231, B232, B233, B234, B235, B236, B237, B238, B240, B241, B242, B243, B244, B245, B247, B248, B249, and a salt of any one thereof. In some embodiments, the compound of formula (III) is selected from compound N3, N4, N5, N6, N7, N8, N9, N10, N12, N13, N14, N15, N16, N18, N19, N21, N23, N24, N26, N28, N31, N33, N34, N35, N36, N37, N39, N41, N44, N47, N50, N54, N55, N59, N60, N62, N68, N72, N74, N77, N80, N81, N83, N84, N87, N88, N93, N94, N95, N98, N99, N101, N102, N103, N104, N106, N108, N109, N110, N111, N112, N114, N115, N116, N117, N118, N119, N121, N122, N123, N124, N125, N126, N127, N128, N129, N130, N132, N133, B1, B2, B4, B6, B7, B8, B9, B12, B13, B14, B16, B17, B18, B23, B25, B27, B28, B29, B30, B31, B32, B33, B34, B35, B36, B37, B38, B39, B41, B42, B43, B44, B45, B46, B49, B52, B53, B54, B55, B56, B57, B58, B59, B60, B62, B63, B64, B65, B68, B69, B70, B72, B73, B74, B75, B76, B77, B78, B79, B80, B81, B82, B83, B84, B85, B87, B88, B89, B91, B92, B93, B94, B95, B96, B97, B99, B100, B101, B102, B103, B104, B105, B106, B108, B110, B112, B113, B114, B116, B117, B118, B119, B120, B121, B122, B123, B124, B125, B126, B127, B128, B129, B130, B132, B133, B134, B135, B136, B137, B138, B139, B140, B141, B142, B144, B145, B146, B147, B148, B150, B152, B154, B155, B156, B157, B160, B161, B163, B164, B169, B170, B172, B176, B178, B181, B182, B188, B189, B191, B194, B199, B200, B202, B203, B204, B205, B206, B210, B212, B214, B217, B218, B221, B222, B223, B225, B226, B227, B228, B229, B230, B231, B232, B233, B234, B235, B236, B237, B238, B241, B243, B244, B245, B247, B248, B249, and a salt of any one thereof. In some embodiments, the compound of formula (III) is selected from compound N4, N5, N7, N9, N10, N13, N15, N16, N18, N23, N26, N28, N31, N33, N37, N47, N54, N62, N68, N74, N81, N83, N87, N88, N94, N98, N101, N102, N103, N104, N110, N111, N112, N115, N117, N118, N119, N121, N122, N123, N124, N125, N126, N128, B1, B2, B4, B6, B7, B8, B9, B12, B13, B14, B16, B17, B23, B25, B29, B30, B31, B32, B33, B34, B35, B36, B37, B38, B39, B42, B43, B44, B45, B46, B52, B53, B54, B55, B57, B59, B60, B62, B64, B65, B69, B70, B75, B76, B77, B78, B79, B80, B81, B82, B83, B84, B85, B87, B88, B89, B91, B92, B94, B99, B100, B101, B102, B103, B105, B106, B108, B110, B113, B114, B116, B117, B118, B119, B120, B121, B123, B124, B126, B127, B128, B129, B130, B132, B133, B135, B136, B137, B139, B141, B142, B144, B145, B147, B148, B150, B152, B154, B155, B160, B164, B169, B176, B181, B188, B189, B191, B199, B202, B204, B206, B210, B214, B217, B221, B222, B223, B225, B226, B227, B228, B229, B230, B231, B232, B233, B234, B236, B237, B238, B241, B243, B245, B247, B248, B249, and a salt of any one thereof. In some embodiments, the compound of formula (III) is selected from compound N4, N5, N13, N15, N33, N87, N111, N123, N124, N128, B1, B4, B6, B9, B13, B17, B23, B30, B31, B33, B36, B39, B43, B45, B53, B54, B55, B57, B62, B65, B75, B77, B78, B79, B80, B81, B82, B83, B89, B92, B94, B100, B103, B106, B110, B118, B120, B123, B126, B128, B132, B133, B139, B142, B145, B147, B164, B176, B189, B191, B199, B206, B214, B221, B222, B225, B227, B229, B232, B233, B236, B238, B247, B248, B249, and a salt of any one thereof.

(333) The method of any one of embodiments 241 to 332, wherein cardiovascular disease or a related condition is selected from: hypertrophic cardiomyopathy (HCM); heart failure with preserved ejection fraction (HFpEF); heart failure with mid ranged ejection fraction disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; right ventricular (RV) hypertrophy; acute myocardial infarction; acute revascularization; ischemia; and angina. (334) The method of embodiment 333, wherein said heart failure with preserved ejection fraction (HFpEF) comprises one or more disorders selected from disorders of relaxation and disorders of chamber stiffness (diabetic HFpEF). (335) The method of embodiment 333, wherein said left ventricular (LV) hypertrophy is malignant left ventricular (LV) hypertrophy. (336) The method of embodiment 333, wherein said restrictive cardiomyopathy comprises one or more subgroups selected from inflammatory subgroups, infiltrative subgroups, storage subgroups, idiopathic/inherited subgroups, congenital heart disease subgroups. (337) The method of embodiment 336, wherein said inflammatory subgroups comprise one or more subgroups selected from Loefilers and EMF. (338) The method of embodiment 336, wherein said inflammatory subgroups comprise one or more subgroups selected from amyloid, sarcoid, and XRT. (339) The method of embodiment 336, wherein said storage subgroups comprise one or more subgroups selected from hemochromatosis, Fabry, and glycogen storage disease. (340) The method of embodiment 336, wherein said idiopathic/inherited subgroups comprise one or more subgroups selected from Trop I (beta myosin HC), Trop T (alpha cardiac actin), and desmin related subgroups. (341) The method of embodiment 336, wherein said congenital heart disease subgroups comprise one or more subgroups selected from pressure-overloaded RV, Tetralogy of Fallot, and pulmonic stenosis. (342) The method of any one of embodiments 241 to 332, wherein cardiovascular disease or a related condition is hypertrophic cardiomyopathy. (343) The method of any one of embodiments 241 to 332, wherein cardiovascular disease or a related condition is obstructive hypertrophic cardiomyopathy. (344) The method of any one of embodiments 241 to 332, wherein cardiovascular disease or a related condition is non-obstructive hypertrophic cardiomyopathy. (345) The method of any one of embodiments 241 to 332, wherein cardiovascular disease or a related condition is heart failure with preserved ejection fraction. (346) The method of any one of embodiments 241 to 332, wherein cardiovascular disease or a related condition is left ventricle stiffness.

EXAMPLES

The invention now being generally described, it will be more readily understood by reference to the following examples which are included merely for purposes of illustration of certain aspects and embodiments of the present invention, and are not intended to limit the invention in any way.

The following synthetic schemes are provided for purposes of illustration, not limitation. The following examples illustrate the various methods of making compounds described herein. It is understood that one skilled in the art may be able to make these compounds by similar methods or by combining other methods known to one skilled in the art. It is also understood that one skilled in the art would be able to make, in a similar manner as described below by using the appropriate starting materials and modifying the synthetic route as needed. In general, starting materials and reagents can be obtained from commercial vendors or synthesized according to sources known to those skilled in the art or prepared as described herein.

In some embodiments, compounds of the disclosure are below in Table 1, Table 2, Table 3, Table 4, Table 5, and Table 6.

The compounds of formula (I), (II), or (III) (e.g., compounds of Table 1, Table 2, Table 3, Table 4, Table 5, and Table 6), can be made using conventional organic syntheses and commercially available starting materials. By way of example and not limitation, compounds of Formula (I), (II), or (III) (e.g., compounds of Table 1, Table 2, Table 3, Table 4, Table 5, and Table 6), can be prepared as outlined in Scheme 1, shown below, as well as in the examples set forth herein.

Scheme 1

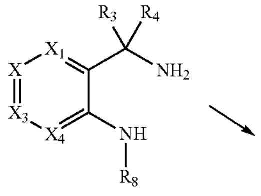

(A)

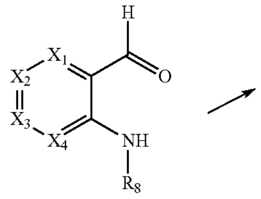

(B)

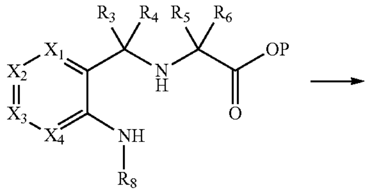

(C)

(E)

+

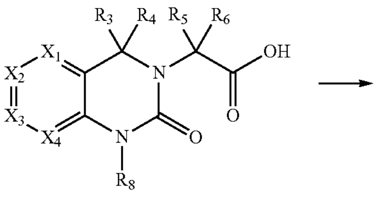

(D)

-continued

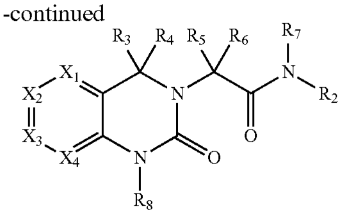

Compounds formula (I), (II), or (III), salt thereof

As shown in Scheme 1, compounds of formula (I), (II), or (III) (e.g., the compounds of Table 1, Table 2, Table 3, Table 4, Table 5, and Table 6), wherein $R^2$, $R^3$, $R^4$, $R^5$, $R^6$ and $R^7$ are as defined herein, can be prepared starting from appropriately derivatized amines (E) and substituted heteroaryl carbamoylglycine (D), wherein $X^1$, $X^2$, $X^3$, and $X^4$ is either C or N. For example, glycine (C) wherein P is either Me, Et, or t-Bu, can be obtained by alkylation of appropriately substituted benzylamine (A) with an alkylating agent, such as methyl or ethyl 2-bromoacetate or tert-butyl 2-bromoacetate, in the presence of a base, such as $K_2CO_3$ or triethyl amine, in a solvent, such as THF or DMF, at temperatures ranging from 0° C. to 25° C. Alternatively, reductive amination of an appropriately substituted aldehydes (B) by treatment with tert-butyl glycinate in a solvent, such as DCE or ACN in the presence of a reducing agent, such as $NaBH(OAc)_3$ or $NaBH_3CN$, at temperatures ranging from 0° C. to 50° C. provides glycine (C). Carbamoylglycine (D) may be obtained by treatment of glycine (C) with CDI or BTC, in the presence of a base, such as DBU or triethylamine, in a solvent, such as DCM or DMF, at temperatures ranging from 0° C. to 50° C. and followed by either subsequent saponification, wherein P is either Me or Et, in the presence of a base, such as LiOH, or NaOH in a solvent, such as MeOH or EtOH and water, at temperatures ranging from 0° C. to 25° C. or hydrolysis, wherein P is t-Bu, in the presence of a acid, such as TFA, in a solvent, such as dichloromethane (DCM), at temperatures ranging from 0° C. to 25° C. Benzylamines (A) aldehydes (B), and amines (E) are commercially available or may be prepared according to known methods (see, e.g., T. A. Engler et al, *J. Med. Chem.* 2004, 47, 16, 3934-3937 and T. Chatterjee et al, *J Org. Chem.* 2018, 83, 14, 7423-7430). Coupling of derivatized amine (E) and substituted heteroaryl carbamoylglycine (D) in a solvent, such as DMF or THF in the presence of a base, such as DIPEA or DMAP, and coupling reagents, such as hydroxybenzotriazole and 1-ethyl-3-(3-dimethylamino-propyl)carbodiimide hydrochloride or propanephosphonic acid anhydride, at temperatures ranging from about 0° C. to about 25° C. provide compounds of Formula (I), (II), or (III).

Intermediate A: (R)-6-(1-Aminoethyl)-5-fluoronicotinonitrile hydrochloride

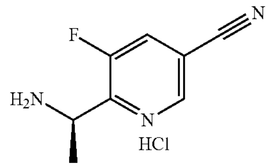

1-(5-Bromo-3-fluoropyridin-2-yl)ethenone. To a solution of 5-bromo-3-fluoropyridine-2-carbonitrile (2200 g, 10945 mmol, 1 equiv) in THF (20 L) was added MeMgBr (7296 mL, 16418 mmol, 2 equiv) dropwise at −10° C. under nitrogen atmosphere for 1 h. The reaction mixture was stirred for an additional 2 h at −10° C. and HCl (3 M) (29187 mL, 87563 mmol, 8 equiv) was added in portions over 1 h at 0° C. The reaction mixture was stirred for 12 h at room temperature and then brought to pH 5 with saturated $NaHCO_3$ (aq.). The reaction mixture was extracted with EtOAc. The combined organic layers were washed with brine, dried over anhydrous $Na_2SO_4$ and filtered. The filtrate was concentrated under reduced pressure. The residue was purified by silica gel column chromatography to afford 1-(5-bromo-3-fluoropyridin-2-yl)ethanone (2000 g, 83.81%).

(R)—N-[1-(5-bromo-3-fluoropyridin-2-yl)ethylidene]-2-methylpropane-2-sulfinamide. To a stirred solution of 1-(5-bromo-3-fluoropyridin-2-yl)ethanone (1000 g, 4586 mmol, 1 equiv) in THF (10 L) was added (S)-2-methylpropane-2-sulfinamide (1111.80 g, 9173.26 mmol, 2 equiv) and $Ti(OEt)_4$ (2092.52 g, 9173.260 mmol, 2 equiv) at room temperature under nitrogen atmosphere. The reaction mixture was stirred for additional 36 h at 40° C. The reaction mixture was concentrated under reduced pressure and purified by silica gel column chromatography to afford (R)—N-[1-(5-bromo-3-fluoropyridin-2-yl)ethylidene]-2-methylpropane-2-sulfinamide (800 g, 54.30%).

N-[1-(5-Bromo-3-fluoropyridin-2-yl)ethyl]-2-methylpropane-2-sulfinamide. To a stirred solution of N-[(1Z)-1-(5-bromo-3-fluoropyridin-2-yl)ethylidene]-2-methylpropane-2-sulfinamide (800 g, 2490.58 mmol, 1 equiv) in THF (8 L) was added L-Selectride (2101 mL, 2101 mmol, 1.5 equiv) dropwise at −78° C. under nitrogen atmosphere for 1 h. The reaction mixture was stirred for additional 1 h at −78° C. The reaction was quenched with sat. $NH_4Cl$ (aq.) at −10° C. The reaction mixture was extracted with EtOAc. The combined organic layers were washed with brine, dried over anhydrous $Na_2SO_4$ and filtered. The filtrate was concentrated under reduced pressure. The residue was purified by silica gel column chromatography to afford N-[1-(5-bromo-3-fluoropyridin-2-yl)ethyl]-2-methylpropane-2-sulfinamide (400 g, 49.69%).

N-[1-(5-Cyano-3-fluoropyridin-2-yl)ethyl]-2-methylpropane-2-sulfinamide. To a stirred solution of N-[1-(5-bromo-3-fluoropyridin-2-yl)ethyl]-2-methylpropane-2-sulfinamide (400 g, 1237 mmol, 1 equiv) in DMF (4 L) were added $Zn(CN)_2$ (290.63 g, 2475 mmol, 2 equiv) and $Pd(PPh_3)_4$ (286 g, 247.5 mmol, 0.2 equiv) at 80° C. under nitrogen atmosphere for 2 h. The reaction mixture was extracted with EtOAc. The combined organic layers were washed with brine, dried over anhydrous $Na_2SO_4$ and filtered. The filtrate was concentrated under reduced pressure. The residue was purified by silica gel column chromatography to afford N-[1-(5-cyano-3-fluoropyridin-2-yl)ethyl]-2-methylpropane-2-sulfinamide (300 g, 90.0%).

(R)-6-(1-Aminoethyl)-5-fluoronicotinonitrile hydrochloride. To a stirred solution of N-[1-(5-cyano-3-fluoropyridin-2-yl)ethyl]-2-methylpropane-2-sulfinamide (300 g, 1113.83 mmol, 1 equiv) in 1,4-dioxane (600 mL) was added 4 M HCl (gas) in 1,4-dioxane (1.1 L, 2227.66 mmol, 2 equiv) dropwise at room temperature under nitrogen atmosphere. The reaction mixture was stirred for additional 0.5 h at room temperature and then diluted with ethyl acetate (3 L). The precipitated solids were collected by filtration and washed with ethyl acetate. The resulting solid were dried under infrared light resulting in (R)-6-(1-aminoethyl)-5-fluoronicotinonitrile hydrochloride (205 g, 92.49%) as a white solid. LCMS-(ES, m/z): 166 $[M+H]^+$ H-NMR: (400 MHz, DMSO-$d_6$) δ 9.03-8.98 (m, 1H), 8.92 (s, 3H), 8.59-8.48 (m, 1H), 4.85-4.64 (m, 1H), 1.62-1.40 (m, 3H).

(S)-6-(1-aminoethyl)-5-fluoronicotinonitrile hydrochloride. LCMS-(ES, m/z): 166 $[M+H]^+$ $^1H$ NMR (300 MHz, DMSO-$d_6$) δ 9.05-8.99 (m, 1H), 8.98-8.85 (m, 3H), 8.60-8.53 (m, 1H), 4.75 (s, 1H), 1.66-1.44 (m, 3H).

Intermediate B: (S)-4-(1-Aminoethyl)-3-fluorobenzonitrile hydrochloride

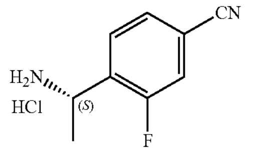

4-Acetyl-3-fluorobenzonitrile. A solution of 4-bromo-3-fluorobenzonitrile (920 g, 4599.77 mmol, 1 equiv), tributyl (1-ethoxyethenyl)stannane (3322.48 g, 9199.54 mmol, 2.0 equiv) and $Pd(PPh_3)_2Cl_2$ (161.43 g, 229.98 mmol, 0.05 equiv) in toluene (10 L) was stirred for 16 h at 110° C. under nitrogen atmosphere. The mixture was cooled to room temperature and 2 N KF (4 L) solution was added to the mixture while stirring. After 30 min, 6 N HCl (5 L) was added to the mixture, and the mixture was stirred for 3 h. The insoluble particulates were filtered, and the filtrate was extracted with EtOAc. The combined organic layers were washed with brine, dried ($Na_2SO_4$), filtered and the solvent was evaporated invacuo. The residue was purified by silica gel column chromatographyto afford 4-acetyl-3-fluorobenzonitrile (700 g, 93.28%).

N-[(1E)-1-(4-Cyano-2-fluorophenyl)ethylidene]-2-methylpropane-2-sulfinamide. A solution of 4-acetyl-3-fluorobenzonitrile (600 g, 3677.57 mmol, 1 equiv), (S)-2-methylpropane-2-sulfinamide (891.44 g, 7355.150 mmol, 2.0 equiv) and $Ti(OEt)_4$ (1677.79 g, 7355.150 mmol, 2.0 equiv) in THF (6 L) was stirred for 16 h at room temperature under nitrogen atmosphere. The residue was purified by silica gel column chromatography to afford N-[(1E)-1-(4-cyano-2-fluorophenyl)ethylidene]-2-methylpropane-2-sulfinamide.

N-[(1S)-1-(4-cyano-2-fluorophenyl)ethyl]-2-methylpropane-2-sulfinamide. To a solution of N-[(1E)-1-(4-cyano-2-fluorophenyl)ethylidene]-2-methylpropane-2-sulfinamide (650 g, 2440.58 mmol, 1 equiv) in THF (3500 mL) under nitrogen atmosphere was added $NaBH_4$ (92.33 g, 2440.581 mmol, 1.0 equiv) in portions at 0° C. The reaction mixture was stirred for 2 h at 0° C. under nitrogen atmosphere. The reaction was quenched by the addition of $NH_4Cl$ (aq.) (500 mL) at 0° C. The reaction mixture was extracted with EtOAc and the combined organic layers were washed with brine, dried over anhydrous $Na_2SO_4$ and filtered. The filtrate was concentrated under reduced pressure. The residue was purified by silica gel column chromatography to afford 450 g (crude) yellow solid. The residue was further purified by trituration with PE/EA (10:1) (3000 mL) resulting in N-[(1S)-1-(4-cyano-2-fluorophenyl)ethyl]-2-methylpropane-2-sulfinamide (300 g, 45.81%).

(S)-4-(1-aminoethyl)-3-fluorobenzonitrile hydrochloride. To a solution of N-[(1S)-1-(4-cyano-2-fluorophenyl)ethyl]-2-methylpropane-2-sulfinamide (300 g, 1117.94 mmol, 1 equiv) in dioxane (3000 mL) under nitrogen atmosphere at 20° C. was added HCl (4M) in 1,4-dioxane (559 mL, 2.0 equiv) dropwise. The reaction mixture was stirred for 2 h at 20° C. under nitrogen atmosphere and then diluted with ethyl acetate (3000 mL). The precipitated solids were collected by filtration and washed with ethyl acetate. The resulting solid was dried under infrared light affording (S)-4-(1-aminoethyl)-3-fluorobenzonitrile hydrochloride (205 g, 92.06%). LCMS (ES, m/z): 165 $[M+H]^+$ H-NMR (300 MHz, DMSO-$d_6$) δ 8.97 (s, 3H), 8.08-7.90 (m, 2H), 7.87-7.77 (m, 1H), 1.65-1.47 (m, 3H).

Example 1: Synthesis of [(1S)-1-(2,4-Difluorophenyl)ethyl]-2-(2-oxo-1,4-dihydroquinazolin-3-yl)acetamide (Compound B249)

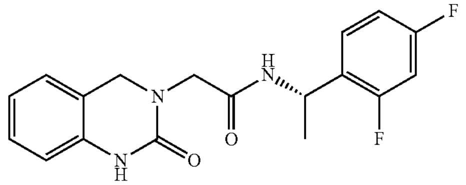 [SMILES: C[C@H](NC(=O)CN1Cc2ccccc2NC1=O)c1ccc(F)cc1F]

Methyl 2-{[(2-nitrophenyl)methyl]amino}acetate. $K_2CO_3$ (3.84 g, 27.774 mmol, 3.0 equiv) was added at 50° C. under air atmosphere to a stirred mixture of 1-(bromomethyl)-2-nitrobenzene (2 g, 9.258 mmol, 1 equiv) and methyl 2-aminoacetate (0.91 g, 10.184 mmol, 1.1 equiv) in DMF (20 mL). The reaction mixture was extracted with EtOAc and the combined organic layers were washed with brine and dried over anhydrous $Na_2SO_4$. The filtrate was concentrated under reduced pressure and the residue was purified by column chromatography to afford methyl 2-{[(2-nitrophenyl)methyl]amino}acetate (1 g, 48.18%). LCMS (ES, m/z): 225 $[M+H]^+$.

Methyl 2-{[(2-aminophenyl)methyl]amino}acetate. A mixture of methyl 2-{[(2-nitrophenyl)methyl]amino}acetate (1 g, 4.460 mmol, 1 equiv) and Pd/C (0.18 g) in MeOH was stirred for 2 h at RT under $H_2$ atmosphere. The reaction mixture was filtered, the filter cake was washed with MeOH. The filtrate was concentrated under reduced pressure. The residue was purified by column chromatography to afford methyl 2-{[(2-aminophenyl)methyl]amino}acetate (0.7 g, 80.81%). LCMS (ES, m/z): 195 $[M+H]^+$.

Methyl 2-(2-oxo-1,4-dihydroquinazolin-3-yl)acetate. DBU (1.37 g, 9.010 mmol, 2.5 equiv) was added at RT under air atmosphere to a stirred mixture of methyl 2-{[(2-aminophenyl)methyl]amino}acetate (0.7 g, 3.604 mmol, 1 equiv) and CDI (1.46 g, 9.010 mmol, 2.5 equiv) in THF (10 mL). The reaction mixture was extracted with EtOAc. The combined organic layers were washed with brine, dried over anhydrous $Na_2SO_4$ $_a$ and the filtrate concentrated under reduced pressure. The residue was purified by column chromatography to afford methyl 2-(2-oxo-1,4-dihydroquinazolin-3-yl)acetate (0.4 g, 50.40%). LCMS (ES, m/z): 221 $[M+H]^+$.

(2-Oxo-1,4-dihydroquinazolin-3-yl)acetic acid. A mixture of methyl 2-(2-oxo-1,4-dihydroquinazolin-3-yl)acetate (0.4 g, 1.816 mmol, 1 equiv) and LiOH (0.13 g, 5.448 mmol, 3 equiv) in MeOH/$H_2O$ (v:v=1:1, 4 mL) was stirred for 4 h at 50° C. under air atmosphere. The mixture was adjusted to pH 4 with conc. HCl. The precipitated solids were collected by filtration and washed with MeCN proving (2-oxo-1,4-dihydroquinazolin-3-yl)acetic acid (350 mg, 93.45%). The crude product was used in the next step directly without further purification. LCMS (ES, m/z): 207 $[M+H]^+$.

N-[(1S)-1-(2,4-difluorophenyl)ethyl]-2-(2-oxo-1,4-dihydroquinazolin-3-yl)acetamide. HATU (344.83 mg, 0.906 mmol, 1.1 equiv) and DIEA (159.83 mg, 1.236 mmol, 1.5 equiv) were added at RT under air atmosphere to a stirred mixture of (2-oxo-1,4-dihydroquinazolin-3-yl)acetic acid (170 mg, 0.824 mmol, 1 equiv) and (1S)-1-(2,4-difluorophenyl)ethanamine (142.53 mg, 0.906 mmol, 1.1 equiv) in DMF (5 mL). The reaction mixture was extracted with EtOAc. The combined organic layers were washed with brine and dried over anhydrous $Na_2SO_4$ and filtered. The filtrate was concentrated under reduced pressure. The residue was purified by reverse flash chromatography with the following conditions: column, C18 silica gel; mobile phase, MeCN in Water (0.1% TFA), 10% to 50% gradient in 10 min; detector, UV 254 nm. This resulted in N-[(1S)-1-(2,4-difluorophenyl)ethyl]-2-(2-oxo-1,4-dihydroquinazolin-3-yl)acetamide (60 mg, 21.07%). LCMS (ES, m/z): 346.25 $[M+H]^+$. $^1H$ NMR (300 MHz, DMSO-$d_6$) δ 9.24 (s, 1H), 8.52 (d, J=7.8 Hz, 1H), 7.55-7.39 (m, 1H), 7.26-7.14 (m, 1H), 7.14-7.03 (m, 2H), 6.87 (d, J=7.2 Hz, 1H), 6.84-6.74 (m, 1H), 5.13 (t, J=7.2 Hz, 1H), 4.45 (s, 2H), 3.97 (s, 2H), 1.36 (d, J=6.9 Hz, 3H).

Example 2: N-[(1S)-1-(2,4-Difluorophenyl)ethyl]-2-(5-fluoro-2-oxo-1,4-dihydroquinazolin-3-yl)acetamide (Compound B248)

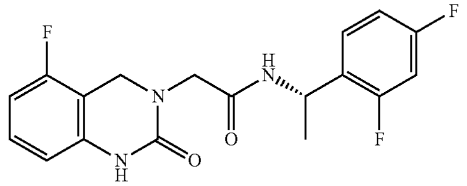 [SMILES: C[C@H](NC(=O)CN1Cc2c(F)cccc2NC1=O)c1ccc(F)cc1F]

Methyl 2-{[(2-fluoro-6-nitrophenyl)methyl]amino}acetate. A mixture of 2-(bromomethyl)-1-fluoro-3-nitrobenzene (1.2 g, 5.128 mmol, 1 equiv) methyl 2-aminoacetate (0.50 g, 5.641 mmol, 1.1 equiv) in DMF (10 mL) was stirred for 2 h at RT under air atmosphere. The reaction mixture was diluted with water and extracted with EtOAc. The combined organic layers were washed with brine and dried over anhydrous $Na_2SO_4$ and filtered. The filtrate was concentrated under reduced pressure and the residue was purified by column chromatography to afford methyl 2-{[(2-fluoro-6-nitrophenyl)methyl]amino}acetate (1.2 g, 96.62%). LCMS (ES, m/z): 243 $[M+H]^+$.

Methyl 2-{[(2-amino-6-fluorophenyl)methyl]amino}acetate. A mixture of methyl 2-{[(2-fluoro-6-nitrophenyl)methyl]amino}acetate (700 mg, 2.890 mmol, 1 equiv) and Pd/C (100 mg) in MeOH (10 mL) was stirred for 3 h at RT under $H_2$ atmosphere. The reaction mixture was filtered, the filter cake was washed with MeOH. The filtrate was concentrated under reduced pressure. The residue was purified by column chromatography to afford methyl 2-{[(2-amino-6-fluorophenyl)methyl]amino}acetate (600 mg, 97.82%). LCMS (ES, m/z): 213[M+H]+.

Methyl 2-(5-fluoro-2-oxo-1,4-dihydroquinazolin-3-yl)acetate. A mixture of methyl 2-{[(2-amino-6-fluorophenyl)methyl]amino}acetate (580 mg, 2.733 mmol, 1 equiv) and DBU (1.04 g, 6.833 mmol, 2.5 equiv) in THF (10 mL) was stirred for 3 h at RT under air atmosphere. The reaction mixture was diluted with water and extracted with EtOAc, dried, filtered and concentrated under reduced pressure. The residue was purified by column chromatography to afford methyl 2-(5-fluoro-2-oxo-1,4-dihydroquinazolin-3-yl)acetate (560 mg, 86.02%). LCMS (ES, m/z): 239[M+H]+.

(5-Fluoro-2-oxo-1,4-dihydroquinazolin-3-yl)acetic acid. A mixture of methyl 2-(5-fluoro-2-oxo-1,4-dihydroquinazolin-3-yl)acetate (540 mg, 2.267 mmol, 1 equiv) and LiOH (271.45 mg, 11.335 mmol, 5 equiv) in THF (5 mL), MeOH (5 mL) and $H_2O$ (5 mL) was stirred for 3 h at RT under air atmosphere. The reaction mixture was concentrated under reduced pressure and diluted with water. The mixture was adjusted to pH 6 with saturated $NH_4Cl$ (aq.) and the precipitated solids were collected by filtration and washed with water affording (5-fluoro-2-oxo-1,4-dihydroquinazolin-3-yl)acetic acid (400 mg, 78.71%). LCMS (ES, m/z): 225[M+H]+.

N-[(1S)-1-(2,4-Difluorophenyl)ethyl]-2-(5-fluoro-2-oxo-1,4-dihydroquinazolin-3-yl)acetamide. HATU (407.05 mg, 1.070 mmol, 1.2 equiv) and DIEA (345.90 mg, 2.676 mmol, 3 equiv) were added in portions at RT under air atmosphere to a stirred mixture of (5-fluoro-2-oxo-1,4-dihydroquinazolin-3-yl)acetic acid (200 mg, 0.892 mmol, 1 equiv) and (1S)-1-(2,4-difluorophenyl)ethanamine (140.21 mg, 0.892 mmol, 1 equiv) in DMF (3 mL). The reaction mixture was stirred for 3 h at RT under air atmosphere and then diluted with water. The reaction mixture was extracted with EtOAc and concentrated under reduced pressure. The residue was purified by reverse flash chromatography with the following conditions: column, C18; mobile phase, MeCN in Water (0.1% FA), 10% to 50% gradient in 40 min; detector, UV 254 nm resulting in N-[(1S)-1-(2,4-difluorophenyl)ethyl]-2-(5-fluoro-2-oxo-1,4-dihydroquinazolin-3-yl)acetamide (173 mg, 53.37%). LCMS (ES, m/z): 364[M+H]+. $^1$H NMR (400 MHz, DMSO-d6) δ 9.49 (d, J=1.8 Hz, 1H), 8.55 (d, J=7.6 Hz, 1H), 7.49-7.40 (m, 1H), 7.24-7.11 (m, 2H), 7.10-7.03 (m, 1H), 6.71 (t, J=8.8 Hz, 1H), 6.60 (d, J=8.0 Hz, 1H), 5.13 (p, J=7.2 Hz, 1H), 4.49 (d, J=2.0 Hz, 2H), 4.00 (s, 2H), 1.36 (d, J=7.2 Hz, 3H).

Example 3: N-[(1S)-1-(2,4-Difluorophenyl)ethyl]-2-(6-fluoro-2-oxo-1,4-dihydroquinazolin-3-yl)acetamide. (Compound B247)

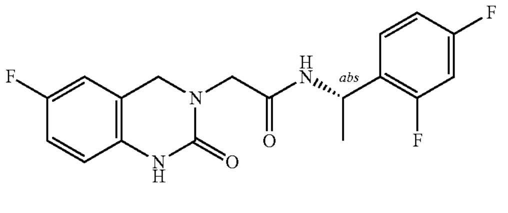 [SMILES: C[C@H](NC(=O)CN1Cc2cc(F)ccc2NC1=O)c1ccc(F)cc1F]

tert-Butyl 2-{[(5-fluoro-2-nitrophenyl)methyl]amino}acetate. $NaBH(OAc)_3$ (31.33 g, 147.8 mmol, 2.5 equiv) was added dropwise at RT under air atmosphere to a stirred solution of 5-fluoro-2-nitrobenzaldehyde (10 g, 59.133 mmol, 1 equiv) and tert-butyl 2-aminoacetate (10.08 g, 76.873 mmol, 1.3 equiv) in DMF (150 mL). The reaction mixture was stirred for 4 h at RT under air atmosphere and extracted with EtOAc. The combined organic layers were washed with brine and dried over anhydrous $Na_2SO_4$ and filtered. The filtrate was concentrated under reduced pressure. The residue was purified by column chromatography to afford tert-butyl 2-{[(5-fluoro-2-nitrophenyl)methyl]amino}acetate (10 g, 59.49%). LCMS (ES, m/z): 285 $[M+H]^+$.

tert-Butyl 2-{[(2-amino-5-fluorophenyl)methyl]amino}acetate. Pd/C (10%, 0.4 g) was added to a solution of tert-butyl 2-{[(5-fluoro-2-nitrophenyl)methyl]amino}acetate (10 g, 35.176 mmol, 1 equiv) in 120 mL MeOH in a pressure vessel. The mixture was held at RT under 40 psi of hydrogen pressure overnight. The reaction mixture was filtered, the filter cake was washed with MeOH. The filtrate was concentrated under reduced pressure. The crude product was used in the next step directly without further purification. to afford tert-butyl 2-{[(2-amino-5-fluorophenyl)methyl]amino}acetate (8 g, 89.43%). LCMS (ES, m/z): 255 [M+H]+.

tert-Butyl 2-(6-fluoro-2-oxo-1,4-dihydroquinazolin-3-yl)acetate. DBU (7.18 g, 47.187 mmol, 1.5 equiv) was added dropwise at RT under air atmosphere to a stirred solution of tert-butyl 2-{[(2-amino-5-fluorophenyl)methyl]amino}acetate (8 g, 31.458 mmol, 1 equiv) and CDI (7.65 g, 47.187 mmol, 1.5 equiv) in DCM (120 mL). The reaction mixture was stirred for 4 h at 40° C. under air atmosphere. The residue was purified by column chromatography to afford tert-butyl 2-(6-fluoro-2-oxo-1,4-dihydroquinazolin-3-yl)acetate (7 g, 79.39%). LCMS (ES, m/z): 281 [M+H]+.

(6-Fluoro-2-oxo-1,4-dihydroquinazolin-3-yl)acetic acid. A solution of tert-butyl 2-(6-fluoro-2-oxo-1,4-dihydroquinazolin-3-yl)acetate (7 g, 24.973 mmol, 1 equiv) in TFA (30 mL) and DCM (100 mL) was stirred for 2 h at RT under air atmosphere. The reaction mixture was concentrated under reduced pressure. The residue was dissolved in MeCN (50 mL). The precipitated solids were collected by filtration and washed with MeCN to afford (6-fluoro-2-oxo-1,4-dihydroquinazolin-3-yl)acetic acid (5 g, 89.30%). LCMS (ES, m/z): 225 [M+H]+.

N-[(1S)-1-(2,4-difluorophenyl)ethyl]-2-(6-fluoro-2-oxo-1,4-dihydroquinazolin-3-yl)acetamide. (1S)-1-(2,4-difluorophenyl)ethanamine (4.21 g, 26.762 mmol, 1.20 equiv) and DIEA (7.21 g, 55.755 mmol, 2.50 equiv) were added dropwise at RT under air atmosphere to a stirred solution of (6-fluoro-2-oxo-1,4-dihydroquinazolin-3-yl)acetic acid (5 g, 22.302 mmol, 1.00 equiv) and HOBT (3.62 g, 26.762 mmol, 1.20 equiv) and EDCI (5.13 g, 26.762 mmol, 1.20 equiv) in DMF (50 mL). The reaction mixture was stirred at RT under air atmosphere for 2 h. The reaction was quenched by the addition of water/ice (50 mL) at 0° C. The precipitated solids were collected by filtration and washed with MeCN. The residue was purified by trituration with MeCN to afford N-[(1S)-1-(2,4-difluorophenyl)ethyl]-2-(6-fluoro-2-oxo-1,4-dihydroquinazolin-3-yl)acetamide (6 g, 72.71%). LCMS (ES, m/z): 364 $[M+H]^+$. $^1$H NMR (400 MHz, DMSO-$d_6$) δ 9.29 (s, 1H), 8.54 (d, J=7.6 Hz, 1H), 7.45 (m, 1H), 7.19 (m, 1H), 7.07 (m, 1H), 6.97 (m, 2H), 6.77 (dd, J=8.4, 4.8 Hz, 1H), 5.13 (m, 1H), 4.45 (s, 2H), 3.97 (s, 2H), 1.36 (d, J=7.2 Hz, 3H).

Example 4: N-[(1S)-1-(2,4-Difluorophenyl)ethyl]-2-(4-methyl-2-oxo-1,4-dihydroquinazolin-3-yl)acetamide (Compound B244)

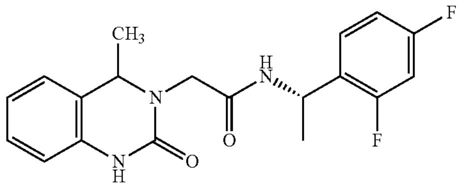 [SMILES: CC1c2ccccc2NC(=O)N1CC(=O)N[C@@H](C)c1ccc(F)cc1F]

1-(2-Nitrophenyl)ethanamine. A mixture of 2-nitroacetophenone (2 g, 12.110 mmol, 1 equiv), $NaBH_3CN$ (3.81 g, 60.550 mmol, 5 equiv) and $CH_3COONH_4$ (5.60 g, 72.660 mmol, 6 equiv) in i-PrOH (40 mL) was stirred overnight at 60° C. The residue was purified by column chromatography, eluted with PE/EA (5:1) to afford 1-(2-nitrophenyl)ethanamine (0.7 g, 34.78%). LC-MS: (ESI, m/z): $[M+H]^+$=167.

2-{[1-(2-Nitrophenyl)ethyl]amino}acetate. A mixture of 1-(2-nitrophenyl)ethanamine (700 mg, 4.212 mmol, 1 equiv), $K_2CO_3$ (1746.48 mg, 12.636 mmol, 3 equiv) and methyl 2-bromoacetate (644.38 mg, 4.212 mmol, 1 equiv) in DMF (11 mL) was stirred for 1 h at RT. The residue was purified by column chromatography to afford methyl 2-{[1-(2-nitrophenyl)ethyl]amino}acetate (650 mg, 64.77%). LC-MS: (ESI, m/z): $[M+H]^+$=239.

2-{[1-(2-Aminophenyl)ethyl]amino}acetate. A mixture of methyl 2-{[1-(2-nitrophenyl)ethyl]amino}acetate (650 mg, 2.728 mmol, 1 equiv) $K_2CO_3$ (1746.48 mg, 12.636 mmol, 3 equiv) and Pd/C (10%, 65 mg) in MeOH (7 mL) was stirred for 2 h at RT under $H_2$ atmosphere. The precipitated solids were collected by filtration and washed with MeOH. The residue was purified by column chromatography to afford methyl 2-{[1-(2-aminophenyl)ethyl]amino}acetate (400 mg, 70.40%). LC-MS: (ESI, m/z): $[M+H]^+$=209.

Methyl 2-(4-methyl-2-oxo-1,4-dihydroquinazolin-3-yl)acetate. A mixture of methyl 2-{[1-(2-aminophenyl)ethyl]amino}acetate (400 mg, 1.921 mmol, 1 equiv), DBU (584.81 mg, 3.842 mmol, 2 equiv) and CDI (622.88 mg, 3.842 mmol, 2 equiv) in THF (5 mL) was stirred for 3 h at RT. The residue was purified by column chromatography to afford methyl 2-(4-methyl-2-oxo-1,4-dihydroquinazolin-3-yl)acetate (400 mg, 88.90%). LC-MS: (ESI, m/z): $[M+H]^+$=235.

(4-Methyl-2-oxo-1,4-dihydroquinazolin-3-yl)acetic acid. A mixture of methyl 2-(4-methyl-2-oxo-1,4-dihydroquinazolin-3-yl)acetate (350 mg, 1.494 mmol, 1 equiv) and LiOH (107.35 mg, 4.482 mmol, 3 equiv) in MeOH (2 mL) and $H_2O$ (2 mL, 111.019 mmol) was stirred for 3 h at RT. The residue was adjusted to pH 5 with conc. HCl to afford (4-methyl-2-oxo-1,4-dihydroquinazolin-3-yl)acetic acid (350 mg crude). LC-MS: (ESI, m/z): $[M+H]^+$=221.

N-[(1S)-1-(2,4-Difluorophenyl)ethyl]-2-(4-methyl-2-oxo-1,4-dihydroquinazolin-3-yl)acetamide. A mixture of (4-methyl-2-oxo-1,4-dihydroquinazolin-3-yl)acetic acid (170 mg, 0.772 mmol, 1 equiv), HATU (322.87 mg, 0.849 mmol, 1.1 equiv), DIEA (149.65 mg, 1.158 mmol, 1.5 equiv) and (1S)-1-(2,4-difluorophenyl)ethanamine (121.32 mg, 0.772 mmol, 1 equiv) in DMF (2 mL) was stirred for 3 h at RT. The residue was purified by reverse flash chromatography with the following conditions: column, C18 silica gel; mobile phase, MeCN in Water (0.10% FA), 0% to 80% gradient in 60 min; detector, UV 254 nm. The reaction mixture was concentrated under reduced pressure to afford N-[(1S)-1-(2,4-difluorophenyl)ethyl]-2-(4-methyl-2-oxo-1,4-dihydroquinazolin-3-yl)acetamide (110 mg, 39.65%). LC-MS: (ESI, m/z): $[M+H]^+$=360.15. $^1H$ NMR (300 MHz, DMSO-$d_6$) δ 9.29 (d, J=4.0 Hz, 1H), 8.48 (d, J=8.0 Hz, 1H), 7.53-7.34 (m, 1H), 7.23-6.98 (m, 4H), 6.91-6.84 (m, 1H), 6.81-6.77 (m, 1H), 5.09 (p, J=8.0 Hz, 1H), 4.57-4.42 (m, 1H), 4.29 (dd, J=16.0, 8.0 Hz, 1H), 3.73 (d, J=16.0 Hz, 1H), 1.34 (d, J=8.0 Hz, 3H), 1.24 (dd, J=8.0, 1.6 Hz, 3H).

Example 5: 2-{5-Chloro-2-oxo-1H,4H-pyrido[4,3-d]pyrimidin-3-yl}-N-[(1S)-1-(2,4-difluorophenyl)ethyl]acetamide (Compound N128)

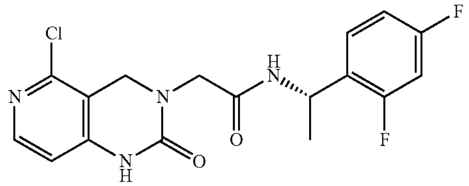 [SMILES: C[C@H](NC(=O)CN1Cc2c(ccnc2Cl)NC1=O)c1ccc(F)cc1F]

tert-Butyl 2-[(E)-[(4-amino-2-chloropyridin-3-yl)methylidene]amino]acetate. TEA (2.91 g, 28.742 mmol, 1.5 equiv) and $MgSO_4$ (3.00 g, 24.909 mmol, 1.3 equiv) were added dropwise at RT under air atmosphere to a stirred solution of 4-amino-2-chloropyridine-3-carbaldehyde (3 g, 19.161 mmol, 1 equiv) and tert-butyl 2-aminoacetate (3.27 g, 24.909 mmol, 1.3 equiv) in MeCN (40 mL). The reaction mixture was stirred overnight at 80° C. under air atmosphere, filtered and the filter cake was washed with MeCN. The filtrate was concentrated under reduced pressure. The crude product was used in the next step directly without further purification, to afford tert-butyl 2-[(E)-[(4-amino-2-chloropyridin-3-yl)methylidene]amino]acetate (3.5 g, 67.72%). LCMS (ES, m/z): 270 $[M+H]^+$.

tert-Butyl 2-{[(4-amino-2-chloropyridin-3-yl)methyl]amino}acetate. A solution of tert-butyl 2-[(E)-[(4-amino-2-chloropyridin-3-yl)methylidene]amino]acetate (3.5 g, 12.976 mmol, 1 equiv) and $NaBH_3CN$ (1.63 g, 25.952 mmol, 2 equiv) in MeOH (40 mL) was stirred for 3 h at RT under air atmosphere. The mixture was concentrated and the residue was purified by column chromatography to afford tert-butyl 2-{[(4-amino-2-chloropyridin-3-yl)methyl]amino}acetate (2 g, 56.72%). LCMS (ES, m/z): 272 $[M+H]^+$.

tert-Butyl 2-{5-chloro-2-oxo-1H,4H-pyrido[4,3-d]pyrimidin-3-yl}acetate. CDI (2.24 g, 13.800 mmol, 1.5 equiv) was added at RT under air atmosphere to a stirred solution of tert-butyl 2-{[(4-amino-2-chloropyridin-3-yl)methyl]amino}acetate (2.5 g, 9.200 mmol, 1 equiv) and DBU (2.10 g, 13.800 mmol, 1.5 equiv) in DCM (40 mL). The reaction mixture was stirred for 4 h at 50° C. under air atmosphere. The residue was purified by column chromatography to afford tert-butyl 2-{5-chloro-2-oxo-1H,4H-pyrido[4,3-d]pyrimidin-3-yl}acetate (2 g, 73.02%). LCMS (ES, m/z): 298 $[M+H]^+$.

{5-Chloro-2-oxo-1H,4H-pyrido[4,3-d]pyrimidin-3-yl}acetic acid. A solution of tert-butyl 2-{5-chloro-2-oxo-1H,4H-pyrido[4,3-d]pyrimidin-3-yl}acetate (2 g, 6.717 mmol, 1 equiv) in TFA (10 mL, 134.631 mmol, 20.04 equiv) and DCM (30 mL, 471.918 mmol, 70.25 equiv) was stirred for 2 h at RT under air atmosphere. The reaction mixture was concentrated under reduced pressure. The crude product was used in the next step directly without further purification, to afford {5-chloro-2-oxo-1H,4H-pyrido[4,3-d]pyrimidin-3-yl}acetic acid (1.4 g, 86.26%). LCMS (ES, m/z): 242 $[M+H]^+$.

2-{5-Chloro-2-oxo-1H,4H-pyrido[4,3-d]pyrimidin-3-yl}-N-[(1S)-1-(2,4-difluorophenyl)ethyl]acetamide. (1S)-1-(2,4-difluorophenyl)ethanamine (0.85 g, 5.381 mmol, 1.3 equiv) and DIEA (1.07 g, 8.278 mmol, 2 equiv) were added dropwise at RT under air atmosphere to a stirred solution of {5-chloro-2-oxo-1H,4H-pyrido[4,3-d]pyrimidin-3-yl}acetic acid (1 g, 4.139 mmol, 1 equiv) and EDCI (1.03 g, 5.381 mmol, 1.3 equiv) and HOBT (0.73 g, 5.381 mmol, 1.3 equiv) in DMF (15 mL). The reaction mixture was stirred for 3 h at RT under air atmosphere and then extracted with EtOAc. The combined organic layers were washed with brine and dried over anhydrous $Na_2SO_4$ and filtered. The filtrate was concentrated under reduced pressure. The residue was purified by reverse flash chromatography with the following conditions: column, C18 silica gel; mobile phase, MeCN in Water (0.1% FA), 0% to 95% gradient in 40 min; detector, UV 254 nm. to afford 2-{5-chloro-2-oxo-1H,4H-pyrido[4,3-d]pyrimidin-3-yl}-N-[(1S)-1-(2,4-difluorophenyl)ethyl]acetamide (800 mg, 50.77%). LCMS (ES, m/z): 381 $[M+H]^+$. $^1$H NMR (400 MHz, DMSO-$d_6$) δ 9.97 (s, 1H), 8.59 (d, J=7.6 Hz, 1H), 8.04 (d, J=5.6 Hz, 1H), 7.44 (m, 1H), 7.19 (m, 1H), 7.11-7.02 (m, 1H), 6.72 (d, J=5.6 Hz, 1H), 5.13 (m, 1H), 4.48 (d, J=2.4 Hz, 2H), 4.02 (s, 2H), 1.36 (d, J=7.2 Hz, 3H).

Example 6: N-[(1S)-1-(2,4-Difluorophenyl)ethyl]-2-{5-methyl-2-oxo-1H,4H-pyrido[4,3-d]pyrimidin-3-yl}acetamide. (N129)

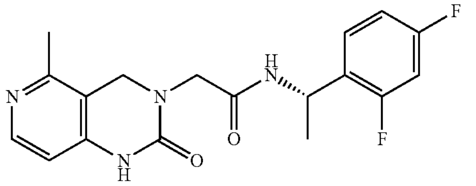 [SMILES: Cc1nccc2c1CN(CC(=O)N[C@@H](C)c1ccc(F)cc1F)C(=O)N2]

N-[(1S)-1-(2,4-Difluorophenyl)ethyl]-2-{5-methyl-2-oxo-1H,4H-pyrido[4,3-d]pyrimidin-3-yl}acetamide. $Pd(dppf)Cl_2$ (76.86 mg, 0.105 mmol, 0.2 equiv) and $K_2CO_3$ (217.77 mg, 1.575 mmol, 3 equiv) were added portionwise at RT under air atmosphere to a stirred solution of 2-{5-chloro-2-oxo-1H,4H-pyrido[4,3-d]pyrimidin-3-yl}-N-[(1S)-1-(2,4-difluorophenyl)ethyl]acetamide (200 mg, 0.525 mmol, 1 equiv) and trimethyl-1,3,5,2,4,6-trioxatriborinane (263.73 mg, 2.100 mmol, 4 equiv) in dioxane (4 mL). The reaction mixture was stirred for 2 h at 110° C. under argon atmosphere. The residue was purified by column chromatography to afford the crude product. The crude product (150 mg) was purified by Prep-HPLC with the following conditions (Column: XBridge Prep C18 OBD Column, 19*150 mm, 5 μm; Mobile Phase A: Water (10 mmoL/L $NH_4HCO_3$), Mobile Phase B: ACN; Flow rate: 25 mL/min; Gradient: 18% B to 32% B in 9 min, 32% B; Wave Length: 254 nm; $RT_1$ (min): 7.84; Number Of Runs: 0) to afford N-[(1S)-1-(2,4-difluorophenyl)ethyl]-2-{5-methyl-2-oxo-1H,4H-pyrido[4,3-d]pyrimidin-3-yl}acetamide (80 mg, 42.27%). LCMS (ES, m/z): 361 $[M+H]^+$. $^1$H NMR (400 MHz, DMSO-$d_6$) δ 9.59 (s, 1H), 8.56 (d, J=7.6 Hz, 1H), 8.06 (d, J=5.6 Hz, 1H), 7.45 (m, 1H), 7.19 (m, 1H), 7.07 (m, 1H), 6.56 (d, J=5.6 Hz, 1H), 5.13 (m, 1H), 4.45 (s, 2H), 3.99 (s, 2H), 2.24 (s, 3H), 1.36 (d, J=7.2 Hz, 3H).

Example 7: N-[(1S)-1-(2,4-Difluorophenyl)ethyl]-2-{5-methoxy-2-oxo-1H,4H-pyrido[4,3-d]pyrimidin-3-yl}acetamide (Compound N125)

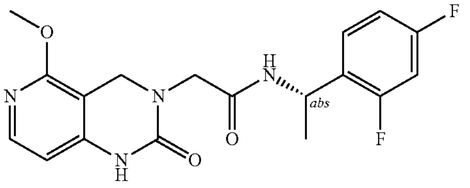 [SMILES: COc1nccc2c1CN(CC(=O)N[C@@H](C)c1ccc(F)cc1F)C(=O)N2]

3-Bromo-2-methoxypyridin-4-amine. A solution of 2-methoxypyridin-4-amine (20 g, 161.105 mmol, 1 equiv) and NBS (28.67 g, 161.105 mmol, 1 equiv) in DCM (200 mL, 3146.120 mmol, 19.53 equiv) was stirred for 2 h at RT under air atmosphere. The reaction mixture was concentrated under vacuum. The residue was purified by column chromatography, eluted with PE/EA (5:1) to afford 3-bromo-2-methoxypyridin-4-amine (20 g, 61.14%). LCMS (ES, m/z): 203 $[M+H]^+$ tert-Butyl N-(3-bromo-2-methoxypyridin-4-yl)carbamate. A solution of 3-bromo-2-methoxypyridin-4-amine (10 g, 49.252 mmol, 1 equiv) and $Boc_2O$ (12.90 g, 59.102 mmol, 1.2 equiv), TEA (9.97 g, 98.504 mmol, 2 equiv), DMAP (0.60 g, 4.925 mmol, 0.1 equiv) in DCM (100 mL) was stirred overnight at RT under air atmosphere. The reaction mixture was concentrated under reduced pressure. The residue was purified by column chromatography to afford tert-butyl N-(3-bromo-2-methoxypyridin-4-yl)carbamate (9 g, 60.28%). LCMS (ES, m/z): 303 $[M+H]^+$ tert-Butyl N-(3-formyl-2-methoxypyridin-4-yl)carbamate. NaH (1.07 g, 44.532 mmol, 1.5 equiv) was added portionwise at 0° C. under argon atmosphere to a stirred solution of tert-butyl N-(3-bromo-2-methoxypyridin-4-yl) carbamate (9 g, 29.688 mmol, 1 equiv) in THF (100 mL). The reaction mixture was stirred for additional 30 min at 0° C. To the above mixture n-BuLi (2.85 g, 44.532 mmol, 1.5 equiv) was added dropwise at −78° C. The reaction mixture was stirred for an additional 30 min at −78° C. To the above mixture DMF (8.68 g, 118.752 mmol, 4 equiv) was added dropwise at −78° C. The reaction mixture was stirred for additional 1 h at −78° C. and then quenched with sat. $NH_4Cl$ (aq.) at RT. The reaction mixture was extracted with EtOAc and the combined organic layers were concentrated under reduced pressure. The residue was purified by column chromatography to afford tert-butyl N-(3-formyl-2-methoxypyridin-4-yl)carbamate (7 g, 93.47%). LCMS (ES, m/z): 253 [M+H]+ tert-Butyl 2-[({4-[(tert-butoxycarbonyl)amino]-2-methoxypyridin-3-yl}methyl)amino]acetate. A solution of tert-butyl N-(3-formyl-2-methoxypyridin-4-yl)carbamate (7 g, 27.748 mmol, 1 equiv) and [2-(tert-butoxy)-2-oxoethyl]aminyl hydrochloride (5.55 g, 33.298 mmol, 1.2 equiv), $MgSO_4$ (5.01 g, 41.622 mmol, 1.5 equiv), TEA (4.21 g, 41.622 mmol, 1.5 equiv) in MeCN (60 mL, 1141.451 mmol, 41.14 equiv) was stirred for 3 h at 80° C. under air atmosphere. To the above mixture $NaBH_3CN$ (8.72 g, 138.740 mmol, 5 equiv) was added dropwise at 0° C. The reaction mixture was stirred for an additional 2 h at RT and then concentrated under reduced pressure. The residue was purified by column chromatography to afford tert-butyl 2-[({4-[(tert-butoxycarbonyl)amino]-2-methoxypyridin-3-yl}methyl)amino]acetate (6 g, 58.85%). LCMS (ES, m/z): 368 $[M+H]^+$ tert-Butyl 2-{5-methoxy-2-oxo-1H,4H-pyrido[4,3-d]pyrimidin-3-yl}acetate. A solution of tert-butyl 2-[({4-[(tert-butoxycarbonyl)amino]-2-methoxypyridin-3-yl}methyl)amino]acetate (6 g, 16.329 mmol, 1 equiv) and CDI (5.30 g, 32.658 mmol, 2 equiv), DBU (4.97 g, 32.658 mmol, 2 equiv) in DCM (50 mL) was stirred overnight at 50° C. under air atmosphere. The reaction mixture was concentrated under vacuum. The residue was purified by column chromatography to afford tert-butyl 2-{5-methoxy-2-oxo-1H,4H-pyrido[4,3-d]pyrimidin-3-yl}acetate (2.3 g, 48.02%). LCMS (ES, m/z): 294 $[M+H]^+$ {5-Methoxy-2-oxo-1H,4H-pyrido[4,3-d]pyrimidin-3-yl}acetic acid. A solution of tert-butyl 2-{5-methoxy-2-oxo-1H,4H-pyrido[4,3-d]pyrimidin-3-yl}acetate (2.3 g, 7.841 mmol, 1 equiv) and TFA (5 mL) in DCM (15 mL) was stirred for 2 h at RT under air atmosphere. The reaction mixture was concentrated under vacuum. The crude product was used in the next step directly without further purification. LCMS (ES, m/z): 238 $[M+H]^+$ N-[(1S)-1-(2,4-Difluorophenyl)ethyl]-2-{5-methoxy-2-oxo-1H,4H-pyrido[4,3-d]pyrimidin-3-yl}acetamide. A solution of {5-methoxy-2-oxo-1H,4H-pyrido[4,3-d]pyrimidin-3-yl}acetic acid (1.7 g, 7.166 mmol, 1 equiv) and (1S)-1-(2,4-difluorophenyl)ethanamine (1.24 g, 7.883 mmol, 1.1 equiv), EDCI (1.65 g, 8.599 mmol, 1.2 equiv), HOBt (1.16 g, 8.599 mmol, 1.2 equiv), DIEA (1.85 g, 14.332 mmol, 2 equiv) in DMF (15 mL) was stirred overnight at 50° C. under air atmosphere. The reaction mixture was extracted with EtOAc and the combined organic layers were concentrated under reduced pressure. The residue was purified by reverse flash chromatography with the following conditions: column, C18; mobile phase, MeCN in Water (0.1% FA), 0% to 100% gradient in 60 min; detector, UV 254 nm to afford N-[(1S)-1-(2,4-difluorophenyl)ethyl]-2-{5-methoxy-2-oxo-1H,4H-pyrido[4,3-d]pyrimidin-3-yl}acetamide (670.9 mg, 24.87%). LCMS (ES, m/z): 377 $[M+H]^+$. $^1$H NMR (300 MHz, DMSO-$d_6$) δ 9.59 (s, 1H), 8.57 (d, J=7.8 Hz, 1H), 7.83 (d, J=5.7 Hz, 1H), 7.47-7.39 (m, 1H), 7.22-7.14 (m, 1H), 7.09-7.02 (m, 1H), 6.40 (d, J=5.7 Hz, 1H), 5.14-5.09 (m, 1H), 4.32 (s, 2H), 3.98 (s, 2H), 3.82 (s, 3H), 1.35 (d, J=7.2 Hz, 3H).

Example 8: 2-[5-Cyclopropyl-2-oxo-1H,4H-pyrido[4,3-d]pyrimidin-3-yl]-N-[(1S)-1-(2,4-difluorophenyl)ethyl]acetamide (Compound N127)

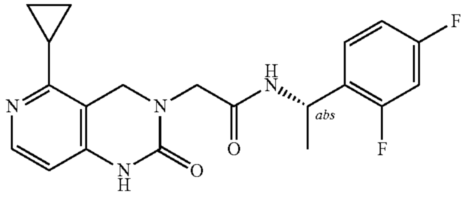 [SMILES: C[C@H](NC(=O)CN1Cc2c(ccnc2C2CC2)NC1=O)c1ccc(F)cc1F]

tert-Butyl 2-{[(4-amino-2-chloropyridin-3-yl)methyl]amino}acetate. A solution of 4-amino-2-chloropyridine-3-carbaldehyde (900 mg, 5.748 mmol, 1 equiv) and [2-(tert-butoxy)-2-oxoethyl]aminyl hydrochloride (1149.39 mg, 6.898 mmol, 1.2 equiv), $MgSO_4$ (1037.79 mg, 8.622 mmol, 1.5 equiv), TEA (1163.36 mg, 11.496 mmol, 2 equiv) in MeCN (10 mL) was stirred for 6 h at 80° C. under air atmosphere. The reaction mixture was filtered, the filtrate was concentrated under reduced pressure. To the above mixture $NaBH_3CN$ (1083.66 mg, 17.244 mmol, 3 equiv) was added portionwise at 0° C. in MeOH (10 mL). The reaction mixture was stirred overnight at RT. The reaction mixture was concentrated under vacuum. The residue was purified by column chromatography to afford tert-butyl 2-{[(4-amino-2-chloropyridin-3-yl)methyl]amino}acetate (600 mg, 38.41%). LCMS (ES, m/z): 272 $[M+H]^+$ tert-Butyl 2-{5-chloro-2-oxo-1H,4H-pyrido[4,3-d]pyrimidin-3-yl}acetate. A solution of tert-butyl 2-{[(4-amino-2-chloropyridin-3-yl)methyl]amino}acetate (600 mg, 2.208 mmol, 1 equiv) in dioxane (6 mL) was treated with triphosgene (262.06 mg, 0.883 mmol, 0.4 equiv) for 5 min at 0° C. under $N_2$ atmosphere followed by the addition of TEA (446.85 mg, 4.416 mmol, 2 equiv) dropwise at 0° C. The reaction mixture was stirred overnight at RT under air atmosphere. The reaction was quenched with water at RT. The reaction mixture was concentrated under reduced pressure. The residue was purified by column chromatography to afford tert-butyl 2-{5-chloro-2-oxo-1H,4H-pyrido[4,3-d]pyrimidin-3-yl}acetate (300 mg, 45.64%). LCMS (ES, m/z): 298 $[M+H]^+$ {5-Chloro-2-oxo-1H,4H-pyrido[4,3-d]pyrimidin-3-yl}acetic acid. A solution of tert-butyl 2-{5-chloro-2-oxo-1H,4H-pyrido[4,3-d]pyrimidin-3-yl}acetate (300 mg, 1.008 mmol, 1 equiv) and TFA (1 mL) in DCM (3 mL) was stirred for 2 h at RT under air atmosphere. The reaction mixture was concentrated under vacuum. The crude product was used in the next step directly without further purification. MS (ES, m/z): 242 $[M+H]^+$ 2-{5-Chloro-2-oxo-1H,4H-pyrido[4,3-d]pyrimidin-3-yl}-N-[(1S)-1-(2,4-difluorophenyl)-ethyl]acetamide. A solution of {5-chloro-2-oxo-1H,4H-pyrido[4,3-d]pyrimidin-3-yl}acetic acid (100 mg, 0.414 mmol, 1 equiv) and (1S)-1-(2,4-difluorophenyl)ethanamine (65.04 mg, 0.414 mmol, 1 equiv), EDCI (95.20 mg, 0.497 mmol, 1.2 equiv), HOBt (67.11 mg, 0.497 mmol, 1.2 equiv), DIEA (160.47 mg, 1.242 mmol, 3 equiv) in DMF (2 mL) was stirred for 2 h at RT under air atmosphere. The reaction mixture was extracted with EtOAc and the combined organic layers were concentrated under reduced pressure. The residue was purified by column chromatography to afford 2-{5-chloro-2-oxo-1H,4H-pyrido[4,3-d]pyrimidin-3-yl}-N-[(1S)-1-(2,4-difluorophenyl)ethyl]acetamide (100 mg, 63.46%). LCMS (ES, m/z): 381 $[M+H]^+$ 2-[5-Cyclopropyl-2-oxo-1H,4H-pyrido[4,3-d]pyrimidin-3-yl]-N-[(1S)-1-(2,4-difluorophenyl)-ethyl]acetamide. A solution of 2-[5-chloro-2-oxo-1H,4H-pyrido[4,3-d]pyrimidin-3-yl]-N-[(1S)-1-(2,4-difluorophenyl)-ethyl]acetamide (100.00 mg, 0.263 mmol, 1.00 equiv), Pd(dppf)$C_{12}$ (19.22 mg, 0.026 mmol, 0.10 equiv) and $K_2CO_3$ (90.74 mg, 0.658 mmol, 2.50 equiv) in dioxane (1.50 mL) was treated with cyclopropylboronic acid (112.79 mg, 1.315 mmol, 5.00 equiv) overnight at 100° C. under $N_2$ atmosphere. The reaction mixture was concentrated under vacuum. The residue was purified by reverse flash chromatography with the following conditions: (column, C18; mobile phase, MeCN in Water (0.1% FA), 0% to 100% gradient in 60 min; detector, UV 254 nm) to afford 2-[5-cyclopropyl-2-oxo-1H,4H-pyrido[4,3-d]pyrimidin-3-yl]-N-[(1S)-1-(2,4-difluorophenyl)ethyl]acetamide (29.8 mg, 29.07%). LCMS (ES, m/z): 387 $[M+H]^+$. $^1$H NMR (300 MHz, DMSO-$d_6$) δ 9.54 (s, 1H), 8.57 (d, J=7.8 Hz, 1H), 8.02 (d, J=5.4 Hz, 1H), 7.49-7.41 (m, 1H), 7.22-7.15 (m, 1H), 7.09-7.02 (m, 1H), 6.48 (d, J=5.4 Hz, 1H), 5.16-5.11 (m, 1H), 4.63 (s, 2H), 4.01 (s, 2H), 1.82-1.75 (m, 1H), 1.37 (d, J=6.9 Hz, 3H), 0.94-0.82 (m, 4H), Example 9: 2-[(4R*)-5,6-Difluoro-4-methyl-2-oxo-1,4-dihydroquinazolin-3-yl]-N-[(1S)-1-(2,4-difluorophenyl)ethyl]acetamide. (Compound B232)

2-[(4S*)-5,6-Difluoro-4-methyl-2-oxo-1,4-dihydroquinazolin-3-yl]-N-[(1S)-1-(2,4-difluorophenyl)ethyl]acetamide. (Compound B231)

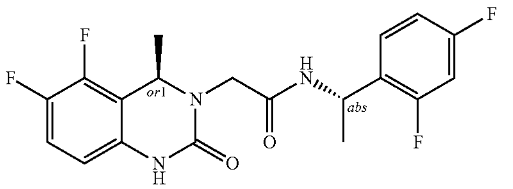

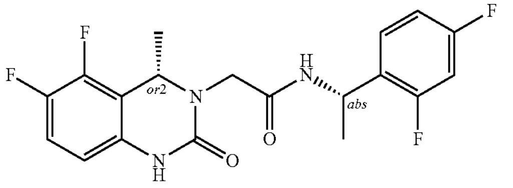

N-(2-Bromo-3,4-difluorophenyl)-2,2-dimethylpropanamide. 2,2-dimethylpropanoyl chloride (6.96 g, 57.690 mmol, 2 equiv) was added dropwise at 0° C. under air atmosphere to a stirred solution of 2-bromo-3,4-difluoroaniline (6 g, 28.845 mmol, 1 equiv) and TEA (5.84 g, 57.690 mmol, 2 equiv) in DCM (60 mL). The reaction mixture was stirred for 3 h at RT under air atmosphere. The reaction mixture was extracted with $CH_2Cl_2$ and the combined organic layers were washed with brine and dried over anhydrous $Na_2SO_4$ and filtered. The filtrate was concentrated under reduced pressure. The residue was purified by column chromatography to afford N-(2-bromo-3,4-difluorophenyl)-2,2-dimethylpropanamide (7 g, 83.07%). LCMS (ES, m/z): 292 $[M+H]^+$.

N-(3,4-Difluoro-2-formylphenyl)-2,2-dimethylpropanamide. A solution of N-(2-bromo-3,4-difluorophenyl)-2,2-dimethylpropanamide (7 g, 23.962 mmol, 1 equiv) and NaH (0.75 g, 31.151 mmol, 1.3 equiv) in THF was stirred for 30 min at 0° C. under $N_2$ atmosphere. To the above mixture n-BuLi (2.30 g, 35.943 mmol, 1.5 equiv) was added dropwise over 10 min at −78° C. The reaction mixture was stirred for an additional 1 h at −78° C. To the above mixture DMF (7.01 g, 95.848 mmol, 4 equiv) was added dropwise over 5 min at −78° C. The reaction mixture was stirred for an additional 1 h at −78° C. The reaction was quenched with sat. $NH_4Cl$ (aq.) at −78° C. and then extracted with EtOAc. The combined organic layers were washed with brine and dried over anhydrous $Na_2SO_4$ and filtered. The filtrate was concentrated under reduced pressure. The residue was purified by column chromatography to afford N-(3,4-difluoro-2-formylphenyl)-2,2-dimethylpropanamide (4.5 g, 77.85%). LCMS (ES, m/z): 242 $[M+H]^+$.

N-[3,4-Difluoro-2-(1-hydroxyethyl)phenyl]-2,2-dimethylpropanamide. Bromo(methyl)magnesium (33.16 mL, 33.162 mmol, 2 equiv) was added dropwise/in portions at 0° C. under argon atmosphere to a stirred solution of N-(3,4-difluoro-2-formylphenyl)-2,2-dimethylpropanamide (4 g, 16.581 mmol, 1 equiv) in THF (50 mL). The reaction mixture was stirred for 2 h at 0° C. under $N_2$ atmosphere. The reaction was quenched with sat. $NH_4Cl$ (aq.) at 0° C. and then extracted with EtOAc. The combined organic layers were washed with brine and dried over anhydrous $Na_2SO_4$ and filtered. The filtrate was concentrated under reduced pressure. The residue was purified by column chromatography to afford N-[3,4-difluoro-2-(1-hydroxyethyl)phenyl]-2,2-dimethylpropanamide (3 g, 70.32%). LCMS (ES, m/z): 258 $[M+H]^+$.

1-(6-Amino-2,3-difluorophenyl)ethanol. A solution of N-[3,4-difluoro-2-(1-hydroxyethyl)phenyl]-2,2-dimethylpropanamide (2 g, 7.774 mmol, 1 equiv) in HCl (20 mL, 3M) and dioxane (20 mL) was stirred overnight at 90° C. under air atmosphere. The mixture/residue was adjusted to pH 8 with saturated $NaHCO_3$ (aq.). The reaction mixture was extracted with EtOAc. The combined organic layers were washed with brine and dried over anhydrous $Na_2SO_4$ and filtered. The filtrate was concentrated under reduced pressure. The residue was purified by column chromatography to afford 1-(6-amino-2,3-difluorophenyl)ethanol (1 g, 74.29%). LCMS (ES, m/z): 174 $[M+H]^+$.

2-(1-Chloroethyl)-3,4-difluoroaniline. A solution of 1-(6-amino-2,3-difluorophenyl)ethanol (1.5 g, 8.662 mmol, 1 equiv) and $SOCl_2$ (5.15 g, 43.310 mmol, 5 equiv) in DCM (20 mL) was stirred for 2 h at RT under air atmosphere. The reaction mixture was concentrated under reduced pressure. The crude product was used in the next step directly without further purification, to afford 2-(1-chloroethyl)-3,4-difluoroaniline (1.5 g, 90.37%). LCMS (ES, m/z): 192 $[M+H]^+$.

tert-Butyl 2-{[1-(6-amino-2,3-difluorophenyl)ethyl]amino}acetate. $K_2CO_3$ (2.16 g, 15.66 mmol, 3 equiv) was added dropwise at RT under air atmosphere to a stirred solution of 2-(1-chloroethyl)-3,4-difluoroaniline (1 g, 5.219 mmol, 1 equiv) and tert-butyl 2-aminoacetate (0.89 g, 6.785 mmol, 1.3 equiv) in DMF (10 mL). The reaction mixture was stirred for 3 h at RT under air atmosphere. The reaction mixture was extracted with EtOAc and the combined organic layers were washed with brine and dried over anhydrous $Na_2SO_4$ and filtered. The filtrate was concentrated under reduced pressure. The residue was purified by column chromatography to afford tert-butyl 2-{[1-(6-amino-2,3-difluorophenyl)ethyl]amino}acetate (800 mg, 53.54%). LCMS (ES, m/z): 287 $[M+H]^+$.

tert-Butyl 2-(5,6-difluoro-4-methyl-2-oxo-1,4-dihydroquinazolin-3-yl)acetate. DBU (638.05 mg, 4.191 mmol, 1.5 equiv) was added dropwise at RT under air atmosphere to a stirred solution of tert-butyl 2-{[1-(6-amino-2,3-difluorophenyl)ethyl]amino}acetate (800 mg, 2.794 mmol, 1 equiv) and CDI (679.59 mg, 4.191 mmol, 1.5 equiv) in DCM (10 mL). The reaction mixture was stirred for 3 h at 40° C. under air atmosphere. The residue was purified by column chromatography to afford tert-butyl 2-(5,6-difluoro-4-methyl-2-oxo-1,4-dihydroquinazolin-3-yl)acetate (700 mg, 80.22%). LCMS (ES, m/z): 313 $[M+H]^+$.

(5,6-Difluoro-4-methyl-2-oxo-1,4-dihydroquinazolin-3-yl)acetic acid. A solution of tert-butyl 2-(5,6-difluoro-4-methyl-2-oxo-1,4-dihydroquinazolin-3-yl)acetate (700 mg, 2.241 mmol, 1 equiv) in TFA (10 mL) and DCM (30 mL) was stirred for 3 h at RT under air atmosphere. The reaction mixture was concentrated under reduced pressure. The crude product was used in the next step directly without further purification, to afford (5,6-difluoro-4-methyl-2-oxo-1,4-dihydroquinazolin-3-yl)acetic acid (650 mg, 90.55%). LCMS (ES, m/z): 257 $[M+H]^+$.

2-(5,6-Difluoro-4-methyl-2-oxo-1,4-dihydroquinazolin-3-yl)-N-[(1S)-1-(2,4-difluorophenyl)ethyl]acetamide. (1S)-

1-(2,4-difluorophenyl)ethanamine (159.49 mg, 1.015 mmol, 1.3 equiv) and DIEA (201.78 mg, 1.562 mmol, 2 equiv) were added dropwise at RT under air atmosphere to a stirred solution of (5,6-difluoro-4-methyl-2-oxo-1,4-dihydroquinazolin-3-yl)acetic acid (200 mg, 0.781 mmol, 1 equiv) and EDCI (194.54 mg, 1.015 mmol, 1.3 equiv) and HOBT (137.13 mg, 1.015 mmol, 1.3 equiv) in DMF (9 mL). The reaction mixture was stirred for 3 h at RT under air atmosphere and then extracted with EtOAc. The combined organic layers were washed with brine and dried over anhydrous $Na_2SO_4$ and filtered. The filtrate was concentrated under reduced pressure. The residue was purified by reverse flash chromatography with the following conditions: column, C18 silica gel; mobile phase, MeCN in Water (0.1% FA), 0% to 100% gradient in 40 min; detector, UV 254 nm. to afford 2-(5,6-difluoro-4-methyl-2-oxo-1,4-dihydroquinazolin-3-yl)-N-[(1S)-1-(2,4-difluorophenyl)ethyl]acetamide (200 mg, 64.80%). LCMS (ES, m/z): 396 $[M+H]^+$.

2-[(4R*)-5,6-difluoro-4-methyl-2-oxo-1,4-dihydroquinazolin-3-yl]-N-[(1S)-1-(2,4-difluorophenyl)ethyl]acetamide. The crude product (150 mg) was purified by CHIRAL-HPLC with the following conditions (Column: CHIRALPAK IE, 2*25 cm, 5 μm; Mobile Phase A: Hex:MtBE=1:1 (0.5% 2 M $NH_3$-MeOH), Mobile Phase B: EtOH-HPLC; Flow rate: 20 mL/min; Gradient: 10% B to 10% B in 16 min; Wave Length: 245/220 nm; $RT_1$ (min): 7.72; $RT_2$ (min): 12; Sample Solvent: MeOH:DCM=1:1; Injection Volume: 1.2 mL; Number Of Runs: 6) to afford 2-[(4R*)-5,6-difluoro-4-methyl-2-oxo-1,4-dihydroquinazolin-3-yl]-N-[(1S)-1-(2,4-difluorophenyl)ethyl]acetamide (60 mg, 40.00%). LCMS (ES, m/z): 396 $[M+H]^+$. $^1H$ NMR (400 MHz, DMSO-$d_6$) δ 9.53 (s, 1H), 8.50 (d, J=7.6 Hz, 1H), 7.41 (m, 1H), 7.29-7.12 (m, 2H), 7.02 (m, 1H), 6.65-6.57 (m, 1H), 5.09 (m, 1H), 4.75 (m, 1H), 4.31 (d, J=16.4 Hz, 1H), 3.78 (d, J=16.4 Hz, 1H), 1.34 (d, J=7.2 Hz, 3H), 1.27 (d, J=6.4 Hz, 3H).

2-[(4S*)-5,6-Difluoro-4-methyl-2-oxo-1,4-dihydroquinazolin-3-yl]-N-[(1S)-1-(2,4-difluorophenyl)ethyl]acetamide. The crude product (150 mg) was purified by CHIRAL-HPLC with the following conditions (Column: CHIRALPAK IE, 2*25 cm, 5 μm; Mobile Phase A: Hex:MtBE=1:1 (0.5% 2 M $NH_3$-MeOH), Mobile Phase B: EtOH-HPLC; Flow rate: 20 mL/min; Gradient: 10% B to 10% B in 16 min; Wave Length: 245/220 nm; $RT_1$ (min): 7.72; $RT_2$ (min): 12; Sample Solvent: MeOH:DCM=1:1; Injection Volume: 1.2 mL; Number Of Runs: 6) to afford 2-[(4S*)-5,6-difluoro-4-methyl-2-oxo-1,4-dihydroquinazolin-3-yl]-N-[(1S)-1-(2,4-difluorophenyl)ethyl]acetamide (60 mg, 40.00%). LCMS (ES, m/z): 396 $[M+H]^+$. $^1H$ NMR (400 MHz, DMSO-$d_6$) δ 9.53 (s, 1H), 8.50 (d, J=7.6 Hz, 1H), 7.41 (m, 1H), 7.29-7.12 (m, 2H), 7.02 (m, 1H), 6.65-6.57 (m, 1H), 5.09 (m, 1H), 4.75 (m, 1H), 4.31 (d, J=16.4 Hz, 1H), 3.78 (d, J=16.4 Hz, 1H), 1.34 (d, J=7.2 Hz, 3H), 1.27 (d, J=6.4 Hz, 3H).

Example 10: N-[(1S)-1-(2,4-Difluorophenyl)ethyl]-2-[2-oxo-6-(trifluoromethyl)-1H,4H-pyrido[3,2-d]pyrimidin-3-yl]acetamide (Compound N112)

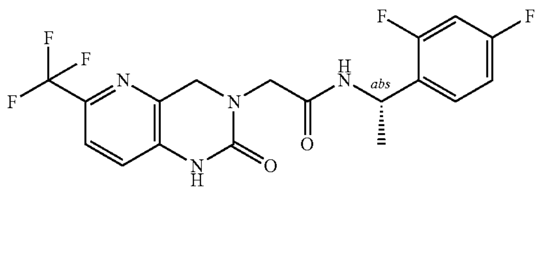 [SMILES: C[C@H](NC(=O)CN1Cc2nc(C(F)(F)F)ccc2NC1=O)c1ccc(F)cc1F]

tert-Butyl N-[2-formyl-6-(trifluoromethyl)pyridin-3-yl]carbamate. NaH (0.21 g, 8.795 mmol, 1.5 equiv) was added portionwise at 0° C. under argon atmosphere to a stirred solution of tert-butyl N-[2-bromo-6-(trifluoromethyl)pyridin-3-yl]carbamate (2 g, 5.863 mmol, 1 equiv) in THF (20 mL). The reaction mixture was stirred for additional 30 min at RT. To the above mixture was added n-BuLi (0.56 g, 8.795 mmol, 1.5 equiv) dropwise at −78° C. The reaction mixture was stirred for additional 30 min at −78° C. To the above mixture was added DMF (1.71 g, 23.452 mmol, 4 equiv) dropwise at −78° C. The reaction mixture was stirred for additional 1 h at −78° C. The reaction was quenched with sat. $NH_4Cl$ (aq.) at 0° C. The reaction mixture was extracted with EtOAc. The combined organic layers were concentrated under reduced pressure. The residue was purified by column chromatography to afford tert-butyl N-[2-formyl-6-(trifluoromethyl)pyridin-3-yl]carbamate (1 g, 58.77%). LCMS (ES, m/z): 291 $[M+H]^+$ Benzyl 2-[({3-[(tert-butoxycarbonyl)amino]-6-(trifluoromethyl)pyridin-2-yl}methyl)amino]acetate. A solution of tert-butyl N-[2-formyl-6-(trifluoromethyl)pyridin-3-yl]carbamate (1 g, 3.445 mmol, 1 equiv) and [2-(benzyloxy)-2-oxoethyl]aminyl hydrochloride (0.83 g, 4.134 mmol, 1.2 equiv), $NaBH(OAc)_3$ (2.19 g, 10.335 mmol, 3 equiv) in DCM (10 mL) was stirred for 2 h at RT under air atmosphere. The reaction mixture was concentrated under vacuum and purified by column chromatography to afford benzyl 2-[({3-[(tert-butoxycarbonyl)amino]-6-(trifluoromethyl)pyridin-2-yl}methyl)amino]acetate (900 mg, 59.44%). LCMS (ES, m/z): 340 $[M+H]^+$ Benzyl 2-({[3-amino-6-(trifluoromethyl)pyridin-2-yl]methyl}amino)acetate. A solution of benzyl 2-[({3-[(tert-butoxycarbonyl)amino]-6-(trifluoromethyl)pyridin-2-yl}methyl)amino]acetate (300 mg, 0.683 mmol, 1 equiv) and TFA (1 mL) in DCM (3 mL) was stirred for 1 h at RT under air atmosphere. The mixture was neutralized to pH 7 with saturated $NaHCO_3$ (aq.) and extracted with $CH_2Cl_2$. The combined organic layers were concentrated under reduced pressure. The residue was purified by column chromatography to afford benzyl 2-({[3-amino-6-(trifluoromethyl)pyridin-2-yl]methyl}amino)acetate (200 mg, 86.34%). LCMS (ES, m/z): 340 $[M+H]^+$ Benzyl 2-[2-oxo-6-(trifluoromethyl)-1H,4H-pyrido[3,2-d]pyrimidin-3-yl]acetate. A solution of benzyl 2-({[3-amino-6-(trifluoromethyl)pyridin-2-yl]methyl}amino)acetate (200 mg, 0.589 mmol, 1 equiv) and CDI (191.15 mg, 1.178 mmol, 2 equiv), DBU (179.47 mg, 1.178 mmol, 2 equiv) in DCM (3 mL) was stirred for overnight at 50° C. under air atmosphere. The reaction mixture was concentrated under vacuum and purified by column chromatography to afford benzyl 2-[2-oxo-6-(trifluoromethyl)-1H,4H-pyrido[3,2-d]pyrimidin-3-yl]acetate (120 mg, 55.73%). LCMS (ES, m/z): 366 $[M+H]^+$

[2-Oxo-6-(trifluoromethyl)-1H,4H-pyrido[3,2-d]pyrimidin-3-yl]acetic acid. A solution of benzyl 2-[2-oxo-6-(trifluoromethyl)-1H,4H-pyrido[3,2-d]pyrimidin-3-yl]acetate (120 mg, 0.328 mmol, 1 equiv) and Pd/C (12 mg) in MeOH (3 mL) was stirred for 2 h at RT under $H_2$ atmosphere. The reaction mixture was filtered, the filtrate was concentrated under reduced pressure. The crude product was used in the next step directly without further purification. LCMS (ES, m/z): 276 $[M+H]^+$ N-[(1S)-1-(2,4-Difluorophenyl)ethyl]-2-[2-oxo-6-(trifluoromethyl)-1H,4H-pyrido[3,2-d]pyrimidin-3-yl]acetamide. A solution of [2-oxo-6-(trifluoromethyl)-1H,4H-pyrido[3,2-d]pyrimidin-3-yl]acetic acid (80.00 mg, 0.291 mmol, 1.00 equiv) and (1S)-1-(2,4-difluorophenyl)

ethanamine (50.26 mg, 0.320 mmol, 1.10 equiv), EDCI (83.59 mg, 0.437 mmol, 1.50 equiv), HOBT (58.92 mg, 0.437 mmol, 1.50 equiv), DIEA (75.14 mg, 0.582 mmol, 2.00 equiv) in DMF (2.00 mL) was stirred overnight at RT under air atmosphere. Water was added to the reaction mixture and extracted with EtOAc. The combined organic layers concentrated under reduced pressure. The residue was purified by reverse flash chromatography with the following conditions: (column, C18; mobile phase, 0.1% HCOOH in water and MeOH, 0% to 100% gradient in 60 min; detector, UV 254 nm) to afford N-[(1S)-1-(2,4-difluorophenyl)ethyl]-2-[2-oxo-6-(trifluoromethyl)-1H,4H-pyrido[3,2-d]pyrimidin-3-yl]acetamide (20.2 mg, 16.70%). LCMS (ES, m/z): 415 $[M+H]^+$. $^1H$ NMR (400 MHz, DMSO-$d_6$) δ 9.86 (s, 1H), 8.58 (d, J=10.4 Hz, 1H), 7.68 (d, J=7.2 Hz, 1H), 7.47-7.39 (m, 1H), 7.27 (d, J=11.2 Hz, 1H), 7.22-7.15 (m, 1H), 7.09-7.03 (m, 1H), 5.15-5.10 (m, 1H), 4.60 (s, 2H), 4.00 (s, 2H), 1.36 (d, J=9.6 Hz, 3H).

Example 11: 2-{6-Chloro-2-oxo-1H,4H-pyrido[3,2-d]pyrimidin-3-yl}-N-[(1S)-1-(2,4-difluorophenyl)ethyl]acetamide (Compound N117)

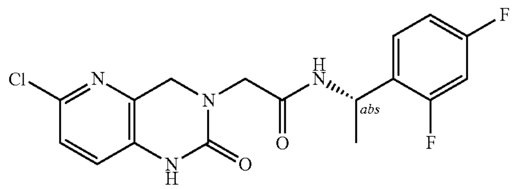 [SMILES: C[C@H](NC(=O)CN1Cc2nc(Cl)ccc2NC1=O)c1ccc(F)cc1F]

tert-Butyl N-(2-bromo-6-chloropyridin-3-yl)carbamate. $(Boc)_2O$ (12.62 g, 57.842 mmol, 1.2 equiv) and DMAP (1.18 g, 9.640 mmol, 0.2 equiv) were added in portions at RT under air atmosphere to a stirred mixture of 2-bromo-6-chloropyridin-3-amine (10 g, 48.202 mmol, 1 equiv) and TEA (9.76 g, 96.404 mmol, 2 equiv) in DCM (200 mL). The reaction mixture was stirred overnight at RT under air atmosphere. The reaction mixture was diluted with water. The aqueous layer was extracted with EtOAc. The reaction mixture was concentrated under reduced pressure. The residue was purified by column chromatography to afford tert-butyl N-(2-bromo-6-chloropyridin-3-yl)carbamate (8.5 g, 57.33%). LCMS (ES, m/z): 307 $[M+H]^+$.

tert-Butyl N-(6-chloro-2-formylpyridin-3-yl)carbamate. A solution of tert-butyl N-(2-bromo-6-chloropyridin-3-yl) carbamate (8.50 g, 27.636 mmol, 1.00 equiv) in THF (150 mL) was treated with NaH (1.33 g, 33.163 mmol, 1.20 equiv, 60%) for 30 min at 0° C. under argon atmosphere followed by the addition of n-BuLi (2.12 g, 33.163 mmol, 1.20 equiv) in portions at −78° C. The reaction mixture was stirred for 30 min at −78° C. under argon atmosphere. To the above mixture DMF (8.08 g, 110.544 mmol, 4.00 equiv) was added dropwise over 10 min at −78° C. The reaction mixture was stirred for additional 30 min at −78° C. The reaction was quenched by the addition of sat. $NH_4Cl$ (aq.) (20 mL) at −20° C. The reaction mixture was extracted with EtOAc. The combined organic layers were washed with brine and dried over anhydrous $Na_2SO_4$ and filtered. The filtrate was concentrated under reduced pressure. The residue was purified by column chromatography to afford tert-butyl N-(6-chloro-2-formylpyridin-3-yl)carbamate (4 g, 56.39%). LCMS (ES, m/z): 257$[M+H]^+$.

tert-Butyl 2-[({3-[(tert-butoxycarbonyl)amino]-6-chloropyridin-2-yl}methyl)amino]acetate. Sodium triacetoxyborohydride (STAB) (3.10 g, 14.610 mmol, 2.5 equiv) was added in portions at 0° C. under air atmosphere to a stirred mixture of tert-butyl N-(6-chloro-2-formylpyridin-3-yl)carbamate (1.5 g, 5.844 mmol, 1 equiv) and tert-butyl 2-aminoacetate (1.15 g, 8.766 mmol, 1.5 equiv) in DMF (20 mL). The reaction mixture was stirred overnight at RT under air atmosphere. The reaction was quenched by the addition of sat. $NH_4Cl$ (aq.) (10 mL) at RT. The reaction mixture was diluted with water. The reaction mixture was extracted with EtOAc. The combined organic layers were washed with brine and dried over anhydrous $Na_2SO_4$ and filtered. The filtrate was concentrated under reduced pressure. The residue was purified by column chromatography to afford tert-butyl 2-[({3-[(tert-butoxycarbonyl)amino]-6-chloropyridin-2-yl}methyl)amino]acetate (1.6 g, 73.63%). LCMS (ES, m/z): 372[M+H]+.

tert-Butyl 3-[2-(tert-butoxy)-2-oxoethyl]-6-chloro-2-oxo-4H-pyrido[3,2-d]pyrimidine-1-carboxylate. A mixture of tert-butyl 2-[({3-[(tert-butoxycarbonyl)amino]-6-chloropyridin-2-yl}methyl)amino]acetate (600 mg, 1.614 mmol, 1 equiv) and ditrichloromethyl carbonate (143.64 mg, 0.484 mmol, 0.3 equiv) in DCM (10 mL) was stirred for 1 h at 0° C. under air atmosphere. The reaction mixture was diluted with water and extracted with $CH_2Cl_2$. The combined organic layers were washed with brine and dried over anhydrous $Na_2SO_4$ and filtered. The filtrate was concentrated under reduced pressure. The residue was purified by column chromatography to afford tert-butyl 3-[2-(tert-butoxy)-2-oxoethyl]-6-chloro-2-oxo-4H-pyrido[3,2-d]pyrimidine-1-carboxylate (350 mg, 54.52%). LCMS (ES, m/z): 398[M+H]+.

6-Chloro-2-oxo-1H,4H-pyrido[3,2-d]pyrimidin-3-yl}acetic acid. A mixture of tert-butyl 3-[2-(tert-butoxy)-2-oxoethyl]-6-chloro-2-oxo-4H-pyrido[3,2-d]pyrimidine-1-carboxylate (300 mg, 0.754 mmol, 1 equiv) and HCl (4 M, 3 mL) in 1,4-dioxane (3 mL) was stirred for 2 h at RT under air atmosphere. The reaction mixture was diluted with $CH_2Cl_2$ (10 mL). The reaction mixture was concentrated under reduced pressure. This resulted in {6-chloro-2-oxo-1H,4H-pyrido[3,2-d]pyrimidin-3-yl}acetic acid (150 mg, 82.33%). LCMS (ES, m/z): 242[M+H]+.

2-{6-Chloro-2-oxo-1H,4H-pyrido[3,2-d]pyrimidin-3-yl}-N-[(1S)-1-(2,4-difluorophenyl)ethyl]acetamide. A mixture of {6-chloro-2-oxo-1H,4H-pyrido[3,2-d]pyrimidin-3-yl}acetic acid (140 mg, 0.579 mmol, 1 equiv), EDCI (133.28 mg, 0.695 mmol, 1.2 equiv) and DMAP (35.39 mg, 0.289 mmol, 0.5 equiv) in DMF (3 mL) was stirred for 2 h at RT under air atmosphere. The reaction mixture was diluted with water. The aqueous layer was extracted with EtOAc. The reaction mixture was concentrated under reduced pressure. The residue was purified by reverse flash chromatography with the following conditions: column, C18; mobile phase, MeCN in Water (0.1% FA), 10% to 50% gradient in 40 min; detector, UV 254 nm resulting in 2-{6-chloro-2-oxo-1H,4H-pyrido[3,2-d]pyrimidin-3-yl}-N-[(1S)-1-(2,4-difluorophenyl)ethyl]acetamide (100 mg, 45.33%). LCMS (ES, m/z): 381$[M+H]^+$. $^1H$ NMR (300 MHz, DMSO-$d_6$) δ 9.98 (s, 1H), 8.60 (d, J=7.7 Hz, 1H), 8.05 (d, J=5.4 Hz, 1H), 7.50-7.39 (m, 1H), 7.27-7.13 (m, 1H), 7.10-7.04 (m, 1H), 6.72 (d, J=5.4 Hz, 1H), 5.14 (p, J=7.2 Hz, 1H), 4.48 (s, 2H), 4.02 (s, 2H), 1.36 (d, J=6.9 Hz, 3H).

Example 12: N-[(1R)-1-(3,5-Difluoropyridin-2-yl)ethyl]-2-[6-fluoro-2-oxo-1H,4H-pyrido[3,2-d]pyrimidin-3-yl]acetamide (Compound N104)

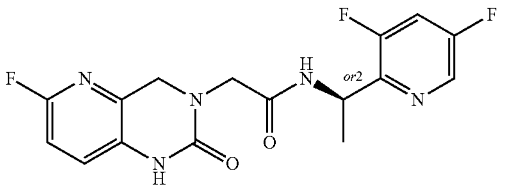 [SMILES: C[C@@H](NC(=O)CN1Cc2nc(F)ccc2NC1=O)c1ncc(F)cc1F]

1-(3,5-Difluoropyridin-2-yl)ethanamine. A mixture of 1-(3,5-difluoropyridin-2-yl)ethanone (600.00 mg, 3.819 mmol, 1.00 equiv), $CH_3COONH_4$ (883.07 mg, 11.456 mmol, 3.00 equiv) and $NaBH_3CN$ (1199.89 mg, 19.094 mmol, 5 equiv) in THF (20.00 mL) was stirred for 3 h at room temperature. The residue was purified by flash chromatography with the following conditions: (column: C18 silica gel; mobile phase, MeCN in water, 0% to 100% gradient in 60 min; detector, UV 254 nm.). The reaction mixture was concentrated under reduced pressure to afford 1-(3,5-difluoropyridin-2-yl)ethanamine (500 mg, 82.79%). LC-MS: (ESI, m/z): 159 $[M+H]^+$.

N-[1-(3,5-Difluoropyridin-2-yl)ethyl]-2-{6-fluoro-2-oxo-1H,4H-pyrido[3,2-d]pyrimidin-3-yl}acetamide. A mixture of 1-(3,5-difluoropyridin-2-yl)ethanamine (130 mg, 0.822 mmol, 1 equiv), HATU (375.06 mg, 0.986 mmol, 1.2 equiv), {6-fluoro-2-oxo-1H,4H-pyrido[3,2-d]pyrimidin-3-yl}acetic acid (222.11 mg, 0.986 mmol, 1.2 equiv) and DIEA (318.72 mg, 2.466 mmol, 3 equiv) in DMF (2 mL) was stirred for 3 h at room temperature. The residue was purified by reverse flash chromatography with the following conditions: (column, C18 silica gel; mobile phase, MeCN in Water (0.1% FA), 0% to 100% gradient in 60 min; detector, UV 254 nm). The reaction mixture was concentrated under reduced pressure to afford N-[1-(3,5-difluoropyridin-2-yl)ethyl]-2-{6-fluoro-2-oxo-1H,4H-pyrido[3,2-d]pyrimidin-3-yl}acetamide (60 mg, 19.98%). LC-MS: (ESI, m/z): 366 $[M+H]^+$.

N-[(1R)-1-(3,5-Difluoropyridin-2-yl)ethyl]-2-[6-fluoro-2-oxo-1H,4H-pyrido[3,2-d]pyrimidin-3-yl]acetamide. The crude product (60 mg) was purified by Chiral-Prep-HPLC (Column name: CHIRALPAK IC-3; Mobile Phase: MtBE (0.1% DEA):EtOH=80:20; Flow rate: 1.0 ml/min; Temperature: Ambient) to afford N-[(1R)-1-(3,5-difluoropyridin-2-yl)ethyl]-2-[6-fluoro-2-oxo-1H,4H-pyrido[3,2-d]pyrimidin-3-yl]acetamide (30 mg). LC-MS: (ESI, m/z): 366.15 $[M+H]^+$. $^1H$ NMR (400 MHz, DMSO-$d_6$) δ 9.43 (s, 1H), 8.58 (d, J=7.2 Hz, 1H), 8.49 (d, J=2.4 Hz, 1H), 7.98-7.88 (m, 1H), 7.27 (t, J=7.6 Hz, 1H), 6.986.96 (m, 1H), 5.27-5.24 (m, 1H), 4.44 (s, 2H), 4.01-3.90 (m, 2H), 1.37 (d, J=7.2 Hz, 3H).

Example 13: N-[(1S)-1-(2,4-Difluorophenyl)ethyl]-2-{2'-oxo-1'H-spiro[cyclopropane-1,4'-quinazolin]-3'-yl}acetamide (Compound B229)

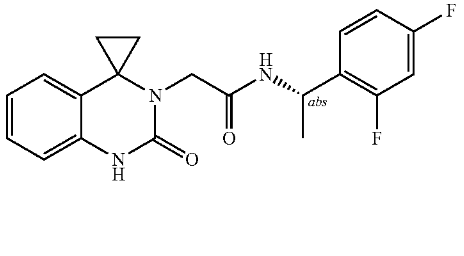 [SMILES: C[C@H](NC(=O)CN1C(=O)Nc2ccccc2C12CC2)c1ccc(F)cc1F]

Methyl 1-(2-nitrophenyl)cyclopropane-1-carboxylate. Diphenylethenyl-lambda4-sulfanyl trifluoromethanesulfonate (2.04 g, 5.636 mmol, 1.1 equiv) was added at RT under argon atmosphere to a stirred solution of methyl 2-(2-nitrophenyl)acetate (1 g, 5.124 mmol, 1.00 equiv) and DBU (2.34 g, 15.372 mmol, 3 equiv) in DMSO (10 mL). The reaction mixture was stirred for 2 h at RT under argon atmosphere. The reaction mixture was extracted with EtOAc. The combined organic layers were dried over anhydrous $Na_2SO_4$ and filtered. The filtrate was concentrated under reduced pressure. The residue was purified by column chromatography to afford methyl 1-(2-nitrophenyl)cyclopropane-1-carboxylate (1 g, 88.23%). LCMS (ES, m/z): 222 $[M+H]^+$ 1-(2-Nitrophenyl)cyclopropane-1-carboxylic acid. To a stirred solution of methyl 1-(2-nitrophenyl)cyclopropane-1-carboxylate (1 g, 4.521 mmol, 1.00 equiv) and $LiOH \cdot H_2O$ (0.57 g, 13.563 mmol, 3 equiv) in MeOH (3 mL), THF (3 mL) and $H_2O$ (3 mL) at RT. The reaction mixture was stirred for 2 h at 60° C. under air atmosphere. The mixture was adjusted to pH 5 with HCl (1 M) and extracted with EtOAc. The combined organic layers were dried over anhydrous $Na_2SO_4$ and filtered. The filtrate was concentrated under reduced pressure. to afford 1-(2-nitrophenyl)cyclopropane-1-carboxylic acid (700 mg, 74.74%). LCMS (ES, m/z): 208 $[M+H]^+$ 1-(2-Nitrophenyl)cyclopropan-1-amine. A solution of 1-(2-nitrophenyl)cyclopropane-1-carboxylic acid (700 mg, 3.379 mmol, 1.00 equiv), DPPA (1394.70 mg, 5.069 mmol, 1.5 equiv) and TEA (512.82 mg, 5.069 mmol, 1.5 equiv) in DCM (10 mL) was stirred at RT. The reaction mixture was stirred for 2 h at RT under argon atmosphere. The reaction mixture was concentrated under reduced pressure. To the above mixture Toluene (10 mL) was added and the mixture was stirred for additional 1 h at 120° C. The mixture was allowed to cool down to RT and HCl (8M, 6 mL) was added. The reaction mixture was stirred for additional 1 h at 80° C. and quenched with sat. $NaHCO_3$ (aq.) at RT. The reaction mixture was extracted with EtOAc. The combined organic layers were dried over anhydrous $Na_2SO_4$ and filtered. The filtrate was concentrated under reduced pressure. The residue was purified by column chromatography to afford 1-(2-nitrophenyl)cyclopropan-1-amine (500 mg, 83.05%). LCMS (ES, m/z): 179 $[M+H]^+$ Methyl 2-{[1-(2-nitrophenyl)cyclopropyl]amino}acetate. A mixture of 1-(2-nitrophenyl)cyclopropan-1-amine (470 mg, 2.638 mmol, 1.00 equiv), $K_2CO_3$ (729.07 mg, 5.276 mmol, 2 equiv) and methyl 2-bromoacetate (484.19 mg, 3.166 mmol, 1.2 equiv) in DMF (10 mL) was stirred at RT. The reaction mixture was stirred overnight at 50° C. and then cooled to 0° C. The reaction mixture was extracted with EtOAc. The combined organic layers were dried over anhydrous $Na_2SO_4$ and filtered. The filtrate was concentrated under reduced pressure. The residue was purified by column chromatography to afford methyl 2-{[1-(2-nitrophenyl)cyclopropyl]amino}acetate (400 mg, 60.60%). LCMS (ES, m/z): 251 $[M+H]^+$ Methyl 2-{[1-(2-aminophenyl)cyclopropyl]amino}acetate. Pd/C (10%, 80 mg) under $H_2$ atmosphere was added to a solution of methyl 2-{[1-(2-nitrophenyl)cyclopropyl]amino}acetate (400 mg, 1.598 mmol, 1.00 equiv) in 10 mL MeOH. The mixture was stirred at RT for 1 h under $H_2$ atmosphere using a hydrogen balloon, filtered through a Celite pad and concentrated under reduced pressure. The residue was purified by column chromatography to afford methyl 2-{[1-(2 aminophenyl)cyclopropyl] amino}acetate (300 mg, 85.21%). LCMS (ES, m/z): 221 [M+H]$^+$ Methyl 2-{2'-oxo-1'H-spiro[cyclopropane-1,4'-quinazolin]-3'-yl}acetate. A solution of methyl 2-{[1-(2-aminophenyl)cyclopropyl]amino}acetate (300 mg, 1.362 mmol, 1.00 equiv), DBU (414.68 mg, 2.724 mmol, 2 equiv) and CDI (441.68 mg, 2.724 mmol, 2 equiv) in DCM (5 mL) was stirred at RT. The reaction mixture was stirred for 1 h at RT. The residue was purified by column chromatography to afford methyl 2-{2'-oxo-1'H-spiro[cyclopropane-1,4'-quinazolin]-3'-yl}acetate (250 mg, 74.54%). LCMS (ES, m/z): 247 [M+H]$^+$ 2'-oxo-1'H-Spiro[cyclopropane-1,4'-quinazolin]-3'-ylacetic acid. To a stirred mixture of methyl 2-{2'-oxo-1'H-spiro[cyclopropane-1,4'-quinazolin]-3'-yl}acetate (240 mg, 0.975 mmol, 1.00 equiv) and LiOH·$H_2O$ (81.79 mg, 1.950 mmol, 2 equiv) in MeOH (3 mL), $H_2O$ (3 mL) at RT. The reaction mixture was stirred for 1 h at RT. The mixture was adjusted to pH 5 with HCl (aq., 1M). The reaction mixture was extracted with EtOAc. The combined organic layers were dried over anhydrous $Na_2SO_4$ and filtered. The filtrate was concentrated under reduced pressure to afford 2'-oxo-1'H-spiro[cyclopropane-1,4'-quinazolin]-3'-ylacetic acid (180 mg, 79.53%). LCMS (ES, m/z): 233 [M+H]$^+$ N-[(1S)-1-(2,4-Difluorophenyl)ethyl]-2-{2'-oxo-1'H-spiro[cyclopropane-1,4'-quinazolin]-3'-yl}acetamide. A mixture of 2'-oxo-1'H-spiro[cyclopropane-1,4'-quinazolin]-3'-ylacetic acid (1.00 equiv), EDCI (1.2 equiv), (1S)-1-(2,4-difluorophenyl)ethanamine (1.2 equiv) and DMAP (0.1 equiv) in DMF (5 mL) was stirred for 2 h at RT. The reaction mixture was extracted with EtOAc. The combined organic layers were dried over anhydrous $Na_2SO_4$ and filtered. The filtrate was concentrated under reduced pressure. The residue was purified by column chromatography to afford N-[(1S)-1-(2,4-difluorophenyl)ethyl]-2-{2'-oxo-1'H-spiro[cyclopropane-1,4'-quinazolin]-3'-yl}acetamide (71.9 mg). LCMS (ES, m/z): 372 [M+H]$^+$ $^1$H NMR (300 MHz, DMSO-$d_6$) δ 9.50 (s, 1H), 8.40 (d, J=7.8 Hz, 1H), 7.47-7.38 (m, 1H), 7.23-7.02 (m, 2H), 6.87-6.79 (m, 3H), 5.12-5.02 (m, 1H), 3.86 (s, 2H), 1.33 (d, J=6.9 Hz, 3H), 1.27-1.21 (m, 2H), 0.98-0.91 (m, 2H).

Example 14: N-[(1S)-1-(2,4-Difluorophenyl)ethyl]-2-{2'-oxo-1'H-spiro[cyclopropane-1,4'-pyrido[4,3-d]pyrimidin]-3'-yl}acetamide (Compound N9)

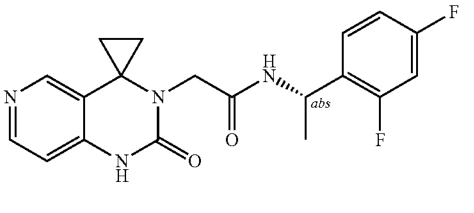 [SMILES: C[C@H](NC(=O)CN1C(=O)Nc2ccncc2C12CC2)c1ccc(F)cc1F]

tert-Butyl N-[3-(1-chlorocyclopropyl)pyridin-4-yl]carbamate. 1,3-dichloro-5,5-dimethylimidazolidine-2,4-dione (1.97 g, 9.990 mmol, 5 equiv) was added at 0° C. to a stirred solution of tert-butyl N-[3-(1-hydroxycyclopropyl)pyridin-4-yl]carbamate (500 mg, 1.998 mmol, 1 equiv) and tetramethylthiourea (132.07 mg, 0.999 mmol, 0.5 equiv) in DCM (5 mL). The reaction mixture was stirred for 2 h at 50° C. The residue was purified by Prep-TLC (PE/EA 15:1) to afford tert-butyl N-[3-(1-chlorocyclopropyl)pyridin-4-yl]carbamate (200 mg, 37.26%). LCMS (ES, m/z): 269 [M+H]$^+$.

Benzyl 2-[(1-{4-[(tert-butoxycarbonyl)amino]pyridin-3-yl}cyclopropyl)amino]acetate. $K_2CO_3$ (262.28 mg, 1.899 mmol, 3 equiv) was added at RT to a stirred mixture of tert-butyl N-[3-(1-chlorocyclopropyl)pyridin-4-yl]carbamate (170 mg, 0.633 mmol, 1 equiv) and benzyl 2-aminoacetate (208.99 mg, 1.266 mmol, 2 equiv) in DMF (3 mL). The reaction mixture was stirred for 3 h at 50° C. The reaction was quenched with NaCl (sat.) at RT and extracted with EtOAc. The combined organic layers were concentrated under reduced pressure. The residue was purified by Prep-TLC (PE/EA 3:1) to afford benzyl 2-[(1-{4-[(tert-butoxycarbonyl) amino]pyridin-3-yl}cyclopropyl)amino]acetate (120 mg, 47.73%). LCMS (ES, m/z): 397 [M+H]$^+$.

Benzyl 2-{[1-(4-aminopyridin-3-yl)cyclopropyl] amino}acetate. TFA (1 mL) was added at RT to a stirred solution of benzyl 2-[(1-{4-[(tert-butoxycarbonyl)amino] pyridin-3-yl}cyclopropyl)amino]acetate (110 mg, 0.277 mmol, 1 equiv) in DCM (4 mL). The reaction mixture was stirred for 2 h at RT. The reaction mixture was concentrated under reduced pressure. This resulted in benzyl 2-{[1-(4-aminopyridin-3-yl)cyclopropyl]amino}acetate (120 mg crude). LCMS (ES, m/z): 298 [M+H]$^+$.

Benzyl 2-{2'-oxo-1'H-spiro[cyclopropane-1,4'-pyrido[4,3-d]pyrimidin]-3'-yl}acetate. CDI (119.97 mg, 0.740 mmol, 2 equiv) was added at RT to a stirred mixture of benzyl 2-{[1-(4-aminopyridin-3-yl)cyclopropyl]amino}acetate (110 mg, 0.370 mmol, 1 equiv) and DBU (281.59 mg, 1.850 mmol, 5 equiv) in DCM (3 mL). The reaction mixture was stirred for 2 h at RT. The residue was purified by Prep-TLC ($CH_2Cl_2$/MeOH=10/1) to afford benzyl 2-{2'-oxo-1'H-spiro [cyclopropane-1,4'-pyrido[4,3-d]pyrimidin]-3'-yl}acetate (65 mg, 54.34%). LCMS (ES, m/z): 324 [M+H]$^+$ 2'-Oxo-1'H-spiro[cyclopropane-1,4'-pyrido[4,3-d]pyrimidin]-3'-ylacetic acid. Pd/C (10%, 0.01 g) under $H_2$ atmosphere was added to a solution of benzyl 2-{2'-oxo-1'H-spiro[cyclopropane-1,4'-pyrido[4,3-d]pyrimidin]-3'-yl}acetate (60 mg, 0.186 mmol, 1 equiv) in 5 mL MeOH. The mixture was stirred at RT for 2 h under $H_2$ atmosphere using a hydrogen balloon, filtered through a Celite pad and concentrated under reduced pressure. This resulted in 2'-oxo-1'H-spiro [cyclopropane-1,4'-pyrido[4,3-d]pyrimidin]-3'-ylacetic acid (40 mg, 92.43%). LCMS (ES, m/z): 234 [M+H]$^+$ N-[(1S)-1-(2,4-Difluorophenyl)ethyl]-2-{2'-oxo-1'H-spiro[cyclopropane-1,4'-pyrido[4,3-d]pyrimidin]-3'-yl}acetamide. EDCI (39.45 mg, 0.206 mmol, 1.2 equiv) and DMAP (2.10 mg, 0.017 mmol, 0.1 equiv) were added at RT to a stirred solution of 2'-oxo-1'H-spiro[cyclopropane-1,4'-pyrido[4,3-d]pyrimidin]-3'-ylacetic acid (40 mg, 0.172 mmol, 1 equiv) and (1S)-1-(2,4-difluorophenyl)ethanamine (32.35 mg, 0.206 mmol, 1.2 equiv) in DMF (1 mL). The reaction mixture was stirred for 2 h at RT. The crude product (50 mg) was purified by Prep-HPLC with the following conditions (Column: XBridge Shield RP18 OBD Column, 30*150 mm, 5 μm; Mobile Phase A: Water (10 mmol/L $NH_4HCO3$+0.1% NH3·H2O), Mobile Phase B: ACN; Flow rate: 60 mL/min; Gradient: 18% B to 18% B in 1 min, 18% B to 38% B in 8 min, 38% B; Wave Length: 254/220 nm; RT1 (min): 7.42) to afford N-[(1S)-1-(2,4-difluorophenyl) ethyl]-2-{2'-oxo-1'H-spiro[cyclopropane-1,4'-pyrido[4,3-d] pyrimidin]-3'-yl}acetamide (15.6 mg, 24.43%). LCMS (ES, m/z): 373 [M+H]$^+$ $^1$H NMR (400 MHz, DMSO-$d_6$): δ 9.92 (s, 1H), 8.46 (d, J=7.2 Hz, 1H), 8.20 (d, J=3.2 Hz, 1H), 7.94

(s, 1H), 7.44-7.39 (m, 1H), 7.20-7.04 (m, 2H), 6.76-6.74 (m, 1H), 5.08-5.05 (m, 1H), 3.86 (s, 2H), 1.34-1.30 (m, 5H), 1.07-1.05 (m, 2H).

Example 15: N—((S)-1-(2,4-difluorophenyl)ethyl)-2-((S)-4-methyl-2-oxo-1,4-dihydropyrido [3,2-d] pyrimidin-3(2H)-yl)acetamide (Compound N78)

N—((S)-1-(2,4-difluorophenyl)ethyl)-2-((R)-4-methyl-2-oxo-1,4-dihydropyrido[3,2-d]pyrimidin-3(2H)-yl)acetamide (Compound N77)

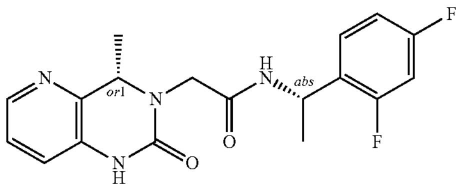

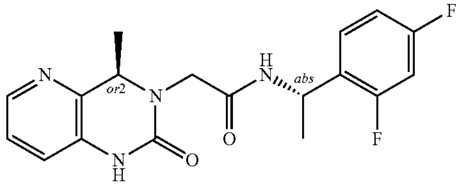

tert-Butyl (2-bromopyridin-3-yl)carbamate. To a stirred solution of 2-bromopyridin-3-amine (5.00 g, 28.900 mmol, 1.00 equiv.) and TEA (5.85 g, 57.800 mmol, 2.00 equiv.) in DCM (50 mL) were added DMAP (0.35 g, 2.890 mmol, 0.10 equiv.) and $Boc_2O$ (6.94 g, 31.790 mmol, 1.10 equiv.) in portions at 0° C. under $N_2$ atmosphere. The reaction mixture was stirred overnight at 30° C. under $N_2$ atmosphere. To the above mixture $K_2CO_3$ (7.99 g, 57.8 mmol, 2.00 equiv) in MeOH (50 mL) was added in portions over 20 min at RT. The reaction mixture was stirred for additional 4 h at 60° C. The reaction mixture was diluted with water. The reaction mixture was extracted with EtOAc. The combined organic layers were washed with brine and dried over anhydrous $Na_2SO_4$ and filtered. The filtrate was concentrated under reduced pressure. The residue was purified by column chromatography to afford tert-butyl (2-bromopyridin-3-yl) carbamate (5.80 g, 73.48%). LCMS (ES, m/z): 273 $[M+H]^+$ tert-butyl (2-acetylpyridin-3-yl)carbamate. To a stirred solution of tert-butyl (2-bromopyridin-3-yl)carbamate (5.50 g, 20.137 mmol, 1.00 equiv) in dry THF (55 mL) was added n-BuLi (16 mL, 2.5 M in n-hexane, 40.274 mmol, 2.00 equiv.) dropwise at −78° C. under argon atmosphere. The reaction mixture was stirred for 1 h at −78° C. under argon atmosphere. To the above mixture was added N-methoxy-N-methylacetamide (2.49 g, 24.164 mmol, 1.20 equiv.) dropwise at −78° C. under argon atmosphere. The reaction mixture was stirred for an additional 1 h at −78° C. The reaction was quenched by the addition of sat. $NH_4Cl$ (aq.) (120 mL) at −60° C. The reaction mixture was diluted with water and extracted with EtOAc. The combined organic layers were washed with brine and dried over anhydrous $Na_2SO_4$ and filtered. The filtrate was concentrated under reduced pressure. The residue was purified by column chromatography to afford tert-butyl (2-acetylpyridin-3-yl) carbamate (2.80 g, 58.85%). LCMS (ES, m/z): 237 $[M+H]^+$ tert-Butyl (E)-(2-(1-(hydroxyimino)ethyl)pyridin-3-yl) carbamate. $NH_2OH{\cdot}HCl$ (1.10 g, 15.871 mmol, 1.50 equiv.) was added in portions at RT under $N_2$ atmosphere to a stirred solution of tert-butyl (2-acetylpyridin-3-yl)carbamate (2.50 g, 10.581 mmol, 1.00 equiv) and NaOAc (1.74 g, 21.162 mmol, 2.00 equiv) in EtOH (25 mL) and $H_2O$ (25 mL). The reaction mixture was stirred overnight at 78° C. under $N_2$ atmosphere and then concentrated under reduced pressure and diluted with water. The reaction mixture was extracted with EtOAc. The combined organic layers were washed with brine and dried over anhydrous $Na_2SO_4$ and filtered. The filtrate was concentrated under reduced pressure. The residue was purified by column chromatography to afford tert-butyl (E)-(2-(1-(hydroxyimino)ethyl)pyridin-3-yl)carbamate (2.30 g, 86.50%). LCMS (ES, m/z): 252 $[M+H]^+$ tert-Butyl (2-(1-aminoethyl)pyridin-3-yl)carbamate. Zinc powder (2.60 g, 39.795 mmol, 5.00 equiv) was added in portions at RT under $N_2$ atmosphere to a stirred solution of tert-butyl (E)-(2-(1-(hydroxyimino)ethyl)pyridin-3-yl)carbamate (2.00 g, 7.959 mmol, 1.00 equiv.) in HOAc (20 mL) and $H_2O$ (10 mL). The reaction mixture was stirred overnight at RT under $N_2$ atmosphere. The reaction mixture was filtered, the filter cake was washed with DCM. The reaction mixture was concentrated under reduced pressure and extracted with EtOAc. The combined organic layers were washed with brine and dried over anhydrous $Na_2SO_4$ and filtered. The filtrate was concentrated under reduced pressure. The residue was purified by column chromatography to afford tert-butyl (2-(1-aminoethyl)pyridin-3-yl)carbamate (1.50 g, 79.42%). LCMS (ES, m/z): 238 $[M+H]^+$ Ethyl (1-(3-((tert-butoxycarbonyl)amino)pyridin-2-yl) ethyl)glycinate. $NaBH_3CN$ (1.19 g, 18.963 mmol, 3.00 equiv.) was added dropwise at 0° C. under $N_2$ atmosphere to a stirred solution of tert-butyl (2-(1-aminoethyl)pyridin-3-yl)carbamate (1.50 g, 6.321 mmol, 1.00 equiv.) and ethyl glyoxylate (1.94 g, 18.963 mmol, 3.00 equiv.) in MeOH (45 mL). The reaction mixture was stirred for 3 h at RT under $N_2$ atmosphere and then diluted with water. The reaction mixture was extracted with EtOAc. The combined organic layers were washed with brine and dried over anhydrous $Na_2SO_4$ and filtered. The filtrate was concentrated under reduced pressure. The residue was purified by column chromatography to afford ethyl (1-(3-((tert-butoxycarbonyl) amino)pyridin-2-yl)ethyl)glycinate (850 mg, 41.58%). LCMS (ES, m/z): 324 $[M+H]^+$ Ethyl (1-(3-aminopyridin-2-yl)ethyl)glycinate. 4M HCl (gas) in 1,4-dioxane (8.5 mL) was added dropwise at 0° C. under $N_2$ atmosphere to a stirred solution of ethyl (1-(3-((tert-butoxycarbonyl)amino)pyridin-2-yl)ethyl)glycinate (850 mg, 2.628 mmol, 1.00 equiv) in 1,4-dioxane (8.5 mL). The reaction mixture was stirred for 1 h at RT under $N_2$ atmosphere. The reaction mixture was concentrated under reduced pressure. The crude product was used in the next step directly without further purification. This resulted in ethyl (1-(3-aminopyridin-2-yl)ethyl)glycinate (800 mg, crude). LCMS (ES, m/z): 224 $[M+H]^+$ Ethyl 2-(4-methyl-2-oxo-1,4-dihydropyrido[3,2-d]pyrimidin-3(2H)-yl)acetate. CDI (697.18 mg, 4.300 mmol, 1.20 equiv.) was added in portions at RT under $N_2$ atmosphere to a stirred solution of ethyl (1-(3-aminopyridin-2-yl)ethyl)glycinate (800 mg, 3.583 mmol, 1.00 equiv.) and DBU (2.18 g, 14.332 mmol, 4.00 equiv.) in DMF (10 mL). The reaction mixture was stirred overnight at 60° C. under $N_2$ atmosphere. The reaction mixture was diluted with EtOAc. The residue was washed with brine and dried over anhydrous $Na_2SO_4$ and filtered. The filtrate was concentrated under reduced pressure. The residue was purified by column chromatography to afford ethyl 2-(4-methyl-2-oxo- 1,4-dihydropyrido[3,2-d]pyrimidin-3(2H)-yl)acetate (460 mg, 51.50%). LCMS (ES, m/z): 250 $[M+H]^+$ 2-(4-methyl-2-oxo-1,4-dihydropyrido[3,2-d]pyrimidin-3(2H)-yl)acetic acid. $LiOH·H_2O$ (227.27 mg, 5.415 mmol, 3.00 equiv.) was added dropwise at 0° C. under $N_2$ atmosphere to a stirred solution of ethyl 2-(4-methyl-2-oxo-1,4-dihydropyrido[3,2-d]pyrimidin-3(2H)-yl)acetate (450 mg, 1.805 mmol, 1.00 equiv.) in THF (4 mL), and $H_2O$ (2 mL). The reaction mixture was stirred overnight at RT under $N_2$ atmosphere. The mixture was adjusted to pH 4 with 1M HCl (aq.). The reaction mixture was diluted with water. The reaction mixture was extracted with EtOAc. The combined organic layers were washed with brine and dried over anhydrous $Na_2SO_4$ and filtered. The filtrate was concentrated under reduced pressure. The crude product was used in the next step directly without further purification. This resulted in 2-(4-methyl-2-oxo-1,4-dihydropyrido[3,2-d]pyrimidin-3(2H)-yl)acetic acid (270 mg, crude). LCMS (ES, m/z): 222 $[M+H]^+$ N—((S)-1-(2,4-difluorophenyl)ethyl)-2-(4-methyl-2-oxo-1,4-dihydropyrido[3,2-d]pyrimidin-3(2H)-yl)acetamide. To a stirred solution of 2-(4-methyl-2-oxo-1,4-dihydropyrido[3,2-d]pyrimidin-3(2H)-yl)acetic acid (250 mg, 1.130 mmol, 1.00 equiv.) and DIEA (438.18 mg, 3.390 mmol, 3.00 equiv.) in DMF (3 mL) were added HATU (515.65 mg, 1.356 mmol, 1.20 equiv.) and (1S)-1-(2,4-difluorophenyl)ethanamine (213.14 mg, 1.356 mmol, 1.20 equiv.) in portions at 0° C. under $N_2$ atmosphere. The reaction mixture was stirred for 3 h at RT under $N_2$ atmosphere. The reaction mixture was diluted with water. The reaction mixture was extracted with EtOAc. The combined organic layers were washed with brine and dried over anhydrous $Na_2SO_4$ and filtered. The filtrate was concentrated under reduced pressure. The residue was purified by column chromatography and then the crude product (250 mg) was purified by Prep-HPLC with the following conditions (Column: XBridge Prep OBD C18 Column, 50*250 mm, 10 μm; Mobile Phase A: Water (10 mmol/L $NH_4HCO_3$), Mobile Phase B: ACN; Flow rate: 100 mL/min; Gradient: 5% B to 30% B in 7 min, 30% B; Wave Length: 254/220 nm; RT1 (min): 6.32;) to afford N—((S)-1-(2,4-difluorophenyl)ethyl)-2-(4-methyl-2-oxo-1,4-dihydropyrido[3,2-d]pyrimidin-3(2H)-yl)acetamide (180 mg). LCMS (ES, m/z): 361 $[M+H]^+$ Chiral separation: The product of N—((S)-1-(2,4-difluorophenyl)ethyl)-2-(4-methyl-2-oxo-1,4-dihydropyrido[3,2-d]pyrimidin-3(2H)-yl)acetamide (180 mg) was purified by Prep-CHIRAL-HPLC with the following conditions (Column: CHIRALPAK ID, 2*25 cm, 5 μm; Mobile Phase A: Hex (10 mM $NH_3$-MeOH), Mobile Phase B: IPA-HPLC; Flow rate: 20 mL/min; Gradient: 50% B to 50% B in 12 min; Wave Length: 200/249 nm; RT1 (min): 5.14; RT2 (min): 7.481; Sample Solvent: THF:MEOH=2:1; Injection Volume: 0.7 mL) to N—((S)-1-(2,4-difluorophenyl)ethyl)-2-((S)-4-methyl-2-oxo-1,4-dihydropyrido[3,2-d]pyrimidin-3(2H)-yl) acetamide (70.8 mg, 7.13%). LCMS (ES, m/z): 361 $[M+H]^+$ $^1H$ NMR (400 MHz, DMSO-$d_6$) δ 9.43 (s, 1H), 8.51 (d, J=7.6 Hz, 1H), 8.07 (dd, J=4.8, 1.6 Hz, 1H), 7.42 (td, J=8.8, 6.6 Hz, 1H), 7.22-7.09 (m, 3H), 7.08-6.99 (m, 1H), 5.09 (m, 1H), 4.54 (q, J=6.6 Hz, 1H), 4.27 (d, J=16.4 Hz, 1H), 3.80 (d, J=16.4 Hz, 1H), 1.32 (dd, J=15.2, 6.8 Hz, 6H).

N—((S)-1-(2,4-difluorophenyl)ethyl)-2-((R)-4-methyl-2-oxo-1,4-dihydropyrido[3,2-d]pyrimidin-3(2H)-yl)acetamide (70.5 mg, 7.12%) as a white solid. LCMS (ES, m/z): 361 $[M+H]^+$ $^1H$ NMR (400 MHz, DMSO-$d_6$) δ 9.44 (s, 1H), 8.51 (d, J=7.6 Hz, 1H), 8.06 (dd, J=4.8, 1.6 Hz, 1H), 7.45 (td, J=8.8, 6.6 Hz, 1H), 7.24-7.13 (m, 3H), 7.08-7.03 (m, 1H), 5.09 (m, 1H), 4.49 (q, J=6.6 Hz, 1H), 4.27 (d, J=16.4 Hz, 1H), 3.80 (d, J=16.4 Hz, 1H), 1.33 (dd, J=15.4, 6.8 Hz, 6H).

Example 16: N-[(1S)-1-(2,4-Difluorophenyl)ethyl]-2-{6'-methoxy-2'-oxo-1'H-spiro[cyclopropane-1,4'-pyrido[3,2-d]pyrimidin]-3'-yl}acetamide (Compound N87)

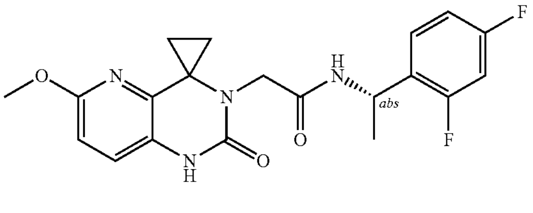 [SMILES: COc1ccc2c(n1)C1(CC1)N(CC(=O)N[C@@H](C)c1ccc(F)cc1F)C(=O)N2]

1,3-Dimethyl 2-(6-methoxy-3-nitropyridin-2-yl)propanedioate. LiHMDS (106.1 mmol, 2 equiv, 1M) was added at 0° C. under argon atmosphere to a solution of dimethyl malonate (14.01 g, 106.1 mmol, 2 equiv) in tetrahydrofuran (150 mL, 2080.242 mmol, 39.23 equiv). After stirring for 30 mins at 0° C. under an argon atmosphere. 2-Chloro-6-methoxy-3-nitropyridine (10 g, 53.031 mmol, 1 equiv) in THF (30 mL) was added dropwise to the mixture and the mixture was stirred at 0° C. Then stirred at 80° C. for 8 h. The reaction was quenched by the addition of $NH_4Cl$ (20 mL, sat.) at 0° C. The aqueous layer was extracted with EtOAc. Combined the organic layer and dried over anhydrous $Na_2SO_4$ and filtered. The filtrate was concentrated under reduced pressure. The reaction mixture was concentrated under reduced pressure. The residue was purified by column chromatography to afford 1,3-dimethyl 2-(6-methoxy-3-nitropyridin-2-yl)propanedioate (6.0 g, 37.82%). LCMS (ES, m/z): 285 $[M+H]^+$ Methyl 2-(6-methoxy-3-nitropyridin-2-yl)acetate. Lithium chloride (8.05 g, 189.990 mmol, 3+3+3 equiv) (three batch) was added to a solution of 1,3-dimethyl 2-(6-methoxy-3-nitropyridin-2-yl)propanedioate (6 g, 21.110 mmol, 1 equiv) in DMSO (40 mL) and water (20 mL). After stirring for 10 h at 120° C. The reaction mixture was diluted with water. The reaction mixture was extracted with EtOAc. The combined organic layers were washed with water and dried over anhydrous $Na_2SO_4$ and filtered. The filtrate was concentrated under reduced pressure. The reaction mixture was concentrated under reduced pressure. The residue was purified by column chromatography to afford methyl 2-(6-methoxy-3-nitropyridin-2-yl)acetate (1.8 g, 33.93%). LCMS (ES, m/z): 227 $[M+H]^+$ Methyl 1-(6-methoxy-3-nitropyridin-2-yl)cyclopropane-1-carboxylate. Diphenylvinylsulfonium triflate (2.26 g, 10.584 mmol, 1.4 equiv) and DBU (3.45 g, 22.680 mmol, 3 equiv) were added to a solution of methyl 2-(6-methoxy-3-nitropyridin-2-yl)acetate (1.71 g, 7.560 mmol, 1 equiv) in DMSO (20 mL). After stirring for 16 h at RT under Ar atmosphere. Then the reaction mixture was diluted with water. The aqueous layer was extracted with EtOAc. The combined organic layers were washed with water and dried over anhydrous $Na_2SO_4$ and filtered. The filtrate was concentrated under reduced pressure. The reaction mixture was concentrated under reduced pressure. The residue was purified by column chromatography to afford methyl 1-(6-methoxy-3-nitropyridin-2-yl)cyclopropane-1-carboxylate (1.95 g, 97.15%). LCMS (ES, m/z): 253 $[M+H]^+$ 1-(6-Methoxy-3-nitropyridin-2-yl)cyclopropane-1-carboxylic acid. LiOH (0.53 g, 22.122 mmol, 3 equiv) was added to a solution of methyl 1-(6-methoxy-3-nitropyridin-2-yl)cyclopropane-1-carboxylate (1.86 g, 7.374 mmol, 1 equiv) in MeOH (16 mL) and water (8 mL). The mixture was stirred for 6 h at 50° C. Then the reaction mixture was concentrated under reduced pressure. The residue was purified by reverse flash chromatography with the following conditions: (column, C18 silica gel; mobile phase, ACN in water, 0% to 100% gradient in 10 min; detector, UV 254 nm.) to afford 1-(6-methoxy-3-nitropyridin-2-yl)cyclopropane-1-carboxylic acid (1.17 g, 63.28%). LCMS (ES, m/z): 239 $[M+H]^+$ tert-Butyl N-[1-(6-methoxy-3-nitropyridin-2-yl)cyclopropyl]carbamate. DPPA (2.08 g, 7.557 mmol, 1.5 equiv) and TEA (0.76 g, 7.557 mmol, 1.5 equiv) were added to a solution of 1-(6-methoxy-3-nitropyridin-2-yl)cyclopropane-1-carboxylic acid (1.2 g, 5.038 mmol, 1 equiv) in Toluene (20 mL). Then 2-methyl-2-propanol (7.47 g, 100.760 mmol, 20 equiv). After stirring for 5 h at 110° C. under an argon atmosphere. Then the reaction mixture was concentrated under reduced pressure. The residue was purified by column chromatography to afford tert-butyl N-[1-(6-methoxy-3-nitropyridin-2-yl)cyclopropyl]carbamate (800 mg, 46.20%). LCMS (ES, m/z): 310 $[M+H]^+$ 1-(6-Methoxy-3-nitropyridin-2-yl)cyclopropan-1-amine. To a solution of tert-butyl N-[1-(6-methoxy-3-nitropyridin-2-yl)cyclopropyl]carbamate (730 mg, 2.360 mmol, 1 equiv) in DCM (9 mL) was added. The mixture was stirred for 2 hours at 0° C. Then the mixture was stirred for 4 h at RT. Then the reaction mixture was concentrated under reduced pressure to afford 1-(6-methoxy-3-nitropyridin-2-yl)cyclopropan-1-amine (480 mg, 87.50%). LC-MS: (ESI, m/z): 210 $[M+H]^+$.

Methyl 2-{[1-(6-methoxy-3-nitropyridin-2-yl)cyclopropyl]amino}acetate. Methyl 2-bromoacetate (584.25 mg, 3.820 mmol, 2 equiv) and potassium methaneperoxoate potassium (1063.37 mg, 7.640 mmol, 4 equiv) were added to a solution of 1-(6-methoxy-3-nitropyridin-2-yl)cyclopropan-1-amine (470 mg, 1.910 mmol, 1 equiv, 85%) in dimethylformamide (6 mL). The mixture was stirred for 12 h at 50° C. Then water (10 mL) was added to the mixture, and the reaction mixture was extracted with EtOAc. The combined organic layers were washed with water and dried over anhydrous $Na_2SO_4$ and filtered. The filtrate was concentrated under reduced pressure. The residue was purified by column flash chromatography with the following conditions: column, silica gel; mobile phase, (PE/EA=2/1) to afford methyl 2-{[1-(6-methoxy-3-nitropyridin-2-yl)cyclopropyl]amino}acetate (340 mg, 56.97%). LC-MS: (ESI, m/z): 282 $[M+H]^+$.

Methyl 2-{[1-(3-amino-6-methoxypyridin-2-yl)cyclopropyl]amino}acetate. Pd/C (50 mg, 10%) in $N_2$ atmosphere was added to a solution of methyl 2-{[1-(6-methoxy-3-nitropyridin-2-yl)cyclopropyl]amino}acetate (340 mg, 1.209 mmol, 1 equiv) in MeOH (5 mL). The mixture was purged with $H_2$ (1 atm) for 3 h at RT for 4 h. Then the reaction mixture was concentrated under reduced pressure to afford methyl 2-{[1-(3-amino-6-methoxypyridin-2-yl)cyclopropyl]amino}acetate (270 mg, 80.00%). LC-MS: (ESI, m/z): 252 $[M+H]^+$.

Methyl 2-{6'-methoxy-2'-oxo-1'H-spiro[cyclopropane-1,4'-pyrido[3,2-d]pyrimidin]-3'-yl}acetate. CDI (335.54 mg, 2.070 mmol, 2 equiv) and DBU (315.03 mg, 2.070 mmol, 2 equiv) were added to a solution of methyl 2-{[1-(3-amino-6-methoxypyridin-2-yl)cyclopropyl]amino}acetate (260 mg, 1.035 mmol, 1 equiv) in DCM (5 mL). The mixture was stirred for 4 h at RT. Then the reaction mixture was concentrated under vacuum. The residue was purified by column flash chromatography with the following conditions: column, silica gel; mobile phase (PE/EA=1/1) to give methyl 2-{6'-methoxy-2'-oxo-1'H-spiro[cyclopropane-1,4'-pyrido[3,2-d]pyrimidin]-3'-yl}acetate (210 mg, 65.88%). LC-MS: (ESI, m/z): 278 $[M+H]^+$.

6'-Methoxy-2'-oxo-1'H-spiro[cyclopropane-1,4'-pyrido[3,2-d]pyrimidin]-3'-ylacetic acid. Lithiumol hydrate (45.40 mg, 1.083 mmol, 3 equiv) was added to a solution of methyl 2-{6'-methoxy-2'-oxo-1'H-spiro[cyclopropane-1,4'-pyrido[3,2-d]pyrimidin]-3'-yl}acetate (100 mg, 0.361 mmol, 1 equiv) in MeOH (4 mL) and water (2 mL). The mixture was stirred for 3 h at RT. Then the reaction mixture was concentrated under reduced pressure to get the residue and water was added. The mixture was adjusted to pH 3 with HCl (1 M). The precipitated solids were collected by filtration and washed with water. The resulting solid was dried under reduced pressure to afford 6'-methoxy-2'-oxo-1'H-spiro[cyclopropane-1,4'-pyrido[3,2-d]pyrimidin]-3'-ylacetic acid (75 mg, 71.10%). LC-MS: (ESI, m/z): 264 $[M+H]^+$.

N-[(1S)-1-(2,4-difluorophenyl)ethyl]-2-{6'-methoxy-2'-oxo-1'H-spiro[cyclopropane-1,4'-pyrido[3,2-d]pyrimidin]-3'-yl}acetamide. HATU (71.42 mg, 0.296 mmol, 1.2 equiv) and DIEA (95.73 mg, 0.741 mmol, 3.0 equiv) were added to a solution of 6'-methoxy-2'-oxo-1'H-spiro[cyclopropane-1,4'-pyrido[3,2-d]pyrimidin]-3'-ylacetic acid (65 mg, 0.247 mmol, 1 equiv) in dimethylformamide (1.5 mL). The mixture was stirred for 2 h at RT. Then the crude product was purified by reverse phase flash with the following conditions: (column, C18 silica gel; mobile phase: 0.5% $NH_4HCO_3$, MeCN in water, 0% to 100% gradient in 60 min; detector, UV 254 nm.) to afford N-[(1S)-1-(2,4-difluorophenyl)ethyl]-2-{6'-methoxy-2'-oxo-1'H-spiro[cyclopropane-1,4'-pyrido[3,2-d]pyrimidin]-3'-yl}acetamide (52 mg, 51.97%). LC-MS: (ESI, m/z): 403 $[M+H]^+$. $^1H$ NMR (400 MHz, DMSO-$d_6$) δ 9.32 (s, 1H), 8.43 (d, J=7.6 Hz, 1H), 7.44-7.20 (m, 1H), 7.18-7.15 (m, 1H), 7.10-7.02 (m, 2H), 6.58 (d, J=8.4 Hz, 1H), 5.0-5.05 (m, 1H), 3.80 (s, 2H), 3.71 (s, 3H), 3.33 (d, J=2.8 Hz, 2H), 1.33 (m, J=7.2 Hz, 3H), 1.22-1.15 (m, 4H).

Example 17: N-[(1S)-1-(2,4-Difluorophenyl)ethyl]-2-{5-fluoro-2-oxo-1H,4H-pyrido[3,4-d]pyrimidin-3-yl}acetamide (Compound N72)

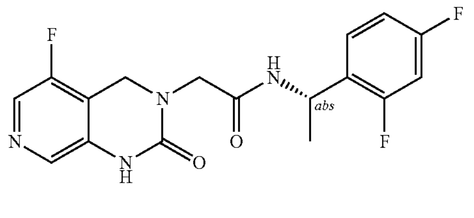

3-Amino-5-fluoropyridine-4-carbonitrile. $Pd(PPh_3)_4$ (2.43 g, 2.101 mmol, 0.2 equiv) was added portion wise at RT under air atmosphere to a stirred mixture of 5-fluoro-4-iodopyridin-3-amine (2.5 g, 10.504 mmol, 1 equiv) and $Zn(CN)_2$ (1.85 g, 15.756 mmol, 1.5 equiv) in DMF (15 mL). The reaction mixture was stirred for 22 h at 12° C. under argon atmosphere. The reaction mixture was extracted with EtOAc. The combined organic layers were washed with brine and dried over anhydrous $Na_2SO_4$ and filtered. The filtrate was concentrated under reduced pressure. The residue was purified by column chromatography to afford 3-amino-5-fluoropyridine-4-carbonitrile (940 mg, 65.27%). LCMS (ES, m/z): 138 $[M+H]^+$.

4-(Aminomethyl)-5-fluoropyridin-3-amine. $LiAlH_4$ (8.26 mL, 8.262 mmol, 1.2 equiv) was added dropwise at 0° C. under air atmosphere to a stirred mixture of 3-amino-5-fluoropyridine-4-carbonitrile (944 mg, 6.885 mmol, 1 equiv) in THF (20 mL). The reaction mixture was stirred for 2 h at RT under air atmosphere. The reaction was quenched with MeOH at 0° C. The reaction mixture was concentrated under reduced pressure. The residue was purified by column chromatography to afford 4-(aminomethyl)-5-fluoropyridin-3-amine (550 mg, 56.60%).

tert-Butyl 2-{[(3-amino-5-fluoropyridin-4-yl)methyl]amino}acetate. $NEt_3$ (1200.13 mg, 11.86 mmol, 3.00 equiv) was added dropwise at RT under air atmosphere to a stirred mixture of 4-(aminomethyl)-5-fluoropyridin-3-amine (558 mg, 3.953 mmol, 1.00 equiv) and tert-butyl 2-bromoacetate (771.11 mg, 3.953 mmol, 1 equiv) in THF (20 mL). The reaction mixture was stirred for 3 h at RT under air atmosphere. The residue was purified by column chromatography to afford tert-butyl 2-{[(3-amino-5-fluoropyridin-4-yl)methyl]amino}acetate (380 mg, 37.65%). LCMS (ES, m/z): 256 $[M+H]^+$.

tert-Butyl 2-{5-fluoro-2-oxo-1H,4H-pyrido[3,4-d]pyrimidin-3-yl}acetate. DBU (923.13 mg, 6.064 mmol, 4 equiv) was added dropwise at RT under air atmosphere to a stirred mixture of tert-butyl 2-{[(3-amino-5-fluoropyridin-4-yl)methyl]amino}acetate (387 mg, 1.516 mmol, 1 equiv) and CDI (983.23 mg, 6.064 mmol, 4 equiv) in DMF (5 mL). The reaction mixture was stirred for 14 h at 50° C. under air atmosphere. The residue was purified by column chromatography to afford tert-butyl 2-{5-fluoro-2-oxo-1H,4H-pyrido[3,4-d]pyrimidin-3-yl}acetate (300 mg, 70.36%). LCMS (ES, m/z): 282 $[M+H]^+$.

{5-fluoro-2-oxo-1H,4H-pyrido[3,4-d]pyrimidin-3-yl}acetic acid. A mixture of tert-butyl 2-{5-fluoro-2-oxo-1H,4H-pyrido[3,4-d]pyrimidin-3-yl}acetate (508 mg, 1.806 mmol, 1 equiv) and HCl (gas) in 1,4-dioxane (10 mL) was stirred for 14 h at RT under air atmosphere. The reaction mixture was concentrated under reduced pressure. The residue was purified by column chromatography to afford {5-fluoro-2-oxo-1H,4H-pyrido[3,4-d]pyrimidin-3-yl}acetic acid (200 mg, 49.18%). LCMS (ES, m/z): 226 $[M+H]^+$.

N-[(1S)-1-(2,4-Difluorophenyl)ethyl]-2-{5-fluoro-2-oxo-1H,4H-pyrido[3,4-d]pyrimidin-3-yl}acetamide. HATU (303.94 mg, 0.800 mmol, 1.5 equiv) and DIEA (206.62 mg, 1.599 mmol, 3 equiv) were added dropwise at RT under air atmosphere to a stirred mixture of {5-fluoro-2-oxo-1H,4H-pyrido[3,4-d]pyrimidin-3-yl}acetic acid (120 mg, 0.533 mmol, 1.00 equiv) and (1S)-1-(2,4-difluorophenyl)ethanamine (125.63 mg, 0.800 mmol, 1.5 equiv) in DMF (3 mL). The reaction mixture was stirred for 14 h at RT under air atmosphere. The residue was purified by reverse flash chromatography with the following conditions: column, silica gel; mobile phase, MeCN in water, 0% to 100% gradient in 60 min; detector, UV 254 nm. This resulted in N-[(1S)-1-(2,4-difluorophenyl)ethyl]-2-{5-fluoro-2-oxo-1H,4H-pyrido[3,4-d]pyrimidin-3-yl}acetamide (38.3 mg, 19.67%). LCMS (ES, m/z): 365.0 $[M+H]^+$ $^1H$ NMR (300 MHz, DMSO-$d_6$) δ 9.77 (d, J=2.1 Hz, 1H), 8.57 (d, J=7.8 Hz, 1H), 8.09 (s, 1H), 7.92 (s, 1H), 7.48-7.40 (m, 1H), 7.24-7.16 (m, 1H), 7.10-7.04 (m, 1H), 5.18-5.08 (m, 1H), 4.59 (s, 2H), 4.01 (s, 2H), 1.36 (d, J=6.9 Hz, 3H).

Example 18: 2-{5-Chloro-2-oxo-1H,4H-pyrido[3,4-d]pyrimidin-3-yl}-N-[(1S)-1-(2,4-difluorophenyl)ethyl]acetamide (Compound N56)

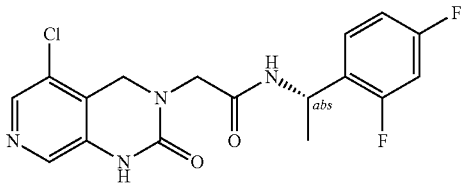 [SMILES: C[C@H](NC(=O)CN1Cc2c(Cl)cncc2NC1=O)c1ccc(F)cc1F]

3-Amino-5-chloropyridine-4-carbonitrile. A mixture of 4-bromo-5-chloropyridin-3-amine (2.5 g, 12.051 mmol, 1 equiv) and CuCN (3.24 g, 36.153 mmol, 3.0 equiv) in DMAc (20 mL) was stirred for 16 h at 120° C. under argon atmosphere. The reaction was quenched by the addition of water at RT. The reaction mixture was extracted with EtOAc. The combined organic layers were washed with saturated NaCl and dried over anhydrous $Na_2SO_4$ and filtered. The filtrate was concentrated under reduced pressure. The residue was purified by column chromatography to afford 3-amino-5-chloropyridine-4-carbonitrile (1.3 g, 70.25%). LCMS (ES, m/z): 155.1 $[M+H]^+$.

4-(Aminomethyl)-5-chloropyridin-3-amine. A solution of 3-amino-5-chloropyridine-4-carbonitrile (650 mg, 4.233 mmol, 1 equiv) in THF (5 mL) was added. The reaction mixture was stirred for 4 h at RT under air atmosphere. The reaction was quenched by the addition of water/ice (50 mL) at RT. The aqueous layer was extracted with EtOAc and concentrated under reduced pressure. The residue was purified by column chromatography, eluted with $CH_2Cl_2$/MeOH (20:1) to afford 4-(aminomethyl)-5-chloropyridin-3-amine (300 mg, 44.97%). LCMS (ES, m/z): 158.0 $[M+H]^+$.

tert-Butyl ((3-amino-5-chloropyridin-4-yl)methyl)glycinate. $K_2CO_3$ (1.3 g, 9.51 mmol, 3 equiv) was added at RT under air atmosphere A mixture of 4-(aminomethyl)-5-chloropyridin-3-amine (500 mg, 3.17 mmol, 1 equiv) and tert-butyl 2-bromoacetate (619 mg, 3.17 mmol, 1 equiv) in DMSO (10 mL) was added. The reaction mixture was stirred for 16 h at RT under air atmosphere. The reaction mixture was evaporated under reduced pressure. The residue was purified by silicon column (PE/EA=5/1) to afford tert-butyl ((3-amino-5-chloropyridin-4-yl)methyl)glycinate (600 mg, 58.3%). LCMS (ES, m/z): 272.0 $[M+H]^+$.

tert-Butyl 2-{5-chloro-2-oxo-1H,4H-pyrido[3,4-d]pyrimidin-3-yl}acetate. CDI (1.55 g, 9.568 mmol, 4 equiv) was added at RT under air atmosphere to a solution of tert-butyl 2-{[(3-amino-5-chloropyridin-4-yl)methyl]amino}acetate (650 mg, 2.392 mmol, 1 equiv) and DBU (1.46 g, 9.568 mmol, 4 equiv) in DCM (10 mL). The reaction mixture was stirred for 4 h at 50° C. under air atmosphere. The reaction mixture was concentrated under reduced pressure. The residue was purified by column chromatography to afford tert-butyl 2-{5-chloro-2-oxo-1H,4H-pyrido[3,4-d]pyrimidin-3-yl}acetate (500 mg, 70.21%). LCMS (ES, m/z): 272.0 $[M+H]^+$.

2-(5-Chloro-2-oxo-1,4-dihydropyrido[3,4-d]pyrimidin-3 (2H)-yl)acetic acid. TFA (2 mL) was added at RT under air atmosphere to a solution of tert-butyl 2-{5-chloro-2-oxo-1H,4H-pyrido[3,4-d]pyrimidin-3-yl}acetate (300 mg, 1.2 mmol, 1 eq.) in DCM (6 mL). The reaction mixture was stirred at RT under air atmosphere for 16 h. The reaction mixture was concentrated under reduced pressure. The residue was purified by trituration with MeCN to afford 2-(5-chloro-2-oxo-1,4-dihydropyrido[3,4-d]pyrimidin-3(2H)-yl) acetic acid (200 mg, 80%). LCMS (ES, m/z): 242.0 $[M+H]^+$.

2-{5-chloro-2-oxo-1H,4H-pyrido[3,4-d]pyrimidin-3-yl}-N-[(1S)-1-(2,4-difluorophenyl)ethyl]acetamide. HATU (207.72 mg, 0.547 mmol, 1.1 equiv) and DIEA (128.38 mg, 0.994 mmol, 2.0 equiv) were added at RT under air atmosphere to a mixture of {5-chloro-2-oxo-1H,4H-pyrido[3,4-d]pyrimidin-3-yl}acetic acid (120 mg, 0.497 mmol, 1 equiv) and (1S)-1-(2,4-difluorophenyl)ethanamine (85.86 mg, 0.547 mmol, 1.1 equiv) in DMF (4 mL). The reaction mixture was stirred for 12 h at RT under air atmosphere. The reaction was quenched by the addition of Water/Ice at RT. The precipitated solids were collected by filtration and washed with MeCN to afford 2-{5-chloro-2-oxo-1H,4H-pyrido[3,4-d]pyrimidin-3-yl}-N-[(1S)-1-(2,4-difluorophenyl)ethyl]acetamide (25.2 mg, 13.27%). LCMS (ES, m/z): 381.1 $[M+H]^+$. $^1$H NMR (300 MHz, DMSO-$d_6$): 9.75 (s, 1H), 8.59 (d, J=7.5, 1H), 8.14 (s, 1H), 7.97 (s, 1H), 7.48-7.40 (m, 1H), 7.24-7.15 (m, 1H), 7.10-7.04 (m, 1H), 5.18-5.08 (m, 1H), 4.61 (s, 2H), 4.02 (s, 2H), 1.36 (d, J=6.9, 3H)

Example 19: N-[(1R)-1-(2,4-difluorophenyl)-2-hydroxyethyl]-2-[(4R*)-4-methyl-2-oxo-1,4-dihydroquinazolin-3-yl]acetamide (Compound B200)

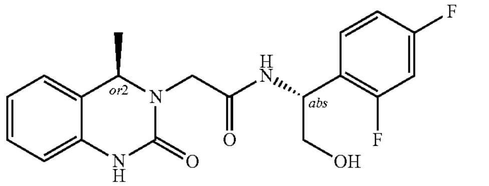 [SMILES: C[C@@H]1c2ccccc2NC(=O)N1CC(=O)N[C@@H](CO)c1ccc(F)cc1F]

tert-Butyl 2-{[1-(2-aminophenyl)ethyl]amino}acetate. Tert-butyl 2-bromoacetate (429.65 mg, 2.203 mmol, 1 equiv) was added dropwise at RT to a stirred solution of 2-(1-aminoethyl)aniline (300 mg, 2.203 mmol, 1.00 equiv) and $K_2CO_3$ (913.27 mg, 6.609 mmol, 3 equiv) in DMF (5 mL). The reaction mixture was stirred for 2 h at RT. The reaction mixture was extracted with EtOAc. The combined organic layers were washed with water and dried over anhydrous $Na_2SO_4$ and filtered. The filtrate was concentrated under reduced pressure. The residue was purified by silica gel column chromatography to afford tert-butyl 2-{[1-(2-aminophenyl)ethyl]amino}acetate (500 mg, 87.05%). LCMS (ES, m/z): 251 [M+H]+.

tert-Butyl 2-(4-methyl-2-oxo-1,4-dihydroquinazolin-3-yl)acetate. Triphosgene (177.79 mg, 0.599 mmol, 0.3 equiv) was added in portions at 0° C. to a stirred solution of tert-butyl 2-{[1-(2-aminophenyl)ethyl]amino}acetate (500 mg, 1.997 mmol, 1.00 equiv) and TEA (404.21 mg, 3.994 mmol, 2 equiv) in THF (5 mL). The reaction mixture was stirred for 3 h at RT. The residue was purified by silica gel column chromatography to afford tert-butyl 2-(4-methyl-2-oxo-1,4-dihydroquinazolin-3-yl)acetate (300 mg, 53.27%). LCMS (ES, m/z): 277 [M+H]+.

(4-methyl-2-oxo-1,4-dihydroquinazolin-3-yl)acetic acid. Into a 25 mL round-bottom flask tert-butyl 2-(4-methyl-2-oxo-1,4-dihydroquinazolin-3-yl)acetate (300 mg, 1.086 mmol, 1.00 equiv) in DCM (5 mL) were added at RT. To the above mixture TFA (1 mL) was added dropwise over 1 min at RT. The reaction mixture was stirred for additional 1 h at RT. The reaction mixture was concentrated under reduced pressure. The reaction mixture was used in the next step directly without further purification, to afford (4-methyl-2-oxo-1,4-dihydroquinazolin-3-yl)acetic acid (210 mg, crude). LCMS (ES, m/z): 221 [M+H]+.

N-[(1R)-1-(2,4-difluorophenyl)-2-hydroxyethyl]-2-(4-methyl-2-oxo-1,4-dihydroquinazolin-3-yl)acetamide. (2R)-2-amino-2-(2,4-difluorophenyl)ethanol (129.74 mg, 0.749 mmol, 1.1 equiv) and DMAP (16.64 mg, 0.136 mmol, 0.2 equiv) were added at RT to a stirred mixture of (4-methyl-2-oxo-1,4-dihydroquinazolin-3-yl)acetic acid (150 mg, 0.681 mmol, 1 equiv) and EDCI (156.68 mg, 0.817 mmol, 1.2 equiv) in DMF (2 mL). The reaction mixture was stirred for 12 h at RT. The residue was purified by reverse flash chromatography with the following conditions: column, silica gel; mobile phase, MeCN in water, 0% to 100% gradient in 50 min; detector, UV 254 nm. to afford N-[(1R)-1-(2,4-difluorophenyl)-2-hydroxyethyl]-2-(4-methyl-2-oxo-1,4-dihydroquinazolin-3-yl)acetamide (210 mg, 81.31%). LCMS (ES, m/z): 376 [M+H]+.

N-[(1R)-1-(2,4-difluorophenyl)-2-hydroxyethyl]-2-[(4R*)-4-methyl-2-oxo-1,4-dihydroquinazolin-3-yl]acetamide. The N-[(1R)-1-(2,4-difluorophenyl)-2-hydroxyethyl]-2-(4-methyl-2-oxo-1,4-dihydroquinazolin-3-yl) acetamide (150 mg, 0.400 mmol, 1 equiv) was purified by Chiral-HPLC: Column Name: CHIRALPAK IG-3, Mobile Phase: Hex (0.1% DEA):EtOH=60:40, Flow Rate: 1.67 ml/min. to afford N-[(1R)-1-(2,4-difluorophenyl)-2-hydroxyethyl]-2-[(4R*)-4-methyl-2-oxo-1,4-dihydroquinazolin-3-yl]acetamide (54.5 mg, 36.08%). LCMS (ES, m/z): 376 [M+H]+. $^1$H NMR (400 MHz, DMSO-$d_6$) δ 9.31 (s, 1H), 8.40 (d, J=8.0 Hz, 1H), 7.47-7.41 (m, 1H), 7.21-7.09 (m, 4H), 7.07-7.02 (m, 1H), 6.88-6.84 (m, 1H), 6.80-6.78 (m, 1H), 5.11-5.01 (m, 1H), 5.01-4.98 (m, 1H), 4.50-4.45 (m, 1H), 4.33-4.29 (m, 1H), 3.78 (d, J=16.4 Hz, 1H), 3.76-3.32 (m, 2H), 1.23 (d, J=6.0 Hz, 3H).

Example 20: N-[(1S)-1-(2,4-Difluorophenyl)ethyl]-2-{6-fluoro-2-oxo-1H,4H-pyrido[2,3-d]pyrimidin-3-yl}acetamide (Compound N71)

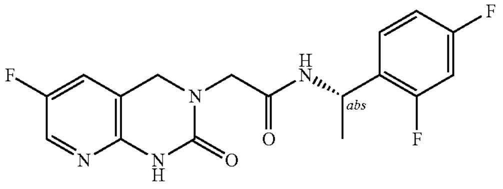 [SMILES: C[C@H](NC(=O)CN1Cc2cc(F)cnc2NC1=O)c1ccc(F)cc1F]

3-(aminomethyl)-5-fluoropyridin-2-amine. A solution of 2-amino-5-fluoropyridine-3-carbonitrile (2 g, 14.586 mmol, 1 equiv) and $LiAlH_4$ (1.66 g, 43.758 mmol, 3 equiv) in THF (20 mg) was stirred for 3 h at RT under argon atmosphere. The reaction mixture was concentrated under reduced pressure. The crude product was used in the next step directly without further purification. LCMS (ES, m/z): 142 $[M+H]^+$ tert-butyl 2-{[(2-amino-5-fluoropyridin-3-yl)methyl]amino}acetate. A solution of 3-(aminomethyl)-5-fluoropyridin-2-amine (800 mg, 5.668 mmol, 1 equiv) and tert-butyl 2-bromoacetate (1216.09 mg, 6.235 mmol, 1.1 equiv), $K_2CO_3$ (1566.63 mg, 11.336 mmol, 2 equiv) in DMF (10 mL) was stirred for 2 h at 50° C. under air atmosphere. The reaction mixture was extracted with EtOAc. The combined organic layers were concentrated under reduced pressure and the residue was purified by column chromatography to afford tert-butyl 2-{[(2-amino-5-fluoropyridin-3-yl)methyl]amino}acetate (600 mg, 41.47%). LCMS (ES, m/z): 256 $[M+H]^+$ tert-butyl 2-{6-fluoro-2-oxo-1H,4H-pyrido[2,3-d]pyrimidin-3-yl}acetate. A solution of tert-butyl 2-{[(2-amino-5-fluoropyridin-3-yl)methyl]amino}acetate (700 mg, 2.742 mmol, 1 equiv) and CDI (889.21 mg, 5.484 mmol, 2 equiv), DBU (834.85 mg, 5.484 mmol, 2 equiv) in DCM (10 mL) was stirred for 2 h at RT under air atmosphere. The reaction mixture was concentrated under reduced pressure. The residue was purified by column chromatography to afford tert-butyl 2-{6-fluoro-2-oxo-1H,4H-pyrido[2,3-d]pyrimidin-3-yl}acetate (500 mg, 64.83%). LCMS (ES, m/z): 282 $[M+H]^+$ {6-fluoro-2-oxo-1H,4H-pyrido[2,3-d]pyrimidin-3-yl}acetic acid. A solution of tert-butyl 2-{6-fluoro-2-oxo-1H,4H-pyrido[2,3-d]pyrimidin-3-yl}acetate (500 mg, 1.778 mmol, 1 equiv) and TFA (2 mL) in DCM (6 mL) was stirred for 2 h at RT under air atmosphere. The reaction mixture was concentrated under reduced pressure. The crude product was used in the next step directly without further purification. LCMS (ES, m/z): 226 $[M+H]^+$ N-[(1S)-1-(2,4-difluorophenyl)ethyl]-2-{6-fluoro-2-oxo-1H,4H-pyrido[2,3-d]pyrimidin-3-yl}acetamide. A solution of {6-fluoro-2-oxo-1H,4H-pyrido[2,3-d]pyrimidin-3-yl}acetic acid (80 mg, 0.355 mmol, 1 equiv) and (1S)-1-(2,4-difluorophenyl)ethanamine (55.84 mg, 0.355 mmol, 1 equiv), EDCI (68.11 mg, 0.355 mmol, 1 equiv), HOBt (48.01 mg, 0.355 mmol, 1 equiv), DIEA (137.75 mg, 1.065 mmol, 3 equiv) in DMF (1 mL) was stirred for 2 h at RT under air atmosphere. Water was added, and the aqueous layer was extracted with EtOAc.

The residue was purified by reverse flash chromatography with the following conditions: (column, C18; mobile phase, 0.1% HCOOH in water and MeOH, 0% to 100% gradient in 60 min; detector, UV 254 nm) to afford N-[(1S)-1-(2,4-difluorophenyl)ethyl]-2-{6-fluoro-2-oxo-1H,4H-pyrido[2,3-d]pyrimidin-3-yl}acetamide (49.9 mg, 37.78%). LCMS (ES, m/z): 365 $[M+H]^+$ $^1H$ NMR (300 MHz, DMSO-$d_6$) δ 9.85 (s, 1H), 8.57 (d, J=7.5 Hz, 1H), 8.07 (d, J=2.7 Hz, 1H), 7.55-7.51 (m, 1H), 7.48-7.40 (m, 1H), 7.23-7.18 (m, 1H), 7.16-7.03 (m, 1H), 5.15-5.10 (m, 1H), 4.48 (s, 2H), 3.98 (s, 2H), 1.36 (d, J=6.9 Hz, 3H).

Example 21: N-[(1S)-1-(2,4-Difluorophenyl)ethyl]-2-{6-fluoro-5-methyl-2-oxo-1H,4H-pyrido[2,3-d]pyrimidin-3-yl}acetamide (Compound N57)

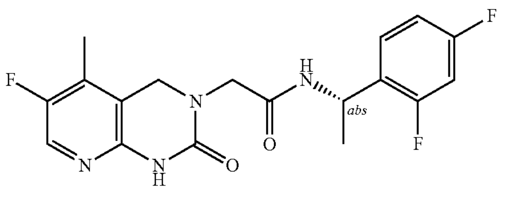 [SMILES: Cc1c(F)cnc2c1CN(CC(=O)N[C@@H](C)c1ccc(F)cc1F)C(=O)N2]

5-fluoro-3-iodo-4-methylpyridin-2-amine. A solution of 5-fluoro-4-methylpyridin-2-amine (2 g, 15.856 mmol, 1 equiv) and NIS (3.57 g, 15.856 mmol, 1 equiv) in AcOH (15 mL) and TFA (0.1 mL) was stirred overnight at RT under air atmosphere. The mixture was adjusted to pH 9-10 with saturated $Na_2CO_3$ (aq.). The reaction mixture was extracted with EtOAc. The combined organic layers were washed with brine and dried over anhydrous $Na_2SO_4$ and filtered. The filtrate was concentrated under reduced pressure. The residue was purified by column chromatography to afford 5-fluoro-3-iodo-4-methylpyridin-2-amine (2.2 g, 55.05%). LCMS (ES, m/z): 253 $[M+H]^+$.

2-amino-5-fluoro-4-methylpyridine-3-carbonitrile. CuI (0.30 g, 1.587 mmol, 0.2 equiv) was added dropwise at RT under argon atmosphere to a stirred solution of 5-fluoro-3-iodo-4-methylpyridin-2-amine (2 g, 7.936 mmol, 1 equiv) and CuCN (1.42 g, 15.872 mmol, 2 equiv) in DMSO (10 mL). The reaction mixture was stirred for overnight at 120° C. under argon atmosphere. The residue was purified by column chromatography to afford 2-amino-5-fluoro-4-methylpyridine-3-carbonitrile (1 g, 83.37%). LCMS (ES, m/z): 152 [M+H]+.

3-(aminomethyl)-5-fluoro-4-methylpyridin-2-amine. $LiAlH_4$ (2M in THF, 19.848 mmol, 3 equiv) was added dropwise at 0° C. under $N_2$ atmosphere to a stirred solution of 2-amino-5-fluoro-4-methylpyridine-3-carbonitrile (1 g, 6.616 mmol, 1 equiv) in THF (15 mL). The reaction mixture was stirred for 2 h at RT under $N_2$ atmosphere. The reaction was quenched with MeOH at 0° C. The residue was purified by column chromatography to afford 3-(aminomethyl)-5-fluoro-4-methylpyridin-2-amine (540 mg, 52.60%). LCMS (ES, m/z): 156 $[M+H]^+$.

Isopropyl 2-{[(2-amino-5-fluoro-4-methylpyridin-3-yl)methyl]amino}acetate. TEA (678.20 mg, 6.702 mmol, 2 equiv) was added dropwise at RT to a stirred solution of 3-(aminomethyl)-5-fluoro-4-methylpyridin-2-amine (520 mg, 3.351 mmol, 1.00 equiv) and tert-butyl 2-bromoacetate (784.37 mg, 4.021 mmol, 1.2 equiv) in THF (8 mL). The residue was purified by column chromatography to afford isopropyl 2-{[(2-amino-5-fluoro-4-methylpyridin-3-yl)methyl]amino}acetate (500 mg, 58.45%). LCMS (ES, m/z): 270 [M+H]+.

tert-butyl 2-{6-fluoro-5-methyl-2-oxo-1H,4H-pyrido[2,3-d]pyrimidin-3-yl}acetate. DBU (367.43 mg, 2.414 mmol, 1.3 equiv) was added dropwise at RT under air atmosphere to a stirred solution of tert-butyl 2-{[(2-amino-5-fluoro-4-methylpyridin-3-yl)methyl]amino}acetate (500 mg, 1.857 mmol, 1 equiv) and CDI (391.35 mg, 2.414 mmol, 1.3 equiv) in DCM (8 mL). The reaction mixture was stirred for overnight at RT under air atmosphere. The residue was purified by column chromatography to afford tert-butyl 2-{6-fluoro-5-methyl-2-oxo-1H,4H-pyrido[2,3-d]pyrimidin-3-yl}acetate (400 mg, 72.96%). LCMS (ES, m/z): 296 [M+H]+.

{6-Fluoro-5-methyl-2-oxo-1H,4H-pyrido[2,3-d]pyrimidin-3-yl}acetic acid. TFA (4 mL) was added dropwise at RT under air atmosphere to a stirred solution of tert-butyl 2-{6-fluoro-5-methyl-2-oxo-1H,4H-pyrido[2,3-d]pyrimidin-3-yl}acetate (400 mg, 1.354 mmol, 1 equiv) in DCM (12 mL). The reaction mixture was stirred for 3 h at RT under air atmosphere. The reaction mixture was concentrated under reduced pressure. The crude product/reaction mixture was used in the next step directly without further purification, to afford {6-fluoro-5-methyl-2-oxo-1H,4H-pyrido[2,3-d]pyrimidin-3-yl}acetic acid (300 mg, 92.59%). LCMS (ES, m/z): 240 [M+H]+.

N-[(1S)-1-(2,4-difluorophenyl)ethyl]-2-{6-fluoro-5-methyl-2-oxo-1H,4H-pyrido[2,3-d]pyrimidin-3-yl}acetamide. EDCI (93.76 mg, 0.489 mmol, 1.3 equiv) and HOBT (66.09 mg, 0.489 mmol, 1.3 equiv) and DIEA (97.26 mg, 0.752 mmol, 2 equiv) were added dropwise at RT under air atmosphere to a stirred solution of {6-fluoro-5-methyl-2-oxo-1H,4H-pyrido[2,3-d]pyrimidin-3-yl}acetic acid (90 mg, 0.376 mmol, 1 equiv) and (1S)-1-(2,4-difluorophenyl)ethanamine (70.96 mg, 0.451 mmol, 1.2 equiv) in DMF (2 mL). The reaction mixture was stirred for 3 h at RT under air atmosphere. The reaction mixture was extracted with EtOAc. The combined organic layers were washed with brine and dried over anhydrous $Na_2SO_4$ and filtered. The filtrate was concentrated under reduced pressure. The crude product (90 mg) was purified by Prep-HPLC with the following conditions (Column: Xselect CSH C18 OBD Column 30*150 mm 5 μm, n; Mobile Phase A: Water (0.1% FA), Mobile Phase B: ACN; Flow rate: 60 mL/min; Gradient: 30% B to 48% B in 7 min, 48% B; Wave Length: 254 nm; RT1 (min): 5.52; Number Of Runs: 0) to afford N-[(1S)-1-(2,4-difluorophenyl)ethyl]-2-{6-fluoro-5-methyl-2-oxo-1H,4H-pyrido[2,3-d]pyrimidin-3-yl}acetamide (50 mg, 35.12%). LCMS (ES, m/z): 379 [M+H]+. $^1$H NMR (300 MHz, DMSO-$d_6$) δ 9.71 (s, 1H), 8.57 (d, J=7.8 Hz, 1H), 7.99 (s, 1H), 7.45 (m, 1H), 7.20 (m, 1H), 7.07 (m, 1H), 5.14 (m, 1H), 4.48 (s, 2H), 3.99 (s, 2H), 2.08 (d, J=1.5 Hz, 3H), 1.36 (d, J=6.9 Hz, 3H)

Example 22: (S)-2-(6-Cyano-2-oxo-1,4-dihydropyrido[3,2-d]pyrimidin-3(2H)-yl)-N-(1-(2,4-difluorophenyl)ethyl)acetamide (Compound N60)

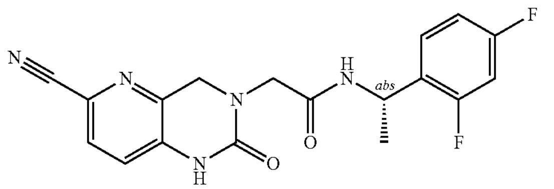 [SMILES: C[C@H](NC(=O)CN1Cc2nc(C#N)ccc2NC1=O)c1ccc(F)cc1F]

tert-butyl N-(2-bromo-6-chloropyridin-3-yl)carbamate. LiHMDS (1M in THF, 120.5 mL, 120.505 mmol, 2.5 equiv) was added dropwise at 0° C. under argon atmosphere to a stirred solution of 2-bromo-6-chloropyridin-3-amine (10 g, 48.202 mmol, 1 equiv) in THF (120 mL). The reaction mixture was stirred for 30 min at RT under argon atmosphere. To the above mixture $Boc_2O$ (10.52 g, 48.202 mmol, 1 equiv) was added dropwise over 20 min at 0° C. The reaction mixture was stirred for additional 2 h at RT. The reaction was quenched with sat. $NH_4Cl$ (aq.) at 0° C. The reaction mixture was extracted with EtOAc. The combined organic layers were washed with water and dried over anhydrous $Na_2SO_4$ and filtered. The filtrate was concentrated under reduced pressure. The residue was purified by column chromatography to afford tert-butyl N-(2-bromo-6-chloropyridin-3-yl)carbamate (13.6 g, 89.90%). LCMS (ES, m/z): 307[M+H]$^+$.

tert-butyl N-(6-chloro-2-formylpyridin-3-yl)carbamate. A mixture of NaH (60% in oil, 780 mg, 19.507 mmol, 1.2 equiv) and tert-butyl N-(2-bromo-6-chloropyridin-3-yl)carbamate (5 g, 16.256 mmol, 1 equiv) in THF (150 mL) was stirred for 30 min at 0° C. under argon atmosphere. To the above mixture was added tert-butyl N-(2-bromo-6-chloropyridin-3-yl)carbamate (5 g, 16.256 mmol, 1 equiv) dropwise over 10 min at −78° C. The reaction mixture was stirred for an additional 30 min at −78° C. To the above mixture DMF (4.75 g, 65.024 mmol, 4 equiv) was added dropwise over 5 min at −78° C. The reaction mixture was stirred for an additional 2 h at −78° C. The reaction was quenched with sat. $NH_4C_1$ (aq.) at 0° C. The reaction mixture was extracted with EtOAc. The combined organic layers were washed with water and dried over anhydrous $Na_2SO_4$ and filtered. The filtrate was concentrated under reduced pressure. The residue was purified by column chromatography to afford tert-butyl N-(6-chloro-2-formylpyridin-3-yl)carbamate (3 g, 66.86%). LCMS (ES, m/z): 257[M+H]$^+$.

tert-Butyl N-(6-chloro-2-formylpyridin-3-yl)carbamate. $MgSO_4$ (93.78 mg, 0.780 mmol, 2 equiv) was added in portions at RT under $N_2$ atmosphere to a stirred mixture of tert-butyl N-(6-chloro-2-formylpyridin-3-yl)carbamate (100 mg, 0.390 mmol, 1 equiv) and methyl 2-aminoacetate hydrochloride (69.42 mg, 0.780 mmol, 2 equiv) in MeCN (3 mL). To the above mixture TEA (78.84 mg, 0.780 mmol, 2 equiv) was added dropwise at RT. The reaction mixture was stirred for an additional 2 h at 80° C. The mixture was allowed to cool down to RT. The reaction mixture was filtered and the filter cake was washed with MeCN. The filtrate was concentrated under reduced pressure. to afford methyl 2-[€-({3-[(tert-butoxycarbonyl)amino]-6-chloropyridin-2-yl}methylidene)amino]acetate (78 mg, crude). LCMS (ES, m/z): 328[M+H]$^+$.

Methyl 2-[({3-[(tert-butoxycarbonyl)amino]-6-chloropyridin-2-yl}methyl)amino]acetate. $NaBH_3CN$ (2.19 g, 34.779 mmol, 3 equiv) was added at 0° C. to a stirred solution of methyl 2-[€-({3-[(tert-butoxycarbonyl)amino]-6-chloropyridin-2-yl}methylidene)amino]acetate (3.8 g, 11.593 mmol, 1 equiv) in MeOH (10 mL). The reaction mixture was stirred for 3 h at 50° C. The residue was purified by column chromatography to afford methyl 2-[({3-[(tert-butoxycarbonyl)amino]-6-chloropyridin-2-yl}methyl)amino]acetate (2.9 g, 62.96%). LCMS (ES, m/z): 330[M+H]$^+$.

Methyl ((3-amino-6-chloropyridin-2-yl)methyl)glycinate. Methyl 2-[({3-[(tert-butoxycarbonyl)amino]-6-chloropyridin-2-yl}methyl)amino]acetate (50 mg, 0.152 mmol, 1 equiv) and TFA (0.2 mL) in DCM (1 mL) were added into a 10 mL sealed tube at RT. The reaction mixture was stirred for 1 h at RT. The reaction mixture was concentrated under reduced pressure. The reaction mixture was used in the next step directly without further purification. LCMS (ES, m/z): 230[M+H]$^+$.

Methyl 2-{6-chloro-2-oxo-1H,4H-pyrido[3,2-d]pyrimidin-3-yl}acetate. CDI (4.13 g, 25.473 mmol, 3 equiv) was added in portions at RT to a stirred solution of methyl 2-{[(3-amino-6-chloropyridin-2-yl)methyl]amino}acetate (1.95 g, 8.491 mmol, 1 equiv) and DBU (6.46 g, 42.455 mmol, 5 equiv) in DCM (20 mL). The reaction mixture was stirred for 3 h at RT. The reaction mixture was concentrated under reduced pressure. The residue was purified by column chromatography to afford methyl 2-{6-chloro-2-oxo-1H,4H-pyrido[3,2-d]pyrimidin-3-yl}acetate (1 g, 44.68%). LCMS (ES, m/z): 256[M+H]$^+$.

{6-Chloro-2-oxo-1H,4H-pyrido[3,2-d]pyrimidin-3-yl}acetic acid. Into a 20 mL vial methyl 2-{6-chloro-2-oxo-1H,4H-pyrido[3,2-d]pyrimidin-3-yl}acetate (100 mg, 0.391 mmol, 1 equiv) and LiOH (28.10 mg, 1.173 mmol, 3 equiv) in $H_2O$ (1 mL) and MeOH (1 mL) were added at RT. The reaction mixture was stirred for 3 h at RT. The reaction mixture was concentrated under vacuum. The mixture was adjusted to pH 4 with HCl (aq. 1M). The reaction mixture was filtered and the filter cake washed with water. The filtrate was concentrated under reduced pressure. To afford {6-chloro-2-oxo-1H,4H-pyrido[3,2-d]pyrimidin-3-yl}acetic acid (80 mg, 71.10%). LCMS (ES, m/z): 242[M+H]$^+$.

(S)-2-(6-chloro-2-oxo-1,4-dihydropyrido[3,2-d]pyrimidin-3(2H)-yl)-N-(1-(2,4-difluorophenyl)ethyl)acetamide. EDCI (47.60 mg, 0.248 mmol, 1.2 equiv) and (1S)-1-(2,4-difluorophenyl)ethanamine (39.03 mg, 0.248 mmol, 1.2 equiv) were added at RT to a stirred mixture of {6-chloro-2-oxo-1H,4H-pyrido[3,2-d]pyrimidin-3-yl}acetic acid (50 mg, 0.207 mmol, 1 equiv) and DMAP (7.58 mg, 0.062 mmol, 0.3 equiv) in DCM (2 mL). The reaction mixture was stirred for 12 h at RT. The residue was purified by Prep-TLC ($CH_2Cl_2$/MeOH 10:1) to afford (S)-2-(6-chloro-2-oxo-1,4-dihydropyrido[3,2-d]pyrimidin-3(2H)-yl)-N-(1-(2,4-difluorophenyl)ethyl)acetamide (35 mg, 43.09%). LCMS (ES, m/z): 381[M+H]$^+$.

(S)-2-(6-cyano-2-oxo-1,4-dihydropyrido[3,2-d]pyrimidin-3(2H)-yl)-N-(1-(2,4-difluorophenyl)ethyl)acetamide. 2-{6-chloro-2-oxo-1H,4H-pyrido[3,2-d]pyrimidin-3-yl}-N-[1-(2,4-difluorophenyl)ethyl]acetamide (150 mg, 0.394 mmol, 1 equiv), $Zn(CN)_2$ (92.53 mg, 0.788 mmol, 2 equiv) and Zn (5.15 mg, 0.079 mmol, 0.2 equiv) in DMSO (5 mL) were added into a 10 mL vial at RT. To the above mixture $Pd(dppf)Cl_2$ (144.12 mg, 0.197 mmol, 0.5 equiv) was added at RT. The reaction mixture was stirred for additional 12 h at 100° C. The residue was purified by reverse flash chromatography with the following conditions: column, silica gel; mobile phase, MeCN in water, 0% to 100% gradient in 50 min; detector, UV 254 nm. To afford (S)-2-(6-cyano-2-oxo-1,4-dihydropyrido[3,2-d]pyrimidin-3(2H)-yl)-N-(1-(2,4-difluorophenyl)ethyl)acetamide (57.8 mg, 39.12%). LCMS (ES, m/z): 372[M+H]$^+$. $^1$H NMR (400 MHz, DMSO-$d_6$) δ 9.98 (s, 1H), 8.58 (d, J=7.6 Hz, 1H), 7.80 (d, J=8.4 Hz, 1H), 7.46-7.40 (m, 1H), 7.22-7.17 (m, 2H), 7.09-7.05 (m, 1H), 5.16-5.09 (m, 1H), 4.58 (d, J=0.8 Hz, 2H), 3.99 (s, 2H), 1.35 (d, J=6.8 Hz, 3H).

Example 23: 2-{6'-Cyano-2'-oxo-1'H-spiro[cyclopropane-1,4'-pyrido[3,2-d]pyrimidin]-3'-yl}-N-[(1S)-1-(3,5-difluoropyridin-2-yl)ethyl]acetamide (Compound N15)

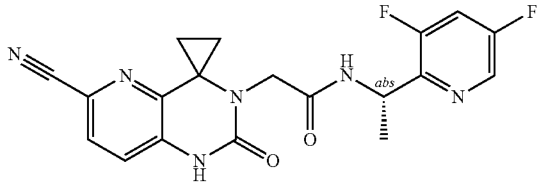 [SMILES: C[C@H](NC(=O)CN1C(=O)Nc2ccc(C#N)nc2C12CC2)c1ncc(F)cc1F]

1-Ethoxycyclopropan-1-ol. A mixture of (1-ethoxycyclopropoxy)trimethylsilane (19.6 g, 112.440 mmol, 1 equiv) and concentrated HCl (one drop) in MeOH (200 mL) was stirred for 14 h at RT under $N_2$ atmosphere. The reaction mixture was concentrated under vacuum. The reaction mixture was used in the next step directly without further purification. This resulted in 1-ethoxycyclopropan-1-ol (9.6 g, 83.60%).

Chloro(1-ethoxycyclopropoxy)magnesium. Chloro(ethyl) magnesium in THF (2M) (61.19 mL, 122.390 mmol, 2.5 equiv) was added dropwise at −78° C. under argon atmosphere to a stirred solution of 1-ethoxycyclopropan-1-ol (5 g, 48.956 mmol, 1 equiv) in THF (50 mL). The mixture was warmed to 0° C. in 2 h. The reaction mixture was used in the next step directly without further purification.

tert-Butyl N-(6-chloro-2-iodopyridin-3-yl)carbamate. $Boc_2O$ (9.43 g, 43.229 mmol, 1.1 equiv) was added in portions at 0° C. under $N_2$ atmosphere to a stirred solution of 6-chloro-2-iodopyridin-3-amine (10 g, 39.299 mmol, 1 equiv) and KOtBu in THF (1 M) (98.25 mL, 98.248 mmol, 2.5 equiv) in THF (100 mL). The reaction mixture was stirred for 5 h at 50° C. under $N_2$ atmosphere. The reaction was quenched with sat. $NH_4Cl$ (aq.) at 0° C. and extracted with EtOAc. The combined organic layers were washed with brine and dried over anhydrous $Na_2SO_4$ and filtered. The filtrate was concentrated under reduced pressure. The residue was purified by column chromatography to afford tert-butyl N-(6-chloro-2-iodopyridin-3-yl)carbamate (11 g, 78.94%). LCMS (ES, m/z): 355 [M+H]$^+$.

N-[6-chloro-2-(1-hydroxycyclopropyl)pyridin-3-yl]carbamate. Chloro(isopropyl)magnesium; lithium chloride in THF (1.3 M) (21.69 mL, 28.204 mmol, 2 equiv) was added dropwise at −40° C. under argon atmosphere to a stirred solution/mixture of tert-butyl N-(6-chloro-2-iodopyridin-3-yl)carbamate (5 g, 14.102 mmol, 1.00 equiv) in THF (65 mL). The reaction mixture was stirred for 1 h at −40° C. under argon atmosphere. The mixture was warmed to 0° C. e and chloro(1-ethoxycyclopropoxy)magnesium (35.25 mL, 15.512 mmol, 1.1 equiv) was added dropwise at 0° C. The reaction mixture was stirred for an additional 1 h at 80° C. and quenched with sat. $NH_4Cl$ (aq.) at 0° C. The reaction mixture was extracted with EtOAc. The combined organic layers were washed with brine and dried over anhydrous $Na_2SO_4$ and filtered. The filtrate was concentrated under reduced pressure. The residue was purified by column chromatography to afford tert-butyl N-[6-chloro-2-(1-hydroxycyclopropyl)pyridin-3-yl]carbamate (1.35 g, 33.62%). LCMS (ES, m/z): 285 [M+H]$^+$.

6-Chloro-2-(1-chlorocyclopropyl)pyridin-3-amine. $SOCl_2$ (1.72 mL, 23.705 mmol, 5 equiv) was added dropwise at 0° C. under air atmosphere to a stirred solution/mixture of tert-butyl N-[6-chloro-2-(1-hydroxycyclopropyl)pyridin-3-yl]carbamate (1.350 g, 4.741 mmol, 1 equiv) in DCM (20 mL). The reaction mixture was stirred for 3 h at 50° C. under air atmosphere. The reaction mixture was extracted with $CH_2Cl_2$. The combined organic layers were washed with saturated $Na_2CO_3$ (aq.) (50 mL) and dried over anhydrous $Na_2SO_4$ and filtered. The filtrate was concentrated under reduced pressure. The reaction mixture was used in the next step directly without further purification. LCMS (ES, m/z): 202 [M+H]$^+$.

2-{[1-(3-amino-6-chloropyridin-2-yl)cyclopropyl] amino}acetate. $K_2CO_3$ (2.21 g, 15.954 mmol, 3 equiv) was added at RT under air atmosphere to a stirred solution/mixture of 6-chloro-2-(1-chlorocyclopropyl)pyridin-3-amine (1.08 g, 5.318 mmol, 1.00 equiv) and methyl 2-aminoacetate hydrochloride (734.49 mg, 5.850 mmol, 1.1 equiv) in DMF (10 mL). The reaction mixture was stirred for 2 h at 80° C. under air atmosphere. The reaction mixture was extracted with EtOAc. The combined organic layers were washed with brine and dried over anhydrous $Na_2SO_4$ and filtered. The filtrate was concentrated under reduced pressure. The residue was purified by column chromatography to afford methyl 2-{[1-(3-amino-6-chloropyridin-2-yl)cyclopropyl]amino}acetate (1.0 g, 73.53%). LCMS (ES, m/z): 256 [M+H]$^+$.

Methyl 2-{6'-chloro-2'-oxo-1'H-spiro[cyclopropane-1,4'-pyrido[3,2-d]pyrimidin]-3'-yl}acetate. DBU (2.69 mL, 17.988 mmol, 4 equiv) was added dropwise at RT under air atmosphere to a stirred solution/mixture of methyl 2-{[1-(3-amino-6-chloropyridin-2-yl)cyclopropyl]amino}acetate (1.15 g, 4.497 mmol, 1 equiv) and CDI (2.92 g, 17.988 mmol, 4 equiv) in DCM (10 mL). The reaction mixture was stirred for 14 h at 50° C. under air atmosphere. The residue was purified by column chromatography to afford methyl 2-{6'-chloro-2'-oxo-1'H-spiro[cyclopropane-1,4'-pyrido[3,2-d]pyrimidin]-3'-yl}acetate (935 mg, 45.02%). LCMS (ES, m/z): 282 [M+H]$^+$.

Methyl 2-{6'-cyano-2'-oxo-1'H-spiro[cyclopropane-1,4'-pyrido[3,2-d]pyrimidin]-3'-yl}acetate. $Pd(dppf)Cl_2$ (382.87 mg, 0.523 mmol, 0.2 equiv) and Zn (85.53 mg, 1.308 mmol, 0.5 equiv) were added at RT under air atmosphere to a stirred solution of methyl 2-{6'-chloro-2'-oxo-1'H-spiro[cyclopropane-1,4'-pyrido[3,2-d]pyrimidin]-3'-yl}acetate (737 mg, 2.616 mmol, 1 equiv) and $Zn(CN)_2$ (614.40 mg, 5.232 mmol, 2 equiv) in DMF (8 mL). The reaction mixture was stirred for 4 h at 120° C. under argon atmosphere. The residue was purified by column chromatography to afford methyl 2-{6'-cyano-2'-oxo-1'H-spiro[cyclopropane-1,4'-pyrido[3,2-d]pyrimidin]-3'-yl}acetate (380 mg, 53.35%). LCMS (ES, m/z): 273 $[M+H]^+$.

6'-Cyano-2'-oxo-1'H-spiro[cyclopropane-1,4'-pyrido[3,2-d]pyrimidin]-3'-ylacetic acid. A solution of methyl 2-{6'-cyano-2'-oxo-1'H-spiro[cyclopropane-1,4'-pyrido[3,2-d]pyrimidin]-3'-yl}acetate (385 mg, 1.414 mmol, 1 equiv) and NaOH in $H_2O$ (1M) (2.83 mL, 2.828 mmol, 2 equiv) in EtOH (8.5 mL) was stirred for 1 h at RT under air atmosphere. The reaction mixture was concentrated under reduced pressure. The reaction mixture was diluted with water. The mixture was adjusted to pH 5 with HCl (aq.). The precipitated solids were collected by filtration and washed with water. This resulted in 6'-cyano-2'-oxo-1'H-spiro[cyclopropane-1,4'-pyrido[3,2-d]pyrimidin]-3'-ylacetic acid (320 mg, 71.86%). LCMS (ES, m/z): 257 $[M-H]^+$.

2-{6'-cyano-2'-oxo-1'H-spiro[cyclopropane-1,4'-pyrido[3,2-d]pyrimidin]-3'-yl}-N-[(1S)-1-(3,5-difluoropyridin-2-yl)ethyl]acetamide. DMAP (13.25 mg, 0.108 mmol, 0.4 equiv) and EDCI (67.55 mg, 0.352 mmol, 1.3 equiv) were added at RT under air atmosphere to a stirred solution of 6'-cyano-2'-oxo-1'H-spiro[cyclopropane-1,4'-pyrido[3,2-d]pyrimidin]-3'-ylacetic acid (70 mg, 0.271 mmol, 1.00 equiv) and (1S)-1-(3,5-difluoropyridin-2-yl)ethanamine (51.44 mg, 0.325 mmol, 1.2 equiv) in DMF (1 mL). The reaction mixture was stirred for 2 h at RT under air atmosphere. The residue was purified by reverse flash chromatography with the following conditions: column, C18 silica gel; mobile phase, MeCN in Water (0.1% FA), 0% to 100% gradient in 60 min; detector, UV 254 nm. This resulted in 2-{6'-cyano-2'-oxo-1'H-spiro[cyclopropane-1,4'-pyrido[3,2-d]pyrimidin]-3'-yl}-N-[(1S)-1-(3,5-difluoropyridin-2-yl)ethyl]acetamide (60.9 mg, 55.10%). LCMS (ES, m/z): 399.10 $[M+H]^+$ 1H NMR (400 MHz, DMSO-$d_6$) δ 10.18 (s, 1H), 8.53-8.46 (m, 2H), 7.94-7.89 (m, 1H), 7.75 (d, J=8.4 Hz, 1H), 7.19 (d, J=8.4 Hz, 1H), 5.25-5.14 (m, 1H), 3.95-3.78 (m, 2H), 1.37-1.11 (m, 7H).

Example 24: 2-(6-cyano-2-oxo-1,4-dihydroquinazolin-3-yl)-N-[(1S)-1-(5-cyano-3-fluoropyridin-2-yl)ethyl]acetamide (Compound B144)

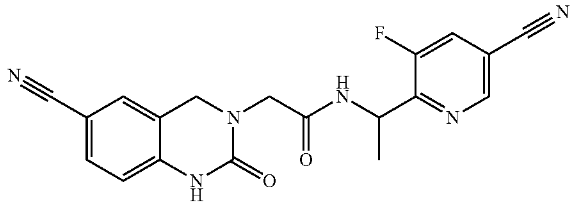 [SMILES: CC(NC(=O)CN1Cc2cc(C#N)ccc2NC1=O)c1ncc(C#N)cc1F]

tert-Butyl 2-(6-cyano-2-oxo-1,4-dihydroquinazolin-3-yl)acetate. A mixture of tert-butyl 2-(6-bromo-2-oxo-1,4-dihydroquinazolin-3-yl)acetate (1.2 g, 3.517 mmol, 1 equiv), $Zn(CN)_2$ (0.83 g, 7.034 mmol, 2 equiv), Zn (0.11 g, 1.758 mmol, 0.5 equiv) and $Pd(dppf)Cl_2$ (0.77 g, 1.055 mmol, 0.3 equiv) in DMSO (15 mL) was stirred for 3 h at 120° C. under argon atmosphere. The residue was purified by flash chromatography with the following conditions: column, silica gel; mobile phase, DCM/MeOH (20/1). The reaction mixture was concentrated under reduced pressure to afford tert-butyl 2-(6-cyano-2-oxo-1,4-dihydroquinazolin-3-yl)acetate (0.6 g, 59.38%). LC-MS: (ESI, m/z): 288 $[M+H]^+$.

(6-Cyano-2-oxo-1,4-dihydroquinazolin-3-yl)acetic acid. A mixture of tert-butyl 2-(6-cyano-2-oxo-1,4-dihydroquinazolin-3-yl)acetate (140 mg, 0.487 mmol, 1 equiv) and $CF_3COOH$ (3 mL) in DCM (3 mL) was stirred for 4 h at RT. The reaction mixture was concentrated under reduced pressure to afford (6-cyano-2-oxo-1,4-dihydroquinazolin-3-yl)acetic acid (100 mg, 88.76%). LC-MS: (ESI, m/z): 232 $[M+H]^+$.

2-(6-cyano-2-oxo-1,4-dihydroquinazolin-3-yl)-N-[(1S)-1-(5-cyano-3-fluoropyridin-2-yl)ethyl]acetamide. A mixture of (6-cyano-2-oxo-1,4-dihydroquinazolin-3-yl)acetic acid (100 mg, 0.433 mmol, 1 equiv), EDCI (99.49 mg, 0.520 mmol, 1.2 equiv), DMAP (15.85 mg, 0.130 mmol, 0.3 equiv) and 6-[(1S)-1-aminoethyl]-5-fluoropyridine-3-carbonitrile (85.72 mg, 0.520 mmol, 1.2 equiv) in DMF (3 mL) was stirred for 3 h at RT. The residue was purified by reverse flash chromatography with the following conditions: column, C18 silica gel; mobile phase, MeCN in Water (0.1% FA), 0% to 100% gradient in 60 min; detector: UV 254 nm. The reaction mixture was concentrated under reduced pressure to afford 2-(6-cyano-2-oxo-1,4-dihydroquinazolin-3-yl)-N-[(1S)-1-(5-cyano-3-fluoropyridin-2-yl)ethyl]acetamide (50 mg, 30.06%). LC-MS: (ESI, m/z): 379.20 $[M+H]^+$. $^1H$ NMR (400 MHz, DMSO-$d_6$) δ 9.77 (s, 1H), 8.90-8.89 (m, 1H), 8.70 (d, J=7.2 Hz, 1H), 8.41-8.38 (m, 1H), 7.59-7.55 (m, 2H), 6.87 (d, J=8.4 Hz, 1H), 5.28-5.25 (m, 1H), 4.48-4.40 (m, 2H), 3.98-3.92 (m, 2H), 1.39 (d, J=7.2 Hz, 3H).

Example 25: 2-(6-Cyano-5-fluoro-2-oxo-1,4-dihydroquinazolin-3-yl)-N-[(1S)-1-(2,4-difluorophenyl)ethyl]acetamide (Compound B160)

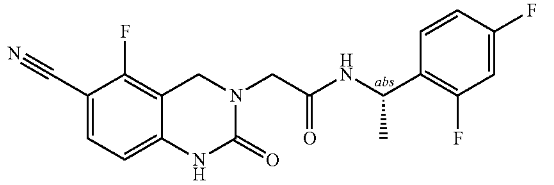 [SMILES: C[C@H](NC(=O)CN1Cc2c(ccc(C#N)c2F)NC1=O)c1ccc(F)cc1F]

tert-butyl 2-{[(6-amino-3-bromo-2-fluorophenyl)methyl]amino}acetate. A mixture of 6-amino-3-bromo-2-fluorobenzaldehyde (500 mg, 2.293 mmol, 1 equiv), $MgSO_4$ (414.04 mg, 3.440 mmol, 1.5 equiv) and TEA (464.13 mg, 4.586 mmol, 2 equiv) in ACN (10 mL) was stirred for 2 h at 80° C. The precipitated solids were collected by filtration and washed with MeOH. The reaction mixture was concentrated under reduced pressure. MeOH (10 mL) and then $NaBH_3CN$ (288.22 mg, 4.586 mmol, 2 equiv) were added. The mixture was stirred for 16 h at RT. The residue was purified by flash chromatography with PE/EA (6/1) to afford tert-butyl 2-{[(6-amino-3-bromo-2-fluorophenyl)methyl]amino}acetate (330 mg, 43.19%). LC-MS: (ESI, m/z): 333 $[M+H]^+$.

tert-butyl 2-(6-bromo-5-fluoro-2-oxo-1,4-dihydroquinazolin-3-yl)acetate). A solution/mixture of tert-butyl 2-{[(6-amino-3-bromo-2-fluorophenyl)methyl]amino}acetate (700 mg, 2.101 mmol, 1 equiv), CDI (681.31 mg, 4.202 mmol, 2 equiv) and DBU (639.67 mg, 4.202 mmol, 2 equiv) in DCM (6 mL) was stirred for 5 h at RT. The residue was purified by flash chromatography with PE/EA (2/1) to afford tert-butyl 2-(6-bromo-5-fluoro-2-oxo-1,4-dihydroquinazolin-3-yl)acetate) (400 mg, 53.01%). LC-MS: (ESI, m/z): 359 $[M+H]^+$.

tert-Butyl 2-(6-cyano-5-fluoro-2-oxo-1,4-dihydroquinazolin-3-yl)acetate. A mixture of tert-butyl 2-(6-bromo-5-fluoro-2-oxo-1,4-dihydroquinazolin-3-yl)acetate (400 mg, 1.114 mmol, 1 equiv), $Zn(CN)_2$ (261.52 mg, 2.228 mmol, 2 equiv), Zn (36.40 mg, 0.557 mmol, 0.5 equiv) and Pd(dppf)$Cl_2$ (244.45 mg, 0.334 mmol, 0.3 equiv) in DMSO (6 mL, 84.475 mmol, 75.86 equiv) was stirred for 16 h at 110° C. under argon atmosphere. The residue was purified by flash chromatography with DCM/MeOH (20/1) to get the crude product. Then the residue was purified by reverse phase with the following conditions: (column, C18 silica gel; mobile phase, 0.10% HCOOH in ACN, 0% to 100% gradient in 50 min; detector, UV 254 nm.) to afford tert-butyl 2-(6-cyano-5-fluoro-2-oxo-1,4-dihydroquinazolin-3-yl)acetate (270 mg, 79.41%). LC-MS: (ESI, m/z): 306 $[M+H]^+$.

(6-Cyano-5-fluoro-2-oxo-1,4-dihydroquinazolin-3-yl) acetic acid. A mixture of tert-butyl 2-(6-cyano-5-fluoro-2-oxo-1,4-dihydroquinazolin-3-yl)acetate (270 mg, 0.884 mmol, 1 equiv) and $CF_3COOH$ (2 mL) in DCM (6 mL) was stirred for 3 h at RT. The reaction mixture was concentrated under reduced pressure to afford (6-cyano-5-fluoro-2-oxo-1,4-dihydroquinazolin-3-yl)acetic acid (200 mg, 90.75%). LC-MS: (ESI, m/z): 250 $[M+H]^+$.

2-(6-Cyano-5-fluoro-2-oxo-1,4-dihydroquinazolin-3-yl)-N-[(1S)-1-(2,4-difluorophenyl) ethyl]acetamide. A mixture of (6-cyano-5-fluoro-2-oxo-1,4-dihydroquinazolin-3-yl) acetic acid (150 mg, 0.602 mmol, 1 equiv), (1S)-1-(2,4-difluorophenyl)ethanamine (113.52 mg, 0.722 mmol, 1.2 equiv), EDCI (138.47 mg, 0.722 mmol, 1.2 equiv) and DMAP (0.98 mg, 0.008 mmol, 0.2 equiv) in DMF (5 mL) was stirred for 3 h at RT. The residue was purified by reverse flash chromatography with the following conditions: (column, C18 silica gel; mobile phase, 0.05% $NH_4HCO_3$ in water and ACN, 0% to 100% gradient in 60 min; detector, UV 254 nm.) to afford 2-(6-cyano-5-fluoro-2-oxo-1,4-dihydroquinazolin-3-yl)-N-[(1S)-1-(2,4-difluorophenyl) ethyl] acetamide (71.8 mg, 30.29%). LC-MS: (ESI, m/z): 389.20 $[M+H]^+$. $^1H$ NMR (400 MHz, DMSO-$d_6$) δ 10.05 (s, 1H), 8.57 (d, J=7.6 Hz, 1H), 7.66 (t, J=7.6 Hz, 1H), 7.44-7.42 (m, 1H), 7.21-7.16 (m, 1H), 7.09-7.06 (m, 1H), 6.71 (d, J=8.4 Hz, 1H), 5.13-5.10 (m, 1H), 4.54 (s, 2H), 4.00 (s, 2H), 1.35 (d, J=7.2 Hz, 3H).

Example 26: 2-(5-Cyano-2-oxo-1,4-dihydroquinazolin-3-yl)-N-[(1S)-1-(5-cyanopyridin-2-yl)ethyl]acetamide (Compound B116)

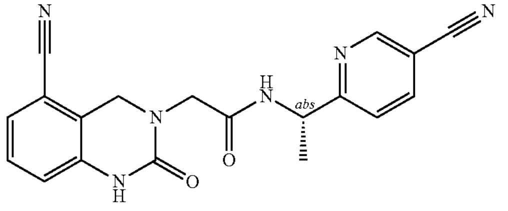 [SMILES: C[C@H](NC(=O)CN1Cc2c(C#N)cccc2NC1=O)c1ccc(C#N)cn1]

2-(Aminomethyl)-3-bromoaniline. 2-amino-6-bromobenzonitrile (5 g, 25.376 mmol, 1 equiv), LAH (1.93 g, 50.752 mmol, 2 equiv) and THF (50 mL) were added together at 80° C. for 2 h. The aqueous layer was extracted with $Et_2O$. The reaction mixture was concentrated under reduced pressure. The residue was purified by column chromatography to afford 2-(aminomethyl)-3-bromoaniline (2.8 g, 54.88%). LCMS (ES, m/z): $[M+H]^+$=201.

tert-Butyl 2-{[(2-amino-6-bromophenyl)methyl] amino}acetate. 2-(aminomethyl)-3-bromoaniline (2.8 g, 13.926 mmol, 1 equiv), tert-butyl 2-bromoacetate (3.26 g, 16.711 mmol, 1.2 equiv), TEA (3.87 mL, 27.852 mmol, 2 equiv) and THF (30 mL) were added into a vial at 80° C. for 2 h. The aqueous layer was extracted with $Et_2O$. The reaction mixture was concentrated under reduced pressure. The residue was purified by column chromatography to afford tert-butyl 2-{[(2-amino-6-bromophenyl)methyl] amino}acetate (3 g, 68.34%). LCMS (ES, m/z): $[M+H]^+$ =315.

tert-Butyl 2-(5-bromo-2-oxo-1,4-dihydroquinazolin-3-yl) acetate. tert-butyl 2-{[(2-amino-6-bromophenyl)methyl] amino}acetate (3 g, 9.517 mmol, 1 equiv), CDI (3.09 g, 19.034 mmol, 2 equiv), DMF (30 mL) and DBU (2.84 mL, 19.034 mmol, 2 equiv) were added together at RT for 3 h. The aqueous layer was extracted with $Et_2O$. The residue was purified by column chromatography to afford tert-butyl 2-(5-bromo-2-oxo-1,4-dihydroquinazolin-3-yl)acetate (2.3 g, 70.83%). LCMS (ES, m/z): $[M+H]^+$=341.

tert-Butyl 2-(5-cyano-2-oxo-1,4-dihydroquinazolin-3-yl) acetate. 5-bromo-3-[2-(tert-butoxy)-2-hydroxyethyl]-2,4-dihydro-1H-quinazolin-2-ol (1 g, 2.897 mmol, 1 equiv), $Zn(CN)_2$ (680.23 mg, 5.794 mmol, 2 equiv), Zn (75.75 mg, 1.159 mmol, 0.4 equiv), Pd(dppf)$Cl_2$ (423.89 mg, 0.579 mmol, 0.2 equiv) and DMF (10 mL) were added into a vial at 120° C. for 2 h. The precipitated solids were collected by filtration and washed with $Et_2O$. The reaction mixture was concentrated under reduced pressure. The residue was purified by column chromatography to afford tert-butyl 2-(5-cyano-2-oxo-1,4-dihydroquinazolin-3-yl)acetate (480 mg, 57.68%). LCMS (ES, m/z): $[M+H]^+$=288.

(5-Cyano-2-oxo-1,4-dihydroquinazolin-3-yl)acetic acid. tert-butyl 2-(5-cyano-2-oxo-1,4-dihydroquinazolin-3-yl)acetate (480 mg, 1.671 mmol, 1 equiv), DCM (6 mL) and TFA (2 mL) were added into a vial at RT for 3 h. The reaction mixture was concentrated under reduced pressure to afford (5-cyano-2-oxo-1,4-dihydroquinazolin-3-yl)acetic acid (380 mg, 99.5%). LCMS (ES, m/z): $[M+H]^+$=232.

N-[(1S)-1-(5-bromopyridin-2-yl)ethyl]-2-(5-cyano-2-oxo-1,4-dihydroquinazolin-3-yl)acetamide. (5-cyano-2-oxo-1,4-dihydroquinazolin-3-yl)acetic acid (200 mg, 0.865 mmol, 1 equiv), (1S)-1-(5-bromopyridin-2-yl)ethanamine (208.71 mg, 1.038 mmol, 1.2 equiv), EDCI (198.99 mg, 1.038 mmol, 1.2 equiv), DIEA (447.20 mg, 3.460 mmol, 4 equiv), HOBT (140.26 mg, 1.038 mmol, 1.2 equiv) and DMF (2 mL) were added together at RT and stirred for 4 h. The residue was purified by reverse flash chromatography with the following conditions: column, C18 silica gel; mobile phase, MeCN in Water (0.1% TFA), 10% to 50% gradient in 10 min; detector, UV 254 nm. to afford N-[(1S)-1-(5-bromopyridin-2-yl)ethyl]-2-(5-cyano-2-oxo-1,4-dihydroquinazolin-3-yl)acetamide (185 mg, 51.63%). LCMS (ES, m/z): $[M+H]^+$=414.

2-(5-Cyano-2-oxo-1,4-dihydroquinazolin-3-yl)-N-[(1S)-1-(5-cyanopyridin-2-yl)ethyl]acetamide. A solution/mixture of N-[(1S)-1-(5-bromopyridin-2-yl)ethyl]-2-(5-cyano-2-oxo-1,4-dihydroquinazolin-3-yl)acetamide (180 mg, 0.435 mmol, 1 equiv), $Zn(CN)_2$ (102.04 mg, 0.870 mmol, 2 equiv), Zn (11.36 mg, 0.174 mmol, 0.4 equiv) and Pd(dppf)$Cl_2$ (63.59 mg, 0.087 mmol, 0.2 equiv) in DMF (3 mL) was stirred for 3 h at 120° C. under air atmosphere. The residue was purified by column chromatography. The reaction mixture was concentrated under reduced pressure. The residue was purified by trituration with DCM and then purified by trituration with MeCN providing 2-(5-cyano-2-oxo-1,4-dihydroquinazolin-3-yl)-N-[(1S)-1-(5-cyanopyridin-2-yl) ethyl]acetamide (75.0 mg, 47.90%). LCMS (ES, m/z): $[M+H]^+$=361.10. $^1$H NMR (400 MHz, DMSO-$d_6$) δ 9.67 (s, 1H), 8.97-8.96 (m, 1H), 8.66 (d, J=7.6 Hz, 1H), 8.28-8.25 (m, 1H), 7.60-7.58 (m, 1H), 7.36-7.31 (m, 2H), 7.09-7.04 (m, 1H), 5.06-5.01 (m, 1H), 4.72-4.59 (m, 2H), 4.08 (s, 2H), 1.42 (d, J=7.2 Hz, 3H).

Example 27: 2-{5-Cyano-2-oxo-1H,4H-pyrido[3,4-d]pyrimidin-3-yl}-N-[(1S)-1-(2,4-difluorophenyl) ethyl]acetamide (Compound N24)

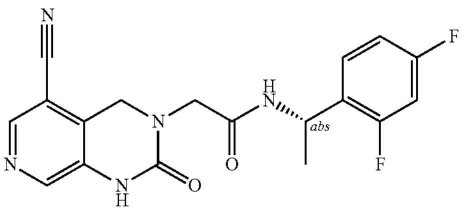 [SMILES: C[C@H](NC(=O)CN1Cc2c(C#N)cncc2NC1=O)c1ccc(F)cc1F]

2-{5-Cyano-2-oxo-1H,4H-pyrido[3,4-d]pyrimidin-3-yl}acetate. $Zn(CN)_2$ (56.57 mg, 0.482 mmol, 2 equiv) and zinc (6.30 mg, 0.096 mmol, 0.4 equiv), then $Pd(dppf)Cl_2$ (35.25 mg, 0.048 mmol, 0.2 equiv) were added under Argon atmosphere to a solution of tert-butyl 2-{5-chloro-2-oxo-1H,4H-pyrido[3,4-d]pyrimidin-3-yl}acetate (100 mg, 0.241 mmol, 1 equiv) in NMP (3 mL). The mixture was stirred for 16 h at 130° C. Then the residue was purified by column chromatography to afford tert-butyl 2-{5-cyano-2-oxo-1H, 4H-pyrido[3,4-d]pyrimidin-3-yl}acetate (26 mg, 35.57%). LCMS (ES, m/z): 289 $[M+H]^+$ 2-{5-Cyano-2-oxo-1H,4H-pyrido[3,4-d]pyrimidin-3-yl}-N-[(1S)-1-(2,4-difluorophenyl)ethyl]acetamide. Trifluoroacetaldehyde (0.4 mL) was added at 0° C. to a solution of tert-butyl 2-{5-cyano-2-oxo-1H,4H-pyrido[3,4-d]pyrimidin-3-yl}acetate (24 mg, 0.083 mmol, 1 equiv) in DCM (1.2 mL). The mixture was stirred for 4 h at RT. The reaction mixture was concentrated under reduced pressure to afford {5-cyano-2-oxo-1H,4H-pyrido[3,4-d]pyrimidin-3-yl}acetic acid (25 mg, 116.40%), the crude product was used for the next step. LCMS (ES, m/z): 233 $[M+H]^+$ 2-{5-Cyano-2-oxo-1H,4H-pyrido[3,4-d]pyrimidin-3-yl}-N-[(1S)-1-(2,4-difluorophenyl)ethyl]acetamide. EDCI (19.22 mg, 0.101 mmol, 1.2 equiv) and DMAP (3.06 mg, 0.025 mmol, 0.3 equiv), then (1S)-1-(2,4-difluorophenyl) ethanamine (15.76 mg, 0.101 mmol, 1.2 equiv) were added to a solution of {5-cyano-2-oxo-1H,4H-pyrido[3,4-d]pyrimidin-3-yl}acetic acid (19.4 mg, 0.084 mmol, 1 equiv) in dimethylformamide (1 mL). The mixture was stirred for 4 h at RT. Then water was added, and the reaction mixture was extracted with EtOAc. The combined organic layers were concentrated under reduced pressure. The residue was purified by reverse flash chromatography with the following conditions: (column, C18 silica gel; mobile phase, ACN in water, 0% to 100% gradient in 30 min; detector, UV 254 nm.) to afford 2-{5-cyano-2-oxo-1H,4H-pyrido[3,4-d]pyrimidin-3-yl}-N-[(1S)-1-(2,4-difluorophenyl)ethyl]acetamide (11 mg, 34.75%). LCMS (ES, m/z): 372 $[M+H]^+$ $^1$H NMR (400 MHz, DMSO-$d_6$) δ 9.90 (s, 1H), 8.61-8.52 (m, 2H), 8.25 (s, 1H), 7.47-7.41 (m, 1H), 7.21-7.16 (m, 1H), 7.09-7.04 (m, 1H), 5.13 (t, J=6.8 Hz, 1H), 4.70 (s, 2H), 4.04 (s, 2H), 1.36 (d, J=6.8 Hz, 3H).

Example 28: (R)—N-(1-(5-cyano-3-fluoropyridin-2-yl)ethyl)-2-(5,6-difluoro-2-oxo-1,4-dihydroquinazolin-3(2H)-yl)acetamide (Compound B141)

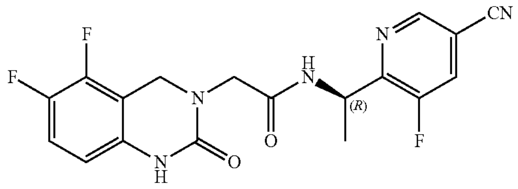

1,2-Difluoro-4-nitro-3-(nitromethyl)benzene. 1,1,3,3-tetramethylguanidine (77.93 g, 677.652 mmol, 2 equiv) was added dropwise at −30° C. a solution of 1,2,3-trifluoro-4-nitrobenzene (60 g, 338.826 mmol, 1 equiv) in nitromethane (206.82 g, 3388.260 mmol, 10 equiv) under $N_2$ atmosphere. The reaction was quenched by the addition of HCl (0.1 M) (5 L) at RT and the precipitated solids were collected by filtration and washed with $H_2O$. The crude product was used in the next step directly without further purification.

2-(Aminomethyl)-3,4-difluoroaniline. Pd/C (10%, 20 g) under $N_2$ atmosphere was added to a solution of 1,2-difluoro-4-nitro-3-(nitromethyl)benzene (60 g, 275.083 mmol, 1 equiv) in MeOH (600 mL). The mixture was stirred at RT for 72 h under $H_2$ atmosphere using a hydrogen balloon, then filtered through a Celite pad and concentrated under reduced pressure. The reaction mixture was filtered, the filter cake was washed with MeOH. The filtrate was concentrated under reduced pressure resulting in 2-(aminomethyl)-3,4-difluoroaniline (30 g, 68.96%).

ethyl 2-{[(6-amino-2,3-difluorophenyl)methyl]amino}acetate. A solution of 2-(aminomethyl)-3,4-difluoroaniline (30 g, 189.691 mmol, 1 equiv) in MeCN (300 mL) was treated with $K_2CO_3$ (78.65 g, 569.073 mmol, 3.0 equiv) under $N_2$ atmosphere followed by dropwise addition of methyl 2-bromoacetate (37.72 g, 246.598 mmol, 1.3 equiv) at 0° C. The reaction mixture was stirred for 30 min at 0° C. under $N_2$ atmosphere. The reaction mixture was filtered and the filter cake was washed with EtOAc. The filtrate was concentrated under reduced pressure and the residue was purified by trituration with tert-butyl methyl ether proving methyl 2-{[(6-amino-2,3-difluorophenyl)methyl]amino}acetate (28 g, 64.12%).

ethyl 2-(5,6-difluoro-2-oxo-1,4-dihydroquinazolin-3-yl)acetate. CDI (29.58 g, 182.438 mmol, 1.5 equiv) was added in portions at RT to a solution of methyl 2-{[(6-amino-2,3-difluorophenyl)methyl]amino}acetate (28 g, 121.625 mmol, 1 equiv) and DBU (55.55 g, 364.875 mmol, 3.0 equiv) in DCM (300 mL) under $N_2$ atmosphere. The reaction mixture was stirred for 30 min at RT under $N_2$ atmosphere. The residue was purified by trituration with PE resulting in methyl 2-(5,6-difluoro-2-oxo-1,4-dihydroquinazolin-3-yl)acetate (13 g, 41.72%).

(5,6-Difluoro-2-oxo-1,4-dihydroquinazolin-3-yl)acetic acid. A solution of methyl 2-(5,6-difluoro-2-oxo-1,4-dihydroquinazolin-3-yl)acetate (13 g, 50.740 mmol, 1 equiv) and LiOH (3.65 g, 152.220 mmol, 3 equiv) in THF (65 mL) and $H_2O$ (65 mL) was stirred for 1 h at RT. The reaction mixture was concentrated under reduced pressure. The mixture was adjusted to pH 3 with HCl (aq.). The precipitated solids were collected by filtration and washed with $H_2O$ resulting in (5,6-difluoro-2-oxo-1,4-dihydroquinazolin-3-yl)acetic acid (11 g, 89.52%).

(R)—N-(1-(5-cyano-3-fluoropyridin-2-yl)ethyl)-2-(5,6-difluoro-2-oxo-1,4-dihydroquinazolin-3(2H)-yl)acetamide. A solution of (5,6-difluoro-2-oxo-1,4-dihydroquinazolin-3-yl)acetic acid (3.5 g, 14.452 mmol, 1 equiv), 6-[(1R)-1-aminoethyl]-5-fluoropyridine-3-carbonitrile (2.90 g, 14.452 mmol, 1 equiv), HATU (6.59 g, 17.342 mmol, 1.2 equiv) and DIEA (7.47 g, 57.808 mmol, 4 equiv) in DMF (35 mL) was stirred for 1 h at RT under $N_2$ atmosphere. The crude product was purified by Flash-Prep-HPLC with the following conditions (IntelFlash-1): Column: Waters XBridge RP18 19*150 mm, 5 um; mobile phase: water (it contains 0.05% ammonia and 10 mM formic acid) and MeCN with a gradient of 20% to 60% MeCN in 20 min; flow rate: 150 mL/min; detector UV wavelength: 254 nm. This resulted in (R)—N-(1-(5-cyano-3-fluoropyridin-2-yl)ethyl)-2-(5,6-difluoro-2-oxo-1,4-dihydroquinazolin-3(2H)-yl)acetamide (3.1 g, 55.09%). LCMS: (ES,m/z): 390 $[M+H]^+$ 1H NMR (300 MHz, DMSO-$d_6$) δ 9.63-9.38 (m, 1H), 8.98-8.82 (m, 1H), 8.78-8.62 (m, 1H), 8.48-8.24 (m, 1H), 7.31-7.08 (m, 1H), 6.68-6.49 (m, 1H), 5.46-5.14 (m, 1H), 4.64-4.37 (m, 2H), 4.27-3.85 (m, 2H), 1.58-1.24 (m, 3H).

Example 29: N-[(7R)-3-Cyano-5H,6H,7H-cyclopenta[b]pyridin-7-yl]-2-(5,6-difluoro-2-oxo-1,4-dihydroquinazolin-3-yl)acetamide (Compound B89)

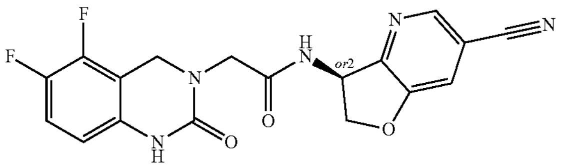 [SMILES: N#Cc1cnc2c(c1)OC[C@H]2NC(=O)CN1Cc2c(ccc(F)c2F)NC1=O]

3-Bromo-5H,6H,7H-1lambda5-cyclopenta[b]pyridin-1-one. m-CPBA (5715.32 mg, 33.120 mmol, 2 equiv) was added in portions at 0° C. under air atmosphere to a stirred solution of 3-bromo-5H,6H,7H-cyclopenta[b]pyridine (4.1 g, 16.560 mmol, 1 equiv, 80%) in $CHCl_3$ (50 mL). The reaction mixture was stirred for 12 h at 80° C. under air atmosphere. The residue was purified by column chromatography to afford 3-bromo-5H,6H,7H-1lambda5-cyclopenta[b]pyridin-1-one (3.3 g, 89.37%). LCMS (ES, m/z): $214[M+H]^+$.

3-Bromo-5H,6H,7H-cyclopenta[b]pyridin-7-ol. TFAA (7.80 g, 37.139 mmol, 1.5 equiv) was added at RT under air atmosphere to a stirred solution of 3-bromo-5H,6H,7H-1lambda5-cyclopenta[b]pyridin-1-one (5.3 g, 24.759 mmol, 1 equiv) in DCM (50 mL). The reaction mixture was stirred for 12 h at 40° C. under air atmosphere. The reaction mixture was concentrated under vacuum. To the above mixture NaOH (2.12 g, 52.984 mmol, 2.14 equiv) was added at RT. The reaction mixture was stirred for additional 3 h at 40° C. The reaction mixture was concentrated under reduced pressure. The residue was purified by column chromatography to afford 3-bromo-5H,6H,7H-cyclopenta[b]pyridin-7-ol (4.2 g, 73.70%). LCMS (ES, m/z): $214[M+H]^+$.

7-Azido-3-bromo-5H,6H,7H-cyclopenta[b]pyridine. DPPA (6.97 g, 25.324 mmol, 1.3 equiv) was added at RT under air atmosphere to a stirred solution of 3-bromo-5H,6H,7H-cyclopenta[b]pyridin-7-ol (4.17 g, 19.480 mmol, 1 equiv) and DBU (3.86 g, 25.324 mmol, 1.3 equiv) in THF (50 mL). The reaction mixture was stirred for 12 h at 50° C. under air atmosphere. The residue was purified by column chromatography to afford 7-azido-3-bromo-5H,6H,7H-cyclopenta[b]pyridine (4.278 g, 83.59%). LCMS (ES, m/z): $239[M+H]^+$.

3-Bromo-5H,6H,7H-cyclopenta[b]pyridin-7-amine. $PPh_3$ (3.00 g, 11.444 mmol, 1.2 equiv) was added at 0° C. under air atmosphere to a stirred solution of 7-azido-3-bromo-5H,6H,7H-cyclopenta[b]pyridine (2.28 g, 9.537 mmol, 1 equiv) and $H_2O$ (4 mL) in THF (16 mL). The reaction mixture was stirred for 3 h at RT under air atmosphere. The reaction mixture was concentrated under vacuum. The residue was purified by column chromatography to afford 3-bromo-5H,6H,7H-cyclopenta[b]pyridin-7-amine (1.78 g, 85.84%). LCMS (ES, m/z): $213[M+H]^+$.

(7R)-3-bromo-5H,6H,7H-cyclopenta[b]pyridin-7-amine. 3-bromo-5H,6H,7H-cyclopenta[b]pyridin-7-amine (1.78 g, 8.396 mmol) was separated by Chiral-HPLC: Column: N-CHIRALPAK IG (Lot No. IG30CS-VL001), 4.6*100 mm, 3.0 um; Mobile Phase B: EtOH (20 mM $NH_3$); Flow rate: 2 mL/min; Gradient: isocratic 10% B; Wave Length: 220 nm; Injection Volume: 5 mL. to afford (7R)-3-bromo-5H,6H,7H-cyclopenta[b]pyridin-7-amine (600 mg, 33.71%). LCMS (ES, m/z): 213[M+H]+.

N-[(7R)-3-bromo-5H,6H,7H-cyclopenta[b]pyridin-7-yl]-2-(5,6-difluoro-2-oxo-1,4-dihydroquinazolin-3-yl)acetamide. (7R)-3-bromo-5H,6H,7H-cyclopenta[b]pyridin-7-amine (179.48 mg, 0.842 mmol, 1.2 equiv) was added at RT under air atmosphere to a stirred solution of (5,6-difluoro-2-oxo-1,4-dihydroquinazolin-3-yl)acetic acid (170 mg, 0.702 mmol, 1 equiv), DMAP (17.15 mg, 0.140 mmol, 0.2 equiv) and EDCI (201.85 mg, 1.053 mmol, 1.5 equiv) in DMF (3 mL). The reaction mixture was stirred for 12 h at RT under air atmosphere. The reaction mixture was diluted with water. The precipitated solids were collected by filtration and washed with MeCN to afford N-[(7R)-3-bromo-5H,6H,7H-cyclopenta[b]pyridin-7-yl]-2-(5,6-difluoro-2-oxo-1,4-dihydroquinazolin-3-yl)acetamide (330 mg, 96.77%). LCMS (ES, m/z): $437[M+H]^+$.

N-[(7R)-3-cyano-5H,6H,7H-cyclopenta[b]pyridin-7-yl]-2-(5,6-difluoro-2-oxo-1,4-dihydroquinazolin-3-yl)acetamide. Zn (5.98 mg, 0.092 mmol, 0.4 equiv) and Pd(dppf)$Cl_2$ (33.47 mg, 0.046 mmol, 0.2 equiv) were added at RT under argon atmosphere to a stirred solution of N-[(7R)-3-bromo-5H,6H,7H-cyclopenta[b]pyridin-7-yl]-2-(5,6-difluoro-2-oxo-1,4-dihydroquinazolin-3-yl)acetamide (100 mg, 0.229 mmol, 1 equiv) and $Zn(CN)_2$ (53.71 mg, 0.458 mmol, 2 equiv) in DMF (2 mL). The reaction mixture was stirred for 12 h at 100° C. under argon atmosphere. The residue was purified by reverse flash chromatography with the following conditions: column, C18 silica gel; mobile phase, MeOH in Water (10 mmol/L $NH_4HCO_3$), 0% to 100% gradient in 50 min; detector, UV 254 nm. to afford N-[(7R)-3-cyano-5H,6H,7H-cyclopenta[b]pyridin-7-yl]-2-(5,6-difluoro-2-oxo-1,4-dihydroquinazolin-3-yl)acetamide (30 mg, 33.70%). LCMS (ES, m/z): $384[M+H]^+$. $^1H$ NMR (400 MHz, DMSO-$d_6$) δ 9.52 (s, 1H), 8.83 (s, 1H), 8.52 (d, J=8.0 Hz, 1H), 8.18 (s, 1H), 7.26-7.19 (m, 1H), 6.58-6.55 (m, 1H), 5.37-5.31 (q, J=8.5 Hz, 1H), 4.59 (s, 2H), 4.03 (s, 2H), 3.31-2.84 (m, 2H), 2.49-2.47 (s, 1H), 1.94-1.84 (m, 1H).

Example 30: rel-2-(5,6-difluoro-2-oxo-1,4-dihydroquinazolin-3-yl)-N-[(3R)-6-fluoro-3,4-dihydro-2H-1-benzopyran-3-yl]acetamide (Compound B87)

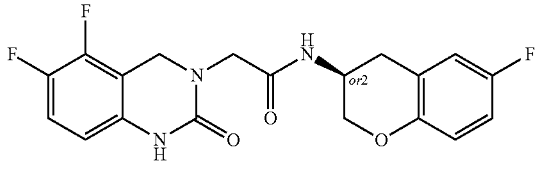 [SMILES: O=C(CN1Cc2c(ccc(F)c2F)NC1=O)N[C@@H]1COc2ccc(F)cc2C1]

6-Fluoro-3-nitro-2H-chromene. A solution of 5-fluoro-2-hydroxybenzaldehyde (9 g, 64.234 mmol, 1 equiv) and phthalic anhydride (19.03 g, 128.468 mmol, 2 equiv), dibutylamine (4.15 g, 32.117 mmol, 0.5 equiv), 2-nitroethanol (11.70 g, 128.468 mmol, 2 equiv) in Toluene (100 mL) was stirred for 48 h at 110° C. under air atmosphere. The reaction mixture was concentrated under vacuum. The residue was purified by column chromatography to afford 6-fluoro-3-nitro-2H-chromene (700 mg, 5.58%). LCMS (ES, m/z): 196 $[M+H]^+$ 6-Fluoro-3,4-dihydro-2H-1-benzopyran-3-amine. A solution of 6-fluoro-3-nitro-2H-chromene (700 mg, 3.587 mmol, 1 equiv) and $NaBH_4$ (339.24 mg, 8.968 mmol, 2.5 equiv) in $CHCl_3$ (5 mL) and IPA (2 mL) was stirred for 0.5 h at RT under air atmosphere. To the above mixture AcOH (0.15 mL) was added dropwise at RT. The reaction mixture was stirred for additional 0.5 h at RT. The reaction mixture was filtered and the filtrate was concentrated under reduced pressure. The residue was purified by column chromatography to afford 6-fluoro-3-nitro-3,4-dihydro-2H-1-benzopyran (470 mg, 66.46%). LCMS (ES, m/z): 198 $[M+H]^+$ 6-Fluoro-3,4-dihydro-2H-1-benzopyran-3-amine. A solution of 6-fluoro-3-nitro-3,4-dihydro-2H-1-benzopyran (470 mg, 2.384 mmol, 1 equiv) and Fe (665.61 mg, 11.920 mmol, 5 equiv), $NH_4Cl$ (1275.09 mg, 23.840 mmol, 10 equiv) in EtOH (8 mL) and $H_2O$ (1.6 mL) was stirred for 2 h at 80° C. under air atmosphere. The reaction mixture was filtered, the filtrate was concentrated under reduced pressure. The residue was purified by column chromatography to afford 6-fluoro-3,4-dihydro-2H-1-benzopyran-3-amine (280 mg, 70.26%). LCMS (ES, m/z): 168 $[M+H]^+$ rel-(3R)-4,6-difluoro-2,3-dihydro-1-benzofuran-3-amine. The product (280 mg) was purified by CHIRAL-HPLC with the following conditions: (Column: CHIRAL ART Amylose-C NEO, 2*25 cm, 5 μm; Mobile Phase A: Hex (10 mM $NH_3$-MeOH), Mobile Phase B: EtOH-HPLC; Flow rate: 20 mL/min; Gradient: 30% B to 30% B in 14 min; Wave Length: 212/284 nm; RT1 (min): 7.415; RT2 (min): 9.475; Sample Solvent: MeOH-HPLC; Injection Volume: 0.55 mL;) to afford rel-(3R)-6-fluoro-3,4-dihydro-2H-1-benzopyran-3-amine (110 mg). LCMS (ES, m/z): 168 $[M+H]^+$ rel-2-(5,6-difluoro-2-oxo-1,4-dihydroquinazolin-3-yl)-N-[(3R)-6-fluoro-3,4-dihydro-2H-1-benzopyran-3-yl]acetamide. A solution of (5,6-difluoro-2-oxo-1,4-dihydroquinazolin-3-yl)acetic acid (130 mg, 0.537 mmol, 1 equiv) and rel-(3R)-6-fluoro-3,4-dihydro-2H-1-benzopyran-3-amine (89.74 mg, 0.537 mmol, 1 equiv), DMAP (32.79 mg, 0.269 mmol, 0.5 equiv), EDCI (123.48 mg, 0.644 mmol, 1.2 equiv) in DMF (2 mL) was stirred for 2 h at RT under air atmosphere. The reaction mixture was extracted with EtOAc. The combined organic layers were concentrated under reduced pressure. The residue was purified by reverse flash chromatography with the following conditions: column, C18 silica gel; mobile phase, MeCN in Water (0.1% FA), 0% to 100% gradient in 30 min; detector, UV 254 nm to afford rel-2-(5,6-difluoro-2-oxo-1,4-dihydroquinazolin-3-yl)-N-[(3R)-6-fluoro-3,4-dihydro-2H-1-benzopyran-3-yl]acetamide (90.5 mg, 42.78%). LCMS (ES, m/z): 392 $[M+H]^+$. $^1H$ NMR (400 MHz, DMSO-$d_6$) δ 9.46 (d, J=1.6 Hz, 1H), 8.16 (d, J=7.2 Hz, 1H), 7.25-7.18 (m, 1H), 6.98-6.90 (m, 2H), 6.81-6.78 (m, 1H), 6.58-6.56 (m, 1H), 4.56 (s, 2H), 4.17-4.13 (m, 2H), 3.97 (s, 2H), 3.90-3.85 (m, 1H), 3.05-2.99 (m, 1H), 2.75-2.69 (m, 1H).

Example 31: rel-2-(5,6-Difluoro-2-oxo-1,4-dihydroquinazolin-3-yl)-N-[(4R)-7-fluoro-3,4-dihydro-1H-2-benzopyran-4-yl (Compound B76)

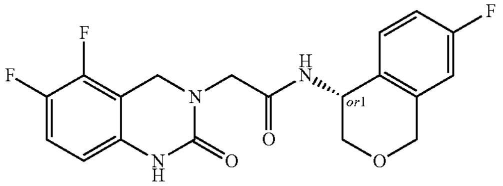 [SMILES: O=C(CN1Cc2c(ccc(F)c2F)NC1=O)N[C@H]1COCc2cc(F)ccc21]

1-Bromo-4-fluoro-2-[(prop-2-en-1-yloxy)methyl]benzene. (2-bromo-5-fluorophenyl)methanol (4.6 g, 22.436 mmol, 1 equiv), allyl bromide (2.71 g, 22.436 mmol, 1 equiv), KOH (2.39 g, 42.628 mmol, 1.9 equiv) and $Bu_4NHSO_4$ (1.52 g, 4.487 mmol, 0.2 equiv) were added into a vial at RT. The reaction mixture was stirred for 4 h at RT under air atmosphere. Then water was added, and the aqueous layer was extracted with EtOAc. The combined organic layers were dried by $Na_2SO_4$, the reaction mixture was concentrated under reduced pressure. The residue was purified by column chromatography to afford 1-bromo-4-fluoro-2-[(prop-2-en-1-yloxy)methyl]benzene (5.3 g, 96.38%). LCMS (ES, m/z): 245 $[Ms+H]^+$.

7-Fluoro-4-methylidene-1,3-dihydro-2-benzopyran. DPPP (1.78 g, 4.325 mmol, 0.2 equiv) and $K_2CO_3$ (5.98 g, 43.250 mmol, 2 equiv) were added in portions at 110° C. under argon atmosphere to a stirred solution of 1-bromo-4-fluoro-2-[(prop-2-en-1-yloxy)methyl]benzene (5.3 g, 21.625 mmol, 1 equiv) and $Pd_2(dba)_3$ (1.24 g, 2.163 mmol, 0.1 equiv) in dioxane (60 mL). The reaction mixture was stirred for overnight at 110° C. under argon atmosphere. The reaction mixture was concentrated under reduced pressure. The residue was purified by column chromatography to afford 7-fluoro-4-methylidene-1,3-dihydro-2-benzopyran (3.9 g, 109.85%). LCMS (ES, m/z): 165 $[Ms+H]^+$.

7-Fluoro-1,3-dihydro-2-benzopyran-4-one. $OsO_4$ (58.84 mg, 0.231 mmol, 0.01 equiv) was added in portions at RT under air atmosphere to a stirred mixture of 7-fluoro-4-methylidene-1,3-dihydro-2-benzopyran (3.8 g, 23.145 mmol, 1 equiv) and $NaIO_4$ (14851.75 mg, 69.435 mmol, 3 equiv) in THF (100 mL). The reaction mixture was stirred for 2 h at RT under air atmosphere. The reaction was quenched with sat. sodium hyposulfite (aq.) at 0° C. And water was added, the aqueous layer was extracted with EtOAc, combined the organic layer, and dried over $Na_2SO_4$. The residue was purified by column chromatography to afford 7-fluoro-1,3-dihydro-2-benzopyran-4-one (3 g, 78.01%). LCMS (ES, m/z): 167 $[M+H]^+$ 7-Fluoro-3,4-dihydro-1H-2-benzopyran-4-amine. $NaBH_3CN$ (1.89 g, 30.095 mmol, 5 equiv) was added in portions at RT under air atmosphere to a stirred mixture of 7-fluoro-1,3-dihydro-2-benzopyran-4-one (1 g, 6.019 mmol, 1 equiv) and $CH_3COONH_4$ (9.28 g, 120.380 mmol, 20 equiv) in MeOH (30 mL). The reaction mixture was stirred for an additional 2 h at RT. The reaction mixture was stirred for overnight at 80° C. under air atmosphere. The reaction mixture was concentrated under reduced pressure. The residue was purified by column chromatography to afford 7-fluoro-3,4-dihydro-1H-2-benzopyran-4-amine (650 mg, 64.60%). LCMS (ES, m/z): 168 $[M+H]^+$ 2-(5,6-Difluoro-2-oxo-1,4-dihydroquinazolin-3-yl)-N-(7-fluoro-3,4-dihydro-1H-2-benzopyran-4-yl)acetamide. EDCI (222.86 mg, 1.435 mmol, 1.2 equiv) and DMAP (58.46 mg, 0.478 mmol, 0.4 equiv) were added at RT under air atmosphere to a stirred mixture of 7-fluoro-3,4-dihydro-1H-2-benzopyran-4-amine (200 mg, 1.196 mmol, 1 equiv) and (5,6-difluoro-2-oxo-1,4-dihydroquinazolin-3-yl)acetic acid (347.67 mg, 1.435 mmol, 1.2 equiv) in DMF (3 mL). The reaction mixture was stirred for 2 h at RT under air atmosphere. Water was added and the precipitated solids were collected by filtration and washed with water. The residue was purified by trituration with MeCN. This resulted in 2-(5,6-difluoro-2-oxo-1,4-dihydroquinazolin-3-yl)-N-(7-fluoro-3,4-dihydro-1H-2-benzopyran-4-yl)acetamide (240 mg, 51.26%). LCMS (ES, m/z): 392 $[M+H]^+$.

rel-2-(5,6-Difluoro-2-oxo-1,4-dihydroquinazolin-3-yl)-N-[(4R)-7-fluoro-3,4-dihydro-1H-2-benzopyran-4-yl]acetamide. The rel-2-(5,6-difluoro-2-oxo-1,4-dihydroquinazolin-3-yl)-N-[(4R)-7-fluoro-3,4-dihydro-1H-2-benzopyran-4-yl]acetamide was separated by Chiral-HPLC, (Column: CHIRAL ART Cellulose-SZ, 3*25 cm, 5 μm; Mobile Phase A: Hex (0.5% 2M $NH_3$-MeOH), Mobile Phase B: EtOH; Flow rate: 40 mL/min; Gradient: 30% B to 30% B in 17 min; Wave Length: 200/247 nm; $RT_1$ (min): 8; RT2 (min): 12; Sample Solvent: DMF; Injection Volume: 1.4 mL), to afford rel-2-(5,6-difluoro-2-oxo-1,4-dihydroquinazolin-3-yl)-N-[(4R)-7-fluoro-3,4-dihydro-1H-2-benzopyran-4-yl]acetamide (99.8 mg, 43.39%). LCMS (ES, m/z): 392.00 $[M+H]^+$. $^1H$ NMR (300 MHz, DMSO-$d_6$): δ 9.48 (s, 1H), 8.46 (d, J=8.1 Hz, 1H), 7.35-6.99 (m, 4H), 6.96-6.56 (m, 1H), 6.62-6.52 (m, 1H), 4.96-4.95 (m, 1H), 4.72-4.69 (m, 2H), 4.59 (s, 2H), 4.00 (s, 2H), 3.85-3.84 (m, 1H), 3.73-3.72 (m, 1H).

Example 32: rel-2-(5,6-difluoro-2-oxo-1,4-dihydroquinazolin-3-yl)-N-[(1R)-1-{1-methyl-2H,3H-pyrido[3,4-b][1,4]oxazin-7-yl}ethyl]acetamide (Compound B74)

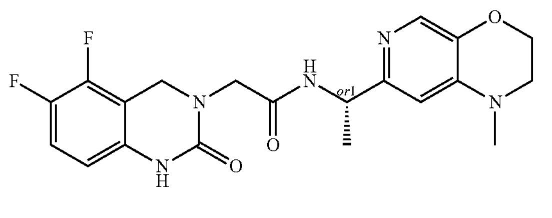 [SMILES: C[C@H](NC(=O)CN1Cc2c(ccc(F)c2F)NC1=O)c1cc2c(cn1)OCCN2C]

7-Bromo-1H,2H,3H-pyrido[3,4-b][1,4]oxazine. $BH_3$-THF (722.32 mg, 8.405 mmol, 2.5 equiv) was added dropwise at 0° C. under Ar atmosphere to a stirred solution of 7-bromo-1H,3H-pyrido[3,4-b][1,4]oxazin-2-one (770 mg, 3.362 mmol, 1 equiv) in THF (10 mL). The reaction mixture was stirred for 2 h at 80° C. under Ar atmosphere. The reaction was quenched with MeOH at 0° C. The reaction mixture was concentrated under reduced pressure. The residue was purified by Prep-TLC ($CH_2Cl_2$/MeOH=20:1) to afford 7-bromo-1H,2H,3H-pyrido[3,4-b][1,4]oxazine (540 mg, 74.69%). LCMS (ES, m/z): 215$[M+H]^+$.

7-Bromo-1-methyl-2H,3H-pyrido[3,4-b][1,4]oxazine. A solution of 7-bromo-1H,2H,3H-pyrido[3,4-b][1,4]oxazine (340 mg, 1.581 mmol, 1 equiv) and t-BuOK (266.12 mg, 2.372 mmol, 1.5 equiv) in THF (5 mL) was stirred at RT under air atmosphere. The reaction mixture was stirred for 30 min at RT under air atmosphere. To the above mixture Mel (224.41 mg, 1.581 mmol, 1 equiv) was added dropwise over 2 min at RT. The reaction mixture was stirred for additional 12 h at RT. The residue was purified by column chromatography to afford 7-bromo-1-methyl-2H,3H-pyrido[3,4-b][1,4]oxazine (300 mg, 82.83%). LCMS (ES, m/z): 229$[M+H]^+$.

1-{1-Methyl-2H,3H-pyrido[3,4-b][1,4]oxazin-7-yl}ethenone. A solution of 7-bromo-1-methyl-2H,3H-pyrido[3,4-b][1,4]oxazine (295 mg, 1.288 mmol, 1 equiv) in THF (3 mL) was treated with n-BuLi (123.74 mg, 1.932 mmol, 1.5 equiv) for 30 min at −78° C. under $N_2$ atmosphere followed by the addition of N-methoxy-N-methylacetamide (663.98 mg, 6.440 mmol, 5 equiv) dropwise at −78° C. The reaction mixture was stirred for 2 h at −78° C. under Ar atmosphere. The reaction was quenched with sat. $NH_4Cl$ (aq.) at 0° C. The reaction mixture was extracted with EtOAc. The combined organic layers were washed with brine and dried over anhydrous $Na_2SO_4$ and filtered. The filtrate was concentrated under reduced pressure. The residue was purified by Prep-TLC (PE/EA 1:1) to afford 1-{1-methyl-2H,3H-pyrido[3,4-b][1,4]oxazin-7-yl}ethanone (180 mg, 67.63%). LCMS (ES, m/z): 193$[M+H]^+$.

1-{1-Methyl-2H,3H-pyrido[3,4-b][1,4]oxazin-7-yl}ethanamine. $NaBH_3CN$ (205.96 mg, 3.279 mmol, 3 equiv) was added in portions at RT under air atmosphere to a stirred solution of 1-{1-methyl-2H,3H-pyrido[3,4-b][1,4]oxazin-7-yl}ethanone (210 mg, 1.093 mmol, 1 equiv) and $NH_4OAc$ (842.14 mg, 10.930 mmol, 10 equiv) in MeOH (3 mL). The reaction mixture was stirred for 12 h at 80° C. under air atmosphere. The residue was purified by Prep-TLC ($CH_2Cl_2$/MeOH 10:1) to afford 1-{1-methyl-2H,3H-pyrido[3,4-b][1,4]oxazin-7-yl}ethanamine (150 mg, 67.49%). LCMS (ES, m/z): 194$[M+H]^+$.

2-(5,6-Difluoro-2-oxo-1,4-dihydroquinazolin-3-yl)-N-(1-{1-methyl-2H,3H-pyrido[3,4-b][1,4]oxazin-7-yl}ethyl)acetamide. EDCI (178.10 mg, 0.928 mmol, 1.5 equiv) and DMAP (15.13 mg, 0.124 mmol, 0.2 equiv) were added at RT under air atmosphere to a stirred solution of (5,6-difluoro-2-oxo-1,4-dihydroquinazolin-3-yl)acetic acid (150 mg, 0.619 mmol, 1 equiv) and 1-{1-methyl-2H,3H-pyrido[3,4-b][1,4]oxazin-7-yl}ethanamine (143.63 mg, 0.743 mmol, 1.2 equiv) in DMF (2 mL). The reaction mixture was stirred for 3 h at RT under air atmosphere. The residue was purified by reverse flash chromatography with the following conditions: (column, C18 silica gel; mobile phase, MeCN in Water (10 mmol/L $NH_4HCO_3$), 0% to 30% gradient in 20 min; detector, UV 254 nm). to afford 2-(5,6-difluoro-2-oxo-1,4-dihydroquinazolin-3-yl)-N-(1-{1-methyl-2H,3H-pyrido[3,4-b][1,4]oxazin-7-yl}ethyl)acetamide (140 mg, 48.74%). LCMS (ES, m/z): 418$[M+H]^+$.

rel-2-(5,6-Difluoro-2-oxo-1,4-dihydroquinazolin-3-yl)-N-[(1R)-1-{1-methyl-2H,3H-pyrido[3,4-b][1,4]oxazin-7-yl}ethyl]acetamide. The 2-(5,6-difluoro-2-oxo-1,4-dihydroquinazolin-3-yl)-N-(1-{1-methyl-2H,3H-pyrido[3,4-b][1,4]oxazin-7-yl}ethyl)acetamide (1 equiv) was separated by Chiral-HPLC (Column: CHIRAL ART Cellulose-SZ, 4.6*50 mm, 3 μm; Mobile Phase A: Hex (0.1% DEA): EtOH=50:50; Flow rate: 1 mL/min; Gradient: 0% B to 0%

B; Injection Volume: 5 ul mL). to afford rel-2-(5,6-difluoro-2-oxo-1,4-dihydroquinazolin-3-yl)-N-[(1R)-1-{1-methyl-2H,3H-pyrido[3,4-b][1,4]oxazin-7-yl}ethyl]acetamide (45.0 mg, 30.82%). LCMS (ES, m/z): 418.10 $[M+H]^+$. $^1H$ NMR (300 MHz, DMSO-$d_6$) δ 9.48 (s, 1H), 8.32 (d, J=8.1 Hz, 1H), 7.68 (s, 1H), 7.27-7.17 (m, 1H), 6.60-6.54 (m, 1H), 4.83-4.78 (m, 1H), 4.57 (s, 2H), 4.18 (t, J=4.5 Hz, 2H), 4.00 (d, J=8.1 Hz, 2H), 3.36-3.34 (m, 2H), 2.91 (s, 3H), 1.32 (d, J=6.9 Hz, 3H).

Example 33: N-[(1S)-1-(4-cyano-2-fluorophenyl)ethyl]-2-(5-fluoro-6-methyl-2-oxo-1,4-dihydroquinazolin-3-yl)acetamide (Compound B31)

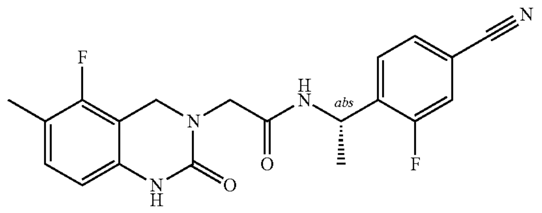 [SMILES: Cc1ccc2c(c1F)CN(CC(=O)N[C@@H](C)c1ccc(C#N)cc1F)C(=O)N2]

2-Fluoro-3-methyl-6-nitrobenzaldehyde. Potassium methaneperoxoate potassium (5.05 g, 36.288 mmol, 3 equiv) and Pd(dppf)$Cl_2$ (0.89 g, 1.210 mmol, 0.1 equiv) were added to a solution of 3-bromo-2-fluoro-6-nitrobenzaldehyde (3 g, 12.096 mmol, 1 equiv) and methylboronic acid (3.62 g, 60.480 mmol, 5 equiv) in dioxane (30 mL) and $H_2O$ (6 mL). After stirring for 6 hours at 95° C. under an Ar atmosphere. The reaction mixture was concentrated under reduced pressure. The residue was purified by column chromatography to afford 2-fluoro-3-methyl-6-nitrobenzaldehyde (1.05 g, 45.03%). LC-MS: (ESI, m/z): 184 $[M+H]^+$ Methyl 2-{[(2-fluoro-3-methyl-6-nitrophenyl)methyl]amino}acetate. Methyl 2-aminoacetate (442.70 mg, 4.969 mmol, 1.3 equiv) at RT to a solution of 2-fluoro-3-methyl-6-nitrobenzaldehyde (700 mg, 3.822 mmol, 1 equiv) in DCM (10 mL). The mixture was stirred for 1 h at 50° C. Then STAB (2025.22 mg, 9.555 mmol, 2.5 equiv) was added at RT. The mixture was stirred for 16 hours at RT. The reaction mixture was concentrated under reduced pressure. The residue was purified by column chromatography to afford methyl 2-{[(2-fluoro-3-methyl-6-nitrophenyl)methyl]amino}acetate (490 mg, 45.03%). LC-MS: (ESI, m/z): 257 $[M+H]^+$ Methyl 2-{[(6-amino-2-fluoro-3-methylphenyl)methyl]amino}acetate. $NH_4Cl$ (1043.78 mg, 19.510 mmol, 10 equiv) and iron (544.87 mg, 9.755 mmol, 5 equiv) were added at RT to a solution of methyl 2-{[(2-fluoro-3-methyl-6-nitrophenyl)methyl]amino}acetate (500 mg, 1.951 mmol, 1 equiv) in isopropyl alcohol (10 mL) and $H_2O$ (2 mL). The mixture was stirred for 5 h at 50° C. The reaction mixture was filtered, the filter cake was washed with MeOH. The filtrate was concentrated under reduced pressure. The residue was purified by column chromatography to afford methyl 2-{[(6-amino-2-fluoro-3-methylphenyl)methyl]amino}acetate (375 mg, 78.14%). LC-MS: (ESI, m/z): 227 $[M+H]^+$ Methyl 2-(5-fluoro-6-methyl-2-oxo-1,4-dihydroquinazolin-3-yl)acetate. CDI (609.19 mg, 3.757 mmol, 2.5 equiv) and DBU (571.95 mg, 3.757 mmol, 2.5 equiv) were added at 0° C. to a solution of methyl 2-{[(6-amino-2-fluoro-3-methylphenyl)methyl]amino}acetate (340 mg, 1.503 mmol, 1 equiv) in DCM (8 mL). The mixture was stirred for 15 h at RT. The reaction mixture was concentrated under reduced pressure. The residue was purified by reverse flash chromatography with the following conditions: (column, C18 silica gel; mobile phase, 0.1% HCOOH in ACN, 0% to 100% gradient in 60 min; detector, UV 254 nm.) to afford methyl 2-(5-fluoro-6-methyl-2-oxo-1,4-dihydroquinazolin-3-yl)acetate (240 mg, 60.15%). LC-MS: (ESI, m/z): 253 $[M+H]^+$ (5-Fluoro-6-methyl-2-oxo-1,4-dihydroquinazolin-3-yl)acetic acid. LiOH (45.57 mg, 1.902 mmol, 2 equiv) was added at RT to a solution of methyl 2-(5-fluoro-6-methyl-2-oxo-1,4-dihydroquinazolin-3-yl)acetate (240 mg, 0.951 mmol, 1 equiv) in MeOH (4 mL) and $H_2O$ (2 mL). The mixture was stirred for 4 h at RT. The reaction mixture was concentrated under reduced pressure. The reaction mixture was diluted with $H_2O$. The mixture was adjusted to pH 5 with HCl (1 M). The reaction mixture was filtered, the filter cake was washed with $H_2O$. The filter cake was concentrated under reduced pressure to afford (5-fluoro-6-methyl-2-oxo-1,4-dihydroquinazolin-3-yl)acetic acid (180 mg, 75.45%). lid. LC-MS: (ESI, m/z): 239 $[M+H]^+$ N-[(1S)-1-(4-cyano-2-fluorophenyl)ethyl]-2-(5-fluoro-6-methyl-2-oxo-1,4-dihydroquinazolin-3-yl)acetamide. HATU (72.85 mg, 0.302 mmol, 1.2 equiv) and DIEA (97.66 mg, 0.756 mmol, 3 equiv), and then 4-[(1S)-1-aminoethyl]-3-fluorobenzonitrile (49.62 mg, 0.302 mmol, 1.2 equiv) were added to a solution of (5-fluoro-6-methyl-2-oxo-1,4-dihydroquinazolin-3-yl)acetic acid (60 mg, 0.252 mmol, 1 equiv) in dimethylformamide (2 mL). The mixture was stirred for 15 h at RT. The residue was purified by reverse flash chromatography with the following conditions: column, C18 silica gel; mobile phase, 0.1% HCOOH in Acetonitrile, 0% to 100% gradient in 60 min; detector, UV 254 nm. to afford N-[(1S)-1-(4-cyano-2-fluorophenyl)ethyl]-2-(5-fluoro-6-methyl-2-oxo-1,4-dihydroquinazolin-3-yl)acetamide (18.2 mg, 18.20%). LC-MS: (ESI, m/z): 385.10 $[M+H]^+$ $^1H$ NMR (400 MHz, DMSO-$d_6$) δ 9.36 (s, 1H), 8.67 (d, J=7.2 Hz, 1H), 7.83-7.80 (m, 1H), 7.69 (dd, J=9.2, 1.2 Hz, 1H), 7.60-7.57 (m, 1H), 7.02 (t, J=8.0 Hz, 1H), 6.49 (d, J=8.0 Hz, 1H), 5.18-5.11 (m, 1H), 4.47 (d, J=2.0 Hz, 2H), 4.00 (s, 2H), 2.11 (s, 3H), 1.37 (d, J=7.2 Hz, 3H).

Example 34: rel-N-[(1R)-1-(5-cyano-4-methylpyridin-2-yl) ethyl]-2-(5,6-difluoro-2-oxo-1,4-dihydroquinazolin-3-yl) acetamide (Compound B35)

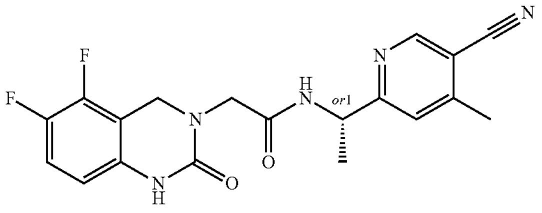 [SMILES: Cc1cc([C@H](C)NC(=O)CN2Cc3c(ccc(F)c3F)NC2=O)ncc1C#N]

5-Bromo-2-(1-ethoxyethenyl)-4-methylpyridine. A solution of 2,5-dibromo-4-methylpyridine (3 g, 11.956 mmol, 1 equiv), $Pd(PPh_3)_4$ (1.38 g, 1.196 mmol, 0.1 equiv) and tributyl(1-ethoxyethenyl) stannane (4.32 g, 11.956 mmol, 1 equiv) in toluene (30 mL) was stirred for 4 h at 100° C. under Ar atmosphere. The residue was purified by column chromatography to afford 5-bromo-2-(1-ethoxyethenyl)-4-methylpyridine (1 g, 34.55%). LCMS (ES, m/z): $[M+H]^+$=242.

1-(5-Bromo-4-methylpyridin-2-yl) ethanone. Into a 10 mL sealed tube were added 5-bromo-2-(1-ethoxyethenyl)-4-methylpyridine (1 g, 4.130 mmol, 1 equiv), HCl (2 mL, 8.000 mmol, 3.16 equiv) and Dioxane (2 mL) at RT. The reaction mixture was stirred for 5 h at RT. The residue was purified by silica gel column chromatography, eluted with PE/EA (10:1) to afford 1-(5-bromo-4-methylpyridin-2-yl) ethanone (500 mg, 56.55%) as a white solid. LCMS (ES, m/z): $[M+H]^+$=214.

1-(5-Bromo-4-methylpyridin-2-yl) ethanamine. Into a 40 mL sealed tube were added 1-(5-bromo-4-methylpyridin-2-yl)ethanone (500 mg, 2.336 mmol, 1 equiv), $CH_3COONH_4$ (3600.97 mg, 46.720 mmol, 20 equiv), $NaBH_3CN$ (733.90 mg, 11.680 mmol, 5 equiv) and MeOH (3 mL) at RT. The reaction mixture was stirred overnight at 80° C. The residue was purified by column chromatography to afford 1-(5-bromo-4-methylpyridin-2-yl)ethanamine (350 mg, 69.66%). LCMS (ES, m/z): $[M+H]^+$=215.

N-[1-(5-Bromo-4-methylpyridin-2-yl) ethyl]-2-(5,6-difluoro-2-oxo-1,4-dihydroquinazolin-3-yl) acetamide. Into a 40 mL sealed tube were added (5,6-difluoro-2-oxo-1,4-dihydroquinazolin-3-yl)acetic acid (281.48 mg, 1.162 mmol, 1 equiv), EDCI (334.21 mg, 1.743 mmol, 1.5 equiv), DMAP (28.40 mg, 0.232 mmol, 0.2 equiv) 1-(5-bromo-4-methylpyridin-2-yl)ethanamine (250 mg, 1.162 mmol, 1 equiv) and DMF (5 mL) at RT. The reaction mixture was stirred for 2 h at RT. The residue was purified by reverse flash chromatography with the following conditions: column, C18 silica gel; mobile phase, MeCN in Water (10 mmol/L $NH_4HCO_3$), 10% to 50% gradient in 30 min; detector, UV 254 nm. to afford N-[1-(5-bromo-4-methylpyridin-2-yl)ethyl]-2-(5,6-difluoro-2-oxo-1,4-dihydroquinazolin-3-yl)acetamide (300 mg, 58.76%). LCMS (ES, m/z): $[M+H]^+$=439.

N-[1-(5-cyano-4-methylpyridin-2-yl) ethyl]-2-(5,6-difluoro-2-oxo-1,4-dihydroquinazolin-3-yl) acetamide. Into a 40 mL sealed tube were added N-[1-(5-bromo-4-methylpyridin-2-yl)ethyl]-2-(5,6-difluoro-2-oxo-1,4-dihydroquinazolin-3-yl)acetamide (300 mg, 0.683 mmol, 1 equiv), Pd(dppf) $Cl_2$ (99.95 mg, 0.137 mmol, 0.2 equiv), $Zn(CN)_2$ (160.39 mg, 1.366 mmol, 2 equiv), Zn (17.86 mg, 0.273 mmol, 0.4 equiv) and DMF (3 mL) at RT. The reaction mixture was stirred for 8 h at 120° C. under Ar atmosphere. The residue was purified by reverse flash chromatography with the following conditions: column, C18 silica gel; mobile phase, MeCN in Water (10 mmol/L $NH_4HCO_3$), 10% to 50% gradient in 30 min; detector, UV 254 nm. This resulted in N-[1-(5-cyano-4-methylpyridin-2-yl)ethyl]-2-(5,6-difluoro-2-oxo-1,4-dihydroquinazolin-3-yl)acetamide (150 mg, 56.99%). LCMS (ES, m/z): $[M+H]^+$=386.

rel-N-[(1R)-1-(5-cyano-4-methylpyridin-2-yl)ethyl]-2-(5,6-difluoro-2-oxo-1,4-dihydroquinazolin-3-yl) acetamide. The crude product (130 mg) was purified by Chiral-Prep-HPLC with the following conditions (Column: CHIRAL ART Amylose-SA, 2*25 cm, 5 μm; Mobile Phase A: Hex: MtBE=1:1 (0.5% 2M $NH_3$-MEOH), Mobile Phase B: MeOH-HPLC; Flow rate: 20 mL/min; Gradient: 30% B to 30% B in 13 min; Wave Length: 254 nm; $RT_1$ (min): 5.65; $RT_2$ (min): 9.345; Sample Solvent: MeOH:DCM=1:1-HPLC; Injection Volume: 0.25 mL; Number Of Runs: 7) to afford rel-N-[(1R)-1-(5-cyano-4-methylpyridin-2-yl)ethyl]-2-(5,6-difluoro-2-oxo-1,4-dihydroquinazolin-3-yl)acetamide (27.4 mg, 21.08%). LCMS (ES, m/z): $[M+H]^+$=386.15 $^1$H NMR (400 MHz, Methanol-$d_4$) δ 8.71 (s, 1H), 7.49 (s, 1H), 7.11-7.04 (m, 1H), 6.57-6.53 (m, 1H), 5.06 (q, J=7.2 Hz, 1H), 4.68-4.59 (m, 2H), 4.20-4.08 (m, 2H), 2.55 (s, 3H), 1.49 (d, J=7.2 Hz, 3H).

Example 35: (R)—N—((R)-1-(2,4-difluorophenyl) ethyl)-2-(6-fluoro-2-oxo-1,4-dihydroquinazolin-3 (2H)-yl)-4-methylpentanamide (Compound B67)

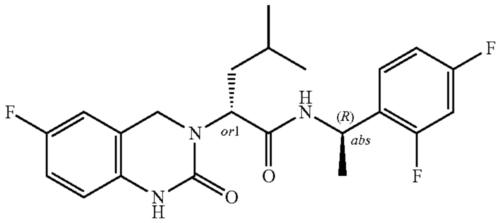

Methyl (5-fluoro-2-nitrobenzyl)leucinate. $NaBH(OAc)_3$ (9.40 g, 44.350 mmol, 2.50 equiv) was added in portions at 0° C. under $N_2$ atmosphere to a stirred mixture of 5-fluoro-2-nitrobenzaldehyde (3.00 g, 17.740 mmol, 1.00 equiv) and methyl leucinate hydrochloride (4.19 g, 23.062 mmol, 1.30 equiv) in DCM (40 mL). The reaction mixture was stirred overnight at RT under $N_2$ atmosphere. The reaction mixture was concentrated under reduced pressure. The reaction mixture was diluted with $H_2O$. The reaction mixture was extracted with EtOAc. The combined organic layers were washed with brine and dried over anhydrous $Na_2SO_4$ and filtered. The filtrate was concentrated under reduced pressure. The residue was purified by column chromatography to afford methyl (5-fluoro-2-nitrobenzyl)leucinate (2.80 g, 48.68%). LCMS (ES, m/z): 299 $[M+H]^+$ Methyl (2-amino-5-fluorobenzyl)leucinate. 10% Pd/C (1.00 g) was added portions at RT under $N_2$. atmosphere to a stirred solution of methyl (5-fluoro-2-nitrobenzyl)leucinate (2.5 g, 8.380 mmol, 1 equiv) in THF (40 mL). The reaction mixture was stirred for 3 h at RT under $H_2$ atmosphere. The reaction mixture was filtered and the filter cake was washed with EtOAc. The filtrate was concentrated under reduced pressure. The residue was purified by column chromatography to afford methyl (2-amino-5-fluorobenzyl) leucinate (2.00 g, 84.49%). LCMS (ES, m/z): 269 $[M+H]^+$ Methyl 2-(6-fluoro-2-oxo-1,4-dihydroquinazolin-3(2H)-yl)-4-methylpentanoate. CDI (3.02 g, 18.635 mmol, 5.00 equiv) was added in portions at RT under $N_2$ atmosphere to a stirred solution of methyl (2-amino-5-fluorobenzyl)leucinate (1.00 g, 3.727 mmol, 1.00 equiv) and DBU (1.70 g, 11.181 mmol, 3.00 equiv) in THF (10 mL). The reaction mixture was stirred for overnight at RT under $N_2$ atmosphere. The reaction mixture was diluted with $H_2O$. The reaction mixture was extracted with EtOAc. The combined organic layers were washed with brine and dried over anhydrous $Na_2SO_4$ and filtered. The filtrate was concentrated under reduced pressure. The residue was purified by column chromatography to afford methyl 2-(6-fluoro-2-oxo-1,4-dihydroquinazolin-3(2H)-yl)-4-methylpentanoate (750 mg, 71.80%). LCMS (ES, m/z): 295 $[M+H]^+$ 2-(6-fluoro-2-oxo-1,4-dihydroquinazolin-3(2H)-yl)-4-methylpentanoic acid. LiOH·$H_2O$ (228.10 mg, 5.436 mmol, 2.00 equiv) was added at 0° C. under $N_2$ atmosphere to a stirred solution of methyl 2-(6-fluoro-2-oxo-1,4-dihydroquinazolin-3(2H)-yl)-4-methylpentanoate (800 mg, 2.718 mmol, 1.00 equiv) in THF (5 mL) and $H_2O$ (5 mL). The reaction mixture was stirred for 3 h at RT under $N_2$ atmosphere. The reaction mixture was diluted with $H_2O$. The mixture was adjusted to pH 6 with 1M HCl (aq.). The reaction mixture was extracted with EtOAc. The combined organic layers were washed with brine and dried over anhydrous $Na_2SO_4$ and filtered. The filtrate was concentrated under reduced pressure. This resulted in 2-(6-fluoro-2-oxo-1, 4-dihydroquinazolin-3(2H)-yl)-4-methylpentanoic acid (520 mg, crude). The crude product was used in the next step directly without further purification. LCMS (ES, m/z): 281 $[M+H]^+$ rel-(R)-2-(6-fluoro-2-oxo-1,4-dihydroquinazolin-3(2H)-yl)-4-methylpentanoic acid. The 2-(6-fluoro-2-oxo-1,4-dihydroquinazolin-3(2H)-yl)-4-methylpentanoic acid (500 mg, purity: 95%) was purified by Prep-HPLC with the following conditions (Column: CHIRALPAK IG, 3*25 cm, 5 μm; Mobile Phase A: $CO_2$, Mobile Phase B: MeOH-HPLC; Flow rate: 60 mL/min; Gradient: isocratic 30% B; Column Temperature (° C.): 35; Back Pressure (bar): 100; Wave Length: 204 nm; Sample Solvent: MeOH-HPLC; Injection Volume: 1.2 mL; Number Of Runs: 17) to afford rel-(R)-2-(6-fluoro-2-oxo-1,4-dihydroquinazolin-3(2H)-yl)-4-methylpentanoic acid (200 mg, assumed, 39.60%) and rel-(S)-2-(6-fluoro-2-oxo-1,4-dihydroquinazolin-3(2H)-yl)-4-methylpentanoic acid (230 mg, assumed, 45.08%). LCMS (ES, m/z): 281 $[M+H]^+$ (R)—N—((R)-1-(2,4-difluorophenyl)ethyl)-2-(6-fluoro-2-oxo-1,4-dihydroquinazolin-3(2H)-yl)-4-methylpentanamide. HATU (406.96 mg, 1.071 mmol, 1.50 equiv) and (R)-1-(2,4-difluorophenyl)ethan-1-amine (134.57 mg, 0.857 mmol, 1.20 equiv) were added at 0° C. under $N_2$ atmosphere to a stirred solution of rel-(R)-2-(6-fluoro-2-oxo-1,4-dihydroquinazolin-3(2H)-yl)-4-methylpentanoic acid (200 mg, 0.714 mmol, 1.00 equiv) and DIEA (276.66 mg, 2.142 mmol, 3.00 equiv) in DMF (4 mL). The reaction mixture was stirred for 2 h at RT under $N_2$ atmosphere. The reaction mixture was diluted with $H_2O$. The reaction mixture was extracted with EtOAc. The combined organic layers were washed with brine and dried over anhydrous $Na_2SO_4$ and filtered. The filtrate was concentrated under reduced pressure. The residue was purified by reverse flash chromatography with the following conditions (Column: C18 spherical 20-35 um, 80 g; Mobile Phase A: Water (0.1% FA), Mobile Phase B: ACN; Flow rate: 40 m/min; Gradient: 30% B to 70% B in 30 min; 254/220 nm; RT1:20 min) to afford (R)—N—((R)-1-(2,4-difluorophenyl)ethyl)-2-(6-fluoro-2-oxo-1,4-dihydroquinazolin-3(2H)-yl)-4-methylpentanamide (70 mg, assumed, 23.39%). LCMS (ES, m/z): 420 $[M+H]^+$ 1H NMR (400 MHz, DMSO-$d_6$) δ 9.30 (s, 1H), 8.56 (d, J=7.6 Hz, 1H), 7.41-7.37 (m, 1H), 7.19-6.95 (m, 4H), 6.78 (dd, J=4.8, 4.8 Hz, 1H), 5.08 (p, J=7.2 Hz, 1H), 4.95 (dd, J=5.6, 5.6 Hz, 1H), 4.51 (d, J=14.8 Hz, 1H), 4.29 (d, J=14.8 Hz, 1H), 1.65-1.64 (m, 1H), 1.55-1.53 (m, 1H), 1.34 (d, J=11.6 Hz, 4H), 0.87 (dd, J=6.8, 8.0 Hz, 6H). $^{19}F$ NMR (377 MHz, DMSO-$d_6$) δ −112.71 (1F), −115.63 (1F), −122.80 (1F).

Example 36: rel-(S)-2-(5,6-Difluoro-2-oxo-1,4-dihydroquinazolin-3(2H)-yl)-N-(1-(5-methylpyridazin-4-yl)ethyl)acetamide (Compound B47)

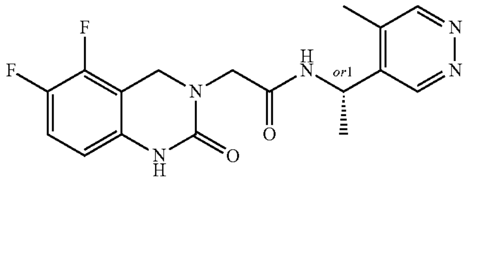 [SMILES: Cc1cnncc1[C@H](C)NC(=O)CN1Cc2c(ccc(F)c2F)NC1=O]

1-(3,6-Dichloro-5-methylpyridazin-4-yl)ethan-1-one. Sodium persulfate (14.61 g, 61.350 mmol, 2.00 equiv) and TFA (4.20 g, 36.810 mmol, 1.20 equiv) and $AgNO_3$ (2.61 g, 15.338 mmol, 0.50 equiv) were added dropwise at RT under $N_2$ atmosphere to a stirred solution of 3,6-dichloro-4-methylpyridazine (5.00 g, 30.675 mmol, 1.00 equiv) and 2-oxopropanoic acid (5.40 g, 61.350 mmol, 2.00 equiv) in MeCN (5 mL) and $H_2O$ (50 mL). The reaction mixture was stirred overnight at 60° C. under $N_2$ atmosphere. The reaction was quenched by the addition of sat. sodium hyposulfite (aq.) (100 mL) at 0° C. The reaction mixture was extracted with EtOAc. The combined organic layers were washed with brine and dried over anhydrous $Na_2SO_4$ and filtered. The filtrate was concentrated under reduced pressure. The residue was purified by reverse flash chromatography with the following conditions: (Column: C18 spherical 20-35 um, 80 g; Mobile Phase A: Water (10 mmol/L $NH_4HCO_3$), Mobile Phase B: ACN; Flow rate: 40 mL/min; Gradient: 30% B to 70% B in 30 min; 254/220 nm; RT1:21 min) to afford 1-(3,6-dichloro-5-methylpyridazin-4-yl)ethan-1-one (1.80 g, 28.62%). LCMS (ES, m/z): 205$[M+H]^+$ 1-(5-methylpyridazin-4-yl)ethan-1-one. Pd/C (10%, 400 mg) was added under $N_2$ atmosphere to a solution of 1-(3,6-dichloro-5-methylpyridazin-4-yl)ethan-1-one (1.80 g, 8.779 mmol, 1.00 equiv) and TEA (3.82 g, 37.750 mmol, 4.30 equiv) in EtOH (30 mL). The mixture was hydrogenated at RT for 3 h under $H_2$ atmosphere using a $H_2$ balloon. The reaction mixture was filtered, the filter cake was washed with EtOH. The filtrate was concentrated under reduced pressure. The residue was purified by column chromatography to afford 1-(5-methylpyridazin-4-yl)ethan-1-one (1.00 g, 83.66%). LCMS (ES, m/z): 137$[M+H]^+$ (E)-2-Methyl-N-(1-(5-methylpyridazin-4-yl)ethylidene) propane-2-sulfinamide. $Ti(Oi-Pr)_4$ (4.17 g, 14.690 mmol, 2.00 equiv) was added dropwise at RT under $N_2$ atmosphere to a stirred solution of 1-(5-methylpyridazin-4-yl)ethan-1-one (1 g, 7.345 mmol, 1.00 equiv) and 2-methylpropane-2-sulfinamide (1.07 g, 8.814 mmol, 1.20 equiv) in THF (10 mL). The reaction mixture was stirred overnight at 80° C. under $N_2$ atmosphere. The mixture was neutralized to pH 8 with saturated $NaHCO_3$ (aq.). The reaction mixture was filtered and the filter cake was washed with EtOAc. The filtrate was concentrated under reduced pressure. The residue was purified by column chromatography to afford (E)-2-methyl-N-(1-(5-methylpyridazin-4-yl)ethylidene)propane-2-sulfinamide (500 mg, 28.44%). LCMS (ES, m/z): 240$[M+H]^+$ 2-Methyl-N-(1-(5-methylpyridazin-4-yl)ethyl)propane-2-sulfinamide. $NaBH_4$ (237.09 mg, 6.267 mmol, 3.00 equiv) was added dropwise at 0° C. under $N_2$ atmosphere to a stirred solution of (E)-2-methyl-N-(1-(5-methylpyridazin-4-yl)ethylidene)propane-2-sulfinamide (500 mg, 2.089 mmol, 1.00 equiv) in THF (5 mL). The reaction mixture was stirred for 1 h at RT under $N_2$ atmosphere. The reaction was quenched with $H_2O$ at 0° C. The reaction mixture was filtered and the filter cake was washed with EtOAc. The filtrate was concentrated under reduced pressure. The residue was purified by column chromatography to afford 2-methyl-N-(1-(5-methylpyridazin-4-yl)ethyl)propane-2-sulfinamide (200 mg, 79.33%). LCMS (ES, m/z): 242$[M+H]^+$ 1-(5-Methylpyridazin-4-yl)ethan-1-amine. 4M HCl (gas) in 1,4-dioxane (151.07 mg, 4.145 mmol, 5.00 equiv) was added dropwise at 0° C. under $N_2$ atmosphere to a stirred solution of 2-methyl-N-(1-(5-methylpyridazin-4-yl)ethyl) propane-2-sulfinamide (200 mg, 0.829 mmol, 1.00 equiv) in DCM (2 mL). The reaction mixture was stirred for 2 h at RT under $N_2$ atmosphere. The reaction mixture was concentrated under reduced pressure and was washed with DCM resulting in 1-(5-methylpyridazin-4-yl)ethanamine (200 mg, HCl salt, crude). The crude product was used in the next step directly without further purification. LCMS (ES, m/z): 138 $[M+H]^+$ 2-(5,6-Difluoro-2-oxo-1,4-dihydroquinazolin-3(2H)-yl)-N-(1-(5-methylpyridazin-4-yl)ethyl)acetamide. DIEA (246.56 mg, 1.908 mmol, 3.00 equiv) was added dropwise at RT under $N_2$ atmosphere to a stirred solution of 2-(5,6-difluoro-2-oxo-1,4-dihydroquinazolin-3(2H)-yl)-N-(1-(5-methylpyridazin-4-yl)ethyl)acetamide acid (154 mg, 0.636 mmol, 1.00 equiv), 1-(5-methylpyridazin-4-yl)ethanamine (200 mg, 1.458 mmol, 2.29 equiv) and HOBt (93.21 mg, 0.762 mmol, 1.20 equiv) and EDCI (146.28 mg, 0.763 mmol, 1.20 equiv) in DMF (5 mL). The reaction mixture was stirred for 3 h at RT under $N_2$ atmosphere. The reaction mixture was diluted with $H_2O$. The reaction mixture was extracted with EtOAc. The combined organic layers were washed with brine and dried over anhydrous $Na_2SO_4$ and filtered. The filtrate was concentrated under reduced pressure. The residue was purified by column chromatography to afford the crude product (150 mg). The crude product (150 mg) was purified by reverse flash chromatography with the following conditions (Column: C18 spherical 20-35 um, 80 g; Mobile Phase A: Water (0.1% FA), Mobile Phase B: ACN; Flow rate: 40 mL/min; Gradient: 30% B to 70% B in 30 min; 254/220 nm; RT1:22 min) to afford 2-(5,6-difluoro-2-oxo-1,4-dihydroquinazolin-3(2H)-yl)-N-(1-(5-methylpyridazin-4-yl)ethyl)acetamide (110 mg, 47.87%). LCMS (ES, m/z): 362$[M+H]^+$ rel-(S)-2-(5,6-difluoro-2-oxo-1,4-dihydroquinazolin-3(2H)-yl)-N-(1-(5-methylpyridazin-4-yl)ethyl)acetamide. The crude product 2-(5,6-difluoro-2-oxo-1,4-dihydroquinazolin-3(2H)-yl)-N-(1-(5-methylpyridazin-4-yl)ethyl)acetamide (100 mg, crude) was purified by Prep-HPLC with the following conditions (Column: CHIRALPAK IA, 2*25 cm, 5 μm; Mobile Phase A: Hex (10 mM $NH_3$-MeOH), Mobile Phase B: EtOH-HPLC; Flow rate: 20 mL/min; Gradient: 30% B to 30% B in 33 min; Wave Length: 246/229 nm; RT1 (min): 16.805; $RT_2$ (min): 23.2675; Sample Solvent: DMSO; Injection Volume: 0.16 mL; Number Of Runs: 15) to afford rel-(S)-2-(5,6-difluoro-2-oxo-1,4-dihydroquinazolin-3(2H)-yl)-N-(1-(5-methylpyridazin-4-yl)ethyl)acetamide (30 mg, assumed, 30.00%). LCMS (ES, m/z): 362 $[M+H]^+$ $^1H$ NMR (300 MHz, DMSO-$d_6$) δ 9.49 (s, 1H), 9.05 (s, 1H), 8.97 (s, 1H), 8.70 (d, J=6.9 Hz, 1H), 7.23 (t, J=9.0 Hz, 1H), 6.57-6.53 (m, 1H), 5.03 (t, J=6.9 Hz, 1H), 4.53 (s, 2H), 4.00 (s, 2H), 2.34 (s, 3H), 1.37 (d, J=7.2 Hz, 3H). $^{19}F$ NMR (282 MHz, DMSO-$d_6$) δ −144.00 (1F), −148.74 (1F).

Example 37: N-[(1S)-1-(4-cyano-2-fluorophenyl)ethyl]-2-(6-fluoro-8-methyl-2-oxo-1,4-dihydroquinazolin-3-yl)acetamide (Compound B59)

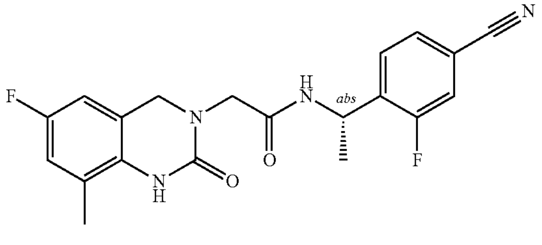 [SMILES: Cc1cc(F)cc2c1NC(=O)N(CC(=O)N[C@@H](C)c1ccc(C#N)cc1F)C2]

2-Amino-5-fluorobenzonitrile. A solution of 2-bromo-4-fluoro-6-methylaniline (4 g, 19.604 mmol, 1 equiv), Zn (0.51 g, 7.842 mmol, 0.4 equiv) and Pd(dppf)$Cl_2$ (2.87 g, 3.921 mmol, 0.2 equiv) in DMF (40 mL) was stirred at 120° C. under Ar atmosphere. The reaction mixture was extracted with EtOAc. The combined organic layers were dried over anhydrous $Na_2SO_4$ and filtered. The filtrate was concentrated under reduced pressure. The residue was purified by column chromatography to afford 2-amino-5-fluorobenzonitrile (2.2 g, 82.44%). LCMS (ES, m/z): 151 $[M+H]^+$.

2-(Aminomethyl)-4-fluoro-6-methylaniline. LAH (1 M, 29 mL, 2 equiv) was added dropwise/in portions at 0° C. under air atmosphere to a stirred solution/mixture of 2-amino-5-fluoro-3-methylbenzonitrile (2.2 g, 14.651 mmol, 1 equiv) in THF (23 mL). The reaction was quenched by the addition of MeOH (30 mL) at 0° C. Then the reaction mixture was concentrated under vacuum. The residue was purified by column chromatography to afford 2-(aminomethyl)-4-fluoro-6-methylaniline (1 g, 44.27%). LCMS (ES, m/z): 155 $[M+H]^+$.

2-{[(2-Amino-5-fluoro-3-methylphenyl)methyl]amino}acetate. Tert-butyl 2-bromoacetate (1.39 g, 7.135 mmol, 1.1 equiv) was added dropwise at RT under air atmosphere to a stirred solution 2-(aminomethyl)-4-fluoro-6-methylaniline (1 g, 6.486 mmol, 1 equiv) and $NEt_3$ (1.31 g, 12.972 mmol, 2 equiv) in THF (10 mL). The reaction mixture was concentrated under reduced pressure and purified by column chromatography to afford tert-butyl 2-{[(2-amino-5-fluoro-3-methylphenyl)methyl]amino}acetate (1.25 g, 71.83%). LCMS (ES, m/z): 269 $[M+H]^+$.

tert-Butyl 2-(6-fluoro-8-methyl-2-oxo-1,4-dihydroquinazolin-3-yl)acetate. Triphosgene (0.40 g, 1.342 mmol, 0.3 equiv) was added in portions at 0° C. under air atmosphere to a stirred solution of tert-butyl 2-{[(2-amino-5-fluoro-3-methylphenyl)methyl]amino}acetate (1.2 g, 4.472 mmol, 1 equiv) and TEA (0.91 g, 8.944 mmol, 2 equiv) in DCM (15 mL). The reaction mixture was stirred for 3 h at RT under air atmosphere. The residue was purified by column chromatography to afford tert-butyl 2-(6-fluoro-8-methyl-2-oxo-1,4-dihydroquinazolin-3-yl)acetate (1.1 g, 70.20%). LCMS (ES, m/z): 295 $[M+H]^+$.

(6-Fluoro-8-methyl-2-oxo-1,4-dihydroquinazolin-3-yl)acetic acid. TFA (3 mL) was added dropwise at 0° C. under air atmosphere to a stirred solution of tert-butyl 2-(6-fluoro-8-methyl-2-oxo-1,4-dihydroquinazolin-3-yl)acetate (1.1 g, 3.737 mmol, 1 equiv) in DCM (15 mL).

The reaction mixture was stirred for 3 h at RT under air atmosphere and was concentrated under reduced pressure. The residue was purified by trituration with MeCN (10 mL). to afford (6-fluoro-8-methyl-2-oxo-1,4-dihydroquinazolin-3-yl)acetic acid (667 mg, 74.92%). LCMS (ES, m/z): 239 $[M+H]^+$.

N-[(1S)-1-(4-cyano-2-fluorophenyl)ethyl]-2-(6-fluoro-8-methyl-2-oxo-1,4-dihydroquinazolin-3-yl)acetamide. DMAP (10.26 mg, 0.084 mmol, 0.2 equiv) and 4-[(1S)-1-aminoethyl]-3-fluorobenzonitrile (75.81 mg, 0.462 mmol, 1.1 equiv) was added in portions at RT under air atmosphere to a stirred mixture of (6-fluoro-8-methyl-2-oxo-1,4-dihydroquinazolin-3-yl)acetic acid (100 mg, 0.420 mmol, 1 equiv) and EDCI (120.71 mg, 0.630 mmol, 1.5 equiv) in DMF (3 mL). The reaction mixture was stirred for 4 h at RT under air atmosphere. The residue was purified by reverse flash chromatography with the following conditions: column, C18 silica gel; mobile phase, MeOH in Water (10 mmol/L $NH_4HCO_3$), 0% to 100% gradient in 50 min; detector, UV 254 nm. to afford N-[(1S)-1-(4-cyano-2-fluorophenyl)ethyl]-2-(6-fluoro-8-methyl-2-oxo-1,4-dihydroquinazolin- 3-yl)acetamide (102.6 mg, 63.33%). LCMS (ES, m/z): 385 $[M+H]^+$. $^1H$ NMR (400 MHz, DMSO-$d_6$) δ 8.65 (d, J=7.2 Hz, 1H), 8.57 (s, 1H), 7.83-7.80 (m, 1H), 7.69-7.67 (m, 1H), 7.59 (t, J=7.6 Hz, 1H), 6.87-6.84 (m, 1H), 6.80-6.77 (m, 1H), 5.18-5.11 (m, 1H), 4.42 (s, 2H), 3.97 (s, 2H), 2.17 (s, 3H), 1.37 (d, J=7.2 Hz, 3H).

Example 38: 2-(7-Chloro-5-fluoro-2-oxo-1,4-dihydroquinazolin-3-yl)-N-[(1S)-1-(4-cyano-2-fluorophenyl)ethyl]acetamide (Compound B33)

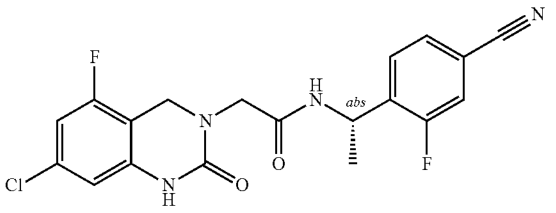 [SMILES: C[C@H](NC(=O)CN1Cc2c(F)cc(Cl)cc2NC1=O)c1ccc(C#N)cc1F]

tert-Butyl N-(5-chloro-3-fluoro-2-iodophenyl)carbamate. Di-tert-butyl dicarbonate (2.25 g, 10.315 mmol, 1 equiv) was added dropwise at 0° C. under air atmosphere to a stirred solution of 5-chloro-3-fluoro-2-iodoaniline (2.8 g, 10.315 mmol, 1 equiv), DMAP (0.25 g, 2.063 mmol, 0.2 equiv) and TEA (2.09 g, 20.630 mmol, 2 equiv) in DCM (40 mL). The reaction mixture was stirred for 12 h at RT under air atmosphere. The residue was purified by column chromatography to afford tert-butyl N-(5-chloro-3-fluoro-2-iodophenyl)carbamate (1.65 g, 43.05%). LCMS (ES, m/z): 372 $[M+H]^+$.

tert-Butyl N-(5-chloro-3-fluoro-2-formylphenyl)carbamate. A solution of tert-butyl N-(5-chloro-3-fluoro-2-iodophenyl)carbamate (5 g, 13.456 mmol, 1 equiv) in THF (50 mL) was treated with NaH (0.48 g, 20.184 mmol, 1.5 equiv) for 30 min at 0° C. under $N_2$ atmosphere followed by the addition of n-BuLi (2.5M, 8.086 mL, 20.184 mmol, 1.5 equiv) dropwise at −78° C. The reaction mixture was stirred for 30 min at −78° C. under Ar atmosphere. To the above mixture DMF (4.92 g, 67.280 mmol, 5 equiv) was added dropwise over 2 min at −78° C. The reaction mixture was stirred for additional 2 h at −78° C. The reaction was quenched with sat. $NH_4Cl$ (aq.) at 0° C. The reaction mixture was extracted with EtOAc. The combined organic layers were washed with brine and dried over anhydrous $Na_2SO_4$ and filtered. The filtrate was concentrated under reduced pressure. The residue was purified by column chromatography to afford tert-butyl N-(5-chloro-3-fluoro-2-formylphenyl)carbamate (3.6 g, 82.11%). LCMS (ES, m/z): 274 $[M+H]^+$.

Methyl 2-{[(2-amino-4-chloro-6-fluorophenyl)methyl]amino}acetate. Into a 8 mL sealed tube were added tert-butyl N-(5-chloro-3-fluoro-2-formylphenyl)carbamate (3.5 g, 12.788 mmol, 1 equiv) and $MgSO_4$ (2.31 g, 19.182 mmol, 1.5 equiv) in ACN (20 mL) at RT. The reaction mixture was stirred for 3 h at 80° C. under air atmosphere. The reaction mixture was filtered, the filter cake was washed with MeOH. The filtrate was concentrated under reduced pressure. To the above mixture was added MeOH (40 mL) and $NaBH_3CN$ (1.61 g, 25.576 mmol, 2 equiv) at 0° C. The reaction mixture was stirred for additional 12 h at 50° C. The residue was purified by column chromatography to afford methyl 2-{[(2-amino-4-chloro-6-fluorophenyl)methyl]amino}acetate (2.05 g, 64.99%). LCMS (ES, m/z): 347 $[M+H]^+$.

2-{[(2-amino-4-chloro-6-fluorophenyl)methyl]amino}acetate. Into a 8 mL sealed tube were added methyl 2-[({2-[(tert-butoxycarbonyl)amino]-4-chloro-6-fluorophenyl}methyl)amino]acetate (2.05 g, 5.912 mmol, 1 equiv) and DCM (20 mL) at RT. To the mixture TFA (4 mL) was added dropwise at 0° C. The reaction mixture was stirred for additional 2 h at RT. The reaction mixture was concentrated under reduced pressure. The mixture was adjusted to pH 8 with saturated $NaHCO_3$ (aq.). The reaction mixture was concentrated under reduced pressure. The residue was purified by column chromatography to afford methyl 2-{[(2-amino-4-chloro-6-fluorophenyl)methyl]amino}acetate (1 g, 61.72%). LCMS (ES, m/z): 247 $[M+H]^+$.

Methyl 2-(7-chloro-5-fluoro-2-oxo-1,4-dihydroquinazolin-3-yl)acetate. Triphosgene (0.36 g, 1.216 mmol, 0.3 equiv) was added in portions at 0° C. under air atmosphere to a stirred solution of methyl 2-{[(2-amino-4-chloro-6-fluorophenyl)methyl]amino}acetate (1 g, 4.054 mmol, 1 equiv) and TEA (0.82 g, 8.108 mmol, 2 equiv) in DCM (15 mL). The reaction mixture was stirred for 12 h at RT under air atmosphere. The residue was purified by column chromatography to afford methyl 2-(7-chloro-5-fluoro-2-oxo-1,4-dihydroquinazolin-3-yl)acetate (600 mg, 54.28%). LCMS (ES, m/z): 273 $[M+H]^+$.

(7-Chloro-5-fluoro-2-oxo-1,4-dihydroquinazolin-3-yl)acetic acid. LiOH (52.70 mg, 2.202 mmol, 3 equiv) in $H_2O$ (1 mL) was added dropwise at RT under air atmosphere to a stirred solution of methyl 2-(7-chloro-5-fluoro-2-oxo-1,4-dihydroquinazolin-3-yl)acetate (200 mg, 0.734 mmol, 1 equiv) and THF (1 mL) in MeOH (1 mL). The reaction mixture was stirred for 3 h at RT under air atmosphere and then concentrated under vacuum. The residue was dissolved in $H_2O$. The mixture was adjusted to pH 4 with HCl (aq. 4 M). The precipitated solids were collected by filtration and washed with MeCN. to afford (7-chloro-5-fluoro-2-oxo-1,4-dihydroquinazolin-3-yl)acetic acid (180 mg, 94.88%). LCMS (ES, m/z): 259 $[M+H]^+$.

2-(7-Chloro-5-fluoro-2-oxo-1,4-dihydroquinazolin-3-yl)-N-[(1S)-1-(4-cyano-2-fluorophenyl)ethyl]acetamide. DMAP (8.50 mg, 0.070 mmol, 0.2 equiv) and 4-[(1S)-1-aminoethyl]-3-fluorobenzonitrile (62.85 mg, 0.383 mmol, 1.1 equiv) were added at RT under air atmosphere to a stirred solution of (7-chloro-5-fluoro-2-oxo-1,4-dihydroquinazolin-3-yl)acetic acid (90 mg, 0.348 mmol, 1 equiv) and EDCI (100.06 mg, 0.522 mmol, 1.5 equiv) in DMF (2 mL). The reaction mixture was stirred for 3 h at RT under air atmosphere. The residue was purified by reverse flash chromatography with the following conditions: (column, C18 silica gel; mobile phase, MeCN in Water (10 mmol/L $NH_4HCO_3$), 0% to 100% gradient in 50 min; detector, UV 254 nm) to afford 2-(7-chloro-5-fluoro-2-oxo-1,4-dihydroquinazolin-3-yl)-N-[(1S)-1-(4-cyano-2-fluorophenyl)ethyl]acetamide (50.6 mg, 35.78%). LCMS (ES, m/z): 405.00 $[M+H]^+$. $^1H$ NMR (300 MHz, DMSO-$d_6$) δ 9.65 (s, 1H), 8.67 (d, J=7.2 Hz, 1H), 7.83-7.80 (m, 1H), 7.70-7.67 (m, 1H), 7.60-7.55 (m, 1H), 6.94-6.90 (m, 1H), 6.64 (s, 1H), 5.19-5.09 (m, 1H), 4.46 (s, 2H), 4.01 (s, 2H), 1.37 (d, J=6.9 Hz, 3H).

Example 39: N-[(1S)-1-(4-Cyano-2-fluorophenyl)ethyl]-2-(5-fluoro-7-methyl-2-oxo-1,4-dihydroquinazolin-3-yl)acetamide (Compound B13)

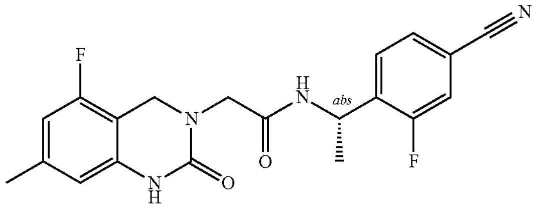 [SMILES: Cc1cc(F)c2c(c1)NC(=O)N(CC(=O)N[C@@H](C)c1ccc(C#N)cc1F)C2]

N-[(1S)-1-(4-Cyano-2-fluorophenyl)ethyl]-2-(5-fluoro-7-methyl-2-oxo-1,4-dihydroquinazolin-3-yl)acetamide. Trimethyl-1,3,5,2,4,6-trioxatriborinane (310.10 mg, 2.470 mmol, 10 equiv) and Pd(dppf)$Cl_2$ (36.15 mg, 0.049 mmol, 0.2 equiv) were added in portions at RT under Ar atmosphere to a stirred mixture of 2-(7-chloro-5-fluoro-2-oxo-1,4-dihydroquinazolin-3-yl)-N-[(1S)-1-(4-cyano-2-fluorophenyl)ethyl]acetamide (100 mg, 0.247 mmol, 1 equiv) and $K_2CO_3$ (102.42 mg, 0.741 mmol, 3 equiv) in DMF (1 mL). The reaction mixture was stirred for 12 h at 100° C. under argon atmosphere. The residue was purified by column chromatography to afford N-[(1S)-1-(4-cyano-2-fluorophenyl)ethyl]-2-(5-fluoro-7-methyl-2-oxo-1,4-dihydroquinazolin-3-yl)acetamide (18.3 mg, 19.18%). LCMS (ES, m/z): 385.05 $[M+H]^+$. $^1H$ NMR (300 MHz, DMSO-$d_6$) δ 9.44 (s, 1H), 8.67 (d, J=7.2 Hz, 1H), 7.84-7.80 (m, 1H), 7.70-7.67 (m, 1H), 7.60-7.55 (m, 1H), 6.54 (d, J=10.5 Hz, 1H), 6.39 (s, 1H), 5.16-5.12 (m, 1H), 4.35 (s, 2H), 4.00 (s, 2H), 2.21 (s, 3H), 1.37 (d, J=6.9 Hz, 3H).

Example 40: rel-2-(5,6-Difluoro-2-oxo-1,4-dihydroquinazolin-3-yl)-N-[(1R)-1-(5-fluoro-4-methylpyridin-2-yl)ethyl]acetamide (Compound B69)

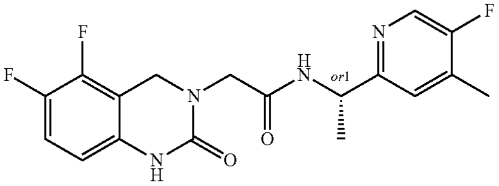 [SMILES: Cc1cc([C@H](C)NC(=O)CN2Cc3c(ccc(F)c3F)NC2=O)ncc1F]

2-(1-Ethoxyethenyl)-5-fluoro-4-methylpyridine). A mixture of 2-bromo-5-fluoro-4-methylpyridine (3 g, 15.788 mmol, 1 equiv), Pd(dppf)$Cl_2$ (7.70 mg, 0.011 mmol, 0.1 equiv) and tributyl(1-ethoxyethenyl)stannane (5.70 g, 15.788 mmol, 1 equiv) in dioxane (1 mL) was stirred for 4 h at 100° C. under Ar atmosphere. The residue was purified by column chromatography to afford 2-(1-ethoxyethenyl)-5-fluoro-4-methylpyridine) (2.5 g, 87.38%). LC-MS: (ESI, m/z): $[M+H]^+$=182.

1-(5-Fluoro-4-methylpyridin-2-yl)ethenone. A mixture of 2-(1-ethoxyethenyl)-5-fluoro-4-methylpyridine (2 g, 11.037 mmol, 1 equiv) in HCl (gas) in 1,4-dioxane (20 mL) was stirred for 3 h at RT. The reaction mixture was concentrated under reduced pressure to afford 1-(5-fluoro-4-methylpyridin-2-yl)ethanone (450 mg, 26.62%). LC-MS: (ESI, m/z): $[M+H]^+$=154.

1-(5-Fluoro-4-methylpyridin-2-yl)ethanamine. A mixture of 1-(5-fluoro-4-methylpyridin-2-yl)ethanone (200 mg, 1.306 mmol, 1 equiv), $NaBH_3CN$ (410.30 mg, 6.530 mmol, 5 equiv) and $CH_3COONH_4$ (2013.19 mg, 26.120 mmol, 20 equiv) in MeOH (2 mL) was stirred for 3 h at RT under $N_2$ atmosphere. The residue was purified by column chromatography to afford 1-(5-fluoro-4-methylpyridin-2-yl)ethanamine (200 mg, 69.53%). LC-MS: (ESI, m/z): $[M+H]^+$=155.

2-(5,6-difluoro-2-oxo-1,4-dihydroquinazolin-3-yl)-N-[1-(5-fluoro-4-methylpyridin-2-yl)ethyl]acetamide. A mixture of (5,6-difluoro-2-oxo-1,4-dihydroquinazolin-3-yl)acetic acid (280 mg, 1.156 mmol, 1 equiv), EDCI (265.96 mg, 1.387 mmol, 1.2 equiv), DMAP (42.37 mg, 0.347 mmol, 0.3 equiv) and 1-(5-fluoro-4-methylpyridin-2-yl)ethanamine (196.09 mg, 1.272 mmol, 1.1 equiv) in DMF (3 mL) was stirred for 3 h at RT. The residue was purified by reverse flash chromatography with the following conditions: column, C18 silica gel; mobile phase, MeCN in Water (0.10% FA), 0% to 70% gradient in 10 min; detector, UV 254 nm to afford 2-(5,6-difluoro-2-oxo-1,4-dihydroquinazolin-3-yl)-N-[1-(5-fluoro-4-methylpyridin-2-yl)ethyl]acetamide (180 mg, 41.15%). LC-MS: (ESI, m/z): $[M+H]^+$=379.

rel-2-(5,6-difluoro-2-oxo-1,4-dihydroquinazolin-3-yl)-N-[(1R)-1-(5-fluoro-4-methylpyridin-2-yl) ethyl]acetamide. The crude product (150 mg) was purified by Prep-Chiral-HPLC with the following conditions (Column: Lux 3 um Cellulose-4, 4.6*50 mm, 3.0 um; Mobile Phase A: $H_2O$ (0.05% DEA):ACN=60:40; Flow rate: 1 mL/min; Gradient: 0% B to 0% B; Injection Volume: 5 ul mL) to afford rel-2-(5,6-difluoro-2-oxo-1,4-dihydroquinazolin-3-yl)-N-[(1R)-1-(5-fluoro-4-methylpyridin-2-yl)ethyl]acetamide (80 mg, 52.96%). LC-MS: (ESI, m/z): $[M+H]^+$=379.05 $^1H$ NMR (400 MHz, DMSO-$d_6$) δ 9.48 (s, 1H), 8.47 (d, J=8.0 Hz, 1H), 8.36 (s, 1H), 7.34 (d, J=6.0 Hz, 1H), 7.22 (q, J=10.0 Hz, 1H), 6.57 (dd, J=8.8, 3.2 Hz, 1H), 4.97-4.93 (m, 1H), 4.56 (d, J=2.0 Hz, 2H), 4.06-3.97 (m, 2H), 2.27 (s, 3H), 1.37 (d, J=6.8 Hz, 3H).

Example 41: N-[(1S)-1-(4-Cyano-2-fluorophenyl)ethyl]-2-(7-cyano-5-fluoro-2-oxo-1,4-dihydroquinazolin-3-yl)acetamide (Compound B11)

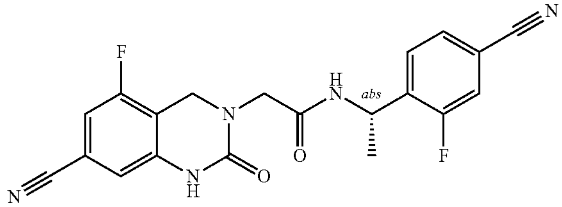 [SMILES: C[C@H](NC(=O)CN1Cc2c(F)cc(C#N)cc2NC1=O)c1ccc(C#N)cc1F]

N-[(1S)-1-(4-Cyano-2-fluorophenyl)ethyl]-2-(7-cyano-5-fluoro-2-oxo-1,4-dihydroquinazolin-3-yl)acetamide. Into a 8 mL sealed tube were added 2-(7-chloro-5-fluoro-2-oxo-1,4-dihydroquinazolin-3-yl)-N-[(1S)-1-(4-cyano-2-fluorophenyl)ethyl]acetamide (100 mg, 0.247 mmol, 1 equiv) and $Zn(CN)_2$ (58.01 mg, 0.494 mmol, 2 equiv) in DMF (3 mL) at RT. To the above mixture was added Zn (6.46 mg, 0.099 mmol, 0.4 equiv) and Pd(dppf)$Cl_2$ (36.15 mg, 0.049 mmol, 0.2 equiv) at RT under Ar atmosphere. The reaction mixture was stirred for additional 12 h at 150° C. The residue was purified by reversed-phase flash chromatography with the following conditions: (column, C18 silica gel; mobile phase, MeOH in Water, 0% to 100% gradient in 50 min; detector, UV 254 nm). to afford N-[(1S)-1-(4-cyano-2-fluorophenyl) ethyl]-2-(7-cyano-5-fluoro-2-oxo-1,4-dihydroquinazolin-3-yl)acetamide (62.9 mg, 63.56%). LCMS (ES, m/z): 396.10 $[M+H]^+$. $^1H$ NMR (400 MHz, DMSO-$d_6$) δ 9.82 (s, 1H), 8.69 (d, J=7.6 Hz, 1H), 7.83-7.80 (m, 1H), 7.70-7.68 (m, 1H), 7.59-7.55 (m, 1H), 7.36 (d, J=8.8 Hz, 1H), 6.92 (s, 1H), 5.16-5.12 (m, 1H), 4.56 (s, 2H), 4.01 (s, 2H), 1.37 (d, J=7.2 Hz, 3H).

Example 42: N-[(1S)-1-(4-cyano-2-fluorophenyl) ethyl]-2-(6,7-difluoro-2-oxo-1,4-dihydroquinazolin-3-yl)acetamide (Compound B45)

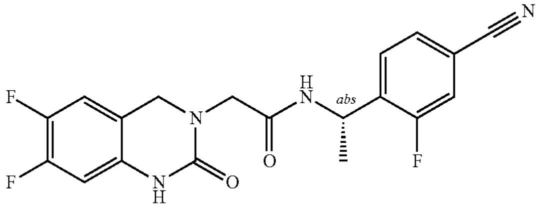 [SMILES: C[C@H](NC(=O)CN1Cc2cc(F)c(F)cc2NC1=O)c1ccc(C#N)cc1F]

2-Amino-4,5-difluorobenzonitrile. A mixture of 2-bromo-4,5-difluoroaniline (5 g, 24.038 mmol, 1 equiv), Zn (1.57 g, 24.038 mmol, 1 equiv), $Zn(CN)_2$ (5.65 g, 48.076 mmol, 2 equiv) and Pd(dppf)$Cl_2$ (3.52 g, 4.808 mmol, 0.2 equiv) in DMF (50 mL) was stirred for 2 h at 120° C. under air atmosphere. The mixture was allowed to cool down to RT. The residue was purified by column chromatography, eluted with PE/EA (1:1) to afford 2-amino-4,5-difluorobenzonitrile (3.5 g, 94.47%). LCMS (ES, m/z): 155 $[M+H]^+$.

2-(Aminomethyl)-4,5-difluoroaniline. A mixture of 2-amino-4,5-difluorobenzonitrile (2 g, 12.977 mmol, 1 equiv) and $BH_3$-THF (1 M, 15 mL) in THF (25 mL) was stirred for 2 h at 0° C. under Ar atmosphere. The reaction was quenched by the addition of MeOH (10 mL) at 0° C. The reaction mixture was concentrated under reduced pressure. The residue was purified by trituration with $CH_2Cl_2$ (5 mL). This resulted in 2-(aminomethyl)-4,5-difluoroaniline (1 g, 48.73%). LCMS (ES, m/z): 159 $[M+H]^+$.

tert-Butyl 2-{[(2-amino-4,5-difluorophenyl)methyl]amino}acetate. A mixture of 2-(aminomethyl)-4, 5-difluoroaniline (1 g, 6.323 mmol, 1 equiv), tert-butyl 2-bromoacetate (1.23 g, 6.323 mmol, 1 equiv) and $K_2CO_3$ (1.75 g, 12.646 mmol, 2 equiv) in THF (20 mL) was stirred overnight at RT under air atmosphere. The mixture was evaporated in vacuum. The residue was purified by column chromatography to afford tert-butyl 2-{[(2-amino-4,5-difluorophenyl)methyl]amino}acetate (1.16 g, 67.37%). LCMS (ES, m/z): 273 $[M+H]^+$.

tert-Butyl 2-(6, 7-difluoro-2-oxo-1,4-dihydroquinazolin-3-yl)acetate. A mixture of tert-butyl 2-{[(2-amino-4,5-difluorophenyl)methyl]amino}acetate (1 g, 3.672 mmol, 1 equiv), CDI (1.19 g, 7.344 mmol, 2 equiv), and DBU (1.12 g, 7.344 mmol, 2 equiv) in THF (20 mL) was stirred for 2 h at 50° C. under air atmosphere. The reaction mixture was diluted with $H_2O$. The aqueous layer was extracted with EtOAc. The reaction mixture was concentrated under reduced pressure. The residue was purified by column chromatography to afford tert-butyl 2-(6,7-difluoro-2-oxo-1,4-dihydroquinazolin-3-yl)acetate (0.9 g, 82.16%). LCMS (ES, m/z): 299 $[M+H]^+$.

(6,7-Difluoro-2-oxo-1,4-dihydroquinazolin-3-yl)acetic acid. A solution of tert-butyl 2-(6,7-difluoro-2-oxo-1,4-dihydroquinazolin-3-yl)acetate (0.9 g, 3.017 mmol, 1 equiv) and TFA (5 mL) in DCM (15 mL) was stirred overnight at RT under air atmosphere. The reaction mixture was concentrated under reduced pressure. This resulted in the crude product (6,7-difluoro-2-oxo-1,4-dihydroquinazolin-3-yl) acetic acid (0.62 g, 84.85%). LCMS (ES, m/z): 243$[M+H]^+$.

N-[(1S)-1-(4-cyano-2-fluorophenyl)ethyl]-2-(6,7-difluoro-2-oxo-1,4-dihydroquinazolin-3-yl)acetamide. A mixture of (6,7-difluoro-2-oxo-1,4-dihydroquinazolin-3-yl)acetic acid (150 mg, 0.619 mmol, 1 equiv), 4-[(1S)-1-aminoethyl]-3-fluorobenzonitrile (122.03 mg, 0.743 mmol, 1.2 equiv), HATU (282.61 mg, 0.743 mmol, 1.2 equiv) and DIEA (240.15 mg, 1.857 mmol, 3 equiv) in DMF (3.00 mL) was stirred for 2 h at RT under air atmosphere. The reaction mixture was diluted with $H_2O$. The precipitated solids were collected by filtration and washed with $H_2O$. The crude product (100 mg) was purified by Prep-HPLC with the following conditions (Column: Xselect CSH C18 OBD Column 30*150 mm 5 μm; Mobile Phase A: Water (0.1% FA), Mobile Phase B: ACN; Flow rate: 60 mL/min; Gradient: 34% B to 49% B in 7 min, 49% B; Wave Length: 254/220 nm; $RT_1$ (min): 5.92) to afford N-[(1S)-1-(4-cyano-2-fluorophenyl)ethyl]-2-(6,7-difluoro-2-oxo-1,4-dihydroquinazolin-3-yl)acetamide (77.5 mg, 32.22%). LCMS (ES, m/z): 389.05 $[M+H]^+$. $^1H$ NMR (300 MHz, DMSO-$d_6$) δ 9.37 (s, 1H), 8.67 (d, J=7.2 Hz, 1H), 7.83 (dd, J=10.5, 1.5 Hz, 1H), 7.71-7.68 (m, 1H), 7.58 (t, J=7.5 Hz, 1H), 7.24-7.18 (m, 1H), 6.72 (dd, J=11.7, 6.9 Hz, 1H), 5.1-5.12 (m, 1H), 4.41 (s, 2H), 3.97 (s, 2H), 1.37 (d, J=7.2 Hz, 3H).

Example 43: rel-N-[(1R)-1-(5-Cyano-3-methylpyrazin-2-yl)ethyl]-2-(5,6-difluoro-2-oxo-1,4-dihydroquinazolin-3-yl)acetamide (Compound B55)

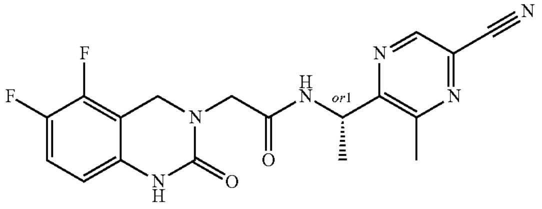 [SMILES: Cc1nc(C#N)cnc1[C@H](C)NC(=O)CN1Cc2c(ccc(F)c2F)NC1=O]

5-Chloro-2-(1-ethoxyethenyl)-3-methylpyrazine. A mixture of 2-bromo-5-chloro-3-methylpyrazine (1 g, 4.820 mmol, 1 equiv), tributyl(1-ethoxyethenyl)stannane (1.76 g, 4.868 mmol, 1.01 equiv) and $Pd(PPh_3)_4$ (1.11 g, 0.964 mmol, 0.2 equiv) in Toluene (10 mL) was stirred for 4 h at 100° C. under Ar atmosphere. The mixture was allowed to cool down to RT. The reaction mixture was diluted with $H_2O$. The reaction mixture was extracted with EtOAc. The reaction mixture was concentrated under reduced pressure. The residue was purified by column chromatography to afford 5-chloro-2-(1-ethoxyethenyl)-3-methylpyrazine (800 mg, 83.55%). LCMS (ES, m/z): 199 $[M+H]^+$.

1-(5-Chloro-3-methylpyrazin-2-yl)ethenone. A mixture of 5-chloro-2-(1-ethoxyethenyl)-3-methylpyrazine (800 mg, 4.027 mmol, 1 equiv) in HCl (4 M in $H_2O$, 8 mL) and 1,4-dioxane (8 mL) was stirred for 3 h at RT under air atmosphere. The reaction mixture was diluted with $H_2O$. The reaction mixture was extracted with EtOAc and concentrated under reduced pressure. The residue was purified by column chromatography to afford 1-(5-chloro-3-methylpyrazin-2-yl)ethanone (600 mg, 87.33%). LCMS (ES, m/z): 171 $[M+H]^+$.

1-(5-Chloro-3-methylpyrazin-2-yl)ethanamine. A mixture of 1-(5-chloro-3-methylpyrazin-2-yl)ethanone (600 mg, 3.517 mmol, 1 equiv), $CH_3COONH_4$ (1355.50 mg, 17.585 mmol, 5 equiv) and $NaBH_3CN$ (665.24 mg, 17.585 mmol, 5 equiv) in MeOH (10 mL) was stirred for 4 h at 80° C. under air atmosphere. The reaction mixture was concentrated under reduced pressure and the residue was purified by column chromatography to afford 1-(5-chloro-3-methylpyrazin-2-yl)ethanamine (400 mg, 66.27%). LCMS (ES, m/z): 172 $[M+H]^+$.

N-[1-(5-chloro-3-methylpyrazin-2-yl)ethyl]-2-(5,6-difluoro-2-oxo-1,4-dihydroquinazolin-3-yl)acetamide. DIEA (677.75 mg, 5.244 mmol, 3 equiv) was added at RT under air atmosphere to a stirred mixture of 1-(5-chloro-3-methylpyrazin-2-yl)ethanamine (300 mg, 1.748 mmol, 1 equiv) and HATU (797.56 mg, 2.098 mmol, 1.2 equiv) in DMF (5 mL). The reaction mixture was stirred for 2 h at RT under air atmosphere. The reaction mixture was diluted with $H_2O$. The reaction mixture was extracted with EtOAc. The reaction mixture was concentrated under reduced pressure. The residue was purified by reverse flash chromatography with the following conditions: (column, C18 silica gel; mobile phase, MeCN in Water (0.1% FA), 10% to 50% gradient in 40 min; detector, UV 254 nm). This resulted in N-[1-(5-chloro-3-methylpyrazin-2-yl)ethyl]-2-(5,6-difluoro-2-oxo-1,4-dihydroquinazolin-3-yl)acetamide (300 mg, 43.36%). LCMS (ES, m/z): 396 $[M+H]^+$.

N-[1-(5-cyano-3-methylpyrazin-2-yl)ethyl]-2-(5,6-difluoro-2-oxo-1,4-dihydroquinazolin-3-yl)acetamide. A mixture of N-[1-(5-chloro-3-methylpyrazin-2-yl)ethyl]-2-(5,6-difluoro-2-oxo-1,4-dihydroquinazolin-3-yl)acetamide (300 mg, 0.758 mmol, 1 equiv), Zn (49.56 mg, 0.758 mmol, 1 equiv) and $Pd(dppf)Cl_2$ (110.92 mg, 0.152 mmol, 0.2 equiv) in DMF (5 mL) was stirred for 4 h at 120° C. under Ar atmosphere. The mixture was allowed to cool down to RT. The residue was purified by column chromatography to afford crude product. The residue was purified by reverse flash chromatography with the following conditions: (column, C18; mobile phase, MeCN in Water (0.1% FA), 10% to 50% gradient in 40 min; detector, UV 254 nm). This resulted in N-[1-(5-cyano-3-methylpyrazin-2-yl)ethyl]-2-(5,6-difluoro-2-oxo-1,4-dihydroquinazolin-3-yl)acetamide (90 mg, 30.73%). LCMS (ES, m/z): 387 $[M+H]^+$.

rel-N-[(1R)-1-(5-cyano-3-methylpyrazin-2-yl)ethyl]-2-(5,6-difluoro-2-oxo-1,4-dihydroquinazolin-3-yl)acetamide. The crude product (90 mg) was purified by Chiral HPLC with the following conditions (Column: CHIRALPAK IA, 2*25 cm, 5 μm; Mobile Phase A: Hex (10 mM $NH_3$-MeOH), Mobile Phase B: IPA-HPLC; Flow rate: 20 mL/min; Gradient: 50% B to 50% B in 18 min; Wave Length: 220/247 nm; RT1 (min): 7.97; RT2 (min): 13.295; Sample Solvent: MeOH:DCM=1:1- HPLC; Injection Volume: 1 mL; Number Of Runs: 3) to afford rel-N-[(1R)-1-(5-cyano-3-methylpyrazin-2-yl)ethyl]-2-(5,6-difluoro-2-oxo-1,4-dihydroquinazolin-3-yl)acetamide (37.2 mg, 41.33%). LCMS (ES, m/z): 387.15 $[M+H]^+$. $^1H$ NMR (400 MHz, DMSO-$d_6$) δ 9.46 (s, 1H), 9.02 (s, 1H), 8.65 (d, J=7.2 Hz, 1H), 7.24-7.17 (m, 1H), 6.56-6.52 (m, 1H), 5.27-5.20 (m, 1H), 4.55-4.46 (m, 2H), 4.02-3.91 (m, 2H), 2.64 (s, 3H), 1.40 (d, J=6.8 Hz, 3H).

Example 44: rel-2-(5,6-Difluoro-2-oxo-1,4-dihydroquinazolin-3-yl)-N-[(1R)-1-(4-methylpyridazin-3-yl)ethyl]acetamide (Compound B25)

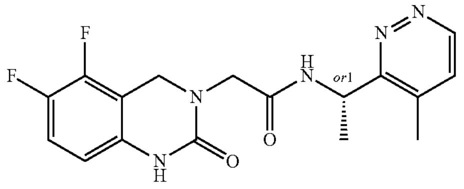 [SMILES: Cc1ccnnc1[C@H](C)NC(=O)CN1Cc2c(ccc(F)c2F)NC1=O]

3-(1-Ethoxyethenyl)-4-methylpyridazine. Into a 40 mL sealed tube were added 3-chloro-4-methylpyridazine (2 g, 15.557 mmol, 1 equiv), tributyl(1-ethoxyethenyl) stannane (5.62 g, 15.557 mmol, 1 equiv), $Pd(PPh_3)_4$ (1.80 g, 1.556 mmol, 0.1 equiv) and Toluene (20 mL) at RT. The reaction mixture was stirred for 4 h at 100° C. under Ar atmosphere. The residue was purified by column chromatography to afford 3-(1-ethoxyethenyl)-4-methylpyridazine (2 g, 78.29%). LCMS (ES, m/z): $[M+H]^+$=165.

1-(4-Methylpyridazin-3-yl) ethanone. Into a 10 mL round-bottom flask were added 3-(1-ethoxyethenyl)-4-methylpyridazine (1.9 g, 11.571 mmol, 1 equiv), HCl (4 M, 10 mL) and dioxane (10 mL) at 0° C. The reaction mixture was stirred for 3 h at RT. The residue was purified by column chromatography to afford 1-(4-methylpyridazin-3-yl)ethanone (1.2 g, 76.17%). LCMS (ES, m/z): $[M+H]^+$=137.

1-(4-Methylpyridazin-3-yl) ethanamine. Into a 100 mL round-bottom flask were added 1-(4-methylpyridazin-3-yl) ethanone (1.2 g, 8.814 mmol, 1 equiv), $NaBH_3CN$ (2.77 g, 44.070 mmol, 5 equiv), $CH_3COONH_4$ (3.40 g, 44.070 mmol, 5 equiv) and MeOH (20 mL) at 0° C. The reaction mixture was stirred for 6 h at 80° C. under Ar atmosphere. The residue was purified by column chromatography to afford 1-(4-methylpyridazin-3-yl)ethanamine (400 mg, 33.08%). LCMS (ES, m/z): $[M+H]^+$=138.

2-(5,6-difluoro-2-oxo-1,4-dihydroquinazolin-3-yl)-N-[1-(4-methylpyridazin-3-yl) ethyl]acetamide. Into a 40 mL sealed tube were added (5,6-difluoro-2-oxo-1,4-dihydroquinazolin-3-yl)acetic acid (150 mg, 0.619 mmol, 1 equiv), 1-(4-methylpyridazin-3-yl)ethanamine (84.97 mg, 0.619 mmol, 1 equiv), HATU (282.61 mg, 0.743 mmol, 1.2 equiv), DIEA (240.15 mg, 1.857 mmol, 3 equiv) and DMF (3 mL) at RT. The reaction mixture was stirred for 3 h at RT. The residue was purified by reversed-phase flash chromatography with the following conditions: column, C18 silica gel; mobile phase, MeCN in Water (10 mmol/L $NH_4HCO_3$), 10% to 50% gradient in 30 min; detector, UV 254 nm. This resulted in 2-(5,6-difluoro-2-oxo-1,4-dihydroquinazolin-3-yl)-N-[1-(4-methylpyridazin-3-yl)ethyl]acetamide (150 mg, 67.02%). LCMS (ES, m/z): $[M+H]^+$=362.

rel-2-(5,6-difluoro-2-oxo-1,4-dihydroquinazolin-3-yl)-N-[(1R)-1-(4-methylpyridazin-3-yl) ethyl]acetamide. The crude product (150 mg) was purified by Chiral-Prep-HPLC with the following conditions (Column: CHIRAL ART Cellulose-SZ, 3*25 cm, 5 μm; Mobile Phase A: Hex (0.1% 2 M $NH_3$-MeOH)-HPLC, Mobile Phase B: EtOH-HPLC; Flow rate: 40 mL/min; Gradient: 50% B to 50% B in 12 min; Wave Length: 254 nm; $RT_1$ (min): 8.8; $RT_2$ (min): 10.8; Sample Solvent: DMSO; Injection Volume: 0.2 mL; Number Of Runs: 15) to afford rel-2-(5,6-difluoro-2-oxo-1,4-dihydroquinazolin-3-yl)-N-[(1R)-1-(4-methylpyridazin-3-yl) ethyl]acetamide (39.2 mg, 26.13%). LCMS (ES, m/z):

$[M+H]^+$=362.10. $^1$H NMR (300 MHz, DMSO-$d_6$) δ 9.47 (s, 1H), 8.99 (d, J=5.1 Hz, 1H), 8.69 (d, J=7.8 Hz, 1H), 7.49-7.47 (m, 1H), 7.23-7.20 (m, 1H), 6.58-6.55 (m, 1H), 5.35 (p, J=7.2 Hz, 1H), 4.53 (d, J=3.0 Hz, 2H), 4.00-3.98 (m, 2H), 2.37 (d, J=0.9 Hz, 3H), 1.48 (d, J=6.9 Hz, 3H).

Example 45: rel-N-[(1R)-1-(6-Cyano-4-methylpyridazin-3-yl)ethyl]-2-(5,6-difluoro-2-oxo-1,4-dihydroquinazolin-3-yl)acetamide (Compound B23)

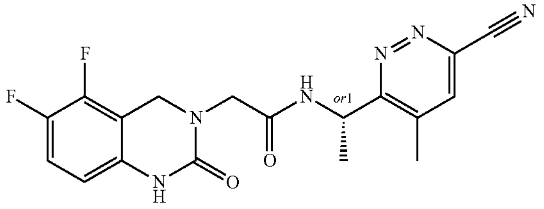 [SMILES: Cc1cc(C#N)nnc1[C@H](C)NC(=O)CN1Cc2c(ccc(F)c2F)NC1=O]

6-Chloro-3-(1-ethoxyethenyl)-4-methylpyridazine. Tributyl(1-ethoxyethenyl)stannane (11.08 g, 30.675 mmol, 1 equiv) was added dropwise at 100° C. under Ar atmosphere to a stirred solution of 3,6-dichloro-4-methylpyridazine (5 g, 30.675 mmol, 1 equiv) and $Pd(PPh_3)_4$ (3.54 g, 3.068 mmol, 0.1 equiv) in dioxane (50 mL). The reaction mixture was concentrated under reduced pressure and purified by column chromatography to afford 6-chloro-3-(1-ethoxyethenyl)-4-methylpyridazine (1 g, 16.41%). LCMS (ES, m/z): 199 $[M+H]^+$.

1-(6-Chloro-4-methylpyridazin-3-yl)ethenone. HCl (4 M, 5 mL) was added dropwise at 0° C. under air atmosphere to a stirred solution of 6-chloro-3-(1-ethoxyethenyl)-4-methylpyridazine (1 g, 5.034 mmol, 1 equiv) in dioxane (5 mL). The aqueous layer was extracted with EtOAc. The reaction mixture was concentrated under reduced pressure and purified by column chromatography to afford 1-(6-chloro-4-methylpyridazin-3-yl)ethanone (400 mg, 46.58%). LCMS (ES, m/z): 171$[M+H]^+$.

1-(6-Chloro-4-methylpyridazin-3-yl)ethanamine. A solution of 1-(6-chloro-4-methylpyridazin-3-yl)ethanone (400 mg, 0.100 mmol, 1 equiv), $NH_4Cl$ (1254.16 mg, 23.450 mmol, 10 equiv) and $NaBH_3CN$ (736.69 mg, 11.725 mmol, 5 equiv) in MeOH (4 mL) was stirred at 80° C. under air atmosphere. The reaction was quenched with $H_2O$ at RT and the aqueous layer was extracted with EtOAc. The reaction mixture was concentrated under reduced pressure and purified by Prep-TLC ($CH_2Cl_2$/MeOH 10:1) to afford 1-(6-chloro-4-methylpyridazin-3-yl)ethanamine (200 mg, 49.70%). LCMS (ES, m/z): 172 $[M+H]^+$.

N-[1-(6-Chloro-4-methylpyridazin-3-yl)ethyl]-2-(5,6-difluoro-2-oxo-1,4-dihydroquinazolin-3-yl)acetamide. 1-(6-chloro-4-methylpyridazin-3-yl)ethanamine (202.68 mg, 1.181 mmol, 1.1 equiv) was added at RT under air atmosphere to a stirred solution of (5,6-difluoro-2-oxo-1,4-dihydroquinazolin-3-yl)acetic acid (260 mg, 1.074 mmol, 1 equiv), EDCI (246.96 mg, 1.289 mmol, 1.2 equiv) and DMAP (52.46 mg, 0.430 mmol, 0.4 equiv) in DMF (3 mL). The residue was purified by reversed-phase flash chromatography with the following conditions: (column, C18 silica gel; mobile phase, MeCN in Water (10 mmol/L $NH_4HCO_3$), 10% to 50% gradient in 10 min; detector, UV 254 nm). to afford N-[1-(6-chloro-4-methylpyridazin-3-yl)ethyl]-2-(5,6-difluoro-2-oxo-1,4-dihydroquinazolin-3-yl)acetamide (240 mg, 56.48%). LCMS (ES, m/z): 396 $[M+H]^+$.

N-[1-(6-Cyano-4-methylpyridazin-3-yl)ethyl]-2-(5,6-difluoro-2-oxo-1,4-dihydroquinazolin-3-yl)acetamide. A solution of N-[1-(6-chloro-4-methylpyridazin-3-yl)ethyl]-2-(5,6-difluoro-2-oxo-1,4-dihydroquinazolin-3-yl)acetamide (220 mg, 0.556 mmol, 1 equiv), $Zn(CN)_2$ (130.54 mg, 1.112 mmol, 2 equiv), Zn (14.54 mg, 0.222 mmol, 0.4 equiv) and $Pd(dppf)Cl_2$ (81.34 mg, 0.111 mmol, 0.2 equiv) in DMSO (2 mL) was stirred at 100° C. under Ar atmosphere. The residue was purified by reversed-phase flash chromatography with the following conditions: (column, C18 silica gel; mobile phase, MeCN in Water (10 mmol/L $NH_4HCO_3$), 0% to 100% gradient in 60 min; detector, UV 254 nm). to afford N-[1-(6-cyano-4-methylpyridazin-3-yl)ethyl]-2-(5,6-difluoro-2-oxo-1,4-dihydroquinazolin-3-yl)acetamide (140 mg, 65.19%). LCMS (ES, m/z): 387 $[M+H]^+$.

rel-N-[(1R)-1-(6-Cyano-4-methylpyridazin-3-yl)ethyl]-2-(5,6-difluoro-2-oxo-1,4-dihydroquinazolin-3-yl)acetamide. A stirred solution of N-[1-(6-cyano-4-methylpyridazin-3-yl)ethyl]-2-(5,6-difluoro-2-oxo-1,4-dihydroquinazolin-3-yl)acetamide (140 mg, 0.362 mmol, 1 equiv) in MeOH (2 mL) and separated by Column Name: (CHIRAL ART Cellulose-SB, 3.0*50 mm; 3 um; Mobile Phase A: MtBE (0.1% DEA):MeOH=90:10; Flow rate: 1 mL/min; Gradient: 0% B to 0% B; Injection Volume: 5 ul mL) to afford rel-N-[(1R)-1-(6-cyano-4-methylpyridazin-3-yl)ethyl]-2-(5,6-difluoro-2-oxo-1,4-dihydroquinazolin-3-yl) acetamide (36.9 mg, 26.36%). LCMS (ES, m/z): 387.10 $[M+H]^+$. $^1$H NMR (400 MHz, DMSO-$d_6$) δ 9.46 (d, J=1.6 Hz, 1H), 8.83 (d, J=7.6 Hz, 1H), 8.20 (s, 1H), 7.24-7.17 (m, 1H), 6.56-6.53 (m, 1H), 5.40-5.33 (m, 1H), 4.56-4.46 (m, 2H), 4.03-3.93 (m, 2H), 2.45 (s, 3H), 1.50 (d, J=6.8 Hz, 3H).

Example 46: N-[(1S)-1-(4-cyano-2-fluorophenyl) ethyl]-2-(6-fluoro-2-oxo-1,4-dihydroquinazolin-3-yl) acetamide (Compound B206)

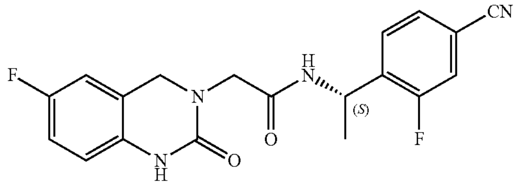

2-(Aminomethyl)-4-fluoroaniline. Borane-tetrahydrofuran complex (2647 mL, 6 equiv) was added dropwise at 0° C. to a solution of 2-amino-5-fluorobenzonitrile (60 g, 440.758 mmol, 1.00 equiv) in tetrahydrofuran (600 mL) under $N_2$ atmosphere. The reaction mixture was stirred for 6 h at RT under $N_2$ atmosphere. The reaction was quenched by the addition of EtOH at 0° C. The mixture was adjusted to pH 4 with HCl (1 M). The precipitated solids were collected by filtration and washed with THF. The reaction mixture was diluted with $H_2O$. The mixture was adjusted to pH 12 with $NH_3 \cdot H_2O$ and extracted with DCM. The combined organic layers were washed with brine and dried over anhydrous $Na_2SO_4$ and filtered. The filtrate was concentrated under reduced pressure. The crude product was used in the next step directly without further purification.

Methyl 2-{[(2-amino-5-fluorophenyl)methyl]amino}acetate. Methyl 2-bromoacetate (54.57 g, 356.733 mmol, 1 equiv) was added dropwise at 0° C. under $N_2$ atmosphere to a solution of 2-(aminomethyl)-4-fluoroaniline (50 g, 356.733 mmol, 1 equiv), $K_2CO_3$ (147.69 g, 1070.199 mmol, 3 equiv) in DMF (500 mL). The reaction mixture was stirred for 30 min at 0° C., filtered, and the filter cake was washed with EtOAc. The residue was washed with brine and dried over anhydrous $Na_2SO_4$ and filtered. The filtrate was concentrated under reduced pressure. The residue was purified by trituration with tert-Butyl methyl ether resulting in methyl 2-{[(2-amino-5-fluorophenyl)methyl]amino}acetate (27 g, 35.66%).

Methyl 2-(6-fluoro-2-oxo-1,4-dihydroquinazolin-3-yl)acetate. CDI (30.94 g, 190.836 mmol, 1.5 equiv) was added batchwise under $N_2$ atmosphere to a solution of methyl 2-{[(2-amino-5-fluorophenyl)methyl]amino}acetate (27 g, 127.224 mmol, 1 equiv), $Et_3N$ (38.62 g, 381.672 mmol, 3.0 equiv) in DCM (300 mL). After the mixture was stirred for 1 h at RT under $N_2$ atmosphere, 300 mL $H_2O$ was added. The reaction mixture was extracted with DCM. The combined organic layers were washed with brine and dried over anhydrous $Na_2SO_4$ and filtered. The filtrate was concentrated under reduced pressure. The residue was purified by column chromatography to afford methyl 2-(6-fluoro-2-oxo-1,4-dihydroquinazolin-3-yl)acetate (17 g, 56.09%).

(6-Fluoro-2-oxo-1,4-dihydroquinazolin-3-yl)acetic acid. A solution of methyl 2-(6-fluoro-2-oxo-1,4-dihydroquinazolin-3-yl)acetate (17 g, 71.363 mmol, 1 equiv), lithiumol (5.13 g, 214.089 mmol, 3 equiv) in tetrahydrofuran (30 mL) and $H_2O$ (150 mL) at RT under $N_2$ atmosphere. The mixture was adjusted to pH 3 with HCl (2 M). The precipitated solids were collected by filtration and washed with $H_2O$ providing (6-fluoro-2-oxo-1,4-dihydroquinazolin-3-yl)acetic acid (14 g, 87.51%).

N-[(1S)-1-(4-cyano-2-fluorophenyl)ethyl]-2-(6-fluoro-2-oxo-1,4-dihydroquinazolin-3-yl)acetamide. A mixture of (6-fluoro-2-oxo-1,4-dihydroquinazolin-3-yl)acetic acid (4 g, 17.842 mmol, 1 equiv), EDCI (5.13 g, 26.763 mmol, 1.5 equiv), DMAP (0.44 g, 3.568 mmol, 0.2 equiv) and 4-[-1-aminoethyl]-3-fluorobenzonitrile (2.93 g, 17.842 mmol, 1 equiv) in DMF was stirred at RT under $N_2$ atmosphere. The crude product was purified by Flash-Prep-HPLC with the following conditions (IntelFlash-1): Column: Waters XBridge RP18 19*150 mm, 5 um; mobile phase: water (it contains 0.05% ammonia and 10 mM formic acid) and acetonitrile with a gradient of 15% to 55% acetonitrile in 20 min; flow rate: 150 mL/min; detector UV wavelength: 254 nm to afford assumed N-[(1S)-1-(4-cyano-2-fluorophenyl) ethyl]-2-(6-fluoro-2-oxo-1,4-dihydroquinazolin-3-yl)acetamide (3.1 g, 46.91%). LCMS (ES,m/z): 371$[M+H]^+$ $^1H$ NMR (300 MHz, DMSO-$d_6$) δ 9.29 (s, 1H), 8.77-8.54 (m, 1H), 7.89-7.77 (m, 1H), 7.75-7.65 (m, 1H), 7.64-7.54 (m, 1H), 7.06-6.91 (m, 2H), 6.85-6.66 (m, 1H), 5.28-5.06 (m, 1H), 4.44 (s, 2H), 1.51-1.2 5 (m, 3H).

Example 47: rel-N-[(1R)-1-(4-Cyano-5-fluoropyridin-2-yl)ethyl]-2-(5,6-difluoro-2-oxo-1,4-dihydroquinazolin-3-yl)acetamide (Compound B53)

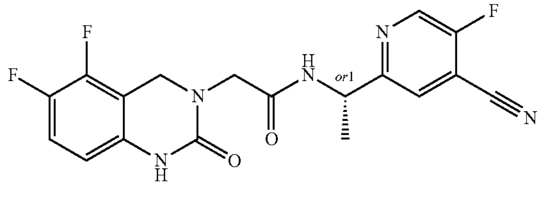 [SMILES: C[C@H](NC(=O)CN1Cc2c(ccc(F)c2F)NC1=O)c1cc(C#N)c(F)cn1]

4-Chloro-2-(1-ethoxyethenyl)-5-fluoropyridine. $Pd(PPh_3)_4$ (1.10 g, 0.950 mmol, 0.1 equiv) was added at RT under Ar atmosphere to a stirred solution of 2-bromo-4-chloro-5-fluoropyridine (2 g, 9.504 mmol, 1 equiv) and tributyl(1-ethoxyethenyl)stannane (3.43 g, 9.504 mmol, 1 equiv) in Toluene (20 mL). The reaction mixture was stirred for 4 h at 100° C. under Ar atmosphere. The reaction mixture was concentrated under reduced pressure. The residue was purified by column chromatography to afford 4-chloro-2-(1-ethoxyethenyl)-5-fluoropyridine (1.5 g, 78.27%). LCMS (ES, m/z): 202 $[M+H]^+$.

1-(4-Chloro-5-fluoropyridin-2-yl)ethenone. HCl (15 mL,4N) was added at RT under air atmosphere to a stirred solution of 4-chloro-2-(1-ethoxyethenyl)-5-fluoropyridine (1.5 g, 7.439 mmol, 1 equiv) in Dioxane (15 mL). The reaction mixture was stirred for 3 h at RT under air atmosphere. The mixture was neutralized to pH 8 with saturated $NaHCO_3$ (aq.). The reaction mixture was extracted with EtOAc. The combined organic layers were washed with brine and dried over anhydrous $Na_2SO_4$ and filtered. The filtrate was concentrated under reduced pressure. The residue was purified by column chromatography to afford 1-(4-chloro-5-fluoropyridin-2-yl)ethanone (1.1 g, 85.19%). LCMS (ES, m/z): 174 $[M+H]^+$.

1-(4-Chloro-5-fluoropyridin-2-yl)ethanamine. $NaBH_3CN$ (1.81 g, 28.805 mmol, 5 equiv) was added at RT under air atmosphere to a stirred solution of 1-(4-chloro-5-fluoropyridin-2-yl)ethanone (1 g, 5.761 mmol, 1 equiv) and $CH_3COONH_4$ (2.22 g, 28.805 mmol, 5 equiv) in i-PrOH (10 mL). The reaction mixture was stirred for overnight at 80° C. under air atmosphere. The reaction mixture was concentrated under reduced pressure. The residue was purified by column chromatography to afford 1-(4-chloro-5-fluoropyridin-2-yl)ethanamine (500 mg, 49.71%) a. LCMS (ES, m/z): 175 $[M+H]^+$.

N-[1-(4-chloro-5-fluoropyridin-2-yl)ethyl]-2-(5,6-difluoro-2-oxo-1,4-dihydroquinazolin-3-yl) acetamide. EDCI (428.20 mg, 2.233 mmol, 1.3 equiv) and HOBt (301.83 mg, 2.233 mmol, 1.3 equiv) and DIEA (444.15 mg, 3.436 mmol, 2 equiv) were added at RT under air atmosphere to a stirred solution of 1-(4-chloro-5-fluoropyridin-2-yl)ethanamine (300 mg, 1.718 mmol, 1 equiv) and (5,6-difluoro-2-oxo-1,4-dihydroquinazolin-3-yl)acetic acid (457.73 mg, 1.890 mmol, 1.1 equiv) in DMF (5 mL). The reaction mixture was stirred for 3 h at RT under air atmosphere. The reaction mixture was extracted with EtOAc. The combined organic layers were washed with brine and dried over anhydrous $Na_2SO_4$ and filtered. The filtrate was concentrated under reduced pressure. The residue was purified by column chromatography to afford N-[1-(4-chloro-5-fluoropyridin-2-yl)ethyl]-2-(5,6-difluoro-2-oxo-1,4-dihydroquinazolin-3-yl) acetamide (350 mg, 51.08%). LCMS (ES, m/z): 399 $[M+H]^+$.

N-[1-(4-cyano-5-fluoropyridin-2-yl)ethyl]-2-(5,6-difluoro-2-oxo-1,4-dihydroquinazolin-3-yl)acetamide. $Pd(dppf)Cl_2$ (55.05 mg, 0.075 mmol, 0.1 equiv) and Zn (19.67 mg, 0.301 mmol, 0.4 equiv) were added at RT under Ar atmosphere to a stirred solution of N-[1-(4-chloro-5-fluoropyridin-2-yl)ethyl]-2-(5,6-difluoro-2-oxo-1,4-dihydroquinazolin-3-yl)acetamide (300 mg, 0.752 mmol, 1 equiv) and $Zn(CN)_2$ (176.67 mg, 1.504 mmol, 2 equiv) in DMSO (3 mL). The reaction mixture was stirred for overnight at 120° C. under Ar atmosphere. The residue was purified by column chromatography to afford the crude product. The residue was purified by reverse flash chromatography with the following conditions: (column, C18 silica gel; mobile phase, MeCN in Water (0.1% FA), 0% to 100% gradient in 40 min; detector, UV 254 nm). to afford N-[1-(4-cyano-5-fluoropyridin-2-yl)ethyl]-2-(5,6-difluoro-2-oxo-1,4-dihydroquinazolin-3-yl)acetamide (140 mg, 47.80%). LCMS (ES, m/z): 409 $[M+H]^+$.

rel-N-[(1R)-1-(4-cyano-5-fluoropyridin-2-yl)ethyl]-2-(5,6-difluoro-2-oxo-1,4-dihydroquinazolin-3-yl)acetamide. The crude product (100 mg) was purified by Chiral-HPLC with the following conditions: (Column: CHIRAL ART Cellulose-SC, 2*25 cm, 5 μm; Mobile Phase A: Hex (10 mM $NH_3$-MeOH), Mobile Phase B: EtOH-HPLC; Flow rate: 20 mL/min; Gradient: 50% B to 50% B in 15 min; Wave Length: 217/247 nm; $RT_1$ (min): 3.69; $RT_2$ (min): 8.24; Sample Solvent: DMSO; Injection Volume: 0.27 mL) to afford rel-N-[(1R)-1-(4-cyano-5-fluoropyridin-2-yl)ethyl]-2-(5,6-difluoro-2-oxo-1,4-dihydroquinazolin-3-yl)acetamide (25 mg, 25.00%). LCMS (ES, m/z): 389.95 $[M+H]^+$ 1H NMR (300 MHz, DMSO-$d_6$) δ 9.52 (s, 1H), 8.87 (s, 1H), 8.61 (d, J=7.5 Hz, 1H), 7.93 (d, J=5.4 Hz, 1H), 7.24-7.18 (m, 1H), 6.60-6.55 (m, 1H), 5.06-4.96 (m, 1H), 4.57 (s, 2H), 4.04 (d, J=2.7 Hz, 2H), 1.41 (d, J=6.9 Hz, 3H).

Example 48: rel-N-[(3S)-6-cyano-2H,3H-furo[3,2-b]pyridin-3-yl]-2-(5,6-difluoro-2-oxo-1,4-dihydroquinazolin-3-yl)acetamide. (Compound B65)

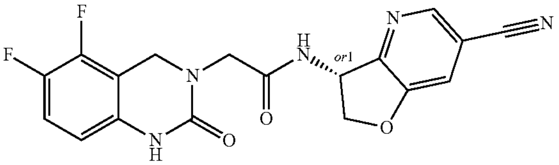 [SMILES: N#Cc1cnc2c(c1)OC[C@@H]2NC(=O)CN1Cc2c(ccc(F)c2F)NC1=O]

5-Bromo-2-iodopyridin-3-ol. 12 (14.59 g, 57.472 mmol, 1 equiv) was added dropwise at 0° C. under air atmosphere to a stirred solution of 5-bromopyridin-3-ol (10 g, 57.472 mmol, 1 equiv) and $Na_2CO_3$ (30.46 g, 287.360 mmol, 5 equiv) in $H_2O$ (200 mL). The reaction mixture was stirred for 4 h at RT under air atmosphere. The mixture was adjusted to pH 7-8 with HCl (2 N, aq.). The precipitated solids were collected by filtration and washed with $H_2O$. The crude product was used in the next step directly without further purification, to afford 5-bromo-2-iodopyridin-3-ol (13 g, 75.43%). LCMS (ES, m/z): 300 $[M+H]^+$.

3-(Benzyloxy)-5-bromo-2-iodopyridine. Benzyl bromide (8.16 g, 47.684 mmol, 1.1 equiv) was added dropwise at 0° C. under air atmosphere to a stirred solution of 5-bromo-2-iodopyridin-3-ol (13 g, 43.349 mmol, 1 equiv) and $K_2CO_3$ (11.98 g, 86.698 mmol, 2 equiv) in MeCN (150 mL). The reaction mixture was stirred for 6 h at RT under air atmosphere. The reaction mixture was concentrated under reduced pressure. The residue was purified by column chromatography to afford 3-(benzyloxy)-5-bromo-2-iodopyridine (14 g, 82.81%). LCMS (ES, m/z): 390 $[M+H]^+$.

3-(Benzyloxy)-5-bromopyridine-2-carbaldehyde. (isopropylmagnesio)(lithio)-1lambda3-dichlorane (30.77 mL, 39.998 mmol, 1.2 equiv) was added dropwise at −40° C. under Ar atmosphere to a stirred solution of 3-(benzyloxy)-5-bromo-2-iodopyridine (13 g, 33.332 mmol, 1 equiv) in THF (120 mL). The reaction mixture was stirred for 2 h at −40° C. under Ar atmosphere. To the above mixture DMF (10.32 mL, 133.328 mmol, 4 equiv) was added dropwise over 10 min at −40° C. The reaction mixture was stirred for additional 1 h at −40° C. The reaction was quenched with sat. $NH_4Cl$ (aq.) at −40° C. The reaction mixture was extracted with EtOAc. The combined organic layers were washed with brine and dried over anhydrous $Na_2SO_4$ and filtered. The filtrate was concentrated under reduced pressure. The residue was purified by column chromatography to afford 3-(benzyloxy)-5-bromopyridine-2-carbaldehyde (7 g, 71.89%). LCMS (ES, m/z): 292 $[M+H]^+$.

5-Bromo-3-hydroxypyridine-2-carbaldehyde. $FeCl_3$ (8.33 g, 51.348 mmol, 2.5 equiv) was added dropwise at 0° C. under air atmosphere to a stirred solution of 3-(benzyloxy)-5-bromopyridine-2-carbaldehyde (6 g, 20.539 mmol, 1 equiv) in DCM (80 mL). The reaction mixture was stirred for 3 h at RT under air atmosphere. The reaction mixture was extracted with $CH_2Cl_2$. The combined organic layers were washed with brine and dried over anhydrous $Na_2SO_4$ and filtered. The filtrate was concentrated under reduced pressure. The residue was purified by column chromatography to afford 5-bromo-3-hydroxypyridine-2-carbaldehyde (2.5 g, 60.26%). LCMS (ES, m/z): 202 $[M+H]^+$.

6-Bromo-2H,3H-furo[3,2-b]pyridin-3-ol. t-BuOK (1.88 g, 16.732 mmol, 1.3 equiv) was added dropwise at 10° C. under air atmosphere to a stirred solution of iodotrimethyl-lambda6-sulfanone (3.68 g, 16.732 mmol, 1.3 equiv) in DMSO (30 mL). The reaction mixture was stirred for 30 min at 10° C. under air atmosphere. To the above mixture 5-bromo-3-hydroxypyridine-2-carbaldehyde (2.6 g, 12.871 mmol, 1 equiv) was added dropwise over 10 min at 10° C. The reaction mixture was stirred for additional 1 h at 10° C. The reaction was quenched with sat. $NH_4Cl$ (aq.) at 0° C. The reaction mixture was extracted with EtOAc. The combined organic layers were washed with brine and dried over anhydrous $Na_2SO_4$ and filtered. The filtrate was concentrated under reduced pressure. The residue was purified by column chromatography to afford 6-bromo-2H,3H-furo[3,2-b]pyridin-3-ol (1 g, 35.96%). LCMS (ES, m/z): 216 $[M+H]^+$.

3-azido-6-bromo-2H,3H-furo[3,2-b]pyridine. DPPA (1910.84 mg, 6.943 mmol, 1.5 equiv) was added dropwise at RT under air atmosphere to a stirred solution of 6-bromo-2H,3H-furo[3,2-b]pyridin-3-ol (1 g, 4.629 mmol, 1 equiv) and DBU (1057.06 mg, 6.943 mmol, 1.5 equiv) in THF (15 mL). The reaction mixture was stirred for 3 h at RT under air atmosphere. The residue was purified by column chromatography to afford 3-azido-6-bromo-2H,3H-furo[3,2-b]pyridine (800 mg, 71.70%). LCMS (ES, m/z): 241 $[M+H]^+$.

6-Bromo-2H,3H-furo[3,2-b]pyridin-3-amine. A solution of 3-azido-6-bromo-2H,3H-furo[3,2-b]pyridine (800 mg, 3.319 mmol, 1 equiv) and $PPh_3$ (1305.76 mg, 4.979 mmol, 1.5 equiv) in THF (8 mL) and $H_2O$ (8 mL) was stirred for 3 h at 50° C. under nitrogen atmosphere. The reaction mixture was concentrated under reduced pressure. The residue was purified by column chromatography to afford 6-bromo-2H,3H-furo[3,2-b]pyridin-3-amine (600 mg, 84.07%). LCMS (ES, m/z): 215 $[M+H]^+$.

N-{6-bromo-2H,3H-furo[3,2-b]pyridin-3-yl}-2-(5,6-difluoro-2-oxo-1,4-dihydroquinazolin-3-yl)acetamide. EDCI (579.42 mg, 3.023 mmol, 1.3 equiv) and HOBt (408.43 mg, 3.023 mmol, 1.3 equiv) and DIEA (601.01 mg, 4.650 mmol, 2 equiv) were added at RT under air atmosphere to a stirred solution of 6-bromo-2H,3H-furo[3,2-b]pyridin-3-amine (500 mg, 2.325 mmol, 1 equiv) and (5,6-difluoro-2-oxo-1,4-dihydroquinazolin-3-yl)acetic acid (619.39 mg, 2.558 mmol, 1.1 equiv) in DMF (10 mL). The reaction mixture was stirred for 3 h at RT under air atmosphere. The product was precipitated by the addition of $H_2O$. The precipitated solids were collected by filtration and washed with MeCN. The reaction mixture was concentrated under reduced pressure, to afford N-{6-bromo-2H,3H-furo[3,2-b]pyridin-3-yl}-2-(5,6-difluoro-2-oxo-1,4-dihydroquinazolin-3-yl)acetamide (600 mg, 58.75%). LCMS (ES, m/z): 439 $[M+H]^+$.

N-{6-Cyano-2H,3H-furo[3,2-b]pyridin-3-yl}-2-(5,6-difluoro-2-oxo-1,4-dihydroquinazolin-3-yl)acetamide. Pd(dppf)$Cl_2$ (83.30 mg, 0.114 mmol, 0.1 equiv) and Zn (29.77 mg, 0.455 mmol, 0.4 equiv) were added at RT under Ar atmosphere to a stirred solution of N-{6-bromo-2H,3H-furo[3,2-b]pyridin-3-yl}-2-(5,6-difluoro-2-oxo-1,4-dihydroquinazolin-3-yl)acetamide (500 mg, 1.138 mmol, 1 equiv) and $Zn(CN)_2$ (200.50 mg, 1.707 mmol, 1.5 equiv) in DMSO (7 mL). The reaction mixture was stirred for overnight at 120° C. under Ar atmosphere.

The residue was purified by column chromatography to afford the crude product. The crude product was purified by reverse flash chromatography with the following conditions: (column, C18 silica gel; mobile phase, MeCN in Water (0.1% FA), 0% to 100% gradient in 40 min; detector, UV 254 nm). to afford N-{6-cyano-2H,3H-furo[3,2-b]pyridin-3-yl}-2-(5,6-difluoro-2-oxo-1,4-dihydroquinazolin-3-yl)acetamide (200 mg, 45.59%). LCMS (ES, m/z): 386 $[M+H]^+$.

rel-N-[(3S)-6-cyano-2H,3H-furo[3,2-b]pyridin-3-yl]-2-(5,6-difluoro-2-oxo-1,4-dihydroquinazolin-3-yl)acetamide. The crude product (100 mg) was purified by Chiral-HPLC with the following conditions (Column: CHIRAL ART Cellulose-SB, 2*25 cm, 5 μm; Mobile Phase A: Hex (10 mM $NH_3$-MeOH), Mobile Phase B: EtOH-HPLC; Flow rate: 20 mL/min; Gradient: 30% B to 30% B in 27 min; Wave Length: 242/228 nm; $RT_1$ (min): 15.755; $RT_2$ (min): 21.56; Sample Solvent: DMSO; Injection Volume: 0.2 mL; Number Of Runs: 7) to afford rel-N-[(3S)-6-cyano-2H,3H-furo[3,2-b]pyridin-3-yl]-2-(5,6-difluoro-2-oxo-1,4-dihydroquinazolin-3-yl)acetamide (20 mg, 20.00%). LCMS (ES, m/z): 386.00 $[M+H]^+$. $^1$H NMR (300 MHz, DMSO-$d_6$) δ 9.52 (s, 1H), 8.83 (d, J=7.8 Hz, 1H), 8.54 (d, J=1.5 Hz, 1H), 7.82 (d, J=1.5 Hz, 1H), 7.24-7.21 (m, 1H), 6.58-6.55 (m, 1H), 5.60-5.52 (m, 1H), 4.91 (t, J=9.6 Hz, 1H), 4.56 (s, 2H), 4.51-4.36 (m, 1H), 4.00 (s, 2H).

In some embodiments, compounds of the disclosure are below in Table 1.

TABLE 1

| Comp. No. | Chemical Structure |
|---|---|
| N1 | 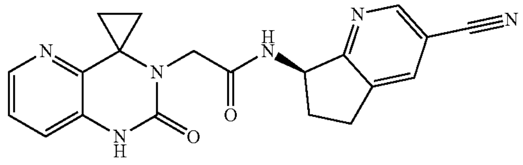 [SMILES: N#Cc1cnc2c(c1)CC[C@H]2NC(=O)CN1C(=O)Nc2cccnc2C12CC2] |
| N2 | 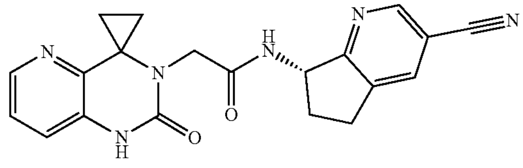 [SMILES: N#Cc1cnc2c(c1)CC[C@@H]2NC(=O)CN1C(=O)Nc2cccnc2C12CC2] |
| N3 | 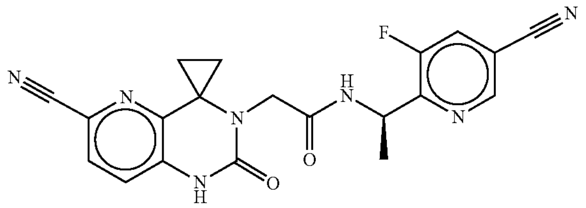 |
| N4 | 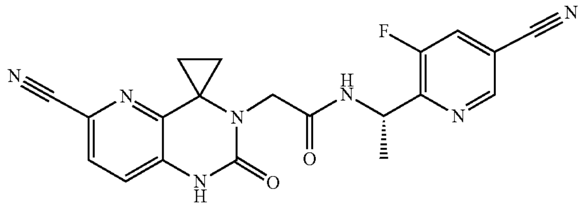 [SMILES: C[C@H](NC(=O)CN1C(=O)Nc2ccc(C#N)nc2C12CC2)c1ncc(C#N)cc1F] |
| N5 | 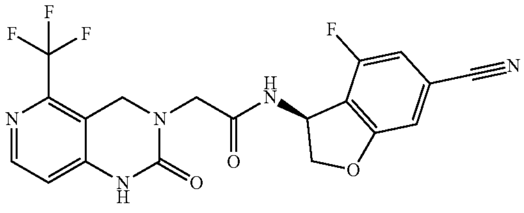 [SMILES: N#Cc1cc(F)c2c(c1)OC[C@H]2NC(=O)CN1Cc2c(ccnc2C(F)(F)F)NC1=O] |

TABLE 1-continued
| Comp. No. | Chemical Structure |
|---|---|
| N6 | 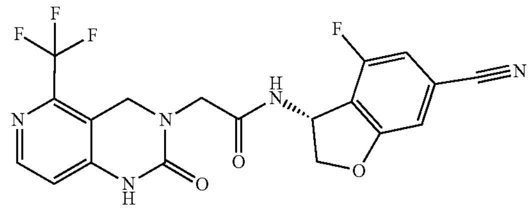 [SMILES: N#Cc1cc(F)c2c(c1)OC[C@@H]2NC(=O)CN1Cc2c(ccnc2C(F)(F)F)NC1=O] |
| N7 | 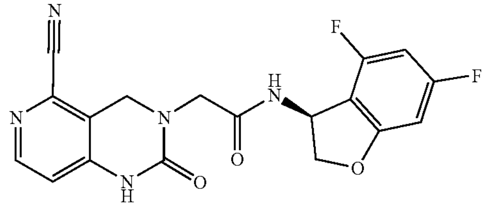 [SMILES: N#Cc1nccc2c1CN(CC(=O)N[C@@H]1COc3cc(F)cc(F)c31)C(=O)N2] |
| N8 | 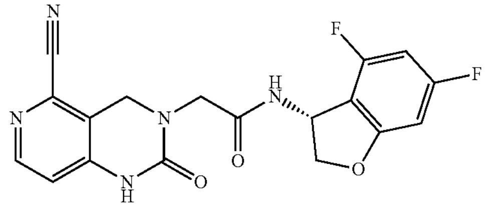 [SMILES: N#Cc1nccc2c1CN(CC(=O)N[C@H]1COc3cc(F)cc(F)c31)C(=O)N2] |
| N9 | 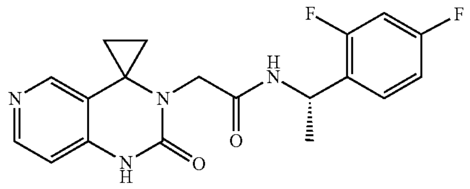 [SMILES: C[C@H](NC(=O)CN1C(=O)Nc2ccncc2C12CC2)c1ccc(F)cc1F] |
| N10 | 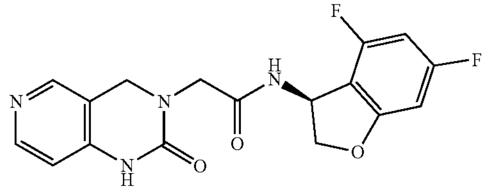 [SMILES: O=C(CN1Cc2cnccc2NC1=O)N[C@@H]1COc2cc(F)cc(F)c21] |
| N11 | 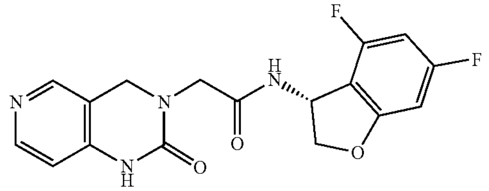 [SMILES: O=C(CN1Cc2cnccc2NC1=O)N[C@H]1COc2cc(F)cc(F)c21] |
| N12 | 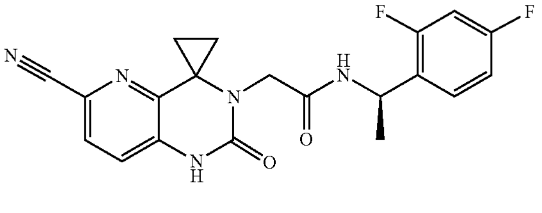 [SMILES: C[C@@H](NC(=O)CN1C(=O)Nc2ccc(C#N)nc2C12CC2)c1ccc(F)cc1F] |

TABLE 1-continued
| Comp. No. | Chemical Structure |
|---|---|
| N13 | 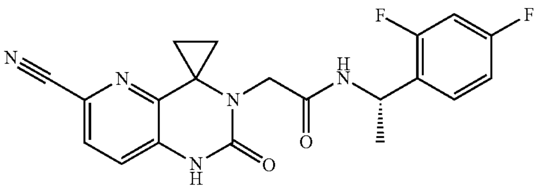 [SMILES: C[C@H](NC(=O)CN1C(=O)Nc2ccc(C#N)nc2C12CC2)c1ccc(F)cc1F] |
| N14 | 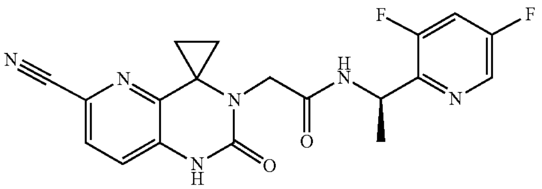 [SMILES: C[C@@H](NC(=O)CN1C(=O)Nc2ccc(C#N)nc2C12CC2)c1ncc(F)cc1F] |
| N15 | 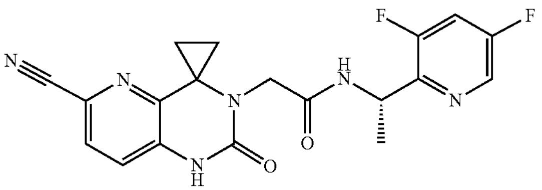 [SMILES: C[C@H](NC(=O)CN1C(=O)Nc2ccc(C#N)nc2C12CC2)c1ncc(F)cc1F] |
| N16 | 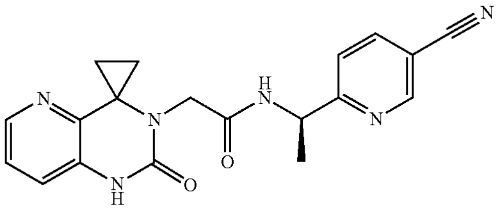 [SMILES: C[C@@H](NC(=O)CN1C(=O)Nc2cccnc2C12CC2)c1ccc(C#N)cn1] |
| N17 | 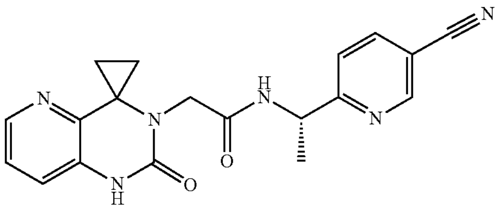 [SMILES: C[C@H](NC(=O)CN1C(=O)Nc2cccnc2C12CC2)c1ccc(C#N)cn1] |
| N18 | 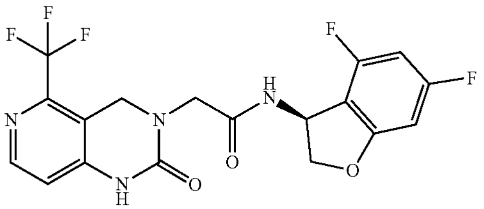 [SMILES: O=C(CN1Cc2c(ccnc2C(F)(F)F)NC1=O)N[C@@H]1COc2cc(F)cc(F)c21] |
| N19 | 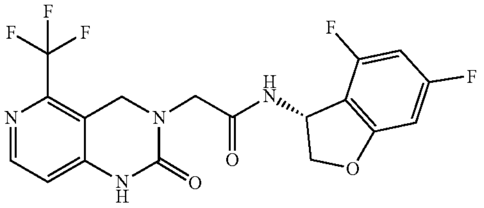 [SMILES: O=C(CN1Cc2c(ccnc2C(F)(F)F)NC1=O)N[C@H]1COc2cc(F)cc(F)c21] |

TABLE 1-continued
| Comp. No. | Chemical Structure |
|---|---|
| N20 | 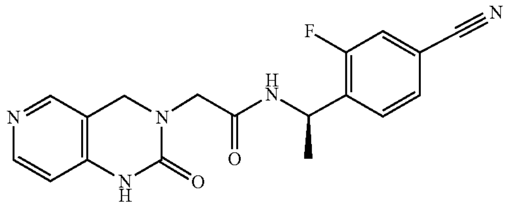 [SMILES: C[C@@H](NC(=O)CN1Cc2cnccc2NC1=O)c1ccc(C#N)cc1F] |
| N21 | 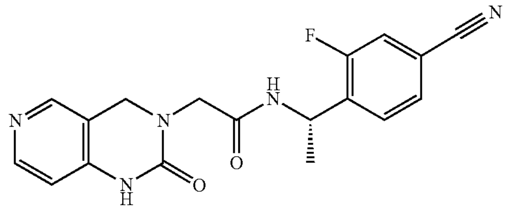 [SMILES: C[C@H](NC(=O)CN1Cc2cnccc2NC1=O)c1ccc(C#N)cc1F] |
| N22 | 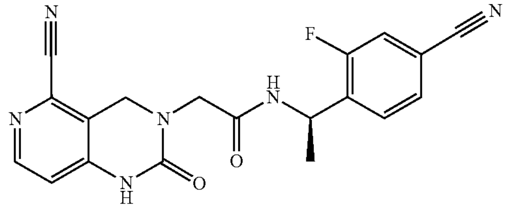 [SMILES: C[C@@H](NC(=O)CN1Cc2c(ccnc2C#N)NC1=O)c1ccc(C#N)cc1F] |
| N23 | 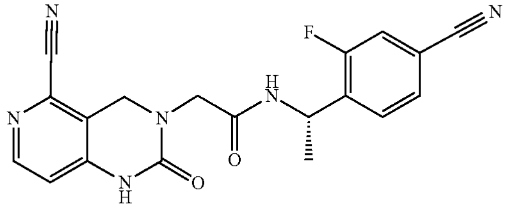 [SMILES: C[C@H](NC(=O)CN1Cc2c(ccnc2C#N)NC1=O)c1ccc(C#N)cc1F] |
| N24 | 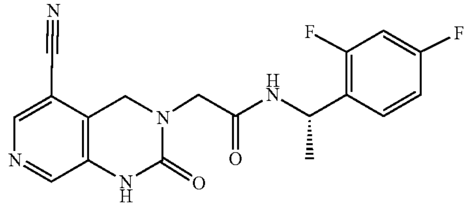 [SMILES: C[C@H](NC(=O)CN1Cc2c(C#N)cncc2NC1=O)c1ccc(F)cc1F] |
| N25 | 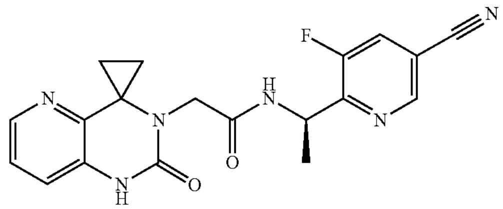 [SMILES: C[C@@H](NC(=O)CN1C(=O)Nc2cccnc2C12CC2)c1ncc(C#N)cc1F] |
| N26 | 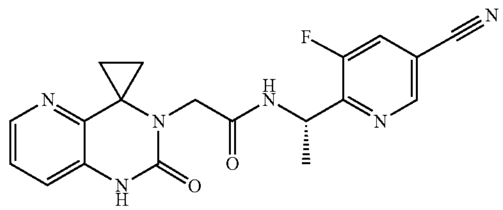 [SMILES: C[C@H](NC(=O)CN1C(=O)Nc2cccnc2C12CC2)c1ncc(C#N)cc1F] |

TABLE 1-continued
| Comp. No. | Chemical Structure |
|---|---|
| N27 | 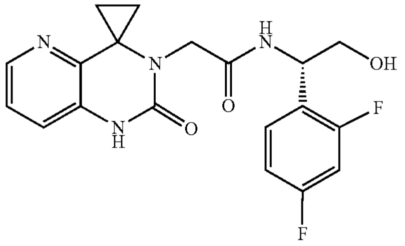 [SMILES: O=C(CN1C(=O)Nc2cccnc2C12CC2)N[C@H](CO)c1ccc(F)cc1F] |
| N28 | 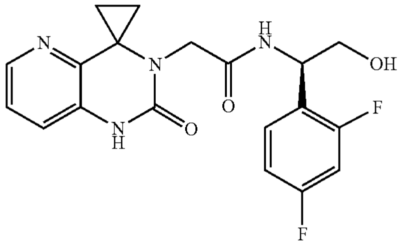 [SMILES: O=C(CN1C(=O)Nc2cccnc2C12CC2)N[C@@H](CO)c1ccc(F)cc1F] |
| 389.1<br>N29 | 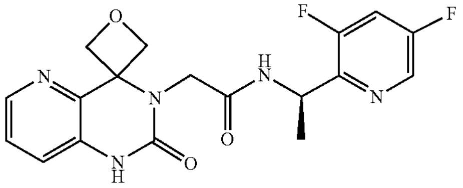 [SMILES: C[C@@H](NC(=O)CN1C(=O)Nc2cccnc2C12COC2)c1ncc(F)cc1F] |
| N30 | 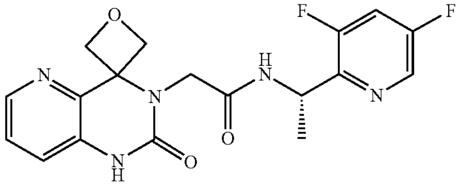 [SMILES: C[C@H](NC(=O)CN1C(=O)Nc2cccnc2C12COC2)c1ncc(F)cc1F] |
| N31 | 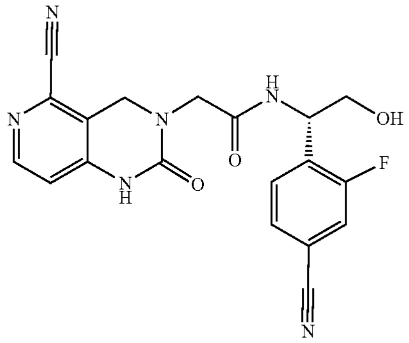 [SMILES: N#Cc1ccc([C@@H](CO)NC(=O)CN2Cc3c(ccnc3C#N)NC2=O)c(F)c1] |
| N32 | 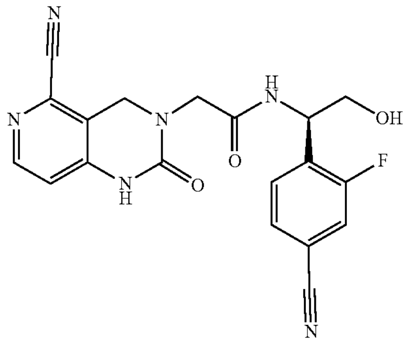 [SMILES: N#Cc1ccc([C@H](CO)NC(=O)CN2Cc3c(ccnc3C#N)NC2=O)c(F)c1] |

TABLE 1-continued
| Comp. No. | Chemical Structure |
| --- | --- |
| N33 | 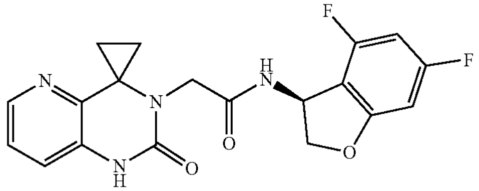 [SMILES: O=C(CN1C(=O)Nc2cccnc2C12CC2)N[C@@H]1COc2cc(F)cc(F)c21] |
| N34 | 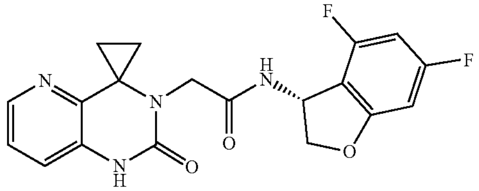 [SMILES: O=C(CN1C(=O)Nc2cccnc2C12CC2)N[C@H]1COc2cc(F)cc(F)c21] |
| N35 | 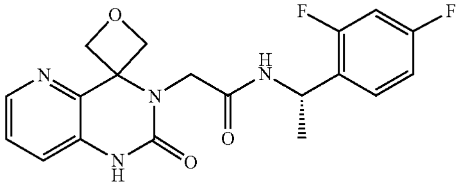 [SMILES: C[C@H](NC(=O)CN1C(=O)Nc2cccnc2C12COC2)c1ccc(F)cc1F] |
| N36 | 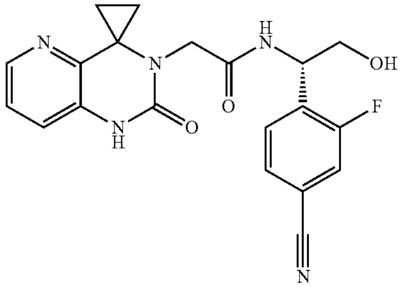 [SMILES: N#Cc1ccc([C@@H](CO)NC(=O)CN2C(=O)Nc3cccnc3C23CC3)c(F)c1] |
| N37 | 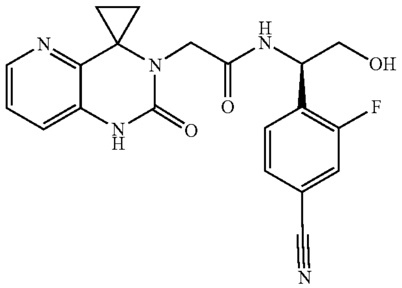 [SMILES: N#Cc1ccc([C@H](CO)NC(=O)CN2C(=O)Nc3cccnc3C23CC3)c(F)c1] |
| N38 | 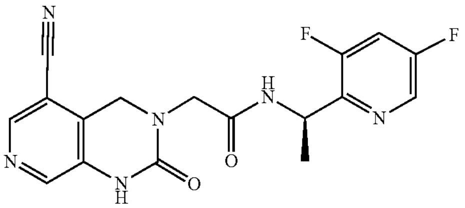 [SMILES: C[C@@H](NC(=O)CN1Cc2c(C#N)cncc2NC1=O)c1ncc(F)cc1F] |

TABLE 1-continued
| Comp. No. | Chemical Structure |
|---|---|
| N39 | 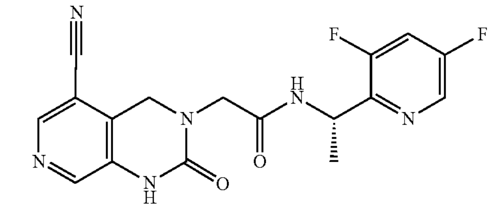 [SMILES: C[C@H](NC(=O)CN1Cc2c(C#N)cncc2NC1=O)c1ncc(F)cc1F] |
| N40 | 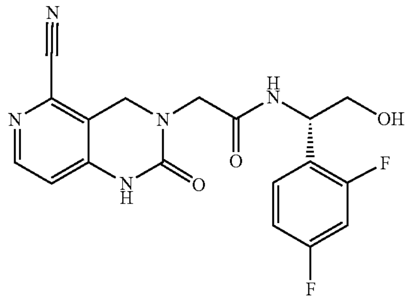 [SMILES: N#Cc1nccc2c1CN(CC(=O)N[C@H](CO)c1ccc(F)cc1F)C(=O)N2] |
| N41 | 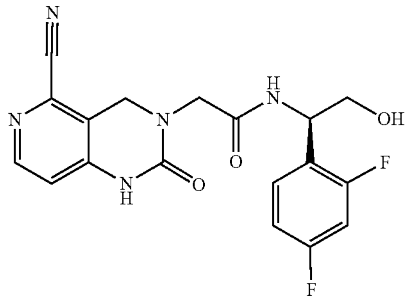 [SMILES: N#Cc1nccc2c1CN(CC(=O)N[C@@H](CO)c1ccc(F)cc1F)C(=O)N2] |
| N42 | 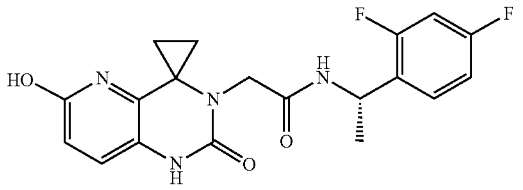 [SMILES: C[C@H](NC(=O)CN1C(=O)Nc2ccc(O)nc2C12CC2)c1ccc(F)cc1F] |
| N43 | 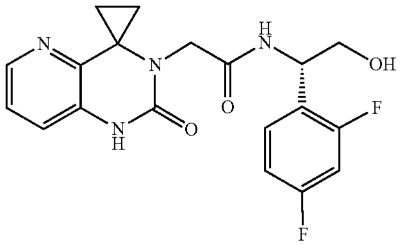 [SMILES: O=C(CN1C(=O)Nc2cccnc2C12CC2)N[C@H](CO)c1ccc(F)cc1F] |
| N44 | 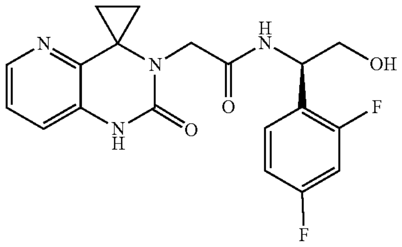 [SMILES: O=C(CN1C(=O)Nc2cccnc2C12CC2)N[C@@H](CO)c1ccc(F)cc1F] |

TABLE 1-continued
| Comp. No. | Chemical Structure |
|---|---|
| N45 | 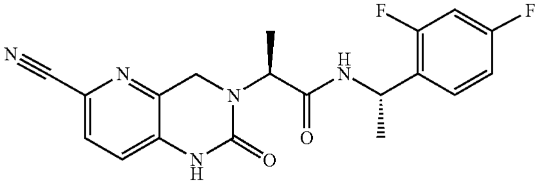 [SMILES: C[C@H](NC(=O)[C@H](C)N1Cc2nc(C#N)ccc2NC1=O)c1ccc(F)cc1F] |
| N46 | 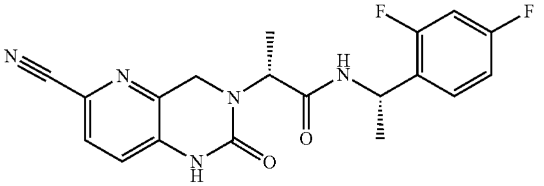 [SMILES: C[C@H](NC(=O)[C@@H](C)N1Cc2nc(C#N)ccc2NC1=O)c1ccc(F)cc1F] |
| N47 | 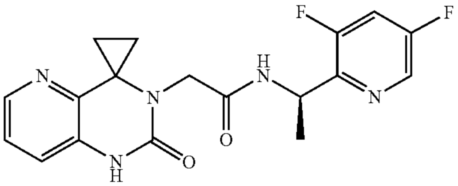 [SMILES: C[C@@H](NC(=O)CN1C(=O)Nc2cccnc2C12CC2)c1ncc(F)cc1F] |
| N48 | 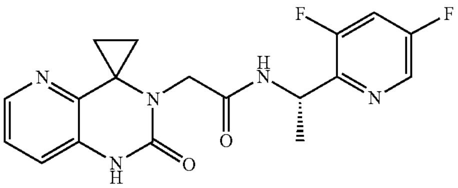 [SMILES: C[C@H](NC(=O)CN1C(=O)Nc2cccnc2C12CC2)c1ncc(F)cc1F] |
| N49 | 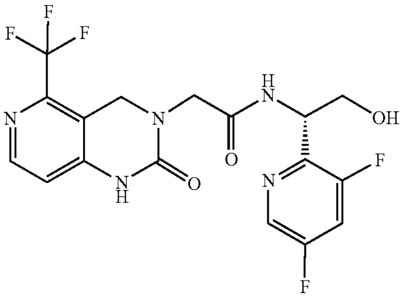 [SMILES: O=C(CN1Cc2c(ccnc2C(F)(F)F)NC1=O)N[C@H](CO)c1ncc(F)cc1F] |
| N50 | 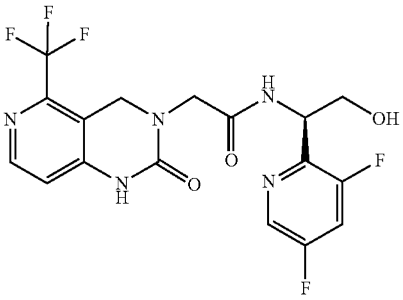 [SMILES: O=C(CN1Cc2c(ccnc2C(F)(F)F)NC1=O)N[C@@H](CO)c1ncc(F)cc1F] |

TABLE 1-continued
| Comp. No. | Chemical Structure |
|---|---|
| N51 | 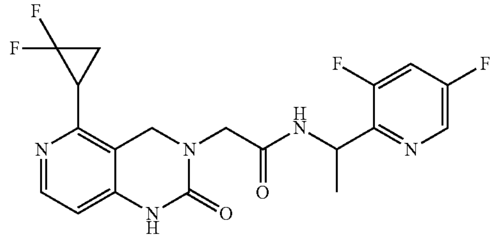 [SMILES: CC(NC(=O)CN1Cc2c(ccnc2C2CC2(F)F)NC1=O)c1ncc(F)cc1F] |
| N52 | 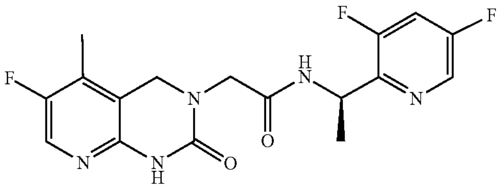 [SMILES: Cc1c(F)cnc2c1CN(CC(=O)N[C@H](C)c1ncc(F)cc1F)C(=O)N2] |
| N53 | 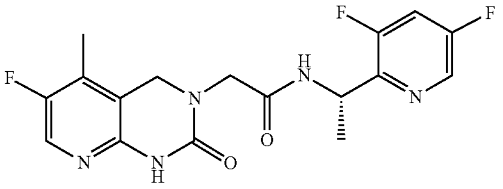 [SMILES: Cc1c(F)cnc2c1CN(CC(=O)N[C@@H](C)c1ncc(F)cc1F)C(=O)N2] |
| N54 | 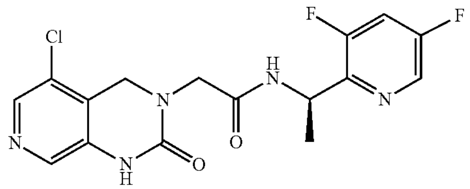 [SMILES: C[C@@H](NC(=O)CN1Cc2c(Cl)cncc2NC1=O)c1ncc(F)cc1F] |
| N55 | 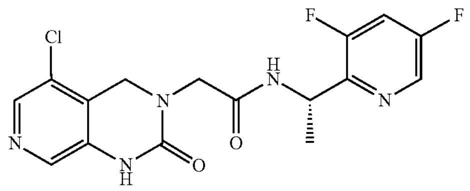 [SMILES: C[C@H](NC(=O)CN1Cc2c(Cl)cncc2NC1=O)c1ncc(F)cc1F] |
| N56 | 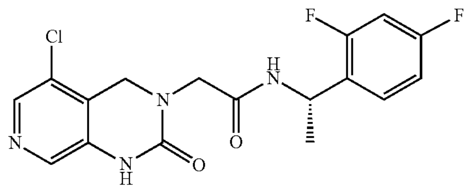 [SMILES: C[C@H](NC(=O)CN1Cc2c(Cl)cncc2NC1=O)c1ccc(F)cc1F] |
| N57 | 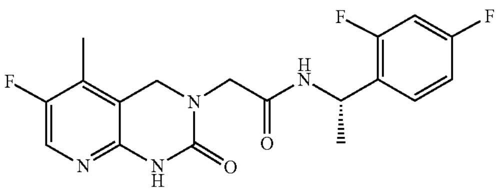 [SMILES: Cc1c(F)cnc2c1CN(CC(=O)N[C@@H](C)c1ccc(F)cc1F)C(=O)N2] |

TABLE 1-continued
| Comp. No. | Chemical Structure |
| --- | --- |
| N58 | 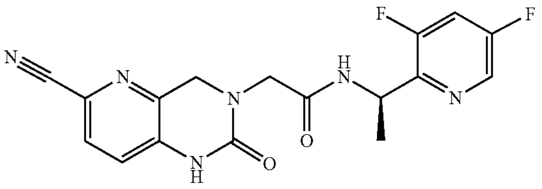 [SMILES: C[C@@H](NC(=O)CN1Cc2nc(C#N)ccc2NC1=O)c1ncc(F)cc1F] |
| N59 | 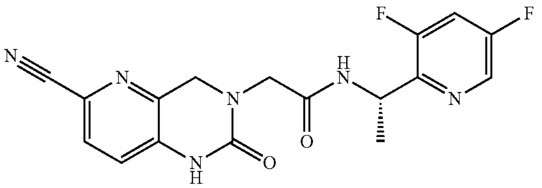 [SMILES: C[C@H](NC(=O)CN1Cc2nc(C#N)ccc2NC1=O)c1ncc(F)cc1F] |
| N60 | 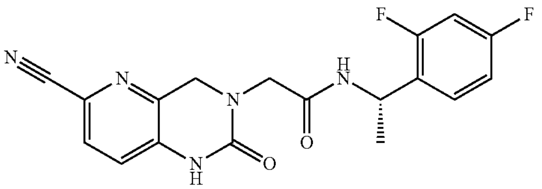 [SMILES: C[C@H](NC(=O)CN1Cc2nc(C#N)ccc2NC1=O)c1ccc(F)cc1F] |
| N61 | 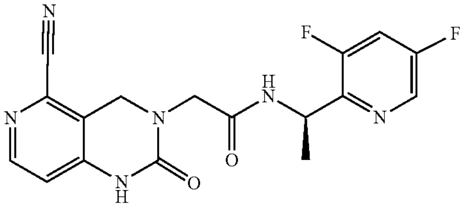 [SMILES: C[C@@H](NC(=O)CN1Cc2c(ccnc2C#N)NC1=O)c1ncc(F)cc1F] |
| N62 | 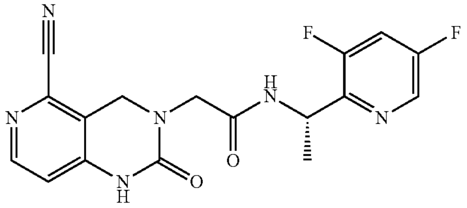 [SMILES: C[C@H](NC(=O)CN1Cc2c(ccnc2C#N)NC1=O)c1ncc(F)cc1F] |
| N63 | 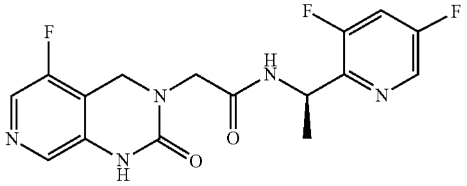 [SMILES: C[C@@H](NC(=O)CN1Cc2c(F)cncc2NC1=O)c1ncc(F)cc1F] |
| N64 | 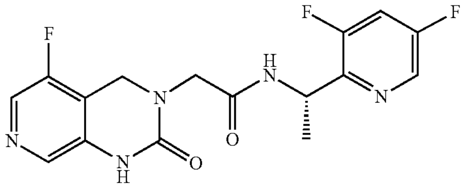 [SMILES: C[C@H](NC(=O)CN1Cc2c(F)cncc2NC1=O)c1ncc(F)cc1F] |

TABLE 1-continued
| Comp. No. | Chemical Structure |
|---|---|
| N65 | 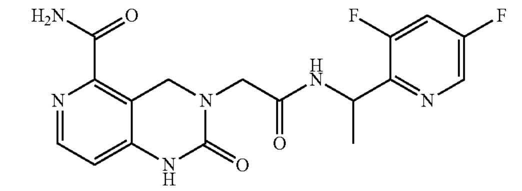 [SMILES: CC(NC(=O)CN1Cc2c(ccnc2C(N)=O)NC1=O)c1ncc(F)cc1F] |
| N66 | 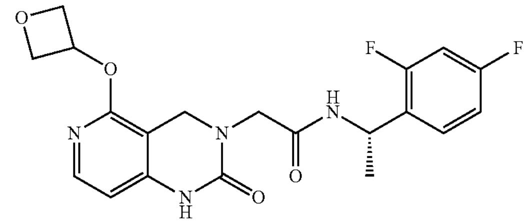 [SMILES: C[C@H](NC(=O)CN1Cc2c(ccnc2OC2COC2)NC1=O)c1ccc(F)cc1F] |
| N67 | 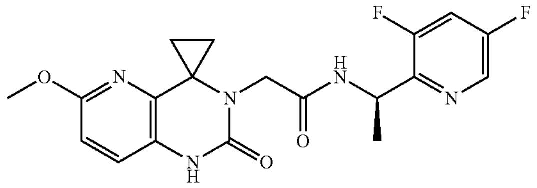 [SMILES: COc1ccc2c(n1)C1(CC1)N(CC(=O)N[C@H](C)c1ncc(F)cc1F)C(=O)N2] |
| N68 | 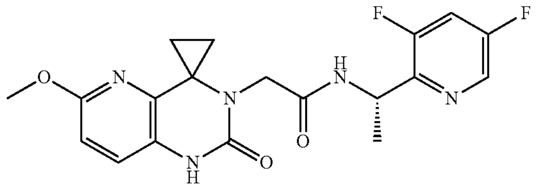 [SMILES: COc1ccc2c(n1)C1(CC1)N(CC(=O)N[C@@H](C)c1ncc(F)cc1F)C(=O)N2] |
| N69 | 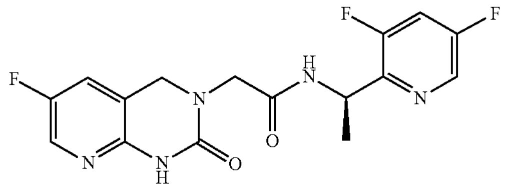 [SMILES: C[C@@H](NC(=O)CN1Cc2cc(F)cnc2NC1=O)c1ncc(F)cc1F] |
| N70 | 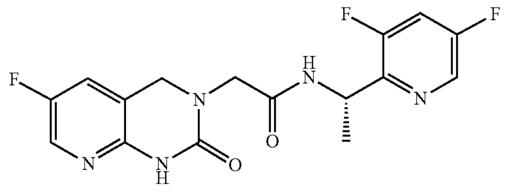 [SMILES: C[C@H](NC(=O)CN1Cc2cc(F)cnc2NC1=O)c1ncc(F)cc1F] |
| N71 | 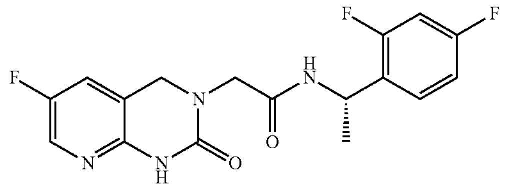 [SMILES: C[C@H](NC(=O)CN1Cc2cc(F)cnc2NC1=O)c1ccc(F)cc1F] |

TABLE 1-continued
| Comp. No. | Chemical Structure |
|---|---|
| N72 | 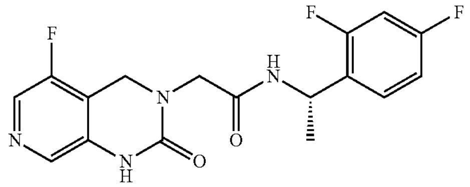 [SMILES: C[C@H](NC(=O)CN1Cc2c(F)cncc2NC1=O)c1ccc(F)cc1F] |
| N73 | 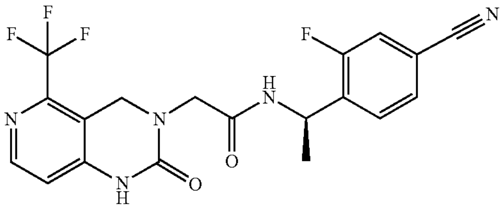 [SMILES: C[C@@H](NC(=O)CN1Cc2c(ccnc2C(F)(F)F)NC1=O)c1ccc(C#N)cc1F] |
| N74 | 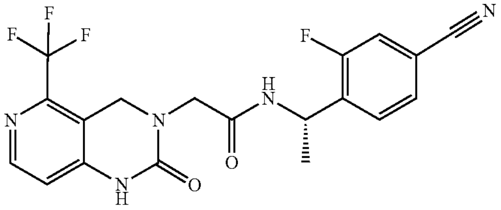 [SMILES: C[C@H](NC(=O)CN1Cc2c(ccnc2C(F)(F)F)NC1=O)c1ccc(C#N)cc1F] |
| N75 | 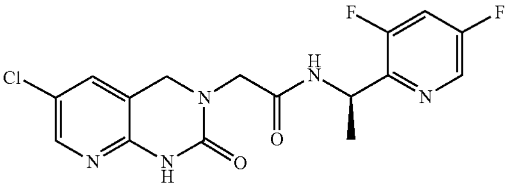 [SMILES: C[C@@H](NC(=O)CN1Cc2cc(Cl)cnc2NC1=O)c1ncc(F)cc1F] |
| N76 | 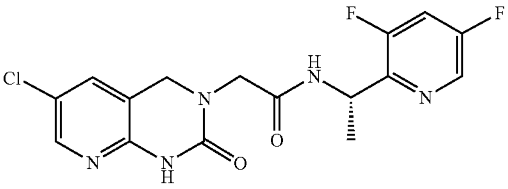 [SMILES: C[C@H](NC(=O)CN1Cc2cc(Cl)cnc2NC1=O)c1ncc(F)cc1F] |
| N77 | 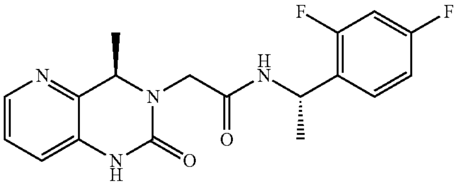 [SMILES: C[C@H](NC(=O)CN1C(=O)Nc2cccnc2[C@H]1C)c1ccc(F)cc1F] |
| N78 | 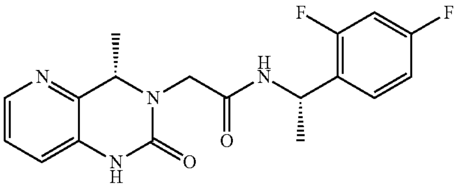 [SMILES: C[C@H](NC(=O)CN1C(=O)Nc2cccnc2[C@@H]1C)c1ccc(F)cc1F] |

TABLE 1-continued
| Comp. No. | Chemical Structure |
| --- | --- |
| N79 | 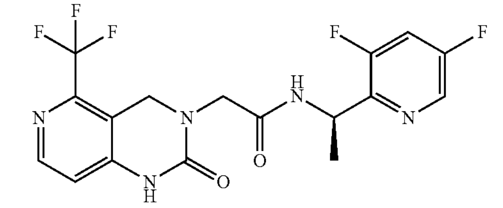 [SMILES: C[C@@H](NC(=O)CN1Cc2c(ccnc2C(F)(F)F)NC1=O)c1ncc(F)cc1F] |
| N80 | 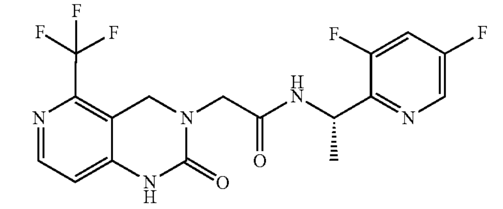 [SMILES: C[C@H](NC(=O)CN1Cc2c(ccnc2C(F)(F)F)NC1=O)c1ncc(F)cc1F] |
| N81 | 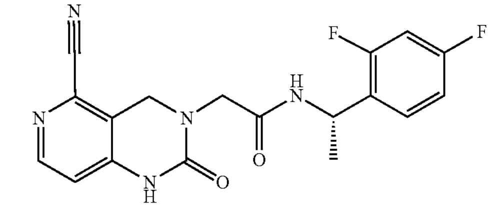 [SMILES: C[C@H](NC(=O)CN1Cc2c(ccnc2C#N)NC1=O)c1ccc(F)cc1F] |
| N82 | 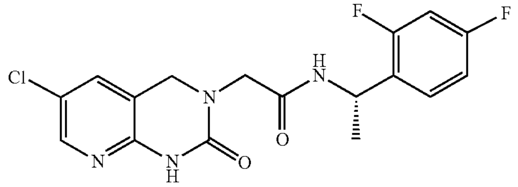 [SMILES: C[C@H](NC(=O)CN1Cc2cc(Cl)cnc2NC1=O)c1ccc(F)cc1F] |
| N83 | 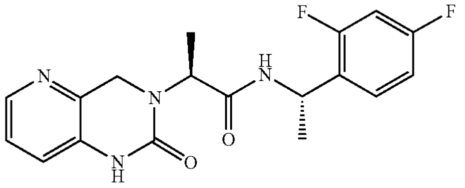 [SMILES: C[C@H](NC(=O)[C@H](C)N1Cc2ncccc2NC1=O)c1ccc(F)cc1F] |
| N84 | 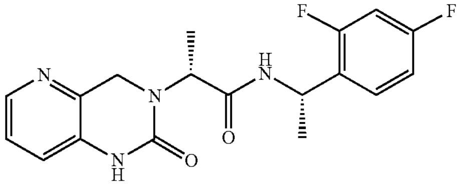 [SMILES: C[C@H](NC(=O)[C@@H](C)N1Cc2ncccc2NC1=O)c1ccc(F)cc1F] |
| N85 | 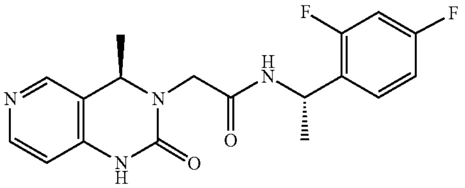 [SMILES: C[C@H](NC(=O)CN1C(=O)Nc2ccncc2[C@H]1C)c1ccc(F)cc1F] |

TABLE 1-continued
| Comp. No. | Chemical Structure |
|---|---|
| N86 | 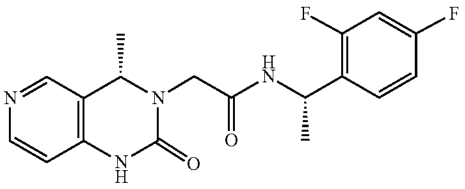 [SMILES: C[C@H](NC(=O)CN1C(=O)Nc2ccncc2[C@@H]1C)c1ccc(F)cc1F] |
| N87 | 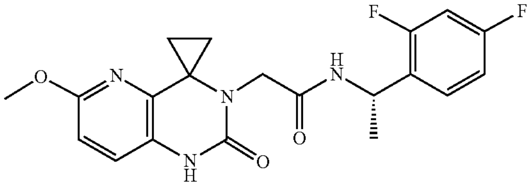 [SMILES: COc1ccc2c(n1)C1(CC1)N(CC(=O)N[C@@H](C)c1ccc(F)cc1F)C(=O)N2] |
| N88 | 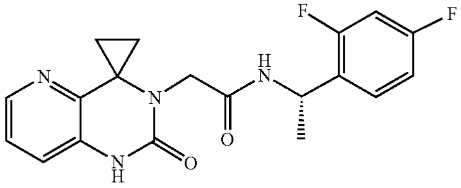 [SMILES: C[C@H](NC(=O)CN1C(=O)Nc2cccnc2C12CC2)c1ccc(F)cc1F] |
| N89 | 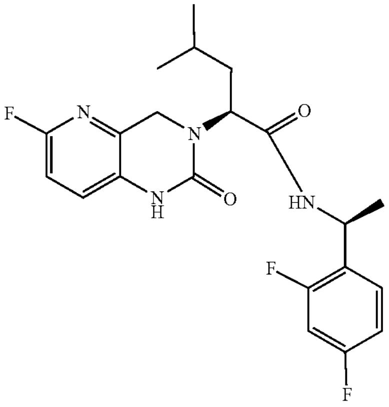 [SMILES: CC(C)C[C@@H](C(=O)N[C@@H](C)c1ccc(F)cc1F)N1Cc2nc(F)ccc2NC1=O] |
| N90 | 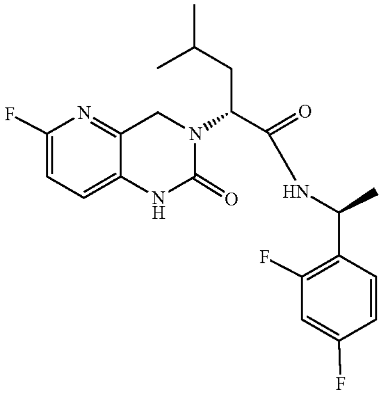 [SMILES: CC(C)C[C@H](C(=O)N[C@@H](C)c1ccc(F)cc1F)N1Cc2nc(F)ccc2NC1=O] |
| N91 | 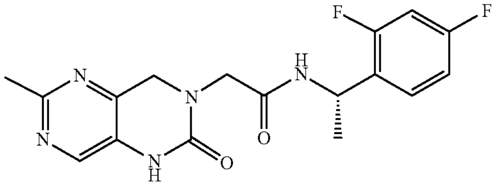 [SMILES: Cc1ncc2c(n1)CN(CC(=O)N[C@@H](C)c1ccc(F)cc1F)C(=O)N2] |

TABLE 1-continued
| Comp. No. | Chemical Structure |
|---|---|
| N92 | 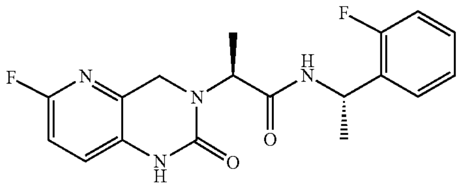 [SMILES: C[C@H](NC(=O)[C@H](C)N1Cc2nc(F)ccc2NC1=O)c1ccccc1F] |
| N93 | 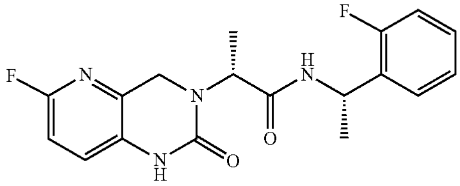 [SMILES: C[C@H](NC(=O)[C@@H](C)N1Cc2nc(F)ccc2NC1=O)c1ccccc1F] |
| N94 | 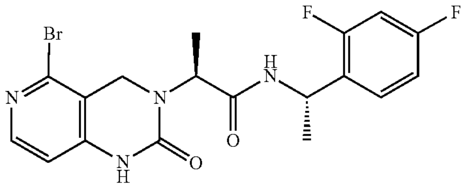 |
| N95 | 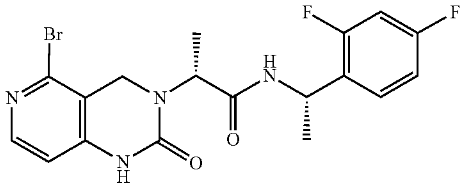 [SMILES: C[C@H](NC(=O)[C@@H](C)N1Cc2c(ccnc2Br)NC1=O)c1ccc(F)cc1F] |
| N96 | 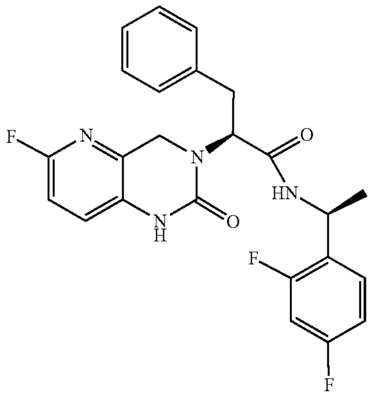 [SMILES: C[C@H](NC(=O)[C@H](Cc1ccccc1)N1Cc2nc(F)ccc2NC1=O)c1ccc(F)cc1F] |

TABLE 1-continued
| Comp. No. | Chemical Structure |
| --- | --- |
| N97 | 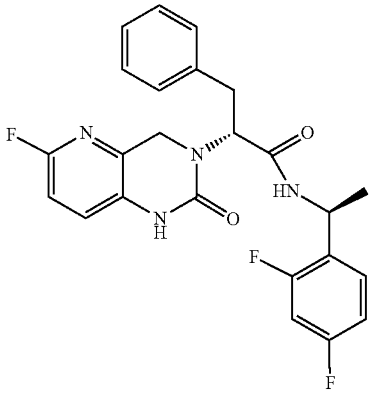 [SMILES: C[C@H](NC(=O)[C@@H](Cc1ccccc1)N1Cc2nc(F)ccc2NC1=O)c1ccc(F)cc1F] |
| N98 | 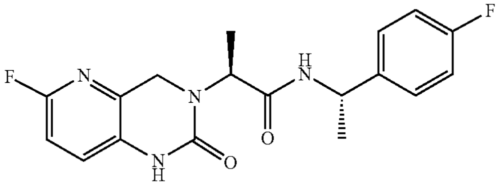 [SMILES: C[C@H](NC(=O)[C@H](C)N1Cc2nc(F)ccc2NC1=O)c1ccc(F)cc1] |
| N99 | 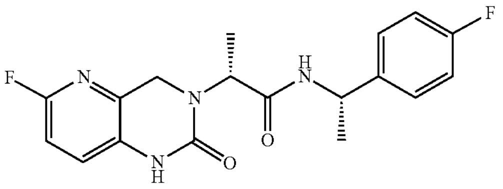 [SMILES: C[C@H](NC(=O)[C@@H](C)N1Cc2nc(F)ccc2NC1=O)c1ccc(F)cc1] |
| N100 | 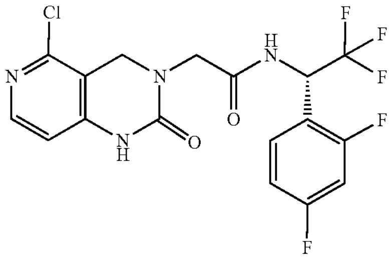 [SMILES: O=C(CN1Cc2c(ccnc2Cl)NC1=O)N[C@@H](c1ccc(F)cc1F)C(F)(F)F] |
| N101 | 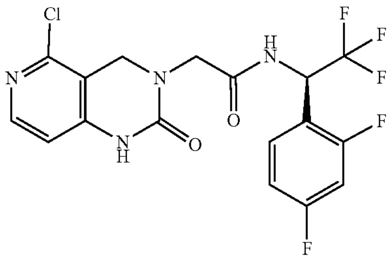 [SMILES: O=C(CN1Cc2c(ccnc2Cl)NC1=O)N[C@H](c1ccc(F)cc1F)C(F)(F)F] |
| N102 | 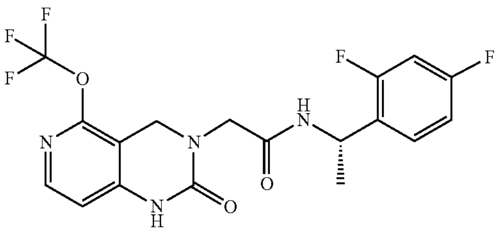 [SMILES: C[C@H](NC(=O)CN1Cc2c(ccnc2OC(F)(F)F)NC1=O)c1ccc(F)cc1F] |

TABLE 1-continued
| Comp. No. | Chemical Structure |
| --- | --- |
| N103 | 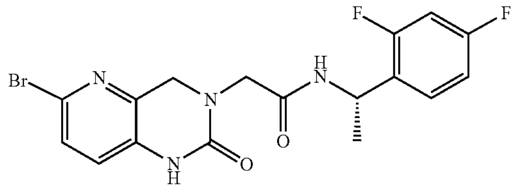 [SMILES: C[C@H](NC(=O)CN1Cc2nc(Br)ccc2NC1=O)c1ccc(F)cc1F] |
| N104 | 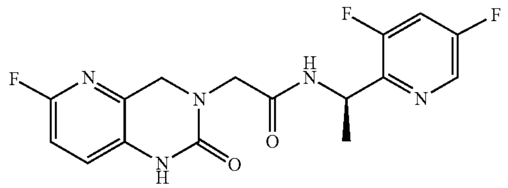 |
| N105 | 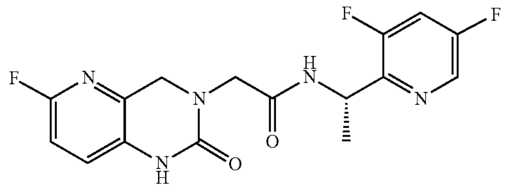 [SMILES: C[C@H](NC(=O)CN1Cc2nc(F)ccc2NC1=O)c1ncc(F)cc1F] |
| N106 | 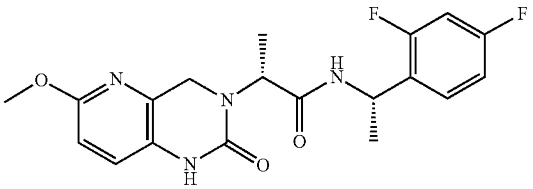 [SMILES: COc1ccc2c(n1)CN([C@H](C)C(=O)N[C@@H](C)c1ccc(F)cc1F)C(=O)N2] |
| N107 | 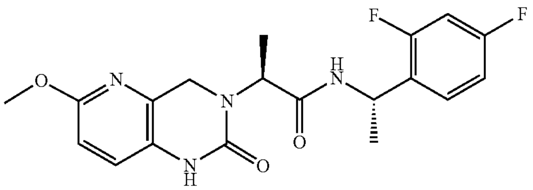 [SMILES: COc1ccc2c(n1)CN([C@@H](C)C(=O)N[C@@H](C)c1ccc(F)cc1F)C(=O)N2] |
| N108 | 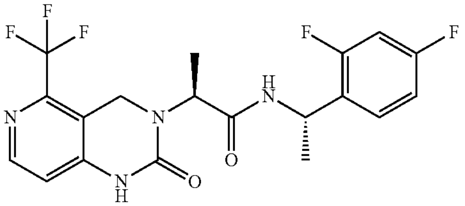 [SMILES: C[C@H](NC(=O)[C@H](C)N1Cc2c(ccnc2C(F)(F)F)NC1=O)c1ccc(F)cc1F] |
| N109 | 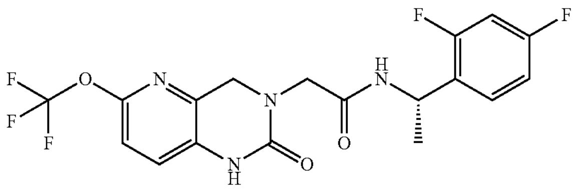 [SMILES: C[C@H](NC(=O)CN1Cc2nc(OC(F)(F)F)ccc2NC1=O)c1ccc(F)cc1F] |

TABLE 1-continued
| Comp. No. | Chemical Structure |
|---|---|
| N110 | 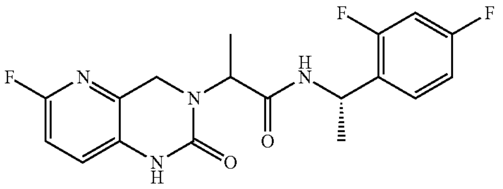 [SMILES: CC(C(=O)N[C@@H](C)c1ccc(F)cc1F)N1Cc2nc(F)ccc2NC1=O] |
| N111 | 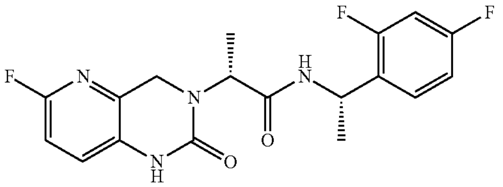 [SMILES: C[C@H](NC(=O)[C@@H](C)N1Cc2nc(F)ccc2NC1=O)c1ccc(F)cc1F] |
| N112 | 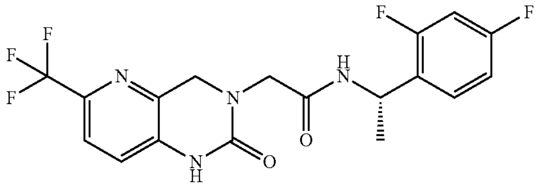 [SMILES: C[C@H](NC(=O)CN1Cc2nc(C(F)(F)F)ccc2NC1=O)c1ccc(F)cc1F] |
| N113 | 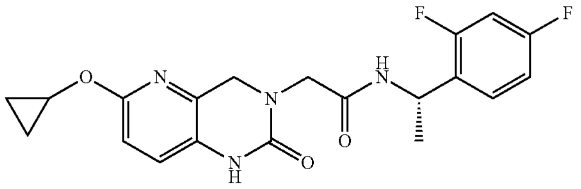 [SMILES: C[C@H](NC(=O)CN1Cc2nc(OC3CC3)ccc2NC1=O)c1ccc(F)cc1F] |
| N114 | 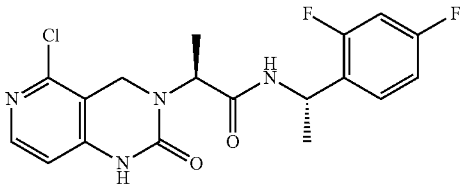 [SMILES: C[C@H](NC(=O)[C@H](C)N1Cc2c(ccnc2Cl)NC1=O)c1ccc(F)cc1F] |
| N115 | 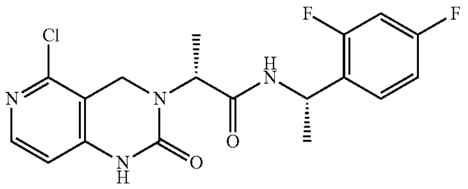 [SMILES: C[C@H](NC(=O)[C@@H](C)N1Cc2c(ccnc2Cl)NC1=O)c1ccc(F)cc1F] |
| N116 | 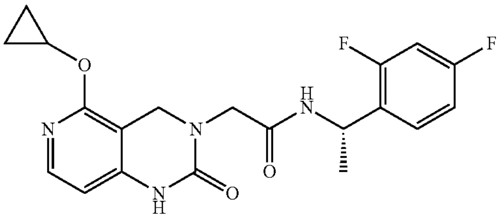 [SMILES: C[C@H](NC(=O)CN1Cc2c(ccnc2OC2CC2)NC1=O)c1ccc(F)cc1F] |

TABLE 1-continued
| Comp. No. | Chemical Structure |
|---|---|
| N117 | 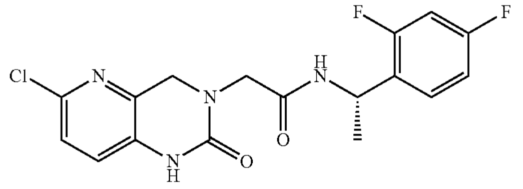 [SMILES: C[C@H](NC(=O)CN1Cc2nc(Cl)ccc2NC1=O)c1ccc(F)cc1F] |
| N118 | 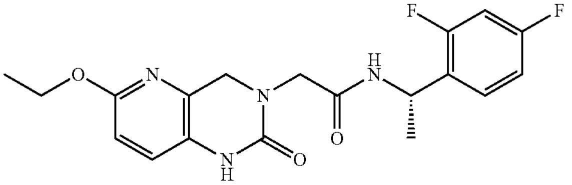 [SMILES: CCOc1ccc2c(n1)CN(CC(=O)N[C@@H](C)c1ccc(F)cc1F)C(=O)N2] |
| N119 | 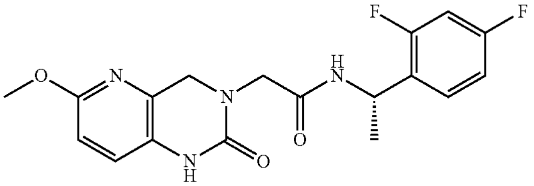 [SMILES: COc1ccc2c(n1)CN(CC(=O)N[C@@H](C)c1ccc(F)cc1F)C(=O)N2] |
| N120 | 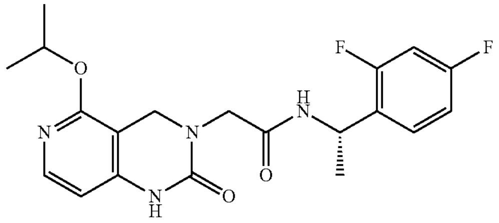 [SMILES: CC(C)Oc1nccc2c1CN(CC(=O)N[C@@H](C)c1ccc(F)cc1F)C(=O)N2] |
| N121 | 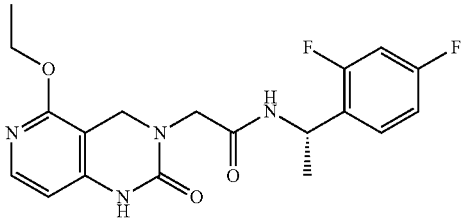 [SMILES: CCOc1nccc2c1CN(CC(=O)N[C@@H](C)c1ccc(F)cc1F)C(=O)N2] |
| N122 | 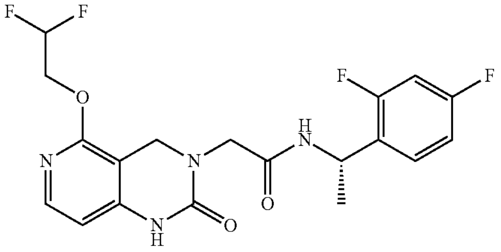 [SMILES: C[C@H](NC(=O)CN1Cc2c(ccnc2OCC(F)F)NC1=O)c1ccc(F)cc1F] |
| N123 | 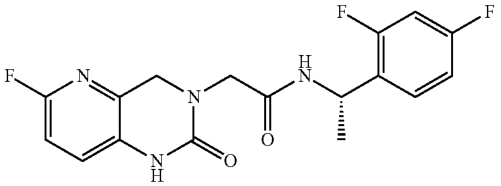 [SMILES: C[C@H](NC(=O)CN1Cc2nc(F)ccc2NC1=O)c1ccc(F)cc1F] |

TABLE 1-continued
| Comp. No. | Chemical Structure |
|---|---|
| N124 | 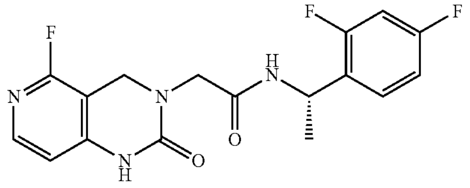 [SMILES: C[C@H](NC(=O)CN1Cc2c(ccnc2F)NC1=O)c1ccc(F)cc1F] |
| N125 | 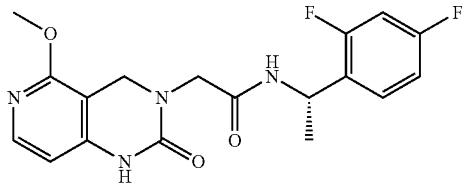 [SMILES: COc1nccc2c1CN(CC(=O)N[C@@H](C)c1ccc(F)cc1F)C(=O)N2] |
| N126 | 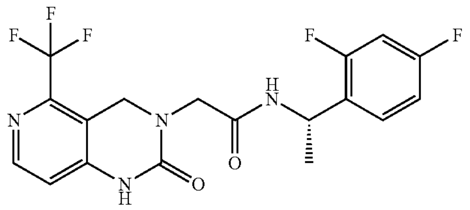 [SMILES: C[C@H](NC(=O)CN1Cc2c(ccnc2C(F)(F)F)NC1=O)c1ccc(F)cc1F] |
| N127 | 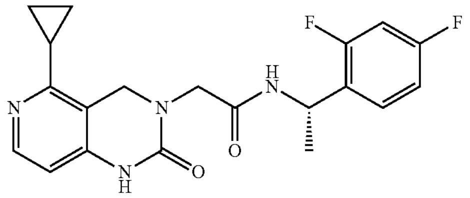 [SMILES: C[C@H](NC(=O)CN1Cc2c(ccnc2C2CC2)NC1=O)c1ccc(F)cc1F] |
| N128 | 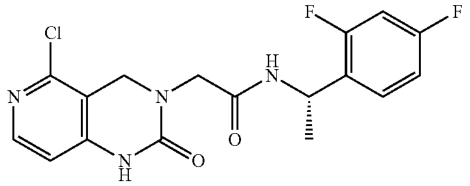 |
| N129 | 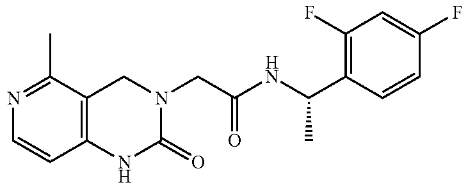 [SMILES: Cc1nccc2c1CN(CC(=O)N[C@@H](C)c1ccc(F)cc1F)C(=O)N2] |
| N130 | 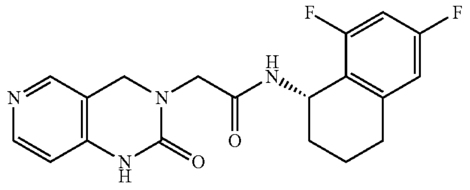 [SMILES: O=C(CN1Cc2cnccc2NC1=O)N[C@H]1CCCc2cc(F)cc(F)c21] |

TABLE 1-continued
| Comp. No. | Chemical Structure |
|---|---|
| N131 | 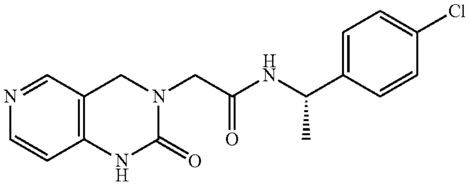 [SMILES: C[C@H](NC(=O)CN1Cc2cnccc2NC1=O)c1ccc(Cl)cc1] |
| N132 | 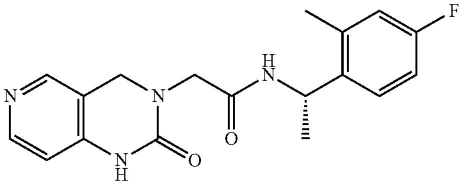 [SMILES: Cc1cc(F)ccc1[C@H](C)NC(=O)CN1Cc2cnccc2NC1=O] |
| N133 | 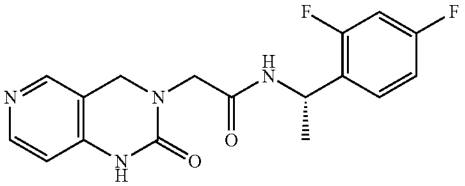 [SMILES: C[C@H](NC(=O)CN1Cc2cnccc2NC1=O)c1ccc(F)cc1F] |
| N135 | 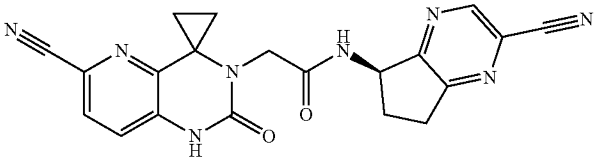 [SMILES: N#Cc1cnc2c(n1)CC[C@H]2NC(=O)CN1C(=O)Nc2ccc(C#N)nc2C12CC2] |
| N136 | 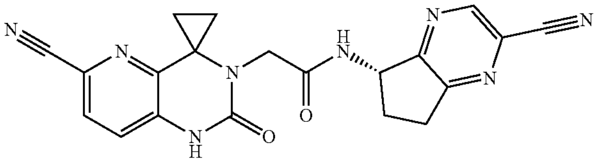 [SMILES: N#Cc1cnc2c(n1)CC[C@@H]2NC(=O)CN1C(=O)Nc2ccc(C#N)nc2C12CC2] |
| N137 | 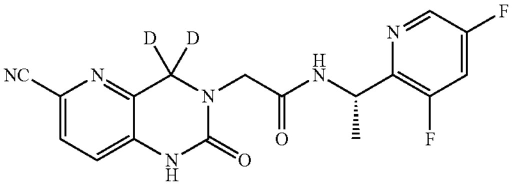 [SMILES: [2H]C1([2H])c2nc(C#N)ccc2NC(=O)N1CC(=O)N[C@@H](C)c1ncc(F)cc1F] |
| N138 | 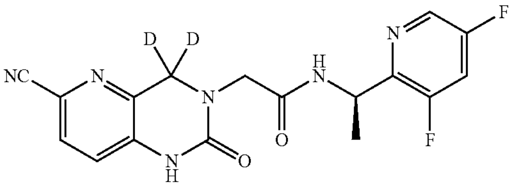 [SMILES: [2H]C1([2H])c2nc(C#N)ccc2NC(=O)N1CC(=O)N[C@H](C)c1ncc(F)cc1F] |
TABLE 2
MS Characterization Data
| Comp. No. | MS |
|---|---|
| N1 | 375 |
| N2 | 375.05 |
TABLE 2-continued
MS Characterization Data
| Comp. No. | MS |
|---|---|
| N3 | 406 |
| N4 | 406 |

TABLE 2-continued

| MS Characterization Data | |
|---|---|
| Comp. No. | MS |
| N5 | 436.1 |
| N6 | 436.05 |
| N7 | 386.05 |
| N8 | 386.05 |
| N9 | 446.1 |
| N10 | 361.05 |
| N11 | 361 |
| N12 | 398.1 |
| N13 | 398.1 |
| N14 | 399.1 |
| N15 | 399.1 |
| N16 | 363.1 |
| N17 | 363.1 |
| N18 | 429.2 |
| N19 | 429.2 |
| N20 | 354.2 |
| N21 | 354.2 |
| N22 | 379.3 |
| N23 | 379.15 |
| N24 | 372.1 |
| N25 | 381 |
| N26 | 381 |
| N27 | 389.1 |
| N28 | 389.1 |
| N29 | 390.15 |
| N30 | 390.15 |
| N31 | 395.15 |
| N32 | 395.2 |
| N33 | 387.1 |
| N34 | 387.1 |
| N35 | 389.2 |
| N36 | 396.14 |
| N37 | 396.14 |
| N38 | 373.15 |
| N39 | 373.15 |
| N40 | 388.15 |
| N41 | 388.15 |
| N42 | 389.1 |
| N43 | 389.05 |
| N44 | 389.05 |
| N45 | 386.2 |
| N46 | 386.1 |
| N47 | 374 |
| N48 | 374 |
| N49 | 432.05 |
| N50 | 432.05 |
| N51 | 424.15 |
| N52 | 380.25 |
| N53 | 380.1 |
| N54 | 381.2 |
| N55 | 381.2 |
| N56 | 381.1 |
| N57 | 379.1 |
| N58 | 373.1 |
| N59 | 373.1 |
| N60 | 372.1 |
| N61 | 373.05 |
| N62 | 373.05 |
| N63 | 366.05 |
| N64 | 366.05 |
| N65 | 391.05 |
| N66 | 419.05 |
| N67 | 404.2 |
| N68 | 403.85 |
| N69 | 366 |
| N70 | 366 |
| N71 | 365 |
| N72 | 365 |
| N73 | 422.15 |
| N74 | 422 |
| N75 | 381.8 |
| N76 | 382 |
| N77 | 361.1 |
| N78 | 361.1 |
| N79 | 415.8 |

TABLE 2-continued

| MS Characterization Data | |
|---|---|
| Comp. No. | MS |
| N80 | 415.8 |
| N81 | 372.2 |
| N82 | 381.1 |
| N83 | 361.2 |
| N84 | 361.2 |
| N85 | 361.2 |
| N86 | 361.2 |
| N87 | 403.1 |
| N88 | 373.2 |
| N89 | 421.15 |
| N90 | 421.15 |
| N91 | 362.2 |
| N92 | 361.1 |
| N93 | 361.15 |
| N94 | 440.95 |
| N95 | 440.95 |
| N96 | 455 |
| N97 | 455.05 |
| N98 | 361 |
| N99 | 361 |
| N100 | 435.1 |
| N101 | 435.15 |
| N102 | 429.1 |
| N103 | 425.2 |
| N104 | 366.15 |
| N105 | 365.85 |
| N106 | 391.05 |
| N107 | 391.05 |
| N108 | 429.2 |
| N109 | 431.1 |
| N110 | 379.05 |
| N111 | 379.05 |
| N112 | 415.1 |
| N113 | 403.1 |
| N114 | 395.05 |
| N115 | 395.05 |
| N116 | 403.1 |
| N117 | 381.1 |
| N118 | 391 |
| N119 | 377.1 |
| N120 | 405 |
| N121 | 390.8 |
| N122 | 427.05 |
| N123 | 365.1 |
| N125 | 376.95 |
| N126 | 415.1 |
| N127 | 387.2 |
| N128 | 381.1 |
| N129 | 361.1 |
| N130 | 373.25 |
| N131 | 345.1 |
| N132 | 343.1 |
| N133 | 347.1 |
| N135 | 401.15 |
| N136 | 401.05 |
| N137 | |
| N138 | |

TABLE 3

NMR Characterization Data

| Comp. No. | NMR |
|---|---|
| N4 | (400 MHz, DMSO-d6) δ 10.17 (s, 1H), 8.88 (t, J = 1.2 Hz, 1H), 8.62 (d, J = 7.2 Hz, 1H), 8.37 (dd, J = 10.0, 1.6 Hz, 1H), 7.74 (d, J = 8.4 Hz, 1H), 7.19 (d, J = 8.4 Hz, 1H), 5.21 (p, J = 7.2 Hz, 1H), 3.95 (d, J = 17.2 Hz, 1H), 3.80 (d, J = 17.2 Hz, 1H), 1.38 (d, J = 7.2 Hz, 3H), 1.35-1.19 (m, 4H). |
| N5 | 400 MHz, DMSO-d6) δ 10.14 (s, 1H), 8.89 (d, J = 7.6 Hz, 1H), 8.34(d, J = 6.4 Hz, 1H), 7.39-7.36 (m, 1H), 7.30 (d, J = 0.8 Hz, 1H), 6.99 (d, J = 6.4Hz, 1H), 5.80-5.75 (m, 1H), 4.84-4.79 (m, 1H), 4.65 (s, 2H), 4.36 (dd, J = 10, 3.6 Hz, 1H), 4.02 (d, J = 2.0 Hz, 2H). |
| N9 | (400 MHz, DMSO-d6) δ 9.92 (s, 1H), 8.46 (d, J = 7.2 Hz, 1H), 8.20 (d, J = 3.2 Hz, 1H), 7.94 (s, 1H), 7.44-7.39 (m, 1H), 7.20-7.04 (m, 2H), 6.76-6.74 (m, 1H), 5.08-5.05 (m, 1H), 3.86 (s, 2H), 1.34-1.30 (m, 5H), 1.07-1.05 (m, 2H). |
| N10 | 400 MHz, DMSO-d6) δ 9.69 (s, 1H), 8.79 (d, J = 7.6 Hz, 1H), 8.23-8.15 (m, 2H), 6.80-6.67 (m, 3H), 5.61-5.66 (m, 1H), 4.78 (dd, J = 9.6, 8.4 Hz, 1H), 4.51 (s, 2H), 4.35 (dd, J = 9.6, 3.6 Hz, 1H), 3.95 (s, 2H). |
| N15 | 400 MHz, DMSO-d6) δ 10.18 (s, 1H), 8.53-8.46 (m, 2H), 7.94-7.89 (m, 1H), 7.75 (d, J = 8.4 Hz, 1H), 7.19 (d, J = 8.4 Hz, 1H), 5.25-5.14 (m, 1H), 3.95-3.78 (m, 2H), 1.37-1.11 (m, 7H) |
| N24 | (400 MHz, DMSO-d6) δ 9.90 (s, 1H), 8.61-8.52 (m, 2H), 8.25 (s, 1H), 7.47-7.41 (m, 1H), 7.21-7.16 (m, 1H), 7.09-7.04 (m, 1H), 5.13 (t, J = 6.8 Hz, 1H), 4.70 (s, 2H), 4.04 (s, 2H), 1.36 (d, J = 6.8 Hz, 3H). |
| N31 | 300 MHz, DMSO-d6) δ 10.17 (s, 1H), 8.68 (d, J = 7.8 Hz, 1H), 8.35 (d, J = 5.4 Hz, 1H), 7.83 (dd, J = 10.2, 1.5 Hz, 1H), 7.70 (dd, J = 8.1, 1.5 Hz, 1H), 7.60 (t, J = 7.5 Hz, 1H), 6.96 (d, J = 5.4 Hz, 1H), 5.24-5.05 (m, 2H), 4.68 (s, 2H), 4.11 (d, J = 2.4 Hz, 2H), 3.61 (t, J = 6.0 Hz, 2H). |
| N33 | 300 MHz, DMSO-d6) δ 9.60 (s, 1H), 8.71 (d, J = 7.8 Hz, 1H), 7.99-7.97 (m, 1H), 7.15-7.06 (m, 2H), 6.78-6.67 (m, 2H), 5.66-5.60 (m, 1H), 4.80-4.74 (m, 1H), 4.31 (dd, J = 9.9, 4.2 Hz, 1H), 3.85-3.79 (m, 2H), 1.27-1.16 (m, 4H). |
| N56 | (300 MHz, DMSO-d6) δ 9.75 (s, 1H), 8.59 (d, J = 7.5, 1H), 8.14 (s, 1H), 7.97 (s, 1H), 7.48-7.40 (m, 1H), 7.24-7.15 (m, 1H), 7.10-7.04 (m, 1H), 5.18-5.08 (m, 1H), 4.61(s, 2H), 4.02 (s, 2H), 1.36 (d,J = 6.9, 3H) |
| N57 | (300 MHz, DMSO-d6) δ 9.71 (s, 1H), 8.57 (d, J = 7.8 Hz, 1H), 7.99 (s, 1H), 7.45 (m, 1H), 7.20 (m,1H), 7.07 (m, 1H), 5.14 (m, 1H), 4.48 (s, 2H), 3.99 (s, 2H), 2.08 (d, J = 1.5 Hz, 3H), 1.36 (d, J = 6.9 Hz, 3H) |
| N60 | (400 MHz, DMSO-d6) δ 9.98 (s, 1H), 8.58 (d, J = 7.6 Hz, 1H), 7.80 (d, J = 8.4 Hz, 1H), 7.46-7.40 (m, 1H), 7.22-7.17 (m, 2H), 7.09-7.05 (m, 1H), 5.16-5.09 (m, 1H), 4.58 (d, J = 0.8 Hz, 2H), 3.99 (s, 2H), 1.35 (d, J = 6.8 Hz, 3H). |
| N68 | 300 MHz, DMSO-d6) δ 9.31 (s, 1H), 8.47 (d, J = 2.1 Hz, 1H), 8.40-8.38 (m, 1H), 7.95-7.88 (m,, 1H), 7.09 (d, J = 8.7 Hz, 1H), 6.93-6.56 (m, 1H), 5.22-5.17 (m, 1H), 3.92-3.86 (m, 1H), 3.77-3.70 (m, 4H), 1.36 (d, J = 6.9 Hz, 3H), 1.23-1.16 (m, 4H). |
| N71 | 300 MHz, DMSO-d6) δ 9.85 (s, 1H), 8.57 (d, J = 7.5 Hz, 1H), 8.07 (d, J = 2.7 Hz, 1H), 7.55-7.51 (m, 1H), 7.48-7.40 (m, 1H), 7.23-7.18 (m, 1H), 7.16-7.03 (m, 1H), 5.15-5.10 (m, 1H), 4.48 (s, 2H), 3.98 (s, 2H), 1.36 (d, J = 6.9 Hz, 3H). |
| N72 | (300 MHz, DMSO-d6) δ 9.77 (d, J = 2.1 Hz, 1H), 8.57 (d, J = 7.8 Hz, 1H), 8.09 (s, 1H), 7.92 (s, 1H), 7.48-7.40 (m, 1H), 7.24-7.16 (m, 1H), 7.10-7.04 (m, 1H), 5.18-5.08 (m, 1H), 4.59 (s, 2H), 4.01 (s, 2H), 1.36 (d, J = 6.9 Hz, 3H). |
| N77 | (400 MHz, DMSO-d6) δ 9.44 (s, 1H), 8.51 (d, J = 7.6 Hz, 1H), 8.06 (dd, J = 4.8, 1.6 Hz, 1H), 7.45 (td, J = 8.8, 6.6 Hz, 1H), 7.24-7.13 (m, 3H), 7.08-7.03 (m, 1H), 5.09 (m, 1H), 4.49 (q, J = 6.6 Hz, 1H), 4.27 (d, J = 16.4 Hz, 1H), 3.80 (d, J = 16.4 Hz, 1H), 1.33 (dd, J = 15.4, 6.8 Hz, 6H). |
| N78 | 400 MHz, DMSO-d6) δ 9.43 (s, 1H), 8.51 (d, J = 7.6 Hz, 1H), 8.07 (dd, J = 4.8, 1.6 Hz, 1H), 7.42 (td, J = 8.8, 6.6 Hz, 1H), 7.22-7.09 (m, 3H), 7.08-6.99 (m, 1H), 5.09 (m, 1H), 4.54 (q, J = 6.6 Hz, 1H), 4.27 (d, J = 16.4 Hz, 1H), 3.80 (d, J = 16.4 Hz, 1H), 1.32 (dd, J = 15.2, 6.8 Hz, 6H). |
| N87 | (400 MHz, DMSO-d6) δ 9.32 (s, 1H), 8.43 (d, J = 7.6 Hz, 1H), 7.44-7.20 (m, 1H), 7.18-7.15 (m, 1H), 7.10-7.02 (m, 2H), 6.58 (d, J = 8.4 Hz, 1H), 5.0-5.05 (m, 1H), 3.80 (s, 2H), 3.71 (s, 3H), 3.33 (d, J = 2.8 Hz, 2H), 1.33 (m, J= 7.2 Hz, 3H), 1.22-1.15 (m, 4H). |
| N104 | 400 MHz, DMSO-d6) δ 9.43 (s, 1H), 8.58 (d, J = 7.2 Hz, 1H), 8.49 (d, J = 2.4 Hz, 1H), 7.98-7.88 (m, 1H), 7.27(t, J = 7.6 Hz, 1H), 6.986.96 (m, 1H), 5.27-5.24 (m, 1H), 4.44 (s, 2H), 4.01-3.90 (m, 2H), 1.37 (d, J = 7.2 Hz, 3H). |
| N112 | 400 MHz, DMSO-d6) δ 9.86 (s, 1H), 8.58 (d, J = 10.4 Hz, 1H), 7.68 (d, J = 7.2 Hz, 1H), 7.47-7.39 (m, 1H), 7.27 (d, J = 11.2 Hz, 1H), 7.22-7.15 (m, 1H), 7.09-7.03 (m, 1H), 5.15-5.10 (m, 1H), 4.60 (s, 2H), 4.00 (s, 2H), 1.36 (d, J = 9.6 Hz, 3H). |
| N117 | (300 MHz, DMSO-d6) δ 9.98 (s, 1H), 8.60 (d, J = 7.7 Hz, 1H), 8.05 (d, J = 5.4 Hz, 1H), 7.50-7.39 (m, 1H), 7.27-7.13 (m, 1H), 7.10-7.04 (m, 1H), 6.72 (d, J = 5.4 Hz, 1H), 5.14 (p, J = 7.2 Hz, 1H), 4.48 (s, 2H), 4.02 (s, 2H), 1.36 (d, J = 6.9 Hz, 3H). |
| N124 | (300 MHz, DMSO-$d_6$) δ 10.07 (d, J = 2.0 Hz, 1H), 8.65 (d, J = 7.6 Hz, 1H), 7.95 (d, J = 5.5 Hz, 1H), 7.45-7.42 (m, 1H), 7.19 (m, 1H), 7.07-7.06 (m, 1H), 6.68-6.65 (m, 1H), 5.12-5.10 (m, 1H), 4.54 (s, 2H), 4.07 (s, 2H), 1.43 (d, J = 7.0 Hz, 3H). |
| N125 | (300 MHz, DMSO-d6) δ 9.59 (s, 1H), 8.57 (d, J = 7.8 Hz, 1H), 7.83 (d, J = 5.7 Hz, 1H), 7.47-7.39 (m, 1H), 7.22-7.14 (m, 1H), 7.09-7.02 (m, 1H), 6.40 (d, J = 5.7 Hz, 1H), 5.14-5.09 (m, 1H), 4.32 (s, 2H), 3.98 (s, 2H), 3.82 (s, 3H), 1.35 (d, J = 7.2 Hz, 3H). |
| N127 | (300 MHz, DMSO-d6) δ 9.54 (s, 1H), 8.57 (d, J = 7.8 Hz, 1H), 8.02 (d, J = 5.4 Hz, 1H), 7.49-7.41 (m, 1H), 7.22-7.15 (m, 1H), 7.09-7.02 (m, 1H), 6.48 (d, J = 5.4 Hz, 1H), 5.16-5.11 (m, 1H), 4.63 (s, 2H), 4.01 (s, 2H), 1.82-1.75 (m, 1H), 1.37 (d, J = 6.9 Hz, 3H), 0.94-0.82 (m, 4H) |
| N128 | (400 MHz, DMSO-d6) δ 9.97 (s, 1H), 8.59 (d, J = 7.6 Hz, 1H), 8.04 (d, J = 5.6 Hz, 1H), 7.44 (m, 1H), 7.19 (m, 1H), 7.11-7.02 (m, 1H), 6.72 (d, J = 5.6 Hz, 1H), 5.13 (m, 1H), 4.48 (d, J = 2.4 Hz, 2H), 4.02 (s, 2H), 1.36 (d, J = 7.2 Hz, 3H). |

TABLE 3-continued
| NMR Characterization Data | |
|---|---|
| Comp. No. | NMR |
| N129 | (400 MHz, DMSO-d6) δ 9.59 (s, 1H), 8.56 (d, J = 7.6 Hz, 1H), 8.06 (d, J = 5.6 Hz, 1H), 7.45 (m, 1H), 7.19 (m, 1H), 7.07 (m, 1H), 6.56 (d, J = 5.6 Hz, 1H), 5.13 (m, 1H), 4.45 (s, 2H), 3.99 (s, 2H), 2.24 (s, 3H), 1.36 (d, J = 7.2 Hz, 3H). |
| N132 | (300 MHz, DMSO-d6) δ 9.67 (s, 1H), 8.48 (d, J = 9.0 Hz, 1H), 8.28-8.11 (m, 2H), 7.45-7.28 (m, 2H), 7.08-6.94 (m, 1H), 6.70 (d, J = 6.0 Hz, 1H), 5.07 (t, J = 7.2 Hz, 1H), 4.48 (s, 2H), 3.95 (s, 2H), 2.32 (s, 3H), 1.32 (d, J = 6.0 Hz, 3H). |
In some embodiments, compounds of the disclosure are below in Table 4.
TABLE 4
| Comp. No. | Chemical Structure |
|---|---|
| B1 | 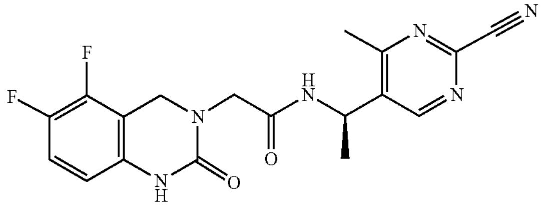 [SMILES: Cc1nc(C#N)ncc1[C@@H](C)NC(=O)CN1Cc2c(ccc(F)c2F)NC1=O] |
| B2 | 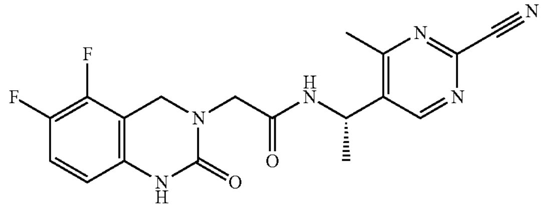 [SMILES: Cc1nc(C#N)ncc1[C@H](C)NC(=O)CN1Cc2c(ccc(F)c2F)NC1=O] |
| B3 | 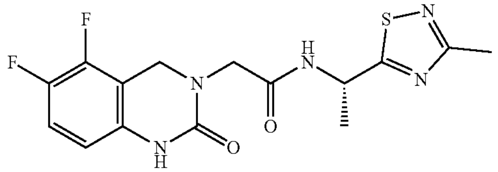 [SMILES: Cc1nsc([C@H](C)NC(=O)CN2Cc3c(ccc(F)c3F)NC2=O)n1] |
| B4 | 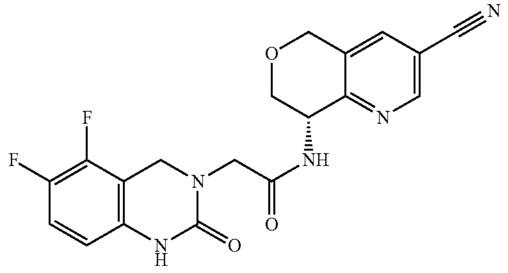 [SMILES: N#Cc1cnc2c(c1)COC[C@H]2NC(=O)CN1Cc2c(ccc(F)c2F)NC1=O] |
| B5 | 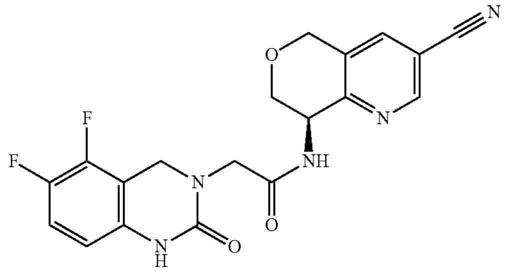 [SMILES: N#Cc1cnc2c(c1)COC[C@@H]2NC(=O)CN1Cc2c(ccc(F)c2F)NC1=O] |

TABLE 4-continued
| Comp. No. | Chemical Structure |
|---|---|
| B6 | 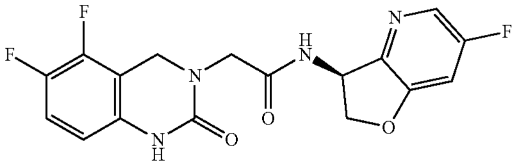 [SMILES: O=C(CN1Cc2c(ccc(F)c2F)NC1=O)N[C@@H]1COc2cc(F)cnc21] |
| B7 | 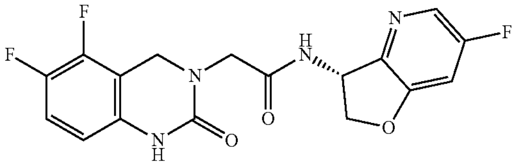 [SMILES: O=C(CN1Cc2c(ccc(F)c2F)NC1=O)N[C@H]1COc2cc(F)cnc21] |
| B8 | 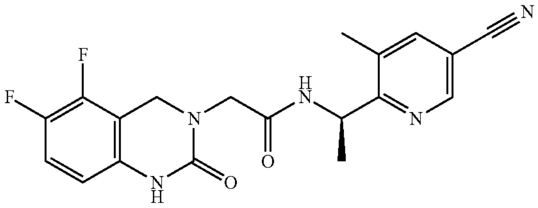 [SMILES: Cc1cc(C#N)cnc1[C@@H](C)NC(=O)CN1Cc2c(ccc(F)c2F)NC1=O] |
| B9 | 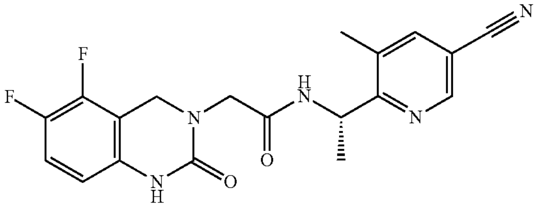 [SMILES: Cc1cc(C#N)cnc1[C@H](C)NC(=O)CN1Cc2c(ccc(F)c2F)NC1=O] |
| B10 | 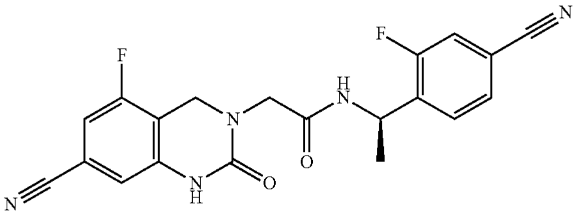 [SMILES: C[C@@H](NC(=O)CN1Cc2c(F)cc(C#N)cc2NC1=O)c1ccc(C#N)cc1F] |
| B11 | 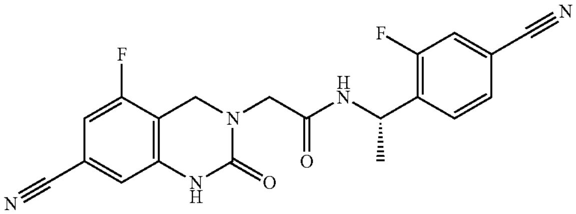 [SMILES: C[C@H](NC(=O)CN1Cc2c(F)cc(C#N)cc2NC1=O)c1ccc(C#N)cc1F] |
| B12 | 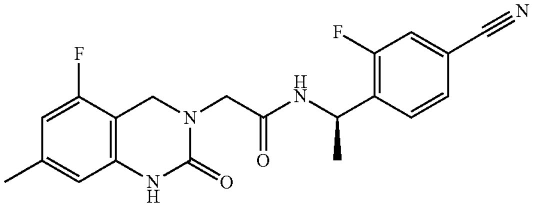 [SMILES: Cc1cc(F)c2c(c1)NC(=O)N(CC(=O)N[C@H](C)c1ccc(C#N)cc1F)C2] |

TABLE 4-continued
| Comp. No. | Chemical Structure |
|---|---|
| B13 | 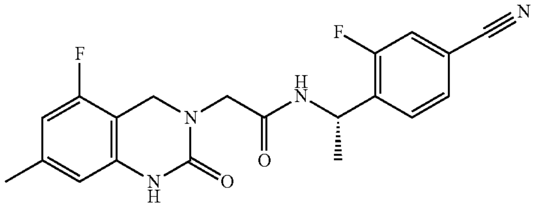 [SMILES: Cc1cc(F)c2c(c1)NC(=O)N(CC(=O)N[C@@H](C)c1ccc(C#N)cc1F)C2] |
| B14 | 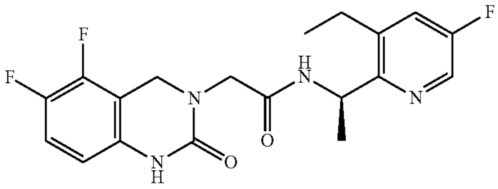 [SMILES: CCc1cc(F)cnc1[C@@H](C)NC(=O)CN1Cc2c(ccc(F)c2F)NC1=O] |
| B15 | 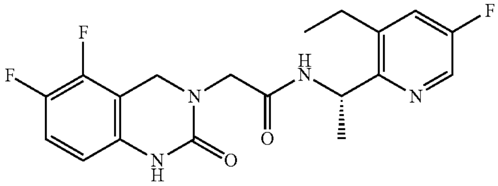 [SMILES: CCc1cc(F)cnc1[C@H](C)NC(=O)CN1Cc2c(ccc(F)c2F)NC1=O] |
| B16 | 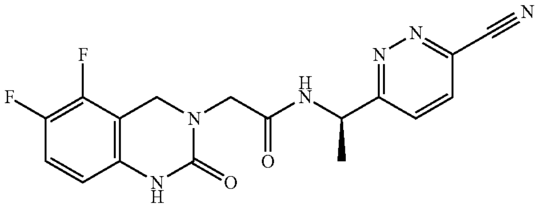 [SMILES: C[C@@H](NC(=O)CN1Cc2c(ccc(F)c2F)NC1=O)c1ccc(C#N)nn1] |
| B17 | 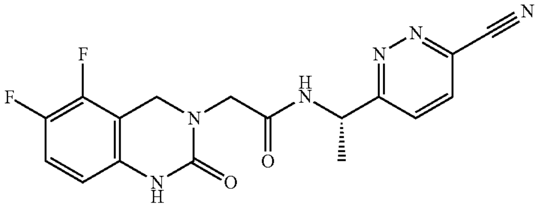 [SMILES: C[C@H](NC(=O)CN1Cc2c(ccc(F)c2F)NC1=O)c1ccc(C#N)nn1] |
| B18 | 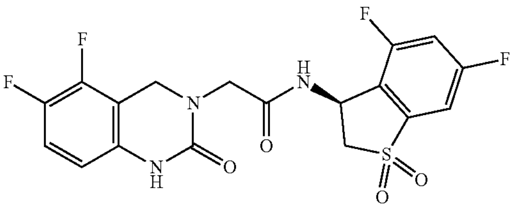 [SMILES: O=C(CN1Cc2c(ccc(F)c2F)NC1=O)N[C@@H]1CS(=O)(=O)c2cc(F)cc(F)c21] |
| B19 | 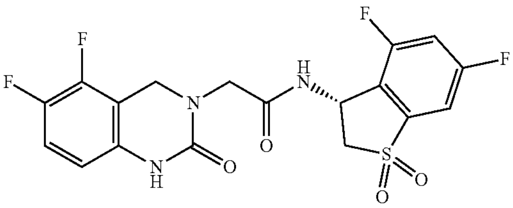 [SMILES: O=C(CN1Cc2c(ccc(F)c2F)NC1=O)N[C@H]1CS(=O)(=O)c2cc(F)cc(F)c21] |

TABLE 4-continued
| Comp. No. | Chemical Structure |
|---|---|
| B20 | 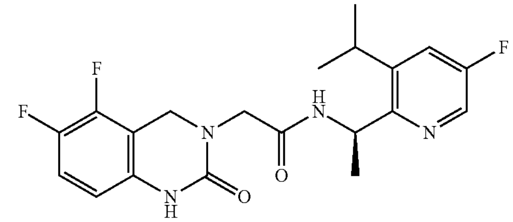 [SMILES: CC(C)c1cc(F)cnc1[C@@H](C)NC(=O)CN1Cc2c(ccc(F)c2F)NC1=O] |
| B21 | 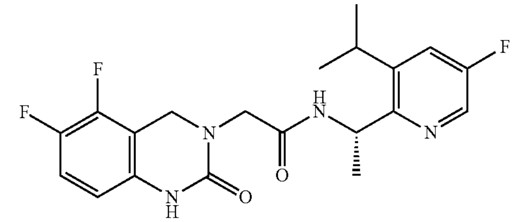 [SMILES: CC(C)c1cc(F)cnc1[C@H](C)NC(=O)CN1Cc2c(ccc(F)c2F)NC1=O] |
| B22 | 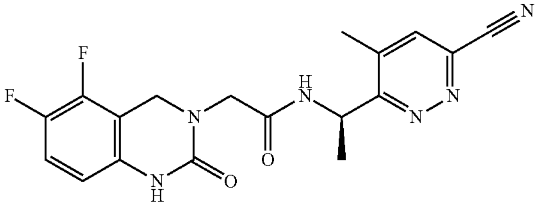 |
| B23 | 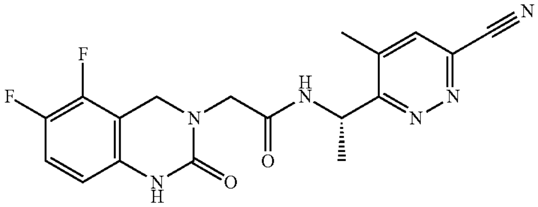 [SMILES: Cc1cc(C#N)nnc1[C@H](C)NC(=O)CN1Cc2c(ccc(F)c2F)NC1=O] |
| B24 | 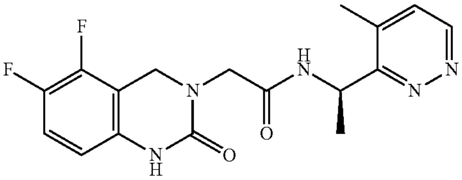 [SMILES: Cc1ccnnc1[C@@H](C)NC(=O)CN1Cc2c(ccc(F)c2F)NC1=O] |
| B25 | 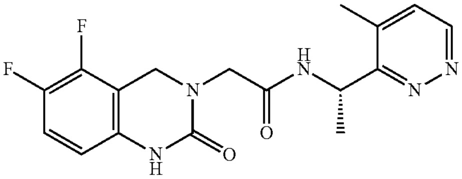 [SMILES: Cc1ccnnc1[C@H](C)NC(=O)CN1Cc2c(ccc(F)c2F)NC1=O] |
| B26 | 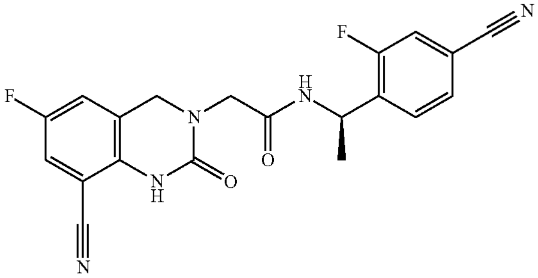 [SMILES: C[C@@H](NC(=O)CN1Cc2cc(F)cc(C#N)c2NC1=O)c1ccc(C#N)cc1F] |

TABLE 4-continued
| Comp. No. | Chemical Structure |
|---|---|
| B27 | 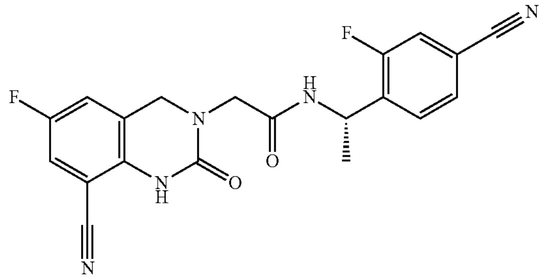 [SMILES: C[C@H](NC(=O)CN1Cc2cc(F)cc(C#N)c2NC1=O)c1ccc(C#N)cc1F] |
| B28 | 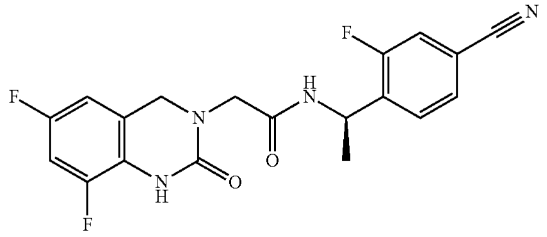 [SMILES: C[C@@H](NC(=O)CN1Cc2cc(F)cc(F)c2NC1=O)c1ccc(C#N)cc1F] |
| B29 | 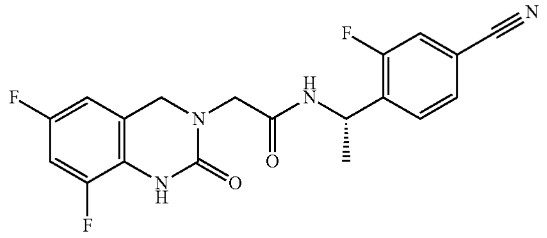 [SMILES: C[C@H](NC(=O)CN1Cc2cc(F)cc(F)c2NC1=O)c1ccc(C#N)cc1F] |
| B30 | 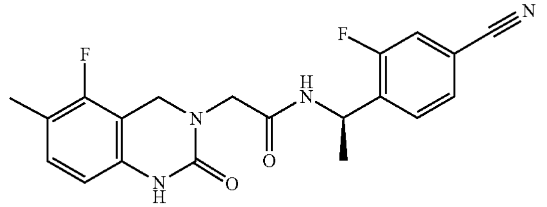 [SMILES: Cc1ccc2c(c1F)CN(CC(=O)N[C@H](C)c1ccc(C#N)cc1F)C(=O)N2] |
| B31 | 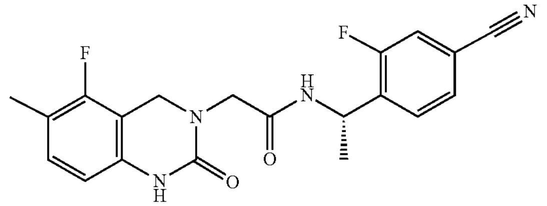 [SMILES: Cc1ccc2c(c1F)CN(CC(=O)N[C@@H](C)c1ccc(C#N)cc1F)C(=O)N2] |
| B32 | 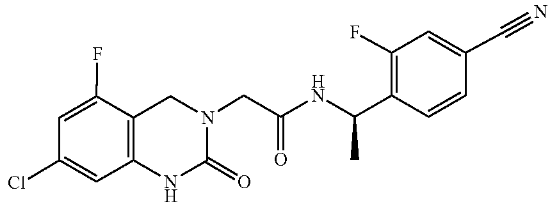 [SMILES: C[C@@H](NC(=O)CN1Cc2c(F)cc(Cl)cc2NC1=O)c1ccc(C#N)cc1F] |

TABLE 4-continued
| Comp. No. | Chemical Structure |
|---|---|
| B33 | 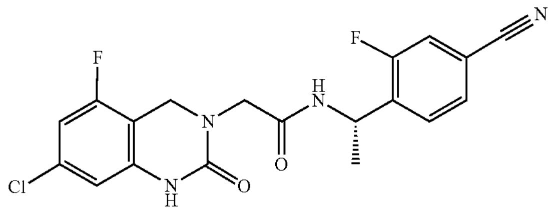 [SMILES: C[C@H](NC(=O)CN1Cc2c(F)cc(Cl)cc2NC1=O)c1ccc(C#N)cc1F] |
| B34 | 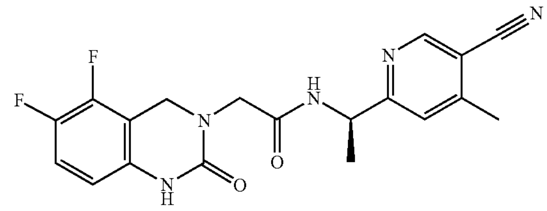 [SMILES: Cc1cc([C@@H](C)NC(=O)CN2Cc3c(ccc(F)c3F)NC2=O)ncc1C#N] |
| B35 | 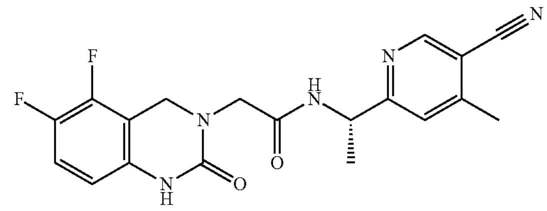 [SMILES: Cc1cc([C@H](C)NC(=O)CN2Cc3c(ccc(F)c3F)NC2=O)ncc1C#N] |
| B36 | 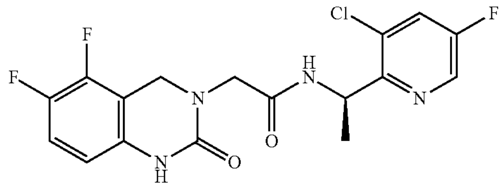 [SMILES: C[C@@H](NC(=O)CN1Cc2c(ccc(F)c2F)NC1=O)c1ncc(F)cc1Cl] |
| B37 | 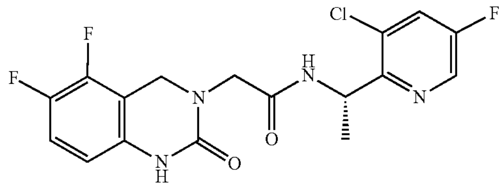 [SMILES: C[C@H](NC(=O)CN1Cc2c(ccc(F)c2F)NC1=O)c1ncc(F)cc1Cl] |
| B38 | 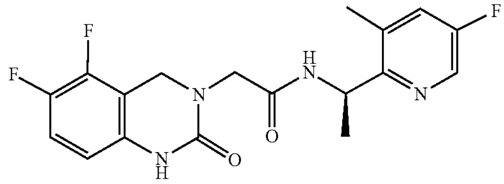 [SMILES: Cc1cc(F)cnc1[C@@H](C)NC(=O)CN1Cc2c(ccc(F)c2F)NC1=O] |
| B39 | 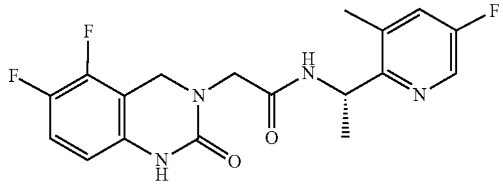 [SMILES: Cc1cc(F)cnc1[C@H](C)NC(=O)CN1Cc2c(ccc(F)c2F)NC1=O] |

TABLE 4-continued
| Comp. No. | Chemical Structure |
| --- | --- |
| B40 | 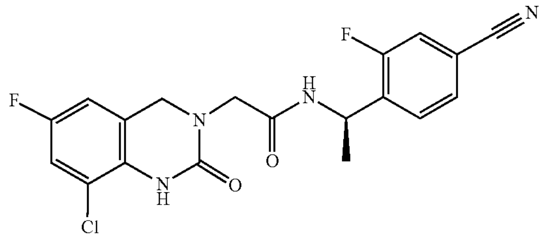 [SMILES: C[C@@H](NC(=O)CN1Cc2cc(F)cc(Cl)c2NC1=O)c1ccc(C#N)cc1F] |
| B41 | 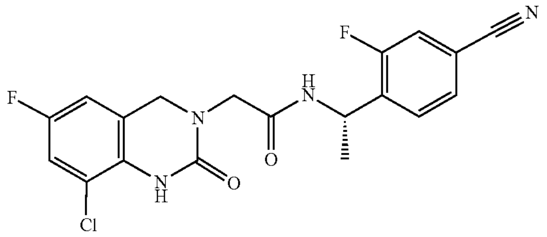 [SMILES: C[C@H](NC(=O)CN1Cc2cc(F)cc(Cl)c2NC1=O)c1ccc(C#N)cc1F] |
| B42 | 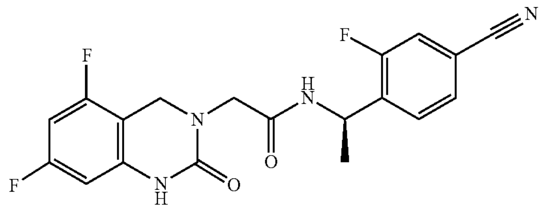 [SMILES: C[C@@H](NC(=O)CN1Cc2c(F)cc(F)cc2NC1=O)c1ccc(C#N)cc1F] |
| B43 | 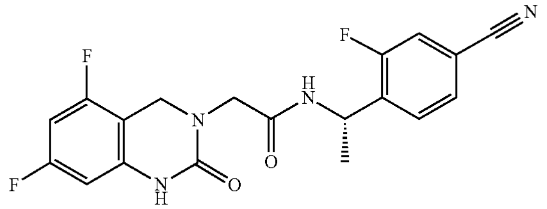 [SMILES: C[C@H](NC(=O)CN1Cc2c(F)cc(F)cc2NC1=O)c1ccc(C#N)cc1F] |
| B44 | 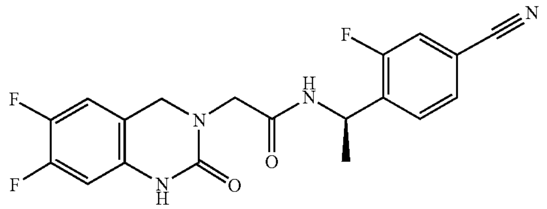 [SMILES: C[C@@H](NC(=O)CN1Cc2cc(F)c(F)cc2NC1=O)c1ccc(C#N)cc1F] |
| B45 | 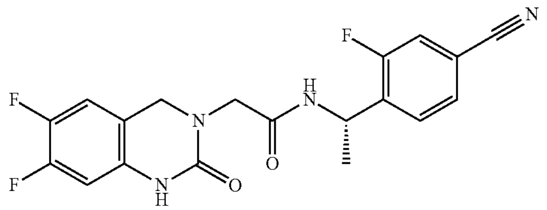 [SMILES: C[C@H](NC(=O)CN1Cc2cc(F)c(F)cc2NC1=O)c1ccc(C#N)cc1F] |
| B46 | 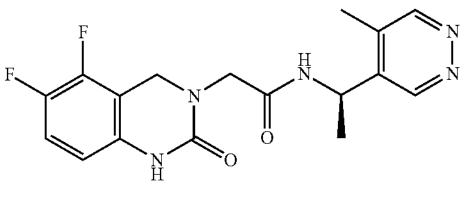 [SMILES: Cc1cnncc1[C@@H](C)NC(=O)CN1Cc2c(ccc(F)c2F)NC1=O] |

TABLE 4-continued
| Comp. No. | Chemical Structure |
|---|---|
| B47 | 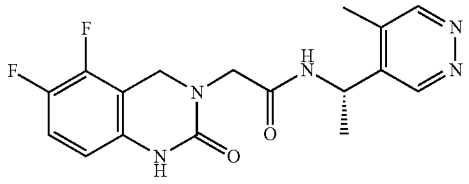 [SMILES: Cc1cnncc1[C@H](C)NC(=O)CN1Cc2c(ccc(F)c2F)NC1=O] |
| B48 | 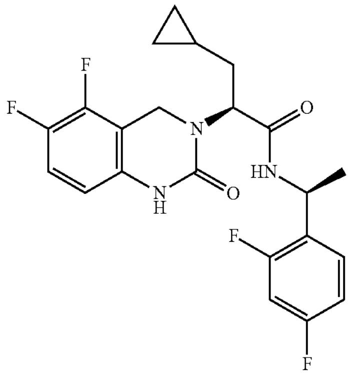 [SMILES: C[C@H](NC(=O)[C@H](CC1CC1)N1Cc2c(ccc(F)c2F)NC1=O)c1ccc(F)cc1F] |
| B49 | 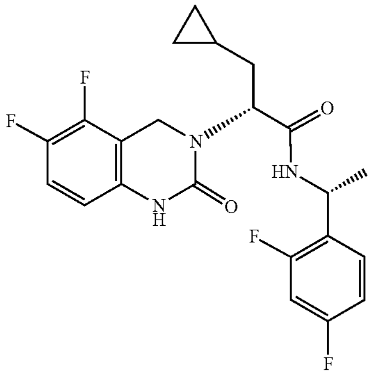 [SMILES: C[C@@H](NC(=O)[C@@H](CC1CC1)N1Cc2c(ccc(F)c2F)NC1=O)c1ccc(F)cc1F] |
| B50 | 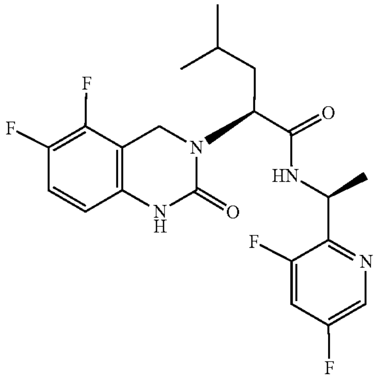 [SMILES: CC(C)C[C@@H](C(=O)N[C@@H](C)c1ncc(F)cc1F)N1Cc2c(ccc(F)c2F)NC1=O] |

TABLE 4-continued
| Comp. No. | Chemical Structure |
|---|---|
| B51 | 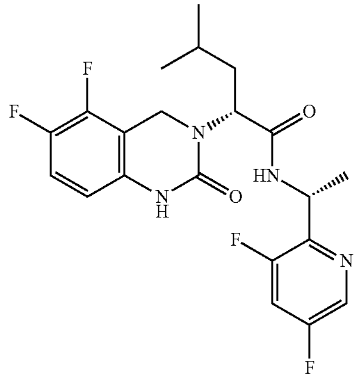 [SMILES: CC(C)C[C@H](C(=O)N[C@H](C)c1ncc(F)cc1F)N1Cc2c(ccc(F)c2F)NC1=O] |
| B52 | 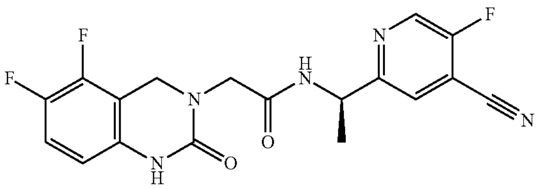 [SMILES: C[C@@H](NC(=O)CN1Cc2c(ccc(F)c2F)NC1=O)c1cc(C#N)c(F)cn1] |
| B53 | 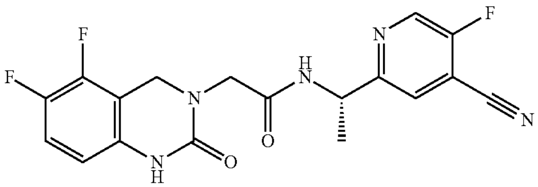 [SMILES: C[C@H](NC(=O)CN1Cc2c(ccc(F)c2F)NC1=O)c1cc(C#N)c(F)cn1] |
| B54 | 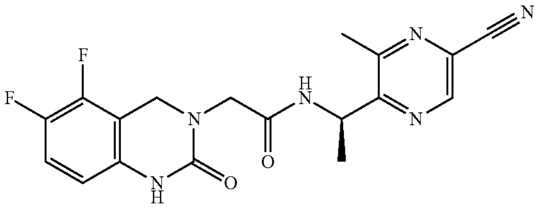 [SMILES: Cc1nc(C#N)cnc1[C@@H](C)NC(=O)CN1Cc2c(ccc(F)c2F)NC1=O] |
| B55 | 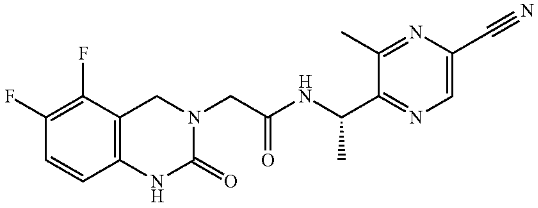 [SMILES: Cc1nc(C#N)cnc1[C@H](C)NC(=O)CN1Cc2c(ccc(F)c2F)NC1=O] |
| B56 | 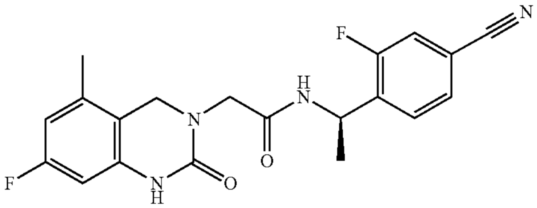 [SMILES: Cc1cc(F)cc2c1CN(CC(=O)N[C@H](C)c1ccc(C#N)cc1F)C(=O)N2] |

TABLE 4-continued
| Comp. No. | Chemical Structure |
|---|---|
| B57 | 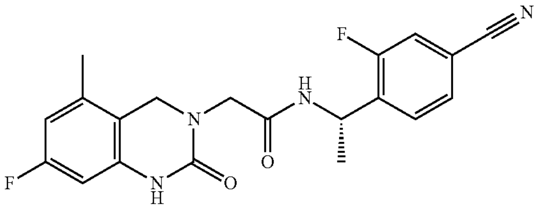 [SMILES: Cc1cc(F)cc2c1CN(CC(=O)N[C@@H](C)c1ccc(C#N)cc1F)C(=O)N2] |
| B58 | 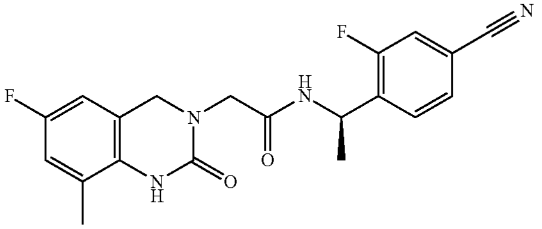 [SMILES: Cc1cc(F)cc2c1NC(=O)N(CC(=O)N[C@H](C)c1ccc(C#N)cc1F)C2] |
| B59 | 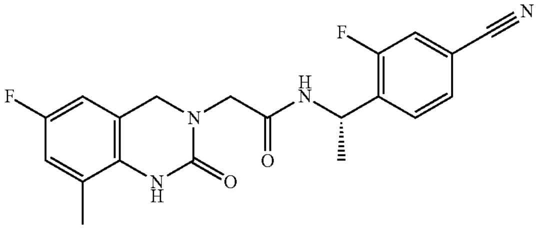 [SMILES: Cc1cc(F)cc2c1NC(=O)N(CC(=O)N[C@@H](C)c1ccc(C#N)cc1F)C2] |
| B60 | 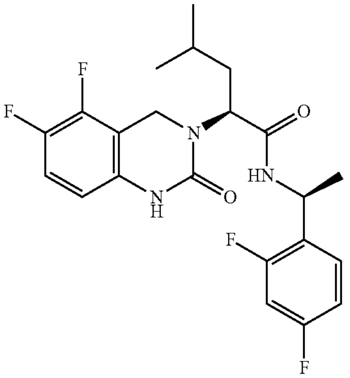 [SMILES: CC(C)C[C@@H](C(=O)N[C@@H](C)c1ccc(F)cc1F)N1Cc2c(ccc(F)c2F)NC1=O] |
| B61 | 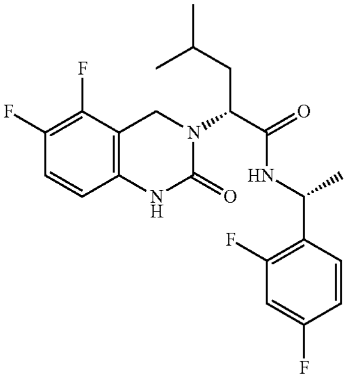 [SMILES: CC(C)C[C@H](C(=O)N[C@H](C)c1ccc(F)cc1F)N1Cc2c(ccc(F)c2F)NC1=O] |

TABLE 4-continued
| Comp. No. | Chemical Structure |
|---|---|
| B62 | 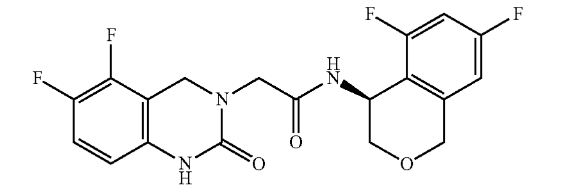 [SMILES: O=C(CN1Cc2c(ccc(F)c2F)NC1=O)N[C@@H]1COCc2cc(F)cc(F)c21] |
| B63 | 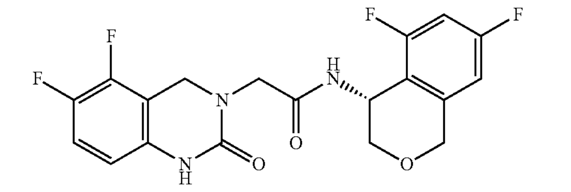 [SMILES: O=C(CN1Cc2c(ccc(F)c2F)NC1=O)N[C@H]1COCc2cc(F)cc(F)c21] |
| B64 | 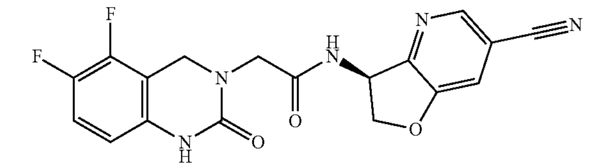 [SMILES: N#Cc1cnc2c(c1)OC[C@H]2NC(=O)CN1Cc2c(ccc(F)c2F)NC1=O] |
| B65 | 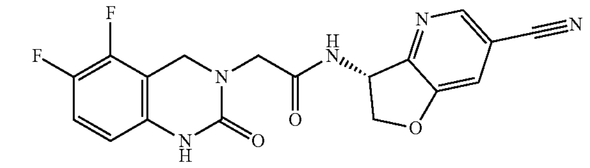 [SMILES: N#Cc1cnc2c(c1)OC[C@@H]2NC(=O)CN1Cc2c(ccc(F)c2F)NC1=O] |
| B66 | 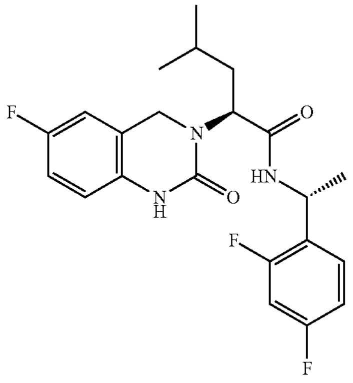 [SMILES: CC(C)C[C@@H](C(=O)N[C@H](C)c1ccc(F)cc1F)N1Cc2cc(F)ccc2NC1=O] |
| B67 | 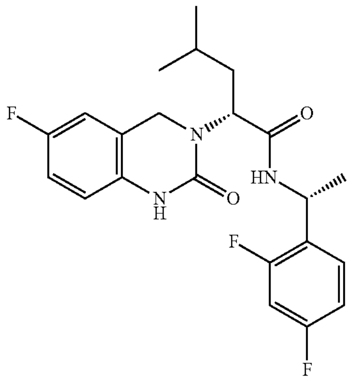 [SMILES: CC(C)C[C@H](C(=O)N[C@H](C)c1ccc(F)cc1F)N1Cc2cc(F)ccc2NC1=O] |

TABLE 4-continued
| Comp. No. | Chemical Structure |
|---|---|
| B68 | 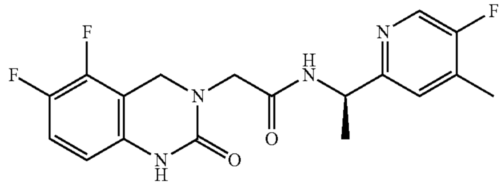 [SMILES: Cc1cc([C@@H](C)NC(=O)CN2Cc3c(ccc(F)c3F)NC2=O)ncc1F] |
| B69 | 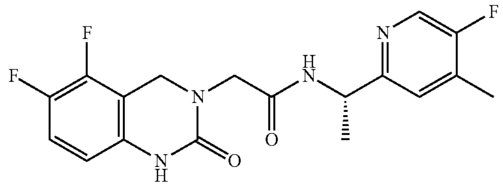 [SMILES: Cc1cc([C@H](C)NC(=O)CN2Cc3c(ccc(F)c3F)NC2=O)ncc1F] |
| B70 | 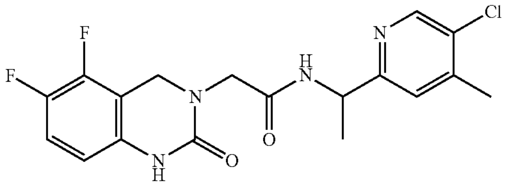 [SMILES: Cc1cc(C(C)NC(=O)CN2Cc3c(ccc(F)c3F)NC2=O)ncc1Cl] |
| B71 | 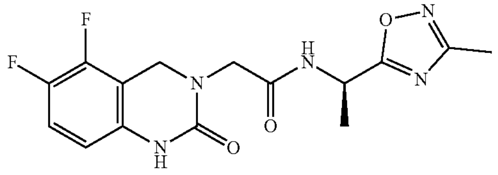 |
| B72 | 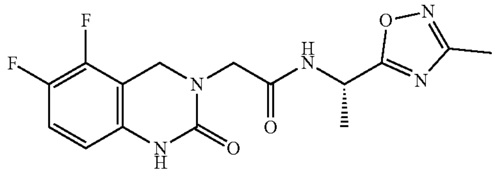 |
| B73 | 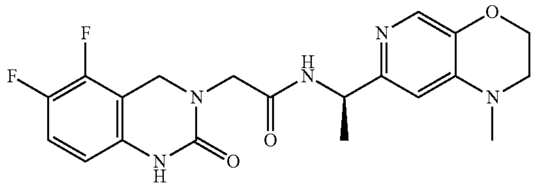 [SMILES: C[C@@H](NC(=O)CN1Cc2c(ccc(F)c2F)NC1=O)c1cc2c(cn1)OCCN2C] |
| B74 | 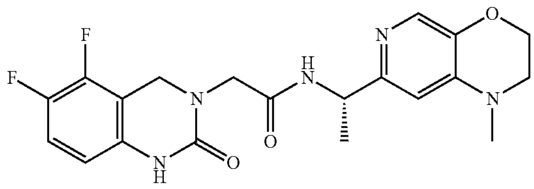 [SMILES: C[C@H](NC(=O)CN1Cc2c(ccc(F)c2F)NC1=O)c1cc2c(cn1)OCCN2C] |
| B75 | 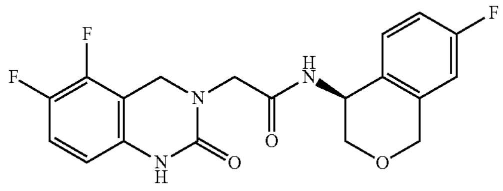 [SMILES: O=C(CN1Cc2c(ccc(F)c2F)NC1=O)N[C@@H]1COCc2cc(F)ccc21] |

TABLE 4-continued
| Comp. No. | Chemical Structure |
| --- | --- |
| B76 | 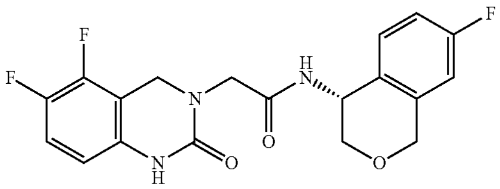 [SMILES: O=C(CN1Cc2c(ccc(F)c2F)NC1=O)N[C@H]1COCc2cc(F)ccc21] |
| B77 | 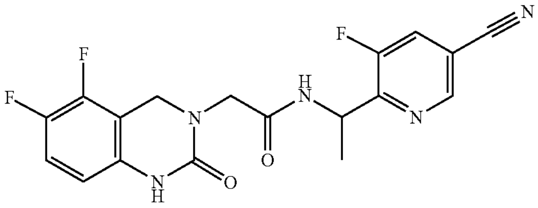 [SMILES: CC(NC(=O)CN1Cc2c(ccc(F)c2F)NC1=O)c1ncc(C#N)cc1F] |
| B78 | 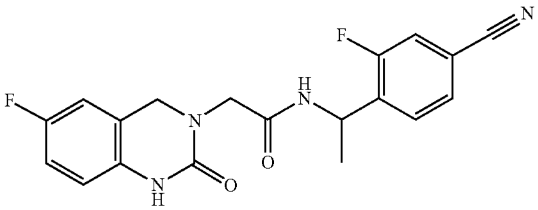 [SMILES: CC(NC(=O)CN1Cc2cc(F)ccc2NC1=O)c1ccc(C#N)cc1F] |
| B79 | 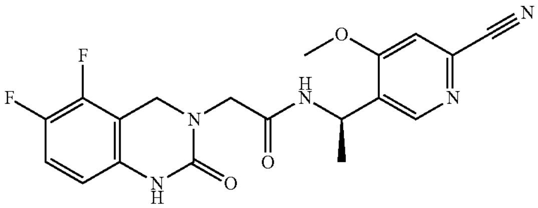 [SMILES: COc1cc(C#N)ncc1[C@@H](C)NC(=O)CN1Cc2c(ccc(F)c2F)NC1=O] |
| B80 | 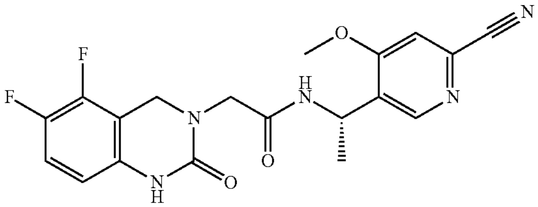 [SMILES: COc1cc(C#N)ncc1[C@H](C)NC(=O)CN1Cc2c(ccc(F)c2F)NC1=O] |
| B81 | 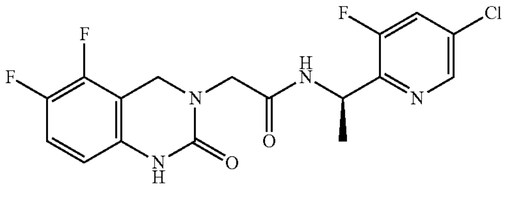 [SMILES: C[C@@H](NC(=O)CN1Cc2c(ccc(F)c2F)NC1=O)c1ncc(Cl)cc1F] |
| B82 | 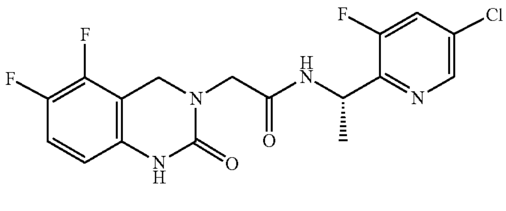 [SMILES: C[C@H](NC(=O)CN1Cc2c(ccc(F)c2F)NC1=O)c1ncc(Cl)cc1F] |

TABLE 4-continued
| Comp. No. | Chemical Structure |
| --- | --- |
| B83 | 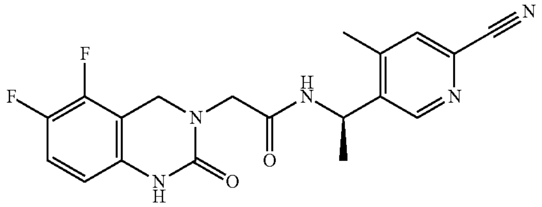 [SMILES: Cc1cc(C#N)ncc1[C@@H](C)NC(=O)CN1Cc2c(ccc(F)c2F)NC1=O] |
| B84 | 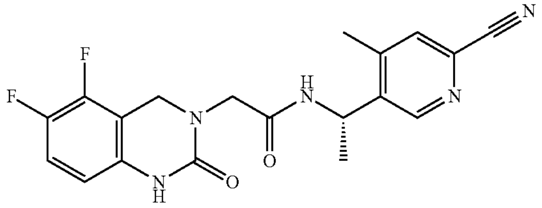 |
| B85 | 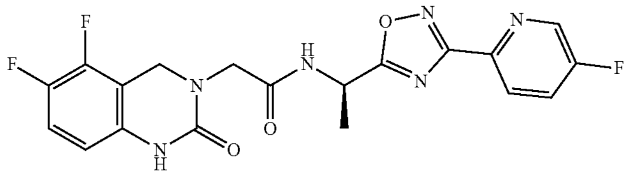 [SMILES: C[C@@H](NC(=O)CN1Cc2c(ccc(F)c2F)NC1=O)c1nc(-c2ccc(F)cn2)no1] |
| B86 | 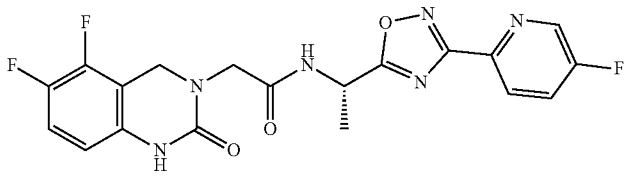 [SMILES: C[C@H](NC(=O)CN1Cc2c(ccc(F)c2F)NC1=O)c1nc(-c2ccc(F)cn2)no1] |
| B87 | 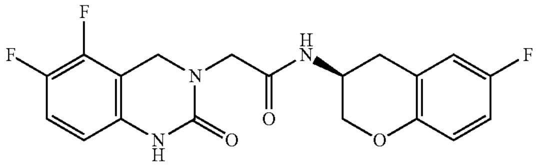 [SMILES: O=C(CN1Cc2c(ccc(F)c2F)NC1=O)N[C@@H]1COc2ccc(F)cc2C1] |
| B88 | 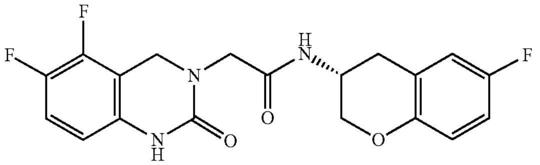 [SMILES: O=C(CN1Cc2c(ccc(F)c2F)NC1=O)N[C@H]1COc2ccc(F)cc2C1] |
| B89 | 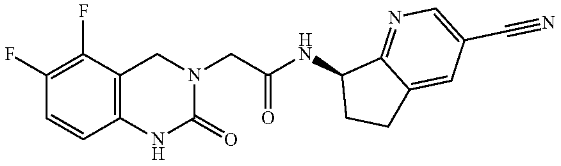 |
| B90 | 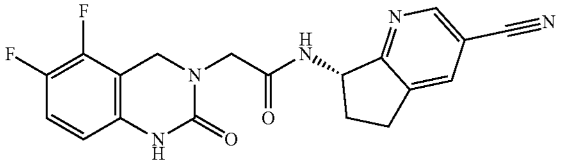 [SMILES: N#Cc1cnc2c(c1)CC[C@@H]2NC(=O)CN1Cc2c(ccc(F)c2F)NC1=O] |

TABLE 4-continued
| Comp. No. | Chemical Structure |
|---|---|
| B91 | 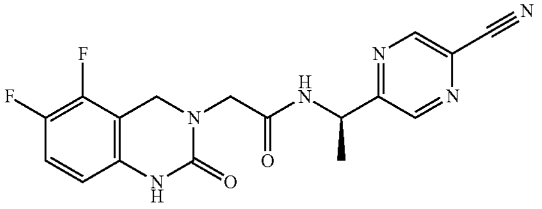 |
| B92 | 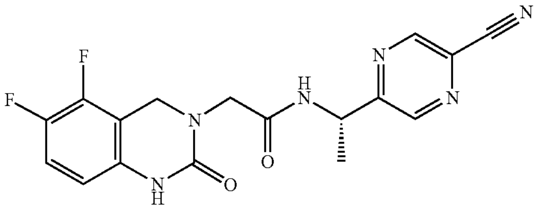 [SMILES: C[C@H](NC(=O)CN1Cc2c(ccc(F)c2F)NC1=O)c1cnc(C#N)cn1] |
| B93 | 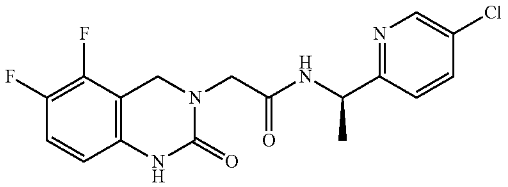 [SMILES: C[C@@H](NC(=O)CN1Cc2c(ccc(F)c2F)NC1=O)c1ccc(Cl)cn1] |
| B94 | 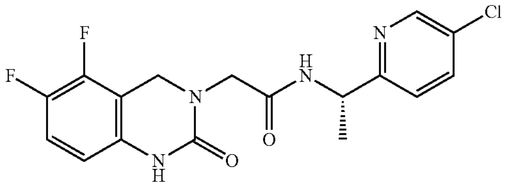 [SMILES: C[C@H](NC(=O)CN1Cc2c(ccc(F)c2F)NC1=O)c1ccc(Cl)cn1] |
| B95 | 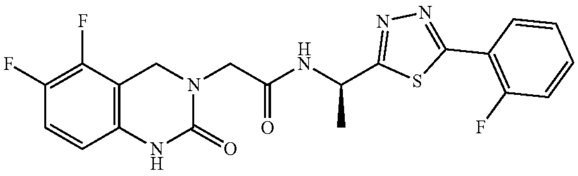 [SMILES: C[C@@H](NC(=O)CN1Cc2c(ccc(F)c2F)NC1=O)c1nnc(-c2ccccc2F)s1] |
| B96 | 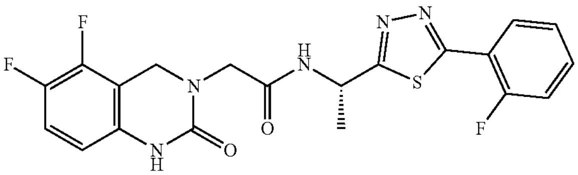 [SMILES: C[C@H](NC(=O)CN1Cc2c(ccc(F)c2F)NC1=O)c1nnc(-c2ccccc2F)s1] |
| B97 | 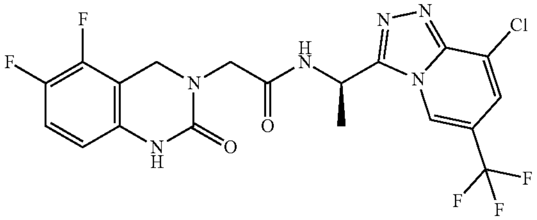 [SMILES: C[C@@H](NC(=O)CN1Cc2c(ccc(F)c2F)NC1=O)c1nnc2c(Cl)cc(C(F)(F)F)cn12] |

TABLE 4-continued
| Comp. No. | Chemical Structure |
|---|---|
| B98 | 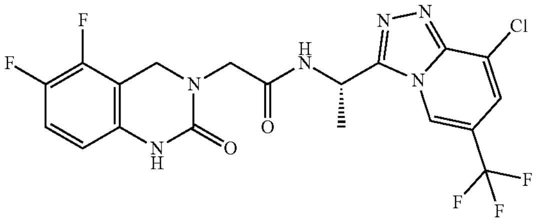 [SMILES: C[C@H](NC(=O)CN1Cc2c(ccc(F)c2F)NC1=O)c1nnc2c(Cl)cc(C(F)(F)F)cn12] |
| B99 | 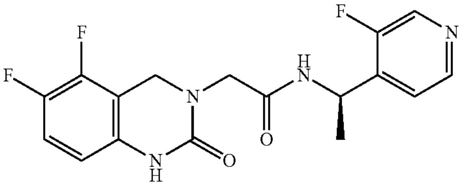 [SMILES: C[C@@H](NC(=O)CN1Cc2c(ccc(F)c2F)NC1=O)c1ccncc1F] |
| B100 | 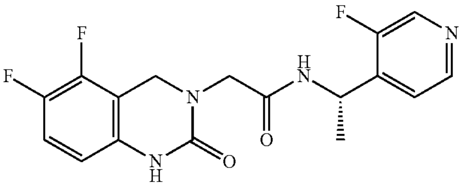 [SMILES: C[C@H](NC(=O)CN1Cc2c(ccc(F)c2F)NC1=O)c1ccncc1F] |
| B101 | 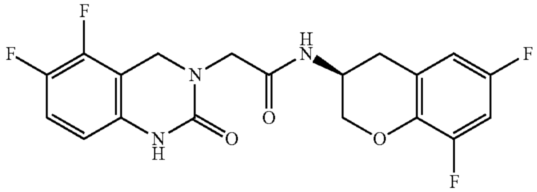 [SMILES: O=C(CN1Cc2c(ccc(F)c2F)NC1=O)N[C@@H]1COc2c(F)cc(F)cc2C1] |
| B102 | 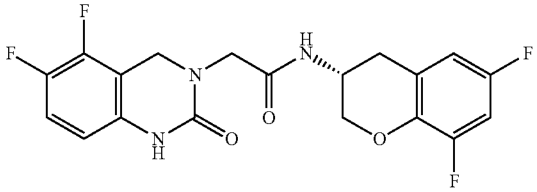 [SMILES: O=C(CN1Cc2c(ccc(F)c2F)NC1=O)N[C@H]1COc2c(F)cc(F)cc2C1] |
| B103 | 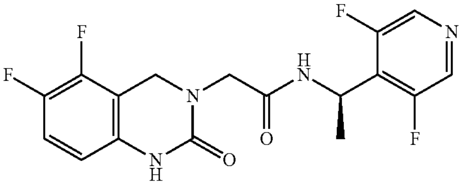 [SMILES: C[C@@H](NC(=O)CN1Cc2c(ccc(F)c2F)NC1=O)c1c(F)cncc1F] |
| B104 | 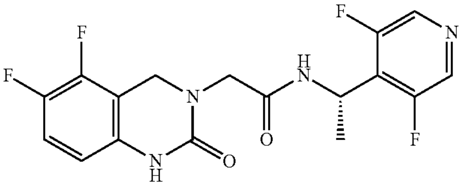 [SMILES: C[C@H](NC(=O)CN1Cc2c(ccc(F)c2F)NC1=O)c1c(F)cncc1F] |

TABLE 4-continued
| Comp. No. | Chemical Structure |
|---|---|
| B105 | 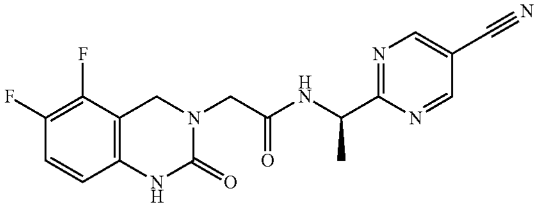 [SMILES: C[C@@H](NC(=O)CN1Cc2c(ccc(F)c2F)NC1=O)c1ncc(C#N)cn1] |
| B106 | 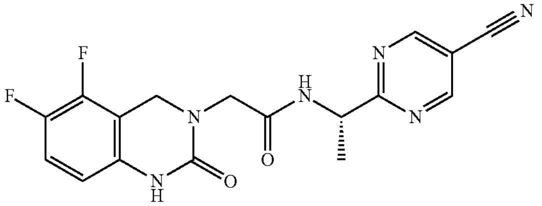 [SMILES: C[C@H](NC(=O)CN1Cc2c(ccc(F)c2F)NC1=O)c1ncc(C#N)cn1] |
| B107 | 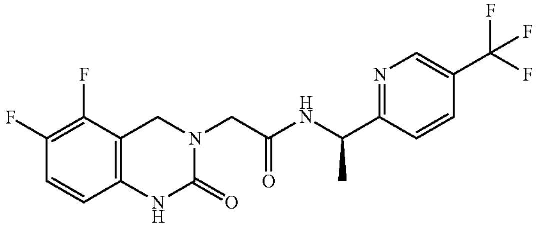 [SMILES: C[C@@H](NC(=O)CN1Cc2c(ccc(F)c2F)NC1=O)c1ccc(C(F)(F)F)cn1] |
| B108 | 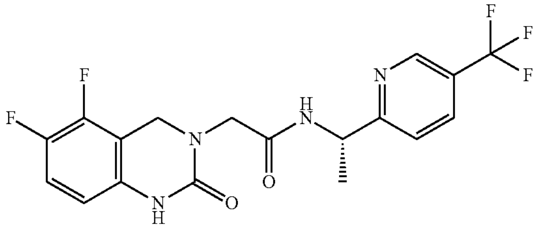 [SMILES: C[C@H](NC(=O)CN1Cc2c(ccc(F)c2F)NC1=O)c1ccc(C(F)(F)F)cn1] |
| B109 | 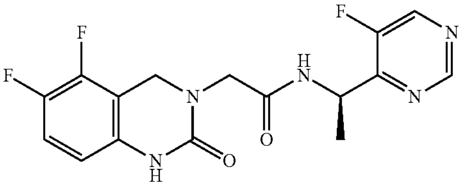 [SMILES: C[C@@H](NC(=O)CN1Cc2c(ccc(F)c2F)NC1=O)c1ncncc1F] |
| B110 | 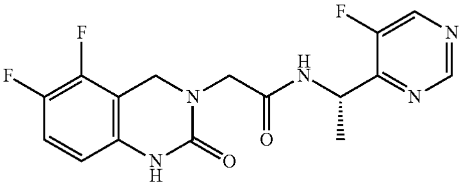 [SMILES: C[C@H](NC(=O)CN1Cc2c(ccc(F)c2F)NC1=O)c1ncncc1F] |
| B111 | 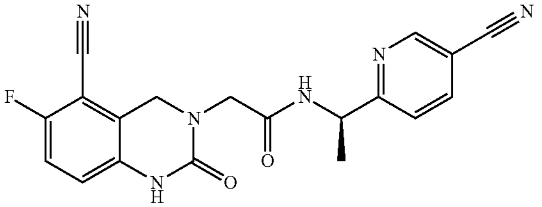 [SMILES: C[C@@H](NC(=O)CN1Cc2c(ccc(F)c2C#N)NC1=O)c1ccc(C#N)cn1] |

TABLE 4-continued
| Comp. No. | Chemical Structure |
|---|---|
| B112 | 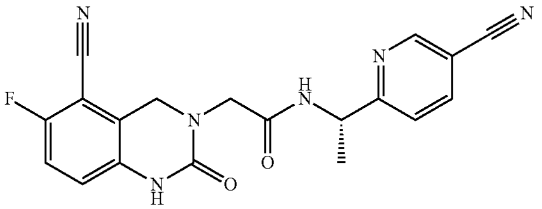 [SMILES: C[C@H](NC(=O)CN1Cc2c(ccc(F)c2C#N)NC1=O)c1ccc(C#N)cn1] |
| B113 | 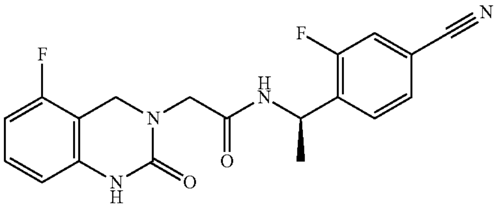 [SMILES: C[C@@H](NC(=O)CN1Cc2c(F)cccc2NC1=O)c1ccc(C#N)cc1F] |
| B114 | 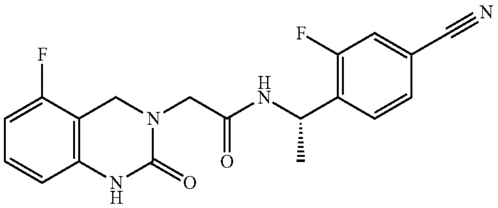 [SMILES: C[C@H](NC(=O)CN1Cc2c(F)cccc2NC1=O)c1ccc(C#N)cc1F] |
| B115 | 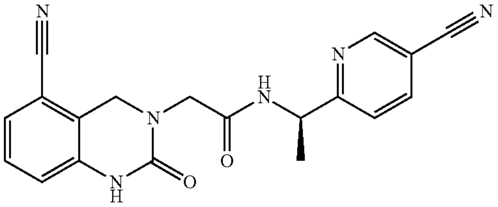 [SMILES: C[C@@H](NC(=O)CN1Cc2c(C#N)cccc2NC1=O)c1ccc(C#N)cn1] |
| B116 | 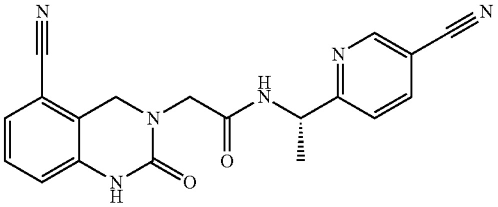 [SMILES: C[C@H](NC(=O)CN1Cc2c(C#N)cccc2NC1=O)c1ccc(C#N)cn1] |
| B117 | 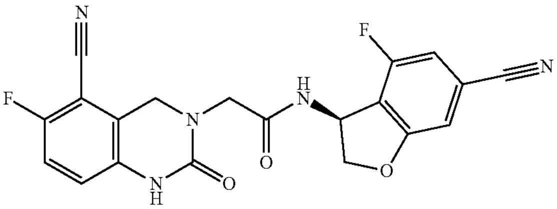 [SMILES: N#Cc1cc(F)c2c(c1)OC[C@H]2NC(=O)CN1Cc2c(ccc(F)c2C#N)NC1=O] |
| B118 | 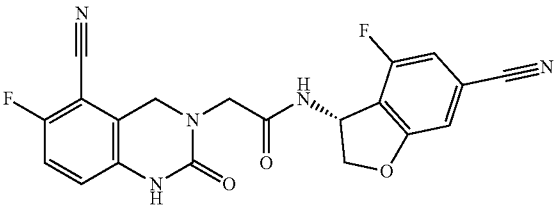 [SMILES: N#Cc1cc(F)c2c(c1)OC[C@@H]2NC(=O)CN1Cc2c(ccc(F)c2C#N)NC1=O] |

TABLE 4-continued
| Comp. No. | Chemical Structure |
| --- | --- |
| B119 | 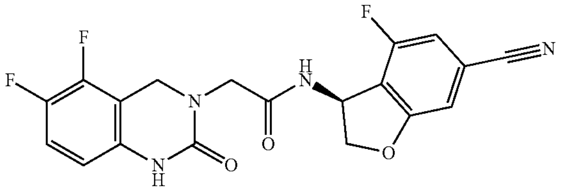 [SMILES: N#Cc1cc(F)c2c(c1)OC[C@H]2NC(=O)CN1Cc2c(ccc(F)c2F)NC1=O] |
| B120 | 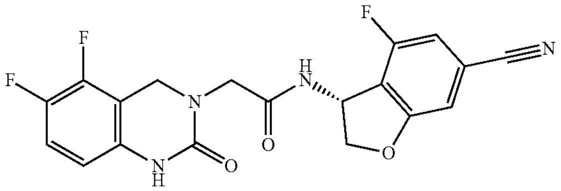 [SMILES: N#Cc1cc(F)c2c(c1)OC[C@@H]2NC(=O)CN1Cc2c(ccc(F)c2F)NC1=O] |
| B121 | 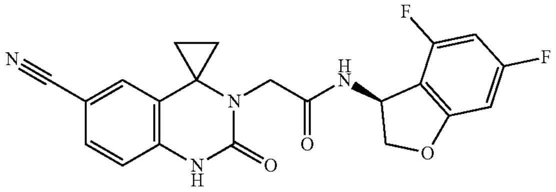 [SMILES: N#Cc1ccc2c(c1)C1(CC1)N(CC(=O)N[C@@H]1COc3cc(F)cc(F)c31)C(=O)N2] |
| B122 | 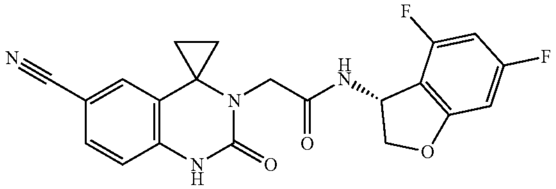 [SMILES: N#Cc1ccc2c(c1)C1(CC1)N(CC(=O)N[C@H]1COc3cc(F)cc(F)c31)C(=O)N2] |
| B123 | 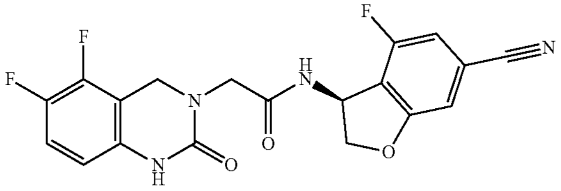 [SMILES: N#Cc1cc(F)c2c(c1)OC[C@H]2NC(=O)CN1Cc2c(ccc(F)c2F)NC1=O] |
| B124 | 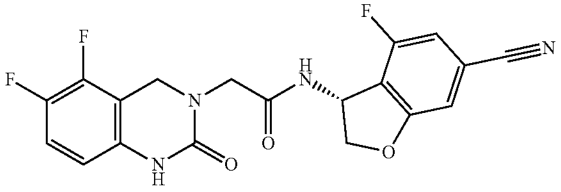 [SMILES: N#Cc1cc(F)c2c(c1)OC[C@@H]2NC(=O)CN1Cc2c(ccc(F)c2F)NC1=O] |
| B125 | 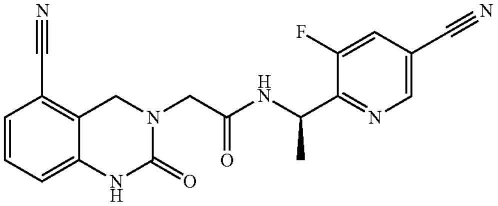 [SMILES: C[C@@H](NC(=O)CN1Cc2c(C#N)cccc2NC1=O)c1ncc(C#N)cc1F] |

TABLE 4-continued
| Comp. No. | Chemical Structure |
|---|---|
| B126 | 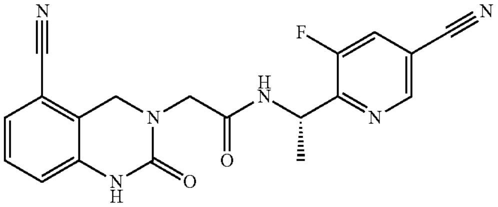 [SMILES: C[C@H](NC(=O)CN1Cc2c(C#N)cccc2NC1=O)c1ncc(C#N)cc1F] |
| B127 | 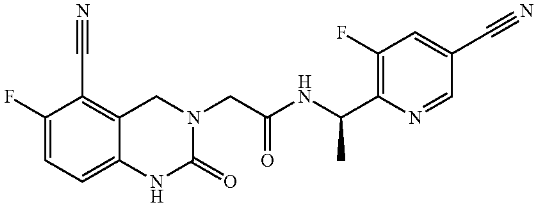 [SMILES: C[C@@H](NC(=O)CN1Cc2c(ccc(F)c2C#N)NC1=O)c1ncc(C#N)cc1F] |
| B128 | 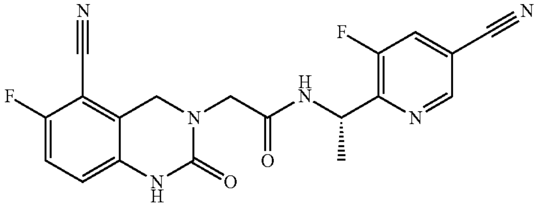 [SMILES: C[C@H](NC(=O)CN1Cc2c(ccc(F)c2C#N)NC1=O)c1ncc(C#N)cc1F] |
| B129 | 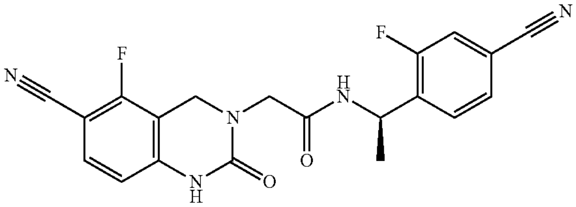 [SMILES: C[C@@H](NC(=O)CN1Cc2c(ccc(C#N)c2F)NC1=O)c1ccc(C#N)cc1F] |
| B130 | 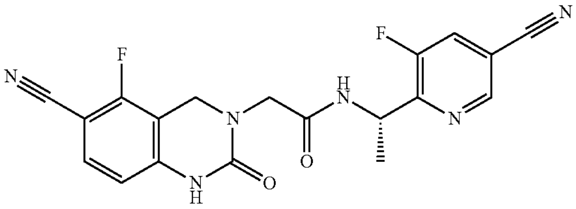 [SMILES: C[C@H](NC(=O)CN1Cc2c(ccc(C#N)c2F)NC1=O)c1ncc(C#N)cc1F] |
| B131 | 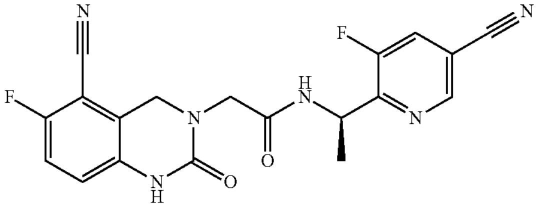 [SMILES: C[C@@H](NC(=O)CN1Cc2c(ccc(F)c2C#N)NC1=O)c1ncc(C#N)cc1F] |
| B132 | 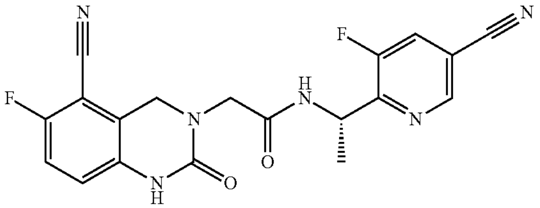 [SMILES: C[C@H](NC(=O)CN1Cc2c(ccc(F)c2C#N)NC1=O)c1ncc(C#N)cc1F] |

TABLE 4-continued
| Comp. No. | Chemical Structure |
|---|---|
| B133 | 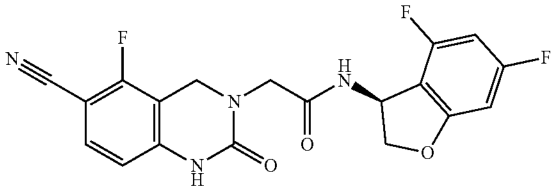 [SMILES: N#Cc1ccc2c(c1F)CN(CC(=O)N[C@@H]1COc3cc(F)cc(F)c31)C(=O)N2] |
| B134 | 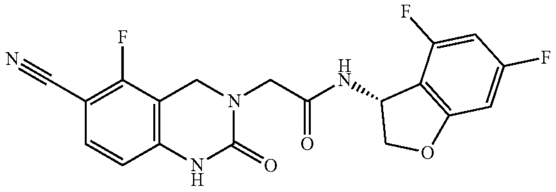 [SMILES: N#Cc1ccc2c(c1F)CN(CC(=O)N[C@H]1COc3cc(F)cc(F)c31)C(=O)N2] |
| B135 | 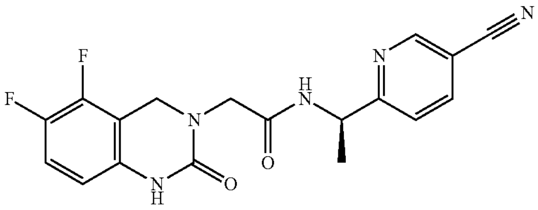 [SMILES: C[C@@H](NC(=O)CN1Cc2c(ccc(F)c2F)NC1=O)c1ccc(C#N)cn1] |
| B136 | 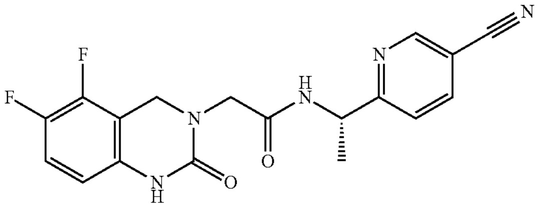 [SMILES: C[C@H](NC(=O)CN1Cc2c(ccc(F)c2F)NC1=O)c1ccc(C#N)cn1] |
| B137 | 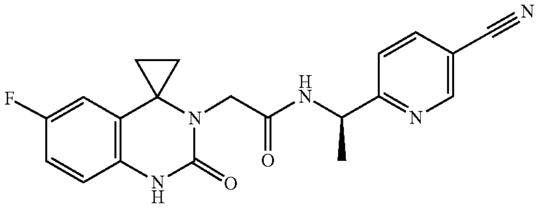 [SMILES: C[C@@H](NC(=O)CN1C(=O)Nc2ccc(F)cc2C12CC2)c1ccc(C#N)cn1] |
| B138 | 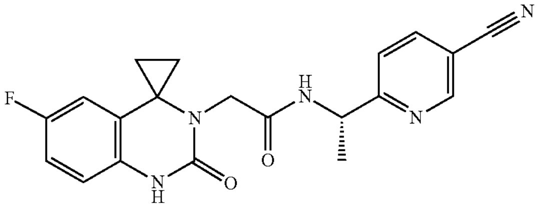 |
| B139 | 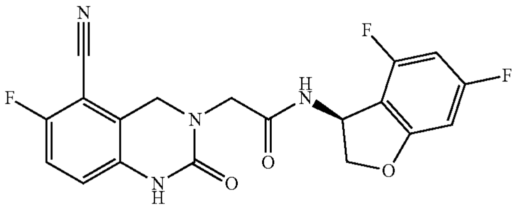 [SMILES: N#Cc1c(F)ccc2c1CN(CC(=O)N[C@@H]1COc3cc(F)cc(F)c31)C(=O)N2] |

TABLE 4-continued
| Comp. No. | Chemical Structure |
|---|---|
| B140 | 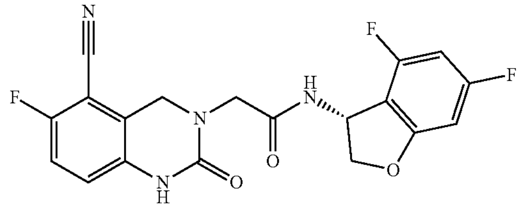 [SMILES: N#Cc1c(F)ccc2c1CN(CC(=O)N[C@H]1COc3cc(F)cc(F)c31)C(=O)N2] |
| B141 | 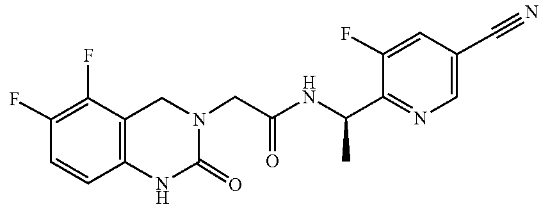 [SMILES: C[C@@H](NC(=O)CN1Cc2c(ccc(F)c2F)NC1=O)c1ncc(C#N)cc1F] |
| B142 | 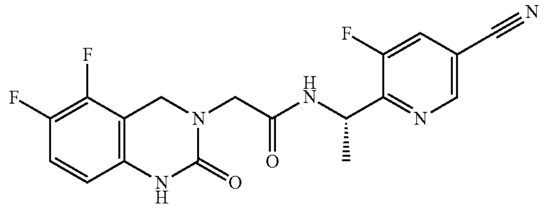 |
| B143 | 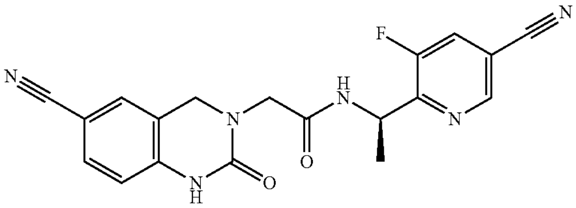 [SMILES: C[C@@H](NC(=O)CN1Cc2cc(C#N)ccc2NC1=O)c1ncc(C#N)cc1F] |
| B144 | 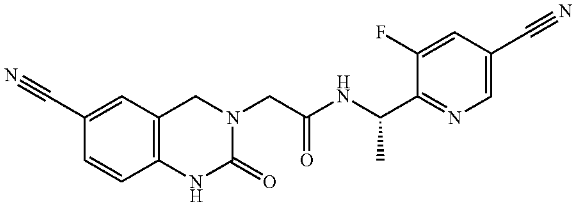 [SMILES: C[C@H](NC(=O)CN1Cc2cc(C#N)ccc2NC1=O)c1ncc(C#N)cc1F] |
| B145 | 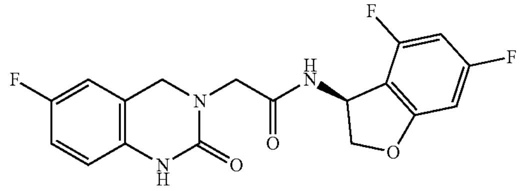 [SMILES: O=C(CN1Cc2cc(F)ccc2NC1=O)N[C@@H]1COc2cc(F)cc(F)c21] |
| B146 | 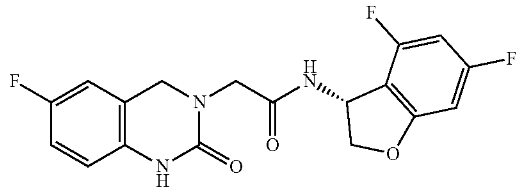 [SMILES: O=C(CN1Cc2cc(F)ccc2NC1=O)N[C@H]1COc2cc(F)cc(F)c21] |

TABLE 4-continued
| Comp. No. | Chemical Structure |
|---|---|
| B147 | 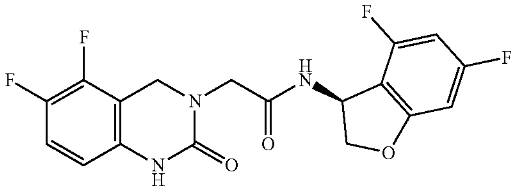 [SMILES: O=C(CN1Cc2c(ccc(F)c2F)NC1=O)N[C@@H]1COc2cc(F)cc(F)c21] |
| B148 | 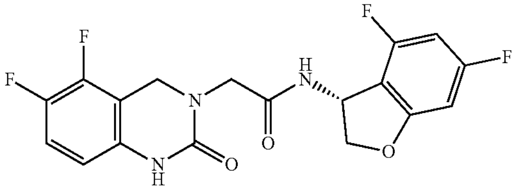 [SMILES: O=C(CN1Cc2c(ccc(F)c2F)NC1=O)N[C@H]1COc2cc(F)cc(F)c21] |
| B149 | 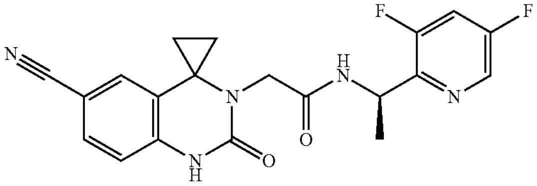 [SMILES: C[C@@H](NC(=O)CN1C(=O)Nc2ccc(C#N)cc2C12CC2)c1ncc(F)cc1F] |
| B150 | 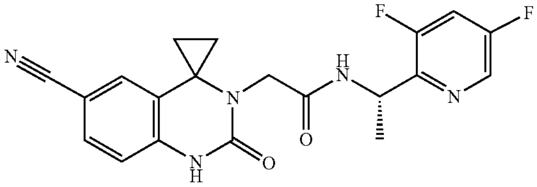 [SMILES: C[C@H](NC(=O)CN1C(=O)Nc2ccc(C#N)cc2C12CC2)c1ncc(F)cc1F] |
| B151 | 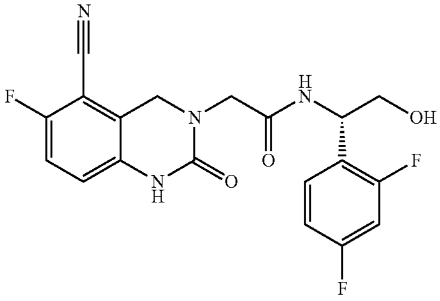 [SMILES: N#Cc1c(F)ccc2c1CN(CC(=O)N[C@H](CO)c1ccc(F)cc1F)C(=O)N2] |
| B152 | 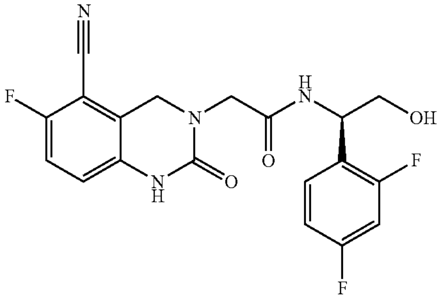 [SMILES: N#Cc1c(F)ccc2c1CN(CC(=O)N[C@@H](CO)c1ccc(F)cc1F)C(=O)N2] |

TABLE 4-continued
| Comp. No. | Chemical Structure |
|---|---|
| B153 | 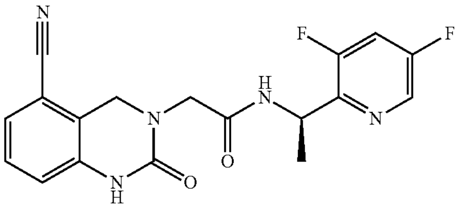 [SMILES: C[C@@H](NC(=O)CN1Cc2c(C#N)cccc2NC1=O)c1ncc(F)cc1F] |
| B154 | 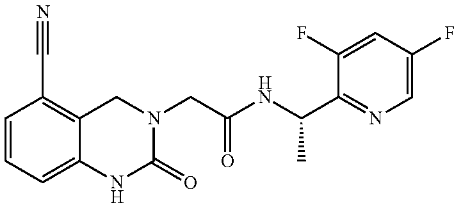 [SMILES: C[C@H](NC(=O)CN1Cc2c(C#N)cccc2NC1=O)c1ncc(F)cc1F] |
| B155 | 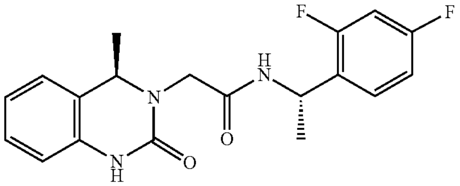 [SMILES: C[C@H](NC(=O)CN1C(=O)Nc2ccccc2[C@H]1C)c1ccc(F)cc1F] |
| B156 | 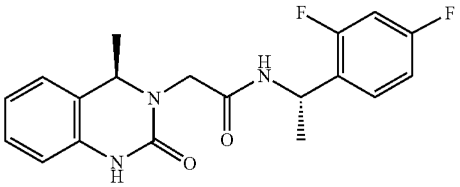 [SMILES: C[C@H](NC(=O)CN1C(=O)Nc2ccccc2[C@H]1C)c1ccc(F)cc1F] |
| B157 | 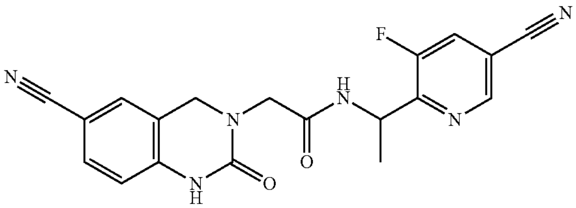 [SMILES: CC(NC(=O)CN1Cc2cc(C#N)ccc2NC1=O)c1ncc(C#N)cc1F] |
| B158 | 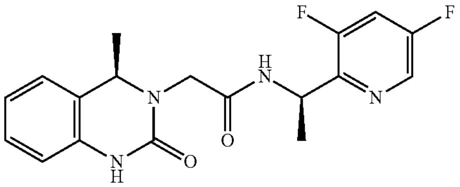 [SMILES: C[C@@H]1c2ccccc2NC(=O)N1CC(=O)N[C@H](C)c1ncc(F)cc1F] |
| B159 | 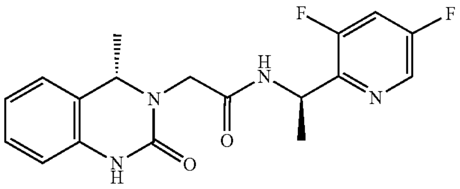 [SMILES: C[C@@H](NC(=O)CN1C(=O)Nc2ccccc2[C@@H]1C)c1ncc(F)cc1F] |

TABLE 4-continued
| Comp. No. | Chemical Structure |
|---|---|
| B160 | 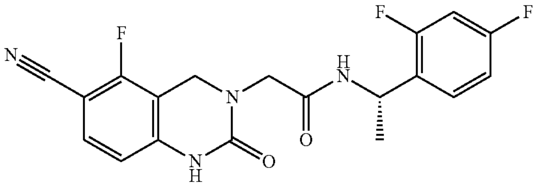 [SMILES: C[C@H](NC(=O)CN1Cc2c(ccc(C#N)c2F)NC1=O)c1ccc(F)cc1F] |
| B161 | 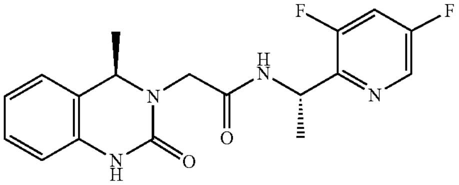 [SMILES: C[C@H](NC(=O)CN1C(=O)Nc2ccccc2[C@H]1C)c1ncc(F)cc1F] |
| B162 | 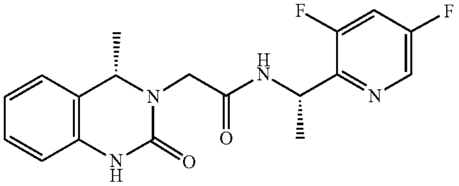 [SMILES: C[C@H](NC(=O)CN1C(=O)Nc2ccccc2[C@@H]1C)c1ncc(F)cc1F] |
| B163 | 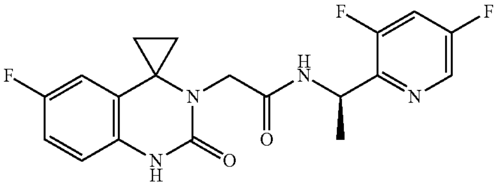 [SMILES: C[C@@H](NC(=O)CN1C(=O)Nc2ccc(F)cc2C12CC2)c1ncc(F)cc1F] |
| B164 | 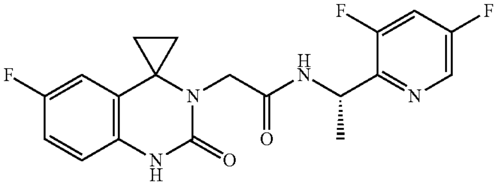 [SMILES: C[C@H](NC(=O)CN1C(=O)Nc2ccc(F)cc2C12CC2)c1ncc(F)cc1F] |
| B165 | 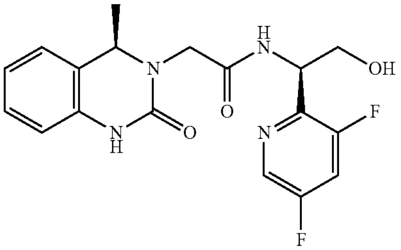 [SMILES: C[C@@H]1c2ccccc2NC(=O)N1CC(=O)N[C@@H](CO)c1ncc(F)cc1F] |
| B166 | 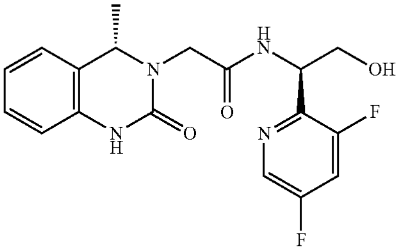 [SMILES: C[C@H]1c2ccccc2NC(=O)N1CC(=O)N[C@@H](CO)c1ncc(F)cc1F] |

TABLE 4-continued
| Comp. No. | Chemical Structure |
|---|---|
| B167 | 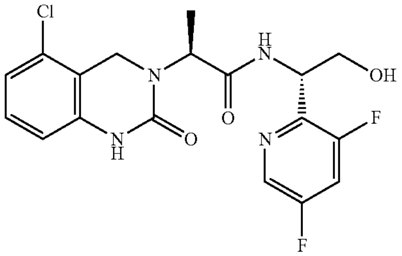 [SMILES: C[C@@H](C(=O)N[C@H](CO)c1ncc(F)cc1F)N1Cc2c(Cl)cccc2NC1=O] |
| B168 | 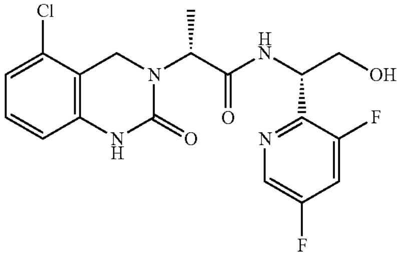 [SMILES: C[C@H](C(=O)N[C@H](CO)c1ncc(F)cc1F)N1Cc2c(Cl)cccc2NC1=O] |
| B169 | 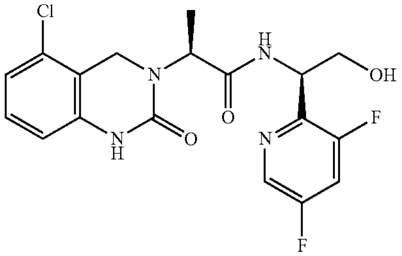 [SMILES: C[C@@H](C(=O)N[C@@H](CO)c1ncc(F)cc1F)N1Cc2c(Cl)cccc2NC1=O] |
| B170 | 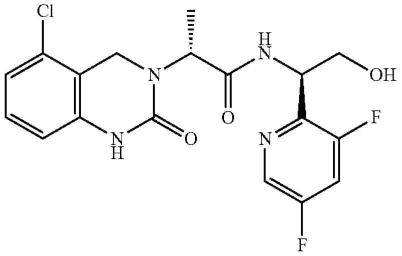 [SMILES: C[C@H](C(=O)N[C@@H](CO)c1ncc(F)cc1F)N1Cc2c(Cl)cccc2NC1=O] |
| B171 | 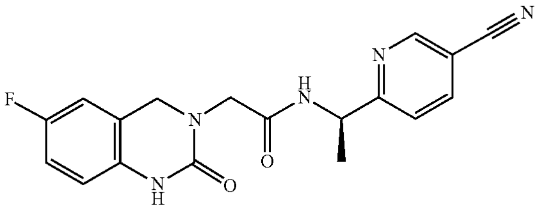 [SMILES: C[C@@H](NC(=O)CN1Cc2cc(F)ccc2NC1=O)c1ccc(C#N)cn1] |
| B172 | 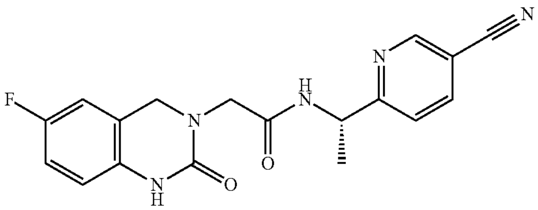 [SMILES: C[C@H](NC(=O)CN1Cc2cc(F)ccc2NC1=O)c1ccc(C#N)cn1] |

TABLE 4-continued
| Comp. No. | Chemical Structure |
|---|---|
| B173 | 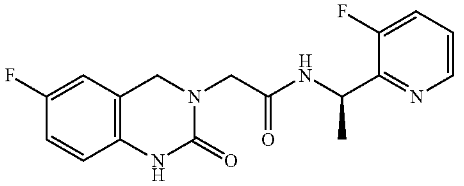 [SMILES: C[C@@H](NC(=O)CN1Cc2cc(F)ccc2NC1=O)c1ncccc1F] |
| B174 | 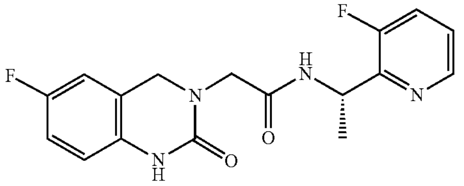 [SMILES: C[C@H](NC(=O)CN1Cc2cc(F)ccc2NC1=O)c1ncccc1F] |
| B175 | 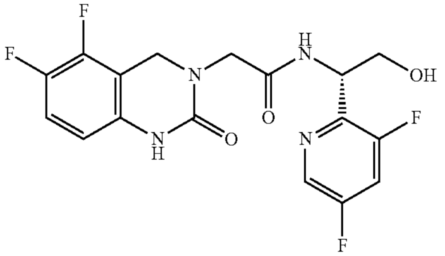 [SMILES: O=C(CN1Cc2c(ccc(F)c2F)NC1=O)N[C@H](CO)c1ncc(F)cc1F] |
| B176 | 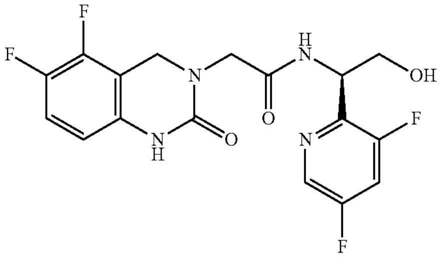 [SMILES: O=C(CN1Cc2c(ccc(F)c2F)NC1=O)N[C@@H](CO)c1ncc(F)cc1F] |
| B177 | 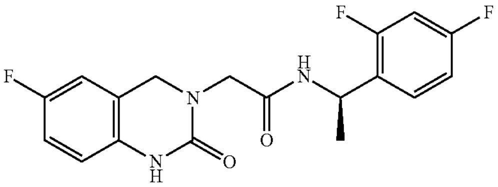 [SMILES: C[C@@H](NC(=O)CN1Cc2cc(F)ccc2NC1=O)c1ccc(F)cc1F] |
| B178 | 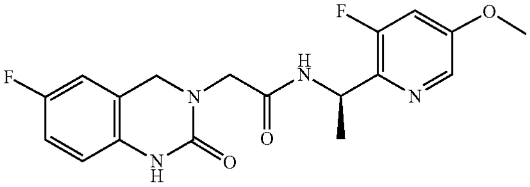 [SMILES: COc1cnc([C@@H](C)NC(=O)CN2Cc3cc(F)ccc3NC2=O)c(F)c1] |
| B179 | 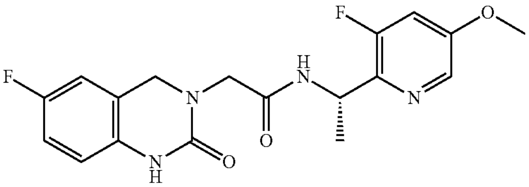 [SMILES: COc1cnc([C@H](C)NC(=O)CN2Cc3cc(F)ccc3NC2=O)c(F)c1] |

TABLE 4-continued
| Comp. No. | Chemical Structure |
| --- | --- |
| B180 | 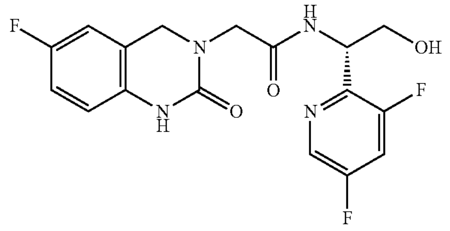 [SMILES: O=C(CN1Cc2cc(F)ccc2NC1=O)N[C@H](CO)c1ncc(F)cc1F] |
| B181 | 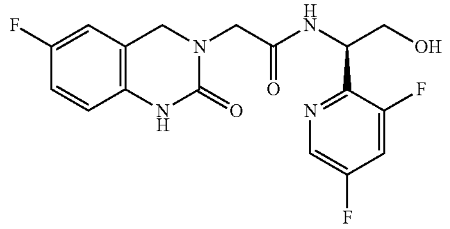 [SMILES: O=C(CN1Cc2cc(F)ccc2NC1=O)N[C@@H](CO)c1ncc(F)cc1F] |
| B182 | 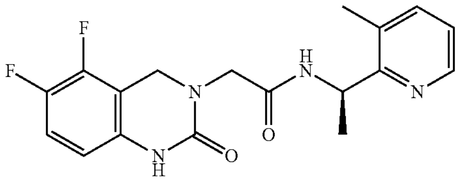 |
| B183 | 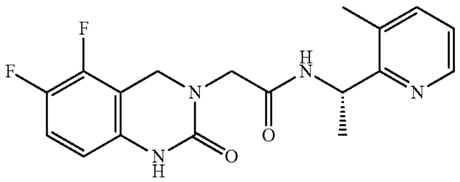 |
| B184 | 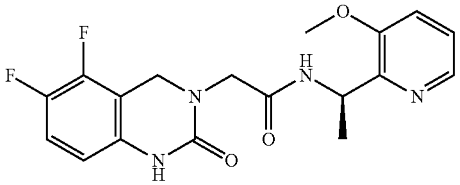 [SMILES: COc1cccnc1[C@@H](C)NC(=O)CN1Cc2c(ccc(F)c2F)NC1=O] |
| B185 | 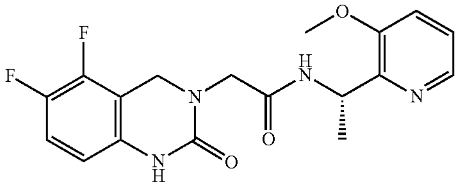 |
| B186 | 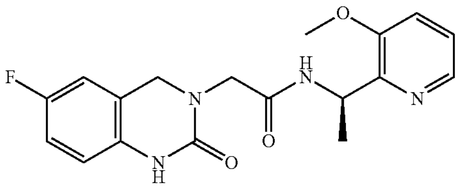 [SMILES: COc1cccnc1[C@@H](C)NC(=O)CN1Cc2cc(F)ccc2NC1=O] |

TABLE 4-continued
| Comp. No. | Chemical Structure |
|---|---|
| B187 | 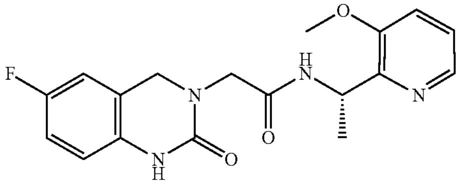 [SMILES: COc1cccnc1[C@H](C)NC(=O)CN1Cc2cc(F)ccc2NC1=O] |
| B188 | 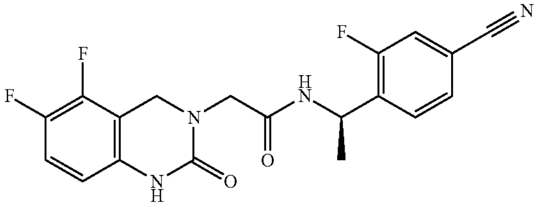 [SMILES: C[C@@H](NC(=O)CN1Cc2c(ccc(F)c2F)NC1=O)c1ccc(C#N)cc1F] |
| B189 | 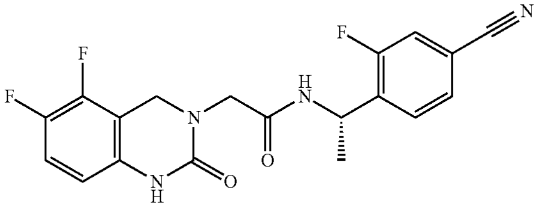 [SMILES: C[C@H](NC(=O)CN1Cc2c(ccc(F)c2F)NC1=O)c1ccc(C#N)cc1F] |
| B190 | 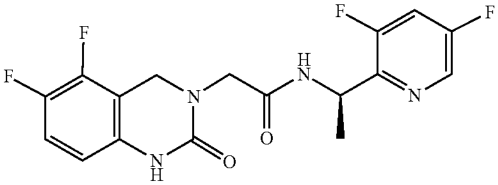 [SMILES: C[C@@H](NC(=O)CN1Cc2c(ccc(F)c2F)NC1=O)c1ncc(F)cc1F] |
| B191 | 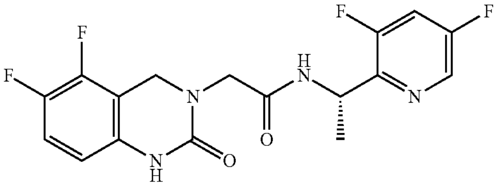 [SMILES: C[C@H](NC(=O)CN1Cc2c(ccc(F)c2F)NC1=O)c1ncc(F)cc1F] |
| B192 | 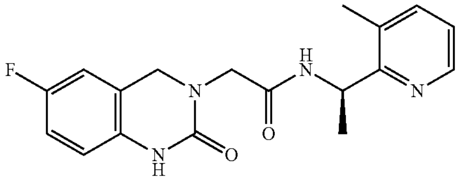 [SMILES: Cc1cccnc1[C@@H](C)NC(=O)CN1Cc2cc(F)ccc2NC1=O] |
| B193 | 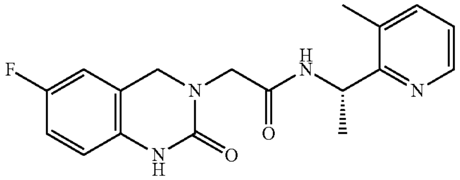 [SMILES: Cc1cccnc1[C@H](C)NC(=O)CN1Cc2cc(F)ccc2NC1=O] |

TABLE 4-continued
| Comp. No. | Chemical Structure |
|---|---|
| B194 | 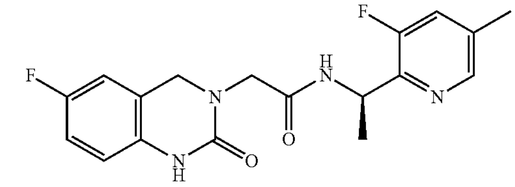 [SMILES: Cc1cnc([C@@H](C)NC(=O)CN2Cc3cc(F)ccc3NC2=O)c(F)c1] |
| B195 | 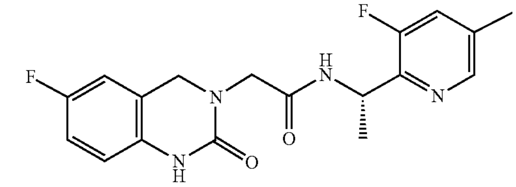 [SMILES: Cc1cnc([C@H](C)NC(=O)CN2Cc3cc(F)ccc3NC2=O)c(F)c1] |
| B196 | 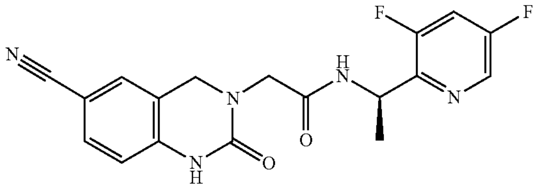 [SMILES: C[C@@H](NC(=O)CN1Cc2cc(C#N)ccc2NC1=O)c1ncc(F)cc1F] |
| B197 | 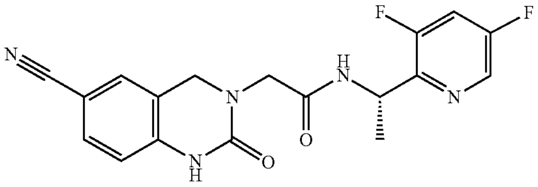 [SMILES: C[C@H](NC(=O)CN1Cc2cc(C#N)ccc2NC1=O)c1ncc(F)cc1F] |
| B198 | 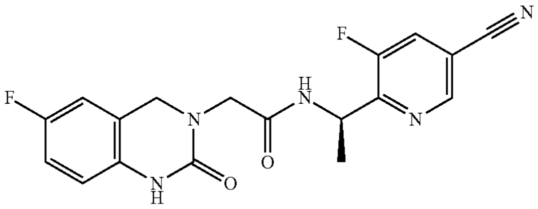 [SMILES: C[C@@H](NC(=O)CN1Cc2cc(F)ccc2NC1=O)c1ncc(C#N)cc1F] |
| B199 | 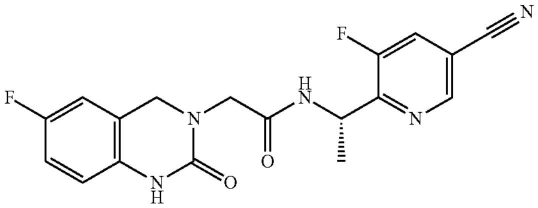 |
| B200 | 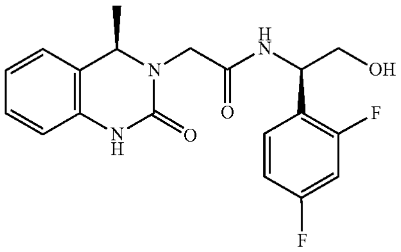 [SMILES: C[C@@H]1c2ccccc2NC(=O)N1CC(=O)N[C@@H](CO)c1ccc(F)cc1F] |

TABLE 4-continued
| Comp. No. | Chemical Structure |
|---|---|
| B201 | 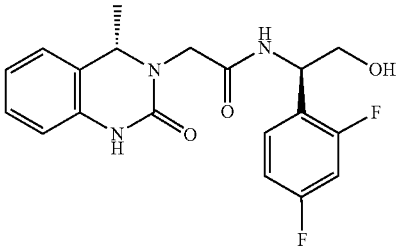 [SMILES: C[C@H]1c2ccccc2NC(=O)N1CC(=O)N[C@@H](CO)c1ccc(F)cc1F] |
| B202 | 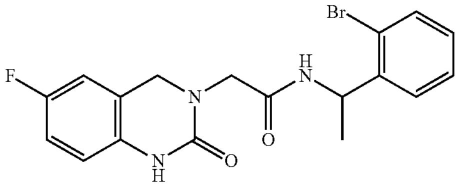 [SMILES: CC(NC(=O)CN1Cc2cc(F)ccc2NC1=O)c1ccccc1Br] |
| B203 | 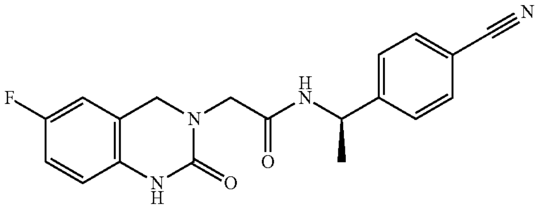 [SMILES: C[C@@H](NC(=O)CN1Cc2cc(F)ccc2NC1=O)c1ccc(C#N)cc1] |
| B204 | 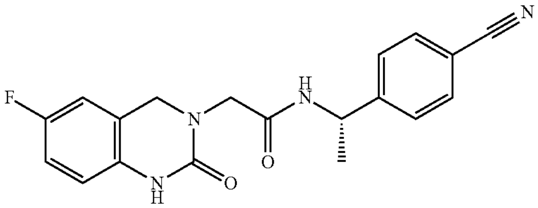 [SMILES: C[C@H](NC(=O)CN1Cc2cc(F)ccc2NC1=O)c1ccc(C#N)cc1] |
| B205 | 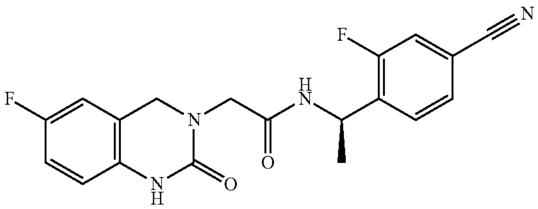 [SMILES: C[C@@H](NC(=O)CN1Cc2cc(F)ccc2NC1=O)c1ccc(C#N)cc1F] |
| B206 | 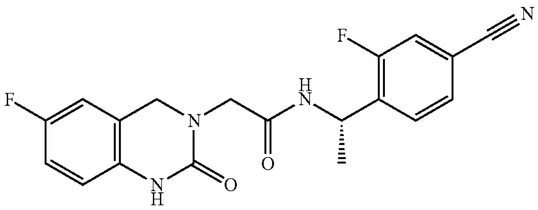 [SMILES: C[C@H](NC(=O)CN1Cc2cc(F)ccc2NC1=O)c1ccc(C#N)cc1F] |

TABLE 4-continued
| Comp. No. | Chemical Structure |
| --- | --- |
| B207 | 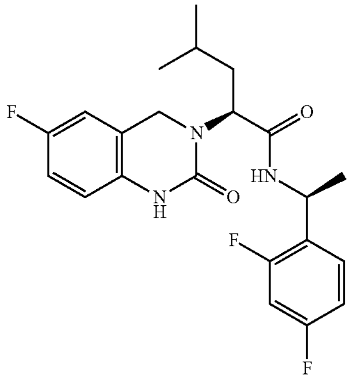 [SMILES: CC(C)C[C@@H](C(=O)N[C@@H](C)c1ccc(F)cc1F)N1Cc2cc(F)ccc2NC1=O] |
| B208 | 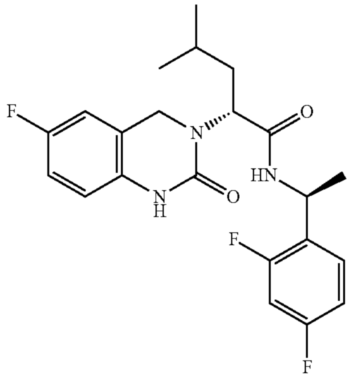 [SMILES: CC(C)C[C@H](C(=O)N[C@@H](C)c1ccc(F)cc1F)N1Cc2cc(F)ccc2NC1=O] |
| B209 | 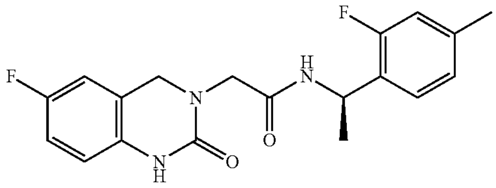 [SMILES: Cc1ccc([C@@H](C)NC(=O)CN2Cc3cc(F)ccc3NC2=O)c(F)c1] |
| B210 | 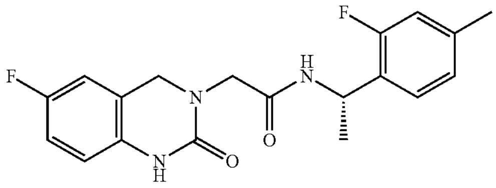 [SMILES: Cc1ccc([C@H](C)NC(=O)CN2Cc3cc(F)ccc3NC2=O)c(F)c1] |
| B211 | 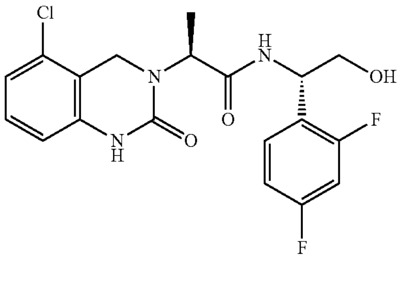 [SMILES: C[C@@H](C(=O)N[C@H](CO)c1ccc(F)cc1F)N1Cc2c(Cl)cccc2NC1=O] |

TABLE 4-continued
| Comp. No. | Chemical Structure |
|---|---|
| B212 | 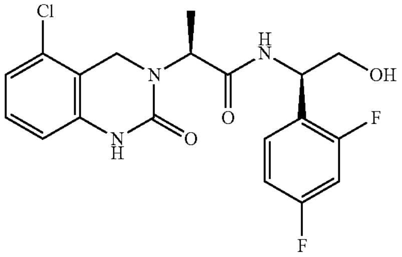 [SMILES: C[C@@H](C(=O)N[C@@H](CO)c1ccc(F)cc1F)N1Cc2c(Cl)cccc2NC1=O] |
| B213 | 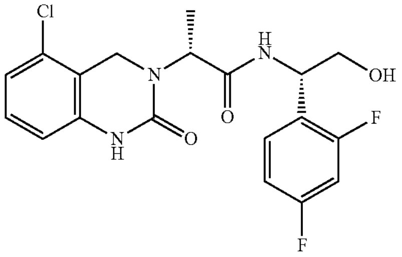 [SMILES: C[C@H](C(=O)N[C@H](CO)c1ccc(F)cc1F)N1Cc2c(Cl)cccc2NC1=O] |
| B214 | 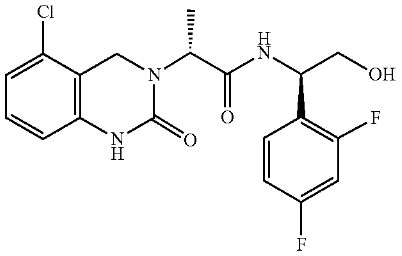 [SMILES: C[C@H](C(=O)N[C@@H](CO)c1ccc(F)cc1F)N1Cc2c(Cl)cccc2NC1=O] |
| B215 | 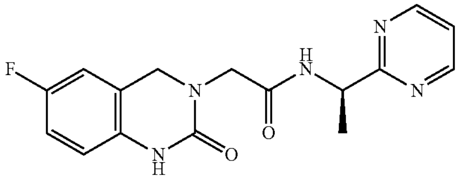 [SMILES: C[C@@H](NC(=O)CN1Cc2cc(F)ccc2NC1=O)c1ncccn1] |
| B216 | 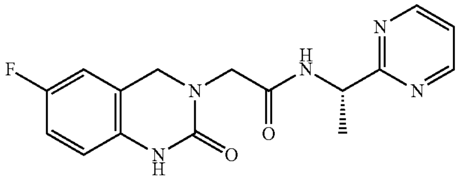 [SMILES: C[C@H](NC(=O)CN1Cc2cc(F)ccc2NC1=O)c1ncccn1] |
| B217 | 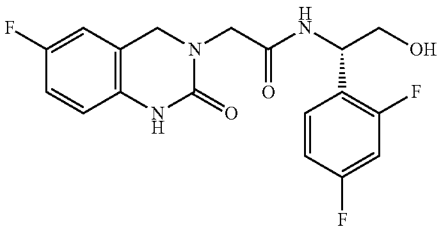 [SMILES: O=C(CN1Cc2cc(F)ccc2NC1=O)N[C@H](CO)c1ccc(F)cc1F] |

TABLE 4-continued
| Comp. No. | Chemical Structure |
|---|---|
| B218 | 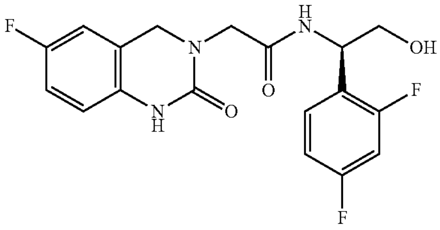 [SMILES: O=C(CN1Cc2cc(F)ccc2NC1=O)N[C@@H](CO)c1ccc(F)cc1F] |
| B219 | 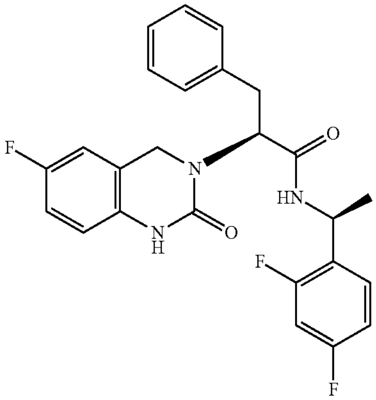 [SMILES: C[C@H](NC(=O)[C@H](Cc1ccccc1)N1Cc2cc(F)ccc2NC1=O)c1ccc(F)cc1F] |
| B220 | 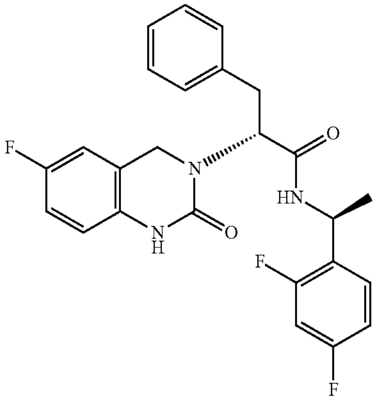 [SMILES: C[C@H](NC(=O)[C@@H](Cc1ccccc1)N1Cc2cc(F)ccc2NC1=O)c1ccc(F)cc1F] |
| B221 | 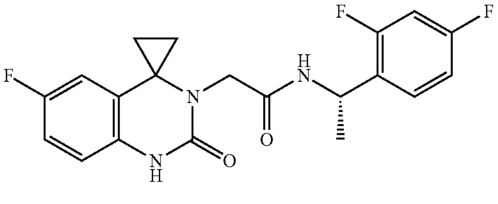 [SMILES: C[C@H](NC(=O)CN1C(=O)Nc2ccc(F)cc2C12CC2)c1ccc(F)cc1F] |
| B222 | 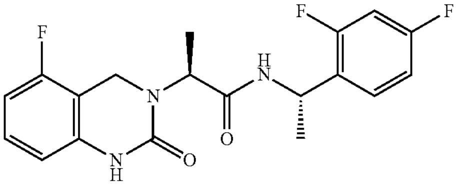 |

TABLE 4-continued
| Comp. No. | Chemical Structure |
|---|---|
| B223 | 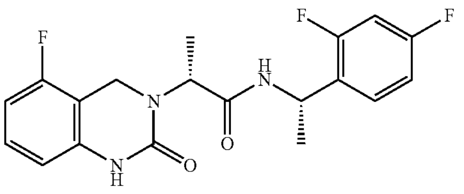 [SMILES: C[C@H](NC(=O)[C@@H](C)N1Cc2c(F)cccc2NC1=O)c1ccc(F)cc1F] |
| B224 | 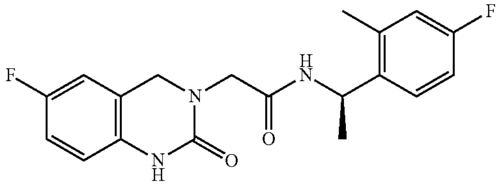 [SMILES: Cc1cc(F)ccc1[C@@H](C)NC(=O)CN1Cc2cc(F)ccc2NC1=O] |
| B225 | 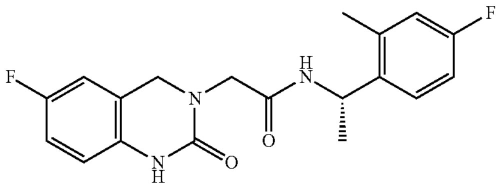 [SMILES: Cc1cc(F)ccc1[C@H](C)NC(=O)CN1Cc2cc(F)ccc2NC1=O] |
| B226 | 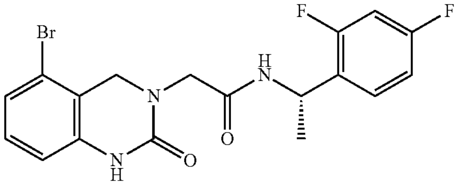 [SMILES: C[C@H](NC(=O)CN1Cc2c(Br)cccc2NC1=O)c1ccc(F)cc1F] |
| B227 | 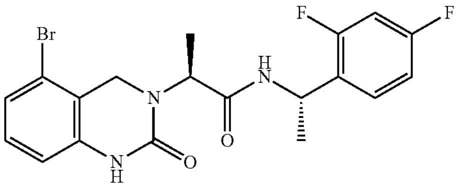 |
| B228 | 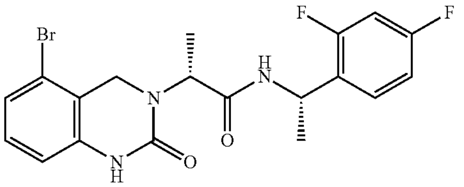 |
| B229 | 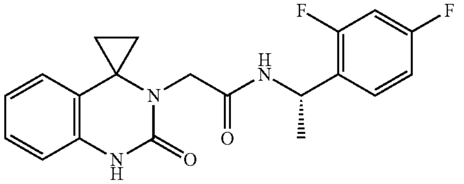 [SMILES: C[C@H](NC(=O)CN1C(=O)Nc2ccccc2C12CC2)c1ccc(F)cc1F] |
| B230 | 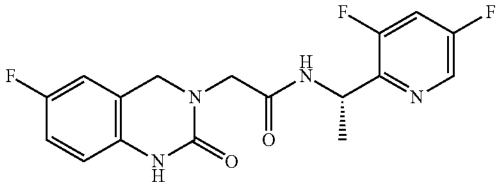 [SMILES: C[C@H](NC(=O)CN1Cc2cc(F)ccc2NC1=O)c1ncc(F)cc1F] |

TABLE 4-continued
| Comp. No. | Chemical Structure |
| --- | --- |
| B231 | 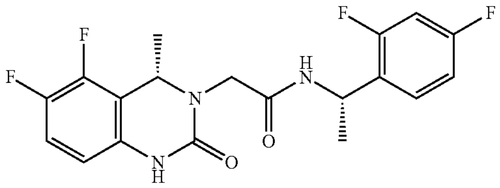 [SMILES: C[C@H](NC(=O)CN1C(=O)Nc2ccc(F)c(F)c2[C@@H]1C)c1ccc(F)cc1F] |
| B232 | 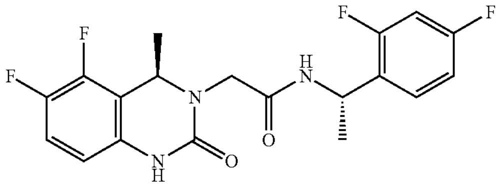 [SMILES: C[C@H](NC(=O)CN1C(=O)Nc2ccc(F)c(F)c2[C@H]1C)c1ccc(F)cc1F] |
| B233 | 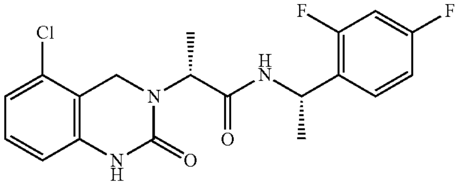 |
| B234 | 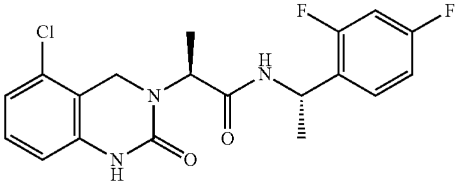 [SMILES: C[C@H](NC(=O)[C@H](C)N1Cc2c(Cl)cccc2NC1=O)c1ccc(F)cc1F] |
| B235 | 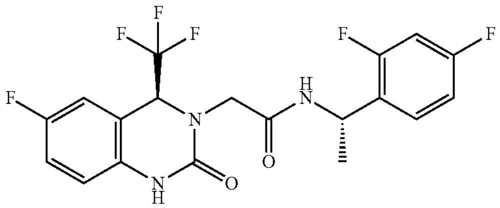 [SMILES: C[C@H](NC(=O)CN1C(=O)Nc2ccc(F)cc2[C@H]1C(F)(F)F)c1ccc(F)cc1F] |
| B236 | 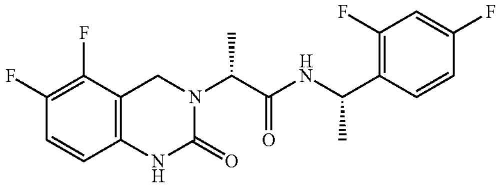 [SMILES: C[C@H](NC(=O)[C@@H](C)N1Cc2c(ccc(F)c2F)NC1=O)c1ccc(F)cc1F] |
| B237 | 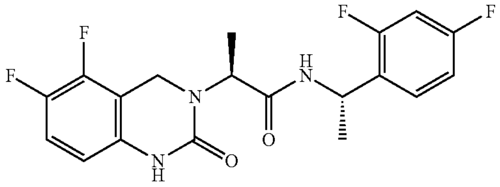 [SMILES: C[C@H](NC(=O)[C@H](C)N1Cc2c(ccc(F)c2F)NC1=O)c1ccc(F)cc1F] |
| B238 | 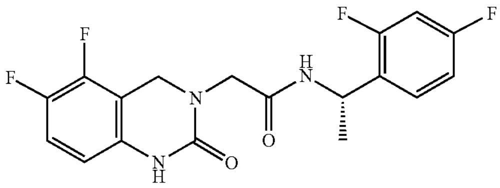 [SMILES: C[C@H](NC(=O)CN1Cc2c(ccc(F)c2F)NC1=O)c1ccc(F)cc1F] |

TABLE 4-continued
| Comp. No. | Chemical Structure |
|---|---|
| B239 | 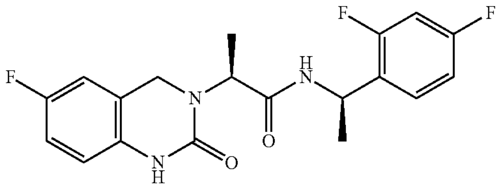 [SMILES: C[C@@H](NC(=O)[C@H](C)N1Cc2cc(F)ccc2NC1=O)c1ccc(F)cc1F] |
| B240 | 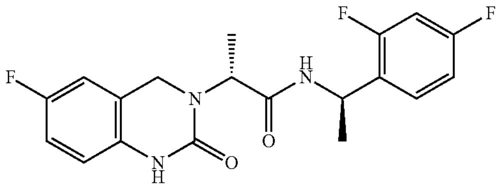 [SMILES: C[C@H](C(=O)N[C@H](C)c1ccc(F)cc1F)N1Cc2cc(F)ccc2NC1=O] |
| B241 | 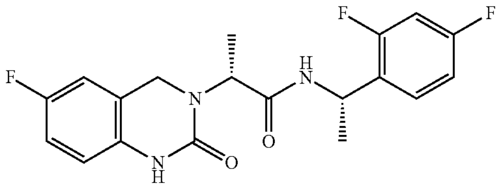 [SMILES: C[C@H](NC(=O)[C@@H](C)N1Cc2cc(F)ccc2NC1=O)c1ccc(F)cc1F] |
| B242 | 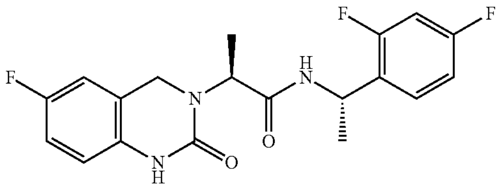 [SMILES: C[C@H](NC(=O)[C@H](C)N1Cc2cc(F)ccc2NC1=O)c1ccc(F)cc1F] |
| B243 | 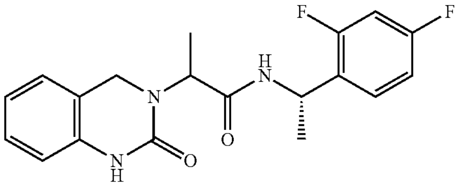 [SMILES: CC(C(=O)N[C@@H](C)c1ccc(F)cc1F)N1Cc2ccccc2NC1=O] |
| B244 | 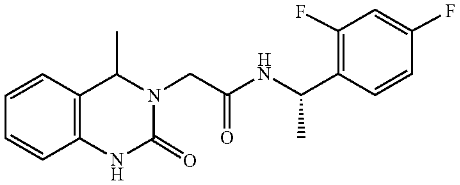 [SMILES: CC1c2ccccc2NC(=O)N1CC(=O)N[C@@H](C)c1ccc(F)cc1F] |
| B245 | 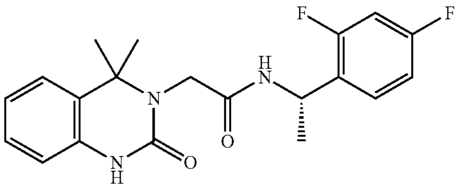 [SMILES: C[C@H](NC(=O)CN1C(=O)Nc2ccccc2C1(C)C)c1ccc(F)cc1F] |

TABLE 4-continued
| Comp. No. | Chemical Structure |
|---|---|
| B246 | 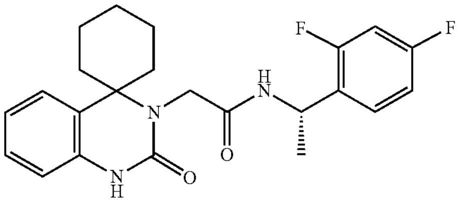 [SMILES: C[C@H](NC(=O)CN1C(=O)Nc2ccccc2C12CCCCC2)c1ccc(F)cc1F] |
| B247 | 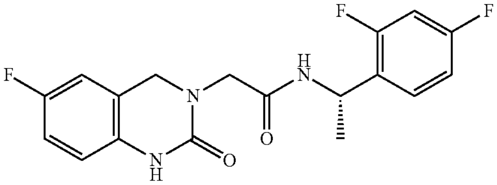 [SMILES: C[C@H](NC(=O)CN1Cc2cc(F)ccc2NC1=O)c1ccc(F)cc1F] |
| B248 | 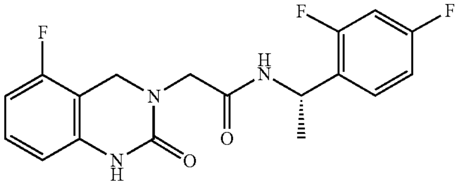 [SMILES: C[C@H](NC(=O)CN1Cc2c(F)cccc2NC1=O)c1ccc(F)cc1F] |
| B249 | 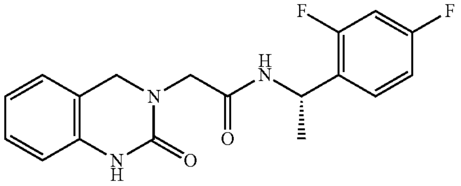 [SMILES: C[C@H](NC(=O)CN1Cc2ccccc2NC1=O)c1ccc(F)cc1F] |
| B250 | 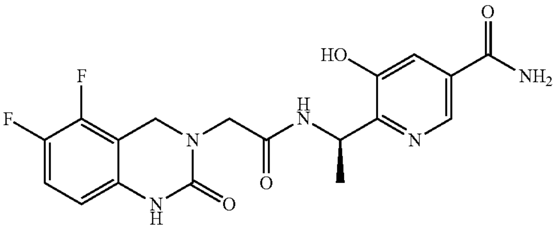 [SMILES: C[C@@H](NC(=O)CN1Cc2c(ccc(F)c2F)NC1=O)c1ncc(C(N)=O)cc1O] |
| B251 | 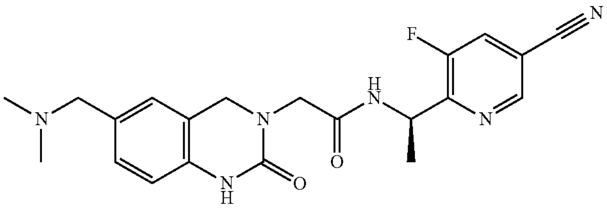 [SMILES: C[C@@H](NC(=O)CN1Cc2cc(CN(C)C)ccc2NC1=O)c1ncc(C#N)cc1F] |
| B252 | 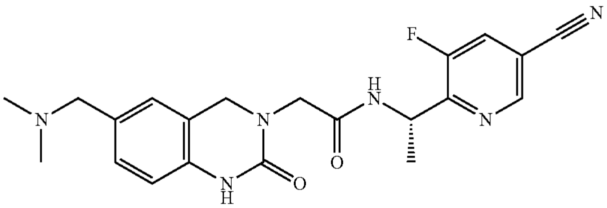 [SMILES: C[C@H](NC(=O)CN1Cc2cc(CN(C)C)ccc2NC1=O)c1ncc(C#N)cc1F] |

TABLE 4-continued
| Comp. No. | Chemical Structure |
|---|---|
| B253 | 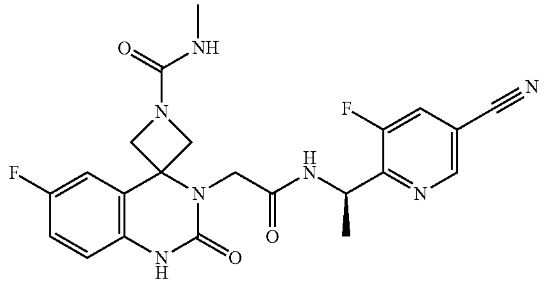 [SMILES: CNC(=O)N1CC2(C1)c1cc(F)ccc1NC(=O)N2CC(=O)N[C@H](C)c1ncc(C#N)cc1F] |
| B254 | 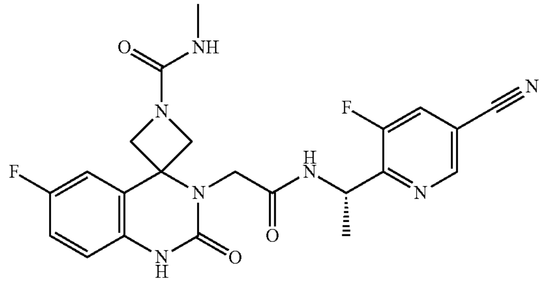 [SMILES: CNC(=O)N1CC2(C1)c1cc(F)ccc1NC(=O)N2CC(=O)N[C@@H](C)c1ncc(C#N)cc1F] |
| B255 | 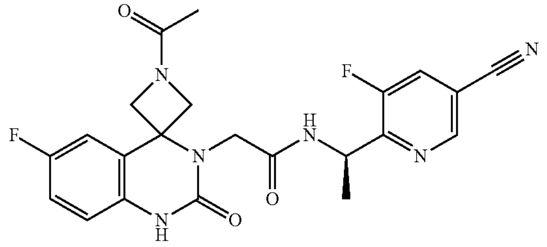 [SMILES: CC(=O)N1CC2(C1)c1cc(F)ccc1NC(=O)N2CC(=O)N[C@H](C)c1ncc(C#N)cc1F] |
| B256 | 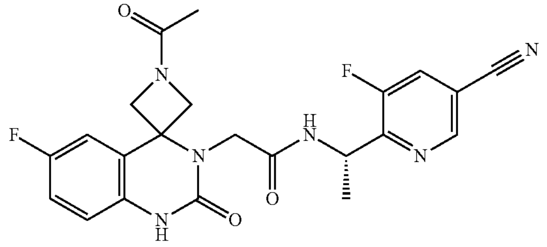 [SMILES: CC(=O)N1CC2(C1)c1cc(F)ccc1NC(=O)N2CC(=O)N[C@@H](C)c1ncc(C#N)cc1F] |
| B257 | 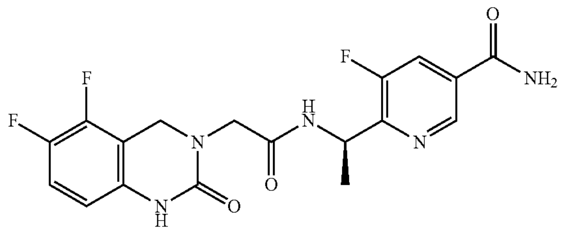 [SMILES: C[C@@H](NC(=O)CN1Cc2c(ccc(F)c2F)NC1=O)c1ncc(C(N)=O)cc1F] |
| B258 | 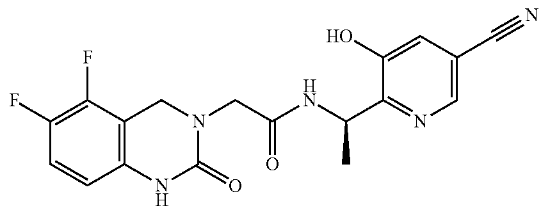 [SMILES: C[C@@H](NC(=O)CN1Cc2c(ccc(F)c2F)NC1=O)c1ncc(C#N)cc1O] |

TABLE 4-continued
| Comp. No. | Chemical Structure |
|---|---|
| B259 | 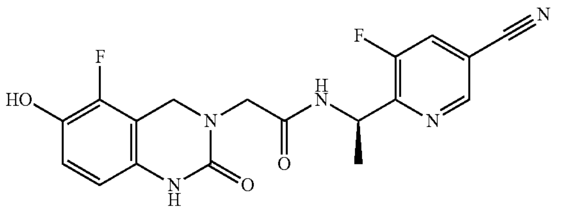 [SMILES: C[C@@H](NC(=O)CN1Cc2c(ccc(O)c2F)NC1=O)c1ncc(C#N)cc1F] |
| B262 | 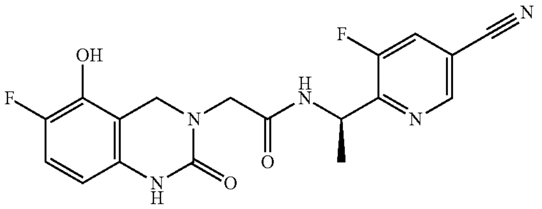 [SMILES: C[C@@H](NC(=O)CN1Cc2c(ccc(F)c2O)NC1=O)c1ncc(C#N)cc1F] |
| B263 | 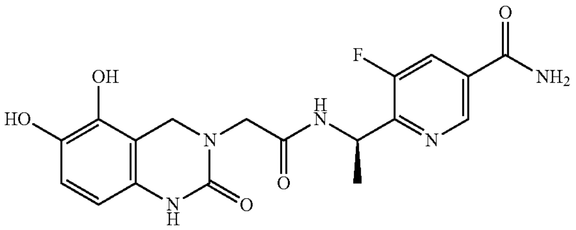 [SMILES: C[C@@H](NC(=O)CN1Cc2c(ccc(O)c2O)NC1=O)c1ncc(C(N)=O)cc1F] |
| B264 | 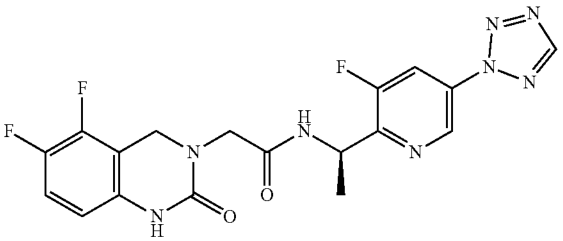 [SMILES: C[C@@H](NC(=O)CN1Cc2c(ccc(F)c2F)NC1=O)c1ncc(-n2ncnn2)cc1F] |
| B265 | 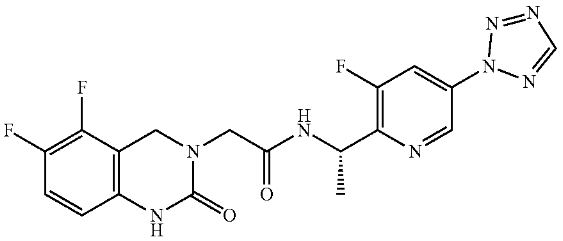 [SMILES: C[C@H](NC(=O)CN1Cc2c(ccc(F)c2F)NC1=O)c1ncc(-n2ncnn2)cc1F] |
| B266 | 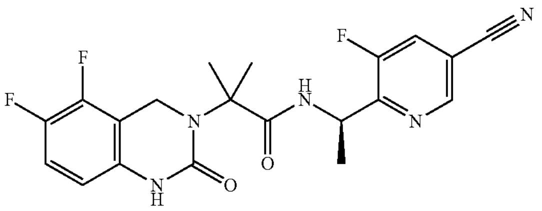 [SMILES: C[C@@H](NC(=O)C(C)(C)N1Cc2c(ccc(F)c2F)NC1=O)c1ncc(C#N)cc1F] |

TABLE 4-continued
| Comp. No. | Chemical Structure |
|---|---|
| B267 | 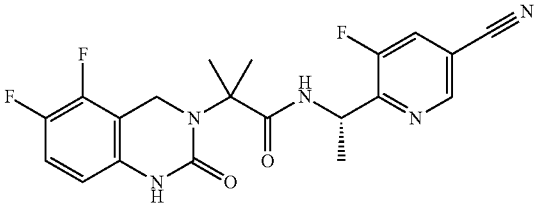 [SMILES: C[C@H](NC(=O)C(C)(C)N1Cc2c(ccc(F)c2F)NC1=O)c1ncc(C#N)cc1F] |
| B268 | 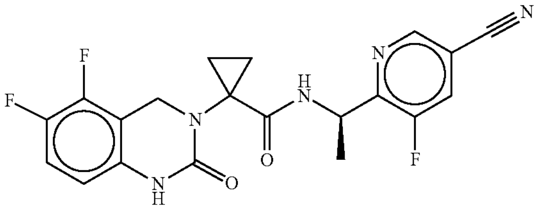 |
| B269 | 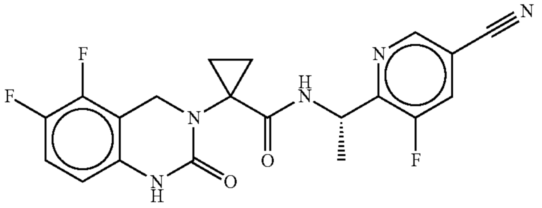 |
| B270 | 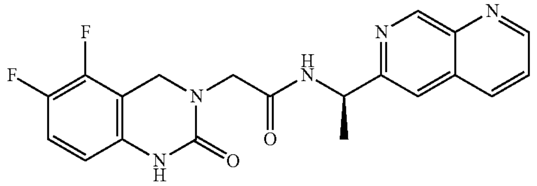 [SMILES: C[C@@H](NC(=O)CN1Cc2c(ccc(F)c2F)NC1=O)c1cc2cccnc2cn1] |
| B271 | 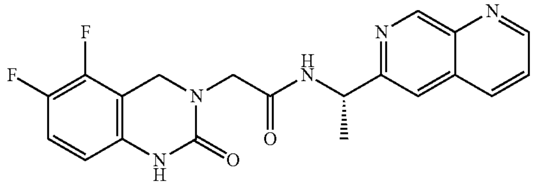 [SMILES: C[C@H](NC(=O)CN1Cc2c(ccc(F)c2F)NC1=O)c1cc2cccnc2cn1] |
| B272 | 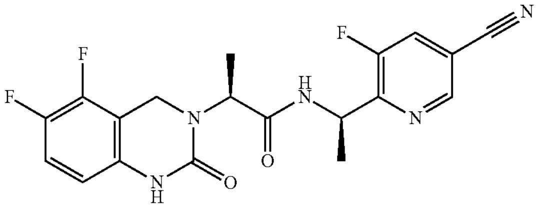 [SMILES: C[C@@H](NC(=O)[C@H](C)N1Cc2c(ccc(F)c2F)NC1=O)c1ncc(C#N)cc1F] |
| B273 | 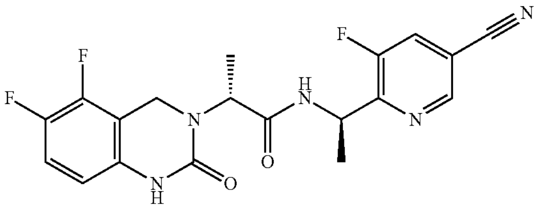 [SMILES: C[C@H](C(=O)N[C@H](C)c1ncc(C#N)cc1F)N1Cc2c(ccc(F)c2F)NC1=O] |

TABLE 4-continued
| Comp. No. | Chemical Structure |
|---|---|
| B274 | 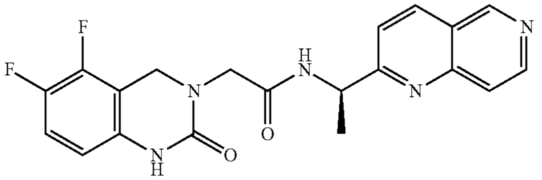 [SMILES: C[C@@H](NC(=O)CN1Cc2c(ccc(F)c2F)NC1=O)c1ccc2cnccc2n1] |
| B275 | 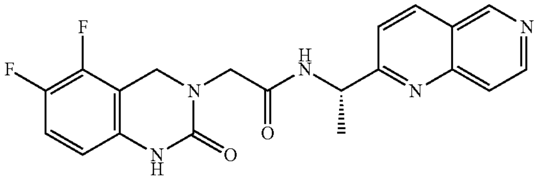 [SMILES: C[C@H](NC(=O)CN1Cc2c(ccc(F)c2F)NC1=O)c1ccc2cnccc2n1] |
| B276 | 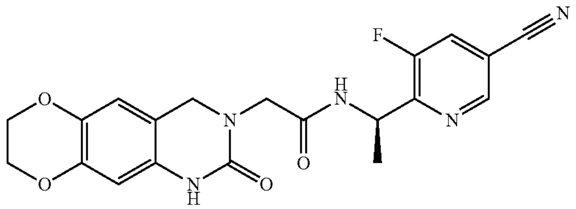 [SMILES: C[C@@H](NC(=O)CN1Cc2cc3c(cc2NC1=O)OCCO3)c1ncc(C#N)cc1F] |
| B277 | 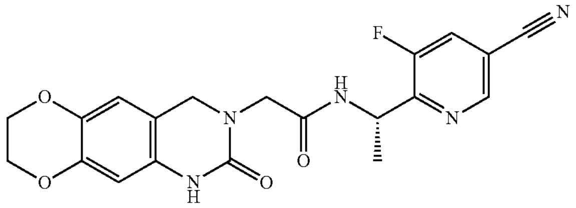 [SMILES: C[C@H](NC(=O)CN1Cc2cc3c(cc2NC1=O)OCCO3)c1ncc(C#N)cc1F] |
| B278 | 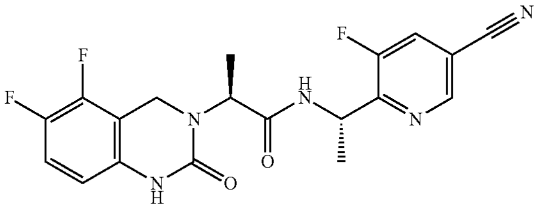 [SMILES: C[C@H](NC(=O)[C@H](C)N1Cc2c(ccc(F)c2F)NC1=O)c1ncc(C#N)cc1F] |
| B279 | 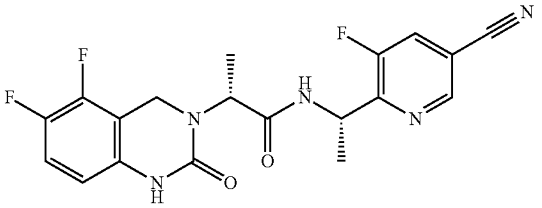 [SMILES: C[C@H](NC(=O)[C@@H](C)N1Cc2c(ccc(F)c2F)NC1=O)c1ncc(C#N)cc1F] |
| B280 | 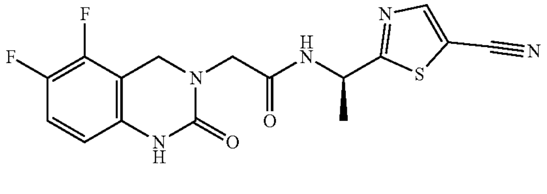 |

TABLE 4-continued
| Comp. No. | Chemical Structure |
|---|---|
| B281 | 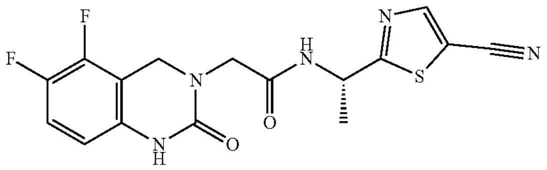 [SMILES: C[C@H](NC(=O)CN1Cc2c(ccc(F)c2F)NC1=O)c1ncc(C#N)s1] |
| B282 | 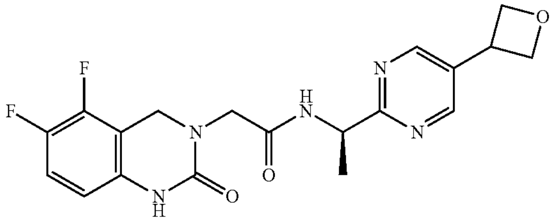 [SMILES: C[C@@H](NC(=O)CN1Cc2c(ccc(F)c2F)NC1=O)c1ncc(C2COC2)cn1] |
| B283 | 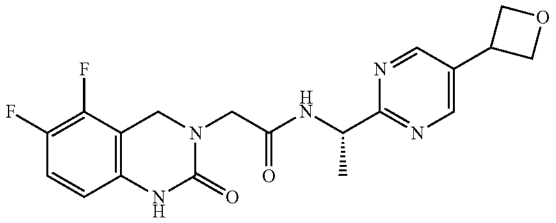 [SMILES: C[C@H](NC(=O)CN1Cc2c(ccc(F)c2F)NC1=O)c1ncc(C2COC2)cn1] |
| B284 | 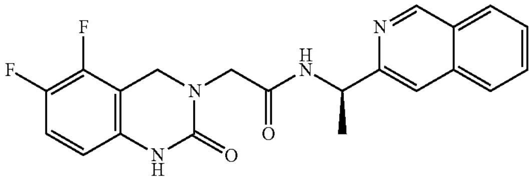 [SMILES: C[C@@H](NC(=O)CN1Cc2c(ccc(F)c2F)NC1=O)c1cc2ccccc2cn1] |
| B285 | 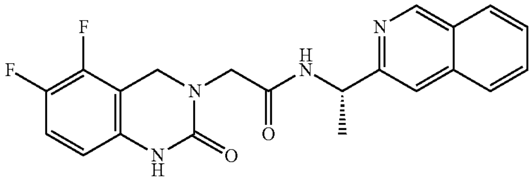 [SMILES: C[C@H](NC(=O)CN1Cc2c(ccc(F)c2F)NC1=O)c1cc2ccccc2cn1] |
| B286 | 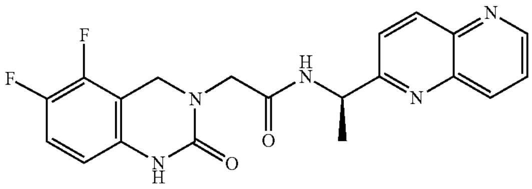 [SMILES: C[C@@H](NC(=O)CN1Cc2c(ccc(F)c2F)NC1=O)c1ccc2ncccc2n1] |
| B287 | 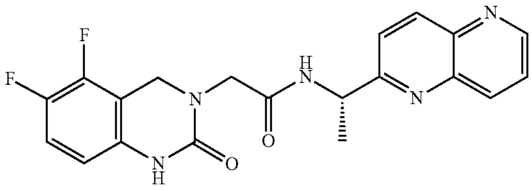 [SMILES: C[C@H](NC(=O)CN1Cc2c(ccc(F)c2F)NC1=O)c1ccc2ncccc2n1] |

TABLE 4-continued
| Comp. No. | Chemical Structure |
|---|---|
| B288 | 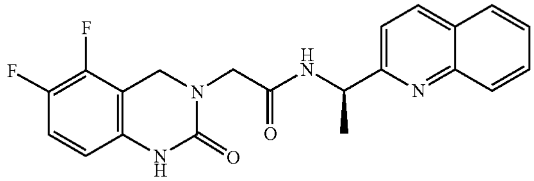 [SMILES: C[C@@H](NC(=O)CN1Cc2c(ccc(F)c2F)NC1=O)c1ccc2ccccc2n1] |
| B289 | 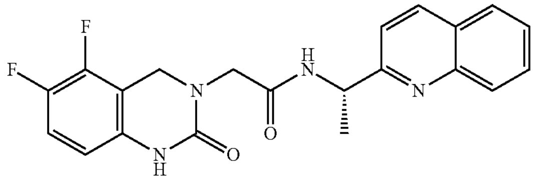 [SMILES: C[C@H](NC(=O)CN1Cc2c(ccc(F)c2F)NC1=O)c1ccc2ccccc2n1] |
| B290 | 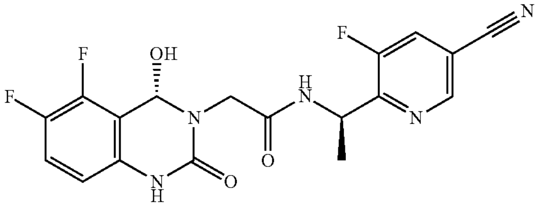 |
| B291 | 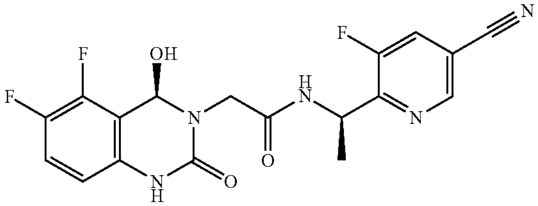 [SMILES: C[C@@H](NC(=O)CN1C(=O)Nc2ccc(F)c(F)c2[C@H]1O)c1ncc(C#N)cc1F] |
| B292 | 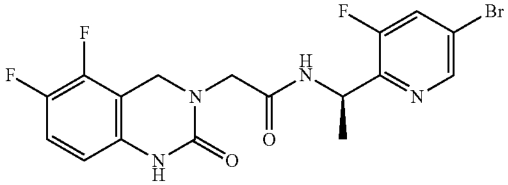 [SMILES: C[C@@H](NC(=O)CN1Cc2c(ccc(F)c2F)NC1=O)c1ncc(Br)cc1F] |
| B293 | 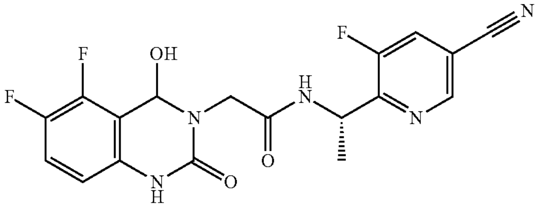 [SMILES: C[C@H](NC(=O)CN1C(=O)Nc2ccc(F)c(F)c2C1O)c1ncc(C#N)cc1F] |
| B294 | 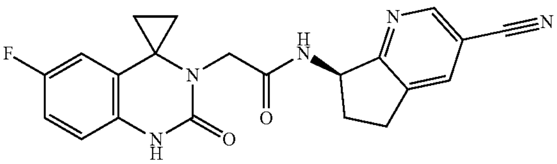 [SMILES: N#Cc1cnc2c(c1)CC[C@H]2NC(=O)CN1C(=O)Nc2ccc(F)cc2C12CC2] |
| B295 | 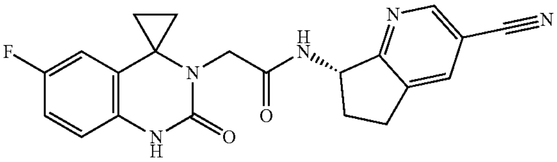 [SMILES: N#Cc1cnc2c(c1)CC[C@@H]2NC(=O)CN1C(=O)Nc2ccc(F)cc2C12CC2] |

TABLE 4-continued
| Comp. No. | Chemical Structure |
|---|---|
| B296 | 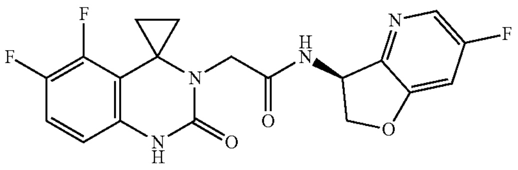 [SMILES: O=C(CN1C(=O)Nc2ccc(F)c(F)c2C12CC2)N[C@@H]1COc2cc(F)cnc21] |
| B297 | 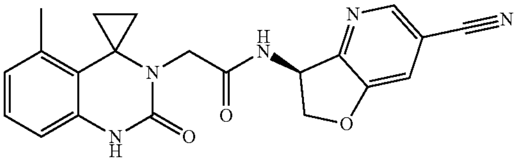 |
| B299 | 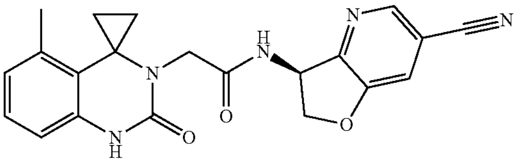 [SMILES: Cc1cccc2c1C1(CC1)N(CC(=O)N[C@@H]1COc3cc(C#N)cnc31)C(=O)N2] |
| B300 | 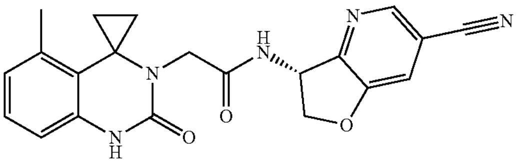 |
| B301 | 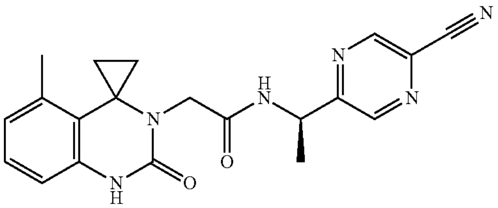 [SMILES: Cc1cccc2c1C1(CC1)N(CC(=O)N[C@H](C)c1cnc(C#N)cn1)C(=O)N2] |
| B302 | 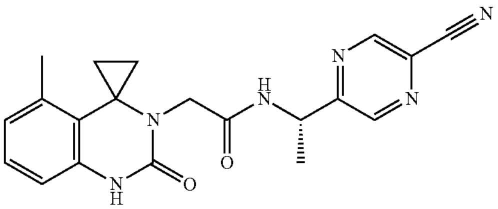 [SMILES: Cc1cccc2c1C1(CC1)N(CC(=O)N[C@@H](C)c1cnc(C#N)cn1)C(=O)N2] |
| B303 | 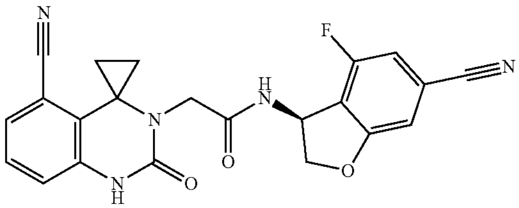 |
| B304 | 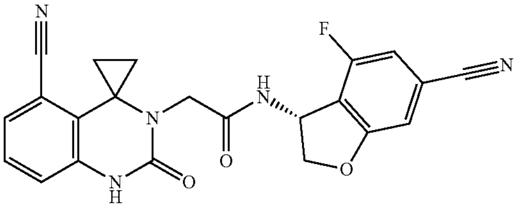 [SMILES: N#Cc1cc(F)c2c(c1)OC[C@@H]2NC(=O)CN1C(=O)Nc2cccc(C#N)c2C12CC2] |

TABLE 4-continued
| Comp. No. | Chemical Structure |
|---|---|
| B306 | 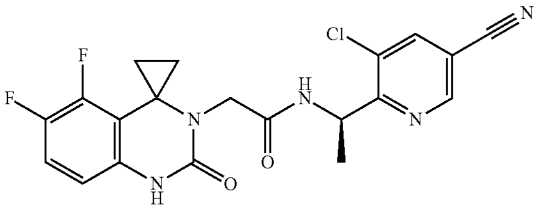 [SMILES: C[C@@H](NC(=O)CN1C(=O)Nc2ccc(F)c(F)c2C12CC2)c1ncc(C#N)cc1Cl] |
| B307 | 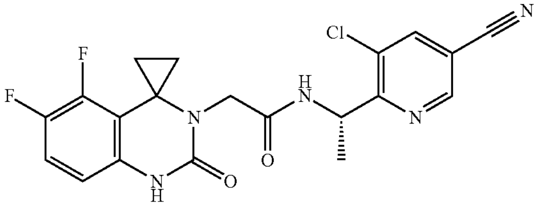 [SMILES: C[C@H](NC(=O)CN1C(=O)Nc2ccc(F)c(F)c2C12CC2)c1ncc(C#N)cc1Cl] |
| B308 | 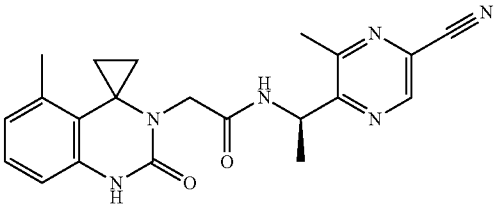 [SMILES: Cc1cccc2c1C1(CC1)N(CC(=O)N[C@H](C)c1ncc(C#N)nc1C)C(=O)N2] |
| B309 | 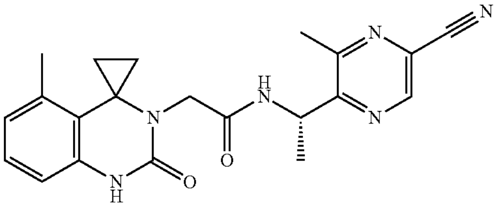 [SMILES: Cc1cccc2c1C1(CC1)N(CC(=O)N[C@@H](C)c1ncc(C#N)nc1C)C(=O)N2] |
| B310 | 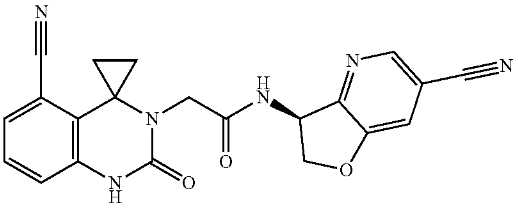 [SMILES: N#Cc1cnc2c(c1)OC[C@H]2NC(=O)CN1C(=O)Nc2cccc(C#N)c2C12CC2] |
| B311 | 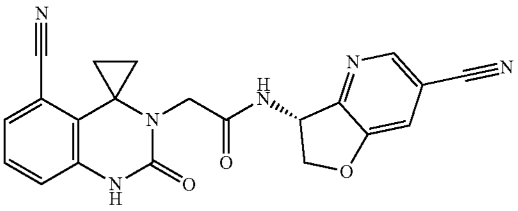 [SMILES: N#Cc1cnc2c(c1)OC[C@@H]2NC(=O)CN1C(=O)Nc2cccc(C#N)c2C12CC2] |
| B312 | 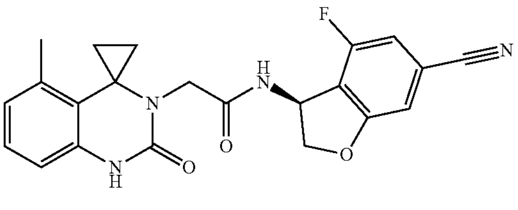 [SMILES: Cc1cccc2c1C1(CC1)N(CC(=O)N[C@@H]1COc3cc(C#N)cc(F)c31)C(=O)N2] |

TABLE 4-continued
| Comp. No. | Chemical Structure |
|---|---|
| B313 | 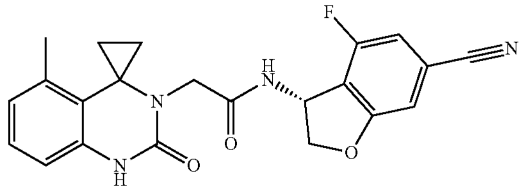 [SMILES: Cc1cccc2c1C1(CC1)N(CC(=O)N[C@H]1COc3cc(C#N)cc(F)c31)C(=O)N2] |
| B314 | 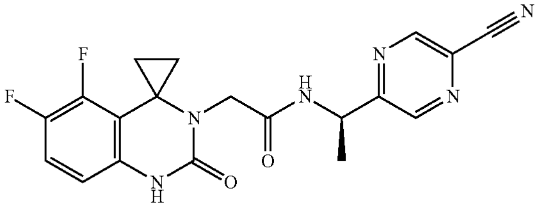 [SMILES: C[C@@H](NC(=O)CN1C(=O)Nc2ccc(F)c(F)c2C12CC2)c1cnc(C#N)cn1] |
| B315 | 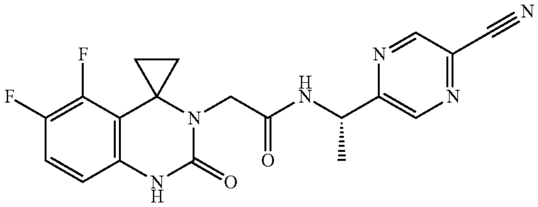 [SMILES: C[C@H](NC(=O)CN1C(=O)Nc2ccc(F)c(F)c2C12CC2)c1cnc(C#N)cn1] |
| B319 | 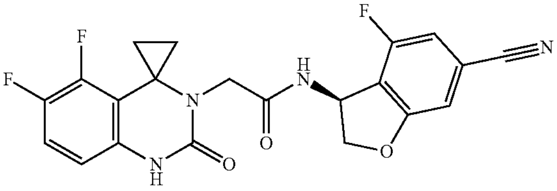 [SMILES: N#Cc1cc(F)c2c(c1)OC[C@H]2NC(=O)CN1C(=O)Nc2ccc(F)c(F)c2C12CC2] |
| B320 | 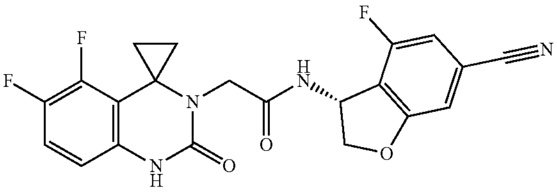 [SMILES: N#Cc1cc(F)c2c(c1)OC[C@@H]2NC(=O)CN1C(=O)Nc2ccc(F)c(F)c2C12CC2] |
| B321 | 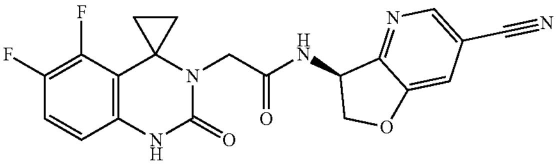 [SMILES: N#Cc1cnc2c(c1)OC[C@H]2NC(=O)CN1C(=O)Nc2ccc(F)c(F)c2C12CC2] |
| B322 | 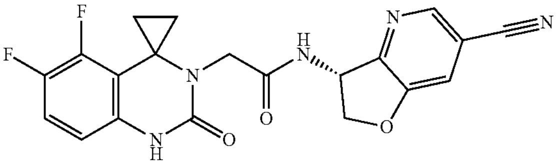 [SMILES: N#Cc1cnc2c(c1)OC[C@@H]2NC(=O)CN1C(=O)Nc2ccc(F)c(F)c2C12CC2] |

TABLE 4-continued
| Comp. No. | Chemical Structure |
|---|---|
| B323 | 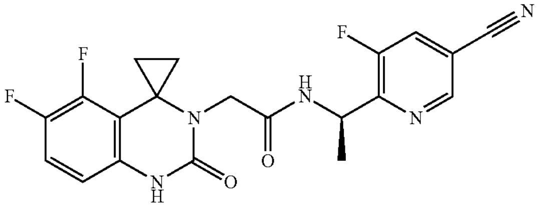 [SMILES: C[C@@H](NC(=O)CN1C(=O)Nc2ccc(F)c(F)c2C12CC2)c1ncc(C#N)cc1F] |
| B324 | 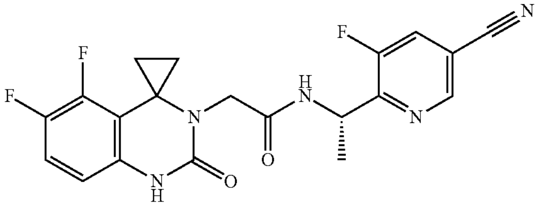 [SMILES: C[C@H](NC(=O)CN1C(=O)Nc2ccc(F)c(F)c2C12CC2)c1ncc(C#N)cc1F] |
| B325 | 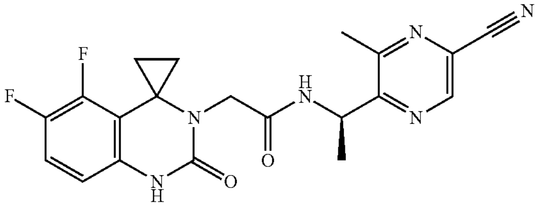 [SMILES: Cc1nc(C#N)cnc1[C@@H](C)NC(=O)CN1C(=O)Nc2ccc(F)c(F)c2C12CC2] |
| B326 | 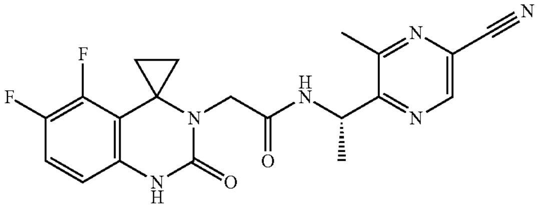 [SMILES: Cc1nc(C#N)cnc1[C@H](C)NC(=O)CN1C(=O)Nc2ccc(F)c(F)c2C12CC2] |
| B327 | 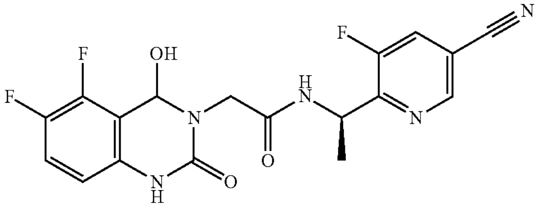 [SMILES: C[C@@H](NC(=O)CN1C(=O)Nc2ccc(F)c(F)c2C1O)c1ncc(C#N)cc1F] |
| B328 | 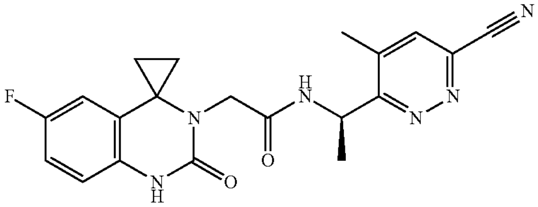 [SMILES: Cc1cc(C#N)nnc1[C@@H](C)NC(=O)CN1C(=O)Nc2ccc(F)cc2C12CC2] |
| B329 | 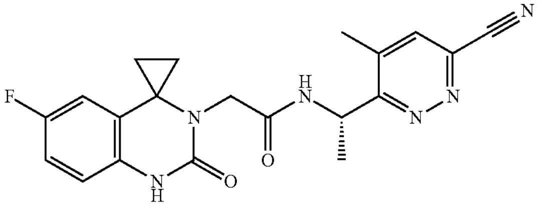 [SMILES: Cc1cc(C#N)nnc1[C@H](C)NC(=O)CN1C(=O)Nc2ccc(F)cc2C12CC2] |

TABLE 4-continued
| Comp. No. | Chemical Structure |
|---|---|
| B330 | 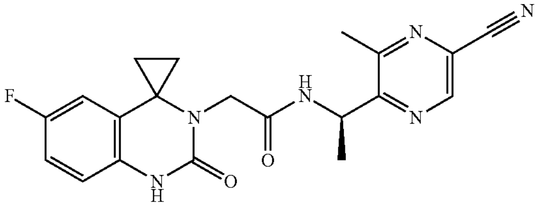 [SMILES: Cc1nc(C#N)cnc1[C@@H](C)NC(=O)CN1C(=O)Nc2ccc(F)cc2C12CC2] |
| B331 | 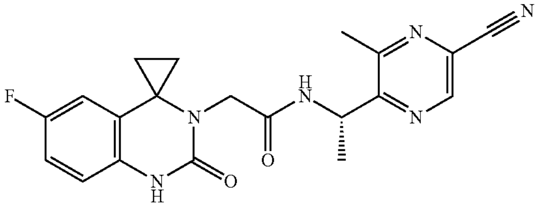 [SMILES: Cc1nc(C#N)cnc1[C@H](C)NC(=O)CN1C(=O)Nc2ccc(F)cc2C12CC2] |
| B332 | 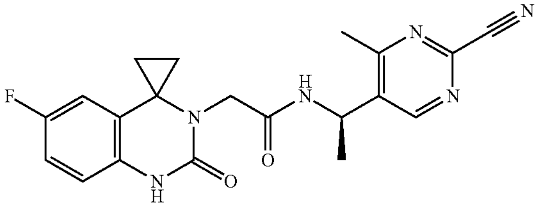 [SMILES: Cc1nc(C#N)ncc1[C@@H](C)NC(=O)CN1C(=O)Nc2ccc(F)cc2C12CC2] |
| B333 | 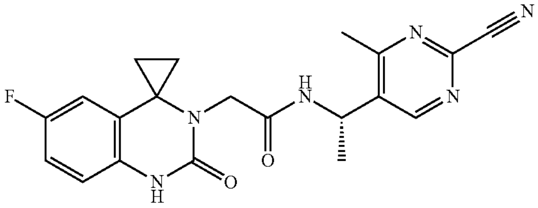 [SMILES: Cc1nc(C#N)ncc1[C@H](C)NC(=O)CN1C(=O)Nc2ccc(F)cc2C12CC2] |
| B334 | 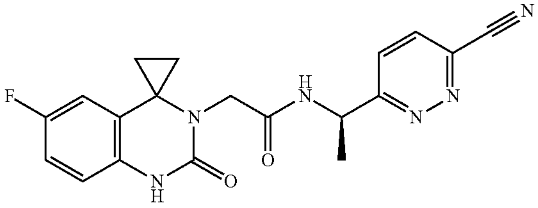 |
| B335 | 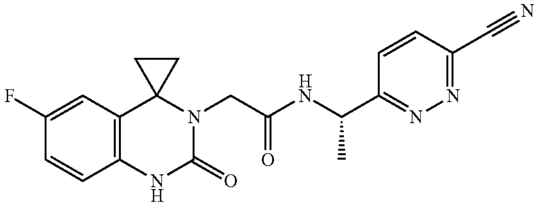 [SMILES: C[C@H](NC(=O)CN1C(=O)Nc2ccc(F)cc2C12CC2)c1ccc(C#N)nn1] |
| B336 | 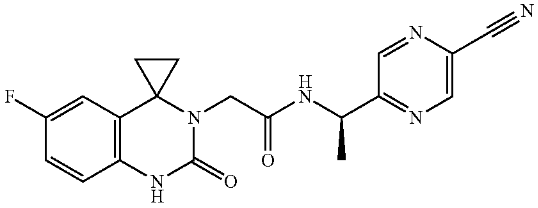 |

TABLE 4-continued
| Comp. No. | Chemical Structure |
|---|---|
| B337 | 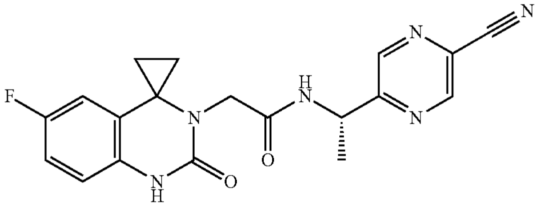 [SMILES: C[C@H](NC(=O)CN1C(=O)Nc2ccc(F)cc2C12CC2)c1cnc(C#N)cn1] |
| B338 | 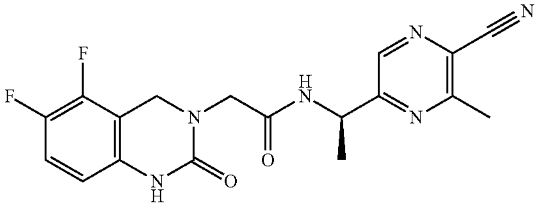 [SMILES: Cc1nc([C@@H](C)NC(=O)CN2Cc3c(ccc(F)c3F)NC2=O)cnc1C#N] |
| B339 | 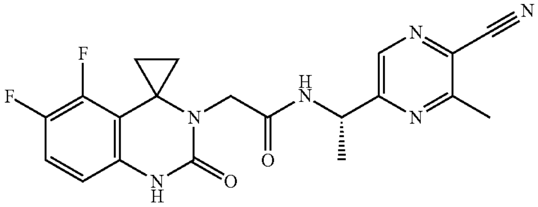 [SMILES: Cc1nc([C@H](C)NC(=O)CN2C(=O)Nc3ccc(F)c(F)c3C23CC3)cnc1C#N] |
| B340 | 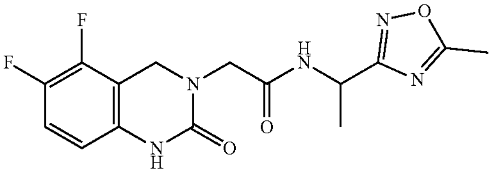 [SMILES: Cc1nc(C(C)NC(=O)CN2Cc3c(ccc(F)c3F)NC2=O)no1] |
| B341 | 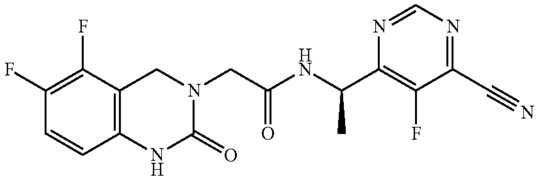 [SMILES: C[C@@H](NC(=O)CN1Cc2c(ccc(F)c2F)NC1=O)c1ncnc(C#N)c1F] |
| B342 | 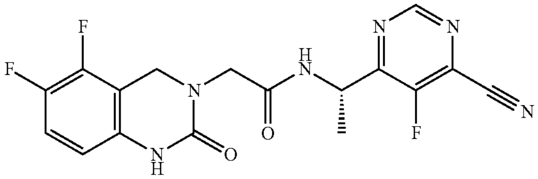 [SMILES: C[C@H](NC(=O)CN1Cc2c(ccc(F)c2F)NC1=O)c1ncnc(C#N)c1F] |
| B343 | 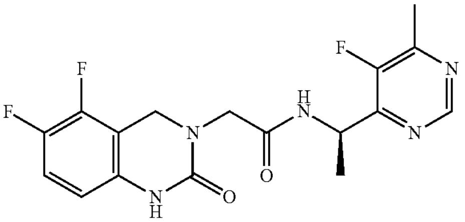 [SMILES: Cc1ncnc([C@@H](C)NC(=O)CN2Cc3c(ccc(F)c3F)NC2=O)c1F] |

TABLE 4-continued
| Comp. No. | Chemical Structure |
|---|---|
| B344 | 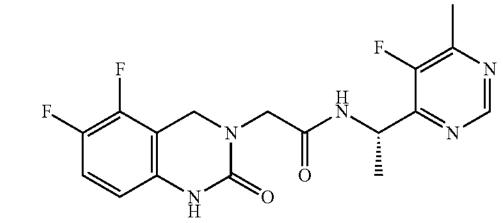 [SMILES: Cc1ncnc([C@H](C)NC(=O)CN2Cc3c(ccc(F)c3F)NC2=O)c1F] |
| B345 | 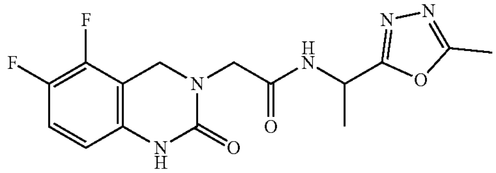 [SMILES: Cc1nnc(C(C)NC(=O)CN2Cc3c(ccc(F)c3F)NC2=O)o1] |
| B346 | 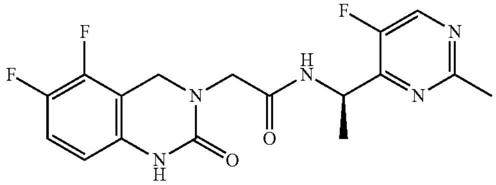 [SMILES: Cc1ncc(F)c([C@@H](C)NC(=O)CN2Cc3c(ccc(F)c3F)NC2=O)n1] |
| B347 | 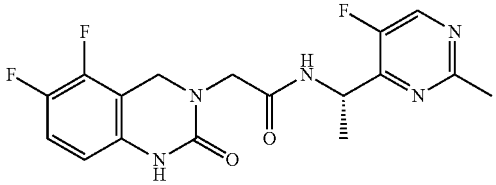 [SMILES: Cc1ncc(F)c([C@H](C)NC(=O)CN2Cc3c(ccc(F)c3F)NC2=O)n1] |
| B348 | 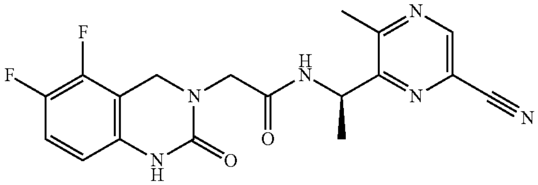 [SMILES: Cc1ncc(C#N)nc1[C@@H](C)NC(=O)CN1Cc2c(ccc(F)c2F)NC1=O] |
| B349 | 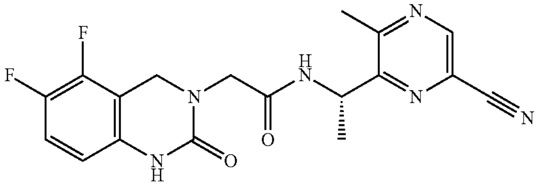 [SMILES: Cc1ncc(C#N)nc1[C@H](C)NC(=O)CN1Cc2c(ccc(F)c2F)NC1=O] |
| B350 | 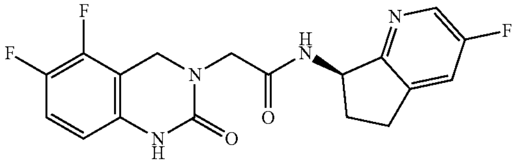 |
| B351 | 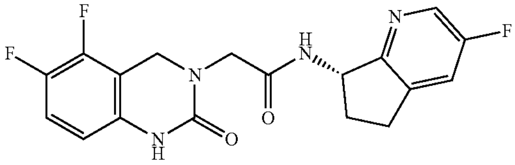 [SMILES: O=C(CN1Cc2c(ccc(F)c2F)NC1=O)N[C@H]1CCc2cc(F)cnc21] |

TABLE 4-continued
| Comp. No. | Chemical Structure |
|---|---|
| B352 | 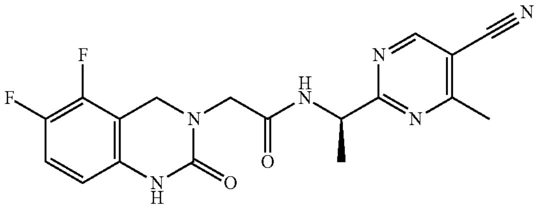 [SMILES: Cc1nc([C@@H](C)NC(=O)CN2Cc3c(ccc(F)c3F)NC2=O)ncc1C#N] |
| B353 | 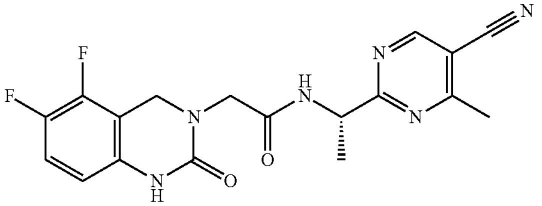 [SMILES: Cc1nc([C@H](C)NC(=O)CN2Cc3c(ccc(F)c3F)NC2=O)ncc1C#N] |
| B354 | 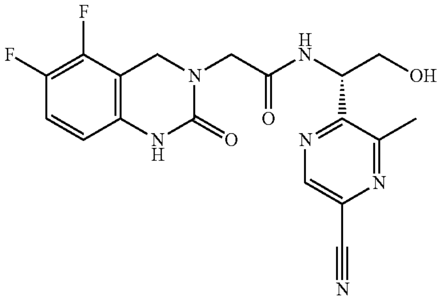 [SMILES: Cc1nc(C#N)cnc1[C@@H](CO)NC(=O)CN1Cc2c(ccc(F)c2F)NC1=O] |
| B355 | 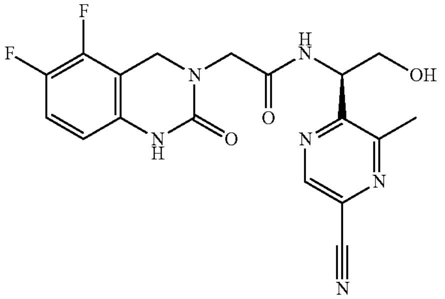 [SMILES: Cc1nc(C#N)cnc1[C@H](CO)NC(=O)CN1Cc2c(ccc(F)c2F)NC1=O] |
| B356 | 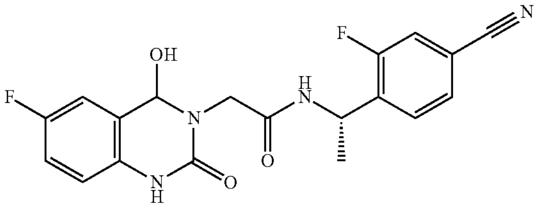 [SMILES: C[C@H](NC(=O)CN1C(=O)Nc2ccc(F)cc2C1O)c1ccc(C#N)cc1F] |
| B357 | 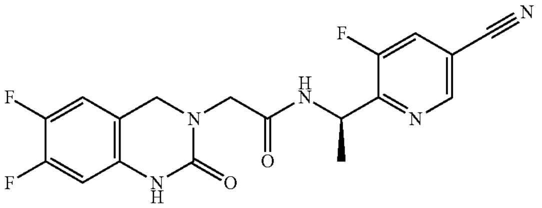 [SMILES: C[C@@H](NC(=O)CN1Cc2cc(F)c(F)cc2NC1=O)c1ncc(C#N)cc1F] |

TABLE 4-continued
| Comp. No. | Chemical Structure |
|---|---|
| B358 | 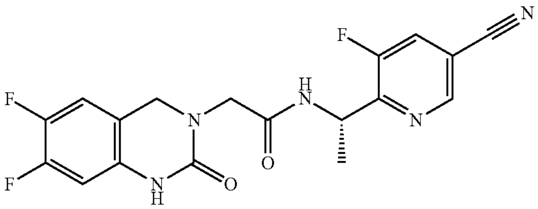 [SMILES: C[C@H](NC(=O)CN1Cc2cc(F)c(F)cc2NC1=O)c1ncc(C#N)cc1F] |
| B359 | 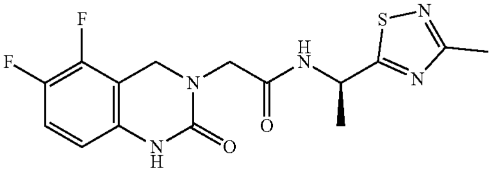 [SMILES: Cc1nsc([C@@H](C)NC(=O)CN2Cc3c(ccc(F)c3F)NC2=O)n1] |
| B360 | 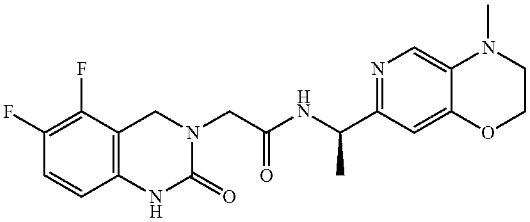 [SMILES: C[C@@H](NC(=O)CN1Cc2c(ccc(F)c2F)NC1=O)c1cc2c(cn1)N(C)CCO2] |
| B361 | 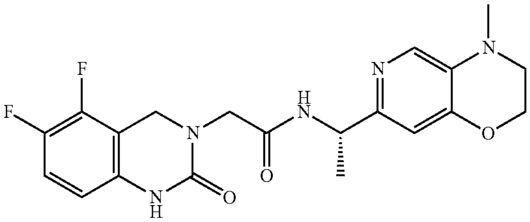 [SMILES: C[C@H](NC(=O)CN1Cc2c(ccc(F)c2F)NC1=O)c1cc2c(cn1)N(C)CCO2] |
| B362 | 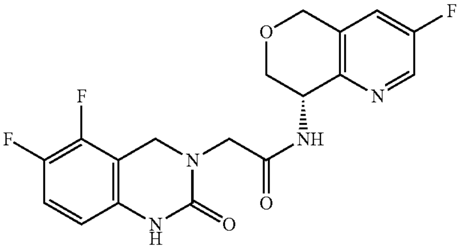 [SMILES: O=C(CN1Cc2c(ccc(F)c2F)NC1=O)N[C@@H]1COCc2cc(F)cnc21] |
| B363 | 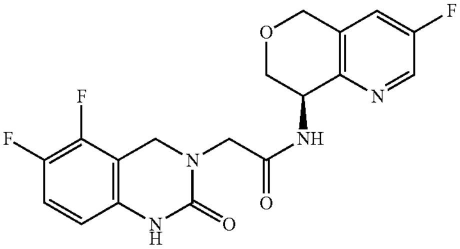 [SMILES: O=C(CN1Cc2c(ccc(F)c2F)NC1=O)N[C@H]1COCc2cc(F)cnc21] |
| B364 | 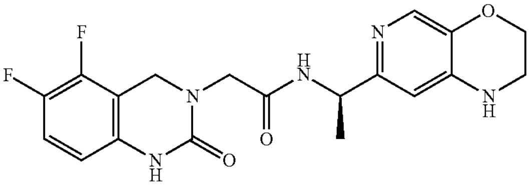 [SMILES: C[C@@H](NC(=O)CN1Cc2c(ccc(F)c2F)NC1=O)c1cc2c(cn1)OCCN2] |

TABLE 4-continued
| Comp. No. | Chemical Structure |
|---|---|
| B365 | 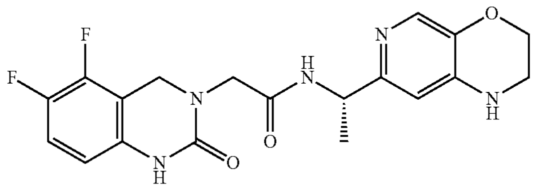 [SMILES: C[C@H](NC(=O)CN1Cc2c(ccc(F)c2F)NC1=O)c1cc2c(cn1)OCCN2] |
| B366 | 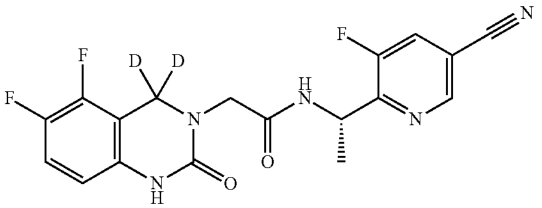 [SMILES: [2H]C1([2H])c2c(ccc(F)c2F)NC(=O)N1CC(=O)N[C@@H](C)c1ncc(C#N)cc1F] |
| B367 | 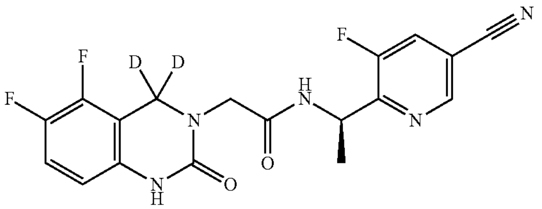 [SMILES: [2H]C1([2H])c2c(ccc(F)c2F)NC(=O)N1CC(=O)N[C@H](C)c1ncc(C#N)cc1F] |
| B368 | 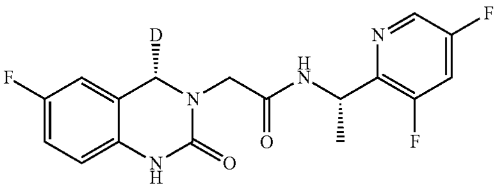 [SMILES: [2H][C@H]1c2cc(F)ccc2NC(=O)N1CC(=O)N[C@@H](C)c1ncc(F)cc1F] |
| B369 | 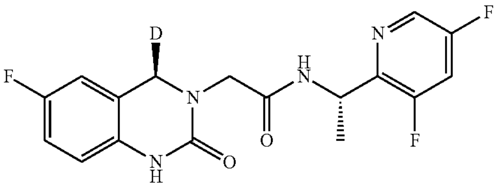 [SMILES: [2H][C@@H]1c2cc(F)ccc2NC(=O)N1CC(=O)N[C@@H](C)c1ncc(F)cc1F] |
| B370 | 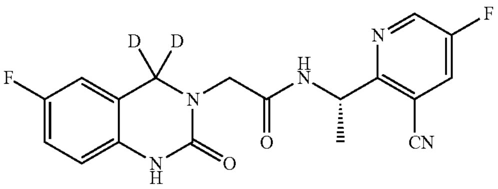 [SMILES: [2H]C1([2H])c2cc(F)ccc2NC(=O)N1CC(=O)N[C@@H](C)c1ncc(F)cc1C#N] |
| B371 | 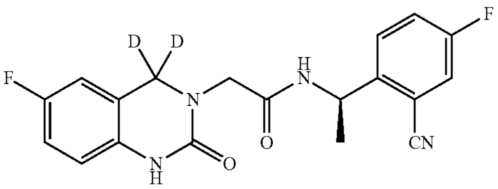 [SMILES: [2H]C1([2H])c2cc(F)ccc2NC(=O)N1CC(=O)N[C@H](C)c1ccc(F)cc1C#N] |

TABLE 4-continued
| Comp. No. | Chemical Structure |
|---|---|
| B372 | 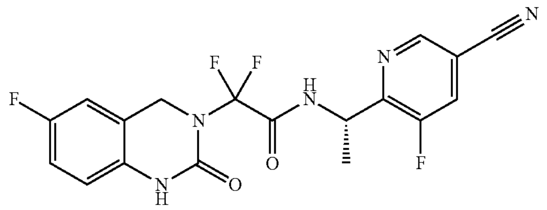 [SMILES: C[C@H](NC(=O)C(F)(F)N1Cc2cc(F)ccc2NC1=O)c1ncc(C#N)cc1F] |
| B373 | 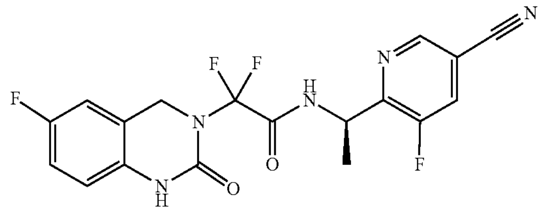 [SMILES: C[C@@H](NC(=O)C(F)(F)N1Cc2cc(F)ccc2NC1=O)c1ncc(C#N)cc1F] |
| B374 | 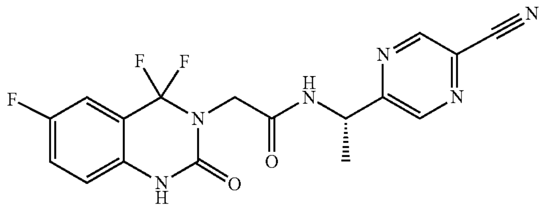 [SMILES: C[C@H](NC(=O)CN1C(=O)Nc2ccc(F)cc2C1(F)F)c1cnc(C#N)cn1] |
| B375 | 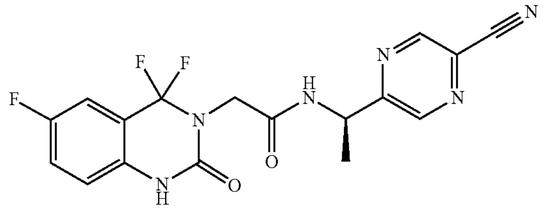 [SMILES: C[C@@H](NC(=O)CN1C(=O)Nc2ccc(F)cc2C1(F)F)c1cnc(C#N)cn1] |
| B376 | 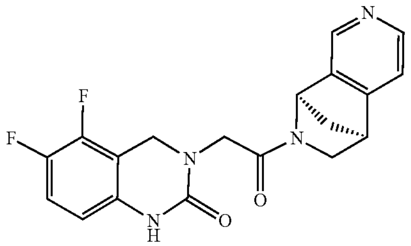 [SMILES: O=C1Nc2ccc(F)c(F)c2CN1CC(=O)N1C[C@H]2C[C@@H]1c1cnccc12] |
| B377 | 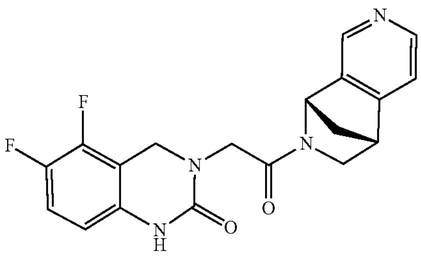 [SMILES: O=C1Nc2ccc(F)c(F)c2CN1CC(=O)N1C[C@@H]2C[C@H]1c1cnccc12] |

TABLE 4-continued
| Comp. No. | Chemical Structure |
|---|---|
| B378 | 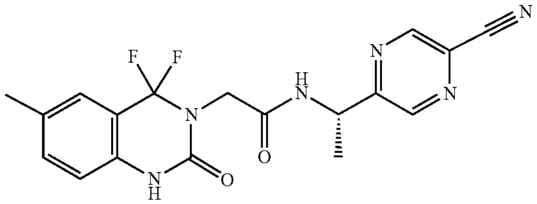 [SMILES: Cc1ccc2c(c1)C(F)(F)N(CC(=O)N[C@@H](C)c1cnc(C#N)cn1)C(=O)N2] |
| B379 | 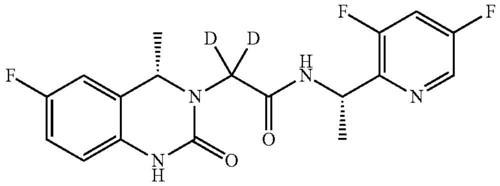 [SMILES: [2H]C([2H])(C(=O)N[C@@H](C)c1ncc(F)cc1F)N1C(=O)Nc2ccc(F)cc2[C@@H]1C] |
| B380 | 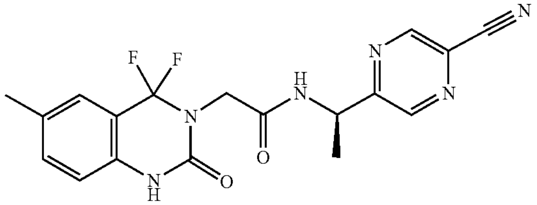 [SMILES: Cc1ccc2c(c1)C(F)(F)N(CC(=O)N[C@H](C)c1cnc(C#N)cn1)C(=O)N2] |
| B381 | 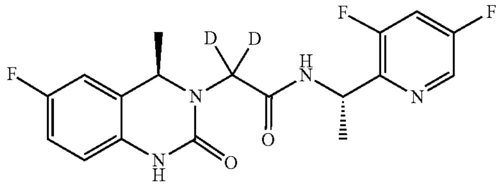 [SMILES: [2H]C([2H])(C(=O)N[C@@H](C)c1ncc(F)cc1F)N1C(=O)Nc2ccc(F)cc2[C@H]1C] |
| B375 | 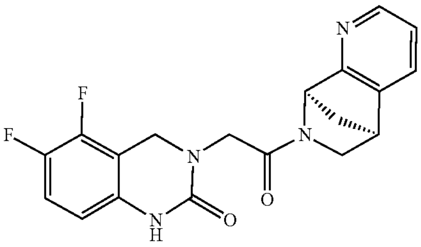 [SMILES: O=C1Nc2ccc(F)c(F)c2CN1CC(=O)N1C[C@H]2C[C@@H]1c1ncccc12] |
| B382 | 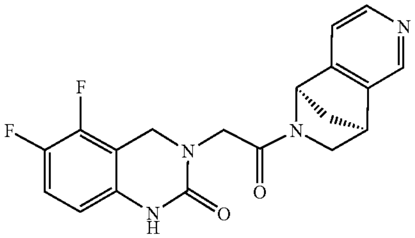 [SMILES: O=C1Nc2ccc(F)c(F)c2CN1CC(=O)N1C[C@H]2C[C@@H]1c1ccncc12] |
| B383 | 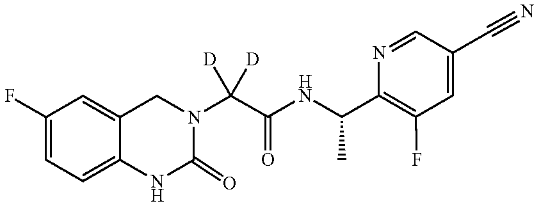 [SMILES: [2H]C([2H])(C(=O)N[C@@H](C)c1ncc(C#N)cc1F)N1Cc2cc(F)ccc2NC1=O] |

TABLE 4-continued
| Comp. No. | Chemical Structure |
|---|---|
| B384 | 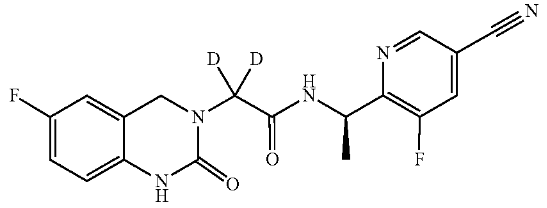 [SMILES: [2H]C([2H])(C(=O)N[C@H](C)c1ncc(C#N)cc1F)N1Cc2cc(F)ccc2NC1=O] |
| B385 | 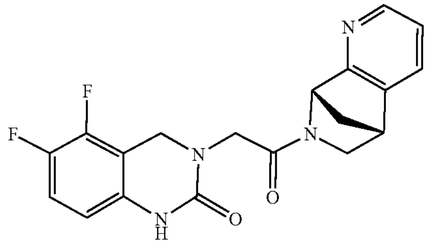 [SMILES: O=C1Nc2ccc(F)c(F)c2CN1CC(=O)N1C[C@@H]2C[C@H]1c1ncccc12] |
| B386 | 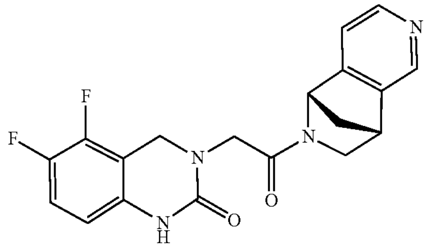 [SMILES: O=C1Nc2ccc(F)c(F)c2CN1CC(=O)N1C[C@@H]2C[C@H]1c1ccncc12] |
TABLE 5
| MS Characterization Data | |
|---|---|
| Comp. No. | MS |
| B1 | 387.05 |
| B2 | 387.05 |
| B3 | 368.1 |
| B4 | 400.15 |
| B5 | 400.15 |
| B6 | 379.05 |
| B7 | 379.05 |
| B8 | 386.1 |
| B9 | 386.1 |
| B10 | 396.15 |
| B11 | 396.1 |
| B12 | 385.1 |
| B13 | 385.05 |
| B14 | 393.1 |
| B15 | 393.1 |
| B16 | 373.2 |
| B17 | 368.4 |
| B18 | 444 |
| B19 | 444 |
| B20 | 407.15 |
| B21 | 407.15 |
| B22 | 387.1 |
| B23 | 387.1 |
| B24 | 362.1 |
| B25 | 362.1 |
| B26 | 396.1 |
| B27 | 396.1 |
| B28 | 389 |
| B29 | 389 |
| B30 | 385.1 |
| B31 | 385.1 |
| B32 | 405 |
TABLE 5-continued
| MS Characterization Data | |
|---|---|
| Comp. No. | MS |
| B33 | 405 |
| B34 | 386.15 |
| B35 | 386.15 |
| B36 | 399 |
| B37 | 399 |
| B38 | 379.05 |
| B39 | 379.05 |
| B40 | 405.05 |
| B41 | 404.95 |
| B42 | 389.1 |
| B43 | 389.05 |
| B44 | 389.05 |
| B45 | 389.05 |
| B46 | 361.95 |
| B47 | 361.95 |
| B48 | 436.1 |
| B49 | 436.1 |
| B50 | 439.1 |
| B51 | 439.05 |
| B52 | 390 |
| B53 | 389.95 |
| B54 | 387.15 |
| B55 | 387.15 |
| B56 | 385.1 |
| B57 | 385.1 |
| B58 | 385.05 |
| B59 | 385.1 |
| B60 | 438.1 |
| B61 | 438.15 |
| B62 | 410.05 |
| B63 | 410 |
| B64 | 386.05 |

TABLE 5-continued

MS Characterization Data

| Comp. No. | MS |
|---|---|
| B65 | 386.05 |
| B66 | 420.15 |
| B67 | 420.15 |
| B68 | 379.05 |
| B69 | 379.05 |
| B70 | 395.05 |
| B71 | 352.1 |
| B72 | 352.1 |
| B73 | 418.1 |
| B74 | 418.1 |
| B75 | 392.05 |
| B76 | 392 |
| B77 | 390.05 |
| B78 | 371.1 |
| B79 | 402.1 |
| B80 | 402.1 |
| B81 | 399 |
| B82 | 398.95 |
| B83 | 386.1 |
| B84 | 412 |
| B85 | 433.1 |
| B86 | 433.1 |
| B87 | 392.1 |
| B88 | 392.05 |
| B89 | 384.05 |
| B90 | 384.05 |
| B91 | 373.1 |
| B92 | 373.15 |
| B93 | 381.05 |
| B94 | 381.05 |
| B95 | 448.1 |
| B96 | 448.1 |
| B97 | 489.1 |
| B98 | 489.1 |
| B99 | 365.15 |
| B100 | 365.15 |
| B101 | 410.2 |
| B102 | 410.2 |
| B103 | 383.1 |
| B104 | 383.15 |
| B105 | 373.05 |
| B106 | 373.15 |
| B107 | 415.15 |
| B108 | 415.05 |
| B109 | 366 |
| B110 | 366.05 |
| B111 | 379.1 |
| B112 | 379.1 |
| B113 | 371.1 |
| B114 | 371.05 |
| B115 | 361.15 |
| B116 | 361.1 |
| B117 | 410 |
| B118 | 409.95 |
| B119 | 401.1 |
| B120 | 401.1 |
| B121 | 411.05 |
| B122 | 411.05 |
| B123 | 401 |
| B124 | 403.05 |
| B125 | 379.05 |
| B126 | 379.05 |
| B127 | 396.15 |
| B128 | 396.1 |
| B129 | 396 |
| B130 | 396.05 |
| B131 | 397.05 |
| B132 | 397.05 |
| B133 | 401 |
| B134 | 401.05 |
| B135 | 372.2 |
| B136 | 372.15 |
| B137 | 380.2 |
| B138 | 380.2 |
| B139 | 403.05 |
| B140 | 403.05 |
| B141 | 390.2 |
| B142 | 390.15 |
| B143 | 379.2 |
| B144 | 379.2 |
| B145 | 378.2 |
| B146 | 378.1 |
| B147 | 396.1 |
| B148 | 396.2 |
| B149 | 398.1 |
| B150 | 398.1 |
| B151 | 427 |
| B152 | 404.95 |
| B153 | 372.12 |
| B154 | 372.12 |
| B155 | 360.2 |
| B156 | 360.2 |
| B157 | 379 |
| B158 | 361.12 |
| B159 | 361.12 |
| B160 | 389.2 |
| B161 | 361.2 |
| B162 | 361.2 |
| B163 | 391.2 |
| B164 | 391.2 |
| B165 | 377.1 |
| B166 | 377.1 |
| B167 | 411 |
| B168 | 411 |
| B169 | 411.1 |
| B170 | 411.15 |
| B171 | 354.05 |
| B172 | 354.3 |
| B173 | 346.85 |
| B174 | 346.85 |
| B175 | 399.05 |
| B176 | 399.1 |
| B177 | 364 |
| B178 | 377.1 |
| B179 | 377.1 |
| B180 | 381.1 |
| B181 | 381.05 |
| B182 | 361.2 |
| B183 | 361.2 |
| B184 | 377.1 |
| B185 | 377 |
| B186 | 359.05 |
| B187 | 359.05 |
| B188 | 389.15 |
| B189 | 389.15 |
| B190 | 383.15 |
| B191 | 383.15 |
| B192 | 343 |
| B193 | 343.05 |
| B194 | 361.1 |
| B195 | 361.1 |
| B196 | 372.1 |
| B197 | 372 |
| B198 | 372.1 |
| B199 | 372.1 |
| B200 | 376.2 |
| B201 | 376.2 |
| B202 | 406 |
| B203 | 353 |
| B204 | 353.15 |
| B205 | 371.05 |
| B206 | 371.1 |
| B207 | 420.15 |
| B208 | 420.15 |
| B209 | 360.3 |
| B210 | 360.3 |
| B211 | 410.3 |
| B212 | 410.3 |
| B213 | 410.15 |
| B214 | 410.15 |

TABLE 5-continued

MS Characterization Data

| Comp. No. | MS |
|---|---|
| B215 | 330.15 |
| B216 | 330.15 |
| B217 | 380.3 |
| B218 | 380.15 |
| B219 | 454 |
| B220 | 454 |
| B221 | 389.85 |
| B222 | 378.2 |
| B223 | 378.15 |
| B224 | 360.15 |
| B225 | 360.1 |
| B226 | 424 |
| B227 | 438.2 |
| B228 | 438.2 |
| B229 | 372.15 |
| B230 | 365.1 |
| B231 | 396.1 |
| B232 | 396.1 |
| B233 | 494.1 |
| B234 | 494.1 |
| B235 | 431.95 |
| B236 | 396.05 |
| B237 | 396.05 |
| B238 | 382.1 |
| B239 | 378.1 |
| B240 | 378.1 |
| B241 | 378.1 |
| B242 | 378.1 |
| B243 | 360.1 |
| B244 | 360.15 |
| B245 | 374.15 |
| B246 | 414.25 |
| B247 | 364.1 |
| B248 | 364.2 |
| B249 | 346.25 |
| B250 | 406.1 |
| B251 | 411.2 |
| B252 | 411.2 |
| B253 | 470.05 |
| B254 | 470.1 |
| B255 | 455.2 |
| B256 | 455.25 |
| B257 | 408 |
| B258 | 388 |
| B259 | 388 |
| B262 | 388.1 |
| B263 | 404.1 |
| B264 | 433.1 |
| B265 | 433.1 |
| B266 | 418.1 |
| B267 | 418.1 |
| B268 | 416.05 |
| B269 | 416.1 |
| B270 | 398.05 |
| B271 | 398.1 |
| B272 | 404.15 |
| B273 | 404.15 |
| B274 | 398.1 |
| B275 | 398.1 |
| B276 | 412.05 |
| B277 | 412.05 |
| B278 | 404.15 |
| B279 | 404.15 |
| B280 | 376 |
| B281 | 376 |
| B282 | 404.2 |
| B283 | 404.15 |
| B284 | 397.05 |
| B285 | 397.15 |
| B286 | 398.15 |
| B287 | 398.05 |
| B288 | 397 |
| B289 | 397.05 |
| B290 | 388.1 |
| B291 | 388.1 |

TABLE 5-continued

MS Characterization Data

| Comp. No. | MS |
|---|---|
| B292 | 444.95 |
| B293 | 388 |
| B294 | 392.2 |
| B295 | 392.15 |
| B296 | 405.1 |
| B297 | 405.05 |
| B299 | 390.2 |
| B300 | 390.25 |
| B301 | 377.15 |
| B302 | 377.25 |
| B303 | 418.05 |
| B304 | 418.05 |
| B306 | 432.15 |
| B307 | 432.15 |
| B308 | 391.25 |
| B309 | 391.25 |
| B310 | 401.05 |
| B311 | 401.05 |
| B312 | 407.25 |
| B313 | 407.2 |
| B314 | 399.2 |
| B315 | 399.2 |
| B319 | 429.1 |
| B320 | 429.15 |
| B321 | 412.15 |
| B322 | 412.15 |
| B323 | 416.05 |
| B324 | 416.05 |
| B325 | 413.1 |
| B326 | 413.05 |
| B327 | 388.4 |
| B328 | 395.2 |
| B329 | 395.2 |
| B330 | 395.2 |
| B331 | 395.15 |
| B332 | 395.15 |
| B333 | 395.15 |
| B334 | 381.15 |
| B335 | 381.2 |
| B336 | 381.2 |
| B337 | 381.2 |
| B338 | 387.05 |
| B339 | 387.1 |
| B340 | 352.05 |
| B341 | 391 |
| B342 | 391.2 |
| B343 | 380.05 |
| B344 | 380.05 |
| B345 | 352.1 |
| B346 | 380.1 |
| B347 | 380.1 |
| B348 | 387.05 |
| B349 | 387.05 |
| B350 | 377.05 |
| B351 | 377.05 |
| B352 | 387.1 |
| B353 | 387.15 |
| B354 | 403.05 |
| B355 | 403.05 |
| B356 | 369.05 |
| B357 | 390.2 |
| B358 | 390.1 |
| B359 | 368.1 |
| B360 | 418.1 |
| B361 | 418.1 |
| B362 | 392.95 |
| B363 | 392.95 |
| B364 | 404.05 |
| B365 | 404.1 |
| B371 | |
| B372 | |
| B373 | |
| B374 | |
| B375 | |
| B376 | |

TABLE 5-continued

| MS Characterization Data | |
|---|---|
| Comp. No. | MS |
| B377 | |
| B378 | |
| B379 | |
| B380 | |

TABLE 6

| NMR Characterization Data | |
|---|---|
| Comp. No. | NMR |
| B76 | (300 MHz, DMSO-d6) δ 9.48 (s, 1H), 8.46 (d, J = 8.1 Hz, 1H), 7.35-6.99 (m, 4H), 6.96-6.56 (m, 1H), 6.62-6.52 (m, 1H), 4.96-4.95 (m, 1H), 4.72-4.69 (m, 2H), 4.59 (s, 2H), 4.00 (s, 2H), 3.85-3.84 (m, 1H), 3.73-3.72 (m, 1H). |
| B87 | (400 MHz, DMSO-$d_6$) δ 9.46 (d, J = 1.6 Hz, 1H), 8.16 (d, J = 7.2 Hz, 1H), 7.25-7.18 (m, 1H), 6.98-6.90 (m, 2H), 6.81-6.78 (m, 1H), 6.58-6.56 (m, 1H), 4.56 (s, 2H), 4.17-4.13 (m, 2H), 3.97 (s, 2H), 3.90-3.85 (m, 1H), 3.05-2.99 (m, 1H), 2.75-2.69 (m, 1H). |
| B89 | (400 MHz, DMSO-$d_6$) δ 9.52 (s, 1H), 8.83 (s, 1H), 8.52 (d, J = 8.0 Hz, 1H), 8.18 (s, 1H), 7.26- 7.19 (m, 1H), 6.58-6.55 (m, 1H), 5.37-5.31 (q, J = 8.5 Hz, 1H), 4.59 (s, 2H), 4.03 (s, 2H), 3.31-2.84 (m, 2H), 2.49-2.47 (s, 1H), 1.94-1.84 (m, 1H). |
| B116 | (400 MHz, DMSO-$d_6$) δ 9.67 (s, 1H), 8.97-8.96 (m, 1H), 8.66 (d, J = 7.6 Hz, 1H), 8.28-8.25 (m, 1H), 7.60-7.58 (m, 1H), 7.36-7.31 (m, 2H), 7.09-7.04 (m, 1H), 5.06-5.01 (m, 1H), 4.72-4.59 (m, 2H), 4.08 (s, 2H), 1.42 (d, J = 7.2 Hz, 3H). |
| B118 | (400 MHz, DMSO-d6) δ 9.69 (s, 1H), 8.88 (d, J = 8.0 Hz, 1H), 7.48-7.26 (m, 3H), 7.09 (dd, J = 8.8, 4.9 Hz, 1H), 5.77 (m, 1H), 4.82 (m, 1H), 4.66 (s, 2H), 4.39 (dd, J = 9.6, 4.4 Hz, 1H), 4.01 (s, 2H) |
| B130 | (400 MHz, DMSO-$d_6$) δ 10.06 (s, 1H), 8.70 (d, J = 7.2 Hz, 1H), 7.84-7.81 (m, 1H), 7.71-7.64 (m, 2H), 7.58-7.56 (m, 1H), 6.71 (d, J = 8.4 Hz, 1H), 5.18- 5.11 (m, 1H), 4.58-4.50 (m, 2H), 4.02 (s, 2H), 1.37 (d, J = 6.8 Hz, 3H). |
| B137 | (300 MHz, DMSO-d6) δ 9.55 (s, 1H), 8.96-8.95 (m, 1H), 8.49 (d, J = 7.5 Hz, 1H), 8.29-8.25 (m, 1H), 7.58 (d, J = 8.1 Hz, 1H), 6.96-6.95 (m, 1H), 6.85-6.71 (m, 2H), 4.95 (q, J = 7.2 Hz, 1H), 3.90 (s, 2H), 1.43-1.21 (m, 6H), 1.03 (s, 2H). |
| B141 | $^1$H NMR (300 MHz, DMSO-d6) δ 9.63-9.38 (m, 1H), 8.98-8.82 (m, 1H), 8.78-8.62 (m, 1H), 8.48-8.24 (m, 1H), 7.31-7.08 (m, 1H), 6.68-6.49 (m, 1H), 5.46-5.14 (m, 1H), 4.64-4.37 (m, 2H), 4.27-3.85 (m, 2H), 1.58-1.24 (m, 3H) |
| B144 | 400 MHz, DMSO-d6) δ 9.77 (s, 1H), 8.90-8.89(m, 1H), 8.70 (d, J = 7.2 Hz, 1H), 8.41-8.38 (m, 1H), 7.59-7.55 (m, 2H), 6.87(d, J = 8.4 Hz, 1H), 5.28-5.25 (m, 1H), 4.48-4.40 (m, 2H), 3.98-3.92 (m, 2H), 1.39 (d, J = 7.2 Hz, 3H). |
| B145 | 400 MHz, DMSO-d6) δ 9.29 (s, 1H), 8.76 (d, J = 7.6 Hz, 1H), 7.00-6.95 (m, 2H), 6.78-6.69 (m, 3H), 5.65-5.60 (m, 1H), 4.80-4.75 (m, 1H), 4.46 (s, 2H), 4.36-4.32 (m, 1H), 3.92 (s, 2H). |
| B155 | (400 MHz, DMSO-d6) δ 9.29 (s, 1H), 8.47 (d, J = 7.6 Hz, 1H), 7.45-7.44 (m, 1H), 7.18-7.02 (m, 3H), 6.86 (t, J = 7.2 Hz, 1H), 6.78(d, J = 8.0 Hz, 1H), 5.09-5.07 (m, 1H), 4.48-4.46 (m, 1H), 4.28-4.24 (m, 1H), 3.74-3.70 (m, 1H), 1.33 (d, J = 6.8 Hz, 3H), 1.23 (d, J = 6.4 Hz, 3H). |
| B172 | 300 MHz, DMSO-d6) δ 9.29 (s,1H), 8.98-8.97 (m, 1H), 8.62 (d, J = 7.5 Hz, 1H), 8.28-8.25 (m, 1H), 7.59-7.57 (m, 1H), 7.00-6.94 (m, 2H), 6.78-6.73 (m, 1H), 5.05-4.96 (m, 1H), 4.46 (s, 2H), 3.99 (s, 2H), 1.40 (d, J = 6.9 Hz, 3H). |
| B175 | (400 MHz, DMSO-d6) δ 9.46 (s, 1H), 8.49 (d, J = 2.4 Hz, 1H), 8.44 (d, J = 8.0 Hz, 1H), 7.90 (td, J = 9.2, 2.4 Hz, 1H), 7.22 (q, J = 9.2Hz, 1H), 6.56 (d, J = 7.6 Hz, 1H), 5.26 (q, J = 7.2 Hz, 1H), 4.96-4.93 (m, 1H), 4.50-4.46 (m, 2H), 4.01 (s, 2H), 3.65 (t, J = 6.4 Hz, 2H). |
| B200 | (400 MHz, DMSO-d6) δ 9.31 (s, 1H), 8.40 (d, J = 8.0 Hz, 1H), 7.47-7.41 (m, 1H), 7.21-7.09 (m, 4H), 7.07-7.02 (m, 1H), 6.88-6.84 (m, 1H), 6.80-6.78 (m, 1H), 5.11-5.01 (m, 1H), 5.01-4.98 (m,1H), 4.50-4.45 (m,1H), 4.33-4.29 (m, 1H), 3.78 (d, J = 16.4 Hz, 1H), 3.76-3.32 (m, 2H), 1.23 (d, J = 6.0 Hz, 3H). |
| B206 | $^1$H NMR (300 MHz, DMSO-d6) δ 9.29 (s, 1H), 8.77-8.54 (m, 1H), 7.89-7.77 (m, 1H), 7.75-7.65 (m, 1H), 7.64-7.54 (m, 1H), 7.06-6.91 (m, 2H), 6.85-6.66 (m, 1H), 5.28-5.06 (m, 1H), 4.44 (s, 2H), 1.51-1.25 (m, 3H) |
| B229 | (300 MHz, DMSO-d6) δ 9.50 (s, 1H), 8.40 (d, J = 7.8 Hz, 1H), 7.47-7.38 (m, 1H), 7.23-7.02 (m, 2H), 6.87-6.79 (m, 3H), 5.12-5.02 (m, 1H), 3.86 (s, 2H), 1.33 (d, J = 6.9 Hz, 3H). |
| B231 | 400 MHz, DMSO-d6) δ 9.53 (s, 1H), 8.50 (d, J = 7.6 Hz, 1H), 7.41 (m, 1H), 7.29-7.12 (m, 2H), 7.02 (m, 1H), 6.65-6.57 (m, 1H), 5.09 (m, 1H), 4.75 (m, 1H), 4.31 (d, J = 16.4 Hz, 1H), 3.78 (d, J = 16.4 Hz, 1H), 1.34 (d, J = 7.2 Hz, 3H), 1.27 (d, J = 6.4 Hz, 3H). |
| B232 | 400 MHz, DMSO-d6) δ 9.53 (s, 1H), 8.50 (d, J = 7.6 Hz, 1H), 7.41 (m, 1H), 7.29-7.12 (m, 2H), 7.02 (m, 1H), 6.65-6.57 (m, 1H), 5.09 (m, 1H), 4.75 (m, 1H), 4.31 (d, J = 16.4 Hz, 1H), 3.78 (d, J= 16.4 Hz, 1H), 1.34 (d, J = 7.2 Hz, 3H), 1.27 (d, J = 6.4 Hz, 3H). |
| B290 | $^1$H-NMR (400 MHz, DMSO, ppm) δ 9.98 (s, 1H), 8.88 (d, J = 8.4 Hz, 1H), 8.73 (d, J = 7.2 Hz, 1H), 8.40 (dd, J = 9.6, 1.6 Hz, 1H), 7.38 (dd, J = 19.2, 8.8 Hz, 1H), 6.79 (d, J = 7.2 Hz, 1H), 6.69 (dd, J = 8.8, 2.4 Hz, 1H), 5.94 (d, J = 6.8 Hz, 1H), 5.29-5.24 (m, 1H), 4.42-4.38 (m, 1H), 3.97-3.92 (m, 1H), 1.40 (d, J = 6.8 Hz, 3H). |
| B291 | $^1$H-NMR (400 MHz, DMSO, ppm) δ 9.99 (s, 1H), 8.88 (s, 1H), 8.72 (d, J = 6.4 Hz, 1H), 8.42 (d, J = 9.2 Hz, 1H), 7.38 (t, J = 18.0, 8.8 Hz, 1H), 6.79-6.66 (m, 2H), 5.87 (d, J = 6.0 Hz, 1H), 5.28-5.25 (m, 1H), 4.44-4.40 (m, 1H), 3.89-3.85 (m, 1H), 1.40 (d, J = 6.0 Hz, 3H). |
| B327 | H-NMR (300 MHz, DMSO, ppm) δ 9.98 (s, 1H), 8.88 (d, J = 6.3 Hz, 1H), 8.74 (d, J = 7.2 Hz, 1H), 8.42-8.37 (m, 1H), 7.40 (dd, J = 19.2, 8.7 Hz, 1H), 6.80 (d, J = 6.9 Hz, 1H), 6.69 (dd, J = 9.0, 2.4 Hz, 1H), 5.95 (d, J = 6.9 Hz, 1H), 5.33-5.26 (m, 1H), 4.45-4.38 (m, 1H), 3.98-3.85 (m, 1H), 1.41 (d, J = 7.2 Hz, 3H). |

Example 49. Myofibril ATPase Assay

Myofibril ATPase assays are known in the art to be useful in evaluating small molecules for the treatment of HCM and other cardiac indications. Myosin ATPase activity is assessed by using a coupled reaction system, in which ADP generated by the myosin ATPase function is coupled to the disappearance of NADH through the pyruvate kinase/lactate dehydrogenase (PK-LDH) system. ATPase activity produces ADP, which is used as a substrate for PK to produce pyruvate and regenerate ATP. The pyruvate is then used as a substrate by LDH to oxidize NADH to NAD+. The rate of the reaction is monitored through the time-dependent disappearance of NADH using absorbance at 340 nm, which, when the couple system is in stoichiometric excess, is directly correlated to the ATPase activity of the myosin. Inhibition of ATPase activity by the assayed compounds is indicated by a reduced rate of NADH loss, relative to vehicle-treated controls, over the experimental time window. Rabbit Skeletal and Porcine Ventricle are the primary sources of myofibril material.

Materials: The following stock solutions and reagents were used in the Myofibril ATPase Assay:

| Stock Solutions |
|---|
| PIPES, 200 mM and 120 mM in $H_2O$, pH 7.0 |
| $MgCl_2$ in $H_2O$, 200 mM |
| PM12 Buffer, 10X: 120 mM PIPES (from 200 mM stock), 20 mM $MgCl_2$ (from 200 mM stock) |
| PBS Buffer, 1X: 135 mM NaCl, 27 mM KCl, 10 mM $Na(PO_4)_2$, 1.8 mM $K_2(PO_4)$, pH 7.4 |
| EGTA in $H_2O$, 250 mM |

-continued

| Stock Solutions |
|---|
| $CaCl_2$ in $H_2O$, 500 mM |
| DTT in $H_2O$, 1M |
| BSA in $H_2O$, 10 mg/mL |
| ATP in 1X PBS, 50 mM |
| NADH in 1X PM12 and 1 mM DTT, 26 mM |
| PEP in 1X PM12, 78 mM, pH 7.0 |

Stock Solutions of pCa buffer. Combine PIPES, $CaCl_2$), and EGTA solutions with water. Adjust pH to 7.0 and bring final volume to 100 mL.

Preparation of Stocks Solutions for 100 mL of pCa buffer

| pCA | 120 mM PIPES (mL) | Approx. Water (mL) | $CaCl_2$ (mL) | EGTA (mL) |
|---|---|---|---|---|
| 4.0 | 10 | 59.797 | 10.203 | 20 |
| 4.5 | 10 | 59.959 | 10.041 | 20 |
| 5.0 | 10 | 60.060 | 9.940 | 20 |
| 5.5 | 10 | 60.244 | 9.756 | 20 |
| 5.75 | 10 | 60.434 | 9.566 | 20 |
| 6.0 | 10 | 60.750 | 9.250 | 20 |
| 6.25 | 10 | 61.262 | 8.738 | 20 |
| 6.5 | 10 | 62.045 | 7.955 | 20 |
| 6.75 | 10 | 63.138 | 6.862 | 20 |
| 7.0 | 10 | 64.484 | 5.516 | 20 |
| 8.0 | 10 | 68.905 | 1.095 | 20 |
| 10.0 | 10 | 69.988 | 0.012 | 20 |

Buffer A & Buffer B. Prepare buffers A and B according to the table below.

| | | Component | Stock Concentrations Value | Unit | Final Concentrations in Specific Buffer | Reaction Concentrations | Volume per well (µL) | Number of Wells Total Volume (µL) 400 | 1200 | |
|---|---|---|---|---|---|---|---|---|---|---|
| Total Well Volume (µL) | 50 | PM12 Buffer | 10 | x | 1.00 x | 1.00 x | 2.50 | 1000.00 | 1300.00 | PM12 Buffer (1 x) |
| | | KCl | 2000 | mM | 0.00 mM | 0.00 mM | 0.00 | 0.00 | 0.00 | KCl (0 mM) |
| | | pCa Solution | 10 | x | 0.00 x | 0.00 x | 0.00 | 0.00 | 0.00 | pCa Solution (0.x) |
| | | Compound | 100% | | 0.00% | 0.00% | 0.00 | 0.00 | 0.00 | Compound (0%) |
| Buffer A (µL) | 25 | BSA | 10 | mg/mL | 0.10 mg/mL | 0.10 mg/mL | 0.25 | 100.00 | 130.00 | BSA (0.1 mg/mL) |
| | | DTT | 1000 | mM | 1.00 mM | 1.00 mM | 0.03 | 10.00 | 13.00 | DTT (1 mM) |
| | | PK/LDH | 200 | x | 2.00 x | 1.00 x | 0.25 | 100.00 | 130.00 | PK/LDH (1x) |
| | | Ventricle Prep 18 | 8.2 | mg/mL | 1.00 mg/mL | 0.50 mg/mL | 3.05 | 1219.51 | 1585.37 | Ventricle Prep 18 (0.5 mg/mL) |
| | | Antifoam | 1.00% | | 0.01% | 0.01% | 0.25 | 100.00 | 130.00 | Antifoam (0.01%) |
| | | Water | | | | | 18.68 | 7470.49 | 9711.63 | Water |
| | | | | | | | 25.00 | 10000.00 | 13000.00 | Total |
| | | PM12 Buffer | 10 | x | 1.00 x | 1.00 x | 2.50 | 1000.00 | 1300.00 | PM12 Buffer (1 x) |

-continued

| | Component | Stock Concentrations Value Unit | Final Concentrations in Specific Buffer | Reaction Concentrations | Volume per well (µL) | Number of Wells Total Volume (µL) | 400 | 1200 |
|---|---|---|---|---|---|---|---|---|
| | KCl | 1000 mM | 0.00 mM | 30.00 mM | 0.00 | 0.00 | 0.00 | KCl (30 mM) |
| | Compound | 100% | 0.00% | 0.00% | 0.00 | 0.00 | 0.00 | Compound (0%) |
| Buffer B 25 (µL) | pCa Solution | 10 x | 2.00 x | 1.00 x | 5.00 | 2000.00 | 2600.00 | pCa Solution (1 x) |
| | BSA | 10 mg/mL | 0.10 mg/mL | 0.10 mg/mL | 0.25 | 100.00 | 130.00 | BSA (0.1 mg/mL) |
| | DTT | 1000 mM | 1.00 mM | 1.00 mM | 0.03 | 10.00 | 13.00 | DTT (1 mM) |
| | ATP | 50 mM | 0.50 mM | 0.25 mM | 0.25 | 100.00 | 130.00 | ATP (0.25 mM) |
| | NADH | 26 mM | 1.00 mM | 0.50 mM | 0.96 | 384.62 | 500.00 | NADH (0.5 mM) |
| | PEP | 78 mM | 3.00 mM | 1.50 mM | 0.96 | 384.62 | 500.00 | PEP (1.5 mM) |
| | Antifoam | 1.00% | 0.01% | 0.01% | 0.25 | 100.00 | 130.00 | Antifoam (0.01%) |
| | Water | | | | 14.80 | 5920.77 | 7697.00 | Water |

Myofibril ATPase Assay Procedure: BSA, ATP, NADH, PEP, and DTT solutions were thawed at room temperature, then transferred to ice. Pellet-frozen myofibrils were transferred with approximately twice the required volume into a sufficiently large tube and capped. Myofibrils were thawed by rolling in a water bath for approximately 15 min at room temperature and cooled on ice. Buffers A and B were prepared by adjusting volumes as necessary for required number of wells and stored on ice. 0.5 µL of the compounds to be assayed were added into wells. 25 µL of Buffer A was dispensed into the wells, followed by 25 µL of Buffer B. The wells were measured for absorbance at 340 nm, using a kinetic protocol in which the wells are read every 1.5-2 min for 75 min. Assay data analysis was performed using a python script that filtered the raw data to retain those points falling between a starting and ending time and between a maximum and minimum absorbance, then used the filtered time-domain 340 nm absorbance data in each well to calculate a slope via linear regression analysis in units of mAU/min. Compound slopes were normalized between 100% and 0% activity, where 100% represented the slope of wells containing only compound vehicle, and fit to a 4-parameter logistic model. In addition to the fit parameters, the $EC_{25\%}$ is calculated, relative to the 100% normalized value. In the case of inhibitors, $EC_{50\%}$ is also calculated, if available. Fit parameters, calculated effective concentrations, filtered raw data, and calculated slopes were exported, in addition to compound-specific graphs of normalized ATPase activity versus concentration in µM. The results are shown in Table 7 and Table 8.

Skeletal Myofibril Isolation:

Myofibrils from various animals and tissue types were acquired from a variety of sources: rabbit psoas muscle was purchased from Pel-Freez Biologicals (Rogers, AR) and porcine cardiac muscle was purchased from Exemplar Genetics. All myofibrils were prepared using a method based upon those described in Herrmann et al. (1993) and summarized here. Minced tissue was homogenized for 50 sec with a Polytron homogenizer into 10 volumes (relative to weight in grams) of Isolation Buffer A (50 mM Tris, pH 8.0, 0.1 M potassium acetate, 5 mM KCl, 2 mM DTT, 5 mM EDTA, 0.5% v/v Triton X-100) supplemented with 0.1 mM PMSF, 10 µM leupeptin, 5 µM pepstatin, and 0.5 mM sodium azide. The myofibrils were recovered by centrifugation (Beckman Allegra 6R, 1200 g, 10 min) and resuspended in 10 volumes Isolation Buffer B (Buffer A above without protease inhibitors or sodium azide). The myofibrils were further homogenized as before and recovered by centrifugation. Cellular membranes and debris were removed by 2 washes in Isolation Buffer B, centrifuging each as before. The myofibrils were then suspended in Isolation Buffer C (Tris, potassium acetate, KCl, and DTT as above, supplemented with 2 mM magnesium acetate) and homogenized as described above. The myofibrils were collected by centrifugation and washed 3 times with Isolation Buffer C before being passed through a 100 µM nylon mesh sheet (Spectrum Laboratories) to remove the larger particles. The sieved myofibrils were centrifuged at 1200 g for 15 min and resuspended in 2 to 3 volumes of PM12-60 buffer (12 mM PIPES, pH 6.8, 2 mM $MgCl_2$, 60 mM KCl, 1 mM DTT). D-sucrose was added to 10% and the myofibril suspension was drop-frozen into liquid nitrogen at stored at −80° C.

Cardiac Myofibril Isolation:

Myofibrils from porcine cardiac muscle was isolated from the left ventricle of Yucatan minipigs. Myofibrils were prepared using a method based upon those described in Herrmann et al. (1993) and summarized here. Minced tissue was homogenized for 50 sec with a Polytron homogenizer into 10 volumes (relative to weight in grams) of Isolation Buffer A (75 mM KCl, 10 mM Imidazole, 2 mM $MgCl_2$, 2 mM EGTA, 1 mM $NaN_3$, 1% v/v Triton X-100) supplemented with 4 mM Phosphocreatine, 1 mM ATP, 50 mM BDM, 1 mM DTT, 1 mM Benzamide HCl, 0.1 mM PMSF, 10 µM leupeptin, 5 µM pepstatin, and 10 mM EDTA. The myofibrils were recovered by centrifugation (Beckman Allegra 6R, 1200 g, 15 min) and resuspended in 10 volumes Isolation Buffer B (Buffer A above without supplemental reagents). The myofibrils were further homogenized described above and recovered by centrifugation for 7 mins.

Cellular membranes and debris were removed by 3 washes in Isolation Buffer B, centrifuging each as before. The myofibrils were then suspended in Isolation Buffer C (Buffer A above without supplemental reagents and Triton) and homogenized as described above. The myofibrils were collected by centrifugation and washed 3 times with Isolation Buffer C before being passed through a 100 μM nylon mesh sheet (Spectrum Laboratories) to remove the larger particles. The sieved myofibrils were centrifuged at 1200 g for 15 min and resuspended in 2 to 3 volumes of PM12-60 buffer (12 mM PIPES, pH 6.8, 2 mM $MgCl_2$, 60 mM KCl, 1 mM DTT). D-sucrose was added to 10% and the myofibril suspension was drop-frozen into liquid nitrogen at stored at −80° C.

Certain compounds of the disclosure have skeletal and ventricle $IC_{25}$ values as in Table 7 and Table 8. In Table 7 and Table 8 the following symbols are defined as follows:

* denotes that absolute stereochemistry is not yet known. Associated $IC_{25}$ values are to a single enantiomer with unknown absolute configuration.

** denotes that absolute stereochemistry is not yet known. Associated $IC_{25}$ values are to a single diastereomer with unknown absolute configuration.

*** denotes a mixture of diastereomers.

****denotes racemic mixtures

TABLE 7

| Comp. No. | Rabbit Psoas $IC_{25}$ (μM) | Porcine Atria $IC_{25}$ (μM) | Porcine Ventricle $IC_{25}$ (μM) |
|---|---|---|---|
| N1* | 100 | 70.94 | 100 |
| N2* | 4.055 | 17.14 | 34.26 |
| N3 | 18.85 | 2.59 | 100 |
| N4 | 0.1067 | 0.07 | 0.474 |
| N5* | 0.0178 | 0.07 | 0.1154 |
| N6* | 2.918 | 2.82 | 38.22 |
| N7* | 0.0355 | 0.11 | 0.266 |
| N8* | 0.3271 | 2.20 | 13.21 |
| N9 | 0.1941 | 0.35 | 3.006 |
| N10* | 0.4579 | 0.82 | 13.44 |
| N11* | 100 | 100.00 | 100 |
| N12 | 100 | 7.63 | 100 |
| N13 | 0.063 | 0.07 | 0.8569 |
| N14 | 100 | 1.16 | 100 |
| N15 | 0.197 | 0.07 | 2.788 |
| N16* | 1.645 | 0.60 | 100 |
| N17* | 100 | 75.12 | 100 |
| N18* | 0.03098 | 0.12 | 1.324 |
| N19* | 2.245 | 2.00 | 11.46 |
| N20 | 0.1315 | 100.00 | 100 |
| N21 | 6.632 | 4.36 | 13.45 |
| N22 | 0.2583 | 100.00 | 100 |
| N23 | 0.0165 | 0.28 | 0.1625 |
| N24 | 0.2119 | 2.97 | 37.65 |
| N25* | 1.324 | 13.11 | 100 |
| N26* | 0.04764 | 0.15 | 1.309 |
| N27 | 100 | 100.00 | 100 |
| N28 | 0.2814 | 0.41 | 6.602 |
| N29* | 100 | 100.00 | 100 |
| N30* | 5.318 | 35.72 | 100 |
| N31* | 0.0533 | 0.38 | 1.237 |
| N32* | 2.872 | 100.00 | 100 |
| N33* | 0.01937 | 0.08 | 0.2832 |
| N34* | 1.366 | 8.44 | 100 |
| N35 | 0.9847 | 6.39 | 100 |
| N36* | 1.604 | 8.01 | 25.16 |
| N37* | 0.0599 | 0.20 | 4.582 |
| N38* | 5.343 | 60.44 | 100 |
| N39* | 1.979 | 9.59 | 51.8 |
| N40 | 4.177 | 87.45 | 100 |
| N41 | 0.0762 | 1.12 | 2.357 |
| N42 | 100 | 100.00 | 100 |

TABLE 7-continued

| Comp. No. | Rabbit Psoas $IC_{25}$ (μM) | Porcine Atria $IC_{25}$ (μM) | Porcine Ventricle $IC_{25}$ (μM) |
|---|---|---|---|
| N43* | 100 | 32.69 | 100 |
| N44* | 0.5658 | 1.18 | 18.96 |
| N45** | 100 | 14.99 | 100 |
| N46** | 100 | 100.00 | 100 |
| N47* | 0.2942 | 0.67 | 6.077 |
| N48* | 100 | 100.00 | 100 |
| N49* | 100 | 100.00 | 100 |
| N50* | 2.278 | 9.91 | 100 |
| N51*** | 100 | 100.00 | 100 |
| N52* | 15.28 | 98.42 | 100 |
| N53* | 100 | 100.00 | 100 |
| N54* | 0.4294 | 0.26 | 2.952 |
| N55* | 7.296 | 4.73 | 100 |
| N56 | 86.07 | 100.00 | 100 |
| N57 | 6.748 | 12.15 | 100 |
| N58* | 100 | 100.00 | 100 |
| N59* | 100 | 6.80 | 100 |
| N60 | 1.385 | 1.15 | 81.4 |
| N61* | 100 | 100.00 | 100 |
| N62* | 0.1508 | 0.97 | 5.161 |
| N63* | 100 | 100.00 | 100 |
| N64* | 16.71 | 25.37 | 100 |
| N65**** | 100 | 100.00 | 100 |
| N66 | 0.3112 | 29.35 | 100 |
| N67* | 100 | 100.00 | 100 |
| N68* | 0.0442 | 0.13 | 1.833 |
| N69* | 100 | 100.00 | 100 |
| N70* | 100 | 100.00 | 100 |
| N71 | 2.804 | 36.26 | 100 |
| N72 | 0.4483 | 3.14 | 39.96 |
| N73* | 35.6 | 100.00 | 100 |
| N74* | 0.07565 | 0.54 | 1.559 |
| N75* | 100 | 100.00 | 100 |
| N76* | 100 | 100.00 | 100 |
| N77** | 2.441 | 2.11 | 24.08 |
| N78** | 11.14 | 26.68 | 31.94 |
| N79* | 100 | 100.00 | 100 |
| N80* | 4.79 | 8.03 | 100 |
| N81 | 0.04549 | 0.24 | 0.545 |
| N82 | 100 | 100.00 | 100 |
| N83** | 1.802 | 0.74 | 100 |
| N84** | 10.25 | 3.69 | 100 |
| N85** | 4.254 | 18.87 | 100 |
| N86** | 10.83 | 30.96 | 100 |
| N87 | 0.0571 | 0.03 | 0.1682 |
| N88 | 0.1726 | 0.13 | 0.7484 |
| N89** | 100 | 100.00 | 100 |
| N90** | 49.64 | 100.00 | 100 |
| N91 | 17.09 | 56.88 | 100 |
| N92** | 100 | 100.00 | 100 |
| N93** | 100 | 1.66 | 100 |
| N94** | 0.0739 | 0.22 | 0.4952 |
| N95** | 0.9565 | 3.69 | 5.968 |
| N96** | 100 | 100.00 | 100 |
| N97** | 90.25 | 100.00 | 100 |
| N98* | 8.57 | 0.36 | 71.64 |
| N99* | 100 | 8.28 | 100 |
| N100* | 9.48 | 100.00 | 100 |
| N101* | 0.1554 | 0.27 | 1.94 |
| N102 | 0.1771 | 0.21 | 2.017 |
| N103 | 1.03 | 0.16 | 9.96 |
| N104* | 0.1699 | 0.16 | 4.155 |
| N105* | 30.96 | 100.00 | 100 |
| N106* | 3.732 | 2.58 | 100 |
| N107* | 100 | 100.00 | 100 |
| N108* | 0.0727 | 1.41 | 49.28 |
| N109 | 0.4553 | 5.44 | 100 |
| N110*** | 0.1674 | 0.19 | 19.54 |
| N111** | 0.1027 | 0.08 | 6.67 |
| N112 | 0.2968 | 0.23 | 9.823 |
| N113 | 0.3281 | 22.12 | 73.85 |
| N114* | 0.2892 | 2.30 | 8.373 |
| N115* | 0.0228 | 0.51 | 0.7516 |
| N116 | 0.1914 | 4.38 | 40.22 |
| N117 | 0.0146 | 0.17 | 0.3795 |

TABLE 7-continued

| Comp. No. | Rabbit Psoas $IC_{25}$ (μM) | Porcine Atria $IC_{25}$ (μM) | Porcine Ventricle $IC_{25}$ (μM) |
|---|---|---|---|
| N118 | 0.152 | 0.75 | 5.896 |
| N119 | 0.1196 | 0.57 | 3.289 |
| N120 | 0.4239 | 100.00 | 27.23 |
| N121 | 0.0218 | 0.51 | 5.985 |
| N122 | 0.0567 | 0.36 | 11.42 |
| N123 | 0.03514 | 0.07 | 0.8592 |
| N124 | 0.0503 | 0.08 | 0.2452 |
| N125 | 0.0423 | 0.68 | 2.663 |
| N126 | 0.07562 | 0.60 | 4.027 |
| N127 | 0.2931 | 3.12 | 73.05 |
| N128 | 0.0418 | 0.08 | 0.2533 |
| N129 | 0.559 | 4.20 | 4.847 |
| N130 | 0.688 | 1.54 | 100 |
| N131 | 8.051 | 36.11 | 100 |
| N132 | 1.636 | 3.75 | 97.09 |
| N133 | 0.8391 | 2.80 | 13.9 |
| N135* | 100.00 | 6.42 | 100.00 |
| N136* | 100.00 | 0.29 | 10.90 |

TABLE 8

| Comp. No. | Rabbit Psoas $IC_{25}$ (μM) | Porcine Atria $IC_{25}$ (μM) | Porcine Ventricle $IC_{25}$ (μM) |
|---|---|---|---|
| B1* | 0.0201 | 0.09 | 0.0599 |
| B2* | 5.739 | 0.96 | 7.734 |
| B3 | 100 | 34.81 | 52.51 |
| B4* | 0.1318 | 0.07 | 0.1161 |
| B5* | 4.565 | 100.00 | 100 |
| B6* | 0.1232 | 0.07 | 0.1483 |
| B7* | 29.14 | 0.45 | 2.786 |
| B8* | 1.018 | 0.43 | 0.6039 |
| B9* | 0.0224 | 0.04 | 0.0379 |
| B10 | 29.08 | 100.00 | 8.204 |
| B11 | 49.64 | 100.00 | 100 |
| B12 | 0.7606 | 0.88 | 0.143 |
| B13 | 0.0132 | 0.06 | 0.086 |
| B14* | 0.0934 | 0.15 | 0.0844 |
| B15* | 100 | 100.00 | 100 |
| B16* | 1.205 | 0.23 | 1.057 |
| B17* | 0.0783 | 0.06 | 0.1841 |
| B18* | 100 | 2.25 | 100 |
| B19* | 100 | 100.00 | 100 |
| B20* | 100 | 100.00 | 100 |
| B21* | 100 | 100.00 | 100 |
| B22* | 0.9012 | 10.83 | 6.451 |
| B23* | 0.0124 | 0.04 | 0.0347 |
| B24* | 30.61 | 100.00 | 100 |
| B25* | 4.823 | 0.70 | 2.494 |
| B26 | 100 | 100.00 | 100 |
| B27 | 0.5422 | 2.10 | 15.59 |
| B28 | 100 | 6.24 | 100 |
| B29 | 0.1245 | 0.11 | 0.6824 |
| B30 | 100 | 0.07 | 100 |
| B31 | 0.01 | 0.02 | 0.0421 |
| B32 | 1.003 | 0.28 | 0.548 |
| B33 | 0.0093 | 0.02 | 0.0667 |
| B34* | 100 | 0.16 | 3.618 |
| B35* | 1.252 | 0.58 | 0.948 |
| B36* | 0.0105 | 0.02 | 0.0148 |
| B37* | 0.3844 | 0.28 | 0.4901 |
| B38* | 10.64 | 0.98 | 3.82 |
| B39* | 0.0203 | 0.02 | 0.0483 |
| B40 | 100 | 100.00 | 17.72 |
| B41 | 0.0857 | 1.74 | 1.384 |
| B42 | 0.7455 | 0.59 | 3.177 |
| B43 | 0.0158 | 0.04 | 0.0473 |
| B44 | 4.901 | 0.45 | 0.5278 |
| B45 | 0.0115 | 0.02 | 0.0457 |
| B46* | 0.6601 | 0.58 | 1.847 |

TABLE 8-continued

| Comp. No. | Rabbit Psoas $IC_{25}$ (μM) | Porcine Atria $IC_{25}$ (μM) | Porcine Ventricle $IC_{25}$ (μM) |
|---|---|---|---|
| B47* | 100 | 100.00 | 96.66 |
| B48** | 12.65 | 100.00 | 62.1 |
| B49** | 100 | 6.51 | 45.96 |
| B50** | 100 | 100.00 | 42.56 |
| B51** | 100 | 49.07 | 100 |
| B52* | 3.964 | 0.42 | 1.456 |
| B53* | 100 | 0.09 | 7.534 |
| B54* | 0.5796 | 0.11 | 0.9628 |
| B55* | 0.0114 | 0.05 | 0.0533 |
| B56 | 1.887 | 1.64 | 1.991 |
| B57 | 0.0139 | 0.04 | 0.0899 |
| B58 | 6.712 | 1.02 | 4.23 |
| B59 | 0.0818 | 0.63 | 0.9519 |
| B60** | 2.769 | 0.80 | 100 |
| B61** | 100 | 100.00 | 100 |
| B62* | 0.0143 | 0.04 | 0.0415 |
| B63* | 100 | 1.81 | 100 |
| B64* | 0.7773 | 0.52 | 0.5798 |
| B65* | 0.0191 | 0.06 | 0.1667 |
| B66** | 100 | 100.00 | 100 |
| B67** | 7.017 | 43.94 | 9.364 |
| B68* | 58.62 | 2.03 | 1.168 |
| B69* | 3.174 | 0.61 | 0.2987 |
| B70**** | 1.912 | 0.35 | 1.114 |
| B71* | 100 | 43.18 | 40.66 |
| B72* | 1.903 | 2.25 | 100 |
| B73* | 23.3 | 1.22 | 2.134 |
| B74* | 100 | 1.24 | 100 |
| B75* | 0.09136 | 0.02 | 0.0144 |
| B76* | 5.359 | 0.39 | 0.3465 |
| B77**** | 0.0488 | 0.04 | 0.0768 |
| B78**** | 0.0417 | 0.04 | 0.1091 |
| B79* | 0.2662 | 0.04 | 0.4454 |
| B80* | 8.828 | 0.06 | 2.778 |
| B81* | 5.776 | 0.09 | 0.4092 |
| B82* | 0.0183 | 0.03 | 0.0561 |
| B83* | 0.0214 | 0.04 | 0.0519 |
| B84* | 3.733 | 0.13 | 1.489 |
| B85* | 4.582 | 0.39 | 28.59 |
| B86* | 100 | 100.00 | 100 |
| B87* | 1.11 | 0.19 | 2.048 |
| B88* | 100 | 0.46 | 2.339 |
| B89* | 0.07847 | 0.07 | 0.2469 |
| B90* | 100 | 10.98 | 100 |
| B91* | 0.3913 | 0.14 | 0.783 |
| B92* | 0.01909 | 0.03 | 0.05126 |
| B93 | 11.45 | 1.26 | 5.574 |
| B94 | 0.1294 | 0.09 | 0.5438 |
| B95* | 100 | 1.56 | 100 |
| B96* | 21.88 | 1.91 | 100 |
| B97* | 8.892 | 1.43 | 4.796 |
| B98* | 93.47 | 100.00 | 72.38 |
| B99* | 100 | 0.70 | 100 |
| B100* | 0.1246 | 0.03 | 0.7409 |
| B101* | 1.059 | 0.15 | 0.5759 |
| B102* | 7.621 | 0.10 | 6.262 |
| B103* | 0.426 | 0.03 | 1.132 |
| B104* | 100 | 2.79 | 100 |
| B105* | 4.205 | 0.11 | 6.381 |
| B106* | 0.3028 | 0.09 | 0.4765 |
| B107 | 100 | 100.00 | 100 |
| B108 | 1.4 | 0.46 | 3.587 |
| B109* | 13.9 | 12.19 | 100 |
| B110* | 0.0558 | 0.04 | 0.5595 |
| B111 | 0.564 | 100.00 | 100 |
| B112 | 0.079 | 1.51 | 2.318 |
| B113 | 0.09089 | 0.16 | 0.233 |
| B114 | 0.0208 | 0.12 | 0.1673 |
| B115 | 100 | 100.00 | 100 |
| B116 | 0.0743 | 0.22 | 0.6721 |
| B117* | 0.2366 | 0.15 | 1.967 |
| B118* | 0.0136 | 0.07 | 0.11 |
| B119* | 0.0521 | 0.55 | 7.599 |
| B120* | 0.0137 | 0.06 | 0.0826 |
| B121* | 0.0677 | 0.12 | 0.1665 |

TABLE 8-continued

| Comp. No. | Rabbit Psoas IC25 (μM) | Porcine Atria IC25 (μM) | Porcine Ventricle IC25 (μM) |
|---|---|---|---|
| B122* | 100 | 1.31 | 100 |
| B123* | 0.0115 | 0.04 | 0.047 |
| B124* | 0.3262 | 0.36 | 1.87 |
| B125 | 1.552 | 1.62 | 100 |
| B126 | 0.04006 | 0.07 | 0.3461 |
| B127 | 0.2455 | 0.25 | 96.35 |
| B128 | 0.01798 | 0.10 | 0.1056 |
| B129 | 3.992 | 0.26 | 100 |
| B130 | 0.1475 | 0.20 | 0.9228 |
| B131 | 0.3456 | 100.00 | 100 |
| B132 | 0.0313 | 0.08 | 0.1715 |
| B133* | 0.2116 | 0.07 | 1.94 |
| B134* | 1.791 | 4.47 | 95.46 |
| B135 | 1.618 | 0.51 | 15.88 |
| B136 | 0.0645 | 0.42 | 0.764 |
| B137* | 0.1155 | 0.12 | 0.6995 |
| B138* | 100 | 1.53 | 100 |
| B139* | 0.01393 | 0.05 | 0.1215 |
| B140* | 1.501 | 1.10 | 55.23 |
| B141 | 0.4228 | 0.13 | 3.094 |
| B142 | 0.02168 | 0.04 | 0.05434 |
| B143 | 100 | 100.00 | 100 |
| B144 | 2.787 | 0.72 | 47.42 |
| B145* | 0.0116 | 0.02 | 0.0512 |
| B146* | 5.163 | 1.52 | 68.33 |
| B147* | 0.01623 | 0.05 | 0.07766 |
| B148* | 0.4985 | 0.85 | 5.833 |
| B149* | 0.1803 | 73.55 | 100 |
| B150* | 100 | 0.98 | 22.65 |
| B151 | 14.21 | 100.00 | 100 |
| B152 | 0.03953 | 0.17 | 0.2946 |
| B153* | 0.5161 | 16.33 | 100 |
| B154* | 0.0315 | 0.18 | 2.518 |
| B155** | 0.0851 | 0.43 | 3.17 |
| B156** | 0.232 | 4.12 | 10.58 |
| B157**** | 100 | 5.96 | 100 |
| B158** | 18.11 | 100.00 | 100 |
| B159** | 100 | 100.00 | 100 |
| B160 | 0.3154 | 0.36 | 4.311 |
| B161* | 1.295 | 4.15 | 45.8 |
| B162* | 0.7039 | 52.14 | 100 |
| B163* | 0.4728 | 2.08 | 31.68 |
| B164* | 0.0273 | 0.10 | 0.3444 |
| B165* | 100 | 17.36 | 100 |
| B166* | 6.966 | 51.60 | 100 |
| B167** | 100 | 100.00 | 100 |
| B168** | 100 | 100.00 | 100 |
| B169** | 0.3955 | 0.15 | 1.354 |
| B170** | 9.578 | 2.85 | 31.8 |
| B171* | 7.545 | 19.79 | 100 |
| B172* | 2.013 | 2.94 | 20.93 |
| B173* | 100 | 100.00 | 100 |
| B174* | 83 | 46.54 | 100 |
| B175* | 100 | 100.00 | 100 |
| B176* | 0.08998 | 0.06 | 0.3872 |
| B177 | 68.51 | 100.00 | 100 |
| B178* | 3.38 | 3.48 | 100 |
| B179* | 100 | | 100 |
| B180* | 100 | 100.00 | 100 |
| B181* | 0.242 | 0.13 | 1.905 |
| B182* | 1.159 | 2.28 | 100 |
| B183* | 100 | 100.00 | 100 |
| B184* | 100 | 57.48 | 56.86 |
| B185* | 100 | 100.00 | 100 |
| B186* | 100 | 100.00 | 100 |
| B187* | 100 | 68.80 | 100 |
| B188* | 0.4649 | 0.42 | 1.834 |
| B189* | 0.01879 | 0.03 | 0.07743 |
| B190* | 9.504 | 17.83 | 50.31 |
| B191* | 0.02019 | 0.04 | 0.1913 |
| B192* | 100 | 100.00 | 100 |
| B193* | 41.67 | 28.17 | 40.61 |
| B194* | 6.088 | 3.71 | 78.56 |
| B195* | 100 | 100.00 | 100 |
| B196* | 100 | 100.00 | 100 |

TABLE 8-continued

| Comp. No. | Rabbit Psoas IC25 (μM) | Porcine Atria IC25 (μM) | Porcine Ventricle IC25 (μM) |
|---|---|---|---|
| B197* | 87.6 | 18.70 | 100 |
| B198* | 100 | 100.00 | 100 |
| B199* | 0.0394 | 0.09 | 0.5693 |
| B200** | 2.863 | 2.45 | 79.13 |
| B201** | 18.61 | 25.98 | 100 |
| B202**** | 0.1741 | 0.18 | 1.035 |
| B203* | 14.19 | 5.48 | 23.26 |
| B204* | 0.1501 | 0.27 | 1.393 |
| B205* | 6.054 | 2.07 | 16.29 |
| B206* | 0.01129 | 0.03 | 0.04769 |
| B207** | 100 | 100.00 | 100 |
| B208** | 100 | 100.00 | 100 |
| B209 | 100 | 12.15 | 100 |
| B210 | 0.1421 | 0.18 | 2.251 |
| B211** | 100 | 100.00 | 100 |
| B212** | 77.91 | 1.52 | 15.17 |
| B213** | 100 | 97.43 | 100 |
| B214** | 0.088 | 0.07 | 0.2408 |
| B215* | 100 | 100.00 | 100 |
| B216* | 100 | 100.00 | 100 |
| B217* | 0.0678 | 0.13 | 0.8987 |
| B218* | 9.306 | 8.55 | 100 |
| B219** | 31.8 | 100.00 | 100 |
| B220** | 47.56 | 53.57 | 100 |
| B221 | 0.0174 | 0.03 | 0.1086 |
| B222** | 0.041 | 0.05 | 0.4365 |
| B223** | 1.426 | 0.44 | 3.783 |
| B224* | 3.991 | 28.57 | 100 |
| B225* | 0.0175 | 0.05 | 0.1849 |
| B226 | 0.0244 | 0.14 | 0.2274 |
| B227* | 0.0127 | 0.06 | 0.2485 |
| B228* | 0.2844 | 0.32 | 2.111 |
| B229 | 0.0356 | 0.06 | 0.156 |
| B230* | 0.182 | 0.22 | 1.835 |
| B231* | 0.02107 | 0.21 | 1.558 |
| B232* | 0.0328 | 0.04 | 0.3963 |
| B233* | 0.0556 | 0.09 | 0.2674 |
| B234* | 100 | 0.26 | 1.527 |
| B235* | 100 | 1.15 | 100 |
| B236* | 0.0333 | 0.03 | 0.2316 |
| B237* | 0.3164 | 0.28 | 8.122 |
| B238 | 0.0116 | 0.03 | 0.1435 |
| B239* | 7.191 | 100.00 | 100 |
| B240* | 0.8825 | 25.37 | 100 |
| B241* | 0.034 | 0.11 | 1.243 |
| B242* | 0.3555 | 58.71 | 100 |
| B243*** | 10.96 | 0.19 | 11.52 |
| B244*** | 0.695 | 2.50 | 4.818 |
| B245 | 9.295 | 0.94 | 11.66 |
| B246 | 19.62 | 100.00 | 73.7 |
| B247 | 0.03205 | 0.06 | 0.2968 |
| B248 | 0.062 | 0.05 | 0.2832 |
| B249 | 0.02766 | 0.07 | 0.6589 |
| B250 | 36.83 | 81.49 | 60.47 |
| B251 | 100.00 | 8.81 | 100.00 |
| B252 | 36.83 | 81.49 | 60.47 |
| B253* | 86.41 | 100.00 | 100.00 |
| B254* | 100.00 | 100.00 | 100.00 |
| B255* | 100.00 | 100.00 | 100.00 |
| B256* | 39.41 | 75.74 | 46.27 |
| B257* | | | |
| B258* | | | |
| B259* | | | |
| B262* | | | |
| B263* | | | |
| B264* | 100.00 | 0.52 | 0.89 |
| B265* | 100.00 | 1.88 | 5.36 |
| B266* | 0.95 | 0.05 | 1.38 |
| B267* | 18.40 | 0.18 | 3.96 |
| B268* | 6.91 | 0.11 | 3.06 |
| B269* | 0.06 | 0.06 | 0.15 |
| B270* | 100.00 | 1.18 | 100.00 |
| B271* | 100.00 | 100.00 | 55.13 |
| B272** | 0.74 | 0.05 | 0.75 |
| B273** | 1.57 | 1.96 | 22.58 |

TABLE 8-continued

| Comp. No. | Rabbit Psoas $IC_{25}$ (μM) | Porcine Atria $IC_{25}$ (μM) | Porcine Ventricle $IC_{25}$ (μM) |
|---|---|---|---|
| B274* | 100.00 | 1.10 | 95.97 |
| B275* | 100.00 | 8.27 | 100.00 |
| B276* | 30.80 | 100.00 | 23.74 |
| B277* | 100.00 | 77.49 | 73.20 |
| B278** | 0.03 | 0.03 | 0.09 |
| B279** | 0.57 | 0.11 | 0.70 |
| B280* | 1.08 | 0.61 | 6.55 |
| B281* | 0.03 | 0.06 | 0.15 |
| B282* | 100.00 | 86.13 | 100.00 |
| B283* | 100.00 | 0.90 | 6.49 |
| B284* | 100.00 | 0.87 | 0.44 |
| B285* | 100.00 | 100.00 | 100.00 |
| B286* | 40.68 | 0.55 | 8.79 |
| B287* | 100.00 | 75.65 | 100.00 |
| B288* | 3.98 | 0.26 | 5.29 |
| B289* | 100.00 | 100.00 | 100.00 |
| B290* | 4.36 | 0.25 | 5.21 |
| B291** | 1.69 | 0.06 | 1.85 |
| B292* | 0.42 | 0.16 | 0.54 |
| B293 | | | |
| B294* | 1.83 | 46.59 | 39.99 |
| B295* | 0.17 | 0.25 | 0.35 |
| B296* | 0.06 | 0.07 | 0.39 |
| B297* | 1.69 | 1.97 | 2.21 |
| B299* | 63.22 | 67.41 | 100.00 |
| B300* | 1.39 | 1.42 | 1.42 |
| B301* | 2.52 | 4.28 | 14.90 |
| B302* | 5.65 | 1.08 | 2.85 |
| B303* | 0.02 | 0.08 | 0.09 |
| B304* | 1.05 | 1.12 | 3.96 |
| B306* | 0.61 | 0.10 | 0.18 |
| B307* | 0.02 | 0.05 | 0.07 |
| B308* | 100.00 | 20.75 | 100.00 |
| B309* | 2.23 | 10.36 | 10.57 |
| B310* | 0.08 | 0.16 | 0.37 |
| B311* | 100.00 | 100.00 | 86.79 |
| B312* | 0.05 | 0.10 | 0.18 |
| B313* | 9.12 | 2.29 | 3.91 |
| B314* | 0.12 | 0.04 | 0.50 |
| B315* | 0.02 | 0.05 | 0.09 |
| B319* | 5.96 | 0.07 | 0.10 |
| B320* | 0.33 | 0.23 | 0.24 |
| B321* | 0.23 | 0.17 | 0.97 |
| B322* | 0.03 | 0.07 | 0.06 |
| B323* | 0.63 | 0.10 | 0.32 |
| B324* | 0.03 | 0.04 | 0.05 |
| B325* | 2.34 | 1.04 | 3.21 |
| B326* | 0.02 | 0.16 | 0.06 |
| B327* | 1.98 | 0.19 | 1.38 |
| B328* | 100.00 | 1.53 | 100.00 |
| B329* | 0.13 | 0.20 | 0.42 |
| B330* | 0.05 | 0.08 | 0.19 |
| B331* | 100.00 | 0.37 | 66.75 |
| B332* | 0.06 | 0.06 | 0.10 |
| B333* | 100.00 | 100.00 | 100.00 |
| B334* | 1.02 | 0.58 | 1.56 |
| B335* | 100.00 | 9.42 | 100.00 |
| B336* | 0.17 | 0.10 | 0.27 |
| B337* | 100.00 | 1.01 | 7.01 |
| B338* | 17.15 | 0.08 | 1.67 |
| B339* | 1.95 | 0.22 | 2.12 |
| B340*** | 100.00 | 3.80 | 100.00 |
| B341* | 1.68 | 0.73 | 0.35 |
| B342* | 2.45 | 0.93 | 4.85 |
| B343* | 100.00 | 4.12 | 100.00 |
| B344* | 2.78 | 1.29 | 8.84 |
| B345* | 100.00 | 57.06 | 100.00 |
| B346* | 59.27 | 0.22 | 1.63 |
| B347* | 100.00 | 100.00 | 100.00 |
| B348* | 9.36 | 10.17 | 6.79 |
| B349* | 5.32 | 0.22 | 0.83 |
| B350* | 0.62 | 0.30 | 0.50 |
| B351* | 100.00 | 100.00 | 100.00 |
| B352* | 4.45 | 0.61 | 2.36 |
| B353* | 2.49 | 1.99 | 2.24 |

TABLE 8-continued

| Comp. No. | Rabbit Psoas $IC_{25}$ (μM) | Porcine Atria $IC_{25}$ (μM) | Porcine Ventricle $IC_{25}$ (μM) |
|---|---|---|---|
| B354* | 68.36 | 0.21 | 3.83 |
| B355* | 0.07 | 0.05 | 0.14 |
| B356* | 0.08 | 0.10 | 0.14 |
| B357* | 50.29 | 1.56 | 100.00 |
| B358* | 0.13 | 0.10 | 0.33 |
| B359* | 13.87 | 4.96 | 100.00 |
| B360* | 100.00 | 44.86 | 9.49 |
| B361* | 100.00 | 100.00 | 100.00 |
| B362* | 0.52 | 100.00 | 1.04 |
| B363* | 100.00 | 100.00 | 100.00 |
| B364* | 100.00 | 20.41 | 100.00 |
| B365* | 100.00 | 100.00 | 100.00 |
| B366* | 0.05 | 0.07 | 0.77 |
| B367* | 0.78 | 0.32 | 0.55 |

Example 50. Myofibril ATPase Assay

Experiments were performed to evaluate the in vivo ability of the compounds of the disclosure to modulate systolic cardiac performance. Non-invasively echocardiography was used to assess cardiac indicators in isoflurane-anesthetized SD rats. A set of conscious rats were treated with either vehicle control (0 mg/kg PO; n=78) or a single dose of an test compound (10 mg/kg PO, n=2 to 6/compound) via oral gavage. Cardiac function/geometry were recorded at two separate time-points/days: once prior to dosing (i.e., at baseline, day −2) and at ~2 hrs post-dosing (day 0).

In these experiments, heart rate (HR), echocardiography-derived indices of left-ventricular systolic performance, as well as dimensions/volumes were measured using a high-frequency transducer and parastemnal long-axis transthoracic views (Vevo3100, VisualSonic). LV fractional shortening (FS), an index of systolic function, was defined as the end-diastole normalized change in internal dimensions divided by the difference in diameter (LVid) of the left ventricle between end-systole (LVids) and end-diastole (LVidd) (i.e., FS=100·[LVidd−LVids]/LVidd). LV volumes were derived using the Teichholz formula (LVV=7·LVid^3/[2.4+LVid]). In addition, a systolic wall-thickening index (SWT) was also evaluated. SWT is defined as the relative ratio (end-diastole normalized) of left-ventricular (anterior and posterior) wall-thickness change during systole; i.e., SWT=I{[(anterior LV wall thickness in systole−anterior LV wall thickness in diastole)]$^{+}$[(posterior LV wall thickness in systole−posterior LV wall thickness in diastole)]}/{2*diastolic thickness}. In all cases, blood samples were taken (via either tail-vein micro-sampling or cardiac-puncture) at the time of each echocardiographic examination in order to establish pharmacokinetic (PK)/pharmacodynamics (PD) relationships.

| Compound No. | HR % vs. VEH | EDV % vs. VEH | FS % vs. VEH | SWT % vs. VEH |
|---|---|---|---|---|
| B247 | 7 | 7 | −31 | −35 |
| B206 | 7 | 29 | −67 | −57 |
| B199 | 22 | 11 | −54 | −55 |
| B191 | 17 | 9 | −59 | −59 |
| B189 | −5 | 19 | −13 | −29 |
| B181 | 8 | −6 | −13 | −5 |
| N33 | 6 | 2 | −10 | −5 |

-continued

| Compound No. | HR % vs. VEH | EDV % vs. VEH | FS % vs. VEH | SWT % vs. VEH |
|---|---|---|---|---|
| B152 | 1 | −6 | 6 | −2 |
| B147 | 10 | 10 | −35 | −37 |
| B145 | 7 | 11 | −42 | −39 |
| B142 | 6 | 21 | −81 | −78 |
| B141 | 13 | −3 | −15 | −19 |
| B327 | 5 | −2 | −1 | 10 |
| B367 | 10 | −6 | −31 | −32 |
| B65 | 22 | 22 | −61 | −53 |
| B357 | −5 | 5 | −8 | −5 |
| B55 | −5 | 70 | −36 | 10 |
| B366 | −2 | 82 | −71 | −41 |

Example 51. RLC Stripping and Swapping in Full Length

Full-length myosin was resuspended to 1 mg/mL in a buffer containing 500 mM KCl, 10 mM KPi, 15 mM CDTA, pH 8.5. Triton-X was then added to a final concentration of 100, and the suspension was agitated for 15 minutes at room temperature to selectively remove the regulatory light chain (RLC). RLC-removed myosin was then precipitated and collected and resuspended in a buffer containing 400 mM KCl, 50 mM Mops, pH 7, 2 mM $MgCl_2$, and 1 mM DTT. Recombinantly expressed and purified human ventricle RLC was added in a 3-fold molar excess to myosin and incubated on ice for 2 hours to allow for reassociation of the RLC onto myosin. Triton (0.1%) was added to the reaction to prevent any non-specific binding events. RLC-exchanged myosin was then precipitated and collected and resuspended in a buffer containing 12 mM PIPES, pH 6.8, 300 nM KCl, 2 mM $MgCl_2$, and 1 mM DTT. RLC removal and exchange were confirmed by SDS-PAGE and proteins were visualized using coomassie stain.

Example 52. Compound Response in NADH-coupled ATPase Assay

Myosin was resuspended in buffer A (f.c.=12 mM PIPES, pH 6.8, 30 mM KCl, 2 mM $MgCl_2$, 1 mM DTT, 0.1 mg/mL BSA, 0.01% (v/v) Antifoam 204, and 0.6% (v/v) PK/LDH (final reaction contains ≥3.6 U/mL PK and >5.4 U/mL LDH)) at final concentrations of 1 μM for myosin+native RLC and 2 μM for myosin+removed RLC and myosin+human ventricle RLC. Buffer A was then mixed with an equal volume of buffer B (f.c.=12 mM PIPES, pH 6.8, 30 mM KCl, 2 mM $MgCl_2$, 1 mM DTT, 0.1 mg/mL BSA, 0.01% (v/v) Antifoam 204, 0.5 mM NADH, 1.5 mM phosphoenolpyruvate, 1 mM ATP, and 0.3 mg/mL filamentous rabbit skeletal actin) in a 384-well plate. Dose-dependent compound effects were assessed by adding the compounds at varying concentrations between 100 μM and 2 nM, all with a constant final DMSO concentration of 1% v/v. The reactions were run at a constant temperature of 25° C. in the plate reader to monitor the change in A340 over time. Measurements were taken every 90 sec for 75 min to generate raw time-domain absorbance data, which was processed to normalized reaction rates. Normalized enzymatic rates were calculated, using rates observed in 1% (v/v) in DMSO as 100% and 0 slope as 0%. Compound-specific activity curves were generated by plotting the normalized rates versus compound concentration and fitting the data to a 4-parameter logistic model. In addition to the fit parameters, the IC25% was calculated, relative to the 100% normalized value. The reported IC25 value is the point of 25% inhibition relative to the vehicle control, which was assigned a normalized value of

| | Potency (μM) | | |
|---|---|---|---|
| Compound Number | Full-length myosin + native porcine ventricle RLC | Full-length myosin + RLC removed | Full-length myosin + exchanged human ventricle RLC |
| B247 | 0.97 | >100.0 | 1.02 |
| B206 | 0.97 | >100.0 | 0.68 |
| B199 | 0.56 | >100.0 | 0.629 |
| B191 | 0.45 | >100.0 | 0.44 |
| B189 | 0.39 | >100.0 | 0.33 |
| B172 | 12.32 | >100.0 | 14.39 |
| N33 | 0.40 | >100.0 | 0.40 |
| N26 | 2.17 | >100.0 | 1.92 |
| B147 | 0.63 | >100.0 | 0.48 |
| B145 | 1.19 | >100.0 | 0.67 |
| B141 | 15.48 | >100.0 | 13.90 |
| B65 | 0.55 | >100.0 | 0.69 |
| B327 | 5.97 | >100.0 | 11.63 |
| B269 | 0.59 | >100.0 | 0.49 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound represented by Formula (II):

(II)

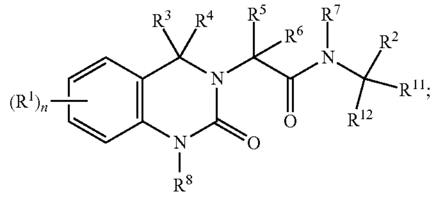

or a salt thereof, wherein:

n is 0, 1, 2, 3, or 4;

each $R^1$ is independently selected from:

halogen, —$NO_2$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, and —$S(O)_2R^{10a}$;

$C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10d}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, =O, =S, =$N(R^{10a})$, —CN, $C_{3-10}$ carbocycle and 3- to 10-membered heterocycle, wherein each $C_{3-10}$ carbocycle and 3- to 10-membered heterocycle is optionally substituted with one or more substituents independently selected from $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —CN, $C_{1-6}$ alkyl, $C_{2-6}$ alkenyl, and $C_{2-6}$ alkynyl, wherein each $C_{1-6}$ alkyl, $C_{2-6}$ alkenyl, and $C_{2-6}$ alkynyl is optionally substituted with one or more substituents independently selected from $R^{9a}$;

$R^2$ is selected from:

halogen, —$NO_2$, —CN, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, and —$S(O)_2R^{10b}$;

$C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —CN, $C_{3-10}$ carbocycle, and 3- to 10-membered heterocycle, wherein each $C_{3-10}$ carbocycle and 3- to 10-membered heterocycle is optionally substituted with one or more substituents independently selected from $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, —CN, $C_{1-6}$ alkyl, $C_{2-6}$ alkenyl, and $C_{2-6}$ alkynyl, wherein each $C_{1-6}$ alkyl, $C_{2-6}$ alkenyl, and $C_{2-6}$ alkynyl is optionally substituted with one or more substituents independently selected from $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more substituents independently selected from $R^{9b'}$;

$R^3$ and $R^4$ are each independently selected from:

hydrogen, halogen, —$OR^{10c}$, —$SR^{10c}$, —$N(R^{10c})_2$, —$NO_2$, and —CN; and $C_{1-6}$ alkyl optionally substituted with one or more substituents independently selected from halogen, —$OR^{10c}$, —$SR^{10c}$, —$N(R^{10c})_2$, —$NO_2$, and —CN; or $R^3$ together with $R^4$ form a 3- to 10-membered heterocycle or $C_{3-10}$ carbocycle, wherein the 3- to 10-membered heterocycle or $C_{3-10}$ carbocycle is optionally substituted with one or more substituents independently selected from $R^{9c}$;

$R^5$ and $R^6$ are each independently selected from:

hydrogen, halogen, —$OR^{10d}$, —$SR^{10d}$, —$N(R^{10d})_2$, —$NO_2$, and —CN; and $C_{1-6}$ alkyl optionally substituted with one or more substituents independently selected from halogen, —$OR^{10d}$, —$SR^{10d}$, —$N(R^{10d})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more substituents independently selected from $R^{9d}$;

$R^7$ is selected from:

hydrogen and $C_{1-6}$ alkyl optionally substituted with one or more substituents independently selected from halogen, —$OR^{10e}$, —$SR^{10e}$, —$N(R^{10e})_2$, —$NO_2$, and —CN;

$R^8$ is selected from:

hydrogen and $C_{1-6}$ alkyl optionally substituted with one or more substituents independently selected from halogen, —$OR^{10f}$, —$SR^{10f}$, —$N(R^{10f})_2$, —$NO_2$, and —CN;

$R^{11}$ is selected from:

halogen, —$NO_2$, —CN, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, and —$S(O)_2R^{10g}$; and $C_{1-6}$ alkyl, $C_{2-6}$ alkenyl, and $C_{2-6}$ alkynyl, each of which is optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, —$OC(O)R^{10g}$, —$N(R^{10g})C(O)N(R^{10g})_2$, —$OC(O)N(R^{10g})_2$, —$N(R^{10g})C(O)OR^{10g}$, —$S(O)R^{10g}$, —$S(O)_2R^{10g}$, —$NO_2$, =S, =$N(R^{10g})$, —CN, $C_{3-10}$ carbocycle and 3- to 10-membered heterocycle, wherein each $C_{3-10}$ carbocycle and 3- to 10-membered heterocycle is optionally substituted with one or more substituents independently selected from $R^{9g}$;

$R^{12}$ is selected from:

hydrogen;

$C_{1-6}$ alkyl optionally substituted with one or more substituents independently selected from the group consisting of halogen, —CN, —OH, —$OR^{10h}$ —$N(R^{10h})_2$, —$NO_2$, —$C(O)R^{10h}$, —$SR^{10h}$, and —$S(O)R^{10h}$; and $C_{3-6}$ carbocycle and 3- to 10-membered heterocycle, each of which is optionally substituted with one or more substituents independently selected from the group consisting of halogen, —CN, —OH, —$OR^{10h}$, —$N(R^{10h})_2$, —$NO_2$, —$C(O)R^{10h}$, —$SR^{10h}$, and —$S(O)R^{10h}$; or $R^{12}$, $R^{11}$, and $R^2$ come together to form a $C_5$-$C_{10}$ bridged ring system;

each $R^{9a}$ is independently selected from:

halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C (O)N($R^{10a}$)$_2$, —OC(O)N($R^{10a}$)$_2$, —N($R^{10a}$)C(O)OR$^{10a}$, —C(O)OR$^{10a}$, —OC(O)R$^{10a}$, —S(O)R$^{10a}$, —S(O)$_2$R$^{10a}$, —NO$_2$, =O, =S, =N($R^{10a}$), and —CN;

each $R^{9b}$ is independently selected from:

halogen, —OR$^{10b}$, —SR$^{10b}$, —N($R^{10b}$)$_2$, —C(O)R$^{10b}$, —C(O)N($R^{10b}$)$_2$, —N($R^{10b}$)C(O)R$^{10b}$, —N($R^{10b}$)C(O)N($R^{10b}$)$_2$, —OC(O)N($R^{10b}$)$_2$, —N($R^{10b}$)C(O)OR$^{10b}$, —C(O)OR$^{10b}$, —OC(O)R$^{10b}$, —S(O)R$^{10b}$, —S(O)$_2$R$^{10b}$, —NO$_2$, =O, =S, =N($R^{10b}$), and —CN; and $C_{1-3}$ alkyl, $C_{2-3}$ alkenyl, and $C_{2-3}$ alkynyl, each of which is optionally substituted with one or more substituents independently selected from halogen, —OR$^{10b}$, —SR$^{10b}$, —N($R^{10b}$)$_2$, —C(O)R$^{10b}$, —C(O)N($R^{10b}$)$_2$, —N($R^{10b}$)C(O)R$^{10b}$, —N($R^{10b}$)C(O)N($R^{10b}$)$_2$, —OC(O)N($R^{10b}$)$_2$, —N($R^{10b}$)C(O)OR$^{10b}$, —C(O)OR$^{10b}$, —OC(O)R$^{10b}$, —S(O)R$^{10b}$, —S(O)$_2$R$^{10b}$, —NO$_2$, =O, =S, =N($R^{10b}$), and —CN;

each $R^{9b'}$ is independently selected from:

halogen, —OR$^{10b}$, —SR$^{10b}$, —N($R^{10b}$)$_2$, —C(O)R$^{10b}$, —C(O)N($R^{10b}$)$_2$, —N($R^{10b}$)C(O)R$^{10b}$, —N($R^{10b}$)C(O)N($R^{10b}$)$_2$, —OC(O)N($R^{10b}$)$_2$, —N($R^{10b}$)C(O)OR$^{10b}$, —C(O)OR$^{10b}$, —OC(O)R$^{10b}$, —S(O)R$^{10b}$, —S(O)$_2$R$^{10b}$, —NO$_2$, =O, =S, =N($R^{10b}$), and —CN; and $C_{1-3}$ alkyl, $C_{2-3}$ alkenyl, and $C_{2-3}$ alkynyl, each of which is optionally substituted with one or more substituents independently selected from halogen, —OR$^{10b}$, —SR$^{10b}$, —N($R^{10b}$)$_2$, —C(O)R$^{10b}$, —C(O)N($R^{10b}$)$_2$, —N($R^{10b}$)C(O)R$^{10b}$, —N($R^{10b}$)C(O)N($R^{10b}$)$_2$, —OC(O)N($R^{10b}$)$_2$, —N($R^{10b}$)C(O)OR$^{10b}$, —C(O)OR$^{10b}$, —OC(O)R$^{10b}$, —S(O)R$^{10b}$, —S(O)$_2$R$^{10b}$, —NO$_2$, =O, =S, =N($R^{10b}$), and —CN;

each $R^{9c}$ is independently selected from:

halogen, —OR$^{10c}$, —SR$^{10c}$, —N($R^{10c}$)$_2$, —C(O)R$^{10c}$, —C(O)N($R^{10c}$)$_2$, —N($R^{10c}$)C(O)R$^{10c}$, —N($R^{10c}$)C(O)N($R^{10c}$)$_2$, —OC(O)N($R^{10c}$)$_2$, —N($R^{10c}$)C(O)OR$^{10c}$, —C(O)OR$^{10c}$, —OC(O)R$^{10c}$, —S(O)R$^{10c}$, —S(O)$_2$R$^{10c}$, —NO$_2$, =O, =S, =N($R^{10c}$), and —CN; and $C_{1-3}$ alkyl, $C_{2-3}$ alkenyl, and $C_{2-3}$ alkynyl, each of which is optionally substituted with one or more substituents independently selected from halogen, —OR$^{10c}$, —SR$^{10c}$, —N($R^{10c}$)$_2$, —C(O)R$^{10c}$, —C(O)N($R^{10c}$)$_2$, —N($R^{10c}$)C(O)R$^{10c}$, —N($R^{10c}$)C(O)N($R^{10c}$)$_2$, —OC(O)N($R^{10c}$)$_2$, —N($R^{10c}$)C(O)OR$^{10c}$, —C(O)OR$^{10c}$, —OC(O)R$^{10c}$, —S(O)R$^{10c}$, —S(O)$_2$R$^{10c}$, —NO$_2$, =O, =S, =N($R^{10c}$), and —CN;

each $R^{9d}$ is independently selected from:

halogen, —OR$^{10d}$, —SR$^{10d}$, —N($R^{10d}$)$_2$, —C(O)R$^{10d}$, —C(O)N($R^{10d}$)$_2$, —N($R^{10d}$)C(O)R$^{10d}$, —N($R^{10d}$)C(O)N($R^{10d}$)$_2$, —OC(O)N($R^{10d}$)$_2$, —N($R^{10d}$)C(O)OR$^{10d}$, —C(O)OR$^{10d}$, —OC(O)R$^{10d}$, —S(O)R$^{10d}$, —S(O)$_2$R$^{10d}$, —NO$_2$, =O, =S, =N($R^{10d}$), and —CN; and $C_{1-3}$ alkyl, $C_{2-3}$ alkenyl, and $C_{2-3}$ alkynyl, each of which is optionally substituted with one or more substituents independently selected from halogen, —OR$^{10d}$, —SR$^{10d}$, —N($R^{10d}$)$_2$, —C(O)R$^{10d}$, —C(O)N($R^{10d}$)$_2$, —N($R^{10d}$)C(O)R$^{10d}$, —N($R^{10d}$)C(O)N($R^{10d}$)$_2$, —OC(O)N($R^{10d}$)$_2$, —N($R^{10d}$)C(O)OR$^{10d}$, —C(O)OR$^{10d}$, —OC(O)R$^{10d}$, —S(O)R$^{10d}$, —S(O)$_2$R$^{10d}$, —NO$_2$, =O, =S, =N($R^{10d}$), and —CN;

each $R^{9g}$ is independently selected from:

halogen, —OR$^{10g}$, —SR$^{10g}$, —N($R^{10g}$)$_2$, —C(O)R$^{10g}$, —C(O)N($R^{10g}$)$_2$, —N($R^{10g}$)C(O)R$^{10g}$, —N($R^{10g}$)C(O)N($R^{10g}$)$_2$, —OC(O)N($R^{10g}$)$_2$, —N($R^{10g}$)C(O)OR$^{10g}$, —C(O)OR$^{10g}$, —OC(O)R$^{10g}$, —S(O)R$^{10g}$, —S(O)$_2$R$^{10g}$, —NO$_2$, =O, =S, =N($R^{10g}$), and —CN; and $C_{1-3}$ alkyl, $C_{2-3}$ alkenyl, and $C_{2-3}$ alkynyl, each of which is optionally substituted with one or more substituents independently selected from halogen, —OR$^{10g}$, —SR$^{10g}$, —N($R^{10g}$)$_2$, —C(O)R$^{10g}$, —C(O)N($R^{10g}$)$_2$, —N($R^{10g}$)C(O)R$^{10g}$, —N($R^{10g}$)C(O)N($R^{10g}$)$_2$, —OC(O)N($R^{10g}$)$_2$, —N($R^{10g}$)C(O)OR$^{10g}$, —C(O)OR$^{10g}$, —OC(O)R$^{10g}$, —S(O)R$^{10g}$, —S(O)$_2$R$^{10g}$, —NO$_2$, =O, =S, =N($R^{10g}$), and —CN; and each $R^{10a}$, $R^{10b}$, $R^{10c}$, $R^{10d}$, $R^{10e}$, $R^{10f}$, $R^{10g}$ and $R^{10h}$ is independently selected from:

hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, and 3- to 10-membered heterocycle; and $C_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

2. The compound or salt of claim 1, wherein n is 1 or 2.

3. The compound or salt of claim 1, wherein each $R^1$ is independently selected from: halogen, —CN, —OR$^{10a}$, —SR$^{10a}$, —N($R^{10a}$)$_2$, and $C_{1-6}$ alkyl, wherein the $C_{1-6}$ alkyl is optionally substituted with one or more substituents independently selected from halogen, —OR$^{10a}$, —SR$^{10a}$, —N($R^{10a}$)$_2$, =O, and —CN, wherein each $R^{10a}$ is independently selected from hydrogen and $C_{1-6}$ alkyl.

4. The compound or salt of claim 1, wherein each $R^1$ is independently selected from: —F, —Br, —CN, —OH, and —CH$_3$.

5. The compound or salt of claim 1, wherein $R^2$ is selected from: optionally substituted $C_{5-10}$ carbocycle and optionally substituted 5- to 10-membered heterocycle.

6. The compound or salt of claim 5, wherein $R^2$ is selected from: optionally substituted $C_{6-10}$ carbocycle and optionally substituted 5- to 10-membered heterocycle.

7. The compound or salt of claim 1, wherein $R^2$ is selected from optionally substituted phenyl and optionally substituted 5- to 10-membered heteroaryl, each of which is optionally substituted with one or more substituents independently selected from halogen, —OR$^{10b}$, —CN, $C_{1-6}$ alkyl, $C_{2-6}$ alkenyl, and $C_{2-6}$ alkynyl, and wherein each $R^{10b}$ is independently selected from hydrogen and $C_{1-6}$ alkyl.

8. The compound or salt of claim 7, wherein $R^2$ is selected from phenyl, pyridinyl, pyrimidinyl, pyrazinyl, and pyridazinyl, any one of which is optionally substituted.

9. The compound or salt of claim 7, wherein $R^2$ is selected from optionally substituted 5- to 10-membered heteroaryl.

10. The compound or salt of claim 1, wherein $R^2$ together with $R^{11}$ form a 6- to 10-membered heterocycle or $C_{3-10}$ carbocycle, wherein the 3- to 10-membered heterocycle or $C_{3-10}$ carbocycle is optionally substituted with one or more substituents independently selected from $R^{9b'}$.

11. The compound or salt of claim 1, wherein $R^3$ and $R^4$ are each independently selected from: hydrogen, —OH, and $C_1$ alkyl.

12. The compound or salt of claim 1, wherein $R^5$ and $R^6$ are each hydrogen.

13. The compound or salt of claim 1, wherein each of $R^7$ and $R^8$ is independently selected from hydrogen and $C_{1-6}$ alkyl.

14. The compound or salt of claim 13, wherein $R^7$ is hydrogen, and $R^8$ is hydrogen.

15. The compound or salt of claim 1, wherein $R^{11}$ is selected from: $C_{1-3}$ alkyl optionally substituted with one or more —OH.

16. The compound or salt of claim 1, wherein $R^{12}$ is hydrogen.

17. The compound of claim 1, wherein the compound is

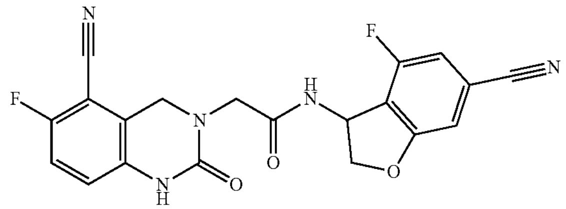 [SMILES: N#Cc1cc(F)c2c(c1)OCC2NC(=O)CN1Cc2c(ccc(F)c2C#N)NC1=O]

or a salt thereof.

18. The compound of claim 1, wherein the compound is

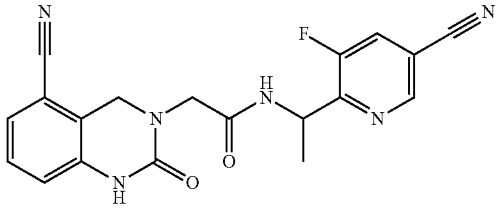

or a salt thereof.

19. The compound of claim 1, wherein the compound is

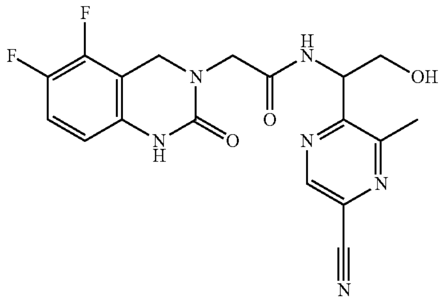

or a salt thereof.

20. The compound of claim 1, wherein the compound is

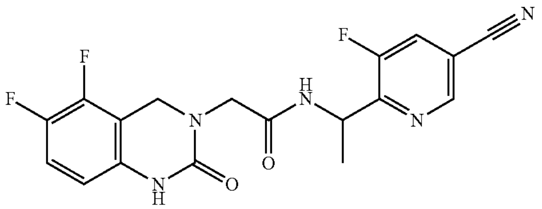 [SMILES: CC(NC(=O)CN1Cc2c(ccc(F)c2F)NC1=O)c1ncc(C#N)cc1F]

or a salt thereof.

21. The compound of claim 1, wherein the compound is

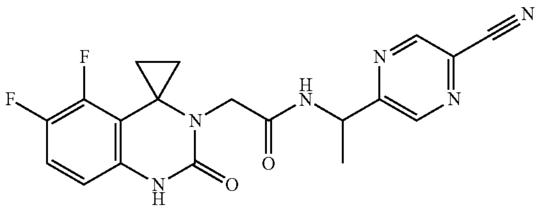 [SMILES: CC(NC(=O)CN1C(=O)Nc2ccc(F)c(F)c2C12CC2)c1cnc(C#N)cn1]

or a salt thereof.

22. The compound of claim 1, wherein the compound is

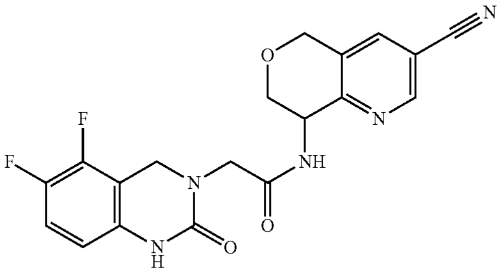

or a salt thereof.

23. The compound of claim 1, wherein the compound is

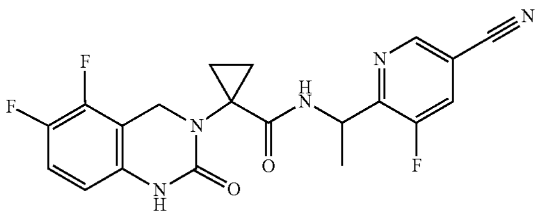 [SMILES: CC(NC(=O)C1(N2Cc3c(ccc(F)c3F)NC2=O)CC1)c1ncc(C#N)cc1F]

or a salt thereof.

24. The compound of claim 1, wherein the compound is

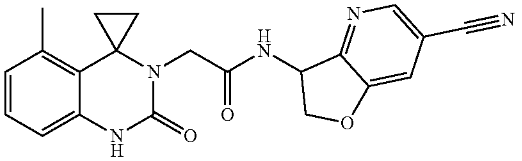 [SMILES: Cc1cccc2c1C1(CC1)N(CC(=O)NC1COc3cc(C#N)cnc31)C(=O)N2]

or a salt thereof.

25. The compound of claim 1, wherein the compound is

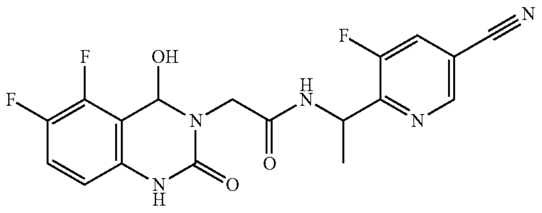 [SMILES: CC(NC(=O)CN1C(=O)Nc2ccc(F)c(F)c2C1O)c1ncc(C#N)cc1F]

or a salt thereof.

26. The compound of claim 1, wherein the compound is

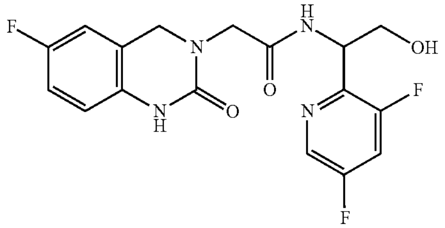 [SMILES: O=C(CN1Cc2cc(F)ccc2NC1=O)NC(CO)c1ncc(F)cc1F]

or a salt thereof.

27. The compound of claim 1, wherein the compound is

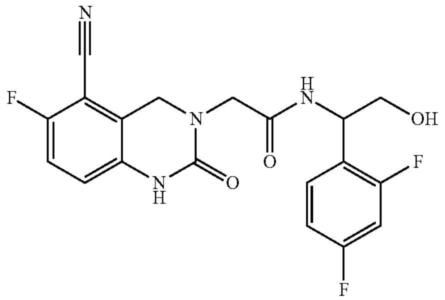

or a salt thereof.

28. A pharmaceutical composition comprising a compound or salt of claim 1 and a pharmaceutically acceptable excipient.

29. The compound of claim 1, wherein the compound is

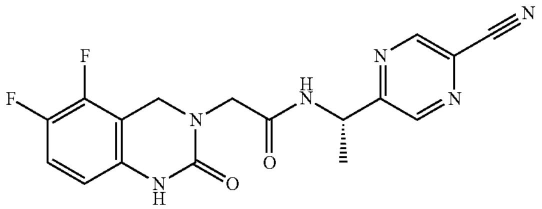

or a salt thereof.

30. The compound of claim 1, wherein the compound is

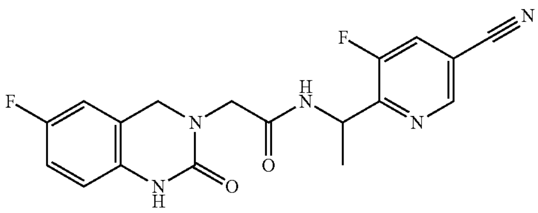 [SMILES: CC(NC(=O)CN1Cc2cc(F)ccc2NC1=O)c1ncc(C#N)cc1F]

or a salt thereof.

31. The compound of claim 1, wherein the compound is

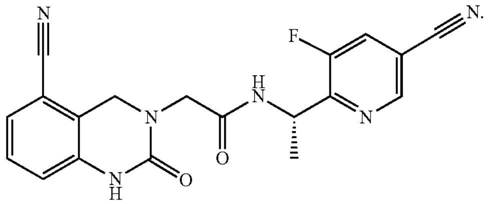

32. The compound of claim 1, wherein the compound is

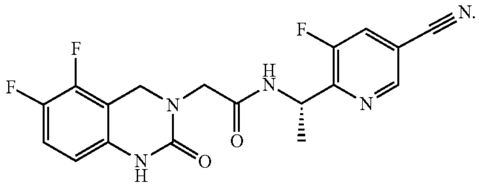

33. The compound of claim 1, wherein the compound is

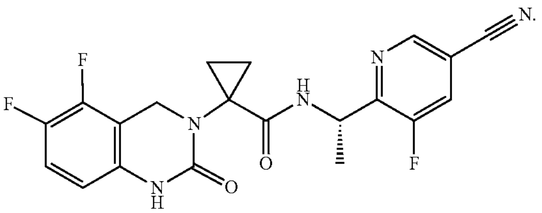

34. The compound of claim 1, wherein the compound is

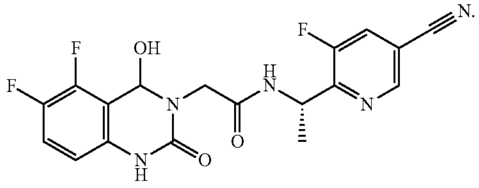

35. The compound of claim 1, wherein the compound is
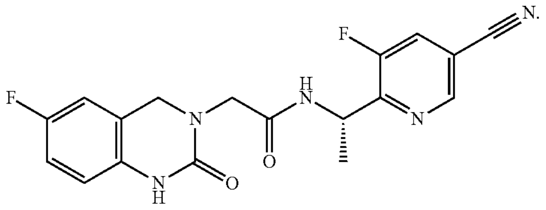
36. The compound of claim 1, wherein the compound is
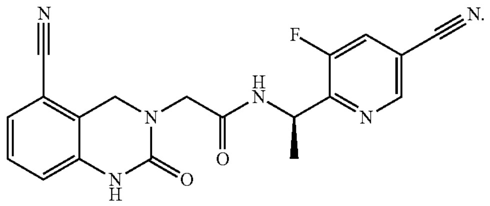
37. The compound of claim 1, wherein the compound is
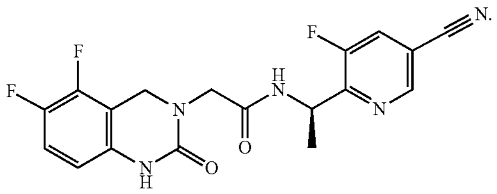
38. The compound of claim 1, wherein the compound is
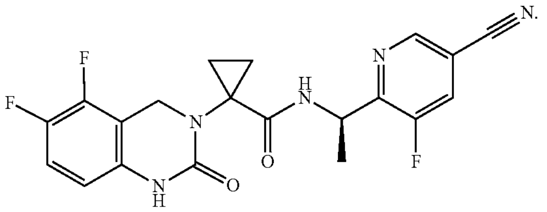
39. The compound of claim 1, wherein the compound is
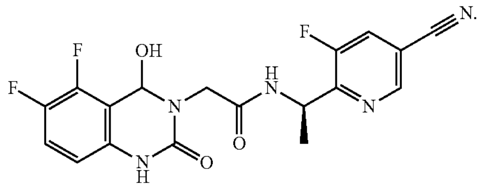
40. The compound of claim 1, wherein the compound is
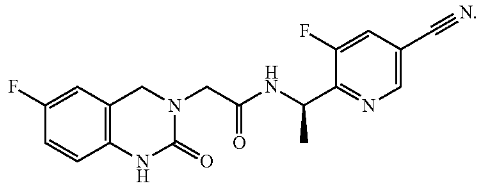
* * * * *